US011168102B1

United States Patent
Gill et al.

(10) Patent No.: US 11,168,102 B1
(45) Date of Patent: *Nov. 9, 2021

(54) BICYCLIC HETEROARYL COMPOUNDS AND USES THEREOF

(71) Applicant: Revolution Medicines, Inc., Redwood City, CA (US)

(72) Inventors: Adrian L. Gill, Menlo Park, CA (US); Andreas Buckl, San Francisco, CA (US); Elena S. Koltun, Foster City, CA (US); Naing Aay, San Mateo, CA (US); Arlyn A. Tambo-ong, South San Francisco, CA (US); Severin Thompson, Belmont, CA (US); Micah James Gliedt, Fremont, CA (US); John E. Knox, Emerald Hills, CA (US); James Cregg, Belmont, CA (US); Anne V. Edwards, San Mateo, CA (US); Yang Liu, Foster City, CA (US); G. Leslie Burnett, San Mateo, CA (US)

(73) Assignee: Revolution Medicines, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/133,340

(22) Filed: Dec. 23, 2020

Related U.S. Application Data

(63) Continuation of application No. 17/090,342, filed on Nov. 5, 2020.

(60) Provisional application No. 63/070,593, filed on Aug. 26, 2020, provisional application No. 63/031,318, filed on May 28, 2020, provisional application No. 62/933,141, filed on Nov. 8, 2019.

(51) Int. Cl.
| | | |
|---|---|---|
| *C07D 471/04* | (2006.01) | |
| *C07F 9/6584* | (2006.01) | |
| *C07D 519/00* | (2006.01) | |

(52) U.S. Cl.
CPC .......... *C07F 9/6584* (2013.01); *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS

| | | | |
|---|---|---|---|
| 8,637,684 B2 | 1/2014 | Shen et al. | |
| 2011/0281942 A1 | 11/2011 | Shen et al. | |
| 2016/0030594 A1 | 2/2016 | Abrams et al. | |

FOREIGN PATENT DOCUMENTS

| | | |
|---|---|---|
| CN | 105418632 A | 3/2016 |
| WO | 2005094314 A2 | 10/2005 |
| WO | 2006119504 A2 | 11/2006 |
| WO | 2007117699 A2 | 10/2007 |
| WO | 2008124815 A1 | 10/2008 |
| WO | 2009049098 A2 | 4/2009 |
| WO | 2009135000 A2 | 11/2009 |
| WO | 2010011666 A2 | 1/2010 |
| WO | 2010121212 A2 | 10/2010 |
| WO | 2011022440 A9 | 2/2011 |
| WO | 2012041524 A1 | 4/2012 |
| WO | 2012087881 A1 | 6/2012 |
| WO | 2014015291 A1 | 1/2014 |
| WO | 2014113584 A1 | 7/2014 |
| WO | 2014176488 A1 | 10/2014 |
| WO | 2015003094 A2 | 1/2015 |
| WO | 2015107493 A1 | 7/2015 |
| WO | 2015107494 A1 | 7/2015 |
| WO | 2015107495 A1 | 7/2015 |
| WO | 2016044772 A1 | 3/2016 |
| WO | 2021074227 A1 | 4/2016 |
| WO | 2016077793 A1 | 5/2016 |
| WO | 2016115434 A1 | 7/2016 |
| WO | 2016191328 A1 | 12/2016 |
| WO | 2016196591 A1 | 12/2016 |
| WO | 2016203404 A1 | 12/2016 |
| WO | 2016203405 A1 | 12/2016 |
| WO | 2016203406 A1 | 12/2016 |

(Continued)

OTHER PUBLICATIONS

Berger et al., "S(+)-4-(1-Phenylethylamino)quinazolines as Inhibitors of Human Immunoglobuline E Synthesis: Potency Is Dictated by Sterochemistry and Atomic Point Charges at N-1", J. Med. Chem., Jan. 1, 2001, vol. 44, No. 18, pp. 3031-3038.

(Continued)

*Primary Examiner* — Emily A Bernhardt
(74) *Attorney, Agent, or Firm* — Armstrong Teasdale LLP

(57) ABSTRACT

The present disclosure is directed to modulators of SOS1 and their use in the treatment of disease. Also disclosed are pharmaceutical compositions comprising the same. Modulators of SOS1 have the following general structure of the Formula (II),

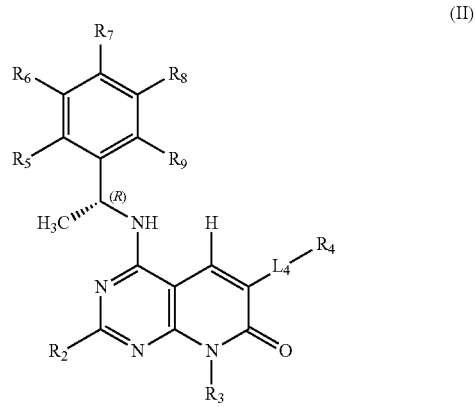

or a pharmaceutically acceptable salt or a stereoisomer thereof, wherein the variables are as defined herein.

18 Claims, No Drawings

(56) References Cited

FOREIGN PATENT DOCUMENTS

| | | | |
|---|---|---|---|
| WO | 2017014323 A1 | 1/2017 | |
| WO | 2017078499 A1 | 5/2017 | |
| WO | 2017079723 A1 | 5/2017 | |
| WO | 2017100279 A1 | 6/2017 | |
| WO | 2017156397 A1 | 9/2017 | |
| WO | 2017210134 A1 | 12/2017 | |
| WO | 2017211303 A1 | 12/2017 | |
| WO | 2018013597 A1 | 1/2018 | |
| WO | 2018057884 A1 | 3/2018 | |
| WO | 2018081091 A1 | 5/2018 | |
| WO | 2018115380 A1 | 6/2018 | |
| WO | 2018129402 A1 | 7/2018 | |
| WO | 2018130928 A1 | 7/2018 | |
| WO | 2018136264 A1 | 7/2018 | |
| WO | 2018136265 A1 | 7/2018 | |
| WO | 2018160731 A1 | 9/2018 | |
| WO | 2018172250 A1 | 9/2018 | |
| WO | 2018172984 A1 | 9/2018 | |
| WO | 2018218133 A1 | 11/2018 | |
| WO | 2019201848 A1 | 1/2019 | |
| WO | 2019051084 A1 | 3/2019 | |
| WO | 2019051469 A1 | 3/2019 | |
| WO | 2019067843 A1 | 4/2019 | |
| WO | 2019122129 A1 | 6/2019 | |
| WO | 2019152454 A1 | 8/2019 | |
| WO | 2019158019 A1 | 8/2019 | |
| WO | 2019165073 A1 | 8/2019 | |
| WO | 2019167000 A1 | 9/2019 | |
| WO | 2019182960 A1 | 9/2019 | |
| WO | 2019183364 A1 | 9/2019 | |
| WO | 2019183367 A1 | 9/2019 | |
| WO | 2019199792 A1 | 10/2019 | |
| WO | 2019213318 A1 | 11/2019 | |
| WO | 2019233810 A1 | 12/2019 | |
| WO | 2020022323 A1 | 1/2020 | |
| WO | 2020033286 A1 | 2/2020 | |
| WO | 2020033828 A1 | 2/2020 | |
| WO | 2020061101 A1 | 3/2020 | |
| WO | 2020061103 A1 | 3/2020 | |
| WO | 2020063760 A1 | 4/2020 | |
| WO | 2020072656 A1 | 4/2020 | |
| WO | 2020073945 A1 | 4/2020 | |
| WO | 2020073949 A1 | 4/2020 | |
| WO | 2020076723 A1 | 4/2020 | |
| WO | 2020081848 A1 | 4/2020 | |
| WO | 2020180768 A1 | 9/2020 | |
| WO | 2020180770 A1 | 9/2020 | |

OTHER PUBLICATIONS

Bullock et al., "Syntheses of 6-Substituted Purines", Journal of the American Chemical Society, Aug. 5, 1956, vol. 78, No. 15, pp. 3693-3696.

Burns et al., "Approach for targeting RAS with small molecules that activate SOS-mediated nucleotide exchange", PNAS, Mar. 4, 2014, vol. 111, No. 9, pp. 3401-3406.

Chakraborti et al., "3D-QSAR Stuies on Thieno[3,2-d]pyrimidines as Phosphodiesterase IV Inhibitors", Bioorganic & Medicinal Chemistry Letters, vol. 13, No. 8, Jan. 1, 2003, pp. 1403-1408.

Chen et al., "Discovery of a Novel Shp2 Protein Tyrosine Phosphatase Inhibitor", Molecular Pharmacology, 2006, vol. 70, No. 2, pp. 562-570.

Crespo et al., "Design, Synthesis, and Biological Activities of New Thieno[3,2-d]pyrimidines as Selective Type 4 Phosphodiesterase Inhibitors", J. of Med. Chem., Jan. 1, 1998, vol. 41, pp. 4021-4035.

Hillig et al., "Discovery of potent SOS1 inhibitors that block RAS activation via disruption of the RAS-SOS1 interaction", PNAS, Feb. 12, 2019, vol. 116, No. 7, pp. 2551-2560.

Igbe et al., "Dietary quercetin potentiates the antiproliferative effect of interferon-α in hepatocellar carcinoma cells through activation of JAK/STAT pathway signaling by inhibition of SHP2 phosphatase", Oncotarget, 2017, vol. 8, No. 69, pp. 113734-113748.

Kaspersen et al., "Activity of 6-aryl-pyrrolo[2,3-d]pyrimidines-4-amines to Tetrahymena", Bioorganic Chemistry, Jan. 1, 2012, vol. 44, pp. 35-41.

Kaspersen et al., "Sythesis and in vitro EGFR (ErbB1) tyrosine kinase inhibitory activity of 4-N-substituted 6-aryl-7Hpyrrolo[2,3-d]pyrimidine-4-amines", European Journal of Medicinal Chemistry, Oct. 6, 2011, vol. 46, No. 12, pp. 6002-6014.

Koshimizu et al., "Structure-Activity Relationships in Optically Active Cytokinins", Phytochemistry, Jan. 1, 1968, vol. 7, pp. 1989-1994.

Ross et al., "Potential Anticancer Agents. XVIII. Synthesis of Substituted 4,5-Trimethylenephyrimidines", J. American Chemical Society, Jan. 1, 1959, vol. 81, pp. 3108-3110.

Sarver et al., "6-Amino-3-methylpyrimidinones as Potent, Selective, and Orally Efficacious SHP2 Inhibitors", J. Med. Chem., 2019, vol. 62, pp. 1793-1802.

Xie et al., "Allosteric Inhibitors of SHP2 with Therapeutic Potential for Cancer Treatment", J. Med. Chem., 2017, vol. 60, pp. 10205-10219.

Lu et al., "Inhibitors of Ras-SOS Interactions", Chem Med Chem, Dec. 2, 2015, vol. 11, No. 8, pp. 814-821.

International Search Report for PCT US/2020/059024, dated Feb. 8, 2021, 3 pages.

Boehringer Ingelheim, A Study to Test Different Doses of BI 1701963 Alone and Combined With Trametinib in Patients with Different Types of Advanced Cancer (Solid Tumours With KRAS Mutation) Bethesda (MD): U.S. National Library of Medicine; 2019. Available from: https://clinicaltrials.gov/ct2/show/NCT04111458 ClinicalTrials.gov, 10 pages.

Boehringer Ingelheim. A Study to Test Different Doses of Bl 1701963 in Combination With Irinotecan in People With Advanced Bowel Cancer With Kirsten Rat Sarcoma Viral Oncogene Homologue (KRAS) Mutation. Bethesda (MD): U.S. National Library of Medicine; 2020. Available from: https://clinicaltrials.gov/ct2/show/NCT04627142 ClinicalTrials.gov, 9 pages.

Boehringer Ingelheim. A Study to Find a Safe and Effective Dose of BI 1701963 Alone and in Combination With Bl 3011441 in Patients With Advanced Cancer and a Certain Mutation (KRAS) Bethesda (MD): U.S. National Library of Medicine; 2021. Available from: https://clinicaltrials.gov/ct2/show/NCT04835714 ClinicalTrials.gov, 11 pages.

Hofmann et al., "BI-3406, a Potent and Selective SOS-1-KRAS Interaction Inhibitor, Is Effective in KRAS-Driven Cancers through Combined MEK Inhibition", Cancer Discovery, Jan. 2021, pp. 142-157.

Ramharter et al., One Atom Makes All the Difference: Getting a Foot in the Door between SOS1 and KRAS:, J. Med. Chem., 2021, vol. 64, pp. 6569-6580.

BICYCLIC HETEROARYL COMPOUNDS AND USES THEREOF

CROSS REFERENCE TO RELATED APPLICATION(S)

This application is a continuation of U.S. application Ser. No. 17/090,342, filed Nov. 5, 2020, the disclosure of which is hereby incorporated by reference as if set forth in its entirety. U.S. application Ser. No. 17/090,342 claims the benefit of priority to U.S. provisional Application Ser. No. 62/933,141, filed Nov. 8, 2019, the disclosure of which is hereby incorporated by reference as if set forth in its entirety. U.S. application Ser. No. 17/090,342 claims the benefit of priority to U.S. provisional Application Ser. No. 63/031,318, filed May 28, 2020, the disclosure of which is hereby incorporated by reference as if set forth in its entirety. U.S. application Ser. No. 17/090,342 claims the benefit of priority to U.S. provisional Application Ser. No. 63/070,593 filed Aug. 26, 2020, the disclosure of which is hereby incorporated by reference as if set forth in its entirety.

FIELD OF THE DISCLOSURE

The present disclosure relates to inhibitors of SOS1 useful in the treatment of diseases or disorders. Specifically, the present disclosure is concerned with compounds and compositions inhibiting SOS1, methods of treating diseases associated with SOS1, and methods of synthesizing these compounds.

BACKGROUND OF THE DISCLOSURE

RAS-family proteins including KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof are small GTPases that exist in cells in either GTP-bound or GDP-bound states (McCormick et al., J. Mol. Med. (Berl), 2016, 94(3):253-8; Nimnual et al., Sci. STKE., 2002, 2002 (145):p 136). The RAS-family proteins have a weak intrinsic GTPase activity and slow nucleotide exchange rates (Hunter et al., Mol. Cancer Res., 2015, 13(9): 1325-35). Binding of GTPase activating proteins (GAPs) such as NF1 increases the GTPase activity of RAS-family proteins. The binding of guanine nucleotide exchange factors (GEFs) such as SOS1 (Son of Sevenless 1) promote release of GDP from RAS-family proteins, enabling GTP binding (Chardin et al., Science, 1993, 260(5112):1338-43). When in the GTP-bound state, RAS-family proteins are active and engage effector proteins including RAF and phosphoinositide 3-kinase (PI3K) to promote the RAF/mitogen or extracellular signal-regulated kinases (MEK/ERK). Published data indicate a critical involvement of SOS1 in mutant KRAS activation and oncogenic signaling in cancer (Jeng et al., Nat. Commun., 2012, 3:1168). Depleting SOS1 levels decreased the proliferation rate and survival of tumor cells carrying a KRAS mutation whereas no effect was observed in KRAS wild type cell lines. The effect of loss of SOS1 could not be rescued by introduction of a catalytic site mutated SOS1, demonstrating the essential role of SOS1 GEF activity in KRAS mutant cancer cells.

SOS1 is critically involved in the activation of RAS-family protein signaling in cancer via mechanisms other than mutations in RAS-family proteins. SOS1 interacts with the adaptor protein Grb2 and the resulting SOS1/Grb2 complex binds to activated/phosphorylated Receptor Tyrosine Kinases (e.g., EGFR, ErbB2, ErbB3, ErbB4, PDGFR-A/B, FGFR1/2/3, IGF1 R, INSR, ALK, ROS, TrkA, TrkB, TrkC, RET, c-MET, VEGFR1/2/3, AXL) (Pierre et al., Biochem. Pharmacol., 2011, 82(9): 1049-56). SOS1 is also recruited to other phosphorylated cell surface receptors such as the T cell Receptor (TCR), B cell Receptor (BCR) and monocyte colony-stimulating factor receptor (Salojin et al., J. Biol. Chem. 2000, 275(8):5966-75). This localization of SOS1 to the plasma membrane, proximal to RAS-family proteins, enables SOS1 to promote RAS-family protein activation. SOS1-activation of RAS-family proteins can also be mediated by the interaction of SOS1/Grb2 with the BCR-ABL oncoprotein commonly found in chronic myelogenous leukemia (Kardinal et al., 2001, Blood, 98:1773-81; Sini et al., Nat. Cell Biol., 2004, 6(3):268-74). Furthermore, alterations in SOS1 have been implicated in cancer. SOS1 mutations are found in embryonal rhabdomyosarcomas, Sertoli cell testis tumors, granular cell tumors of the skin (Denayer et al., Genes Chromosomes Cancer, 2010, 49(3):242-52) and lung adenocarcinoma (Cancer Genome Atlas Research Network., Nature, 2014, 511 (751 1):543-50). Meanwhile over-expression of SOS1 has been described in bladder cancer (Watanabe et al., IUBMB Life, 2000, 49(4):317-20) and prostate cancer (Timofeeva et al., Int. J. Oncol., 2009; 35(4):751-60). In addition to cancer, hereditary SOS1 mutations are implicated in the pathogenesis of RASopathies like e.g., Noonan syndrome (NS), cardio-facio-cutaneous syndrome (CFC) and hereditary gingival fibromatosis type 1 (Pierre et al., Biochem. Pharmacol., 2011, 82(9):1049-56).

SOS1 is also a GEF for the activation of the GTPases RAC1 (Ras-related C3 botulinum toxin substrate 1) (Innocenti et al., J. Cell Biol., 2002, 156(1):125-36). RAC1, like RAS-family proteins, is implicated in the pathogenesis of a variety of human cancers and other diseases (Bid et al., Mol. Cancer Ther. 2013, 12(10):1925-34).

Son of Sevenless 2 (SOS2), a homolog of SOS1 in mammalian cells, also acts as a GEF for the activation of RAS-family proteins (Pierre et al., Biochem. Pharmacol., 2011, 82(9): 1049-56; Buday et al., Biochim. Biophys. Acta., 2008, 1786(2):178-87). Published data from mouse knockout models suggests a redundant role for SOS1 and SOS2 in homeostasis in the adult mouse. Whilst germline knockout of SOS1 in mice results in lethality during mid-embryonic gestation (Qian et al., EMBO J., 2000, 19(4): 642-54), systemic conditional SOS1 knockout adult mice are viable (Baltanas et al., Mol. Cell. Biol., 2013, 33(22): 4562-78). SOS2 gene targeting did not result in any overt phenotype in mice (Esteban et al., Mol. Cell. Biol., 2000, 20(17):6410-3). In contrast, double SOS1 and SOS2 knockout leads to rapid lethality in adult mice (Baltanas et al., Mol. Cell. Biol., 2013, 33(22):4562-78). These published data suggest that selective targeting of individual SOS isoforms (e.g., selective SOS1 targeting) may be adequately tolerated to achieve a therapeutic index between SOS1/RAS-family protein driven cancers (or other SOS1/RAS-family protein pathologies) and normal cells and tissues.

Selective pharmacological inhibition of the binding of the catalytic site of SOS1 to RAS-family proteins is expected to prevent SOS1-mediated activation of RAS-family proteins to the GTP-bound form. Such SOS1 inhibitor compounds are be expected to consequently inhibit signaling in cells downstream of RAS-family proteins (e.g., ERK phosphorylation). In cancer cells associated with dependence on RAS-family proteins (e.g., KRAS mutant cancer cell lines), SOS1 inhibitor compounds are be expected to deliver anti-cancer efficacy (e.g., inhibition of proliferation, survival, metastasis, etc.). High potency towards inhibition of SOS1: RAS-family protein binding (nanomolar level $IC_{50}$ values) and ERK phosphorylation in cells (nanomolar level $IC_{50}$ values) are desirable characteristics for a SOS1 inhibitor compound. Furthermore, a desirable characteristic of a SOS1 inhibitor compound would be the selective inhibition of SOS1 over SOS2. This conclusion is based on the viable phenotype of SOS1 knockout mice and lethality of SOS1/SOS2 double knockout mice, as described above.

These characteristics have not been achieved in previously described SOS1 inhibitor compounds. In the last decades, the RAS family proteins-SOS1 protein interaction has gained increasing recognition. Several efforts to identify and optimize binders, which target either the effector binding site of RAS or the catalytic binding site of SOS1 (for a selected review see: Lu et al., ChemMedChem. 2016, 11(8): 814-21), have been made with limited success.

Recently, small activating molecules have been identified, which bind to a lipophilic pocket of SOS1 in close proximity to the RAS binding site (Burns et al., Proc. Natl. Acad. Sci. 2014, 111(9):3401-6). However, binding of these molecules seems to lead to increased nucleotide exchange and thereby activation of RAS instead of deactivation.

In an effort to stabilize the protein-protein-interaction of RAS-family proteins with SOS1 and to prevent reloading of RAS-family proteins with GTP, several different fragments were subsequently identified (Winter et al., J. Med. Chem. 2015, 58(5):2265-74). However, reversible binding of fragments to SOS1 did not translate into a measurable effect on the nucleotide exchange and only a weak effect was observed for fragments covalently bound to RAS.

Also recently, studies have been conducted to combine rational design and screening platforms to identify small molecule inhibitors of SOS1 (Evelyn et al., Chem. Biol. 2014, 21 (12):1618-28; Evelyn et al., J. Biol. Chem. 2015, 290(20):12879-98; Zheng et al., WO 2016/077793), i.e. compounds which bind to SOS1 and inhibit protein-protein interaction with RAS-family proteins. Although compounds with a slight inhibitory effect on SOS1 have been identified, the effects on guanine nucleotide exchange and cellular signal transduction modulation (e.g., ERK phosphorylation) are weak.

BRIEF SUMMARY

The present disclosure relates to compounds capable of inhibiting the activity of SOS1. The present disclosure further provides a process for the preparation of compounds, pharmaceutical preparations comprising such compounds and methods of using such compounds and compositions in the management of diseases or disorders associated with the aberrant activity of SOS1.

One aspect of the present disclosure relates to compounds of Formula (I):

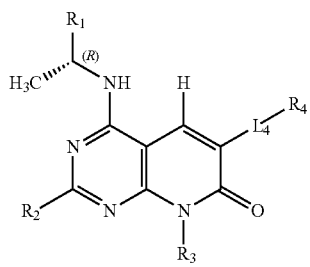

(I)

or a pharmaceutically acceptable salt, solvate, isomer, prodrug, or tautomer thereof, wherein:

$R_1$ is selected from the group consisting of optionally substituted 3-6 membered cycloalkyl, optionally substituted 3-6 membered heterocyclyl, optionally substituted 6-membered aryl, and optionally substituted 5-6 membered heteroaryl;

$R_2$ is selected from the group consisting of H, $C_{1-6}$ alkyl, halogen, —$NHR_{2a}$, —$OR_{2a}$, cyclopropyl, and —CN; wherein $C_{1-6}$ alkyl is optionally substituted with halogen, —$NHR_{2a}$, —$OR_{2a}$, or 5-6 membered heterocyclyl, and further wherein $R_{2a}$ is selected from the group consisting of H, $C_{1-6}$ alkyl, 3-6 membered heterocyclyl, and $C_{1-6}$ haloalkyl;

$R_3$ is selected from the group consisting of H, $C_{1-3}$ alkyl, —$OR_{3a}$, cyclopropyl, and 3-6 membered heterocyclyl, wherein each of $C_{1-3}$ alkyl, cyclopropyl, and 3-6 membered heterocyclyl is optionally substituted with $R_{3a}$, and further wherein $R_{3a}$ is selected from the group consisting of $C_{1-3}$ alkyl, halogen, —OH, or —CN;

$L_4$ is selected from the group consisting of bond, —C(O)—, —C(O)O—, —C(O)NH($CH_2$)$_o$—, —NH—, —S—, —S(O)$_2$—,

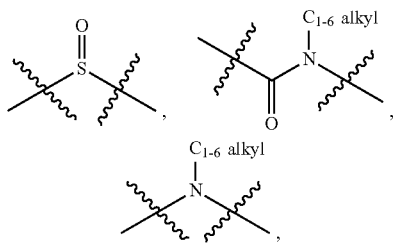

—($CH_2$)$_p$—, and —O—; wherein o is 0, 1, or 2; and wherein p is a number from 1 to 6; and $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl, —$R_{4a}$, —$OR_{4a}$, —O—$C_{1-6}$ alkyl-$R_{4a}$, =O, halogen, —C(O)$R_{4a}$, —C(OO)$R_{4a}$, —C(O)$NR_{4b}R_{4c}$, —$NR_{4b}$C(O)$R_{4c}$, —CN, =$NR_{4a}$, —$NR_{4b}R_{4c}$, —$SO_2R_{4a}$, 3-6 membered cycloalkyl optionally substituted with $R_{4a}$, 3-7 membered heterocyclyl optionally substituted with $R_{4a}$, 6-10 membered aryl optionally substituted with $R_{4a}$, or 5-10 membered heteroaryl optionally substituted with $R_{4a}$;

wherein $R_{4a}$ is H, $C_{1-6}$ alkyl, $C_{1-6}$ haloalkyl, —C(O)$R_{4b}$, —C(O)$NR_{4b}R_{4c}$, =O, 3-6 membered cycloalkyl, 6-10 membered aryl optionally substituted with —$OR_{4b}$, —CN, =N-3-6 membered cycloalkyl, 3-7 membered heterocyclyl, —($CH_2$)$_r$$OCH_3$, or —($CH_2$)$_r$OH wherein r is 1, 2, or 3;

wherein each $R_{4b}$ is independently H, $C_{1-6}$ alkyl; and wherein each $R_{4c}$ is independently H or $C_{1-6}$ alkyl.

Another aspect of the present disclosure relates to compounds of Formula (II):

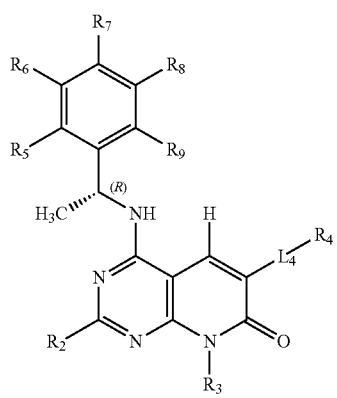

(II)

or a pharmaceutically acceptable salt, solvate, isomer, prodrug, or tautomer thereof, wherein $R_2$, $R_3$, $L_4$, and $R_4$ are as defined in Formula (I);

$R_5$, $R_6$, and $R_7$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —$NO_2$, —CN, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, —$C(O)R_{10}$, —$CO_2R_{10}$, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl, halogen, —$NO_2$, oxo, —CN, —$R_{10}$, —$OR_{10}$, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, 3-8 membered cycloalkyl, 3-14 membered heterocyclyl, 6-10 membered aryl, or 5-10 membered heteroaryl, or any two adjacent $R_5$, $R_6$, $R_7$, $R_8$, and $R_9$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —$OR_{13}$, —$SR_{13}$, halogen, —$NR_{13}R_{14}$, —$NO_2$, and —CN; and $R_{13}$ and $R_{14}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —$NH_2$, —$NO_2$, or —CN.

Another aspect of the present disclosure relates to compounds of Formula (III),

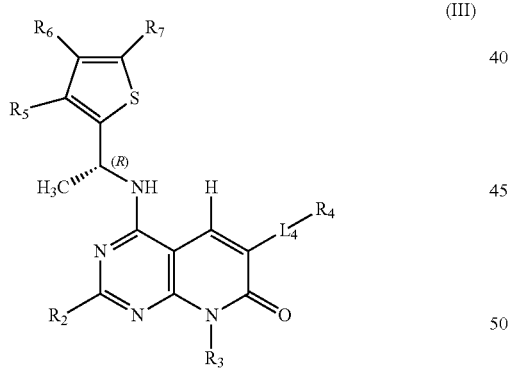

(III)

or a pharmaceutically acceptable salt, solvate, isomer, prodrug, or tautomer thereof, wherein $R_2$, $R_3$, $L_4$, and $R_4$ are as defined in Formula (I);

$R_5$, $R_6$, and $R_7$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —$NO_2$, —CN, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, —$C(O)R_{10}$, —$CO_2R_{10}$, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl, halogen, —$NO_2$, oxo, —CN, —$R_{10}$, —$OR_{10}$, —$NR_1R_2$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, 3-8 membered cycloalkyl, 3-14 membered heterocyclyl, 6-10 membered aryl, or 5-10 membered heteroaryl, or any two adjacent $R_5$, $R_6$, and $R_7$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —$OR_{13}$, —$SR_{13}$, halogen, —$NR_{13}R_{14}$, —$NO_2$, and —CN; and $R_{13}$ and $R_{14}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —$NH_2$, —$NO_2$, or —CN.

Another aspect of the present disclosure relates to compounds of Formula (IV-a), (IV-b), or (IV-c),

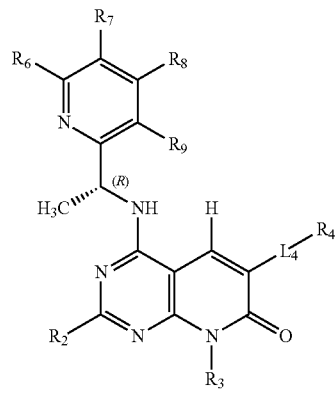

(IV-a)

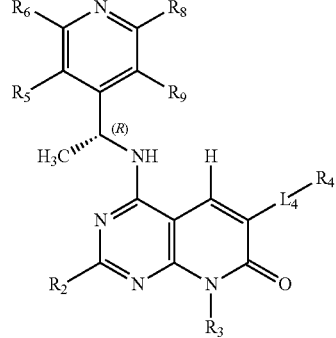

(IV-b)

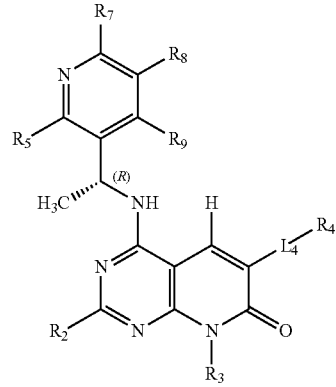

(IV-c)

or a pharmaceutically acceptable salt, solvate, isomer, prodrug, or tautomer thereof, wherein $R_2$, $R_3$, $L_4$, and $R_4$ are as defined in Formula (I);

$R_5$, $R_6$, $R_7$, $R_8$, and $R_9$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —$NO_2$, —CN, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, —$C(O)R_{10}$, —$CO_2R_{10}$, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl, halogen, —$NO_2$, oxo, —CN, —$R_{10}$, —$OR_{10}$, —$NR_1R_2$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, 3-8 membered cycloalkyl, 3-14 membered heterocyclyl, 6-10 membered aryl, or 5-10 membered heteroaryl, or any two adjacent $R^5$, $R^6$, $R^7$, $R^8$, and $R^9$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —$OR_{13}$, —$SR_{13}$, halogen, —$NR_{13}R_{14}$, —$NO_2$, and —CN; and $R_{13}$ and $R_{14}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —$NH_2$, —$NO_2$, or —CN.

One aspect of the present disclosure relates to a method of inhibiting SOS1 in a subject in need thereof, comprising administering to the subject a SOS1 inhibitor of the present invention, or a pharmaceutically acceptable salt, solvate, hydrate, tautomer, or isomer thereof.

Another aspect of the present disclosure relates to methods of treating or preventing a disease that is effected by inhibition of the interaction of SOS1 and a RAS-family protein and/or RAC1 in a subject in need thereof, comprising administering to the subject an effective amount of a compound of any one of Formula (I)-(IV), and pharmaceutically acceptable salts, prodrugs, solvates, hydrates, tautomers, and isomers thereof.

Another aspect of the present disclosure relates to methods of treating or preventing cancer in a subject in need thereof, comprising administering to the subject an effective amount of a compound of any one of Formula (I)-(IV), and pharmaceutically acceptable salts, prodrugs, solvates, hydrates, tautomers, and isomers thereof.

Another aspect of the present disclosure relates to methods of inhibiting SOS1. The method comprises administering to a patient in need thereof, an effective amount of a compound of any one of Formula (I)-(IV), and pharmaceutically acceptable salts, prodrugs, solvates, hydrates, tautomers, and isomers thereof.

Another aspect of the present disclosure is directed to pharmaceutical compositions comprising a compound of any one of Formula (I)-(IV), and pharmaceutically acceptable salts, prodrugs, solvates, hydrates, tautomers, and isomers thereof, and a pharmaceutically acceptable carrier. The pharmaceutically acceptable carrier can further comprise an excipient, diluent, or surfactant. The pharmaceutical composition can be effective for treating or preventing a disease associated with SOS1 modulation in a subject in need thereof. The pharmaceutical composition can be effective for treating or preventing a cancer in a subject in need thereof.

Another aspect of the present disclosure relates to a compound of any one of Formula (I)-(IV), and pharmaceutically acceptable salts, prodrugs, solvates, hydrates, tautomers, and isomers thereof, for use in treating or preventing a disease associated with SOS1 modulation. Another aspect of the present disclosure relates to a compound of any one of Formula (I)-(IV), and pharmaceutically acceptable salts, prodrugs, solvates, hydrates, tautomers, and isomers thereof, for use in treating or preventing a disease cancer.

Another aspect of the present disclosure relates to the use of a compound of any one of Formula (I)-(IV), and pharmaceutically acceptable salts, prodrugs, solvates, hydrates, tautomers, and isomers thereof, in the manufacture of a medicament for treating or preventing a disease associated with SOS1 modulation. Another aspect of the present disclosure relates to the use of a compound of any one of Formula (I)-(IV) and pharmaceutically acceptable salts, prodrugs, solvates, hydrates, tautomers, and isomers thereof, in the manufacture of a medicament for treating or preventing cancer.

The present disclosure also provides compounds that are useful in inhibiting SOS1.

DETAILED DESCRIPTION OF THE DISCLOSURE

The details of the present disclosure are set forth in the accompanying description below. Although methods and materials similar or equivalent to those described herein can be used in the practice or testing of the present disclosure, illustrative methods and materials are now described. Other features, objects, and advantages of the present disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which the present disclosure belongs. All patents and publications cited in this specification are incorporated herein by reference in their entireties.

Terms

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise. The use of the term "or" is used to mean "and/or" unless explicitly indicated to refer to alternatives only or the alternative are mutually exclusive, although the disclosure supports a definition that refers to only alternatives and "and/or."

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%>, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment, an optionally substituted group has 2 substituents. In another embodiment, an optionally substituted group has 3 substituents. In another embodiment, an optionally substituted group has 4 substituents. In another embodiment, an optionally substituted group has 5 substituents. For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

As used herein, "alkyl" may mean a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight or branched. As used herein, "lower alkyl" means an alkyl having from 1 to 6 carbon atoms.

As used herein, the term "heteroalkyl" refers to an "alkyl" group (as defined herein), in which at least one carbon atom has been replaced with a heteroatom (e.g., an O, N, or S atom). The heteroatom may appear in the middle or at the end of the radical.

The term "alkenyl" means an aliphatic hydrocarbon group containing a carbon carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

As used herein, the term "halo" or "halogen" means a fluoro, chloro, bromo, or iodo group.

The term "oxo" as used herein refers to an "=O" group. When an oxo group is bonded to a carbon atom, it can also be abbreviated herein as C(O) or as C=O. An oxo group can also be bonded to a sulfur atom (e.g., S=O and $S(O)_2$) or at phosphorous atom (e.g., P=O, $PO_2$, $PO_3$, $PO_4$, etc.).

The term "imine" as used herein refers to an "=N" group. When an imine is bonded to a carbon atom, it can also be abbreviated herein as C=N. Nitrogen can also be double bonded to sulfur, e.g., S=N, which is referred to as a thioimine.

The term "annular atoms" used in conjunction with terms relating to ring systems described herein (e.g., cycloalkyl, cycloalkenyl, aryl, heterocyclyl, and heteroaryl) refers to the total number of ring atoms present in the system. "Annular atoms" therefore does not include the atoms present in a substituent attached to the ring. Thus, the number of "annular atoms" includes all atoms present in a fused ring. For example, a 2-indolyl ring,

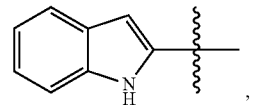 [SMILES: *c1cc2ccccc2[nH]1]

is considered a 5-membered heteroaryl, but is also a heteroaryl containing 9 annular atoms. In another example, pyridine is considered a 6-membered heteroaryl, and is a heteroaryl containing 6 annular atoms.

"Cycloalkyl" refers to a single saturated all carbon ring having 3 to 20 annular carbon atoms (i.e., $C_3$-$C_{20}$ cycloalkyl), for example from 3 to 15 annular atoms, for example, from 3 to 12 annular atoms. In certain embodiments, the cycloalkyl group is either monocyclic ("monocyclic cycloalkyl") or contains a fused, bridged or spiro ring system such as a bicyclic system ("bicyclic cycloalkyl") and can be saturated. "Cycloalkyl" includes ring systems where the cycloalkyl ring, as defined above, is fused with one or more cycloalkyl, cycloalkenyl, heterocyclyl, aryl or heteroaryl groups, wherein the point of attachment is on a cycloalkyl ring, and, in such instances, the number of carbon atoms recited continues to designate the number of carbons in the cycloalkyl ring containing the point of attachment. Examples of cycloalkyl groups include cyclohexyl, cycloheptyl, 2-adamantyl

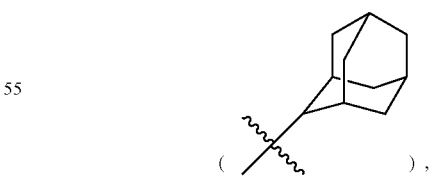

2-(2,3-dihydro-1H-indene)

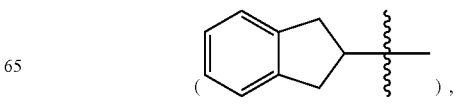

and 9-fluorenyl

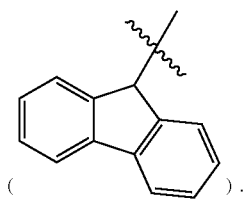 [SMILES: *C1c2ccccc2-c2ccccc21]

As noted above, cycloalkyl rings can be further characterized by the number of annular atoms. For example, a cyclohexyl ring is a $C_6$ cycloalkyl ring with 6 annular atoms, while 2-(2,3-dihydro-1H-indene) is a $C_5$ cycloalkyl ring with 9 annular atoms. Also, for example, 9-fluorenyl is a $C_5$ cycloalkyl ring with 13 annular atoms and 2-adamantyl is a $C_6$ cycloalkyl with 10 annular atoms.

As used herein, the term "cycloalkenyl" may refer to a partially saturated, monocyclic, fused or spiro polycyclic, all carbon ring having from 3 to 18 carbon atoms per ring and contains at least one double bond. "Cycloalkenyl" includes ring systems where the cycloalkenyl ring, as defined above, is fused with one or more cycloalkyl, cycloalkenyl, heterocyclyl, aryl or heteroaryl groups, wherein the point of attachment is on a cycloalkenyl ring, and, in such instances, the number of carbon atoms recited continues to designate the number of carbons in the cycloalkenyl ring containing the point of attachment. Cycloalkenyl rings can be further characterized by the number of annular atoms. Examples of cycloalkenyl include 1-cyclohex-1-enyl and cyclopent-1-enyl.

The term "aryl" as used herein refers to a single all carbon aromatic ring or a multiple condensed all carbon ring system wherein at least one of the rings is aromatic. For example, in certain embodiments, an aryl group has 5 to 20 annular carbon atoms, 5 to 14 annular carbon atoms, or 5 to 12 annular carbon atoms. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl). "Aryl" includes ring systems where the aryl ring, as defined above, is fused with one or more cycloalkyl, cycloalkenyl, heterocyclyl, aryl or heteroaryl groups, and wherein the point of attachment is on an aryl ring, and, in such instances, the number of carbon atoms recited continues to designate the number of carbon atoms in the aryl ring containing the point of attachment. Examples of aryl groups include phenyl and 5-(2,3-dihydro-1H-indene):

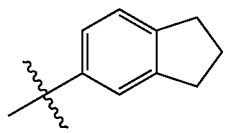

As noted above, aryl rings can be further characterized by the number of annular atoms. For example, phenyl is a $C_6$ aryl with 6 annular atoms, while 5-(2,3-dihydro-1H-indene) is a $C_6$ aryl with 9 annular atoms.

"Heterocyclyl" as used herein refers to a single saturated or partially unsaturated non-aromatic ring or a non-aromatic multiple ring system (including fused and spiro polycyclic) that has at least one heteroatom in the ring (at least one annular heteroatom selected from oxygen, nitrogen, phosphorus, and sulfur). Unless otherwise specified, a heterocyclyl group has from 5 to about 20 annular atoms, for example from 5 to 15 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen, phosphorus, and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen, phosphorus, and sulfur in the ring. "Heterocyclyl" includes ring systems where the heterocyclyl ring, as defined above, is fused with one or more cycloalkyl, cycloalkenyl, heterocyclyl, aryl or heteroaryl groups, wherein the point of attachment is on a heterocyclic ring, and, in such instances, the number of ring members recited continues to designate the number of annular atoms in the heterocyclic ring containing the point of attachment. Heterocyclic rings can be further characterized by the number of annular atoms. Examples of heterocyclic groups include piperidinyl (6-membered heterocycle with 6 annular atoms), azepanyl (7-membered heterocycle with 7 annular atoms), and 3-chromanyl (6-membered heterocycle with 10 annular atoms)

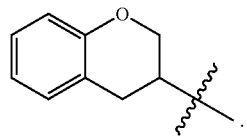 [SMILES: *C1COc2ccccc2C1]

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring. Thus, the term includes single heteroaryl rings of from about 1 to 10 annular carbon atoms and about 1-5 annular heteroatoms selected from the group consisting of oxygen, nitrogen and sulfur in the rings. The sulfur and nitrogen atoms may also be present in an oxidized form provided the ring is aromatic. "Heteroaryl" includes ring systems where the heteroaryl ring, as defined above, is fused with one or more cycloalkyl, cycloalkenyl, heterocyclyl, aryl or heteroaryl groups, wherein the point of attachment is on a heteroaryl ring, and, in such instances, the number of ring members continues to designate the number of ring members in the heteroaryl ring containing the point of attachment. Heteroaryl rings can be further characterized by the number of annular atoms. For example, pyridine is a 6-membered heteroaryl having 6 annular atoms.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the present disclosure.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{13}$F, $^{36}$Cl, $^{123}$I and $^{125}$I. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements). In some embodiments, one or more hydrogen atoms are replaced by $^2$H or $^3$H, or one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the present disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds herein may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers.

An "effective amount" when used in connection with a compound is an amount effective for treating or preventing a disease in a subject as described herein.

The term "carrier", as used in this disclosure, encompasses excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "prevent" or "preventing" with regard to a subject refers to keeping a disease or disorder from afflicting the subject. Preventing includes prophylactic treatment. For instance, preventing can include administering to the subject a compound disclosed herein before a subject is afflicted with a disease and the administration will keep the subject from being afflicted with the disease.

The terms "inhibiting" and "reducing," or any variation of these terms, includes any measurable or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., SOS1.Ras-family protein binding activity) compared to normal.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds of Disclosed Formulae

In some embodiments, the present disclosure relates to compounds of the following formula (A):

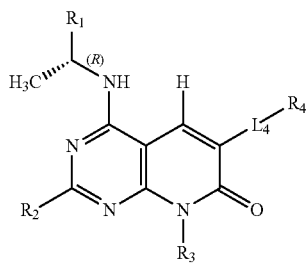

(A)

or a pharmaceutically acceptable salt, solvate, isomer, prodrug, or tautomer thereof, wherein:

$R_1$ is selected from the group consisting of optionally substituted 3-6 membered cycloalkyl, optionally substituted 3-6 membered heterocycloalkyl, optionally substituted 6-membered aryl, and optionally substituted 5-6 membered heteroaryl;

$R_2$ is selected from the group consisting of H, $C_{1-6}$ alkyl, halogen, —$NHR_{2a}$, —$OR_{2a}$, cyclopropyl, and —CN; wherein $C_{1-6}$ alkyl is optionally substituted with halogen, —$NHR_{2a}$, —$OR_{2a}$, or 5-6 membered heterocycloalkyl, and further wherein $R_{2a}$ is selected from the group consisting of H, $C_{1-6}$ alkyl, 3-6 membered heterocyclyl, and $C_{1-6}$ haloalkyl;

$R_3$ is selected from the group consisting of H, C1.3 alkyl, cyclopropyl, and 3-6 membered heterocycloalkyl, wherein each of $C_{1-3}$ alkyl, cyclopropyl, and 3-6 membered heterocycloalkyl is optionally substituted with halogen, —OH, or —CN;

$L_4$ is selected from the group consisting of bond, —C(O)—, —C(O)O—, —C(O)NH(CH$_2$)$_o$—, —NH—, —S—, —S(O)$_2$—,

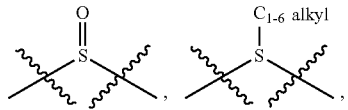

—(CH$_2$)$_p$—, and —O—; wherein p is a number from 1 to 6; and $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl, —$OR_{4a}$, =O, halogen, —$C(O)R_{4a}$, —$C(OO)R_{4a}$, —$C(O)NR_{4b}R_{4c}$, —CN, —$NR_{4b}R_{4c}$, 3-6 membered cycloalkyl, 3-7 membered heterocyclyl, 6-10 membered aryl, or 5-10 membered heteroaryl;

wherein $R_{4a}$ is H, $C_{1-6}$ alkyl, $C_{1-6}$ haloalkyl, 3-7 membered heterocyclyl, or —(CH$_2$)OCH$_3$, wherein r is 1, 2, or 3;
wherein $R_{4b}$ is H or $C_{1-6}$ alkyl; and
wherein $R_{4c}$ is H or $C_{1-6}$ alkyl.

In other embodiments, the present disclosure relates to compounds of the following formula (B):

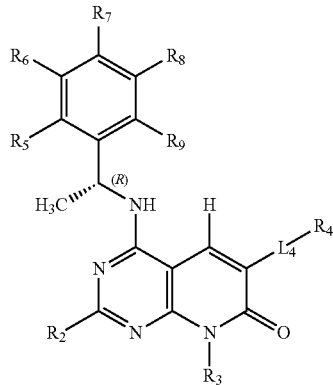

(B)

or a pharmaceutically acceptable salt, solvate, isomer, prodrug, or tautomer thereof, wherein:

$R_2$ is selected from the group consisting of H, $C_{1-6}$ alkyl, halogen, —$NHR_{2a}$, —$OR_{2a}$, cyclopropyl, and —CN; wherein $C_{1-6}$ alkyl is optionally substituted with halogen, —$NHR_{2a}$, —$OR_{2a}$, or 5-6 membered heterocycloalkyl, and further wherein $R_{2a}$ is selected from the group consisting of H, $C_{1-6}$ alkyl, 3-6 membered heterocyclyl, and $C_{1-6}$ haloalkyl;

$R_3$ is selected from the group consisting of H, $C_{1-3}$ alkyl, cyclopropyl, and 3-6 membered heterocycloalkyl, wherein each of $C_{1-3}$ alkyl, cyclopropyl, and 3-6 membered heterocycloalkyl is optionally substituted with halogen, —OH, or —CN;

$L_4$ is a bond; and $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl, —$OR_{4a}$, =O, halogen, —$C(O)R_{4a}$, —$C(OO)R_{4a}$, —$C(O)NR_{4b}R_{4c}$, —CN, —$NR_{4b}R_{4c}$, 3-6 membered cycloalkyl, 3-7 membered heterocyclyl, 6-10 membered aryl, or 5-10 membered heteroaryl;

wherein $R_{4a}$ is H, $C_{1-6}$ alkyl, $C_{1-6}$ haloalkyl, 3-7 membered heterocyclyl, or —(CH$_2$)OCH$_3$, wherein r is 1, 2, or 3;
wherein $R_{4b}$ is H or $C_{1-6}$ alkyl;
wherein $R_{4c}$ is H or $C_{1-6}$ alkyl;

$R_5$, $R_6$, $R_7$, $R_8$, and $R_9$ are independently selected from the group consisting of H, D, $C_1$-$C_6$ alkyl, $C_2$-$C_6$ alkenyl, $C_4$-$C_8$ cycloalkenyl, $C_2$-$C_6$ alkynyl, $C_3$-$C_8$ cycloalkyl, —OH, halogen, —NO$_2$, —CN, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R^{12}$, —$NR_{10}S(O)R_{11}$, —$C(O)R_{10}$, —$CO_2R_{10}$, aryl, and heteroaryl, wherein each alkyl, alkenyl, cycloalkenyl, alkynyl, cycloalkyl, and aryl is optionally substituted with —OH, $C_1$-$C_6$ alkyl optionally substituted with —OH, $NR_{11}R_{12}$, or heterocyclyl, halogen, —$NO_2$, oxo, —CN, —$R_{10}$, —$OR_{10}$, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, heterocycle, aryl, or heteroaryl;

$R_{10}$, $R_{11}$, and $R_{12}$ are independently, at each occurrence, H, D, $C_1$-$C_6$ alkyl, $C_2$-$C_6$ alkenyl, $C_4$-$C_8$cycloalkenyl, $C_2$-$C_6$ alkynyl, $C_3$-$C_8$cycloalkyl, 3-14 membered heterocyclyl, —$OR_{13}$, —$SR_{13}$, halogen, —$NR_{13}R_{14}$, —$NO_2$, or —CN; and $R_{13}$ and $R_{14}$ are independently, at each occurrence, H, D, $C_1$-$C_6$ alkyl, $C_2$-$C_6$ alkenyl, $C_4$-$C_8$ cycloalkenyl, $C_2$-$C_6$ alkynyl, $C_3$-$C_8$ cycloalkyl, 3-14 membered heterocyclyl, wherein each alkyl, alkenyl, cycloalkenyl, alkynyl, cycloalkyl, and heterocyclyl is optionally substituted with —OH, —SH, —$NH_2$, —$NO_2$, or —CN.

Additional Compounds of Disclosed Formulae

In some embodiments, the present disclosure relates to compounds having the structure of Formula (I),

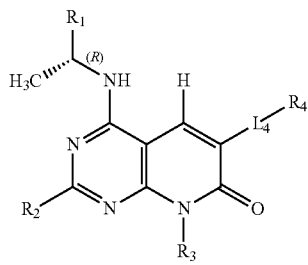

(I)

or a pharmaceutically acceptable salt, solvate, isomer, prodrug, or tautomer thereof, wherein:

$R_1$ is selected from the group consisting of optionally substituted 3-6 membered cycloalkyl, optionally substituted 3-6 membered heterocyclyl, optionally substituted 6-membered aryl, and optionally substituted 5-6 membered heteroaryl;

$R_2$ is selected from the group consisting of H, $C_{1-6}$ alkyl, halogen, —$NHR_{2a}$, —$OR_{2a}$, cyclopropyl, and —CN; wherein $C_{1-6}$ alkyl is optionally substituted with halogen, —$NHR_{2a}$, —$OR_{2a}$, or 5-6 membered heterocyclyl, and further wherein $R_{2a}$ is selected from the group consisting of H, $C_{1-6}$ alkyl, 3-6 membered heterocyclyl, and $C_{1-6}$ haloalkyl;

$R_3$ is selected from the group consisting of H, $C_{1-3}$ alkyl, —$OR_3a$, cyclopropyl, and 3-6 membered heterocyclyl, wherein each of $C_{1-3}$ alkyl, cyclopropyl, and 3-6 membered heterocyclyl is optionally substituted with $R_{3a}$, and further wherein $R_{3a}$ is selected from the group consisting of $C_{1-3}$ alkyl, halogen, —OH, or —CN;

$L_4$ is selected from the group consisting of bond, —C(O)—, —C(O)O—, —C(O)NH(CH$_2$)$_o$—, —NH—, —S—, —S(O)$_2$—,

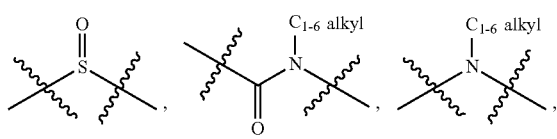

—(CH$_2$)$_p$—, and —O—; wherein o is 0, 1, or 2; and wherein p is a number from 1 to 6; and $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl, —$R_{4a}$, —$OR_{4a}$, —O—$C_{1-6}$ alkyl-$R_{4a}$, =O, halogen, —$C(O)R_{4a}$, —$C(OO)R_{4a}$, —$C(O)NR_{4b}R_{4c}$, —$NR_bC(O)R_{4c}$, —CN, =$NR_{4a}$, —$NR_{4b}R_{4c}$, —$SO_2R_{4a}$, 3-6 membered cycloalkyl optionally substituted with $R_{4a}$, 3-7 membered heterocyclyl optionally substituted with $R_{4a}$, 6-10 membered aryl optionally substituted with $R_{4a}$, or 5-10 membered heteroaryl optionally substituted with $R_{4a}$;

wherein $R_{4a}$ is H, $C_{1-6}$ alkyl, $C_{1-6}$ haloalkyl, —$C(O)R_{4b}$, —$C(O)NR_{4b}R_{4c}$, =O, 3-6 membered cycloalkyl, 6-10 membered aryl optionally substituted with —$OR_{4b}$, —CN, =N-3-6 membered cycloalkyl, 3-7 membered heterocyclyl, —(CH$_2$)OCH$_3$, or —(CH$_2$)OH, wherein r is 1, 2, or 3;

wherein each $R_{4b}$ is independently H, $C_{1-6}$ alkyl; and wherein each $R_{4c}$ is independently H or $C_{1-6}$ alkyl.

In some embodiments of compounds of Formula (I), $R_1$ is the optionally substituted 6-membered aryl. In some embodiments, the 6-membered aryl has the following structure:

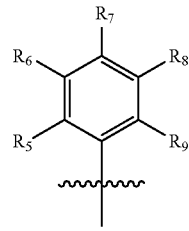

wherein $R_5$, $R_6$, $R_7$, $R_8$, and $R_9$ are as defined below in connection with Formula (II)-(IV).

In some embodiments of compounds of Formula (I), $R_1$ is the optionally substituted 5-6 membered heteroaryl. In some embodiments, $R_1$ is a 6-membered heteroaryl having any of the following structures:

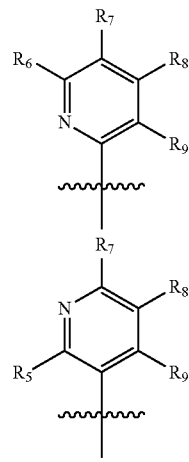

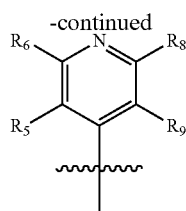

wherein $R_5$, $R_6$, $R_7$, $R_8$, and $R_9$ are as defined below in connection with Formula (II)-(IV).

In some embodiments of compounds of Formula (I), $R_1$ is the optionally substituted 5-6 membered heteroaryl. In some embodiments, $R_1$ is a 5-membered heteroaryl having the following structure:

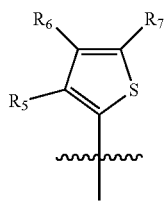

wherein $R_5$, $R_6$, and $R_7$ are as defined below in connection with Formula (II)-(IV).

In some embodiments, the present disclosure relates to compounds having the structure of Formula (II),

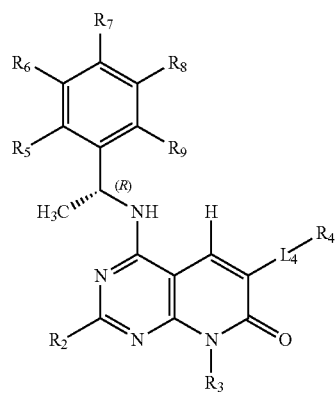

(II)

or a pharmaceutically acceptable salt, solvate, isomer, prodrug, or tautomer thereof, wherein $R_2$, $R_3$, $L_4$, and $R_4$ are as defined in Formula (I);

$R_5$, $R_6$, $R_7$, $R_8$, and $R_9$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —NO$_2$, —CN, —NR$_{11}$R$_{12}$, —SR$_{10}$, —S(O)$_2$NR$_{11}$R$_{12}$, —S(O)$_2$R$_{10}$, —NR$_{10}$S(O)$_2$NR$_{11}$R$_{12}$, —NR$_{10}$S(O)$_2$R$_{11}$, —S(O)NR$_{11}$R$_{12}$, —S(O)R$_{10}$, —NR$_{10}$S(O)NR$_{11}$R$_{12}$, —NR$_{10}$S(O)R$_{11}$, —C(O)R$_{10}$, —CO$_2$R$_{10}$, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl optionally substituted with —R$_{10}$, halogen, —NO$_2$, oxo, —CN, —R$_{10}$, —OR$_{10}$, —NR$_{11}$R$_{12}$, —SR$_{10}$, —S(O)$_2$NR$_{11}$R$_{12}$, —S(O)$_2$R$_{10}$, —NR$_{10}$S(O)$_2$NR$_{11}$R$_{12}$, —NR$_{10}$S(O)$_2$R$_{11}$, —S(O)NR$_{11}$R$_{12}$, —S(O)R$_{10}$, —NR$_{10}$S(O)NR$_1$R$_{12}$, —NR$_{10}$S(O)R$_{11}$, 3-8 membered cycloalkyl, 3-14 membered heterocyclyl optionally substituted with R$_{10}$, 6-10 membered aryl, or 5-10 membered heteroaryl, or any two adjacent $R_5$, $R_6$, $R_7$, $R_8$, and $R_9$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OR$_{13}$, —SR$_{13}$, halogen, —NR$_{13}$R$_{14}$, —NO$_2$, and —CN; and $R_{13}$ and $R_{14}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —NH$_2$, —NO$_2$, or —CN.

In some embodiments, the present disclosure relates to compounds having the structure of Formula (III),

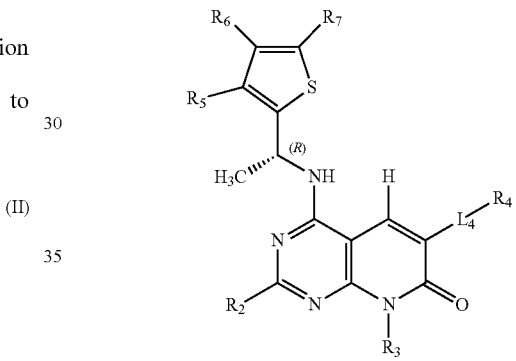

(III)

or a pharmaceutically acceptable salt, solvate, isomer, prodrug, or tautomer thereof, wherein $R_2$, $R_3$, $L_4$, and $R_4$ are as defined Formula (I);

$R_5$, $R_6$, and $R_7$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —NO$_2$, —CN, —NR$_{11}$R$_{12}$, —SR$_{10}$, —S(O)$_2$NR$_{11}$R$_{12}$, —S(O)$_2$R$_{10}$, —NR$_{10}$S(O)$_2$NR$_{11}$R$_{12}$, —NR$_{10}$S(O)$_2$R$_{11}$, —S(O)NR$_{11}$R$_{12}$, —S(O)R$_{10}$, —NR$_{10}$S(O)NR$_{11}$R$_{12}$, —NR$_{10}$S(O)R$_{11}$, —C(O)R$_{10}$, —CO$_2$R$_{10}$, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl optionally substituted with —R$_{10}$, halogen, —NO$_2$, oxo, —CN, —R$_{10}$, —OR$_{10}$, —NR$_{11}$R$_{12}$, —SR$_{10}$, —S(O)$_2$NR$_{11}$R$_{12}$, —S(O)$_2$R$_{10}$, —NR$_{10}$S(O)$_2$NR$_{11}$R$_{12}$, —NR$_{10}$S(O)$_2$R$_{11}$, —S(O)NR$_{11}$R$_{12}$, —S(O)R$_{10}$, —NR$_{10}$S(O)NR$_{11}$R$_{12}$, —NR$_{10}$S(O)R$_{11}$, 3-8 membered cycloalkyl, 3-14 membered heterocyclyl optionally substituted with R$_{10}$, 6-10 membered aryl, or 5-10 membered heteroaryl, or any two adjacent $R_5$, $R_6$, and $R_7$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OR₁₃, —SR₁₃, halogen, —NR₁₃R₁₄, —NO₂, and —CN; and

R₁₃ and R₁₄ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —NH₂, —NO₂, or —CN.

In some embodiments, the present disclosure relates to compounds having the structure of Formula (IV-a), (IV-b), or (IV-c),

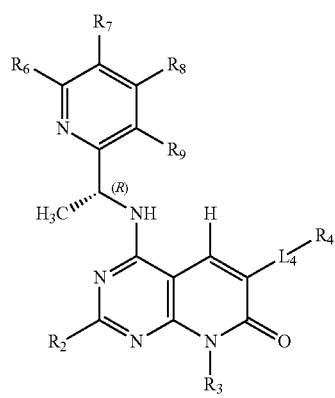

(IV-a)

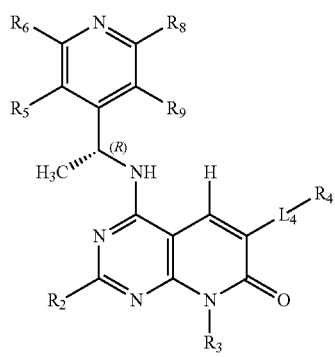

(IV-b)

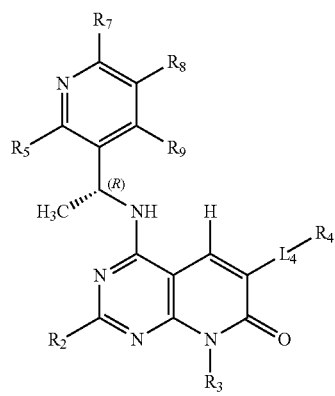

(IV-c)

or a pharmaceutically acceptable salt, solvate, isomer, prodrug, or tautomer thereof, wherein $R_2$, $R_3$, $L_4$, and $R_4$ are as defined Formula (I);

$R_5$, $R_6$, $R_7$, $R_8$, and $R_9$ are independently selected from the group consisting of H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OH, halogen, —NO₂, —CN, —NR₁₁R₁₂, —SR₁₀, —S(O)₂NR₁₁R₁₂, —S(O)₂R₁₀, —NR₁₀S(O)₂NR₁₁R₁₂, —NR₁₀S(O)₂R₁₁, —S(O)NR₁₁R₁₂, —S(O)R₁₀, —NR₁₀S(O)NR₁₁R₁₂, —NR₁₀S(O)R₁₁, —C(O)R₁₀, —CO₂R₁₀, 6-10 membered aryl, and 5-10 membered heteroaryl, wherein each $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, 6-10 membered aryl, and 5-10 membered heteroaryl is optionally substituted with —OH, $C_{1-6}$ alkyl optionally substituted with —R₁₀, halogen, —NO₂, oxo, —CN, —R₁₀, —OR₁₀, —NR₁₁R₁₂, —SR₁₀, —S(O)₂NR₁₁R₁₂, —S(O)₂R₁₀, —NR₁₀S(O)₂NR₁₁R₁₂, —NR₁₀S(O)₂R₁₁, —S(O)NR₁₁R₁₂, —S(O)R₁₀, —NR₁₀S(O)NR₁₁R₁₂, —NR₁₀S(O)R₁₁, 3-8 membered cycloalkyl, 3-14 membered heterocyclyl optionally substituted with R₁₀, 6-10 membered aryl, or 5-10 membered heteroaryl, or any two adjacent $R_5$, $R_6$, $R_7$, $R_8$, and $R^9$ forms an optionally substituted 3-14 membered fused ring;

$R_{10}$, $R_{11}$, and $R_{12}$ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, 3-14 membered heterocyclyl, —OR₁₃, —SR₁₃, halogen, —NR₁₃R₁₄, —NO₂, and —CN; and R₁₃ and R₁₄ are at each occurrence independently selected from H, D, $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl, wherein each $C_{1-6}$ alkyl, $C_{2-6}$ alkenyl, 4-8 membered cycloalkenyl, $C_{2-6}$ alkynyl, 3-8 membered cycloalkyl, and 3-14 membered heterocyclyl are independently optionally substituted with —OH, —SH, —NH₂, —NO₂, or —CN.

In some embodiments, the present disclosure relates to compounds having the structure of Formula (IV-a) or Formula (IV-b).

In some embodiments of compounds of Formula (II)-(IV), one to three of $R_5$, $R_6$, $R_7$, $R_8$, and $R_9$ is $C_{1-6}$ alkyl, wherein the alkyl is optionally substituted with halogen.

In some embodiments of compounds of Formula (II)-(IV), one to three of $R_5$, $R_6$, $R_7$, $R_8$, and $R_9$ is $C_{1-6}$ alkyl, wherein the alkyl is optionally substituted with halogen or —OH.

In some embodiments of compounds of Formula (II)-(IV), one to three of $R_5$, $R_6$, $R_7$, $R_8$, and $R_9$ is $C_{1-6}$ alkyl, and one to three of $R_5$, $R_6$, $R_7$, $R_8$, and $R_9$ is $C_{1-6}$ alkyl optionally substituted with halogen.

In some embodiments of compounds of Formula (II)-(IV), one to three of $R_5$, $R_6$, $R_7$, $R_8$, and $R_9$ is halogen, and one to three of $R_5$, $R_6$, $R_7$, $R_8$, and $R_9$ is $C_{1-6}$ alkyl optionally substituted with halogen.

In some embodiments of compounds of Formula (II)-(IV), one to three of $R_5$, $R_6$, $R_7$, $R_8$, and $R_9$ is —NH₂.

In some embodiments of compounds of Formula (II)-(IV), one of $R_5$, $R_6$, $R_7$, $R_8$, and $R_9$ is —NH₂; and one of $R_5$, $R_6$, $R_7$, $R_8$, and $R_9$ is $C_{1-6}$ alkyl optionally substituted with halogen.

In some embodiments of compounds of Formula (II)-(IV), any two adjacent $R_5$, $R_6$, $R_7$, $R_8$, and $R_9$ forms a 3-14 membered fused ring. In some embodiments of compounds of Formula (II)-(IV), any two adjacent $R_5$, $R_6$, $R_7$, $R_8$, and $R_9$ forms a 3-8 membered fused ring. In some embodiments of compounds of Formula (II)-(IV), any two adjacent $R_5$, $R_6$, $R_7$, $R_8$, and $R_9$ forms a 4-8 membered fused ring. In some embodiments of compounds of Formula (II)-(IV), any two adjacent $R_5$, $R_6$, $R_7$, $R_8$, and $R_9$ forms a 4-membered fused ring or a 5-membered fused ring. In some embodiments, the fused ring is a 3-8 membered heterocyclyl or a 3-8 membered cycloalkyl. In some embodiments, the fused ring is a 4-8 membered heterocyclyl or a 4-8 membered cycloalkyl. In some embodiments, the fused ring is a 4-membered heterocyclyl or a 5-membered heterocyclyl. In some embodiments, the fused ring is a 4-membered cycloalkyl or a 5-membered cycloalkyl. In some embodiments, the fused ring is optionally substituted with —OH, $C_{1-6}$ alkyl, halogen, —$NO_2$, oxo, —CN, —$R_{10}$, —$OR_{10}$, —$NR_{11}R_{12}$, —$SR_{10}$, —$S(O)_2NR_{11}R_{12}$, —$S(O)_2R_{10}$, —$NR_{10}S(O)_2NR_{11}R_{12}$, —$NR_{10}S(O)_2R_{11}$, —$S(O)NR_{11}R_{12}$, —$S(O)R_{10}$, —$NR_{10}S(O)NR_{11}R_{12}$, —$NR_{10}S(O)R_{11}$, 3-8 membered cycloalkyl, 3-14 membered heterocyclyl, 6-10 membered aryl, or 5-10 membered heteroaryl. In some embodiments, the fused ring is optionally substituted with halogen.

In some embodiments of compounds of Formula (II)-(IV), one or more of $R_5$, $R_6$, $R_7$, $R_8$, and $R_9$ is selected from among —$CF_3$, —$NH_2$, —F, and —$CF_2CH_2OH$. In some embodiments of compounds of Formula (II), one of $R_5$, $R_6$, $R_7$, $R_8$, and $R_9$ is-$CF_3$ and one of $R_5$, $R_6$, $R_7$, $R_8$, and $R_9$ is —$NH_2$. In some embodiments of compounds of Formula (II), one of $R_5$, $R_6$, $R_7$, $R_8$, and $R_9$ is-F and one of $R_5$, $R_6$, $R_7$, $R_8$, and $R_9$ is —$CF_2CH_2OH$.

In some embodiments of compounds of Formula (I), $R_1$ is selected from among:

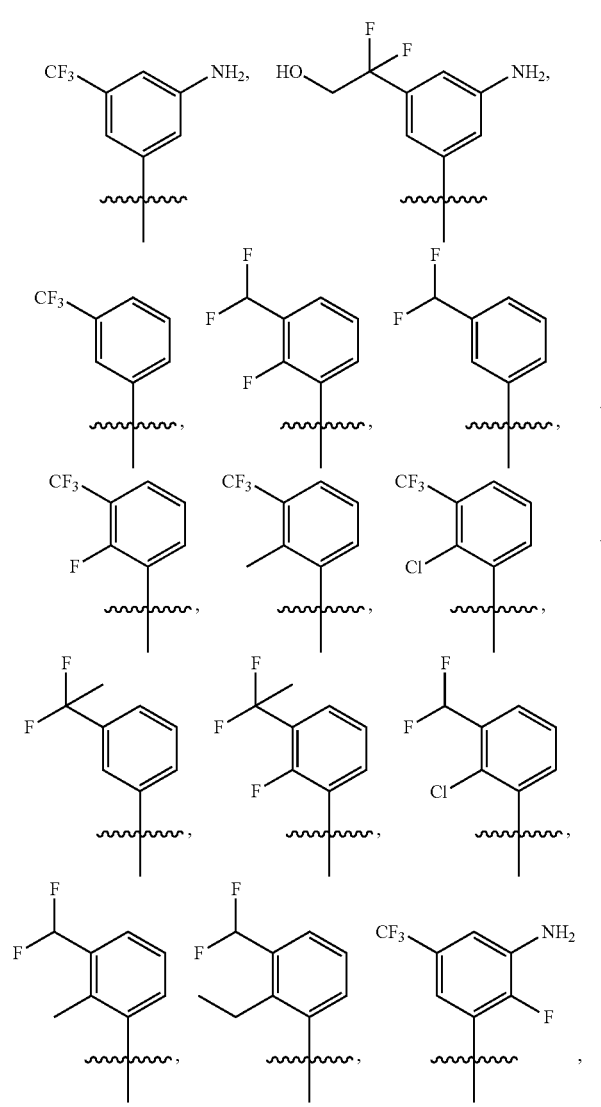

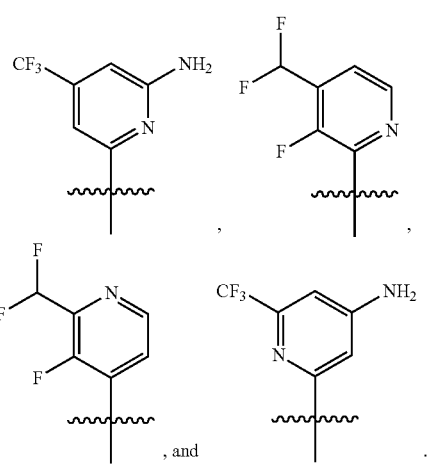

In some embodiments of compounds of Formula (I), $R_1$ is selected from among:

, and .

In some embodiments of compounds of Formula (I), $R_1$ is selected from among:

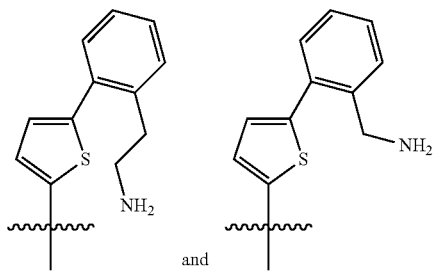

and .

In some embodiments of compounds of Formula (I), $R_1$ is selected from among:

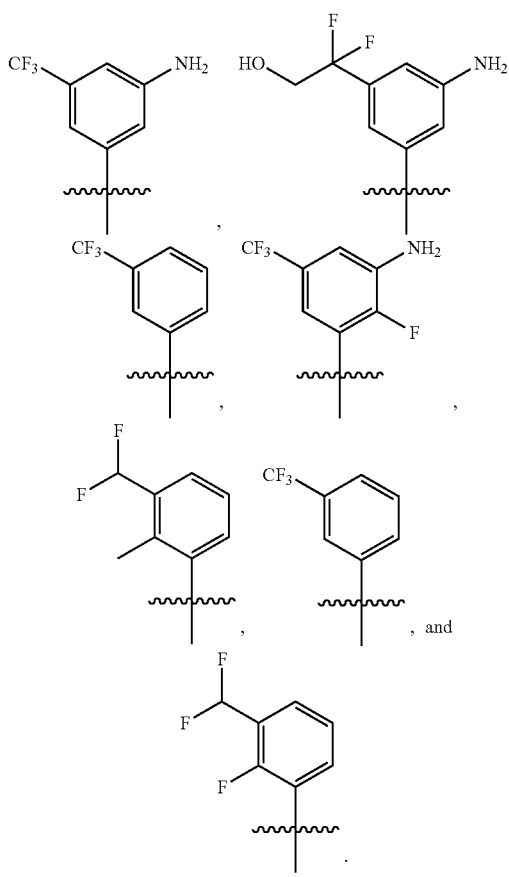

, , , and

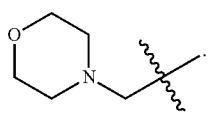 [SMILES: *CN1CCOCC1]

.

In some embodiments of compounds of Formula (I)-(IV), $R_2$ is H.

In some embodiments of compounds of Formula (I)-(IV), $R_2$ is $C_{1-6}$ alkyl. In some embodiments of compounds of Formula (I)-(IV), $R_2$ is —$CH_3$.

In some embodiments of compounds of Formula (I)-(IV), $R_2$ is $C_{1-6}$ alkyl substituted with 5-6 membered heterocycloalkyl. In some embodiments of compounds of Formula (I)-(IV), $R_2$ is

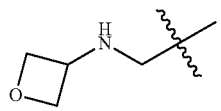 [SMILES: *CNC1COC1]

.

In some embodiments of compounds of Formula (I)-(IV), $R_2$ is $C_{1-6}$ alkyl substituted with —$NHR_{2a}$, wherein $R_{2a}$ is $C_{1-6}$ alkyl or 3-6 membered heterocyclyl. In some embodiments of compounds of Formula (I)-(IV), $R_2$ is selected from among

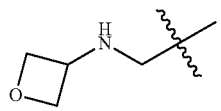 [SMILES: *CNC1COC1]

and —$CH_2NHCH_3$.

In some embodiments of compounds of Formula (I)-(IV), $R_2$ is $C_{1-6}$ alkyl substituted with —$OR_{2a}$, wherein $R_{2a}$ is H or $C_{1-6}$ alkyl. In some embodiments of compounds of Formula (I)-(IV), $R_2$ is —$CH_2OH$.

In some embodiments of compounds of Formula (I)-(IV), $R_2$ is —$NHR_{2a}$, wherein $R_{2a}$ is $C_{1-6}$ alkyl. In some embodiments of compounds of Formula (I)-(IV), $R_2$ is —$NHCH_3$.

In some embodiments of compounds of Formula (I)-(IV), $R_2$ is —$OR_{2a}$; wherein $R_{2a}$ is $C_{1-6}$ alkyl. In some embodiments of compounds of Formula (I)-(IV), $R_2$ is —$OCH_3$.

In some embodiments of compounds of Formula (I)-(IV), $R_3$ is $C_{1-3}$ alkyl. In some embodiments of compounds of Formula (I)-(IV), $R_3$ is —$CH_3$. In some embodiments of compounds of Formula (I)-(IV), $R_3$ is —$CD_3$.

In some embodiments of compounds of Formula (I)-(IV), $R_3$ is $C_{1-3}$ alkyl substituted with —OH. In some embodiments of compounds of Formula (I)-(IV), $R_3$ is —$CH_2CH_2OH$.

In some embodiments of compounds of Formula (I)-(IV), $R_3$ is H.

In some embodiments of compounds of Formula (I)-(IV), $R_3$ is —$OR_{3a}$. In some embodiments of compounds of Formula (I)-(IV), $R_3$ is —$OCH_3$.

In some embodiments of compounds of Formula (I)-(IV), $R_3$ is cyclopropyl.

In some embodiments of compounds of Formula (I)-(IV), $R_3$ is 3-6 membered heterocyclyl. In some embodiments of compounds of Formula (I)-(IV), $R_3$ is

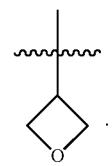 [SMILES: *C1COC1]

In some embodiments of compounds of Formula (I)-(IV), $L_4$ is selected from the group consisting of bond, —C(O)—, —C(O)O—, —C(O)NH(CH_2)_o—, —NH—, —S—, —S(O)_2—,

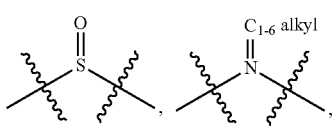

—(CH_2)_p—, and —O—; wherein o is 0, 1, or 2; and wherein p is a number from 1 to 6.

In some embodiments of compounds of Formula (I)-(IV), $L_4$ is a bond.

In some embodiments of compounds of Formula (I)-(IV), $L_4$ is —C(O)—.

In some embodiments of compounds of Formula (I)-(IV), $L_4$ is —(CH$_2$)$_p$—. In some embodiments of compounds of Formula (I), $L_4$ is —(CH$_2$)—.

In some embodiments of compounds of Formula (I)-(IV), $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl, —$R_{4a}$, —$OR_{4a}$, —O—$C_{1-6}$ alkyl-$R_{4a}$, =O, halogen, —C(O)$R_{4a}$, —C(OO)$R_{4a}$, —C(O)$NR_{4b}R_{4c}$, —$NR_{4b}$C(O)$R_{4c}$, —CN, =$NR_{4a}$, —$NR_{4b}R_{4c}$, —$SO_2R_{4a}$, 3-6 membered cycloalkyl, 3-7 membered heterocyclyl, 6-10 membered aryl, or 5-10 membered heteroaryl.

In some embodiments of compounds of Formula (I)-(IV), $R_4$ is selected from the group consisting of H, $C_{1-6}$ alkyl, 3-14 membered cycloalkyl, 3-14 membered cycloalkenyl, 3-14 membered heterocyclyl, 6-10 membered aryl, and 5-10 membered heteroaryl; wherein each $C_{1-6}$ alkyl, 3-14 membered cycloalkyl, 3-14 membered cycloalkenyl, 3-14 membered heterocyclyl, 6-10 membered aryl, and 5-10 membered heteroaryl is optionally substituted with $C_{1-6}$ alkyl —$OR_{4a}$, =O, halogen, —C(O)$R_{4a}$, —C(OO)$R_{4a}$, —C(O)$NR_{4b}R_{4c}$, —CN, —$NR_{4b}R_{4c}$, 3-6 membered cycloalkyl, 3-7 membered heterocyclyl, 6-10 membered aryl, or 5-10 membered heteroaryl.

In some embodiments of compounds of Formula (I)-(IV), $R_{4a}$ is H, $C_{1-6}$ alkyl, $C_{1-6}$ haloalkyl, —C(O)$R_4$, —C(O)$NR_{4b}R_{4c}$, =O, 3-6 membered cycloalkyl, 6-10 membered aryl optionally substituted with —$OR_{4b}$, —CN, =N-3-6 membered cycloalkyl, 3-7 membered heterocyclyl, —(CH$_2$)$_r$OCH$_3$, or —(CH$_2$)$_r$OH, wherein r is 1, 2, or 3; wherein each $R_{4b}$ is independently H, $C_{1-6}$ alkyl; and wherein each $R_{4c}$ is independently H or $C_{1-6}$ alkyl.

In some embodiments of compounds of Formula (I)-(IV), $R_{4a}$ is H, $C_{1-6}$ alkyl, $C_{1-6}$ haloalkyl, —C(O)$R_{4b}$, —C(O)$NR_{4b}R_{4c}$, 3-6 membered cycloalkyl, 6-10 membered aryl optionally substituted with —$OR_{4b}$, —CN, 3-7 membered heterocyclyl, —(CH$_2$)OCH$_3$, or —(CH$_2$)OH, wherein r is 1, 2, or 3; wherein each $R_4$ is independently H, $C_{1-6}$ alkyl; and wherein each $R_{4c}$ is independently H or $C_{1-6}$ alkyl.

In some embodiments of compounds of Formula (I)-(IV), $R_4$ is 3-14 membered heterocyclyl. In some embodiments of compounds of Formula (I)-(IV), $R_4$ is substituted 3-14 membered heterocyclyl.

In some embodiments of compounds of Formula (I)-(IV), $R_4$ is 3-14 membered heterocyclyl substituted with 3-6 membered heterocyclyl. In some embodiments, the heterocyclyl substituent is oxetanyl.

In some embodiments of compounds of Formula (I)-(IV), $R_4$ is 3-14 membered heterocyclyl substituted with $C_{1-6}$ alkyl. In some embodiments of compounds of Formula (I)-(IV), $R_4$ is 3-14 membered heterocyclyl substituted with —CH$_3$. In some embodiments of compounds of Formula (I)-(IV), $R_4$ is 3-14 membered heterocyclyl substituted with —CH$_2$—, i.e., the substituent is a methylene bridge bridging 2 carbon atoms in the heterocyclyl ring.

In some embodiments of compounds of Formula (I)-(IV), $R_4$ is 3-14 membered heterocyclyl substituted with 3-6 membered cycloalkyl. In some embodiments, the cycloalkyl substituent is cyclopropyl.

In some embodiments of compounds of Formula (I)-(IV), $R_4$ is 3-14 membered heterocyclyl substituted with =O.

In some embodiments, the $R_4$ is a heterocyclyl selected from among:

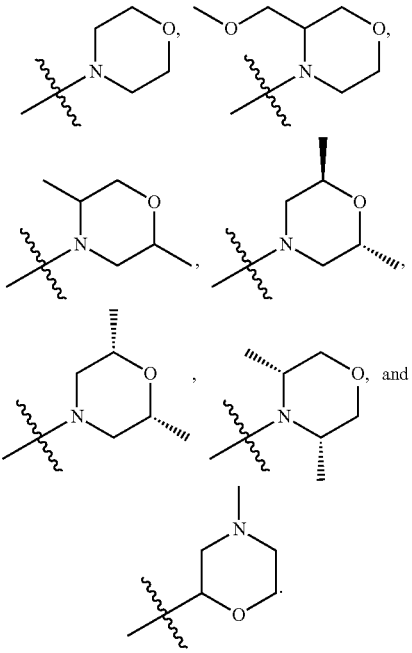

In some embodiments, the $R_4$ is a heterocyclyl selected from among:

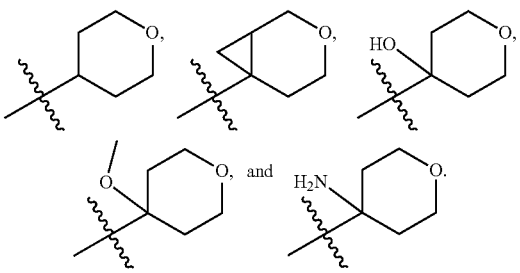

In some embodiments the $R_4$ is a heterocyclyl selected from among:

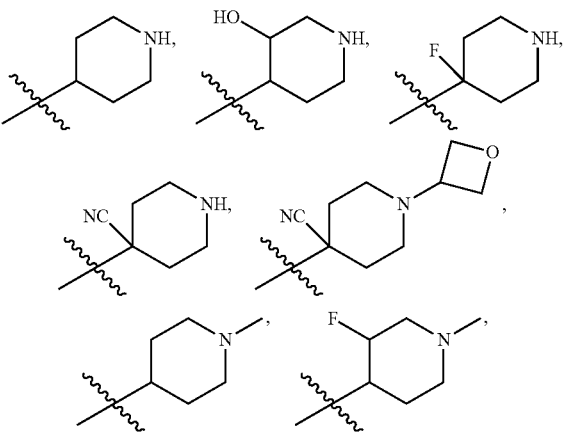

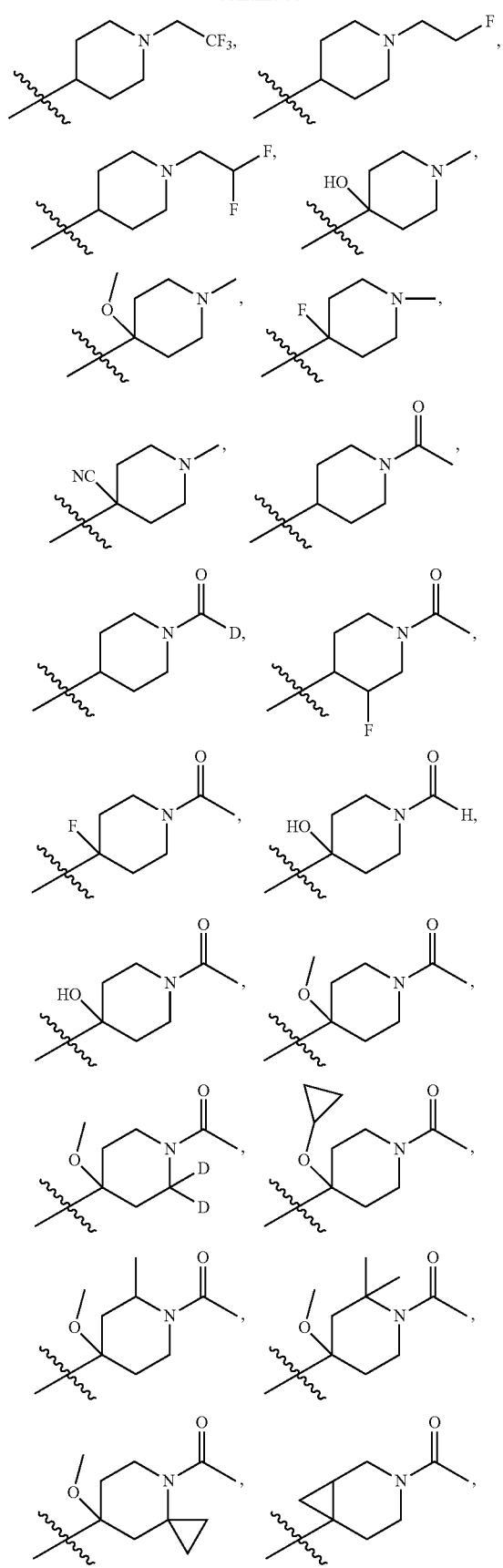
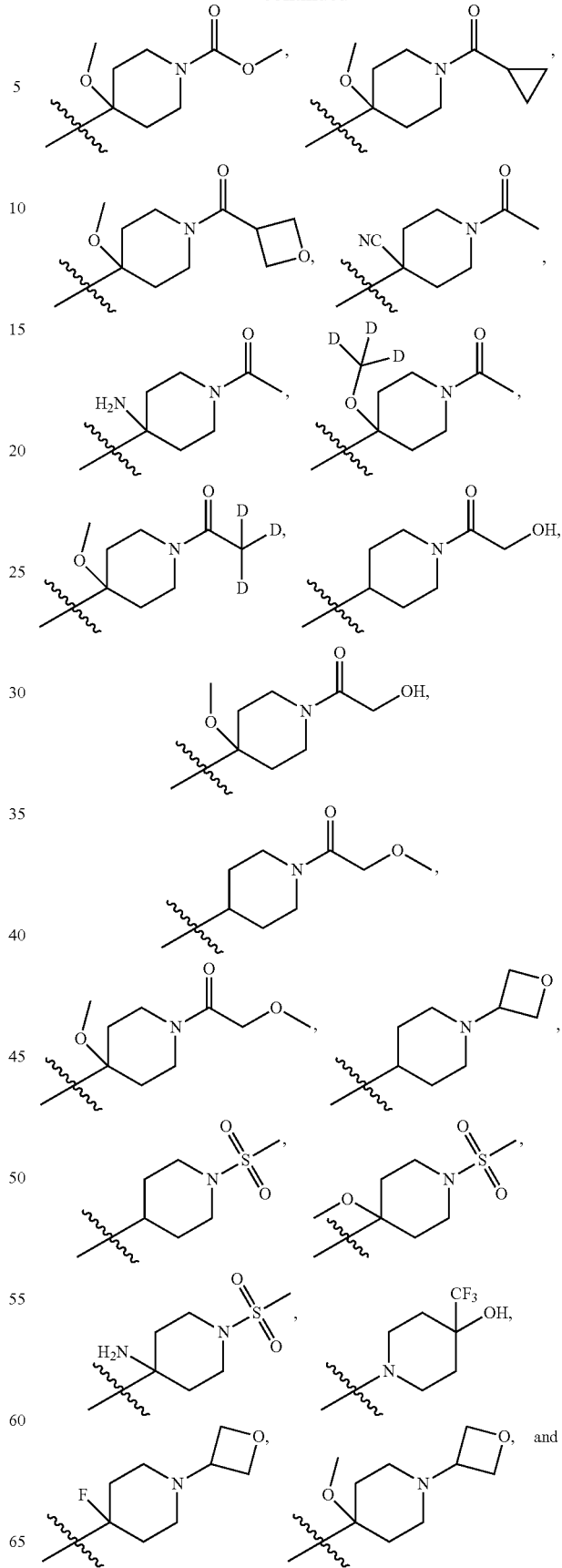

-continued
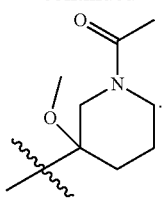
In some embodiments, the $R_4$ is a heterocyclyl selected from among:
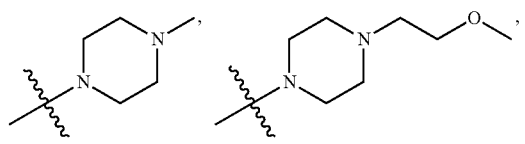
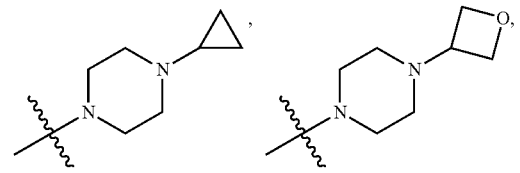
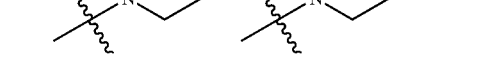, and
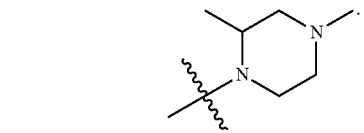
In some embodiments, the $R_4$ is a heterocyclyl selected from among:
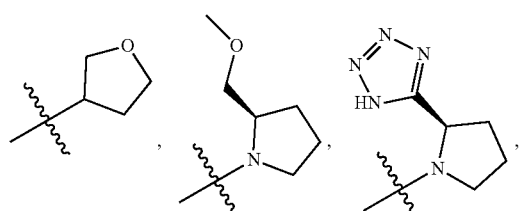
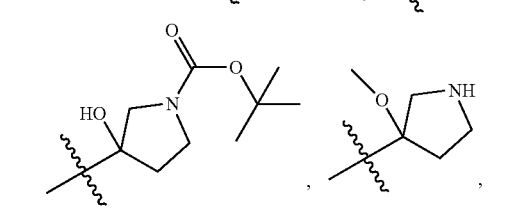
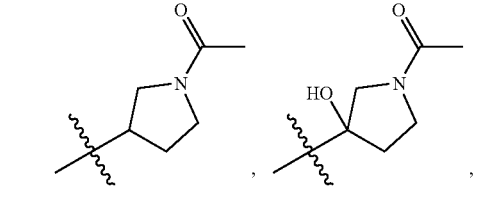
-continued
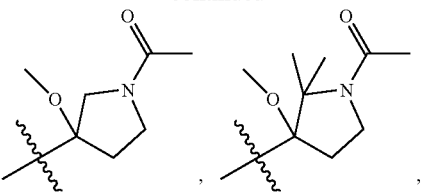
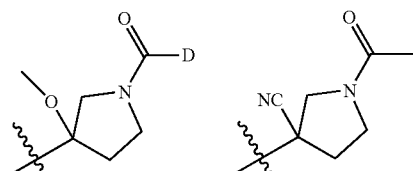
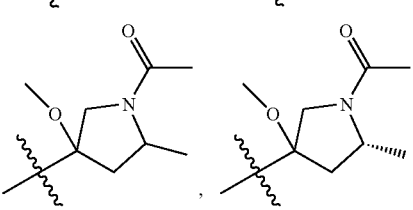
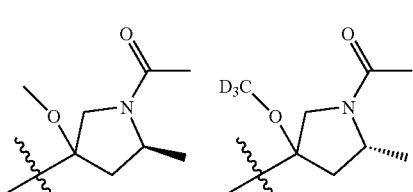
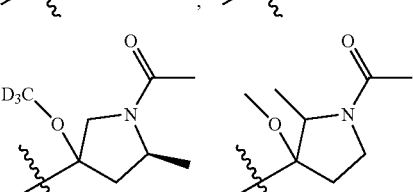
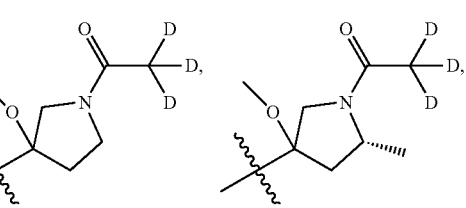
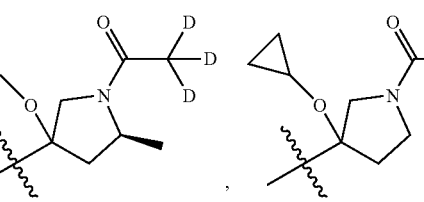
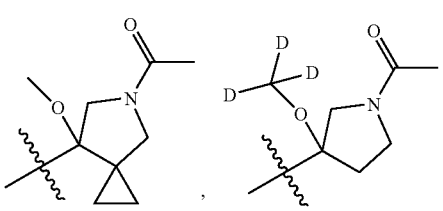

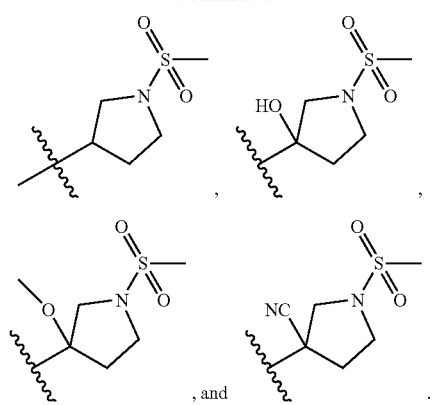
In some embodiments, the $R_4$ is a heterocyclyl selected from among:
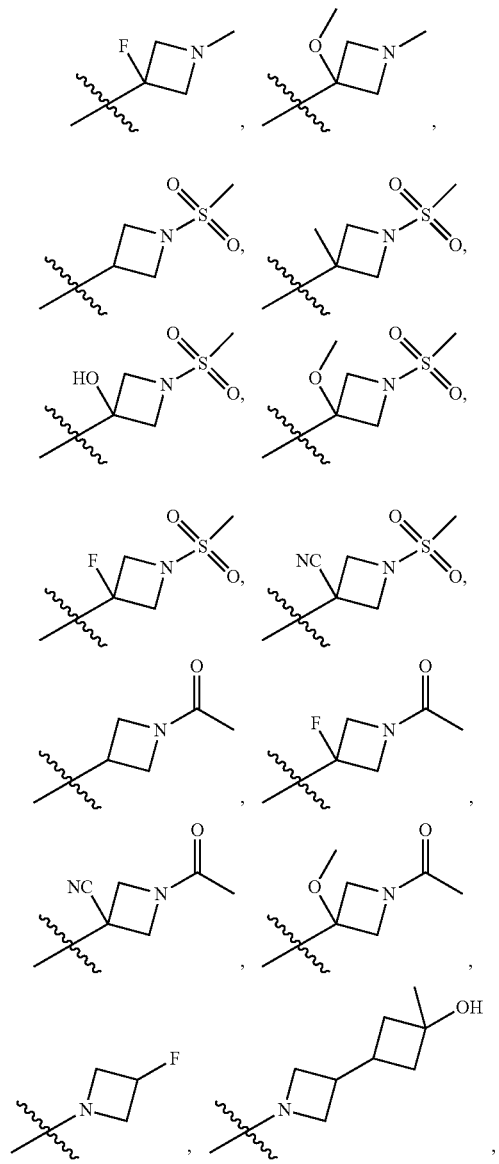
In some embodiments, the $R_4$ is a heterocyclyl selected from among:
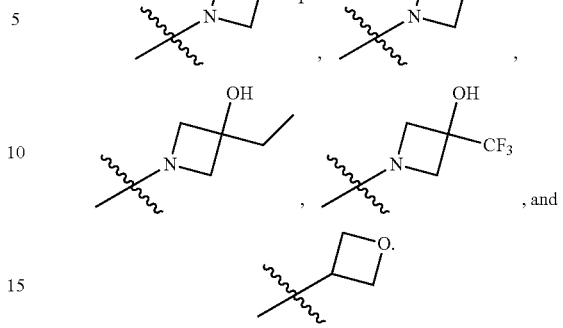
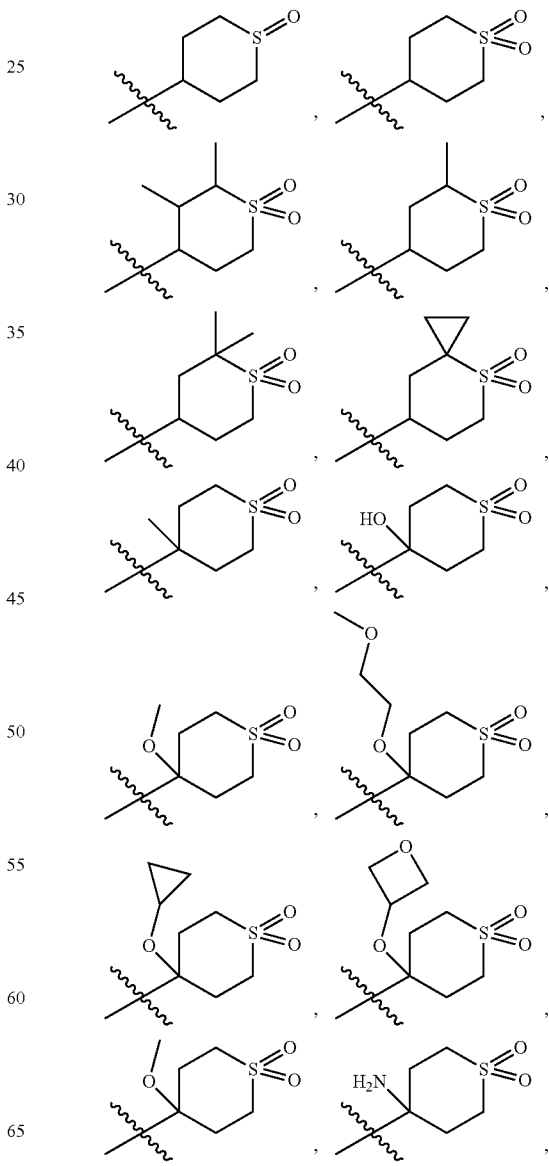

-continued
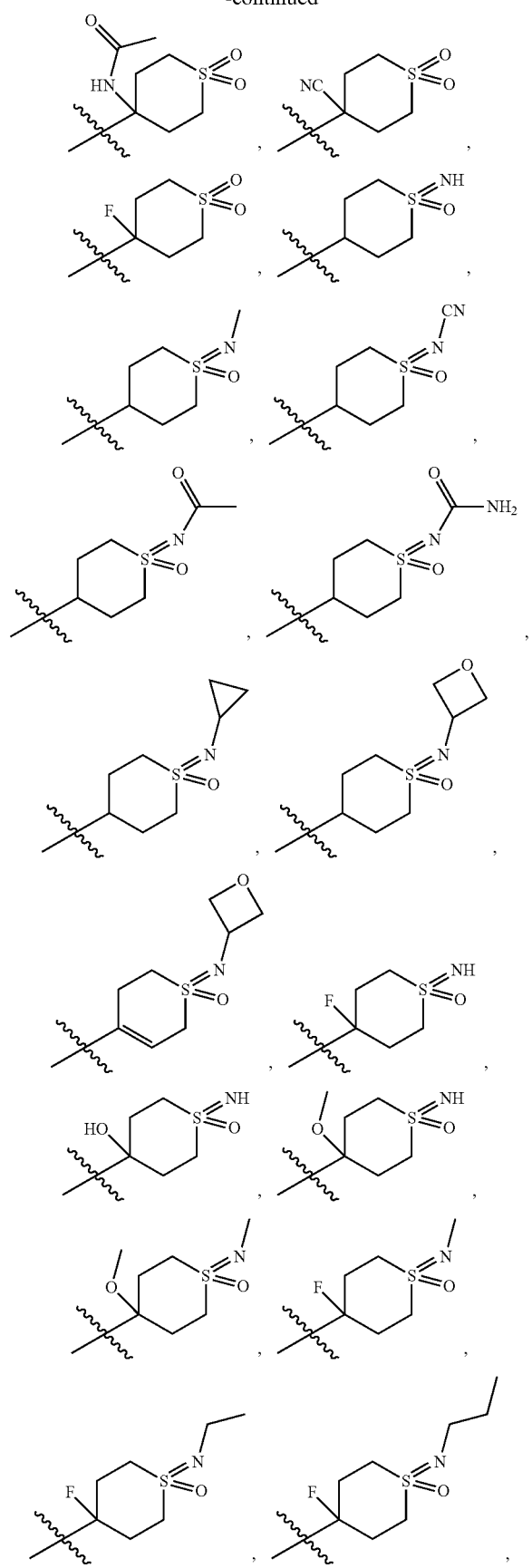
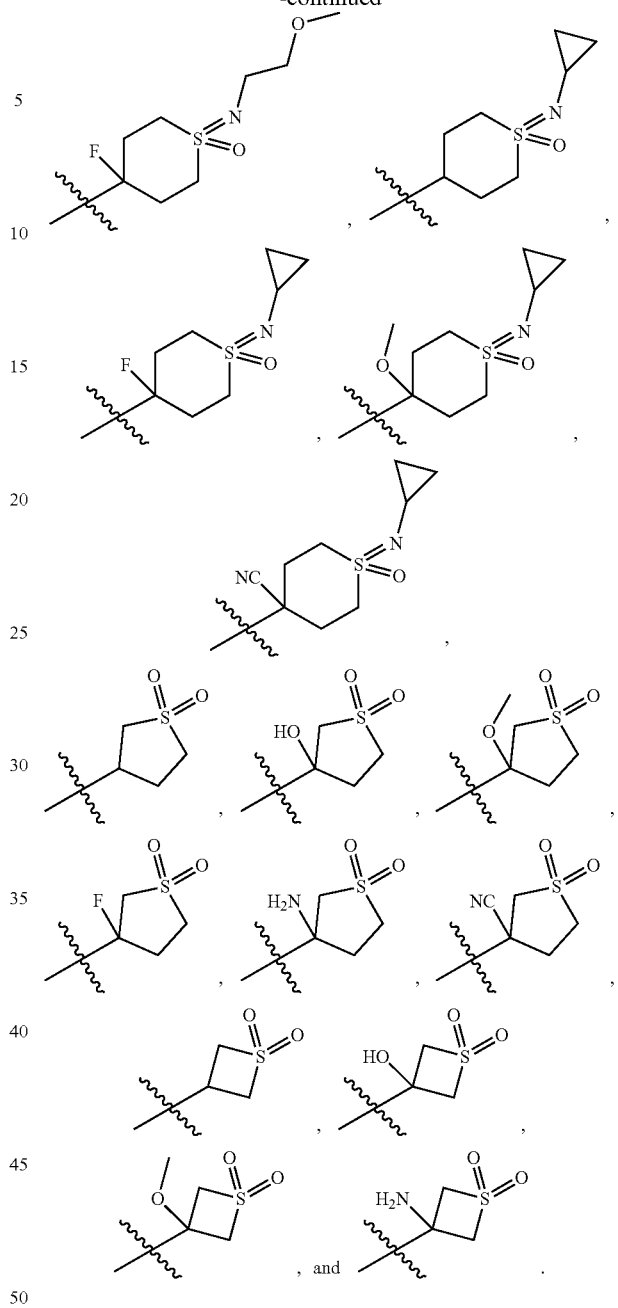
In some embodiments, the $R_4$ is a heterocyclyl selected from among:
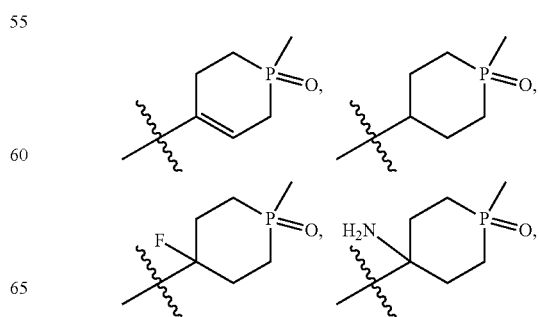

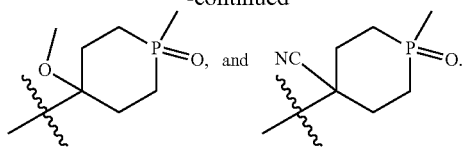
In some embodiments, the $R_4$ is a heterocyclyl selected from among:
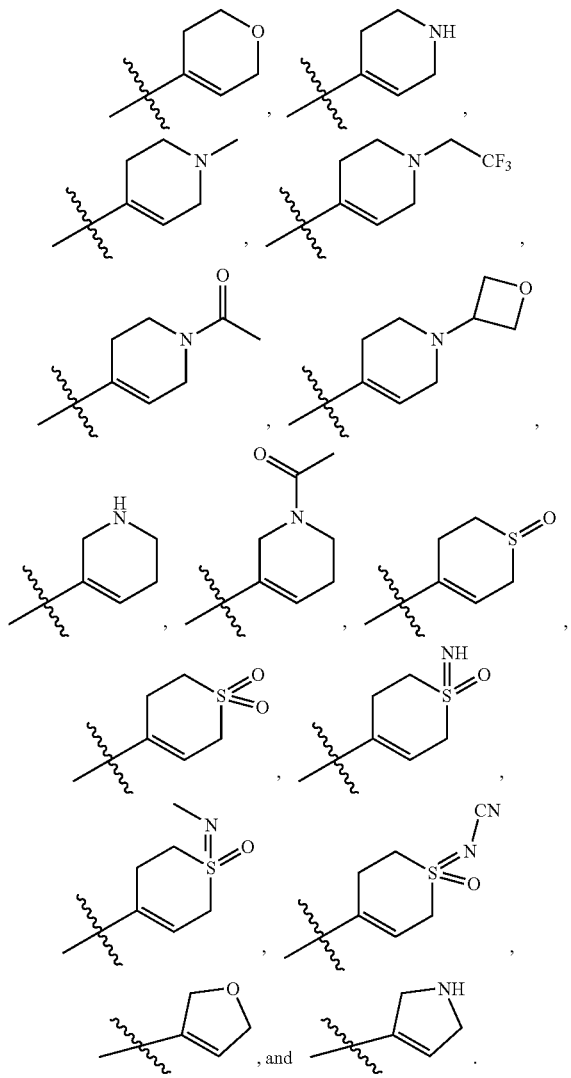
In some embodiments, the $R_4$ is a heterocyclyl selected from among:
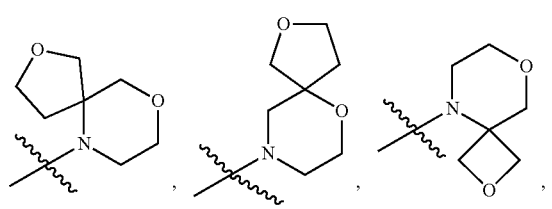
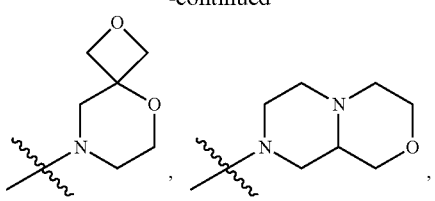
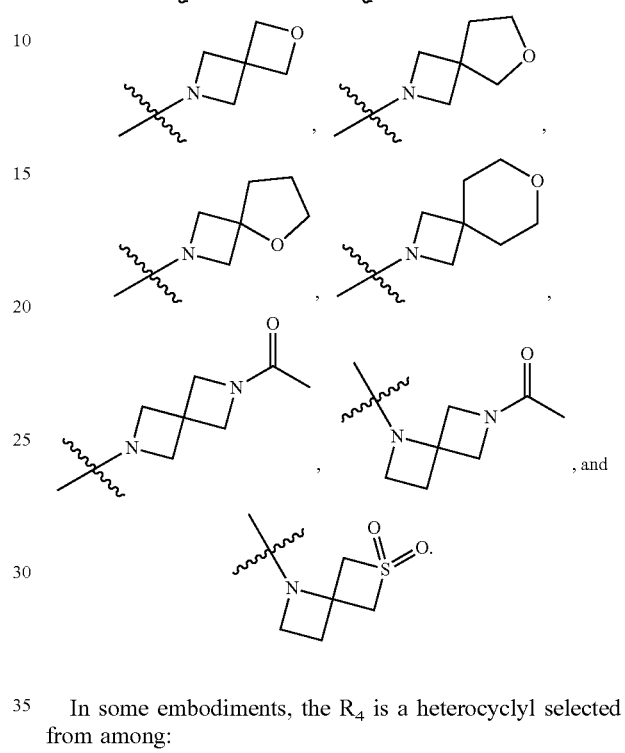
In some embodiments, the $R_4$ is a heterocyclyl selected from among:
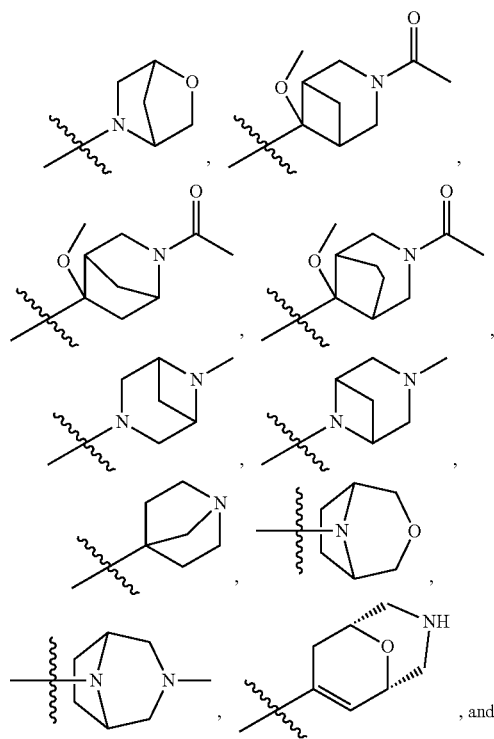

-continued

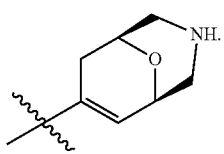

In some embodiments, the $R_4$ is a heterocyclyl selected from among:

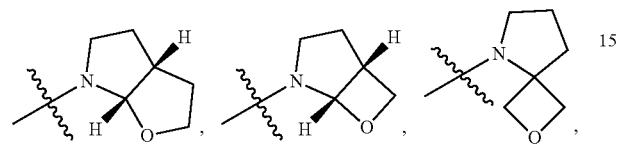

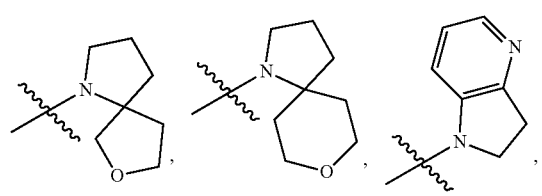

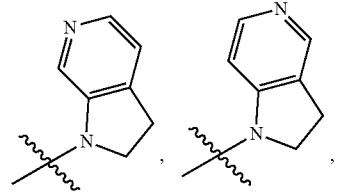

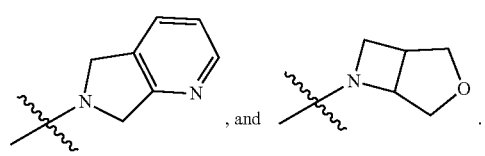

In some embodiments, the $R_4$ is a heterocyclyl selected from among:

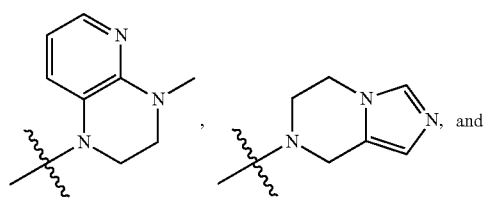

In some embodiments, the $R_4$ is a heterocyclyl selected from among:

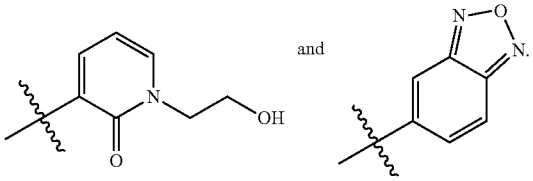 [SMILES: *c1cccn(CCO)c1=O ; *c1ccc2nonc2c1]

In some embodiments, the $R_4$ is a heterocyclyl selected from among:

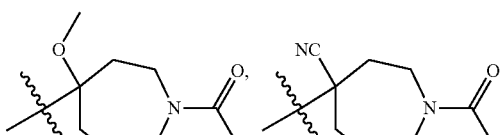

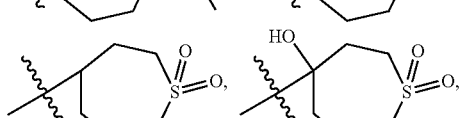

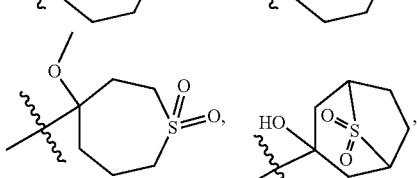

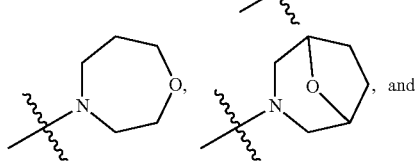

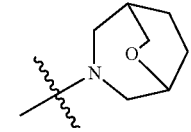

In some embodiments, $R_4$ is selected from among:

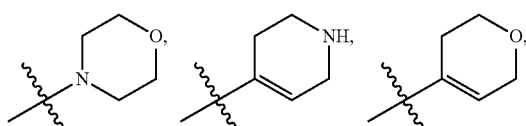

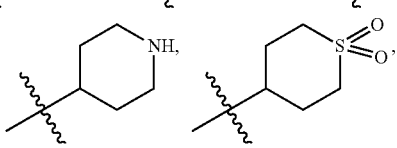

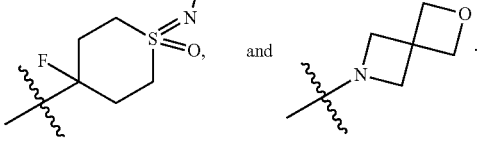

In some embodiments, $R_4$ is 3-14 membered cycloalkyl. In some embodiments, $R_4$ is substituted 3-14 membered cycloalkyl.

In some embodiments, R₄ is selected from among:
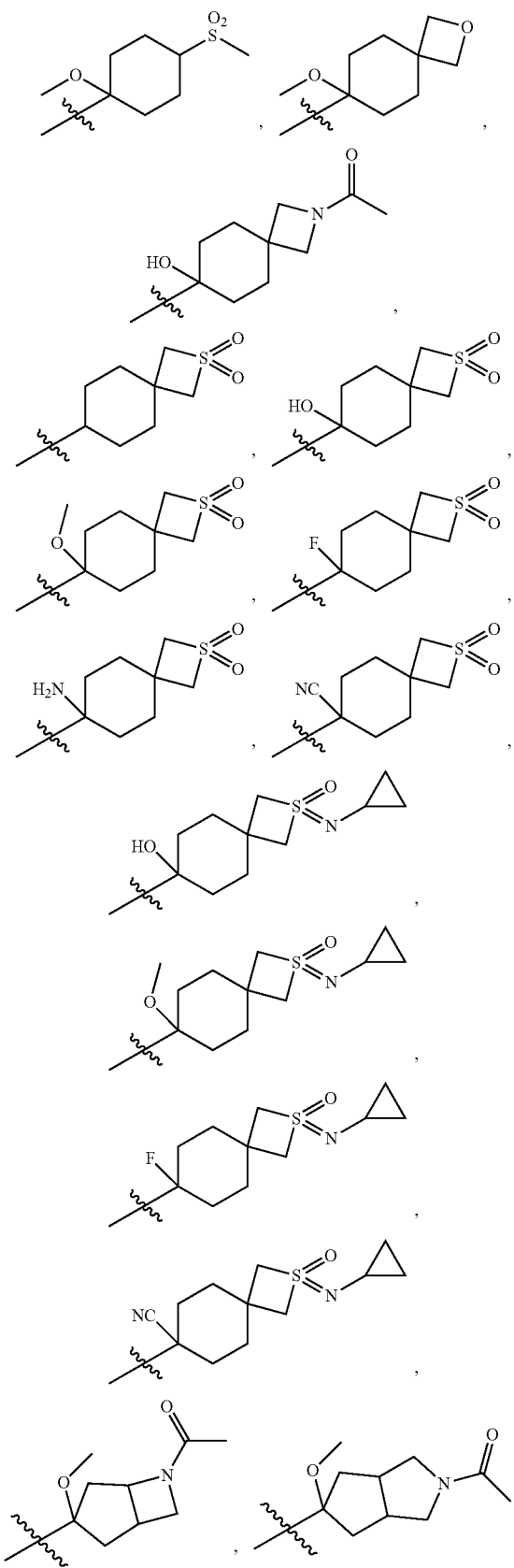
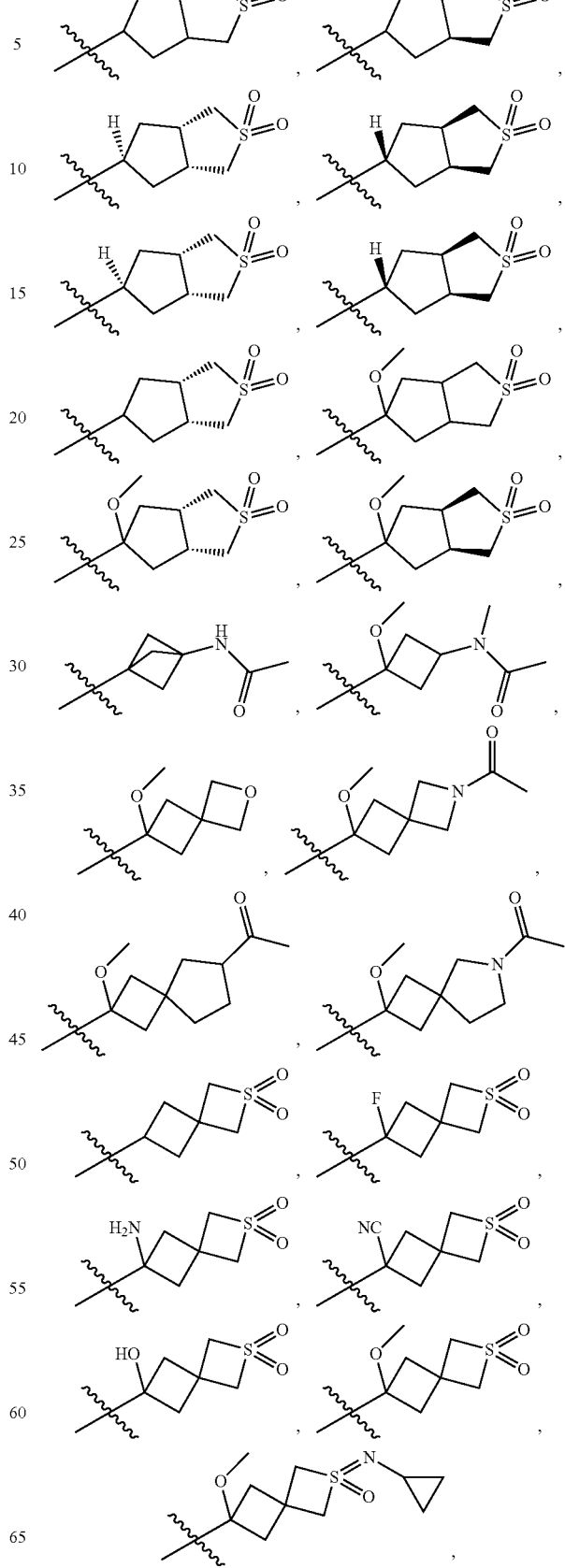

43

-continued

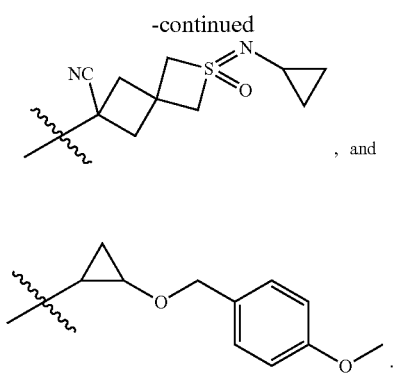

, and

In some embodiments, $R_4$ is 6-10 membered aryl. In some embodiments, $R_4$ is substituted 6-10 membered aryl. In some embodiments, $R_4$ is phenyl. In some embodiments, $R_4$ is phenyl substituted with one or two group selected from among —$OCH_3$ and —CN.

In some embodiments, $R_4$ is 5-10 membered heteroaryl. In some embodiments, $R_4$ is substituted 5-10 membered heteroaryl. In some embodiments, $R_4$ is selected from among 1H-pyrrole, thiazole, pyridine, pyridazine, pyrimidine, each of which is optionally substituted with a group selected from among —F, —$OCH_3$, and —$OCH_2CH_2OH$.

44

In some embodiments, $R_4$ is selected from among:

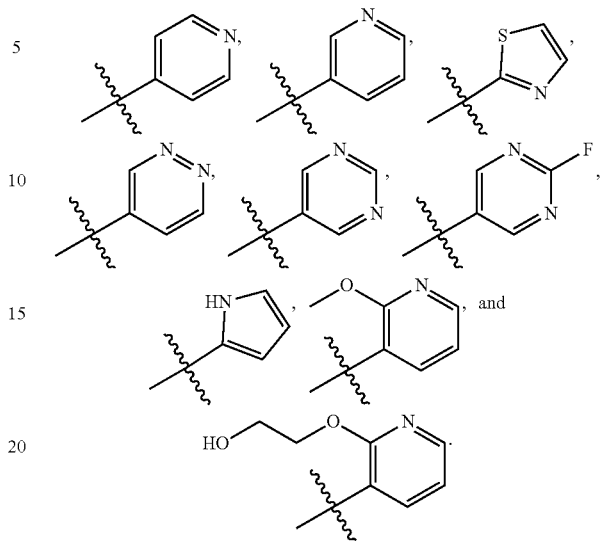

The present disclosure provides a compound, and pharmaceutically acceptable salts, solvates, stereoisomers, and tautomers thereof, selected from the group consisting of compounds of Table A:

TABLE A

| Example # | Structure |
|---|---|
| Example 1. | 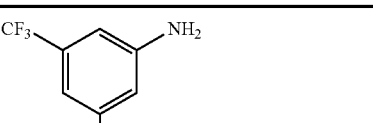 |
| Example 1-1. | 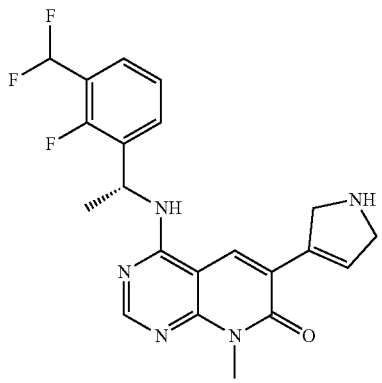 [SMILES: C[C@@H](Nc1ncnc2c1cc(C1=CCNC1)c(=O)n2C)c1cccc(C(F)F)c1F] |

TABLE A-continued
| Example # | Structure |
|---|---|
| Example 1-2. | 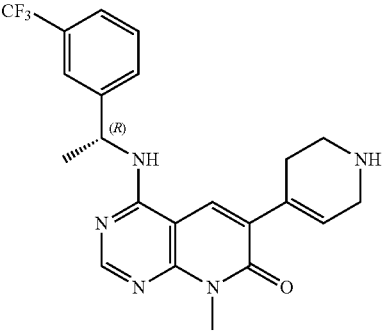 |
| Example 1-3. | 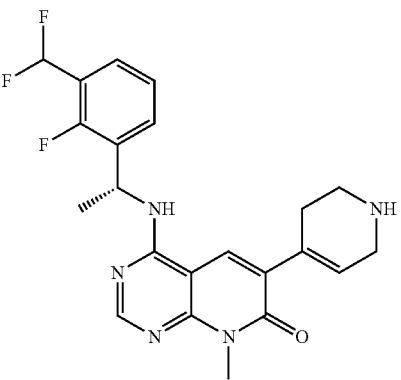 [SMILES: C[C@@H](Nc1ncnc2c1cc(C1=CCNCC1)c(=O)n2C)c1cccc(C(F)F)c1F] |
| Example 1-4. | 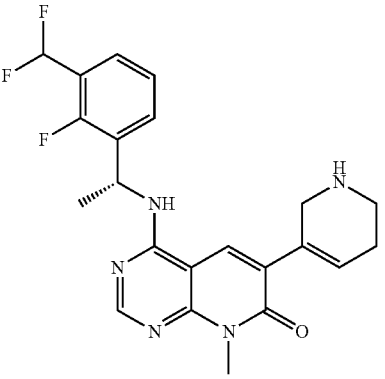 [SMILES: C[C@@H](Nc1ncnc2c1cc(C1=CCCNC1)c(=O)n2C)c1cccc(C(F)F)c1F] |
| Example 1-5. | 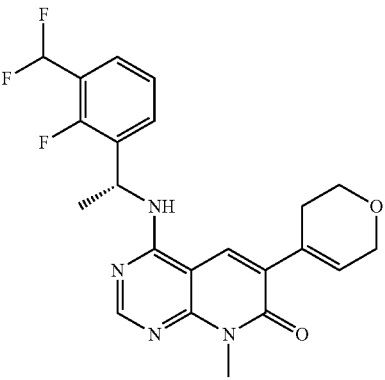 |

TABLE A-continued

| Example # | Structure |
|---|---|
| Example 1-6. | (structure) |
| Example 1-7. | (structure) |
| Example 1-8. | (structure) |
| Example 1-9. | (structure) |

TABLE A-continued
| Example # | Structure |
|---|---|
| Example 1-10. | 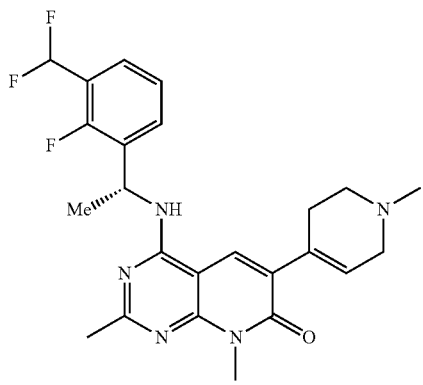 [SMILES: Cc1nc(N[C@H](C)c2cccc(C(F)F)c2F)c2cc(C3=CCN(C)CC3)c(=O)n(C)c2n1] |
| Example 1-11. | 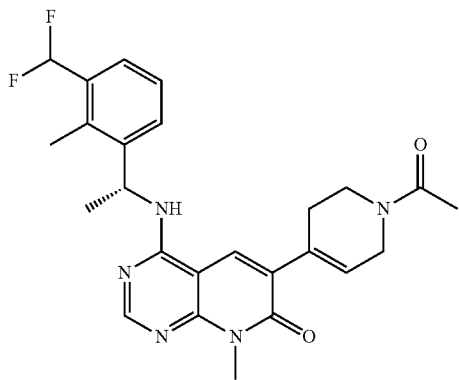 [SMILES: CC(=O)N1CC=C(c2cc3c(N[C@H](C)c4cccc(C(F)F)c4C)ncnc3n(C)c2=O)CC1] |
| Example 1-12. | 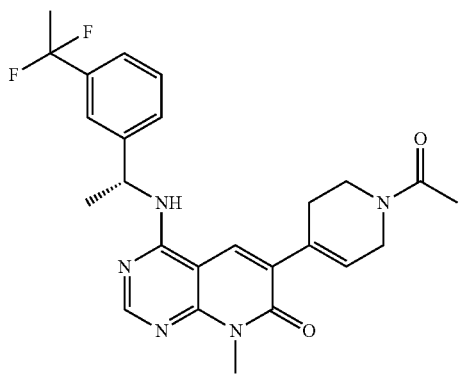 [SMILES: CC(=O)N1CC=C(c2cc3c(N[C@H](C)c4cccc(C(C)(F)F)c4)ncnc3n(C)c2=O)CC1] |
| Example 1-13. | 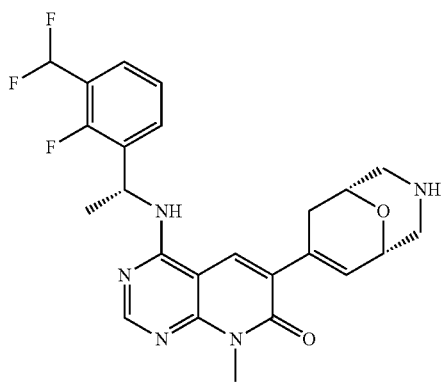 [SMILES: C[C@@H](Nc1ncnc2c1cc(C1=C[C@H]3CNC[C@@H](C1)O3)c(=O)n2C)c1cccc(C(F)F)c1F] |

TABLE A-continued
| Example # | Structure |
|---|---|
| Example 1-14. | 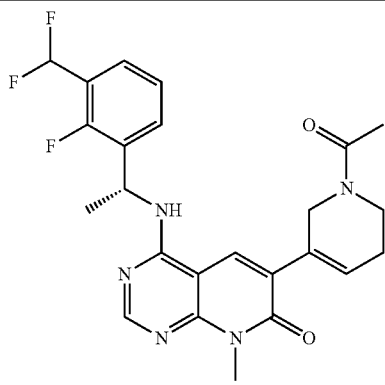 |
| Example 1-15. | 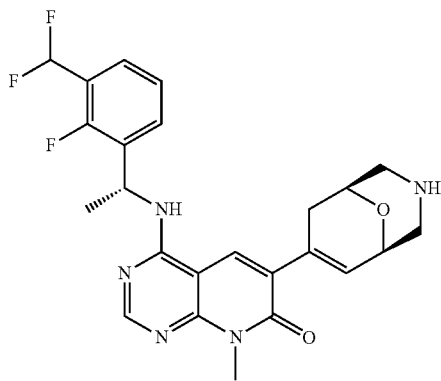 [SMILES: C[C@@H](Nc1ncnc2c1cc(C1=C[C@@H]3CNC[C@H](C1)O3)c(=O)n2C)c1cccc(C(F)F)c1F] |
| Example 1-16. | 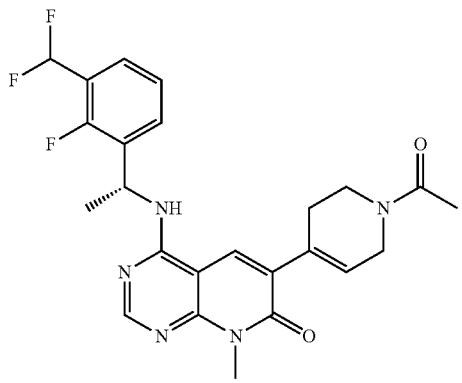 [SMILES: CC(=O)N1CC=C(c2cc3c(N[C@H](C)c4cccc(C(F)F)c4F)ncnc3n(C)c2=O)CC1] |
| Example 1-17. | 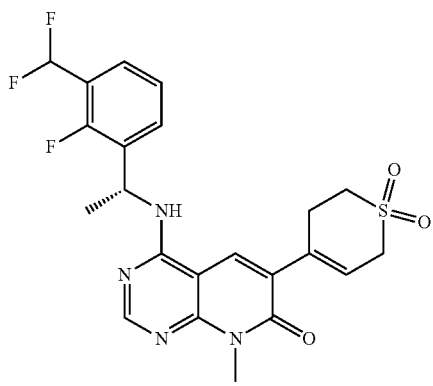 [SMILES: C[C@@H](Nc1ncnc2c1cc(C1=CCS(=O)(=O)CC1)c(=O)n2C)c1cccc(C(F)F)c1F] |

TABLE A-continued
| Example # | Structure |
|---|---|
| Example 1-18. | 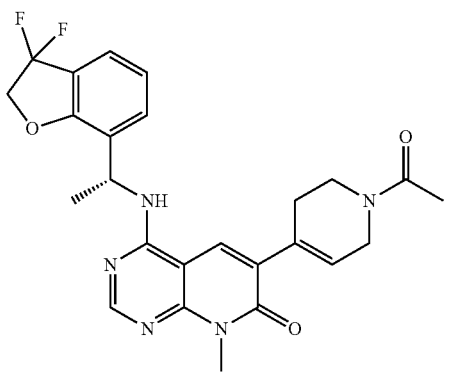 [SMILES: CC(=O)N1CC=C(c2cc3c(N[C@H](C)c4cccc5c4OCC5(F)F)ncnc3n(C)c2=O)CC1] |
| Example 1-19. | 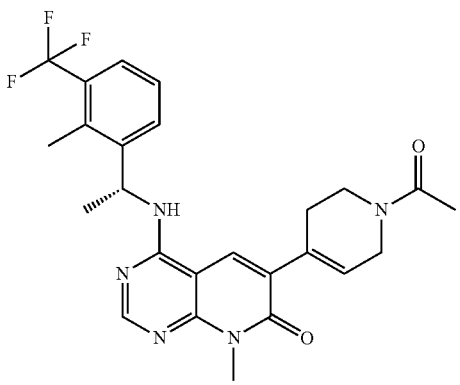 |
| Example 1-20. | 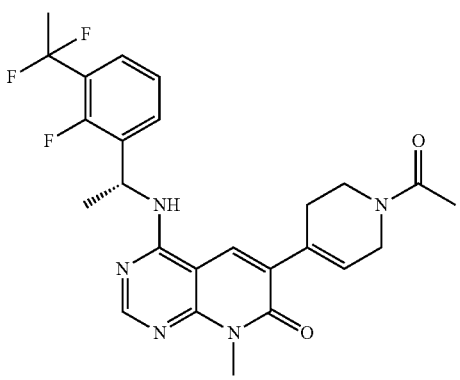 [SMILES: CC(=O)N1CC=C(c2cc3c(N[C@H](C)c4cccc(C(C)(F)F)c4F)ncnc3n(C)c2=O)CC1] |
| Example 1-21. | 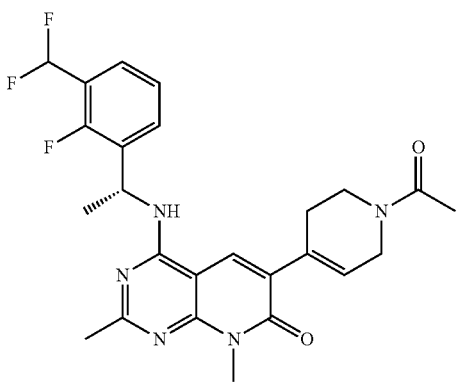 [SMILES: CC(=O)N1CC=C(c2cc3c(N[C@H](C)c4cccc(C(F)F)c4F)nc(C)nc3n(C)c2=O)CC1] |

TABLE A-continued
| Example # | Structure |
|---|---|
| Example 1-22. | 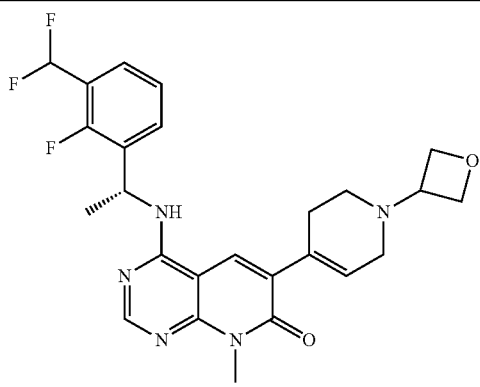 |
| Example 1-23. | 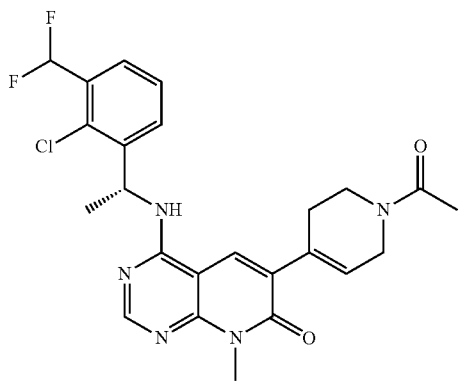 [SMILES: CC(=O)N1CC=C(c2cc3c(N[C@H](C)c4cccc(C(F)F)c4Cl)ncnc3n(C)c2=O)CC1] |
| Example 1-24. | 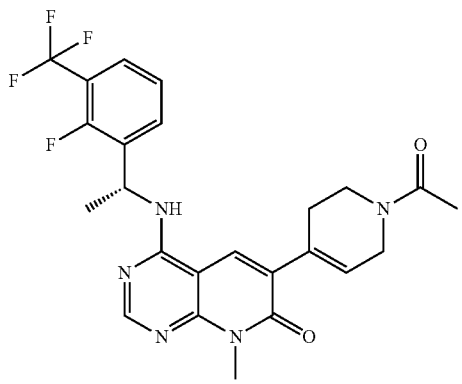 |
| Example 1-25. | 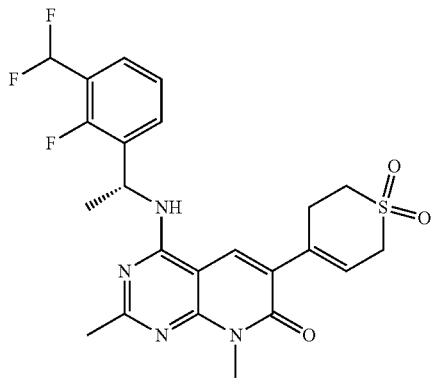 |

TABLE A-continued

| Example # | Structure |
|---|---|
| Example 1-26. | (structure) |
| Example 1-27. | (structure) |
| Example 1-28. | (structure) |
| Example 1-29. | (structure) |

TABLE A-continued

| Example # | Structure |
|---|---|
| Example 1-30. | 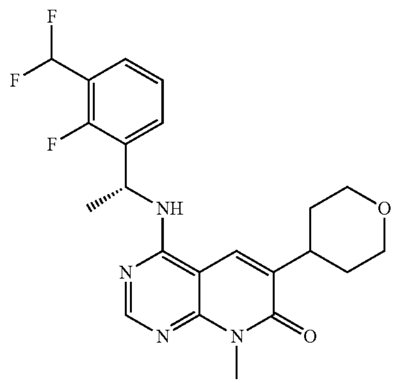 [SMILES: C[C@@H](Nc1ncnc2c1cc(C1CCOCC1)c(=O)n2C)c1cccc(C(F)F)c1F] |
| Example 1-31. | 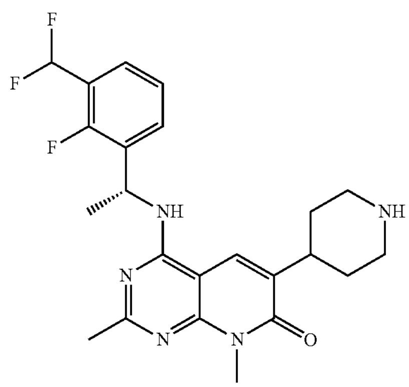 [SMILES: Cc1nc(N[C@H](C)c2cccc(C(F)F)c2F)c2cc(C3CCNCC3)c(=O)n(C)c2n1] |
| Example 1-32. | 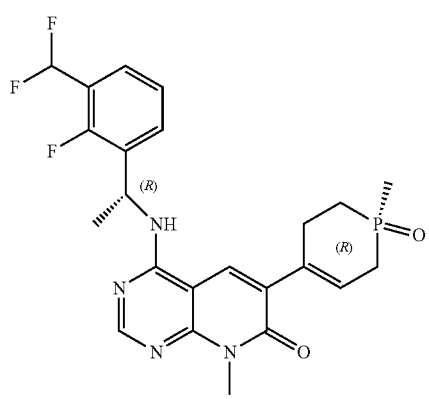 |
| Example 1-33. | 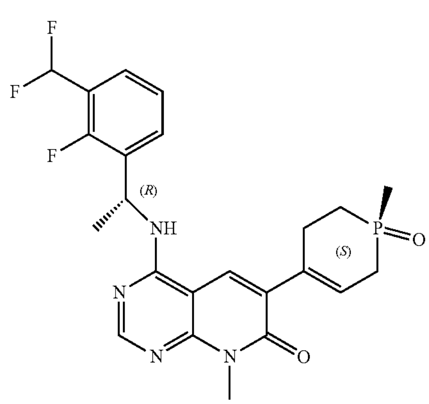 |

TABLE A-continued
| Example # | Structure |
|---|---|
| Example 2. | 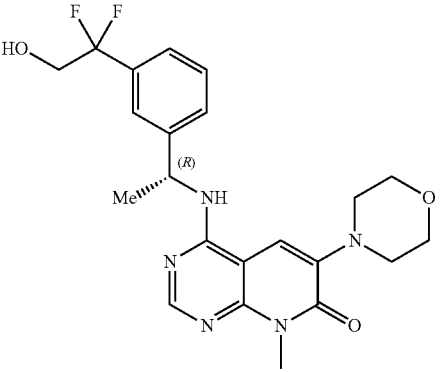 |
| Example 2-1. | 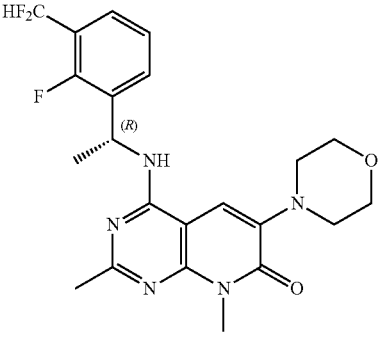 |
| Example 2-2. | 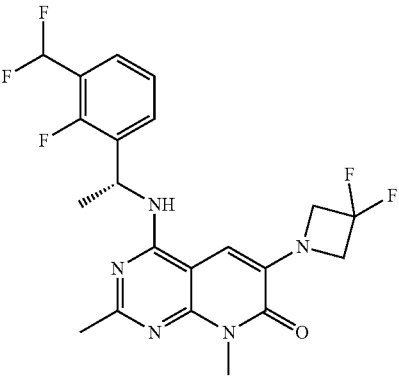 [SMILES: Cc1nc(N[C@H](C)c2cccc(C(F)F)c2F)c2cc(N3CC(F)(F)C3)c(=O)n(C)c2n1] |
| Example 2-3. | 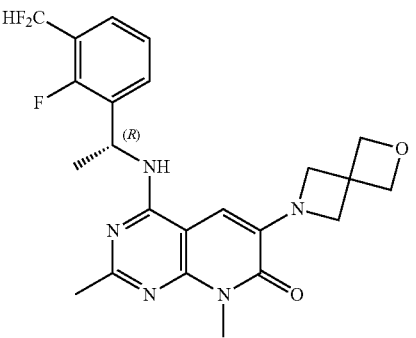 |

TABLE A-continued
| Example # | Structure |
|---|---|
| Example 2-4. | 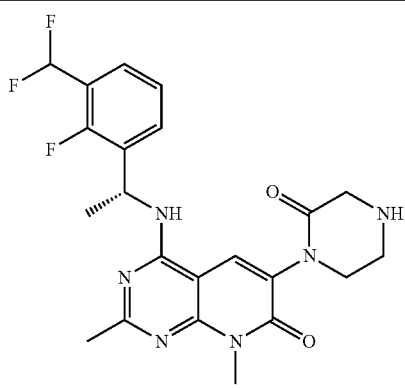 |
| Example 2-5. | 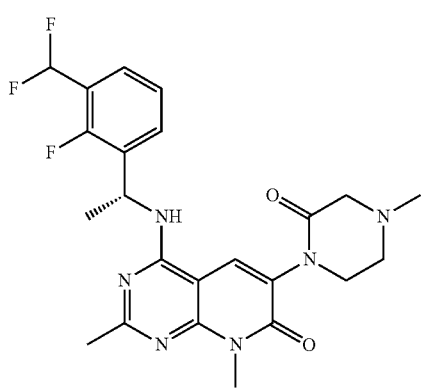 [SMILES: Cc1nc(N[C@H](C)c2cccc(C(F)F)c2F)c2cc(N3CCN(C)CC3=O)c(=O)n(C)c2n1] |
| Example 3. | 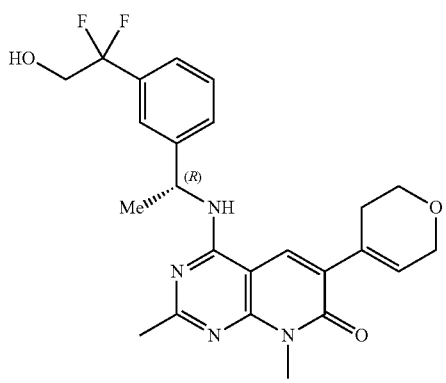 |
| Example 4. | 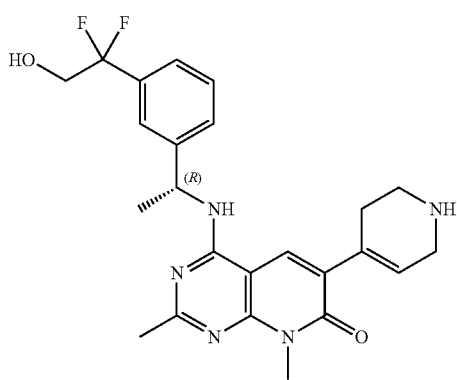 |

TABLE A-continued
| Example # | Structure |
| --- | --- |
| Example 5. | 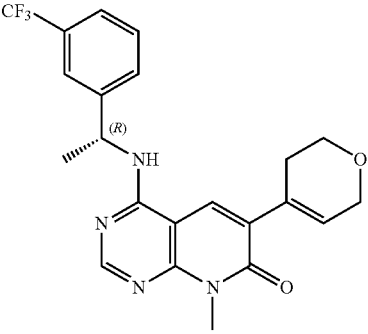 |
| Example 6. | 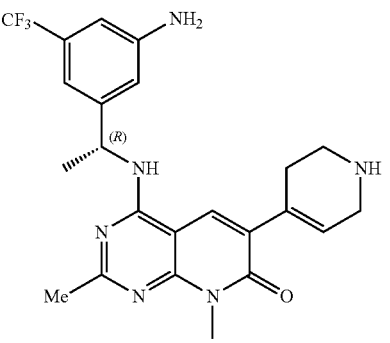 |
| Example 7. | 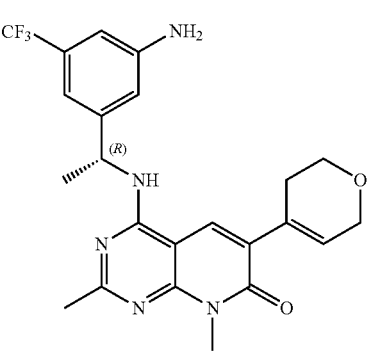 |
| Example 8. | 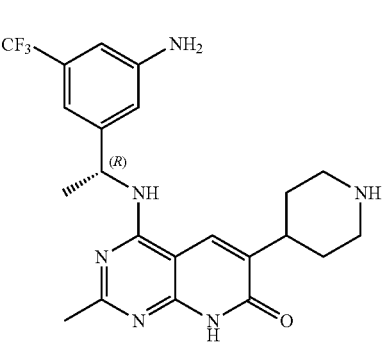 |

TABLE A-continued
| Example # | Structure |
|---|---|
| Example 8-1. | 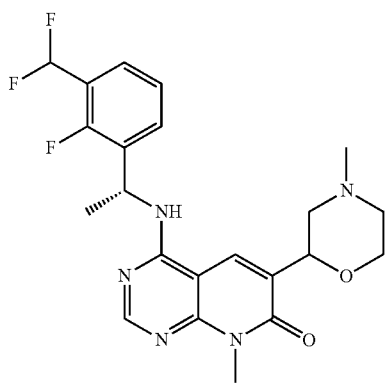 [SMILES: C[C@@H](Nc1ncnc2c1cc(C1CN(C)CCO1)c(=O)n2C)c1cccc(C(F)F)c1F] |
| Example 8-2. | 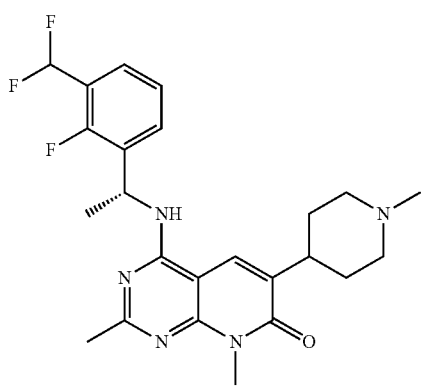 [SMILES: Cc1nc(N[C@H](C)c2cccc(C(F)F)c2F)c2cc(C3CCN(C)CC3)c(=O)n(C)c2n1] |
| Example 8-3. | 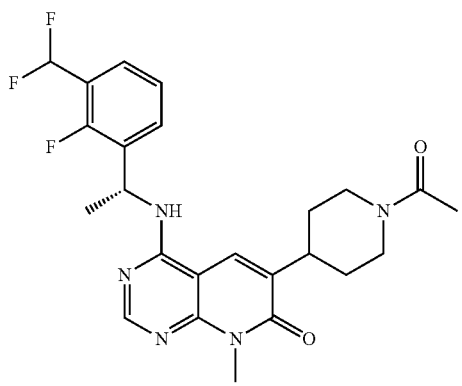 |
| Example 8-4. | 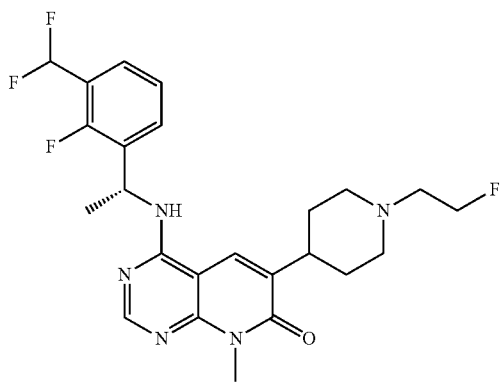 [SMILES: C[C@@H](Nc1ncnc2c1cc(C1CCN(CCF)CC1)c(=O)n2C)c1cccc(C(F)F)c1F] |

TABLE A-continued
| Example # | Structure |
|---|---|
| Example 8-5. | 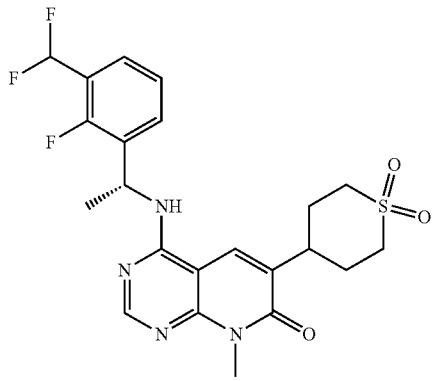 |
| Example 8-6. | 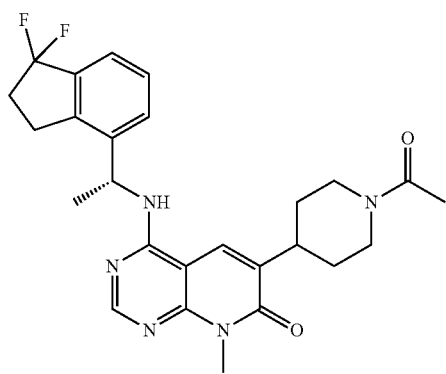 [SMILES: CC(=O)N1CCC(c2cc3c(N[C@H](C)c4cccc5c4CCC5(F)F)ncnc3n(C)c2=O)CC1] |
| Example 8-7. | 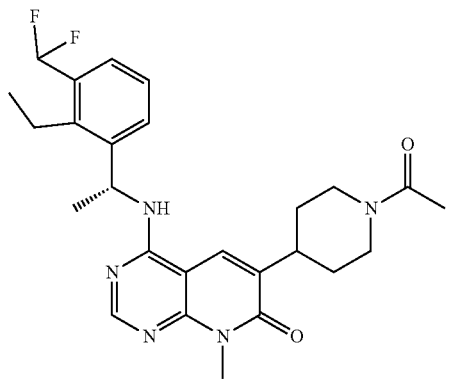 [SMILES: CCc1c(C(F)F)cccc1[C@@H](C)Nc1ncnc2c1cc(C1CCN(C(C)=O)CC1)c(=O)n2C] |
| Example 8-8. | 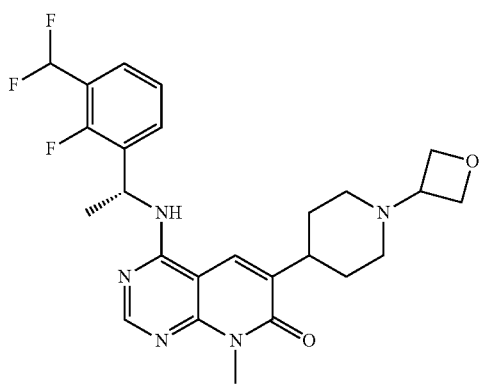 [SMILES: C[C@@H](Nc1ncnc2c1cc(C1CCN(C3COC3)CC1)c(=O)n2C)c1cccc(C(F)F)c1F] |

TABLE A-continued
| Example # | Structure |
|---|---|
| Example 8-9. | 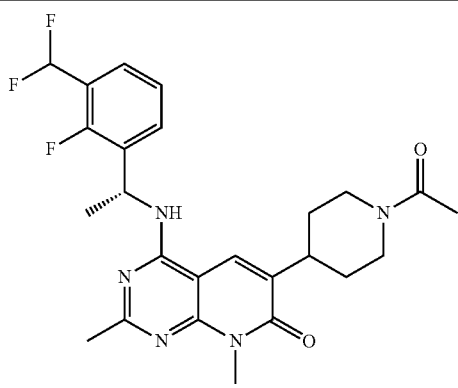 |
| Example 8-10. | 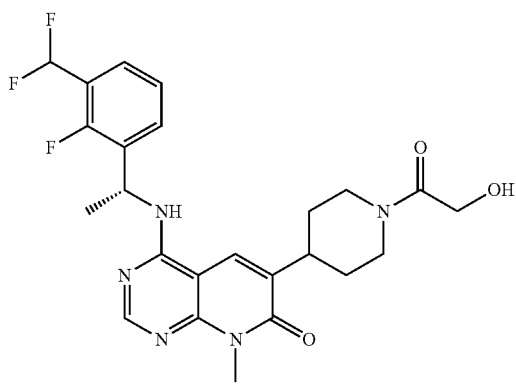 [SMILES: C[C@@H](Nc1ncnc2c1cc(C1CCN(C(=O)CO)CC1)c(=O)n2C)c1cccc(C(F)F)c1F] |
| Example 8-11. | 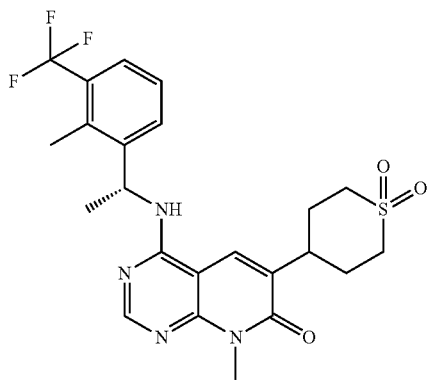 [SMILES: Cc1c([C@@H](C)Nc2ncnc3c2cc(C2CCS(=O)(=O)CC2)c(=O)n3C)cccc1C(F)(F)F] |
| Example 8-12. | 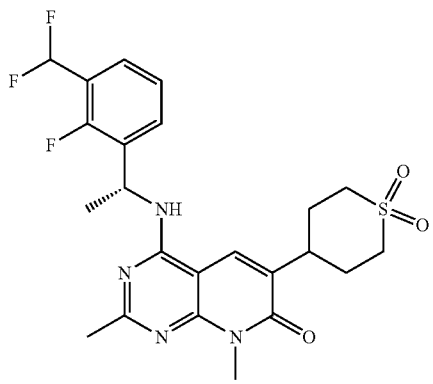 [SMILES: Cc1nc(N[C@H](C)c2cccc(C(F)F)c2F)c2cc(C3CCS(=O)(=O)CC3)c(=O)n(C)c2n1] |

TABLE A-continued

| Example # | Structure |
|---|---|
| Example 8-13. | 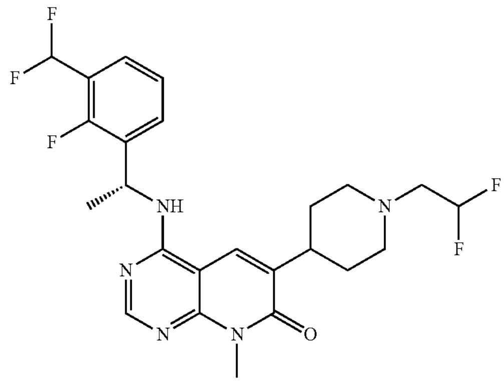 [SMILES: C[C@@H](Nc1ncnc2c1cc(C1CCN(CC(F)F)CC1)c(=O)n2C)c1cccc(C(F)F)c1F] |
| Example 8-14. | 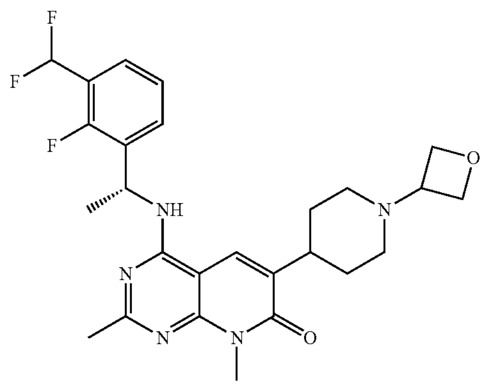 |
| Example 8-15. | 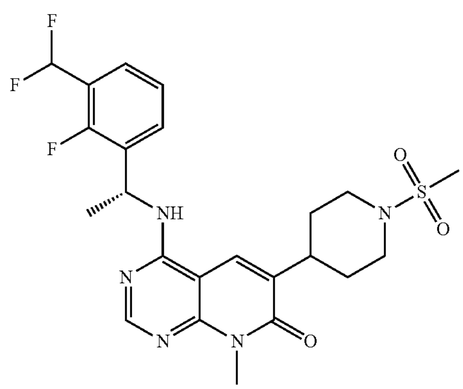 [SMILES: C[C@@H](Nc1ncnc2c1cc(C1CCN(S(C)(=O)=O)CC1)c(=O)n2C)c1cccc(C(F)F)c1F] |
| Example 8-16. | 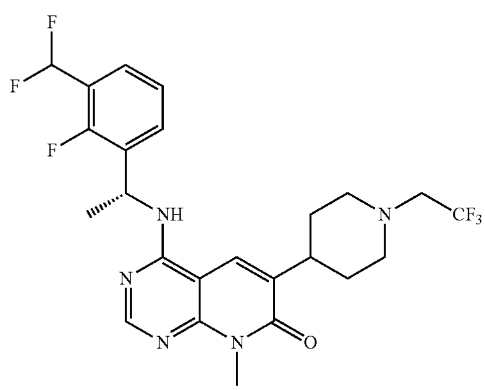 |

TABLE A-continued
| Example # | Structure |
|---|---|
| Example 8-17. | 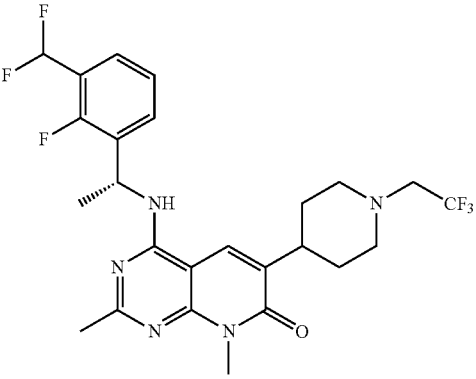 [SMILES: Cc1nc(N[C@H](C)c2cccc(C(F)F)c2F)c2cc(C3CCN(CC(F)(F)F)CC3)c(=O)n(C)c2n1] |
| Example 9. | 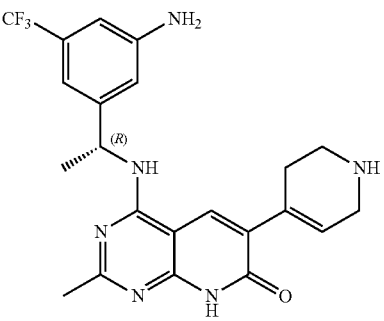 |
| Example 10. | 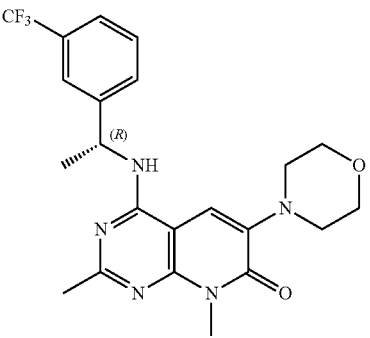 |
| Example 11. | 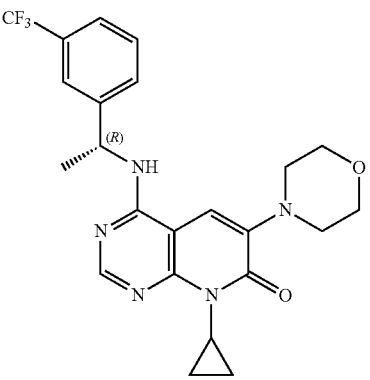 |

TABLE A-continued
| Example # | Structure |
|---|---|
| Example 11-1. | 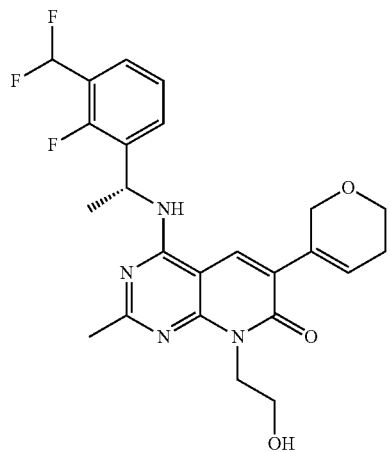 [SMILES: Cc1nc(N[C@H](C)c2cccc(C(F)F)c2F)c2cc(C3=CCCOC3)c(=O)n(CCO)c2n1] |
| Example 11-2. | 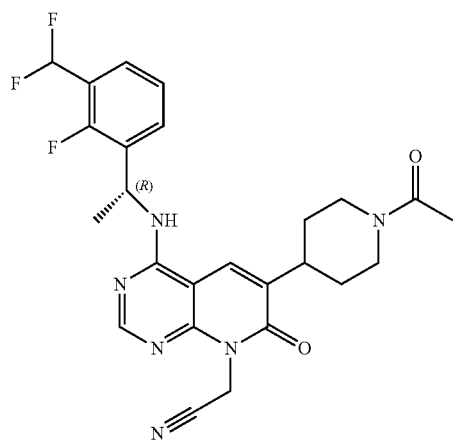 |
| Example 11-3. | 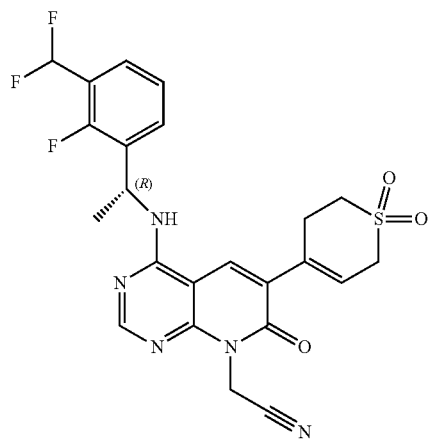 |

TABLE A-continued
| Example # | Structure |
|---|---|
| Example 11-4. | 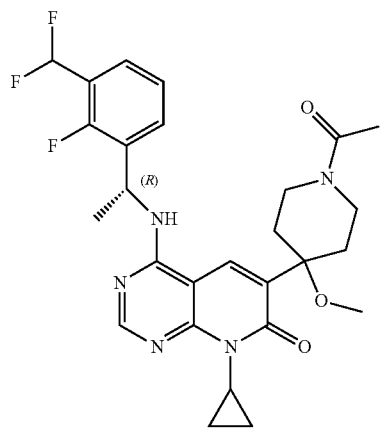 |
| Example 12. | 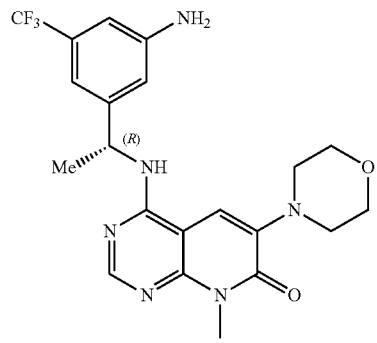 |
| Example 13. | 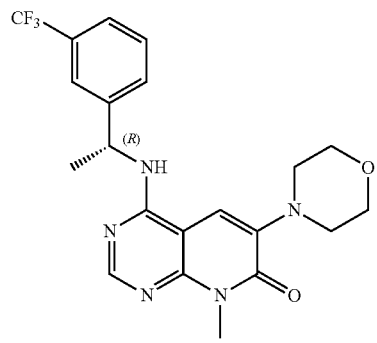 |
| Example 14. | 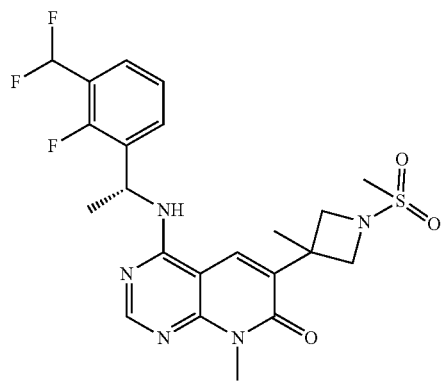 [SMILES: C[C@@H](Nc1ncnc2c1cc(C1(C)CN(S(C)(=O)=O)C1)c(=O)n2C)c1cccc(C(F)F)c1F] |

TABLE A-continued

| Example # | Structure |
|---|---|
| Example 15. | 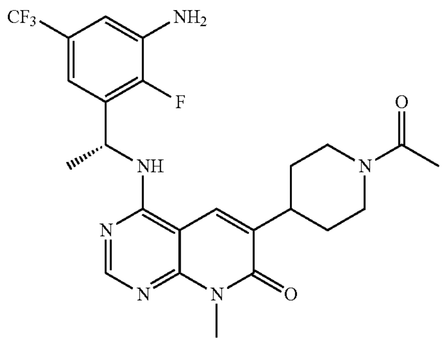 [SMILES: CC(=O)N1CCC(c2cc3c(N[C@H](C)c4cc(C(F)(F)F)cc(N)c4F)ncnc3n(C)c2=O)CC1] |
| Example 16. | 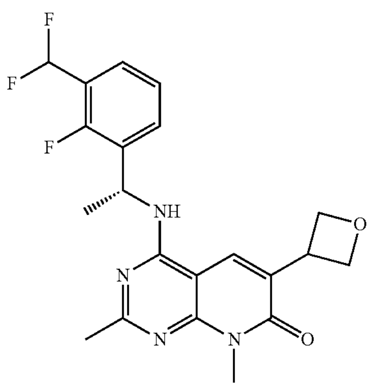 [SMILES: Cc1nc(N[C@H](C)c2cccc(C(F)F)c2F)c2cc(C3COC3)c(=O)n(C)c2n1] |
| Example 17. | 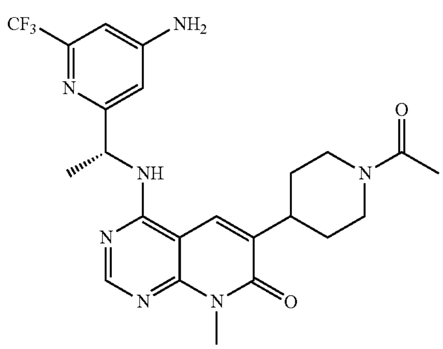 [SMILES: CC(=O)N1CCC(c2cc3c(N[C@H](C)c4cc(N)cc(C(F)(F)F)n4)ncnc3n(C)c2=O)CC1] |
| Example 18. | 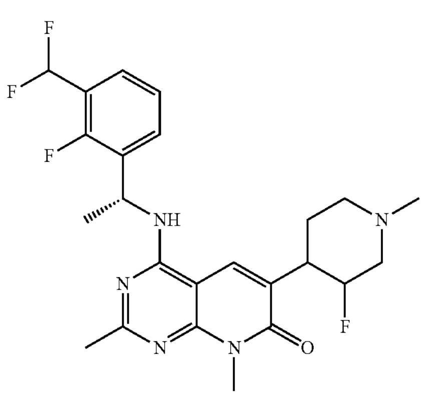 [SMILES: Cc1nc(N[C@H](C)c2cccc(C(F)F)c2F)c2cc(C3CCN(C)CC3F)c(=O)n(C)c2n1] |

TABLE A-continued

| Example # | Structure |
| --- | --- |
| Example 19. | 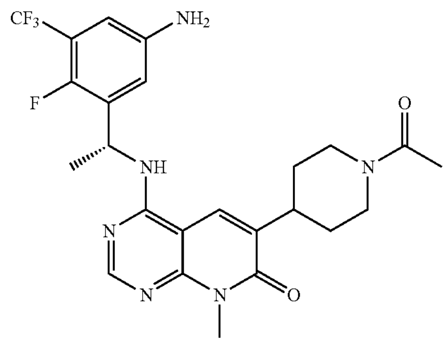 |
| Example 20. | 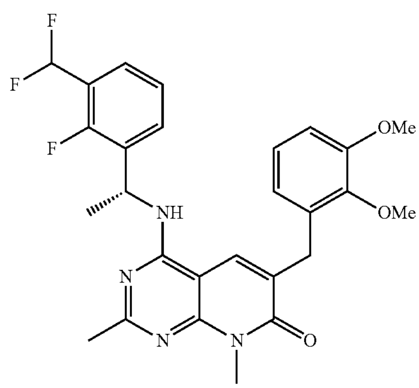 [SMILES: COc1cccc(Cc2cc3c(N[C@H](C)c4cccc(C(F)F)c4F)nc(C)nc3n(C)c2=O)c1OC] |
| Example 20-1. | 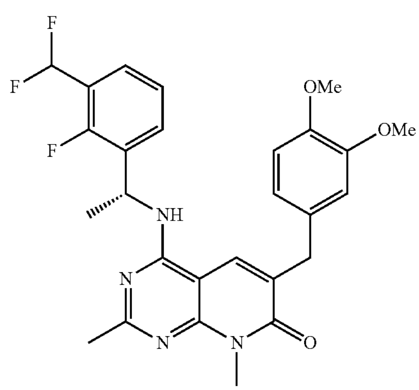 [SMILES: COc1ccc(Cc2cc3c(N[C@H](C)c4cccc(C(F)F)c4F)nc(C)nc3n(C)c2=O)cc1OC] |
| Example 20-2. | 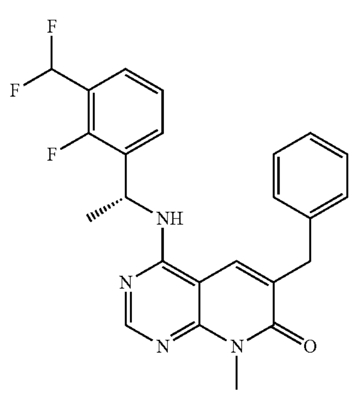 [SMILES: C[C@@H](Nc1ncnc2c1cc(Cc1ccccc1)c(=O)n2C)c1cccc(C(F)F)c1F] |

TABLE A-continued
| Example # | Structure |
|---|---|
| Example 20-3. | 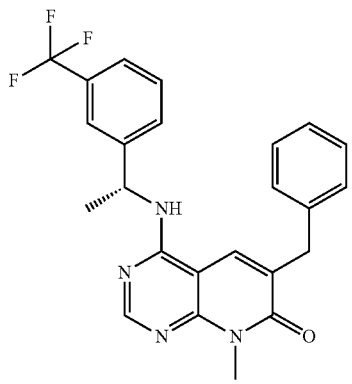 [SMILES: C[C@@H](Nc1ncnc2c1cc(Cc1ccccc1)c(=O)n2C)c1cccc(C(F)(F)F)c1] |
| Example 20-4. | 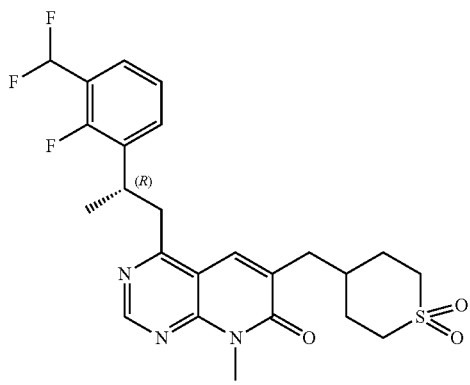 |
| Example 21. | 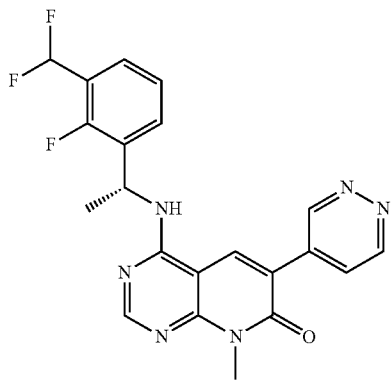 |
| Example 21-1. | 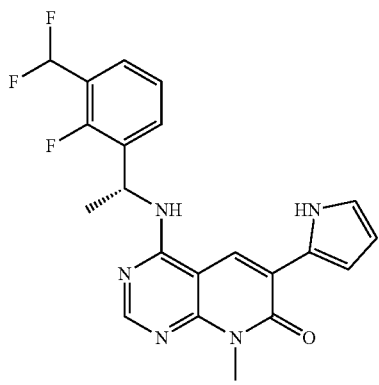 [SMILES: C[C@@H](Nc1ncnc2c1cc(-c1ccc[nH]1)c(=O)n2C)c1cccc(C(F)F)c1F] |

TABLE A-continued
| Example # | Structure |
|---|---|
| Example 21-2. | 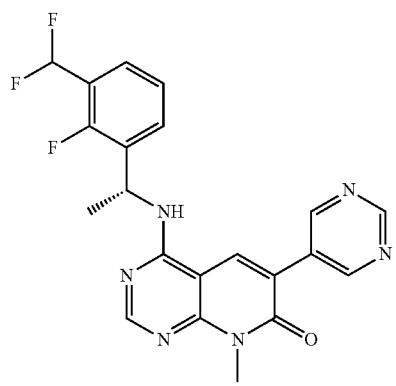 [SMILES: C[C@@H](Nc1ncnc2c1cc(-c1cncnc1)c(=O)n2C)c1cccc(C(F)F)c1F] |
| Example 21-3. | 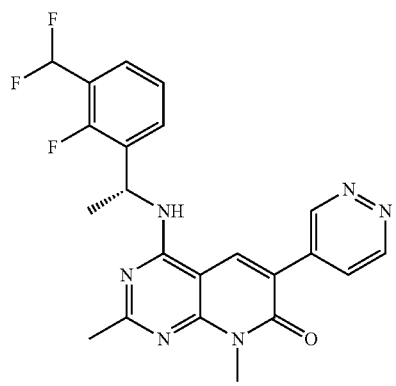 [SMILES: Cc1nc(N[C@H](C)c2cccc(C(F)F)c2F)c2cc(-c3ccnnc3)c(=O)n(C)c2n1] |
| Example 21-4. | 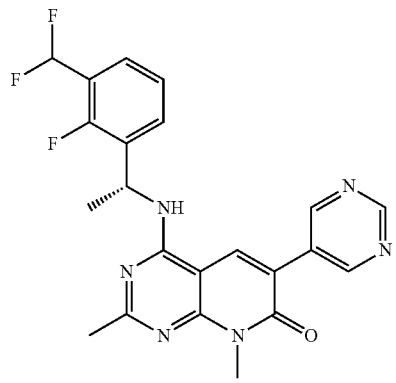 [SMILES: Cc1nc(N[C@H](C)c2cccc(C(F)F)c2F)c2cc(-c3cncnc3)c(=O)n(C)c2n1] |
| Example 21-5. | 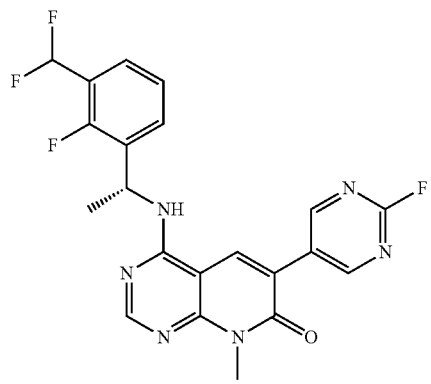 [SMILES: C[C@@H](Nc1ncnc2c1cc(-c1cnc(F)nc1)c(=O)n2C)c1cccc(C(F)F)c1F] |

TABLE A-continued
| Example # | Structure |
|---|---|
| Example 21-6. | 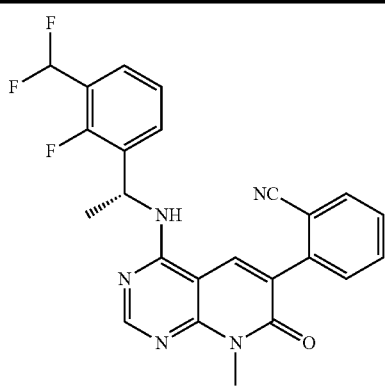 |
| Example 21-7. | 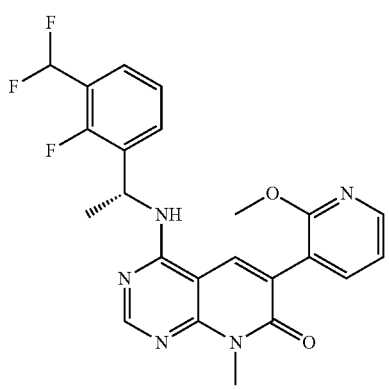 [SMILES: COc1ncccc1-c1cc2c(N[C@H](C)c3cccc(C(F)F)c3F)ncnc2n(C)c1=O] |
| Example 21-8. | 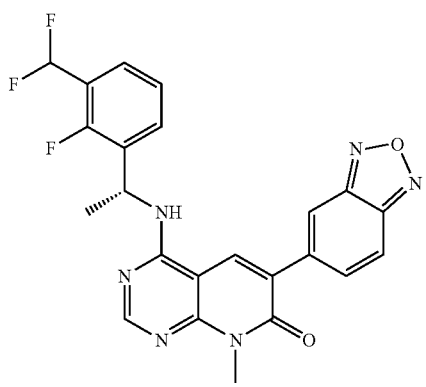 [SMILES: C[C@@H](Nc1ncnc2c1cc(-c1ccc3nonc3c1)c(=O)n2C)c1cccc(C(F)F)c1F] |
| Example 21-9. | 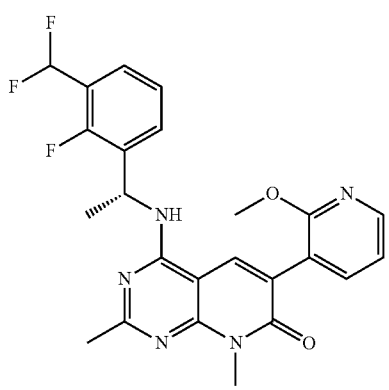 [SMILES: COc1ncccc1-c1cc2c(N[C@H](C)c3cccc(C(F)F)c3F)nc(C)nc2n(C)c1=O] |

TABLE A-continued
| Example # | Structure |
|---|---|
| Example 21-10. | 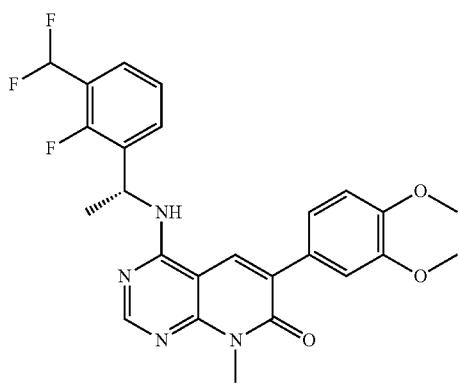 [SMILES: COc1ccc(-c2cc3c(N[C@H](C)c4cccc(C(F)F)c4F)ncnc3n(C)c2=O)cc1OC] |
| Example 21-11. | 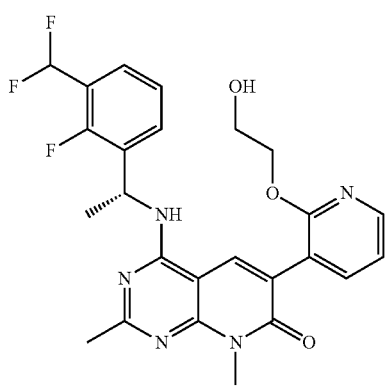 [SMILES: Cc1nc(N[C@H](C)c2cccc(C(F)F)c2F)c2cc(-c3cccnc3OCCO)c(=O)n(C)c2n1] |
| Example 21-12. | 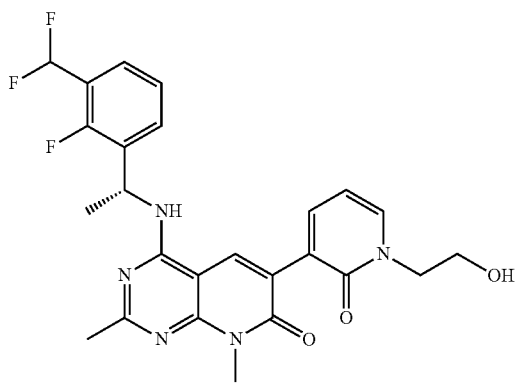 [SMILES: Cc1nc(N[C@H](C)c2cccc(C(F)F)c2F)c2cc(-c3cccn(CCO)c3=O)c(=O)n(C)c2n1] |
| Example 21-13. | 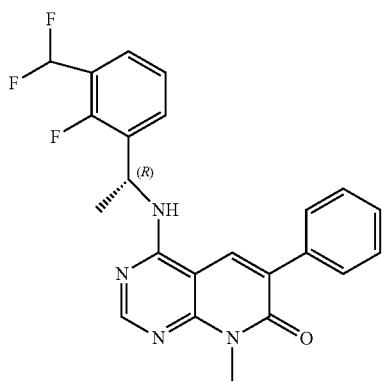 |

TABLE A-continued
| Example # | Structure |
|---|---|
| Example 21-14. | 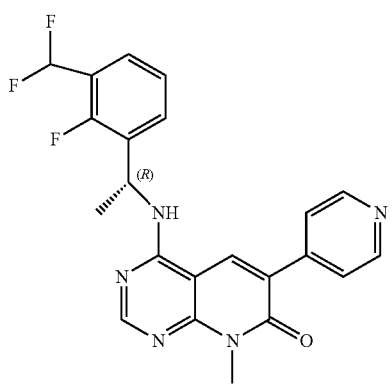 |
| Example 21-15. | 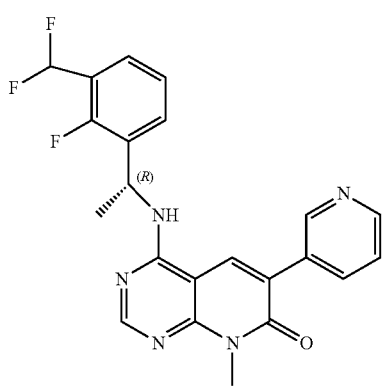 |
| Example 22. | 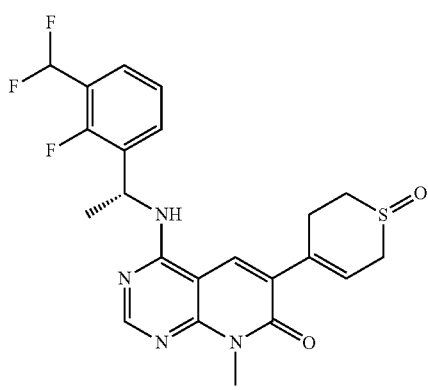 [SMILES: C[C@@H](Nc1ncnc2c1cc(C1=CCS(=O)CC1)c(=O)n2C)c1cccc(C(F)F)c1F] |
| Example 23. | 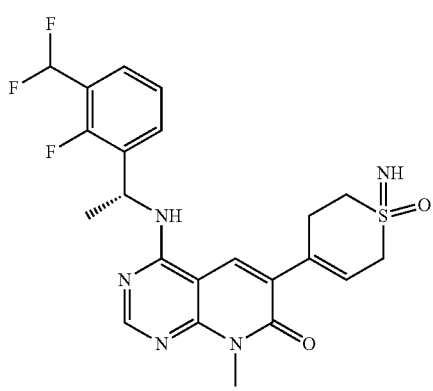 [SMILES: C[C@@H](Nc1ncnc2c1cc(C1=CCS(=N)(=O)CC1)c(=O)n2C)c1cccc(C(F)F)c1F] |

TABLE A-continued

| Example # | Structure |
| --- | --- |
| Example 23-1. | 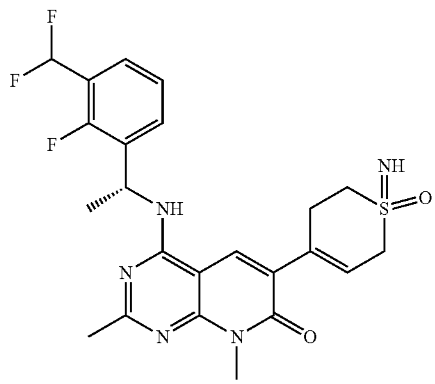 [SMILES: Cc1nc(N[C@H](C)c2cccc(C(F)F)c2F)c2cc(C3=CCS(=N)(=O)CC3)c(=O)n(C)c2n1] |
| Example 24. | 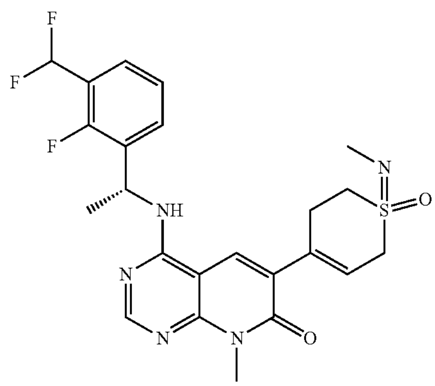 [SMILES: CN=S1(=O)CC=C(c2cc3c(N[C@H](C)c4cccc(C(F)F)c4F)ncnc3n(C)c2=O)CC1] |
| Example 25. | 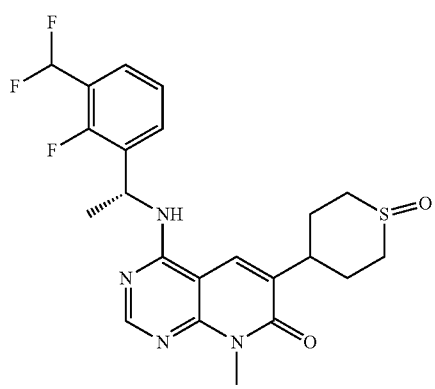 [SMILES: C[C@@H](Nc1ncnc2c1cc(C1CCS(=O)CC1)c(=O)n2C)c1cccc(C(F)F)c1F] |
| Example 26. | 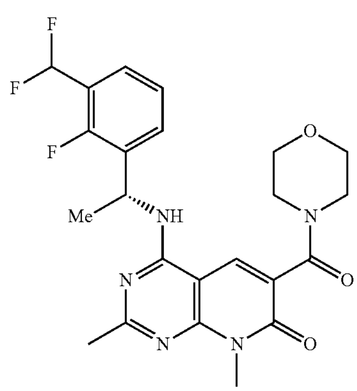 [SMILES: Cc1nc(N[C@H](C)c2cccc(C(F)F)c2F)c2cc(C(=O)N3CCOCC3)c(=O)n(C)c2n1] |

TABLE A-continued
| Example # | Structure |
|---|---|
| Example 26-1. | 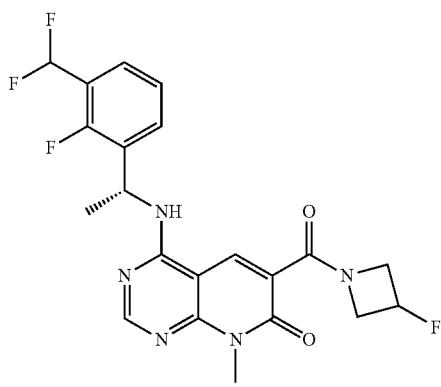 [SMILES: C[C@@H](Nc1ncnc2c1cc(C(=O)N1CC(F)C1)c(=O)n2C)c1cccc(C(F)F)c1F] |
| Example 26-2. | 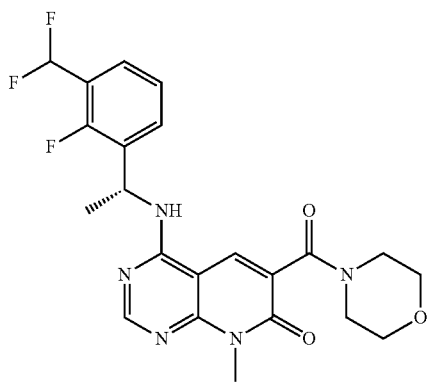 [SMILES: C[C@@H](Nc1ncnc2c1cc(C(=O)N1CCOCC1)c(=O)n2C)c1cccc(C(F)F)c1F] |
| Example 26-3. | 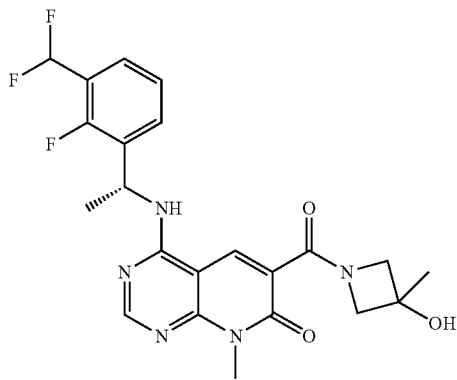 [SMILES: C[C@@H](Nc1ncnc2c1cc(C(=O)N1CC(C)(O)C1)c(=O)n2C)c1cccc(C(F)F)c1F] |
| Example 26-4. | 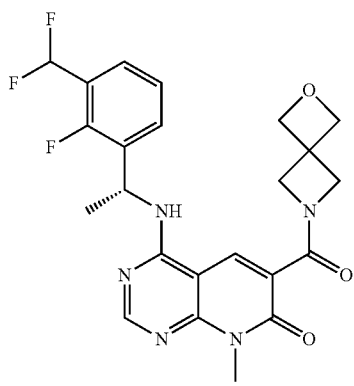 [SMILES: C[C@@H](Nc1ncnc2c1cc(C(=O)N1CC3(COC3)C1)c(=O)n2C)c1cccc(C(F)F)c1F] |

TABLE A-continued
| Example # | Structure |
|---|---|
| Example 26-5. | 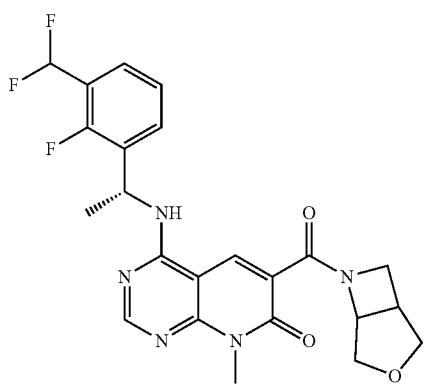 [SMILES: C[C@@H](Nc1ncnc2c1cc(C(=O)N1CC3COCC31)c(=O)n2C)c1cccc(C(F)F)c1F] |
| Example 26-6. | 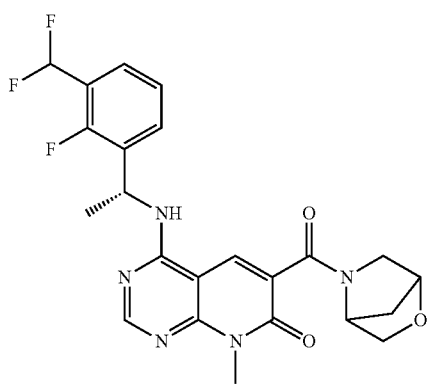 |
| Example 26-7. | 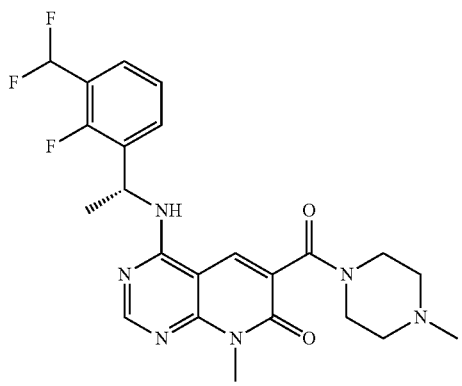 [SMILES: C[C@@H](Nc1ncnc2c1cc(C(=O)N1CCN(C)CC1)c(=O)n2C)c1cccc(C(F)F)c1F] |
| Example 26-8. | 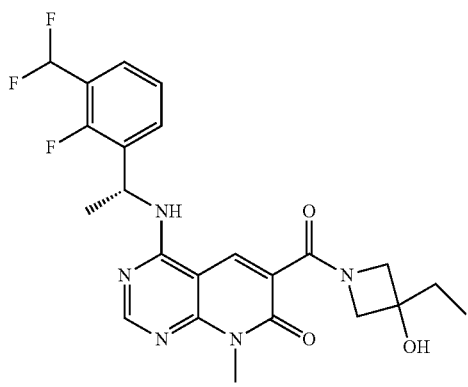 [SMILES: CCC1(O)CN(C(=O)c2cc3c(N[C@H](C)c4cccc(C(F)F)c4F)ncnc3n(C)c2=O)C1] |

TABLE A-continued
| Example # | Structure |
|---|---|
| Example 26-9. | 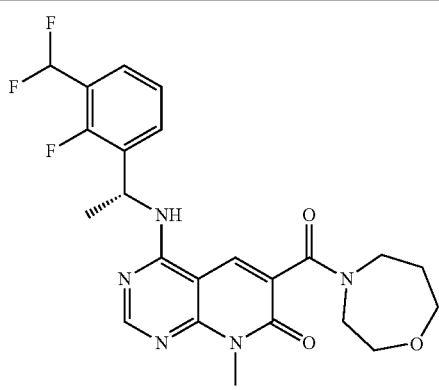 [SMILES: C[C@@H](Nc1ncnc2c1cc(C(=O)N1CCCOCC1)c(=O)n2C)c1cccc(C(F)F)c1F] |
| Example 26-10. | 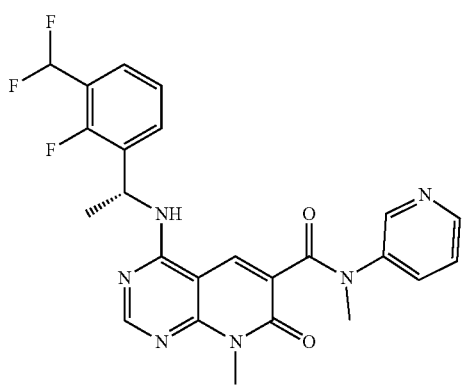 [SMILES: C[C@@H](Nc1ncnc2c1cc(C(=O)N(C)c1cccnc1)c(=O)n2C)c1cccc(C(F)F)c1F] |
| Example 26-11. | 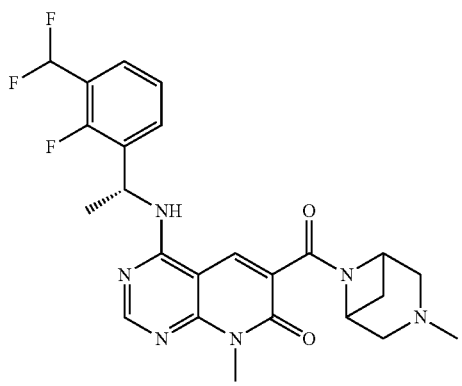 [SMILES: C[C@@H](Nc1ncnc2c1cc(C(=O)N1C3CC1CN(C)C3)c(=O)n2C)c1cccc(C(F)F)c1F] |
| Example 26-12. | 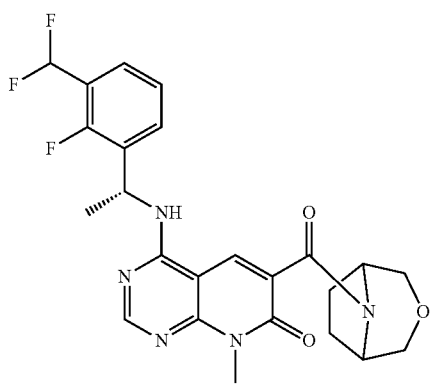 [SMILES: C[C@@H](Nc1ncnc2c1cc(C(=O)N1C3CCC1COC3)c(=O)n2C)c1cccc(C(F)F)c1F] |

103
104
TABLE A-continued
| Example # | Structure |
|---|---|
| Example 26-13. | 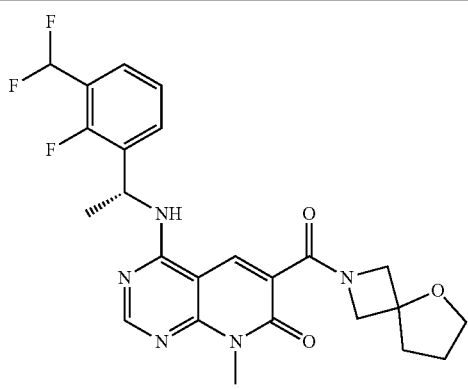 [SMILES: C[C@@H](Nc1ncnc2c1cc(C(=O)N1CC3(CCCO3)C1)c(=O)n2C)c1cccc(C(F)F)c1F] |
| Example 26-14. | 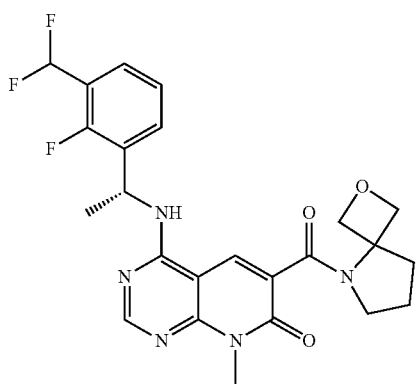 [SMILES: C[C@@H](Nc1ncnc2c1cc(C(=O)N1CCCC13COC3)c(=O)n2C)c1cccc(C(F)F)c1F] |
| Example 26-15. | 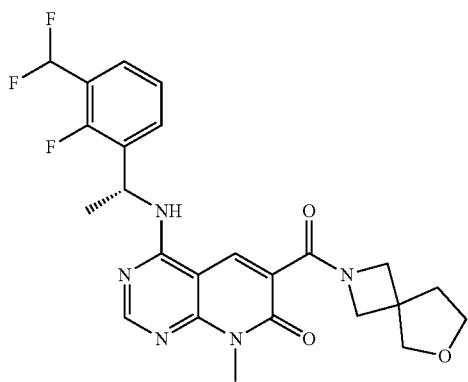 [SMILES: C[C@@H](Nc1ncnc2c1cc(C(=O)N1CC3(CCOC3)C1)c(=O)n2C)c1cccc(C(F)F)c1F] |
| Example 26-16. | 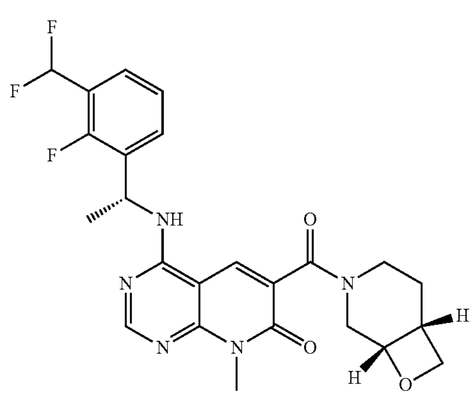 [SMILES: C[C@@H](Nc1ncnc2c1cc(C(=O)N1CC[C@@H]3CO[C@@H]3C1)c(=O)n2C)c1cccc(C(F)F)c1F] |

TABLE A-continued
| Example # | Structure |
|---|---|
| Example 26-17. | 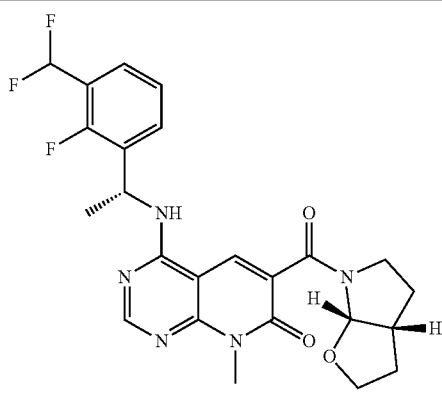 [SMILES: C[C@@H](Nc1ncnc2c1cc(C(=O)N1CC[C@@H]3CCO[C@@H]31)c(=O)n2C)c1cccc(C(F)F)c1F] |
| Example 26-18. | 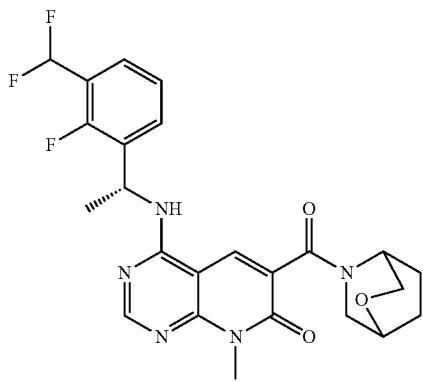 [SMILES: C[C@@H](Nc1ncnc2c1cc(C(=O)N1CC3CCC1CO3)c(=O)n2C)c1cccc(C(F)F)c1F] |
| Example 26-19. | 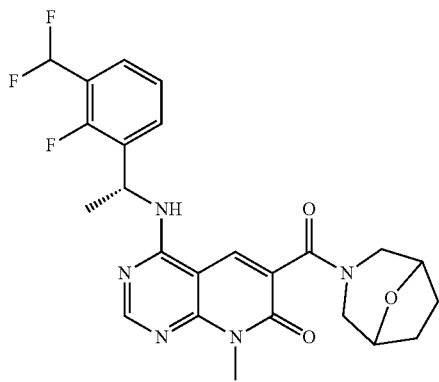 [SMILES: C[C@@H](Nc1ncnc2c1cc(C(=O)N1CC3CCC(C1)O3)c(=O)n2C)c1cccc(C(F)F)c1F] |
| Example 26-20. | 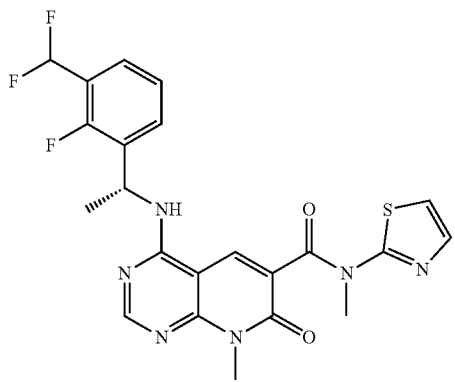 [SMILES: C[C@@H](Nc1ncnc2c1cc(C(=O)N(C)c1nccs1)c(=O)n2C)c1cccc(C(F)F)c1F] |

TABLE A-continued
| Example # | Structure |
|---|---|
| Example 26-21. | 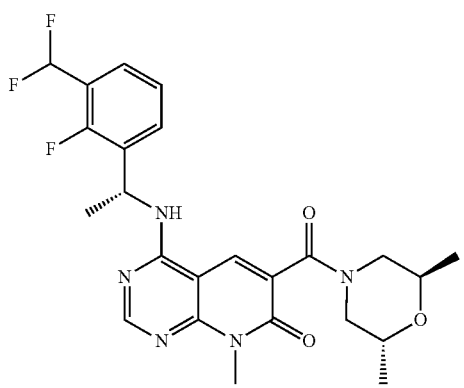 [SMILES: C[C@@H]1CN(C(=O)c2cc3c(N[C@H](C)c4cccc(C(F)F)c4F)ncnc3n(C)c2=O)C[C@@H](C)O1] |
| Example 26-22. | 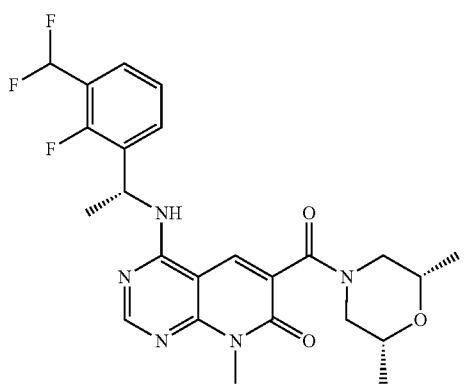 [SMILES: C[C@@H]1CN(C(=O)c2cc3c(N[C@H](C)c4cccc(C(F)F)c4F)ncnc3n(C)c2=O)C[C@H](C)O1] |
| Example 26-23. | 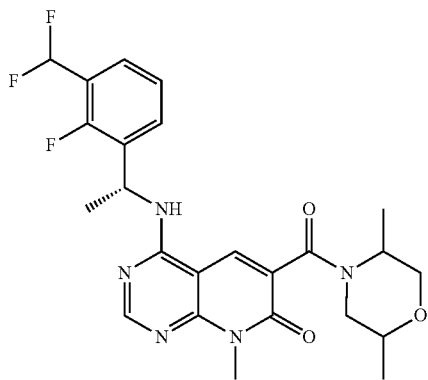 [SMILES: CC1CN(C(=O)c2cc3c(N[C@H](C)c4cccc(C(F)F)c4F)ncnc3n(C)c2=O)C(C)CO1] |
| Example 26-24. | 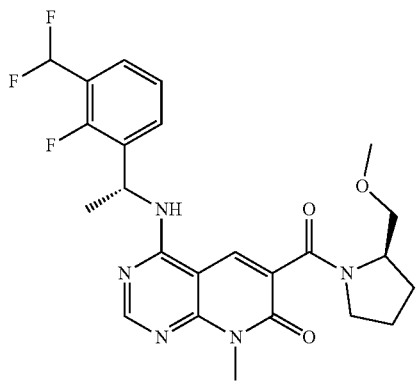 [SMILES: COC[C@H]1CCCN1C(=O)c1cc2c(N[C@H](C)c3cccc(C(F)F)c3F)ncnc2n(C)c1=O] |

TABLE A-continued

| Example # | Structure |
|---|---|
| Example 26-25. | 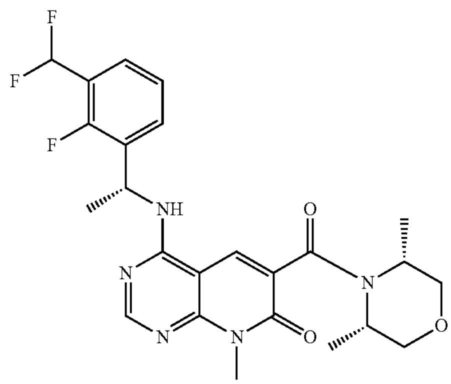 [SMILES: C[C@@H]1COC[C@H](C)N1C(=O)c1cc2c(N[C@H](C)c3cccc(C(F)F)c3F)ncnc2n(C)c1=O] |
| Example 26-26. | 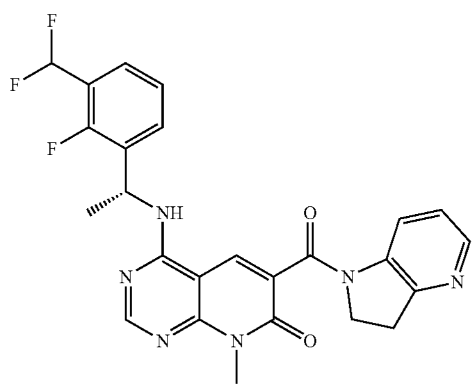 |
| Example 26-27. | 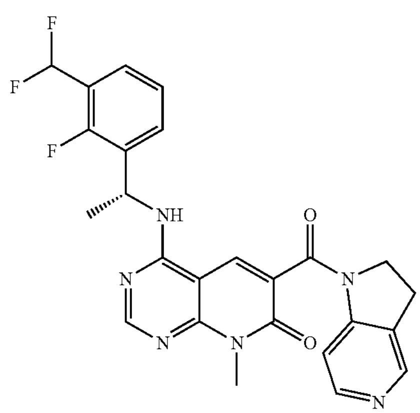 [SMILES: C[C@@H](Nc1ncnc2c1cc(C(=O)N1CCc3cnccc31)c(=O)n2C)c1cccc(C(F)F)c1F] |
| Example 26-28. | 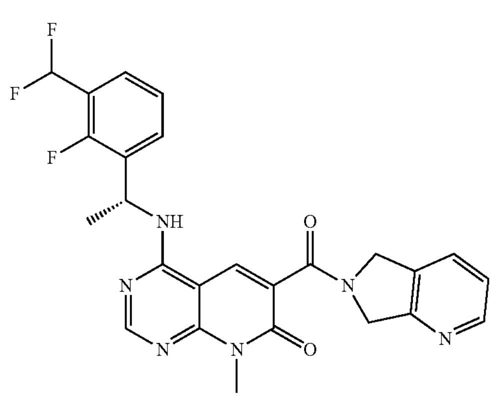 [SMILES: C[C@@H](Nc1ncnc2c1cc(C(=O)N1Cc3cccnc3C1)c(=O)n2C)c1cccc(C(F)F)c1F] |

TABLE A-continued
| Example # | Structure |
|---|---|
| Example 26-29. | 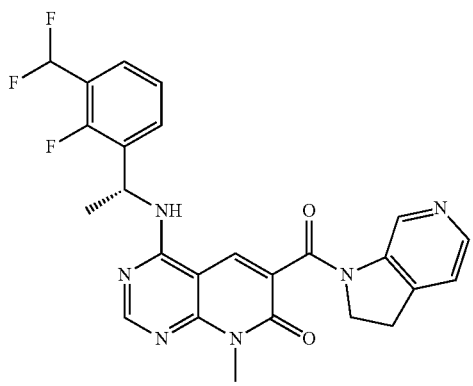 |
| Example 26-30. | 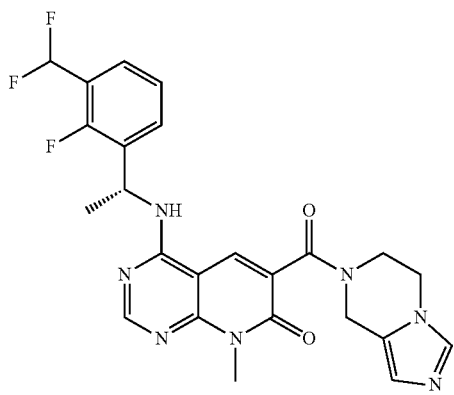 [SMILES: C[C@@H](Nc1ncnc2c1cc(C(=O)N1CCn3cncc3C1)c(=O)n2C)c1cccc(C(F)F)c1F] |
| Example 26-31. | 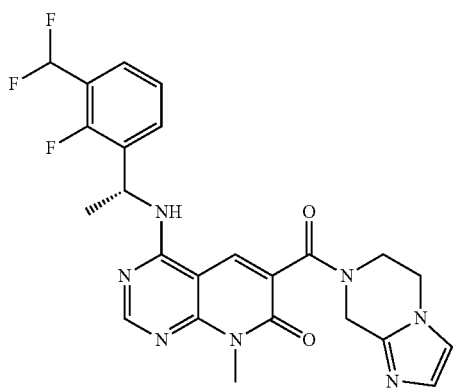 [SMILES: C[C@@H](Nc1ncnc2c1cc(C(=O)N1CCn3ccnc3C1)c(=O)n2C)c1cccc(C(F)F)c1F] |
| Example 26-32. | 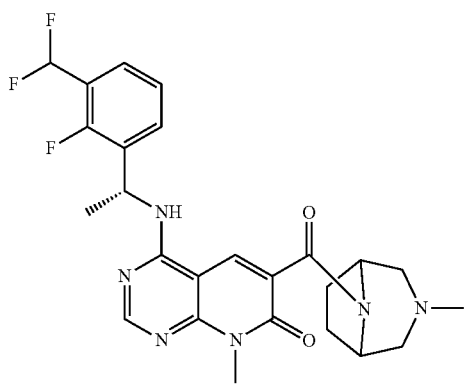 [SMILES: C[C@@H](Nc1ncnc2c1cc(C(=O)N1C3CCC1CN(C)C3)c(=O)n2C)c1cccc(C(F)F)c1F] |

TABLE A-continued
| Example # | Structure |
|---|---|
| Example 26-33. | 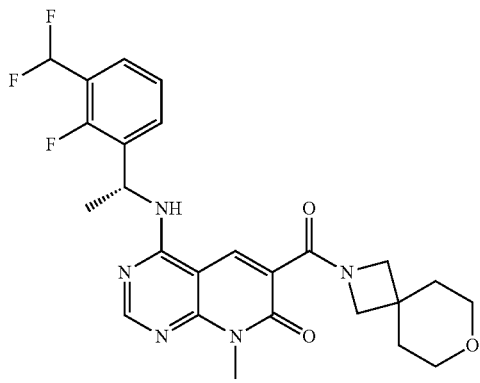 [SMILES: C[C@@H](Nc1ncnc2c1cc(C(=O)N1CC3(CCOCC3)C1)c(=O)n2C)c1cccc(C(F)F)c1F] |
| Example 26-34. | 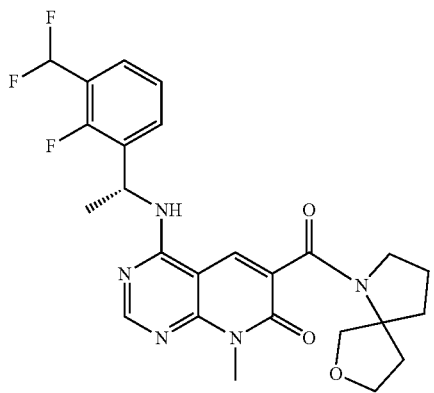 [SMILES: C[C@@H](Nc1ncnc2c1cc(C(=O)N1CCCC13CCOC3)c(=O)n2C)c1cccc(C(F)F)c1F] |
| Example 26-35. | 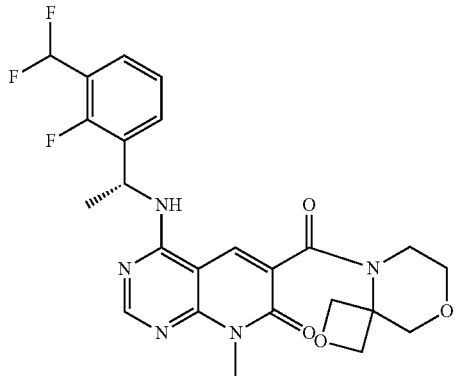 [SMILES: C[C@@H](Nc1ncnc2c1cc(C(=O)N1CCOCC13COC3)c(=O)n2C)c1cccc(C(F)F)c1F] |
| Example 26-36. | 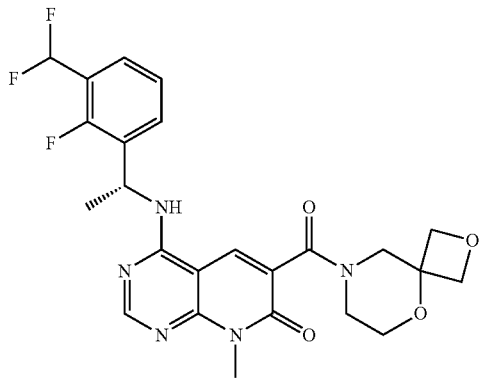 [SMILES: C[C@@H](Nc1ncnc2c1cc(C(=O)N1CCOC3(COC3)C1)c(=O)n2C)c1cccc(C(F)F)c1F] |

TABLE A-continued
| Example # | Structure |
|---|---|
| Example 26-37. | 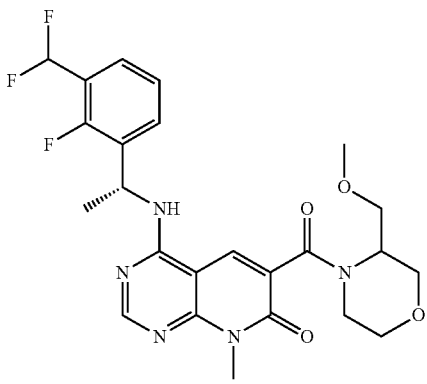 [SMILES: COCC1COCCN1C(=O)c1cc2c(N[C@H](C)c3cccc(C(F)F)c3F)ncnc2n(C)c1=O] |
| Example 26-38. | 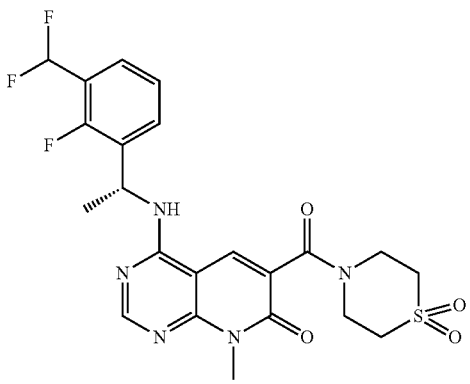 [SMILES: C[C@@H](Nc1ncnc2c1cc(C(=O)N1CCS(=O)(=O)CC1)c(=O)n2C)c1cccc(C(F)F)c1F] |
| Example 26-39. | 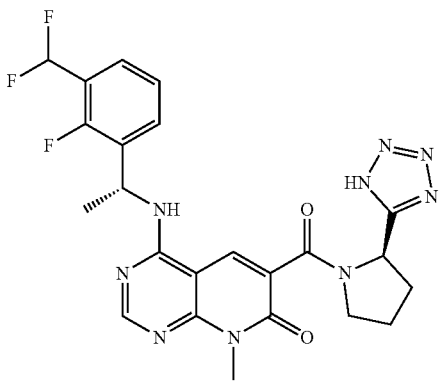 [SMILES: C[C@@H](Nc1ncnc2c1cc(C(=O)N1CCC[C@@H]1c1nnn[nH]1)c(=O)n2C)c1cccc(C(F)F)c1F] |
| Example 26-40. | 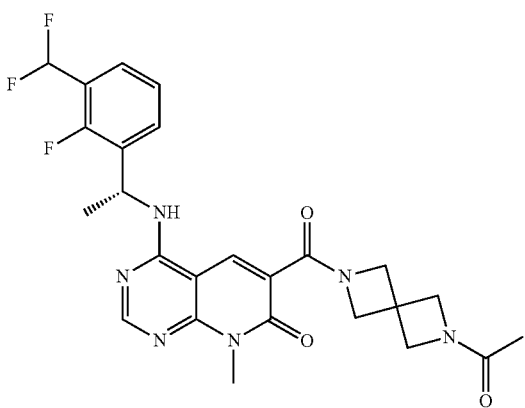 [SMILES: CC(=O)N1CC2(C1)CN(C(=O)c1cc3c(N[C@H](C)c4cccc(C(F)F)c4F)ncnc3n(C)c1=O)C2] |

TABLE A-continued
| Example # | Structure |
|---|---|
| Example 26-41. | 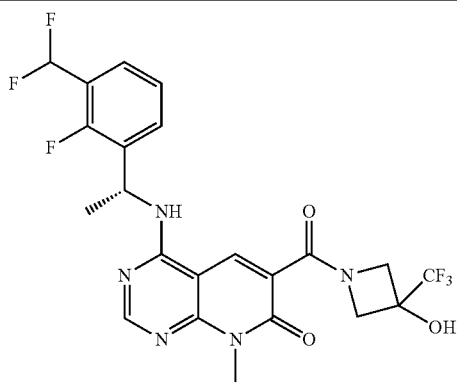 |
| Example 26-42. | 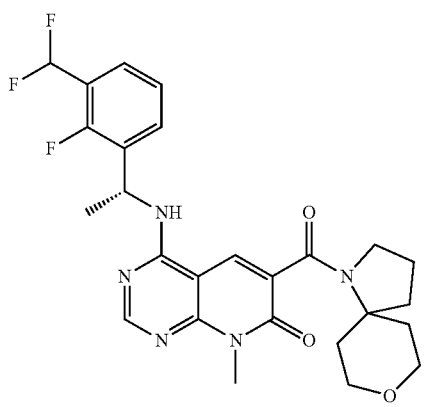 [SMILES: C[C@@H](Nc1ncnc2c1cc(C(=O)N1CCCC13CCOCC3)c(=O)n2C)c1cccc(C(F)F)c1F] |
| Example 26-43. | 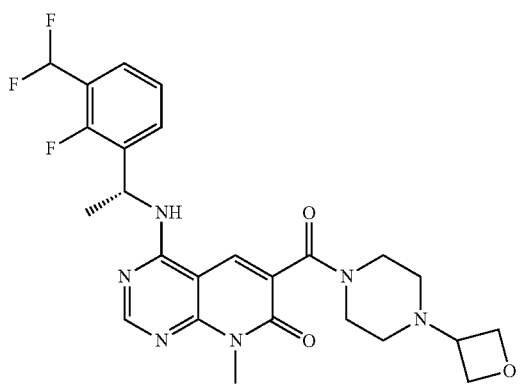 [SMILES: C[C@@H](Nc1ncnc2c1cc(C(=O)N1CCN(C3COC3)CC1)c(=O)n2C)c1cccc(C(F)F)c1F] |
| Example 26-44. | 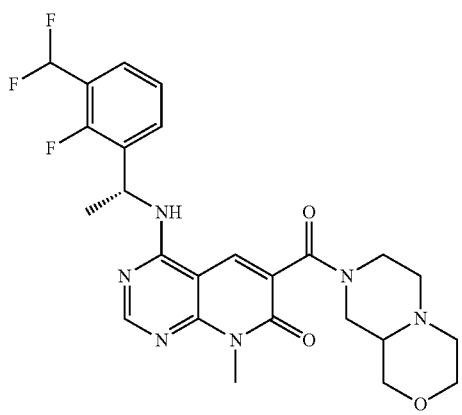 [SMILES: C[C@@H](Nc1ncnc2c1cc(C(=O)N1CCN3CCOCC3C1)c(=O)n2C)c1cccc(C(F)F)c1F] |

TABLE A-continued
| Example # | Structure |
|---|---|
| Example 26-45. | 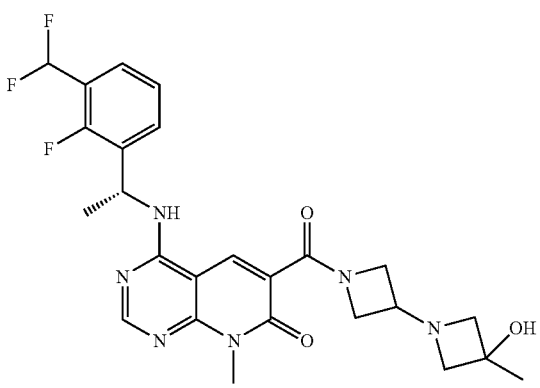 [SMILES: C[C@@H](Nc1ncnc2c1cc(C(=O)N1CC(N3CC(C)(O)C3)C1)c(=O)n2C)c1cccc(C(F)F)c1F] |
| Example 26-46. | 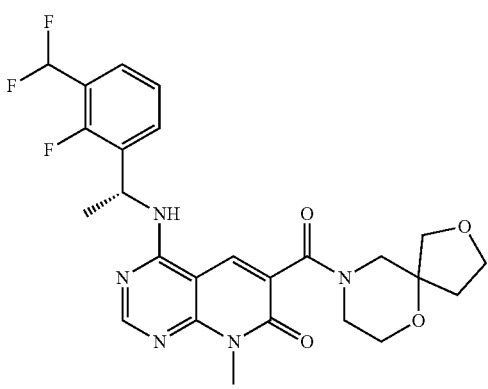 [SMILES: C[C@@H](Nc1ncnc2c1cc(C(=O)N1CCOC3(CCOC3)C1)c(=O)n2C)c1cccc(C(F)F)c1F] |
| Example 26-47. | 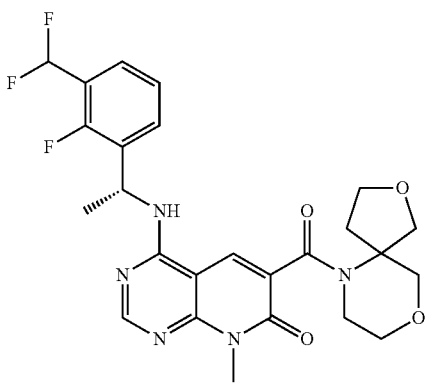 [SMILES: C[C@@H](Nc1ncnc2c1cc(C(=O)N1CCOCC13CCOC3)c(=O)n2C)c1cccc(C(F)F)c1F] |
| Example 26-48. | 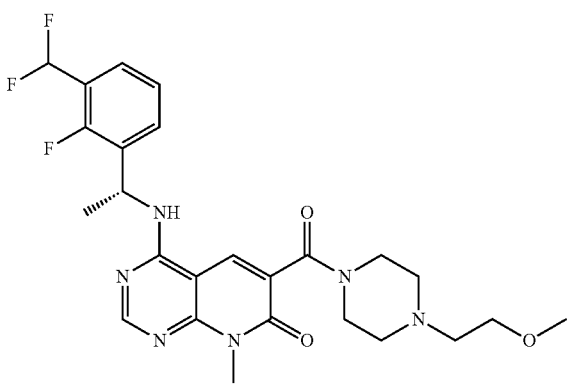 [SMILES: COCCN1CCN(C(=O)c2cc3c(N[C@H](C)c4cccc(C(F)F)c4F)ncnc3n(C)c2=O)CC1] |

TABLE A-continued
| Example # | Structure |
|---|---|
| Example 26-49. | 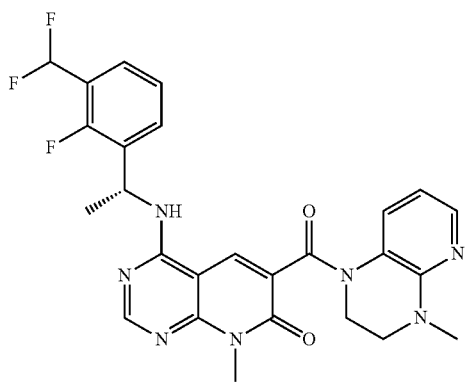 [SMILES: C[C@@H](Nc1ncnc2c1cc(C(=O)N1CCN(C)c3ncccc31)c(=O)n2C)c1cccc(C(F)F)c1F] |
| Example 26-50. | 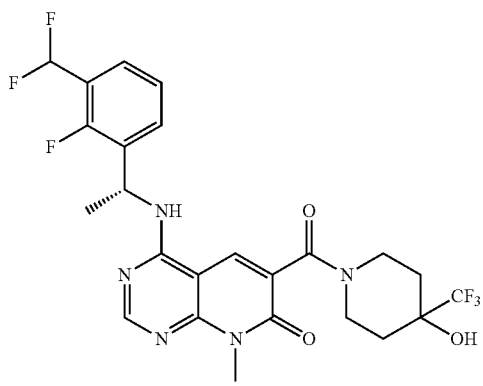 [SMILES: C[C@@H](Nc1ncnc2c1cc(C(=O)N1CCC(O)(C(F)(F)F)CC1)c(=O)n2C)c1cccc(C(F)F)c1F] |
| Example 26-51. | 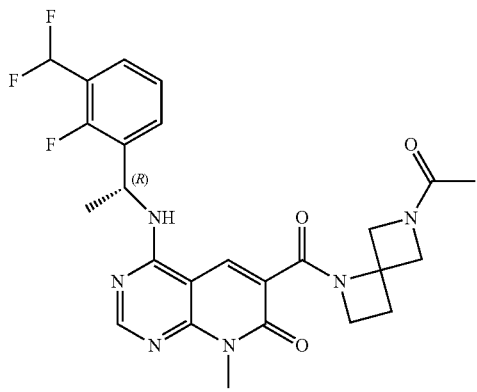 |
| Example 26-52. | 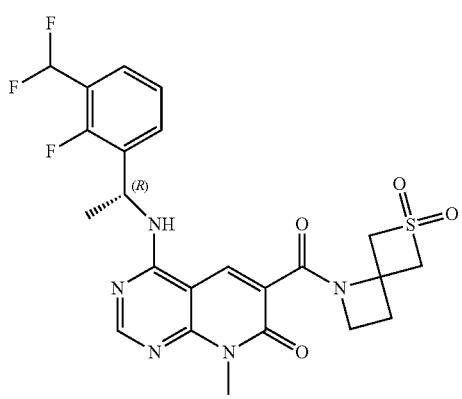 |

TABLE A-continued
| Example # | Structure |
|---|---|
| Example 27. | 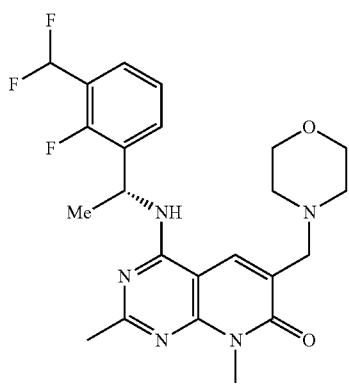 [SMILES: Cc1nc(N[C@H](C)c2cccc(C(F)F)c2F)c2cc(CN3CCOCC3)c(=O)n(C)c2n1] |
| Example 28. | 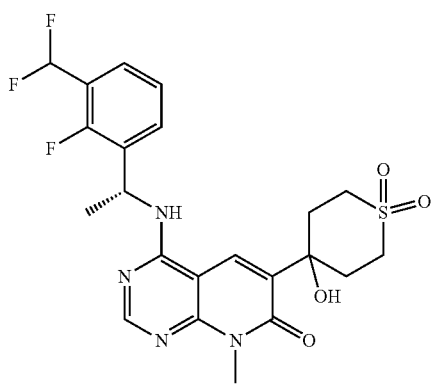 |
| Example 28-1. | 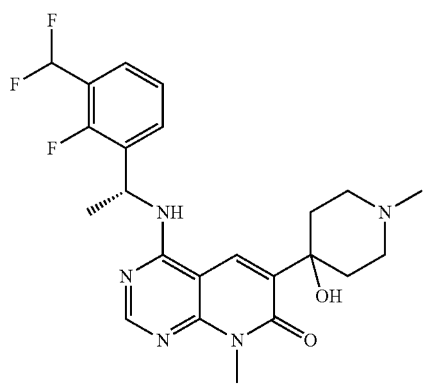 [SMILES: C[C@@H](Nc1ncnc2c1cc(C1(O)CCN(C)CC1)c(=O)n2C)c1cccc(C(F)F)c1F] |
| Example 28-2. | 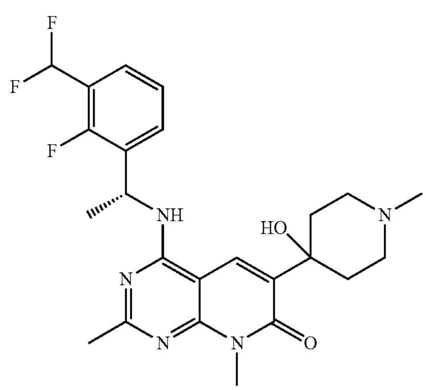 [SMILES: Cc1nc(N[C@H](C)c2cccc(C(F)F)c2F)c2cc(C3(O)CCN(C)CC3)c(=O)n(C)c2n1] |

TABLE A-continued
| Example # | Structure |
|---|---|
| Example 28-3. | 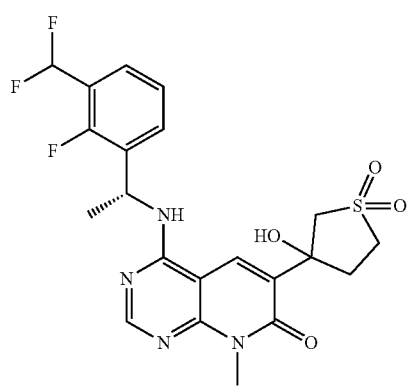 [SMILES: C[C@@H](Nc1ncnc2c1cc(C1(O)CCS(=O)(=O)C1)c(=O)n2C)c1cccc(C(F)F)c1F] |
| Example 28-4. | 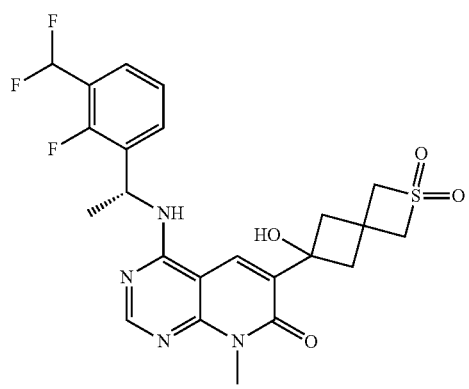 [SMILES: C[C@@H](Nc1ncnc2c1cc(C1(O)CC3(C1)CS(=O)(=O)C3)c(=O)n2C)c1cccc(C(F)F)c1F] |
| Example 28-5. | 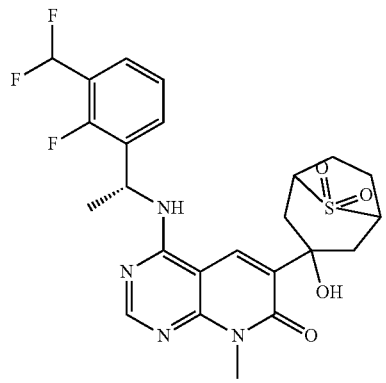 [SMILES: C[C@@H](Nc1ncnc2c1cc(C1(O)CC3CCC(C1)S3(=O)=O)c(=O)n2C)c1cccc(C(F)F)c1F] |
| Example 28-6. | 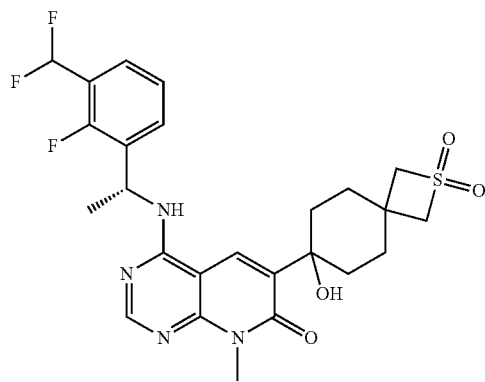 [SMILES: C[C@@H](Nc1ncnc2c1cc(C1(O)CCC3(CC1)CS(=O)(=O)C3)c(=O)n2C)c1cccc(C(F)F)c1F] |

TABLE A-continued
| Example # | Structure |
|---|---|
| Example 28-7. | 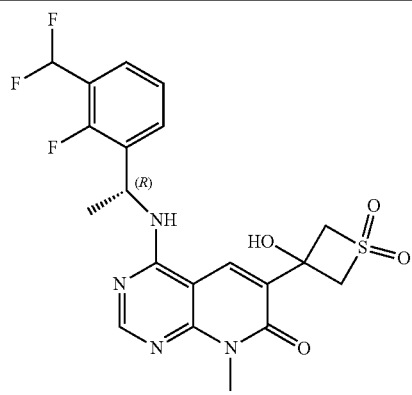 |
| Example 28-8. | 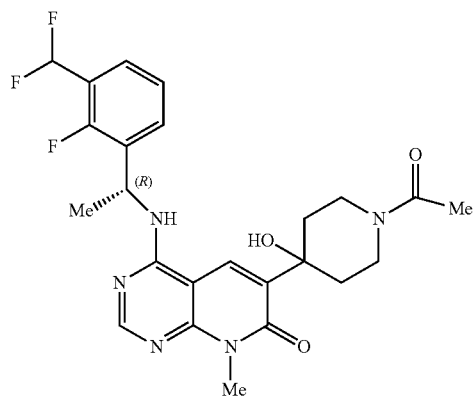 |
| Example 28-9. | 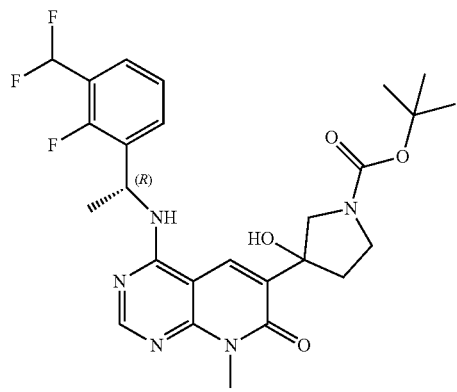 |
| Example 29. | 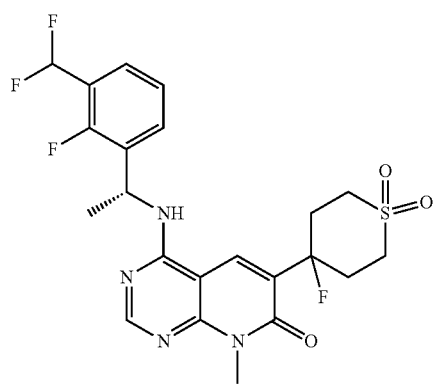 [SMILES: C[C@@H](Nc1ncnc2c1cc(C1(F)CCS(=O)(=O)CC1)c(=O)n2C)c1cccc(C(F)F)c1F] |

TABLE A-continued
| Example # | Structure |
|---|---|
| Example 29-1. | 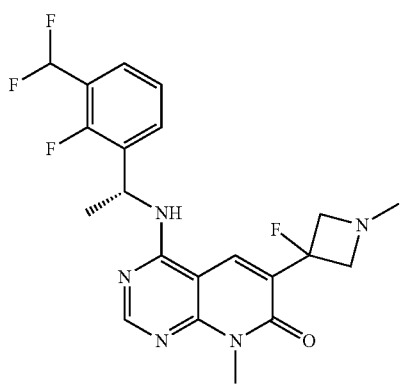 [SMILES: C[C@@H](Nc1ncnc2c1cc(C1(F)CN(C)C1)c(=O)n2C)c1cccc(C(F)F)c1F] |
| Example 29-2. | 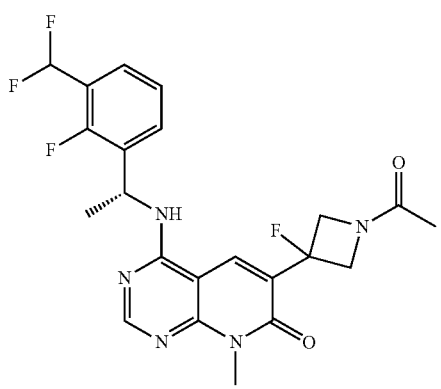 [SMILES: CC(=O)N1CC(F)(c2cc3c(N[C@H](C)c4cccc(C(F)F)c4F)ncnc3n(C)c2=O)C1] |
| Example 29-3. | 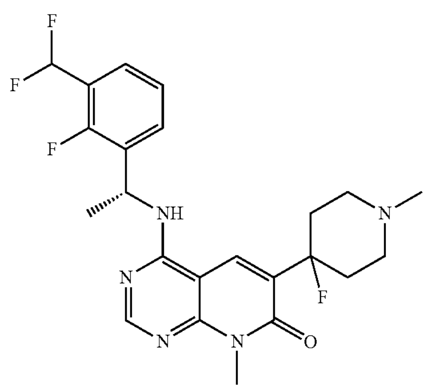 [SMILES: C[C@@H](Nc1ncnc2c1cc(C1(F)CCN(C)CC1)c(=O)n2C)c1cccc(C(F)F)c1F] |
| Example 29-4. | 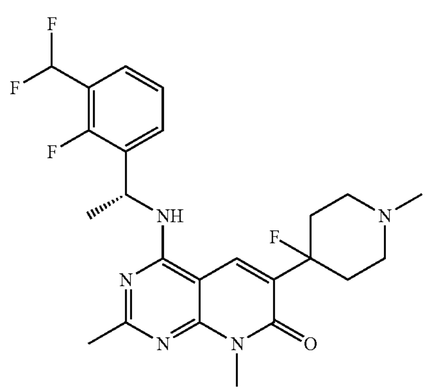 [SMILES: Cc1nc(N[C@H](C)c2cccc(C(F)F)c2F)c2cc(C3(F)CCN(C)CC3)c(=O)n(C)c2n1] |

TABLE A-continued
| Example # | Structure |
|---|---|
| Example 29-5. | 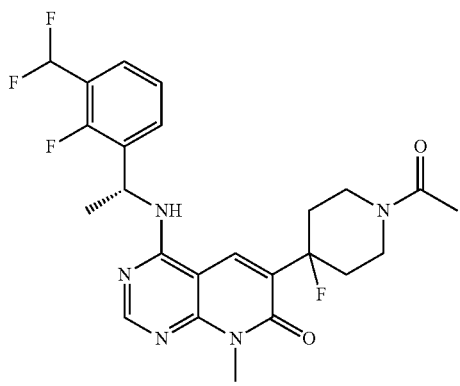 |
| Example 29-6. | 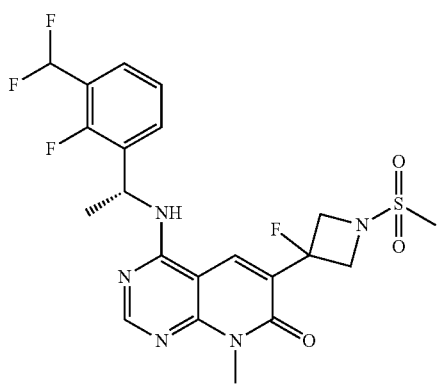 [SMILES: C[C@@H](Nc1ncnc2c1cc(C1(F)CN(S(C)(=O)=O)C1)c(=O)n2C)c1cccc(C(F)F)c1F] |
| Example 29-7. | 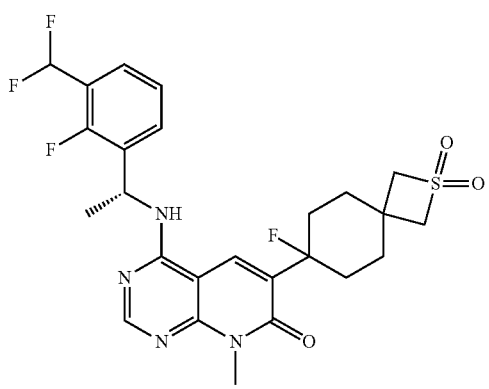 [SMILES: C[C@@H](Nc1ncnc2c1cc(C1(F)CCC3(CC1)CS(=O)(=O)C3)c(=O)n2C)c1cccc(C(F)F)c1F] |
| Example 29-8. | 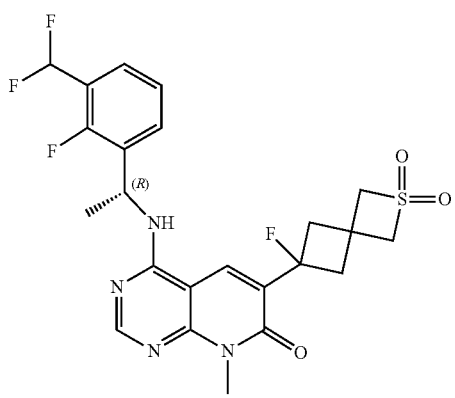 |

TABLE A-continued
| Example # | Structure |
|---|---|
| Example 29-9. | 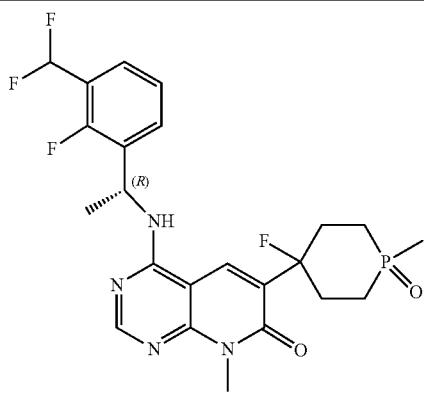 |
| Example 29-10. | 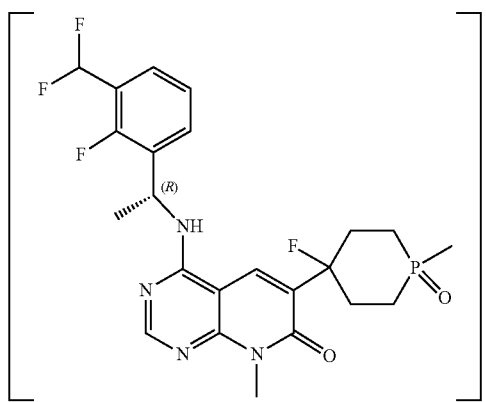 |
| Example 29-11. | 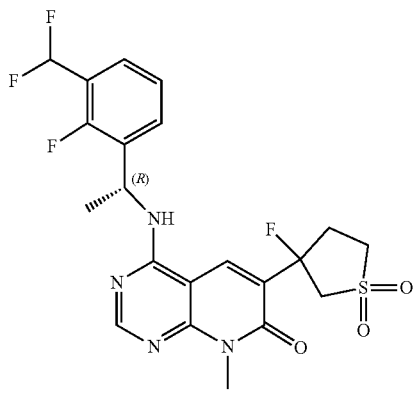 |
| Example 29-12. | 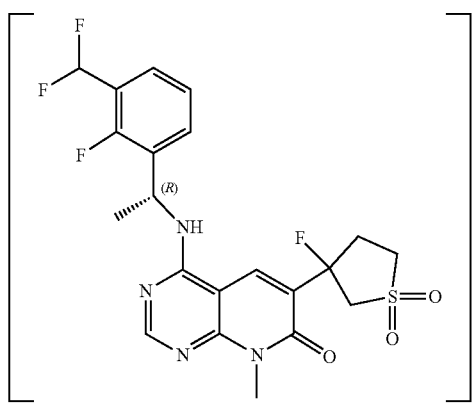 |

TABLE A-continued
| Example # | Structure |
|---|---|
| Example 29-13. | 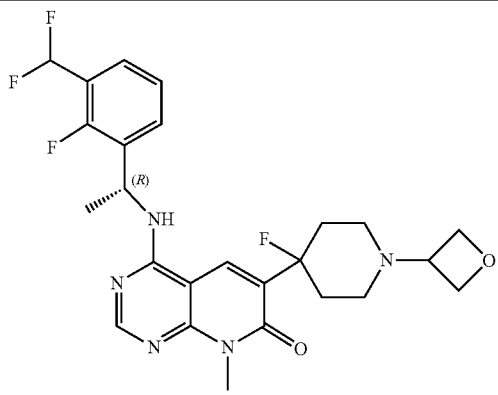 |
| Example 29-14. | 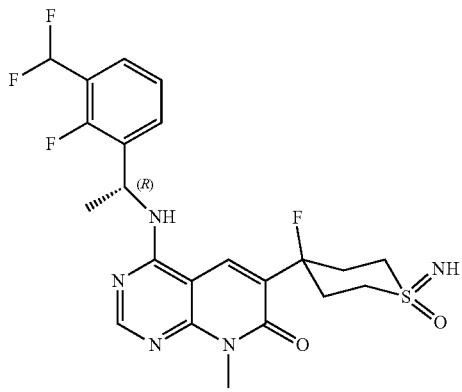 |
| Example 29-15. | 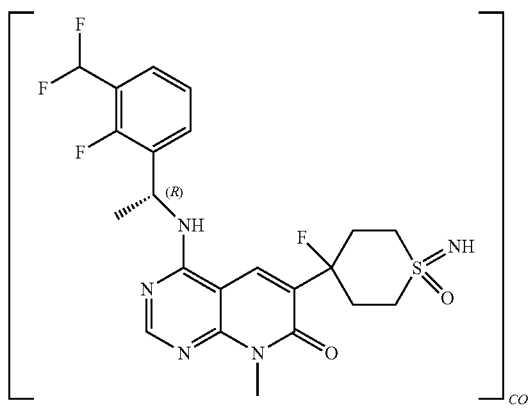 |
| Example 30. | 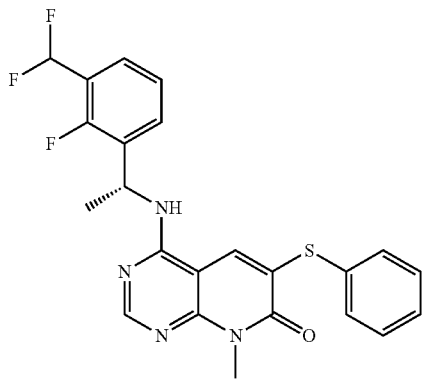 [SMILES: C[C@@H](Nc1ncnc2c1cc(Sc1ccccc1)c(=O)n2C)c1cccc(C(F)F)c1F] |

TABLE A-continued
| Example # | Structure |
|---|---|
| Example 31. | 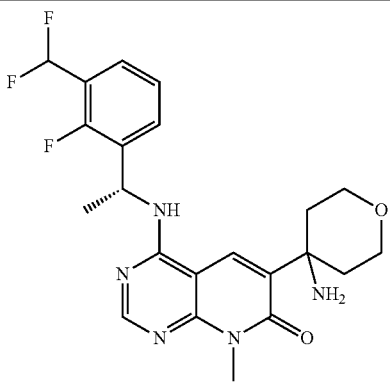 |
| Example 31-1. | 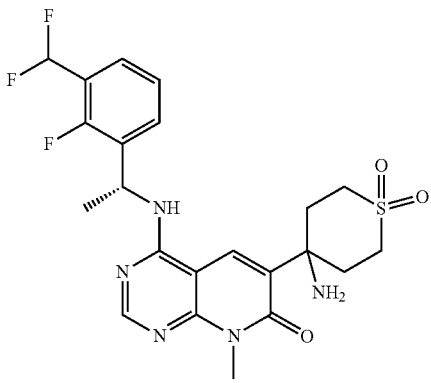 [SMILES: C[C@@H](Nc1ncnc2c1cc(C1(N)CCS(=O)(=O)CC1)c(=O)n2C)c1cccc(C(F)F)c1F] |
| Example 31-2. | 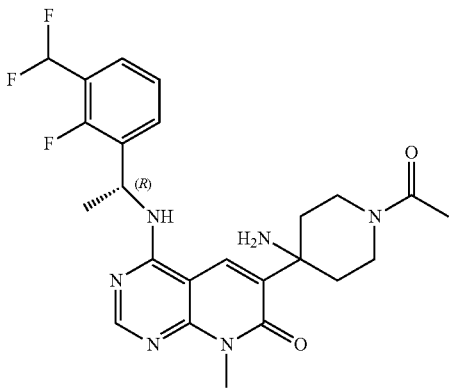 |
| Example 31-3. | 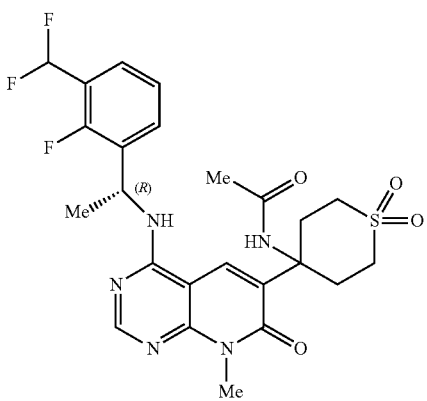 |

TABLE A-continued

| Example # | Structure |
|---|---|
| Example 31-4. | 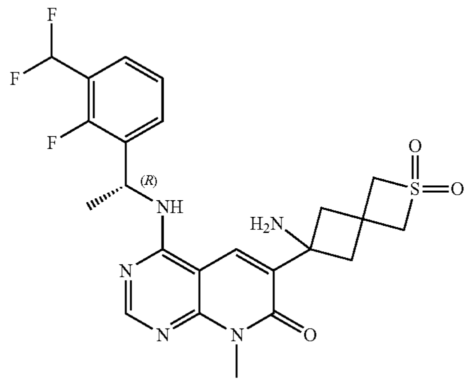 |
| Example 31-5. | 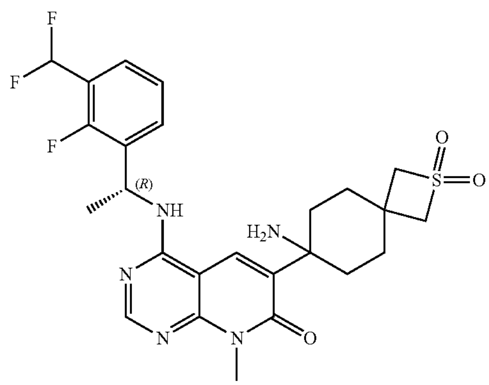 |
| Example 31-6. | 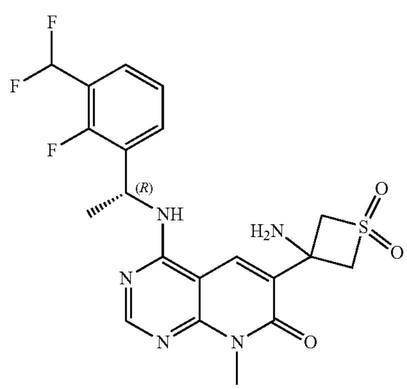 |
| Example 31-7. | 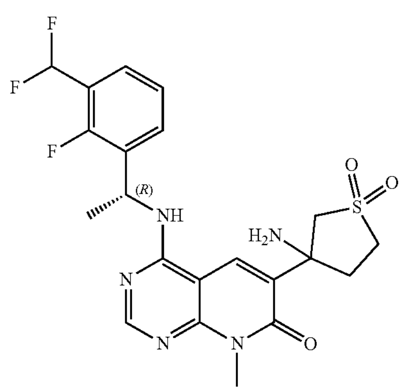 |

TABLE A-continued
| Example # | Structure |
|---|---|
| Example 31-8. | 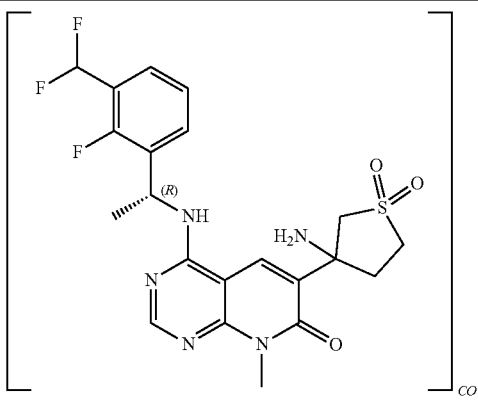 |
| Example 31-9. | 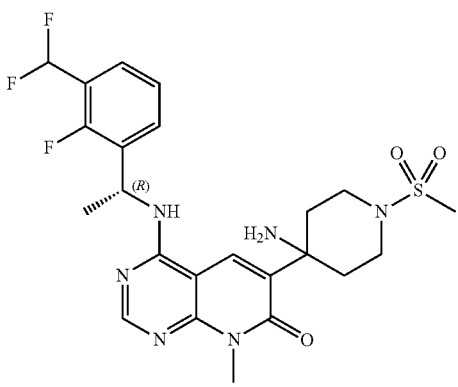 |
| Example 31-10. | 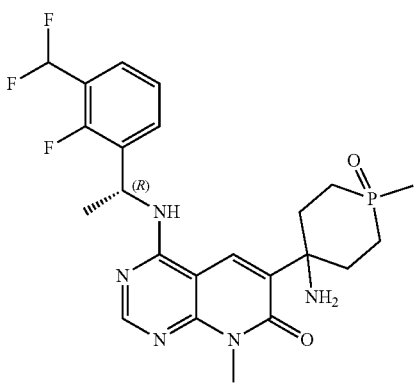 |
| Example 31-11. | 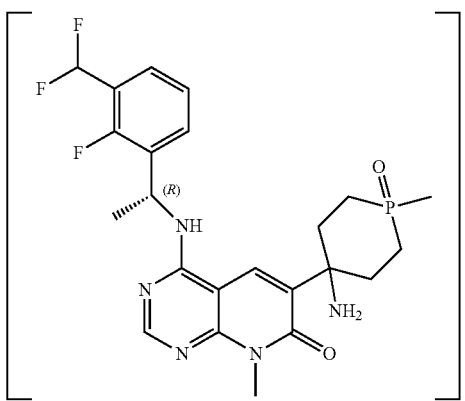 |

TABLE A-continued
| Example # | Structure |
|---|---|
| Example 32. | 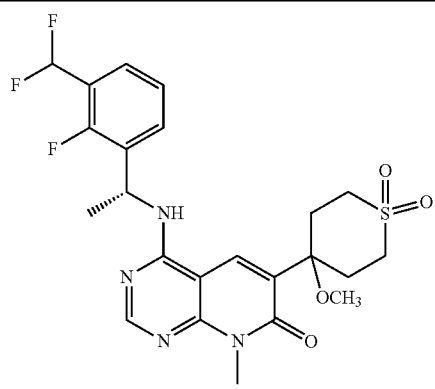 |
| Example 32-1. | 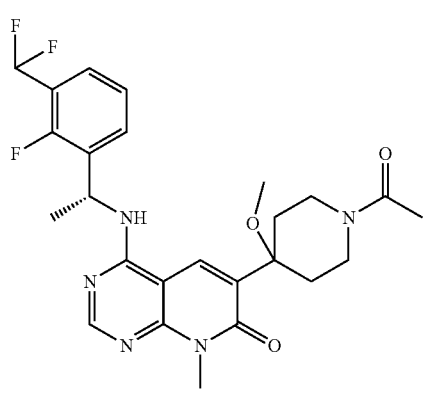 [SMILES: COC1(c2cc3c(N[C@H](C)c4cccc(C(F)F)c4F)ncnc3n(C)c2=O)CCN(C(C)=O)CC1] |
| Example 32-2. | 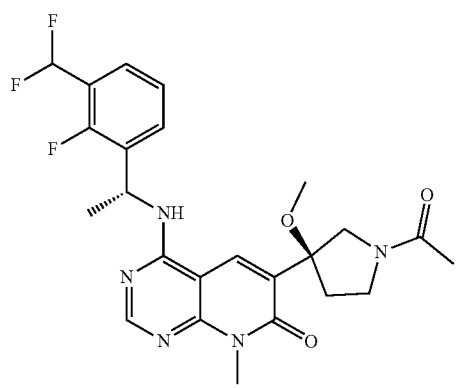 [SMILES: CO[C@]1(c2cc3c(N[C@H](C)c4cccc(C(F)F)c4F)ncnc3n(C)c2=O)CCN(C(C)=O)C1] |
| Example 32-3. | 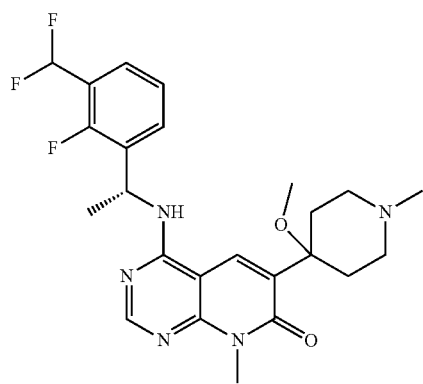 [SMILES: COC1(c2cc3c(N[C@H](C)c4cccc(C(F)F)c4F)ncnc3n(C)c2=O)CCN(C)CC1] |

TABLE A-continued
| Example # | Structure |
|---|---|
| Example 32-4. | 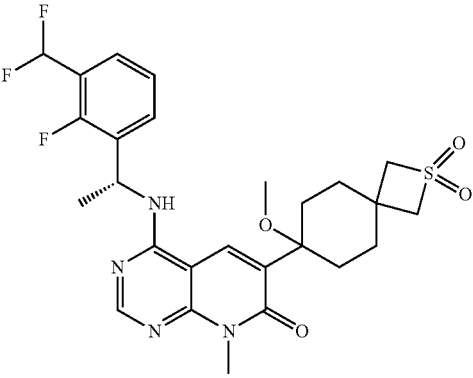 [SMILES: COC1(c2cc3c(N[C@H](C)c4cccc(C(F)F)c4F)ncnc3n(C)c2=O)CCC2(CC1)CS(=O)(=O)C2] |
| Example 32-5. | 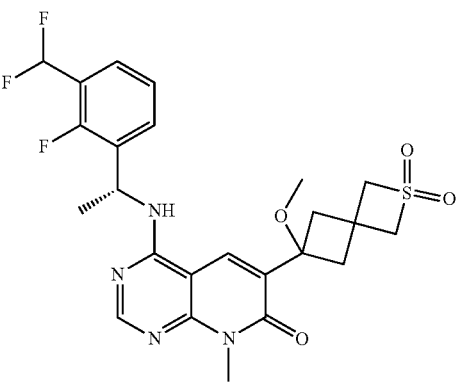 [SMILES: COC1(c2cc3c(N[C@H](C)c4cccc(C(F)F)c4F)ncnc3n(C)c2=O)CC2(C1)CS(=O)(=O)C2] |
| Example 32-6. | 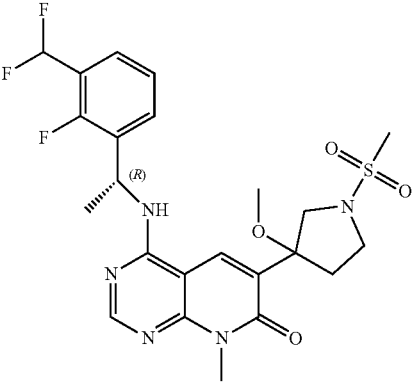 |
| Example 32-7. | 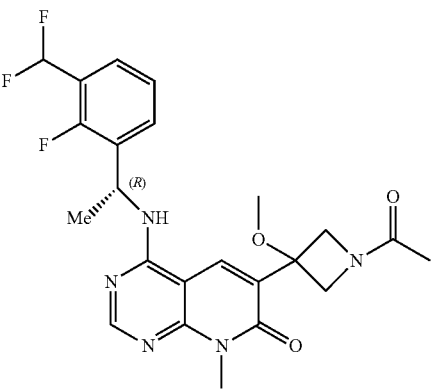 |

TABLE A-continued
| Example # | Structure |
|---|---|
| Example 32-8. | 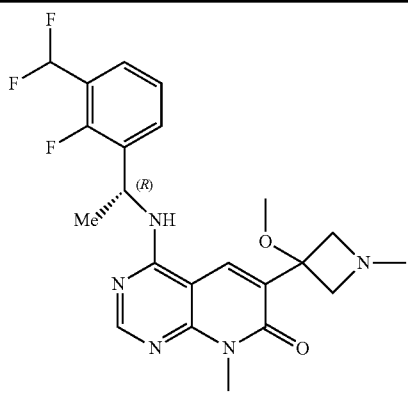 |
| Example 32-9. | 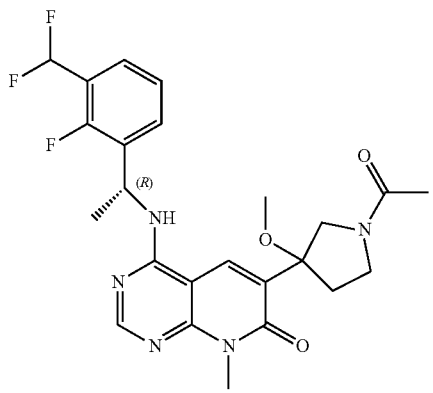 |
| Example 32-10. | 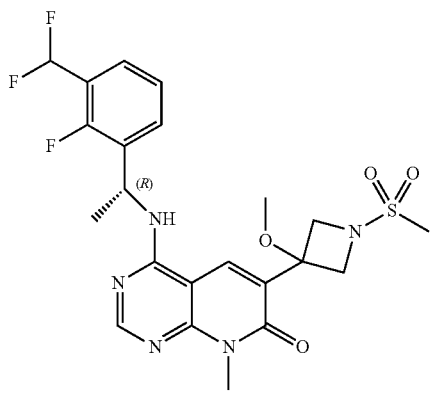 |
| Example 32-11. | 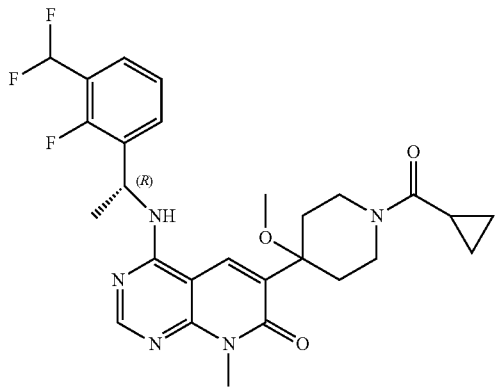 |

TABLE A-continued
| Example # | Structure |
|---|---|
| Example 32-12. | 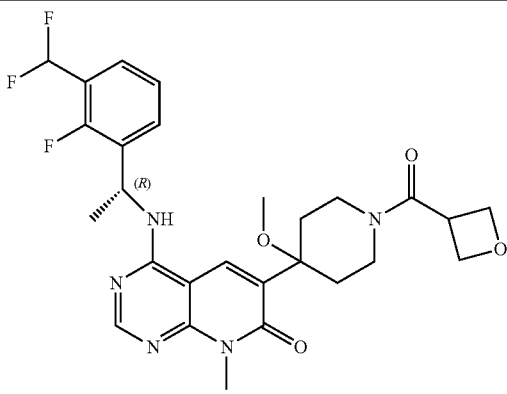 |
| Example 32-13. | 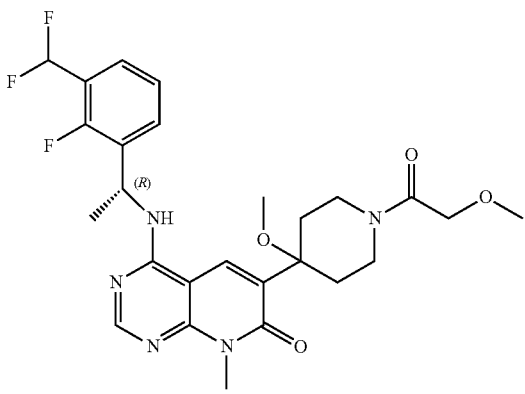 |
| Example 32-14. | 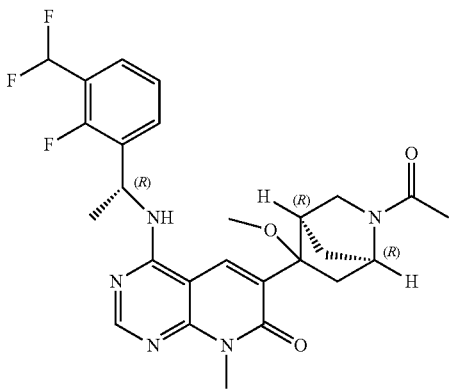 |
| Example 32-15. | 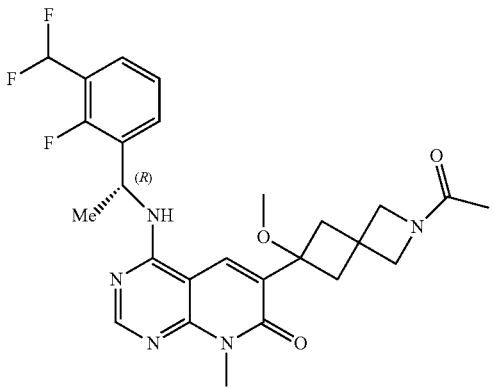 |

TABLE A-continued
| Example # | Structure |
|---|---|
| Example 32-16. | 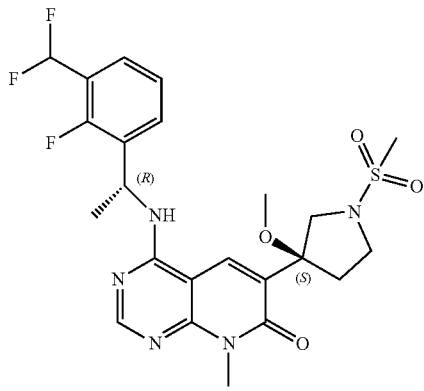 |
| Example 32-17. | 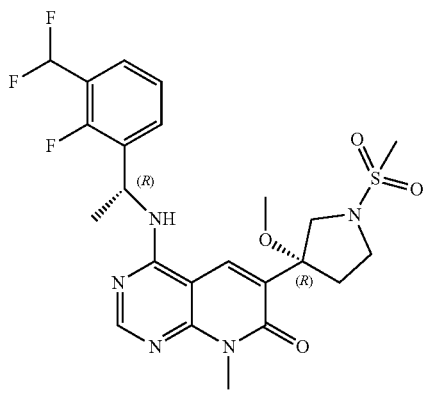 |
| Example 32-18. | 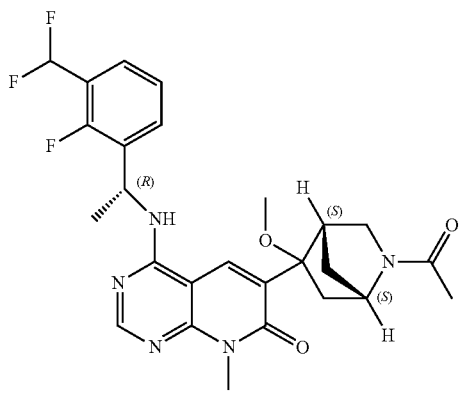 |
| Example 32-19. | 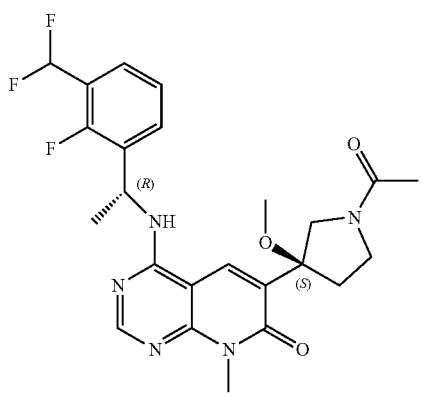 |

TABLE A-continued
| Example # | Structure |
|---|---|
| Example 32-20. | 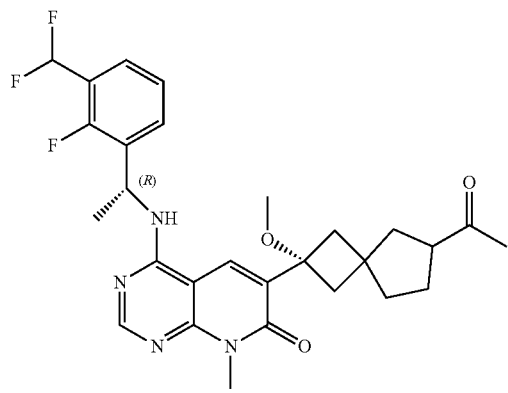 |
| Example 32-21. | 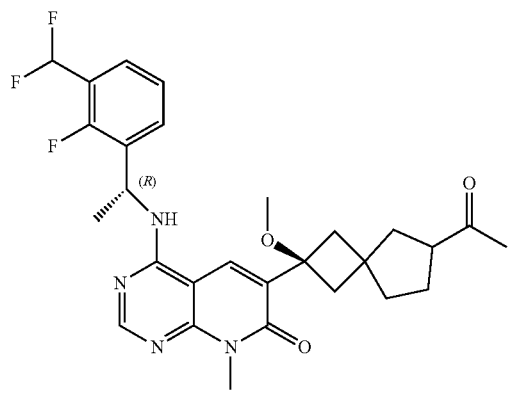 |
| Example 32-22. | 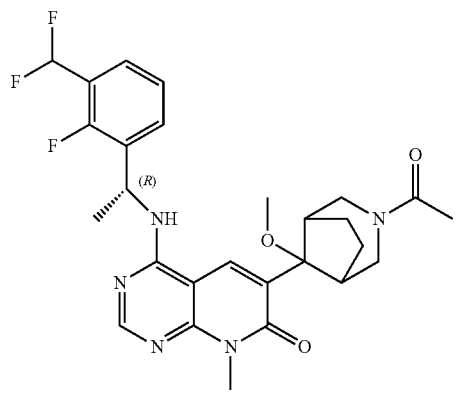 |
| Example 32-23. | 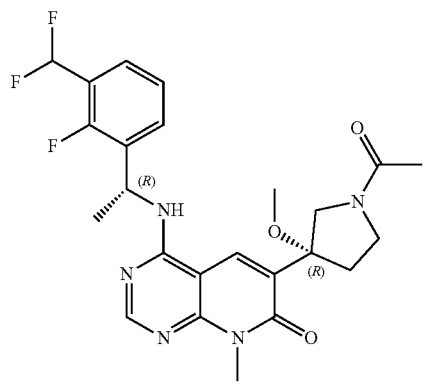 |

TABLE A-continued
| Example # | Structure |
|---|---|
| Example 32-24. | 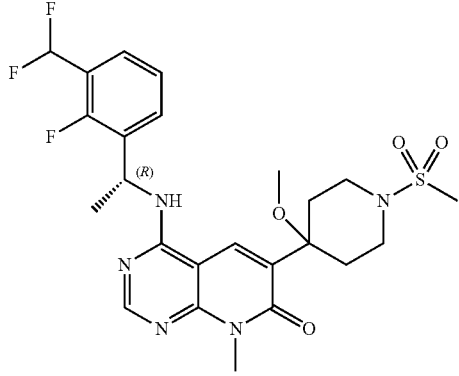 |
| Example 32-25. | 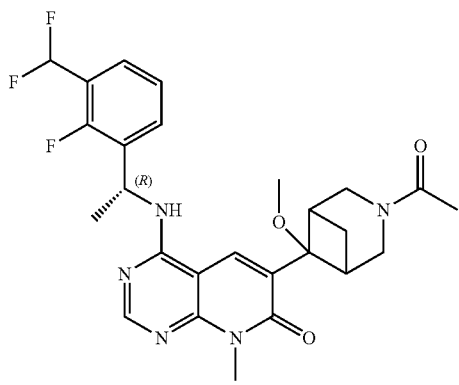 |
| Example 32-26. | 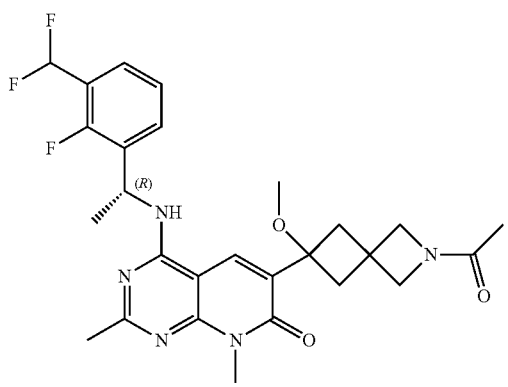 |
| Example 32-27. | 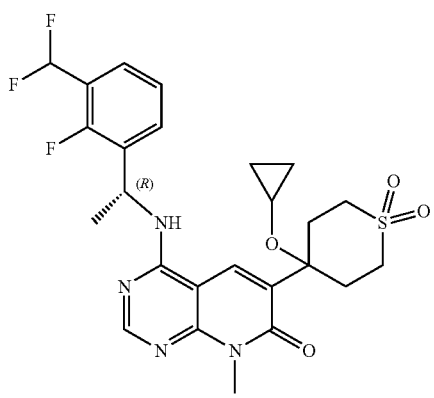 |

| Example # | Structure |
|---|---|
| Example 32-28. | 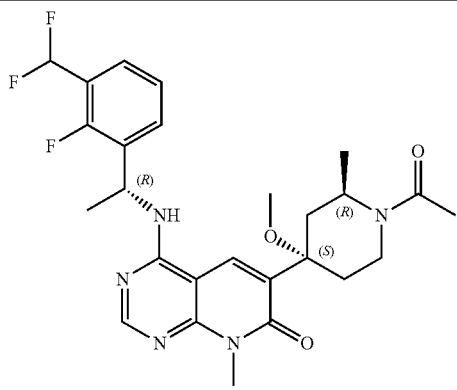 |
| Example 32-29. | 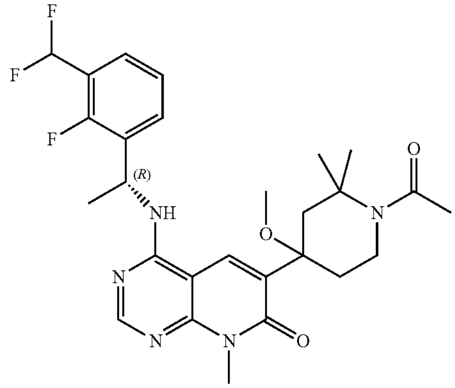 |
| Example 32-30. | 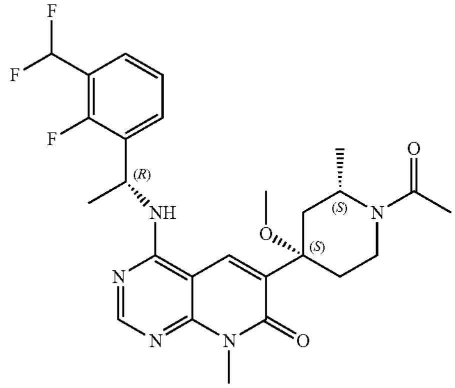 |
| Example 32-31. | 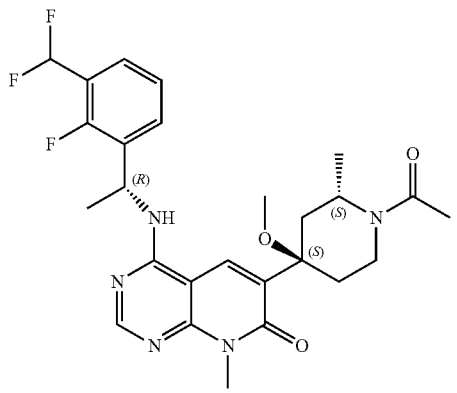 |

TABLE A-continued
| Example # | Structure |
|---|---|
| Example 32-32. | 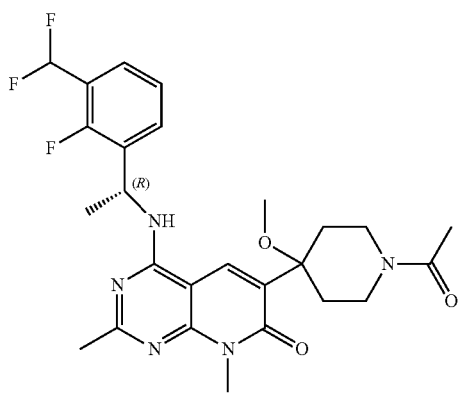 |
| Example 32-33. | 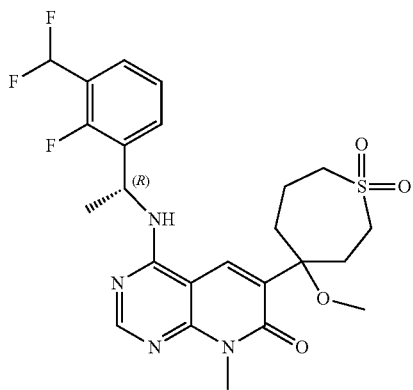 |
| Example 32-34. | 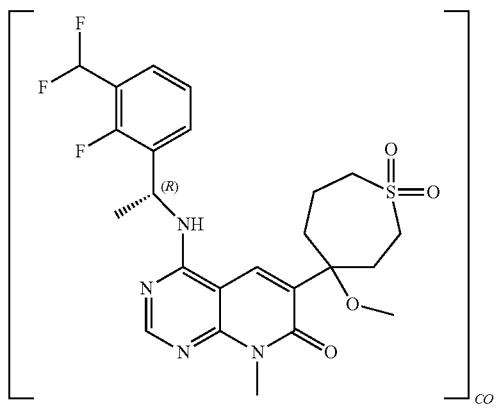 |
| Example 32-35. | 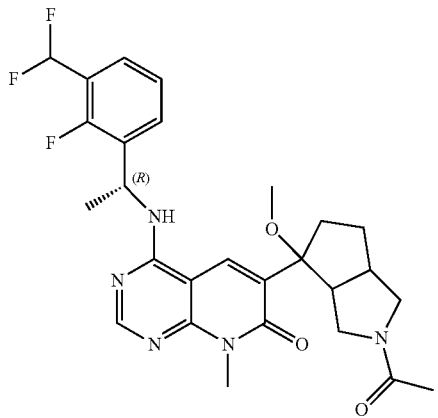 |

TABLE A-continued
| Example # | Structure |
|---|---|
| Example 32-36. | 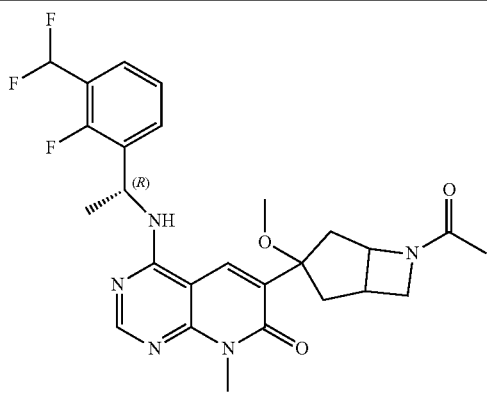 |
| Example 32-37. | 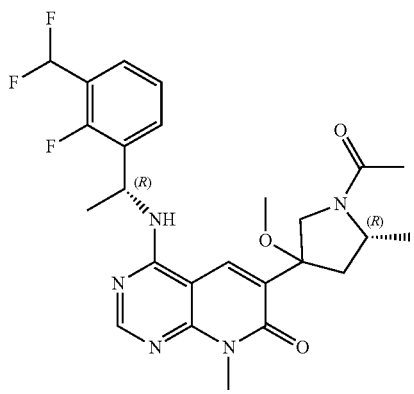 |
| Example 32-38. | 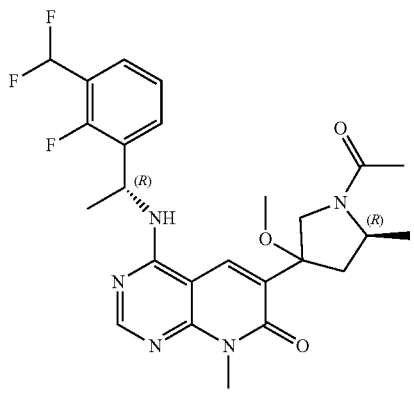 |
| Example 32-39. | 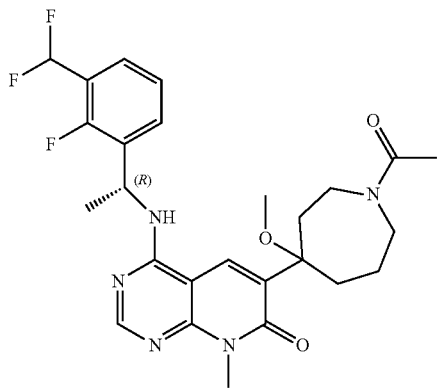 |

TABLE A-continued
| Example # | Structure |
|---|---|
| Example 32-40. | 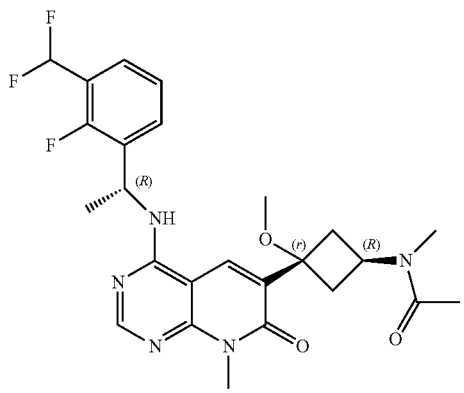 |
| Example 32-41. | 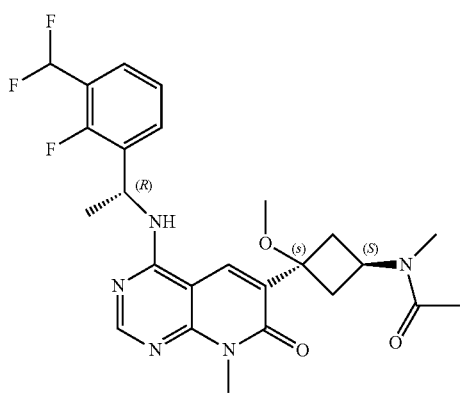 |
| Example 32-42. | 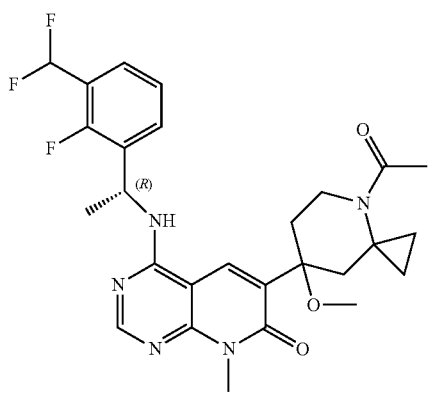 |
| Example 32-43. | 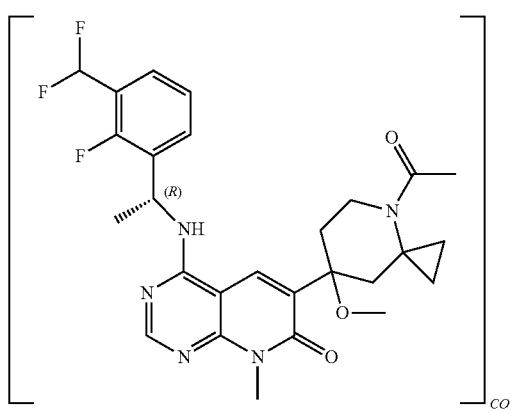 |

TABLE A-continued
| Example # | Structure |
|---|---|
| Example 32-44. | 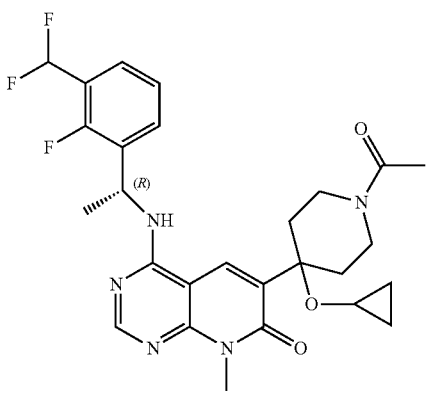 |
| Example 32-45. | 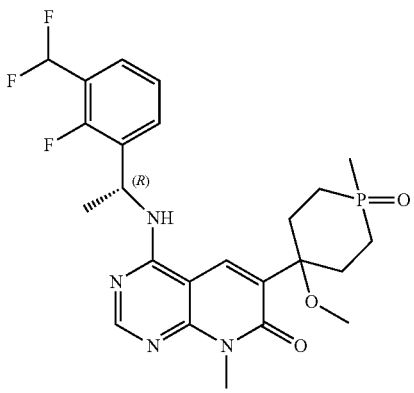 |
| Example 32-46. | 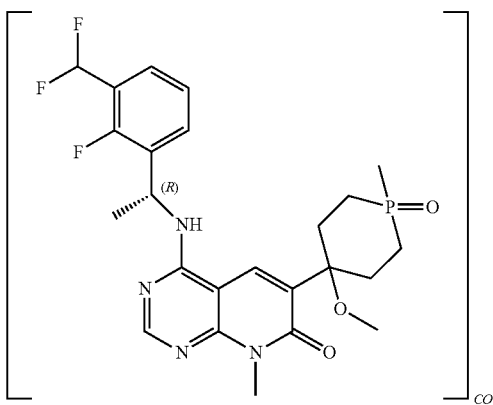 |
| Example 32-47. | 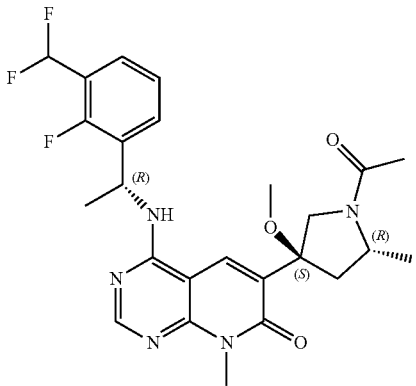 |

TABLE A-continued
| Example # | Structure |
|---|---|
| Example 32-48. | 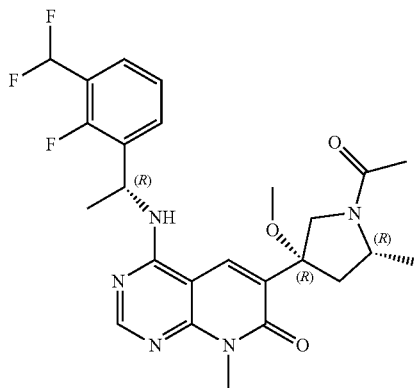 |
| Example 32-49. | 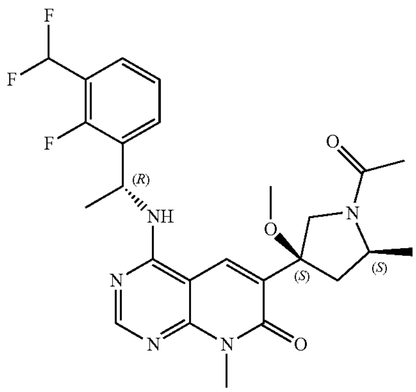 |
| Example 32-50. | 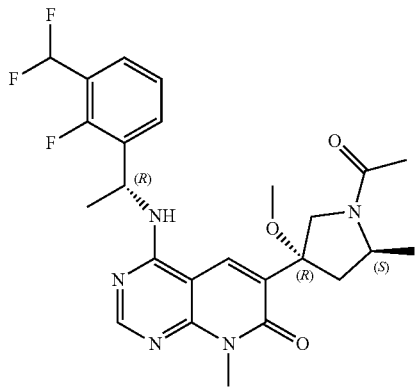 |
| Example 32-51. | 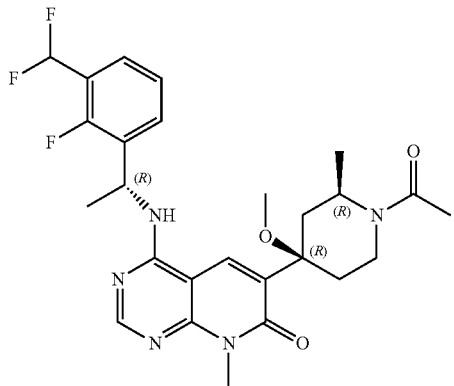 |

TABLE A-continued
| Example # | Structure |
|---|---|
| Example 32-52. | 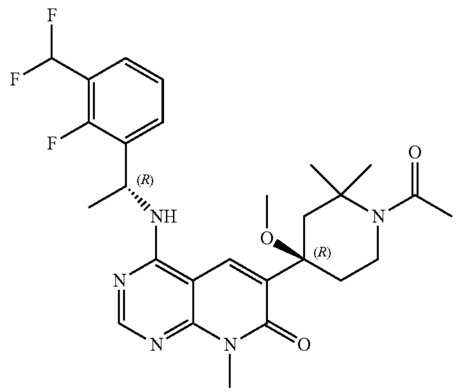 |
| Example 32-53. | 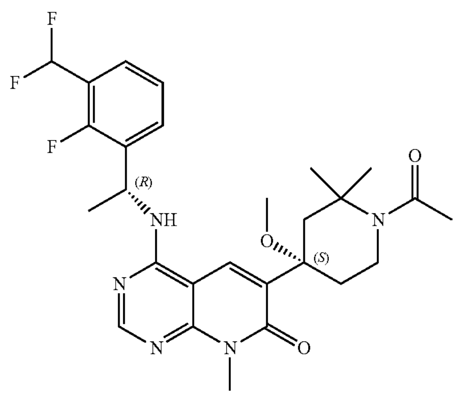 |
| Example 32-54. | 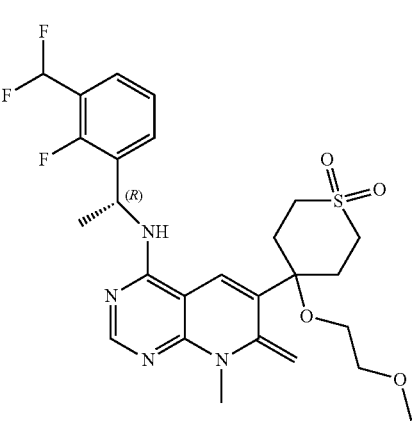 |
| Example 32-55. | 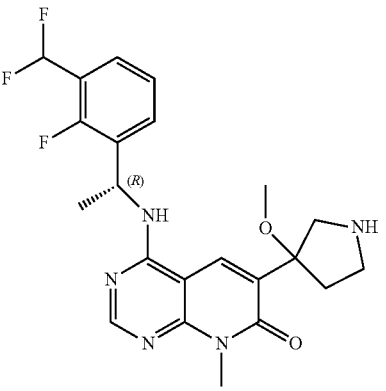 |

171 172
TABLE A-continued
| Example # | Structure |
| --- | --- |
| Example 32-56. | 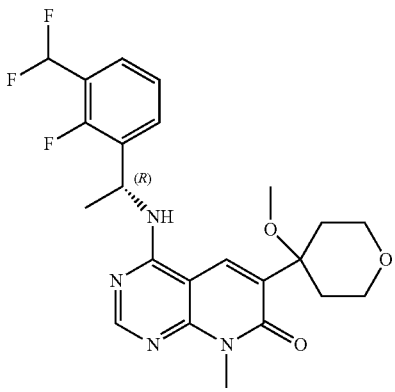 |
| Example 32-57. | 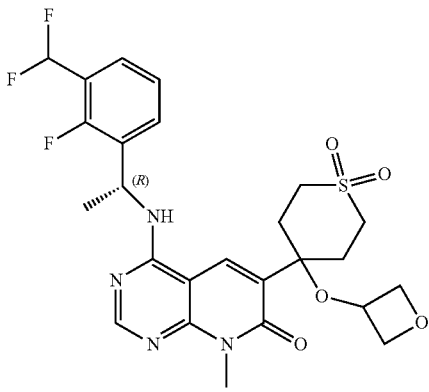 |
| Example 32-58. | 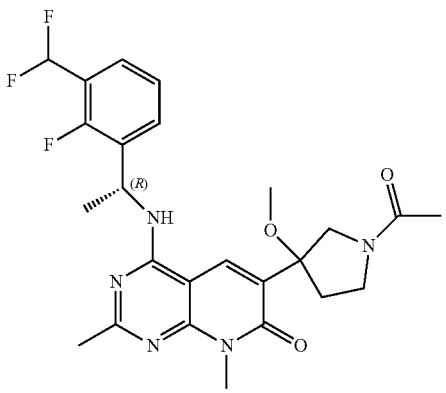 |
| Example 32-59. | 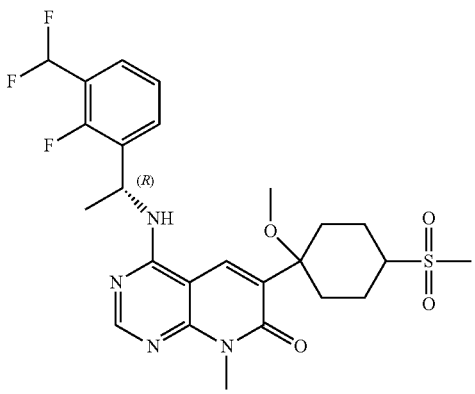 |

TABLE A-continued
| Example # | Structure |
|---|---|
| Example 32-60. | 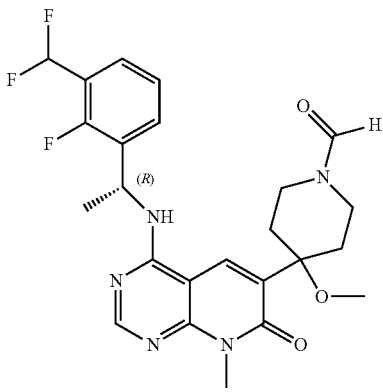 |
| Example 32-61. | 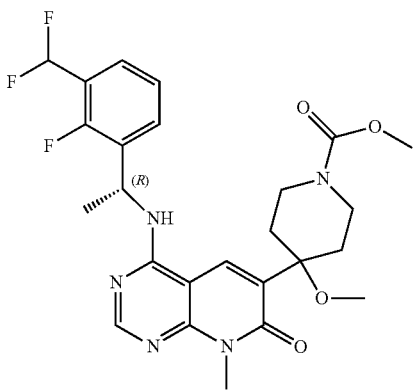 |
| Example 32-62. | 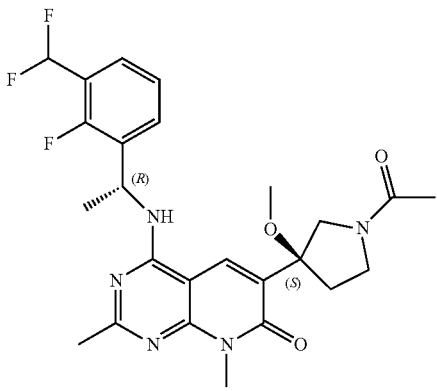 |
| Example 32-63. | 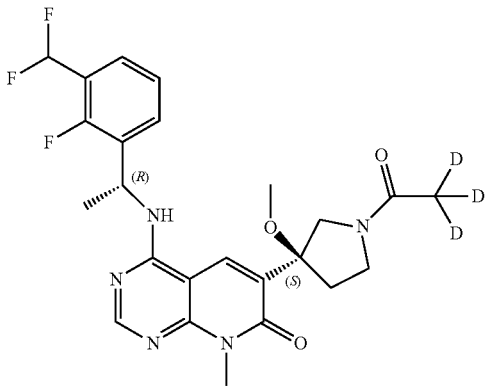 |

TABLE A-continued
| Example # | Structure |
|---|---|
| Example 32-64. | 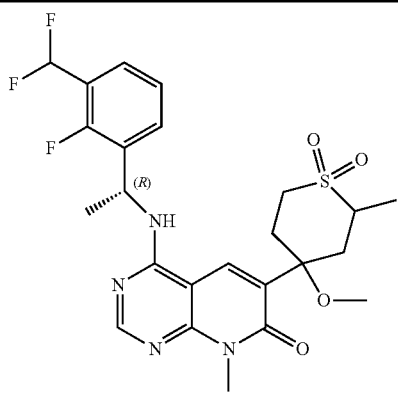 |
| Example 32-65. | 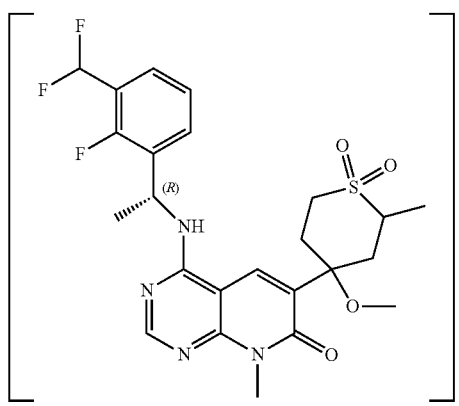 |
| Example 32-66. | 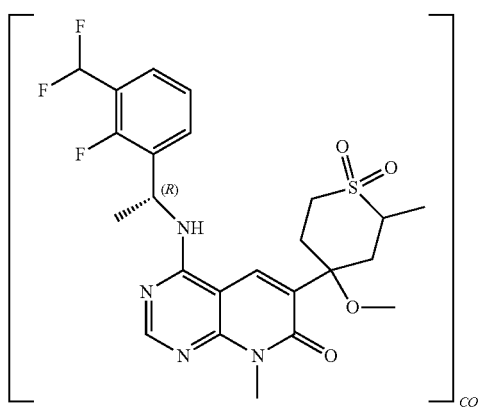 |
| Example 32-67. | 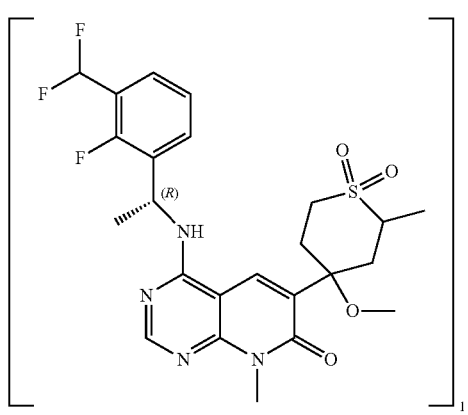 |

TABLE A-continued
| Example # | Structure |
|---|---|
| Example 32-68. | 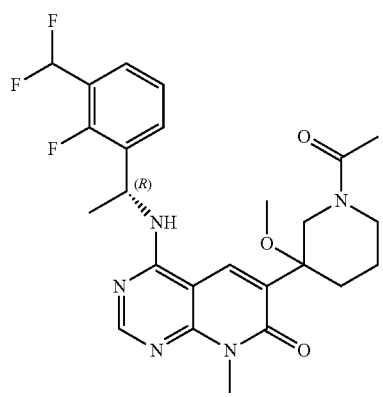 |
| Example 32-69. | 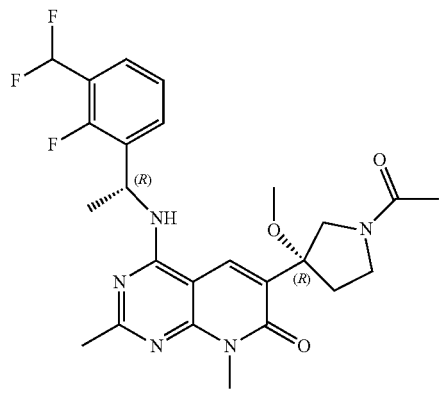 |
| Example 32-70. | 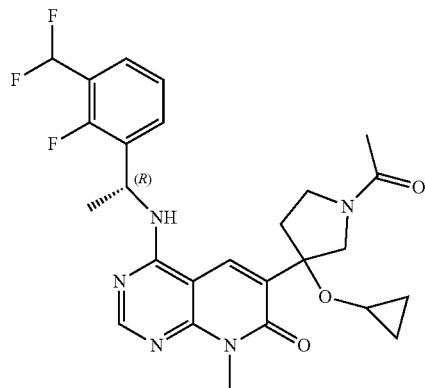 |
| Example 32-71. | 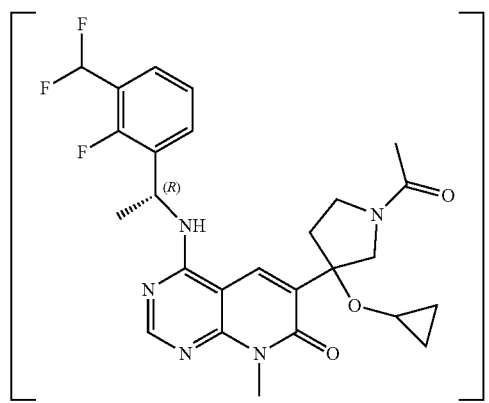 |

TABLE A-continued
| Example # | Structure |
|---|---|
| Example 32-72. | 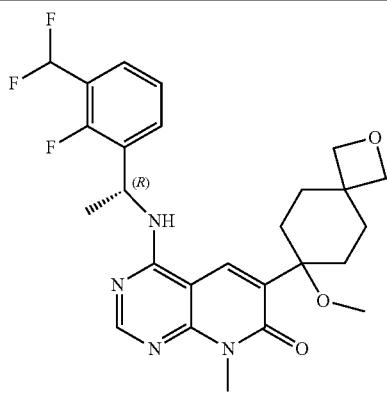 |
| Example 32-73. | 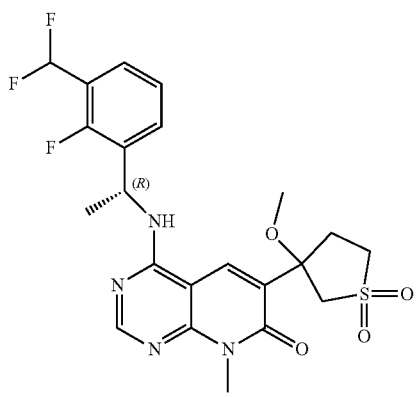 |
| Example 32-74. | 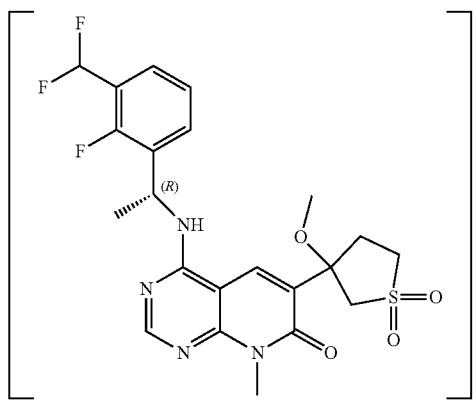 |
| Example 32-75. | 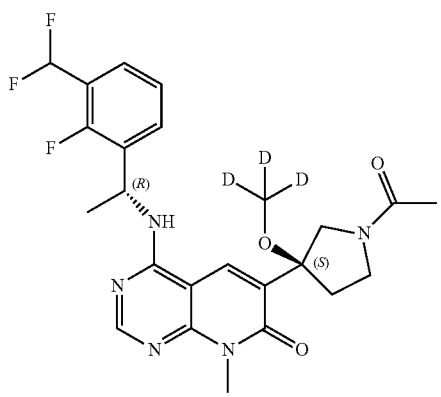 |

TABLE A-continued
| Example # | Structure |
|---|---|
| Example 32-76. | 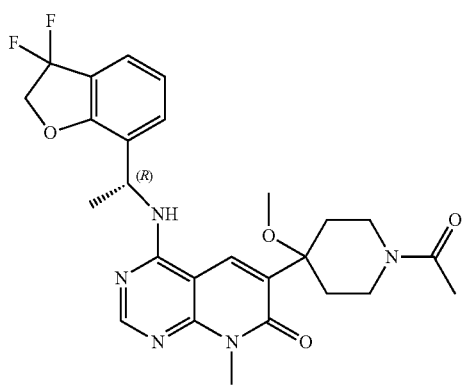 |
| Example 32-77. | 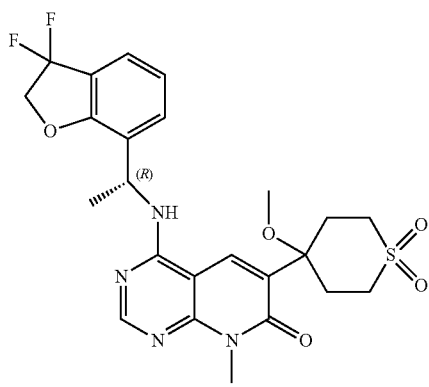 |
| Example 32-78. | 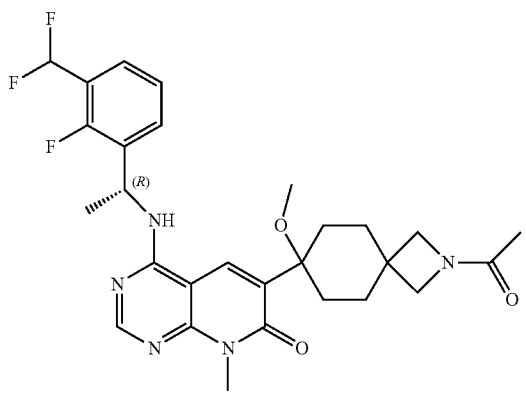 |
| Example 32-79. | 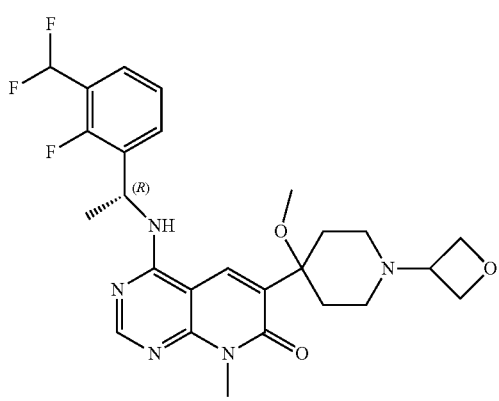 |

TABLE A-continued
| Example # | Structure |
|---|---|
| Example 32-80. | 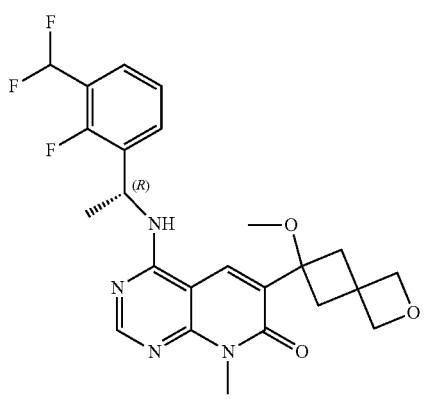 |
| Example 32-81. | 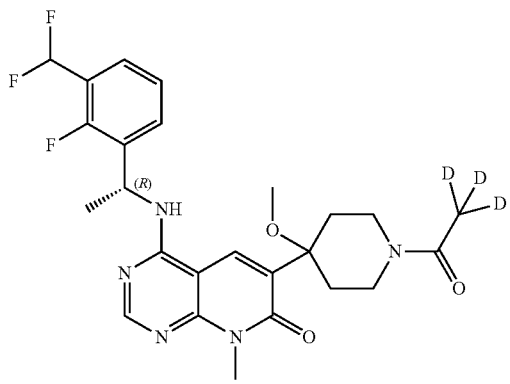 |
| Example 32-82. | 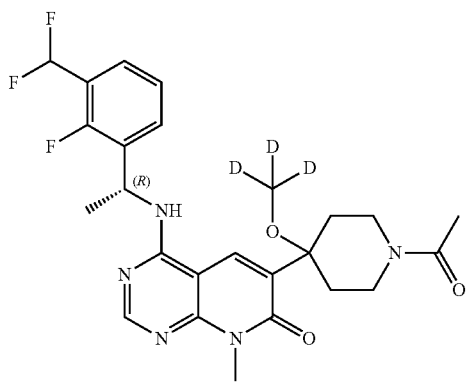 |
| Example 32-83. | 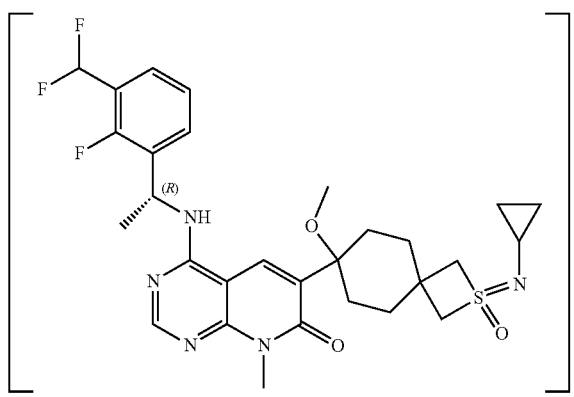 |

TABLE A-continued
| Example # | Structure |
|---|---|
| Example 32-84. | 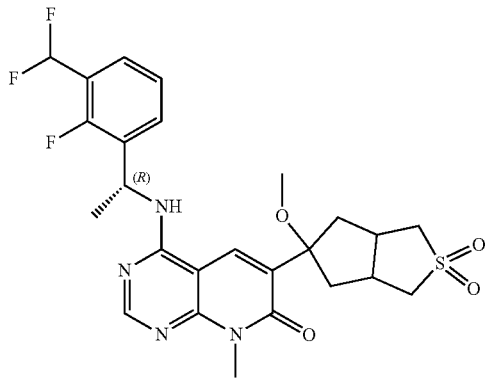 |
| Example 32-85. | 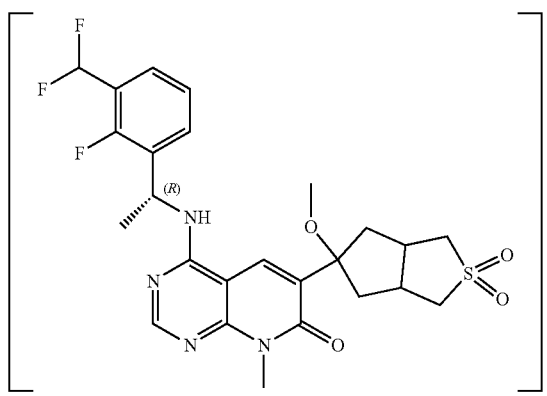 |
| Example 32-86. | 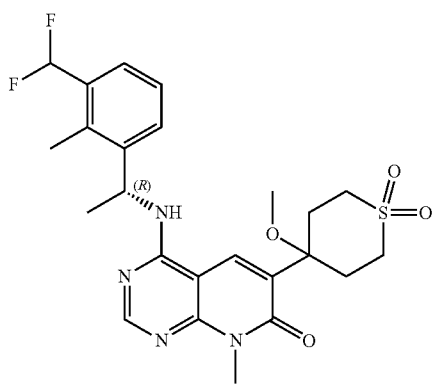 |
| Example 32-87. | 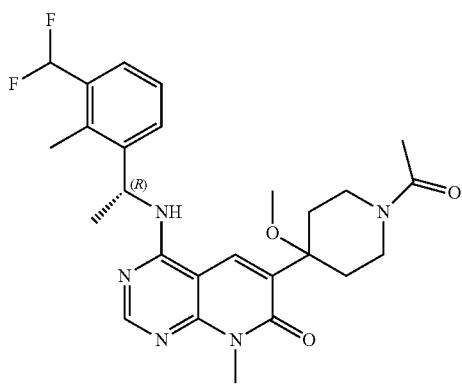 |

US 11,168,102 B1
187
TABLE A-continued
188
| Example # | Structure |
|---|---|
| Example 32-88. | 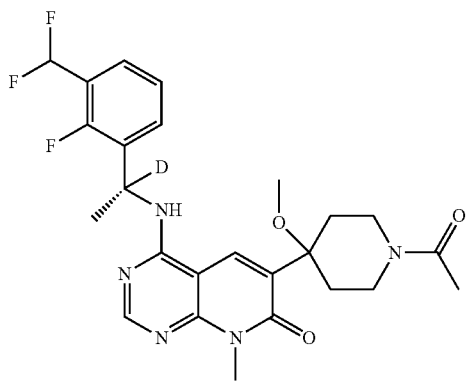 [SMILES: [2H][C@@](C)(Nc1ncnc2c1cc(C1(OC)CCN(C(C)=O)CC1)c(=O)n2C)c1cccc(C(F)F)c1F] |
| Example 32-89. | 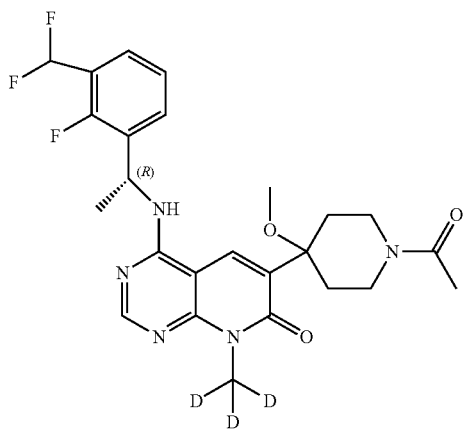 |
| Example 32-90. | 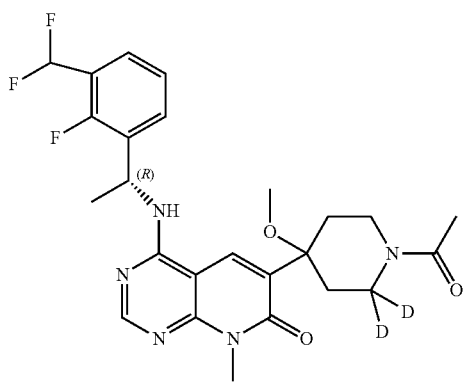 |
| Example 32-91. | 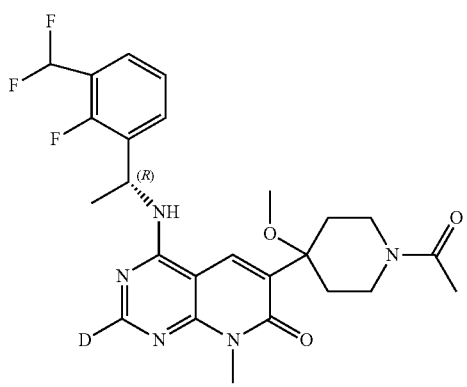 |

TABLE A-continued
| Example # | Structure |
|---|---|
| Example 32-92. | 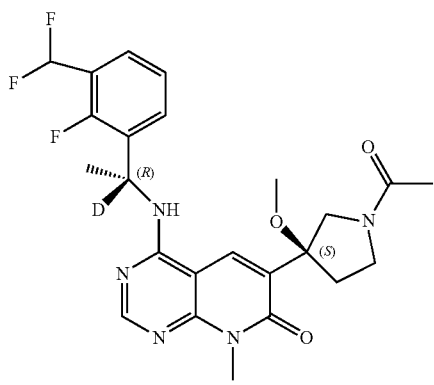 |
| Example 32-93. | 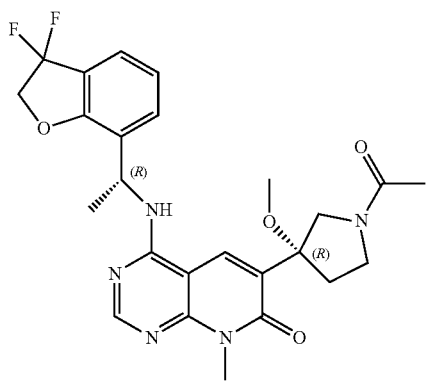 |
| Example 32-94. | 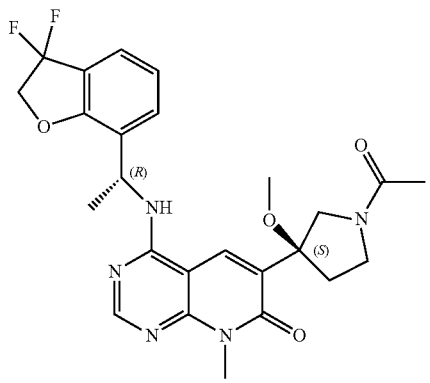 |
| Example 32-95. | 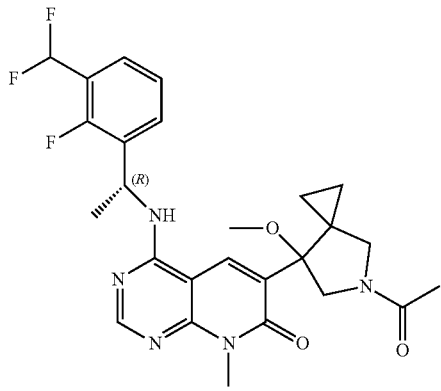 |

TABLE A-continued
| Example # | Structure |
| --- | --- |
| Example 32-96. | 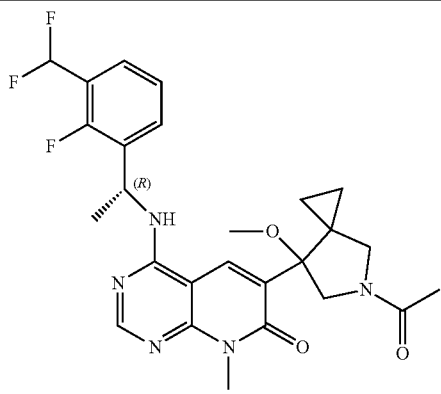 |
| Example 32-97. | 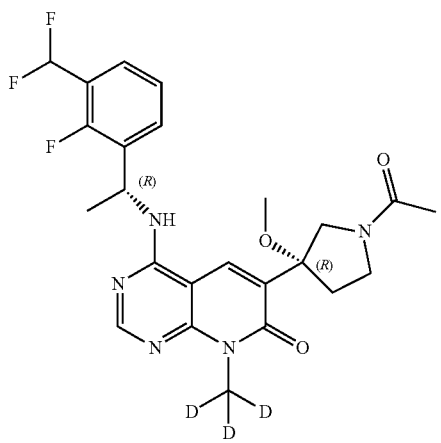 |
| Example 32-98. | 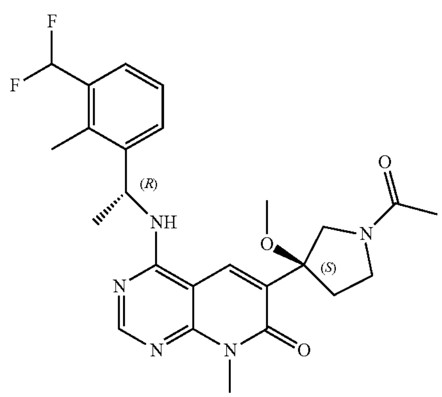 |
| Example 32-99. | 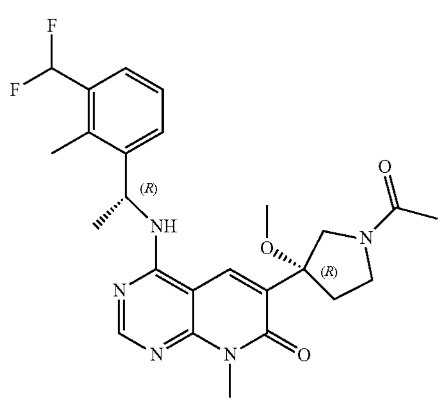 |

TABLE A-continued
| Example # | Structure |
|---|---|
| Example 32-100. | 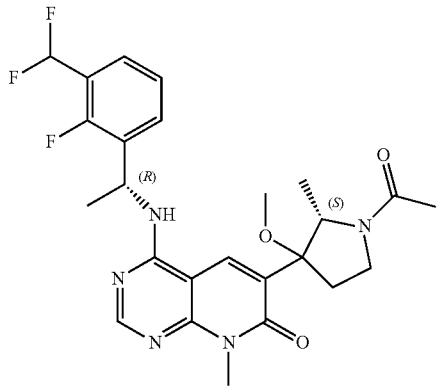 |
| Example 32-101. | 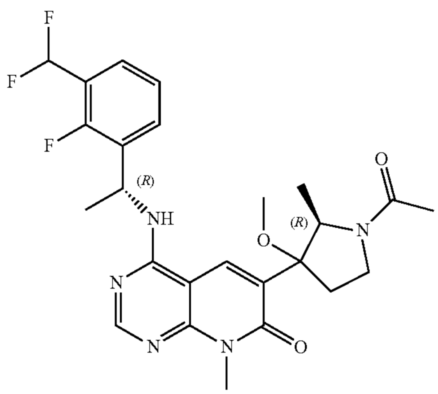 |
| Example 32-102. | 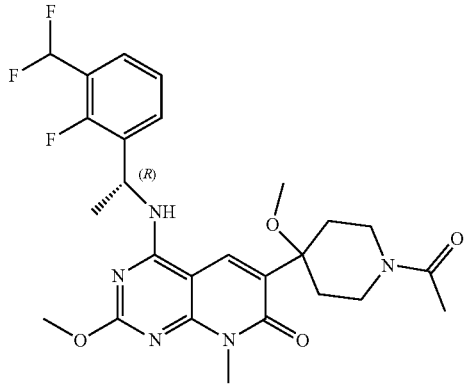 |
| Example 32-103. | 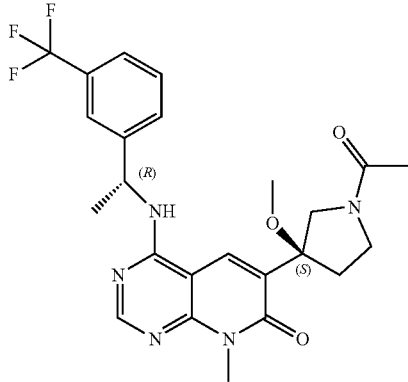 |

TABLE A-continued
| Example # | Structure |
|---|---|
| Example 32-104. | 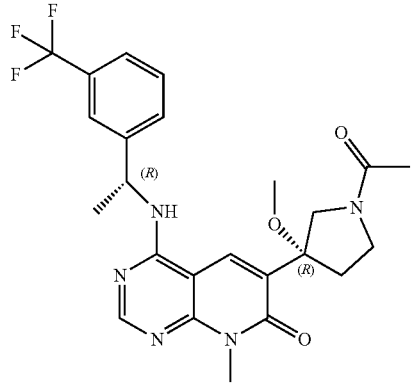 |
| Example 32-105. | 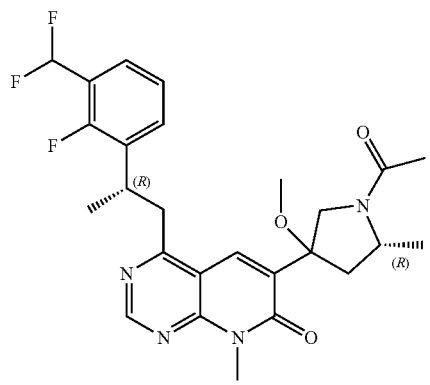 |
| Example 32-106. | 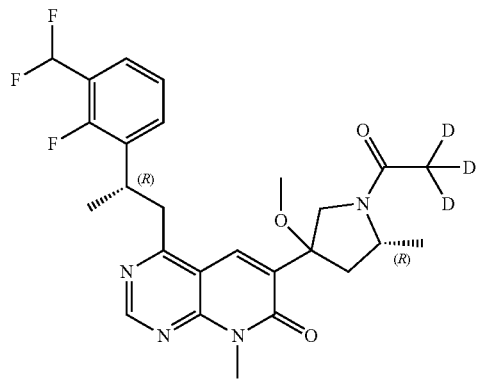 |
| Example 32-107. | 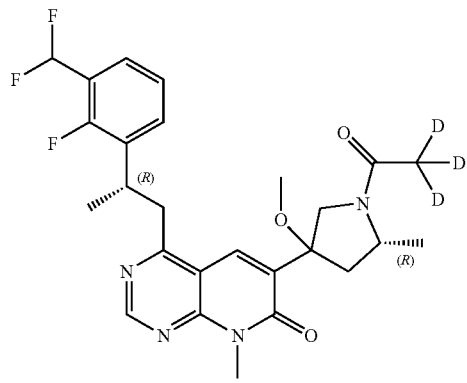 |

TABLE A-continued

| Example # | Structure |
| --- | --- |
| Example 32-108. | 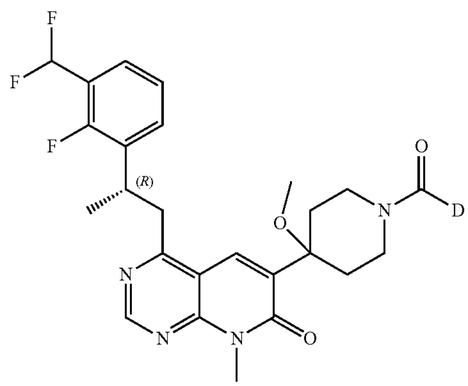 |
| Example 32-109. | 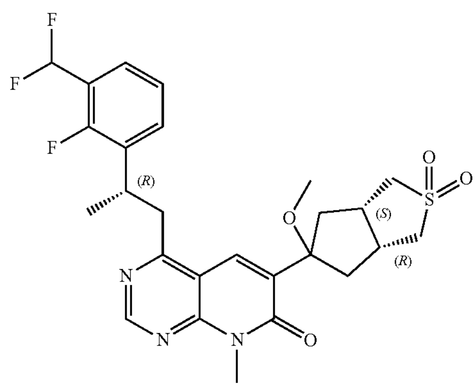 |
| Example 32-110. | 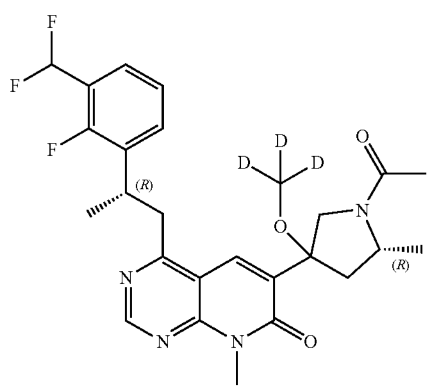 |
| Example 32-111. | 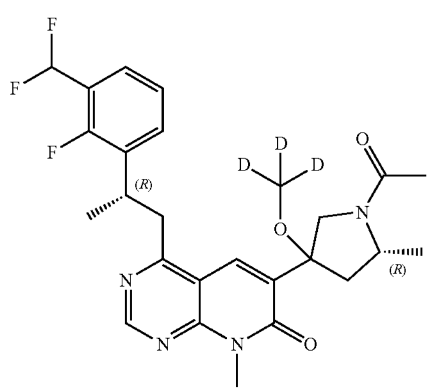 |

TABLE A-continued
| Example # | Structure |
|---|---|
| Example 32-112. | 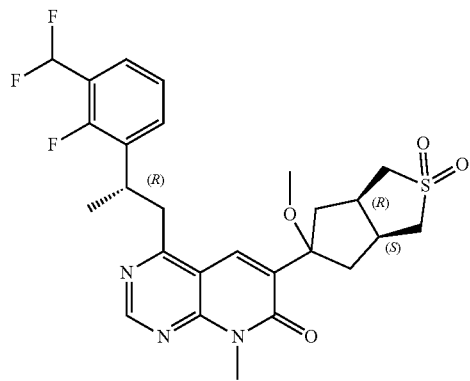 |
| Example 32-113. | 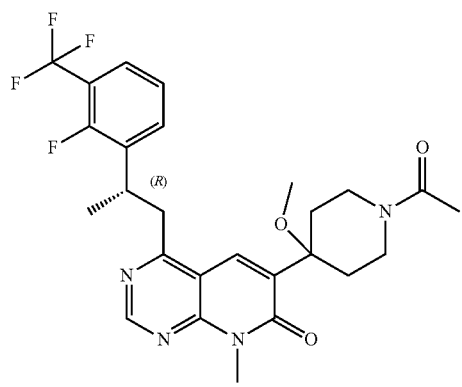 |
| Example 32-114. | 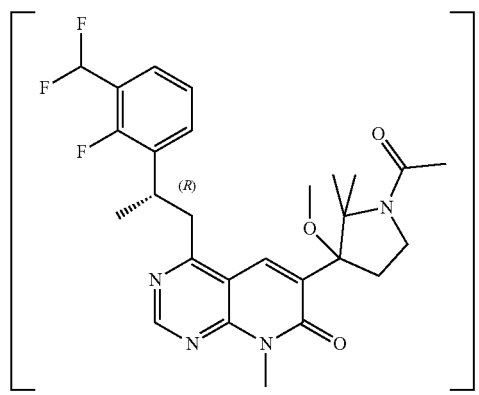 |
| Example 32-115. | 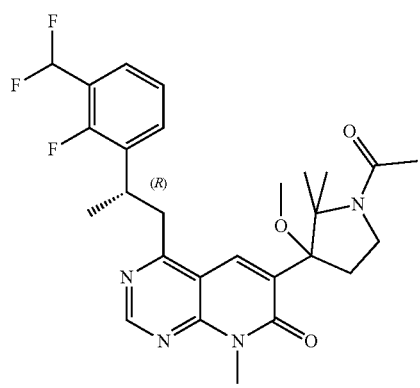 |

TABLE A-continued

| Example # | Structure |
|---|---|
| Example 33. | 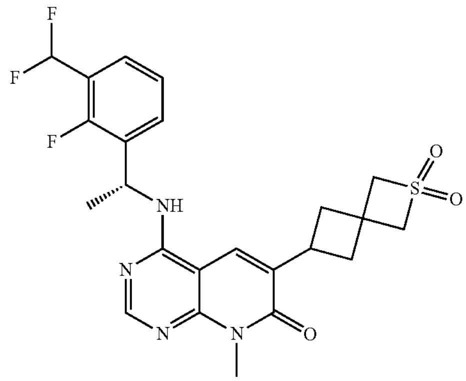 [SMILES: C[C@@H](Nc1ncnc2c1cc(C1CC3(C1)CS(=O)(=O)C3)c(=O)n2C)c1cccc(C(F)F)c1F] |
| Example 33-1. | 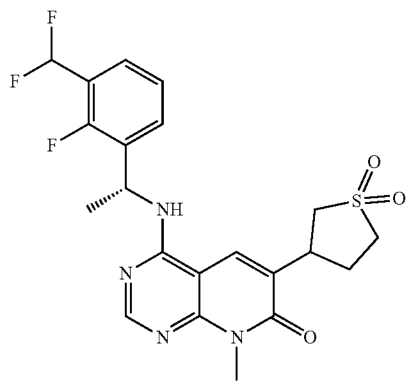 [SMILES: C[C@@H](Nc1ncnc2c1cc(C1CCS(=O)(=O)C1)c(=O)n2C)c1cccc(C(F)F)c1F] |
| Example 33-2. | 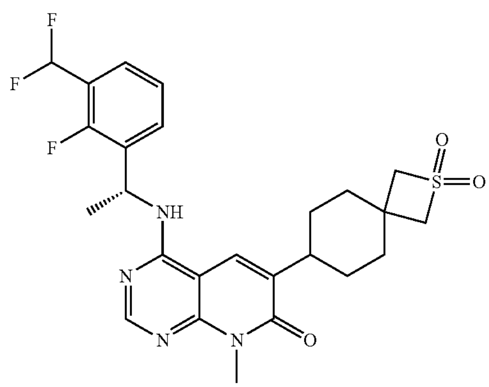 [SMILES: C[C@@H](Nc1ncnc2c1cc(C1CCC3(CC1)CS(=O)(=O)C3)c(=O)n2C)c1cccc(C(F)F)c1F] |
| Example 33-3. | 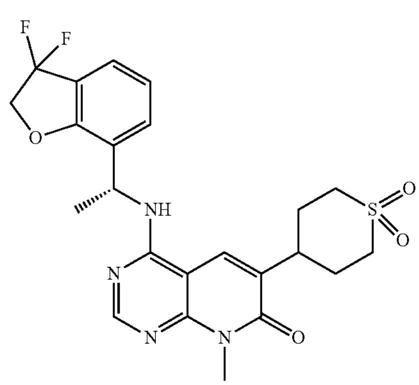 [SMILES: C[C@@H](Nc1ncnc2c1cc(C1CCS(=O)(=O)CC1)c(=O)n2C)c1cccc2c1OCC2(F)F] |

TABLE A-continued

| Example # | Structure |
| --- | --- |
| Example 33-4. | 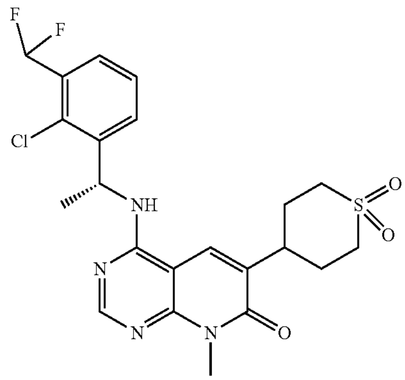 [SMILES: C[C@@H](Nc1ncnc2c1cc(C1CCS(=O)(=O)CC1)c(=O)n2C)c1cccc(C(F)F)c1Cl] |
| Example 33-5. | 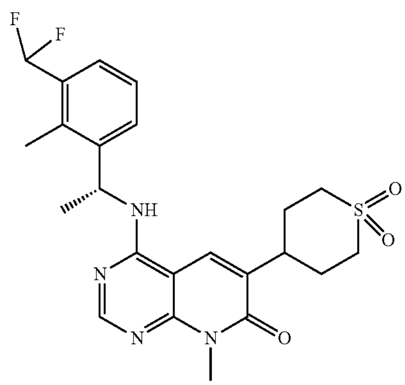 [SMILES: Cc1c(C(F)F)cccc1[C@@H](C)Nc1ncnc2c1cc(C1CCS(=O)(=O)CC1)c(=O)n2C] |
| Example 33-6. | 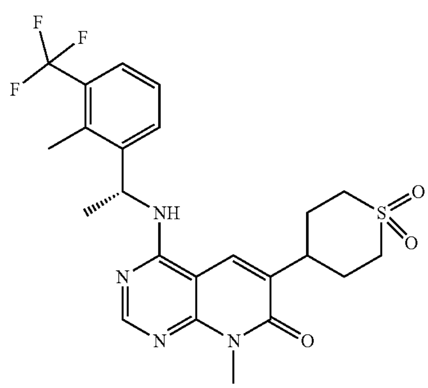 [SMILES: Cc1c([C@@H](C)Nc2ncnc3c2cc(C2CCS(=O)(=O)CC2)c(=O)n3C)cccc1C(F)(F)F] |
| Example 33-7. | 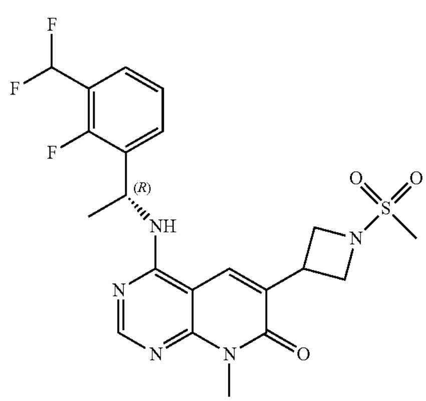 |

TABLE A-continued
| Example # | Structure |
|---|---|
| Example 33-8. | 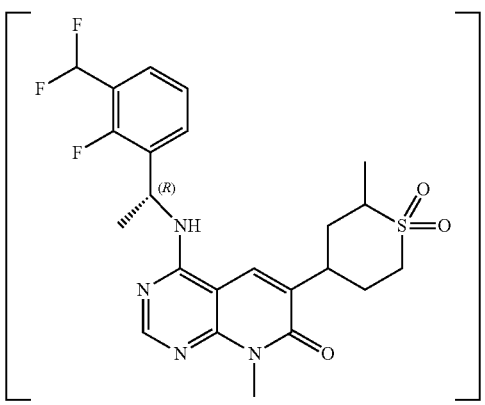 |
| Example 33-9. | 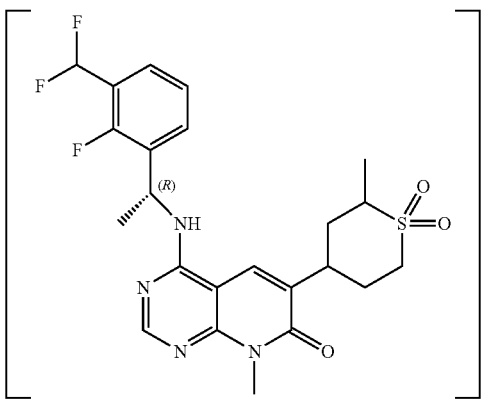 |
| Example 33-10. | 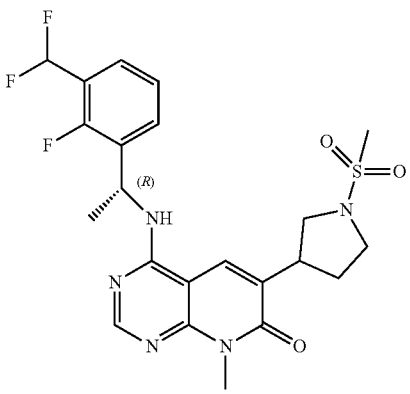 |
| Example 33-11. | 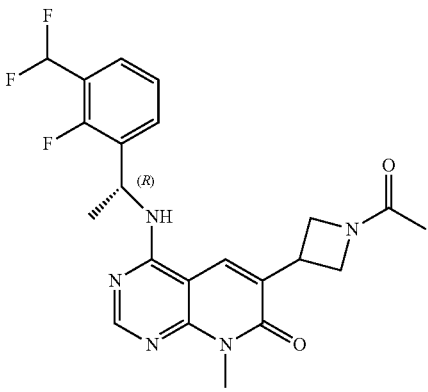 |

TABLE A-continued
| Example # | Structure |
|---|---|
| Example 33-12. | 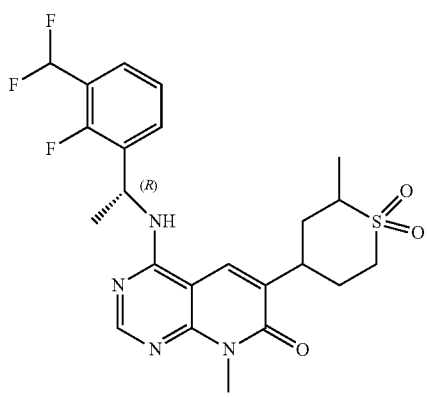 |
| Example 33-13. | 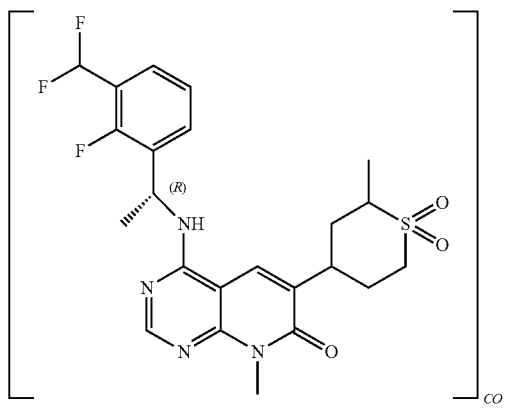 |
| Example 33-14. | 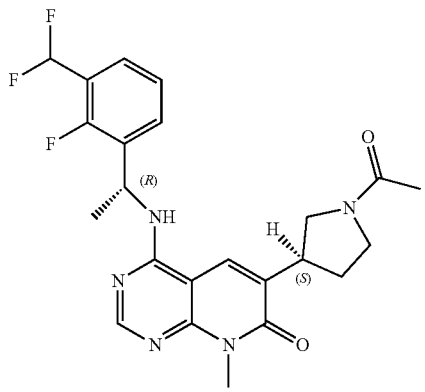 |
| Example 33-15. | 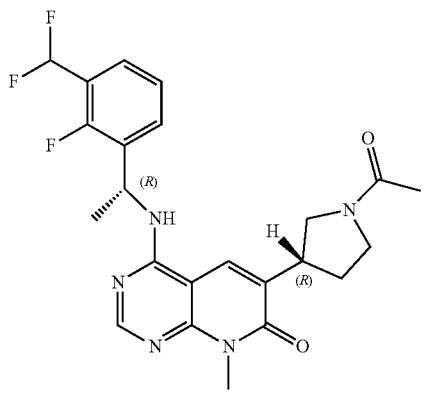 |

TABLE A-continued
| Example # | Structure |
|---|---|
| Example 33-16. | 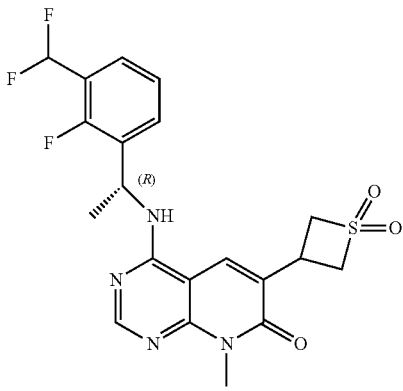 |
| Example 33-17. | 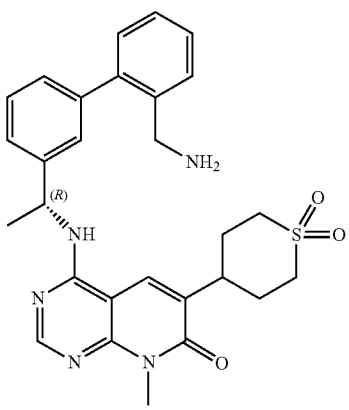 |
| Example 33-18. | 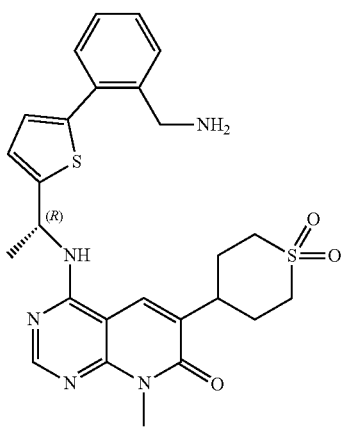 |
| Example 33-19. | 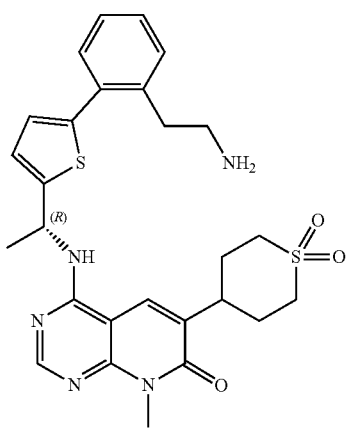 |

TABLE A-continued
| Example # | Structure |
|---|---|
| Example 33-20. | 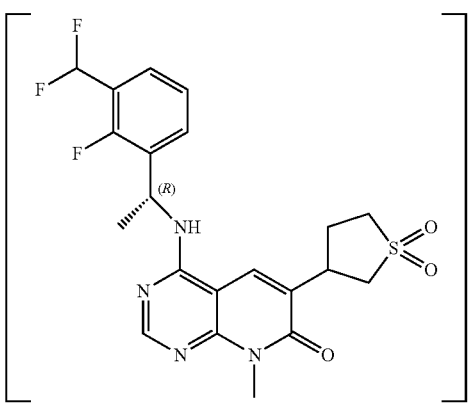 |
| Example 33-21. | 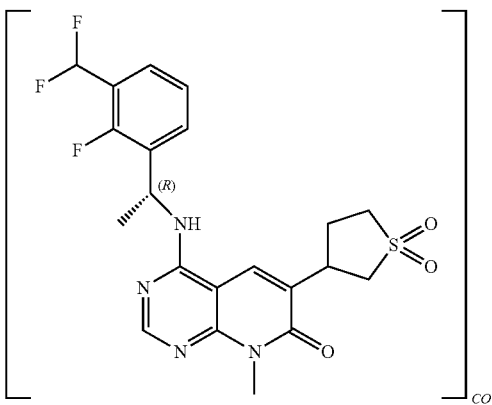 |
| Example 33-22. | 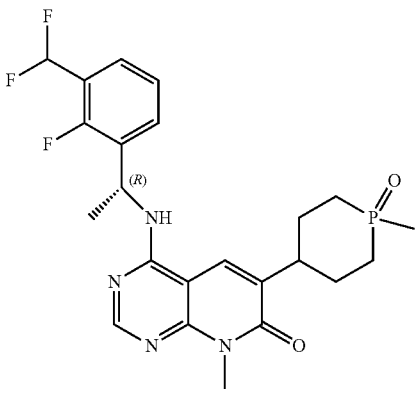 |
| Example 33-23. | 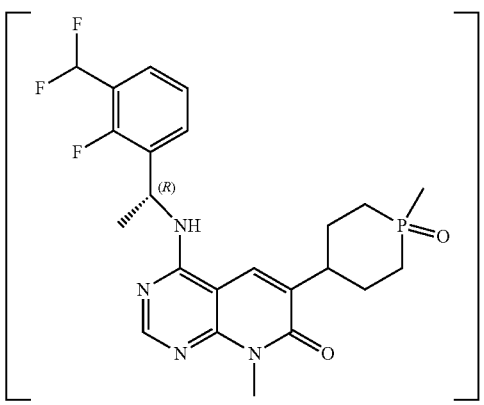 |

TABLE A-continued
| Example # | Structure |
|---|---|
| Example 33-24. | 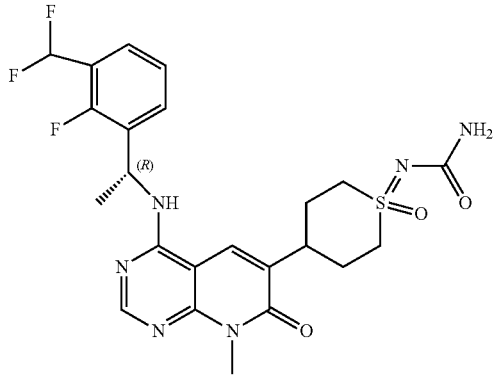 |
| Example 33-25. | 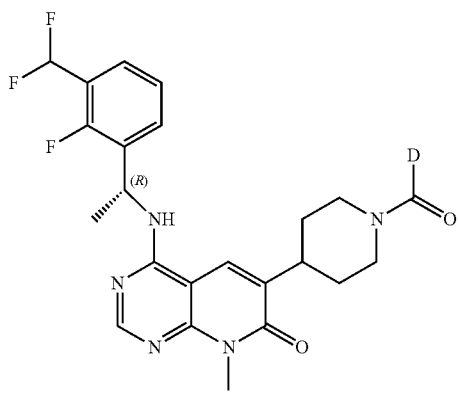 |
| Example 33-26. | 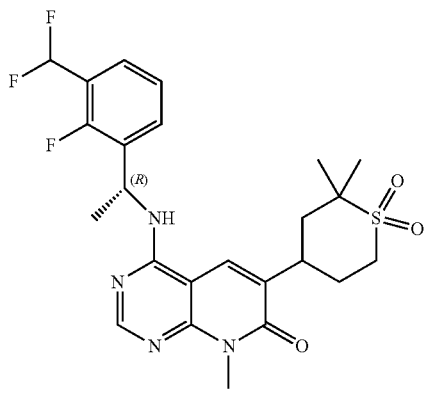 |
| Example 33-27. | 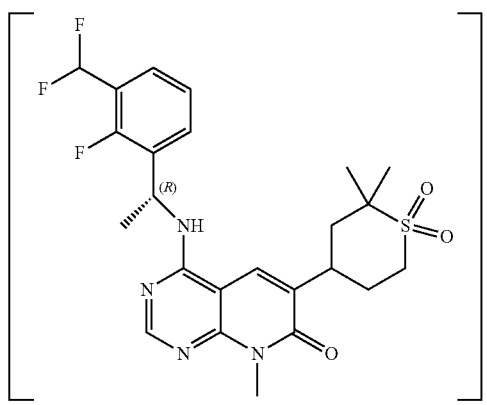 |

215 216
TABLE A-continued
| Example # | Structure |
|---|---|
| Example 33-28. | 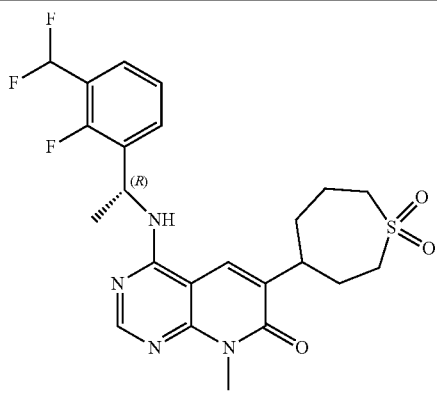 |
| Example 33-29. | 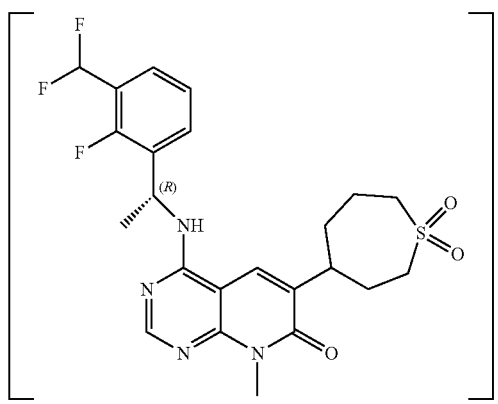 |
| Example 33-30. | 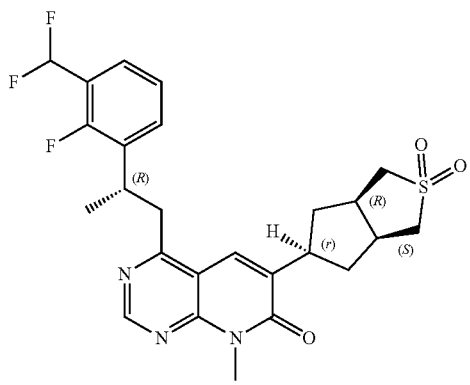 |
| Example 33-31. | 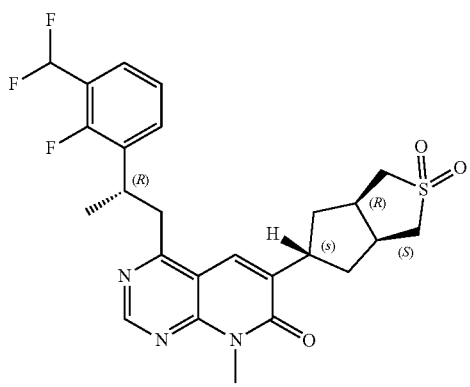 |

TABLE A-continued
| Example # | Structure |
|---|---|
| Example 33-32. | 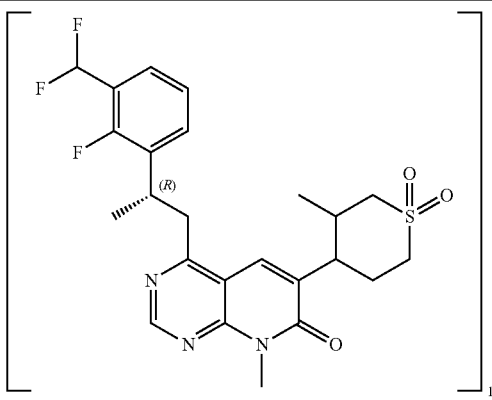 |
| Example 33-33. | 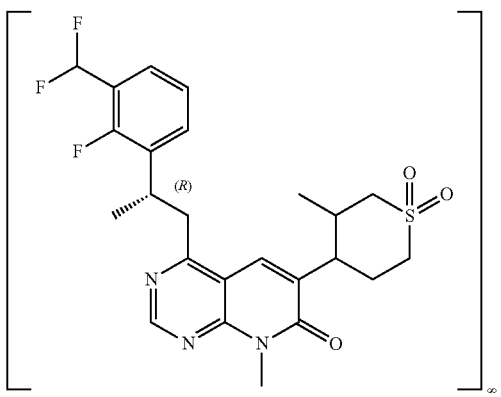 |
| Example 33-34. | 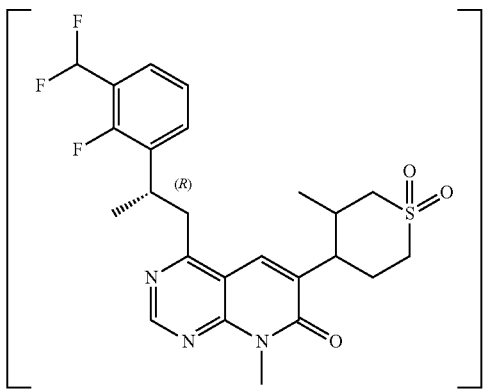 |
| Example 33-35. | 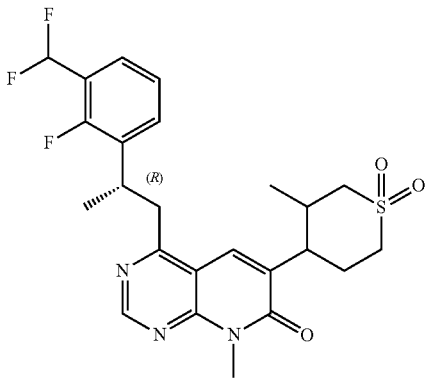 |

TABLE A-continued
| Example # | Structure |
|---|---|
| Example 33-36. | 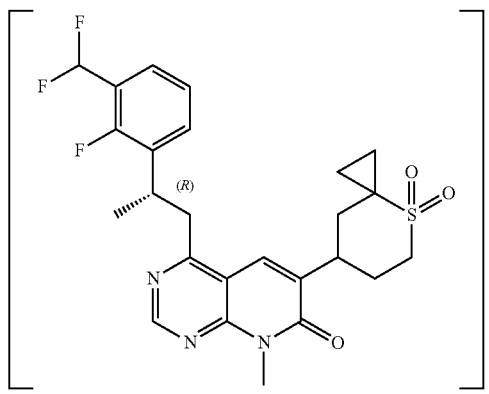 |
| Example 33-37. | 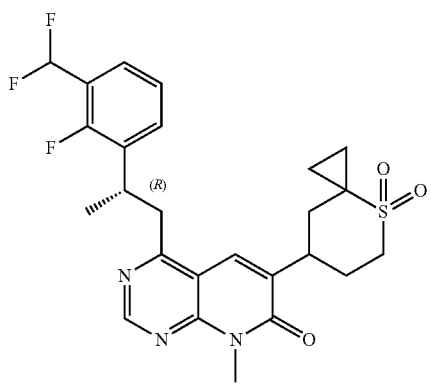 |
| Example 34. | 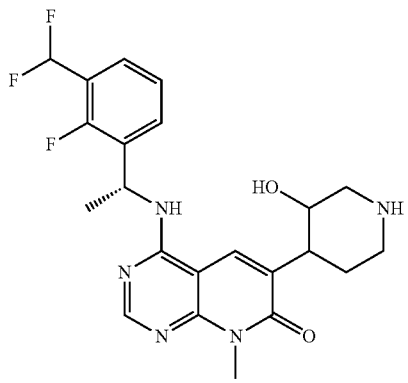 [SMILES: C[C@@H](Nc1ncnc2c1cc(C1CCNCC1O)c(=O)n2C)c1cccc(C(F)F)c1F] |
| Example 35. | 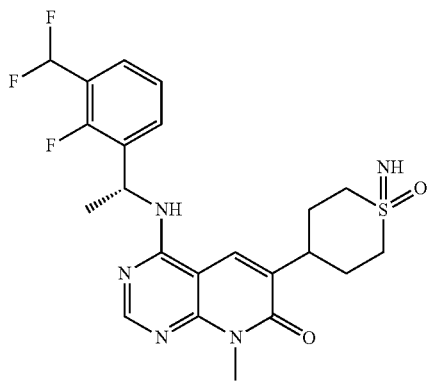 [SMILES: C[C@@H](Nc1ncnc2c1cc(C1CCS(=N)(=O)CC1)c(=O)n2C)c1cccc(C(F)F)c1F] |

TABLE A-continued
| Example # | Structure |
|---|---|
| Example 36. | 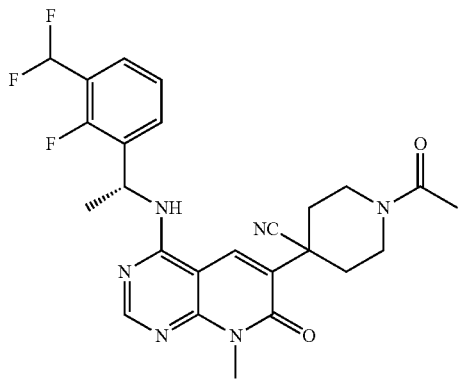 [SMILES: CC(=O)N1CCC(C#N)(c2cc3c(N[C@H](C)c4cccc(C(F)F)c4F)ncnc3n(C)c2=O)CC1] |
| Example 36-1. | 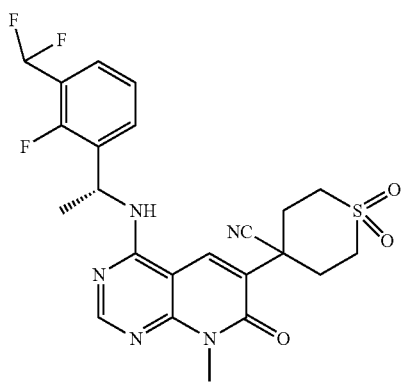 [SMILES: C[C@@H](Nc1ncnc2c1cc(C1(C#N)CCS(=O)(=O)CC1)c(=O)n2C)c1cccc(C(F)F)c1F] |
| Example 36-2. | 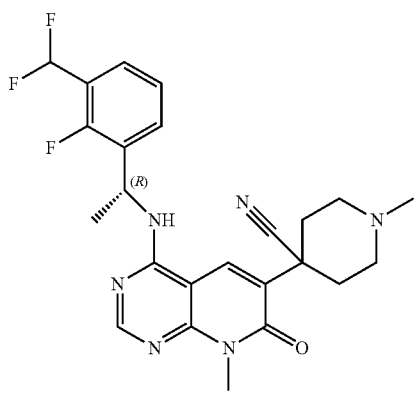 |
| Example 36-3. | 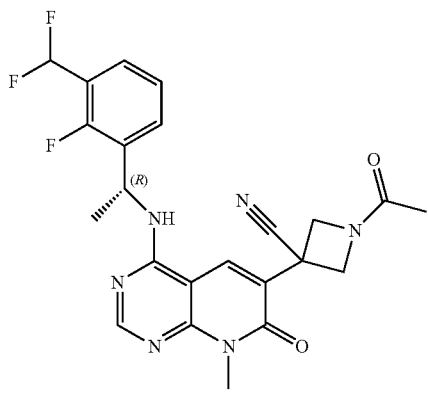 |

TABLE A-continued
| Example # | Structure |
|---|---|
| Example 36-4. | 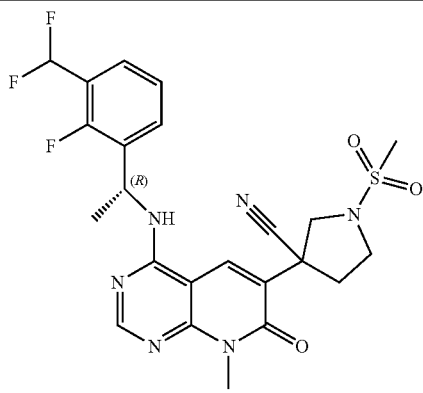 |
| Example 36-5. | 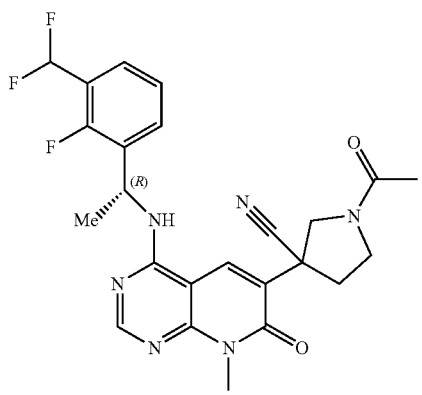 |
| Example 36-6. | 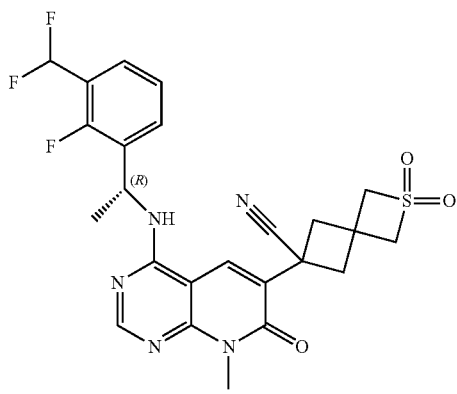 |
| Example 36-7. | 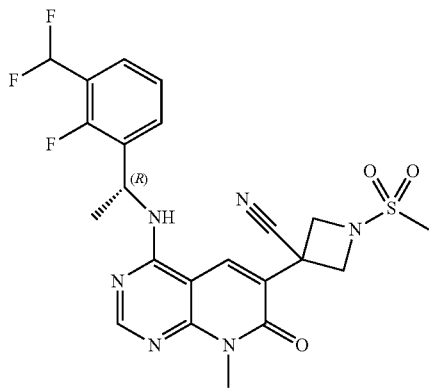 |

TABLE A-continued

| Example # | Structure |
|---|---|
| Example 36-8. | 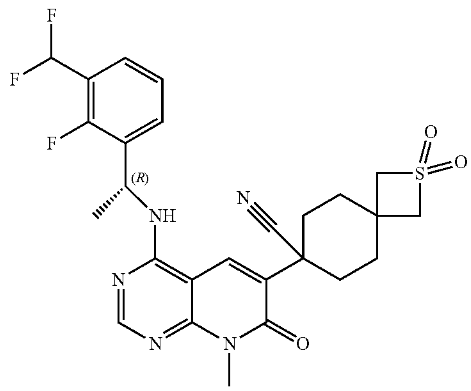 |
| Example 36-9. | 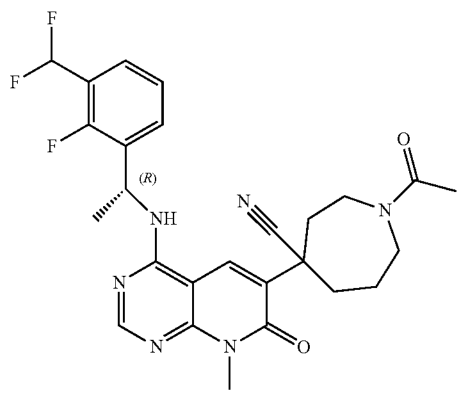 |
| Example 36-10. | 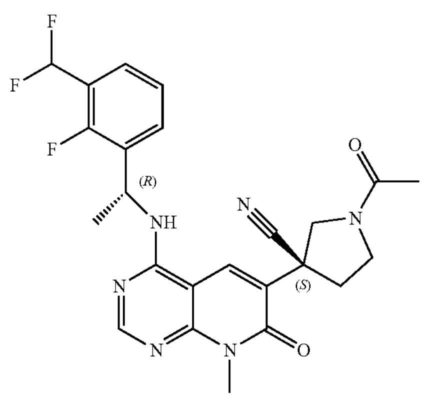 |
| Example 36-11. | 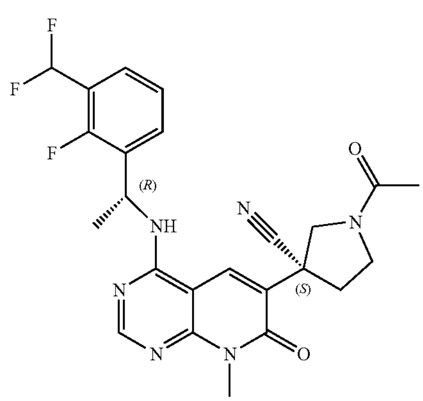 |

TABLE A-continued
| Example # | Structure |
|---|---|
| Example 36-12. | 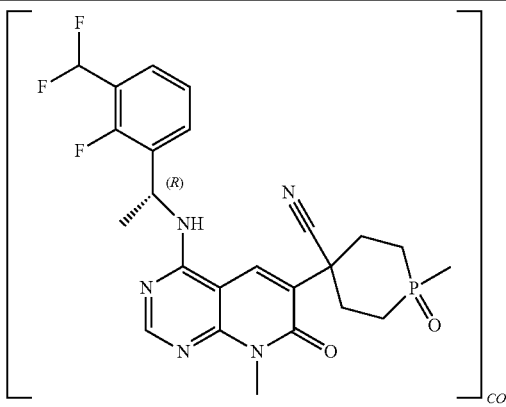 |
| Example 36-13. | 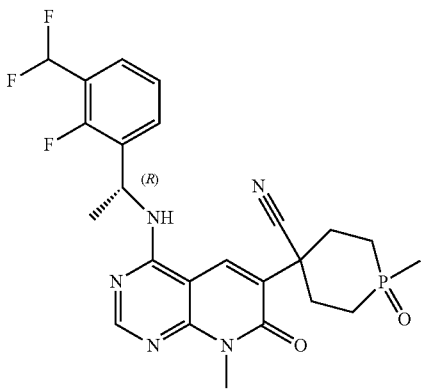 |
| Example 36-14. | 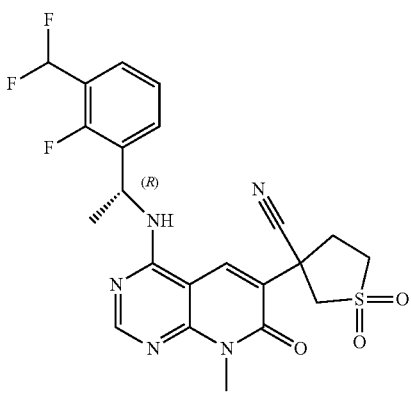 |
| Example 36-15. | 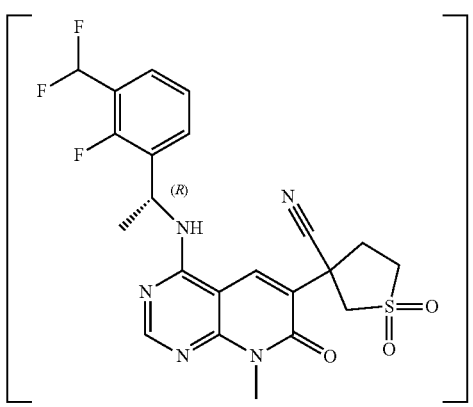 |

TABLE A-continued
| Example # | Structure |
|---|---|
| Example 36-16. | 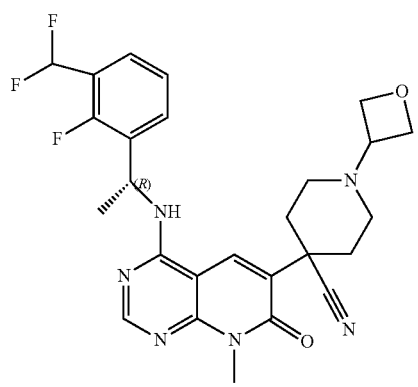 |
| Example 37. | 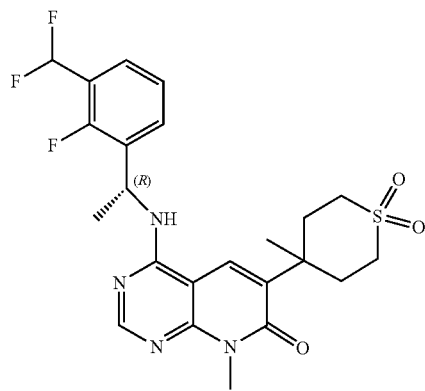 |
| Example 38. | 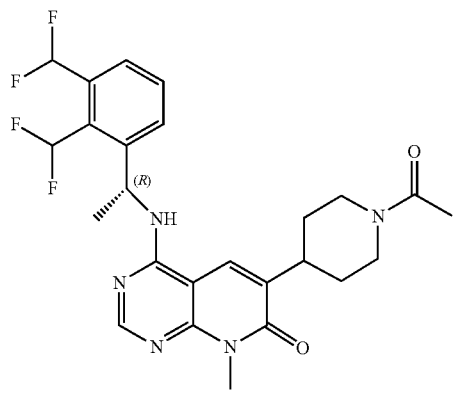 |
| Example 39. | 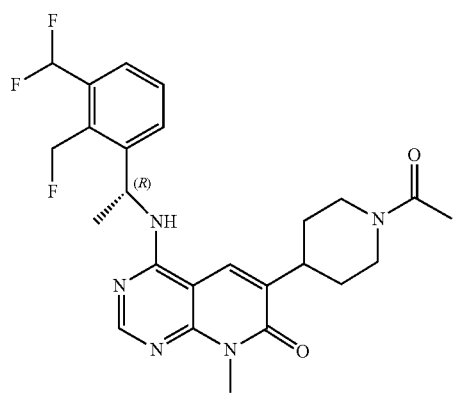 |

TABLE A-continued
| Example # | Structure |
|---|---|
| Example 40. | 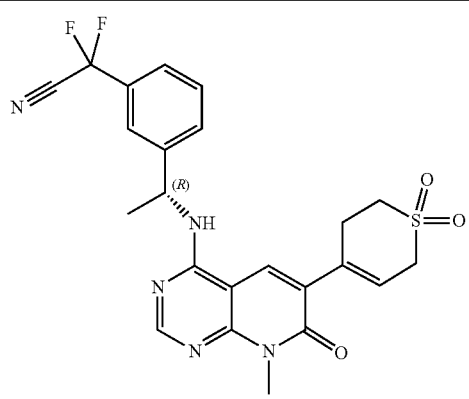 |
| Example 41. | 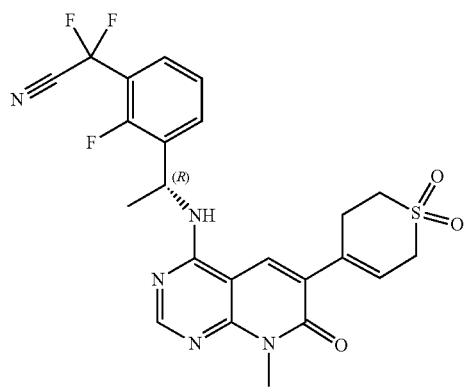 |
| Example 41-1. | 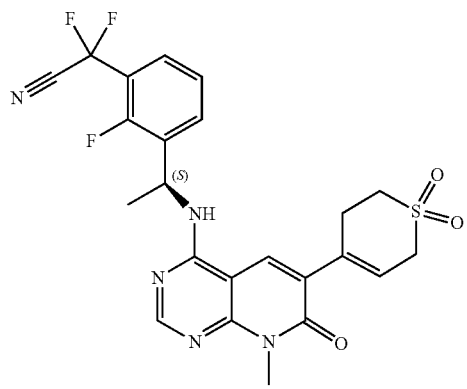 |
| Example 42. | 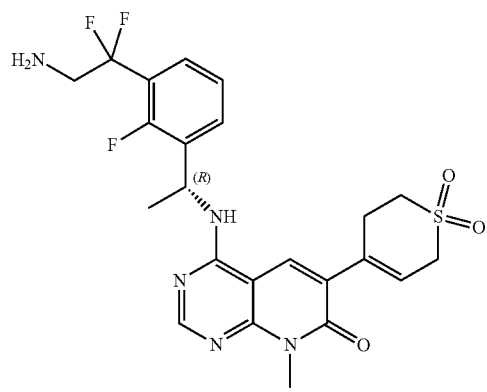 |

TABLE A-continued
| Example # | Structure |
| --- | --- |
| Example 43. | 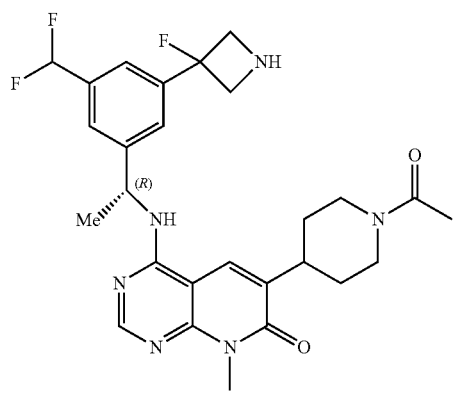 |
| Example 44. | 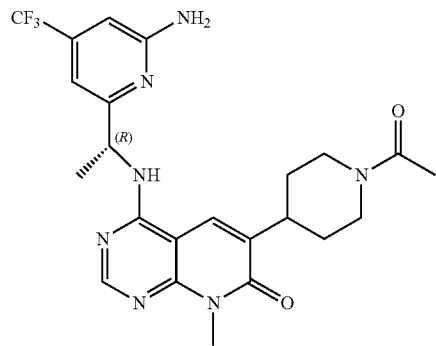 |
| Example 45. | 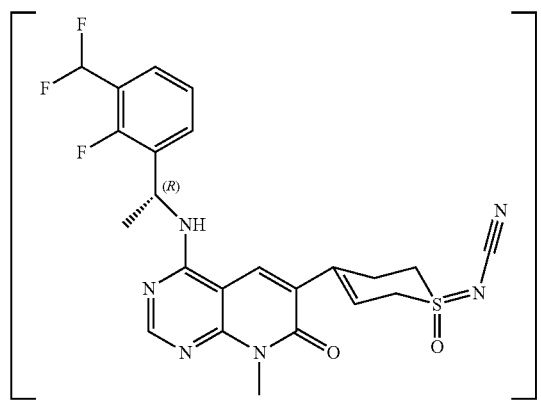 |
| Example 46. | 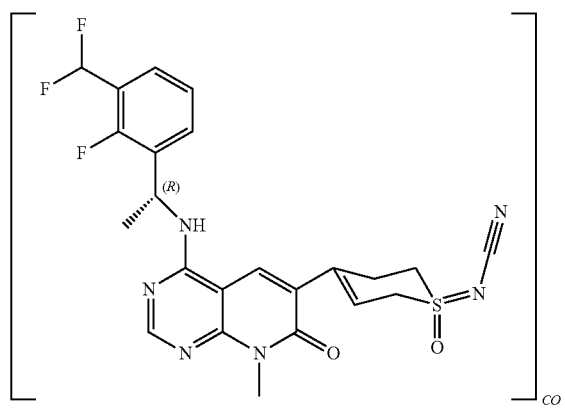 |

TABLE A-continued
| Example # | Structure |
|---|---|
| Example 47. | 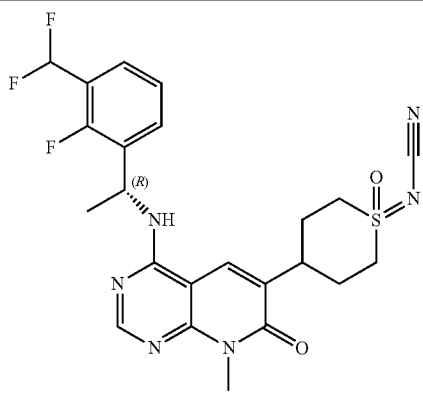 |
| Example 48. | 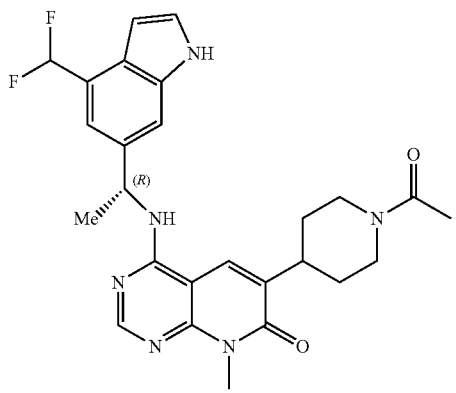 |
| Example 49. | 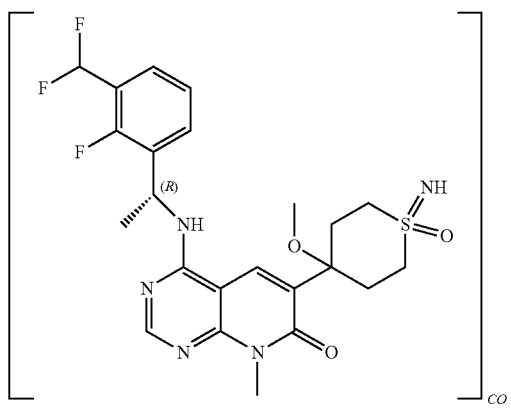 |
| Example 50. | 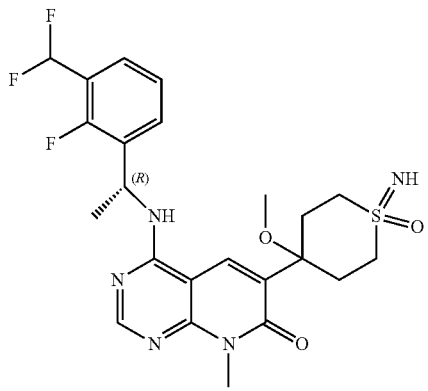 |

TABLE A-continued

| Example # | Structure |
|---|---|
| Example 51. | 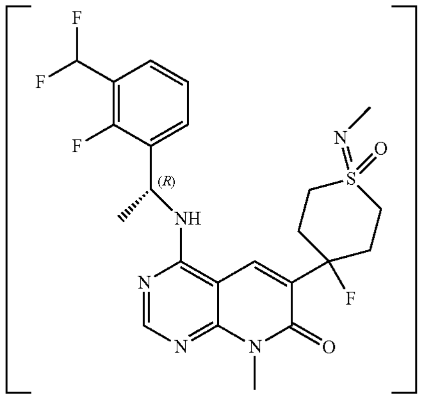 |
| Example 51-1. | 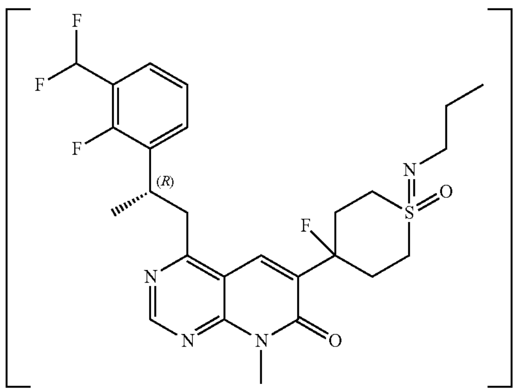 |
| Example 51-2. | 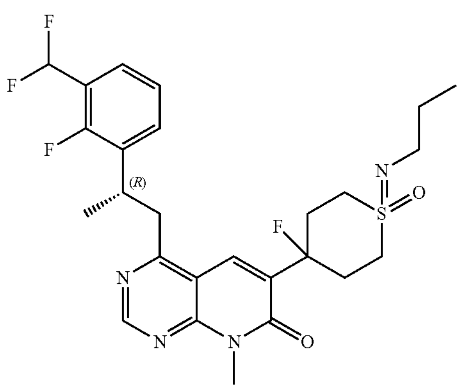 |
| Example 51-3. | 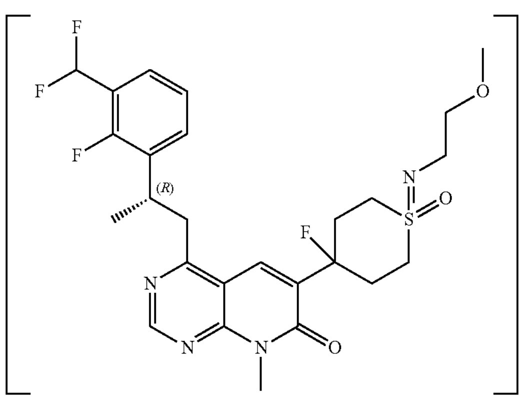 |

TABLE A-continued
| Example # | Structure |
|---|---|
| Example 51-4. | 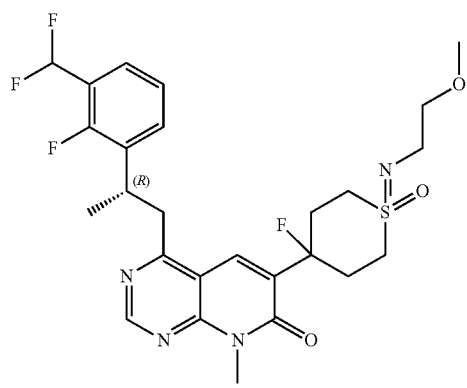 |
| Example 51-5. | 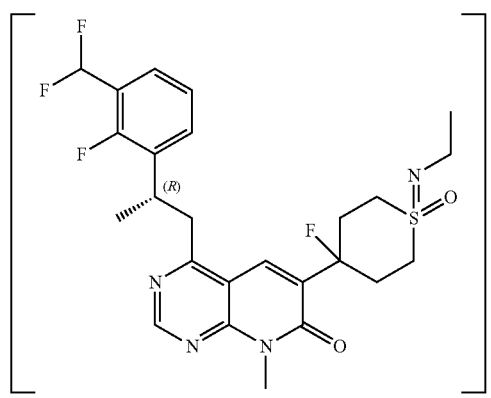 |
| Example 51-6. | 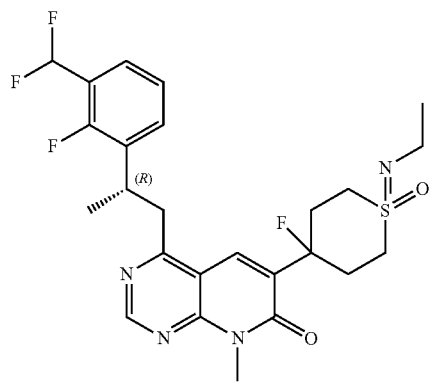 |
| Example 52. | 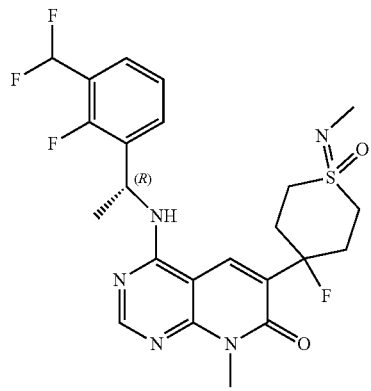 |

TABLE A-continued
| Example # | Structure |
|---|---|
| Example 53. | 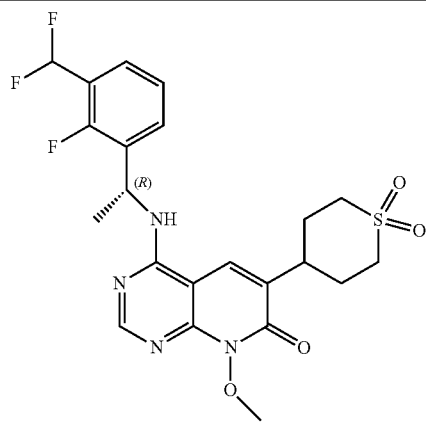 |
| Example 54. | 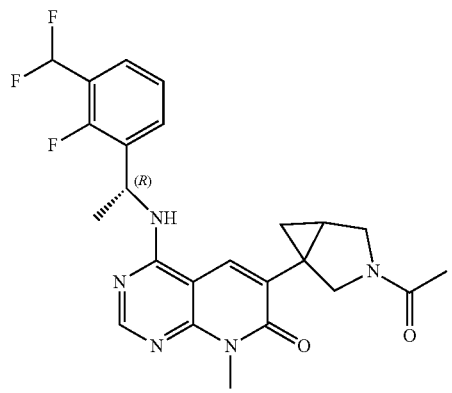 |
| Example 54-1. | 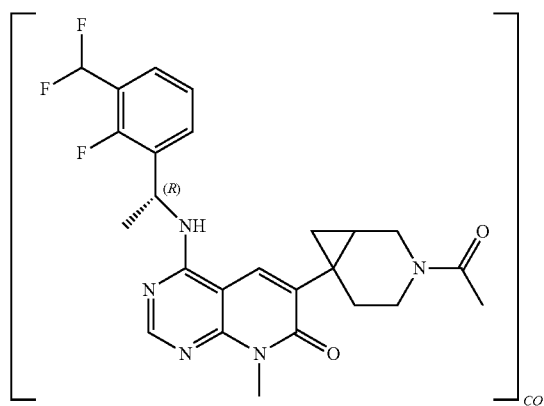 |
| Example 54-2. | 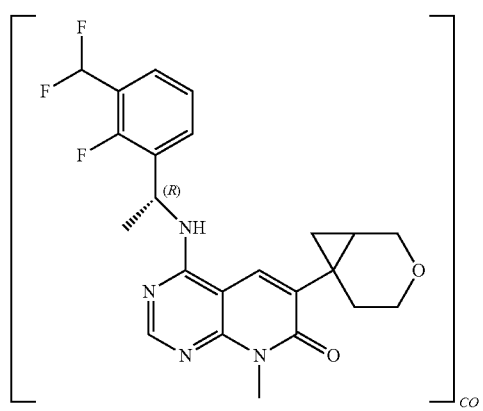 |

TABLE A-continued
| Example # | Structure |
|---|---|
| Example 54-3. | 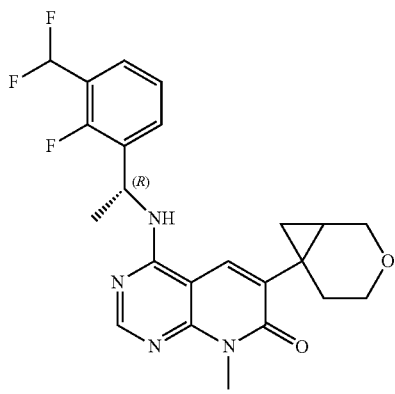 |
| Example 54-4. | 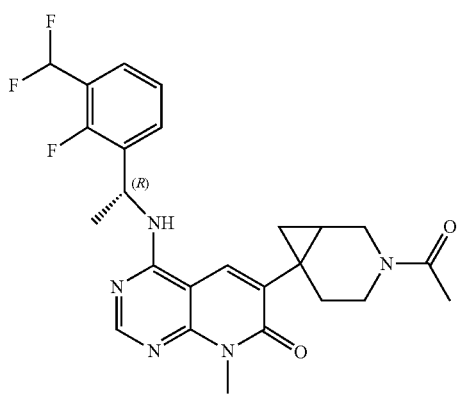 |
| Example 55. | 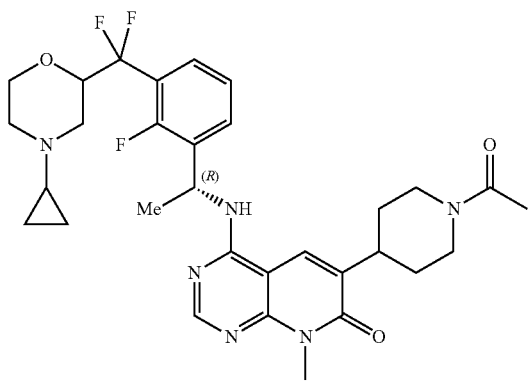 |
| Example 56. | 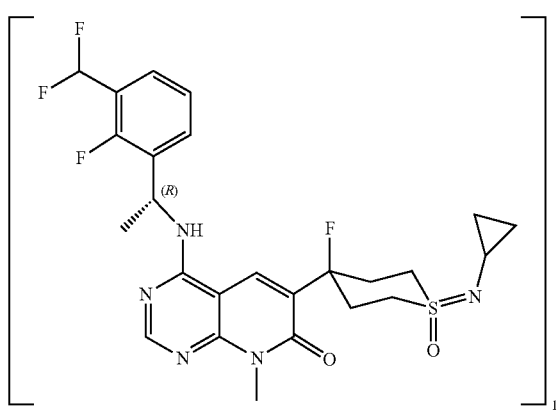 |

TABLE A-continued
| Example # | Structure |
|---|---|
| Example 56-1. | 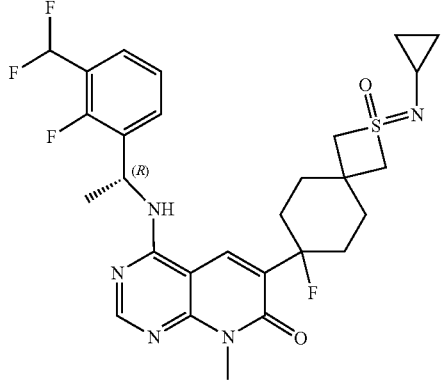 |
| Example 56-2. | 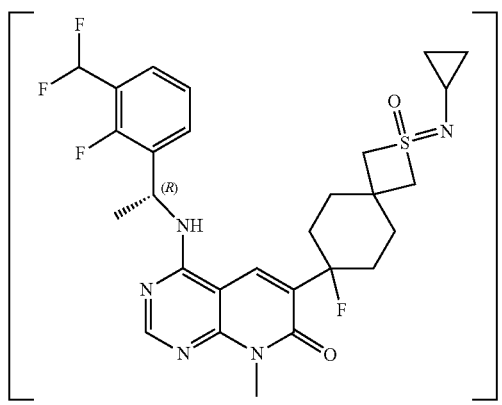 |
| Example 56-3. | 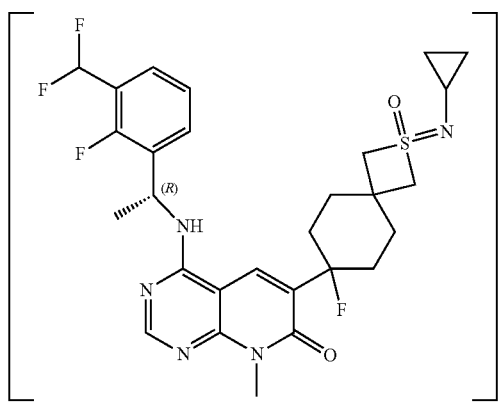 |
| Example 56-4. | 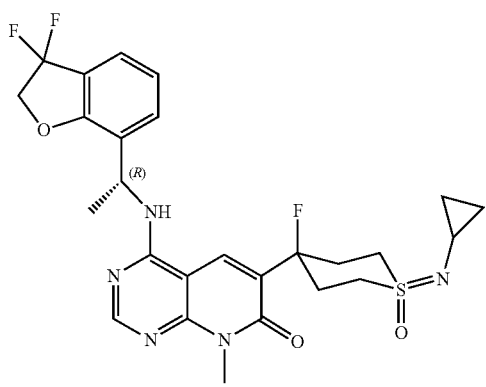 |

TABLE A-continued

| Example # | Structure |
|---|---|
| Example 56-5. | 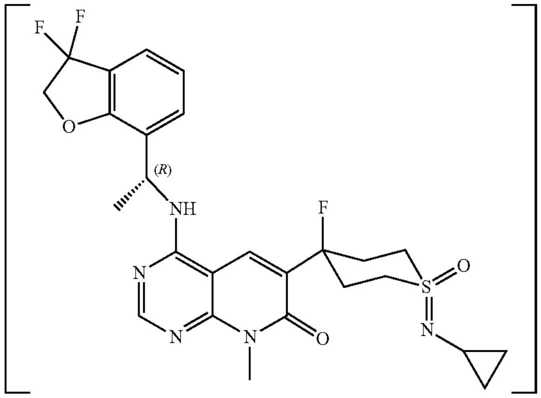 |
| Example 57. | 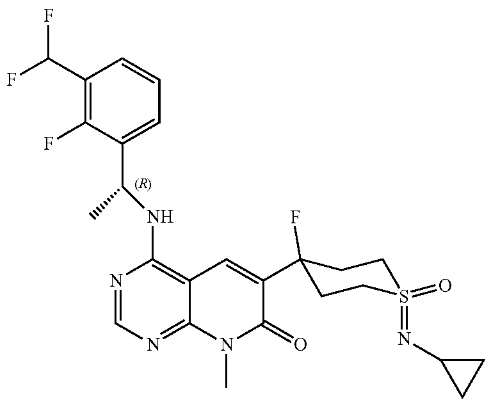 |
| Example 58. | 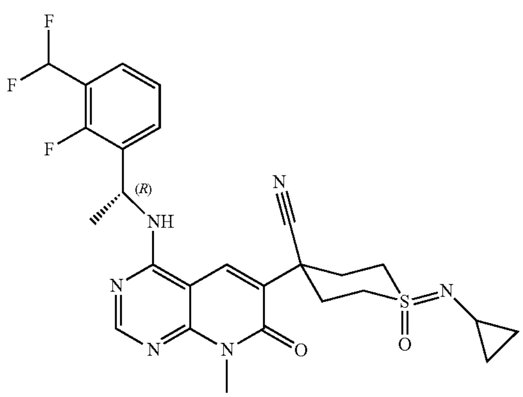 |
| Example 58-1. | 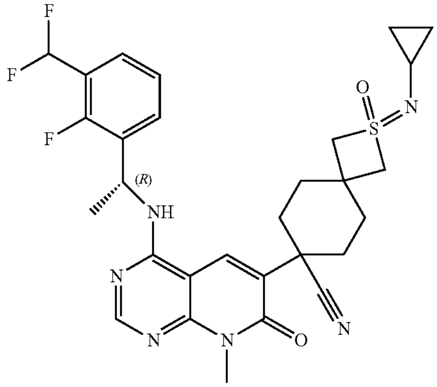 |

249 250
TABLE A-continued
| Example # | Structure |
|---|---|
| Example 58-2. | 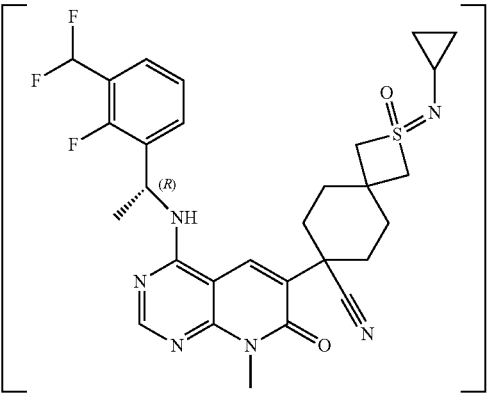 |
| Example 58-3. | 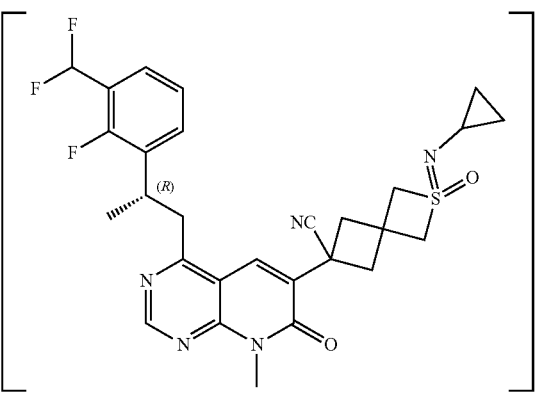 |
| Example 58-4. | 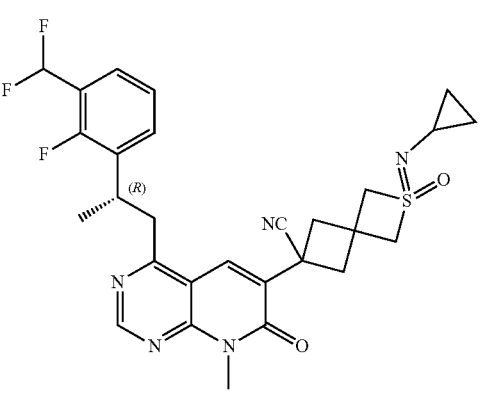 |
| Example 59. | 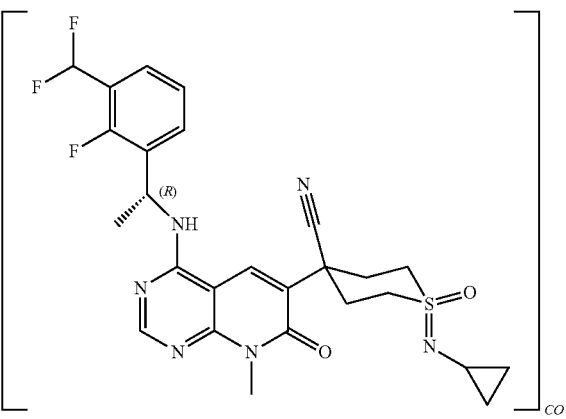 |

251 252
TABLE A-continued
| Example # | Structure |
|---|---|
| Example 60. | 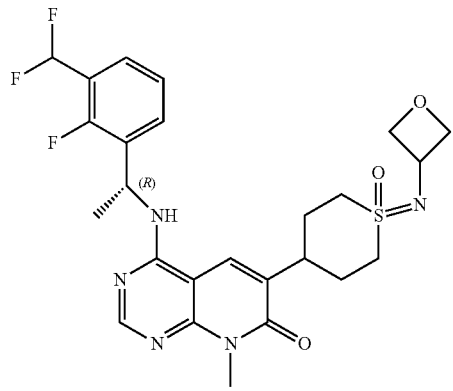 |
| Example 61. | 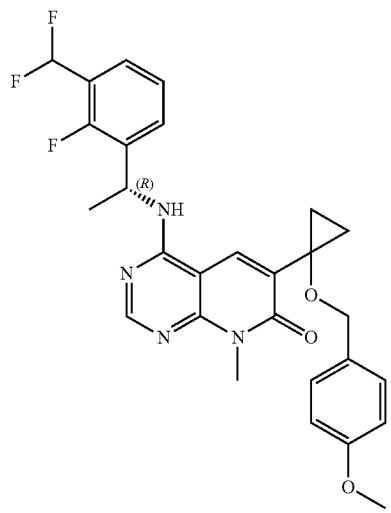 |
| Example 62. | 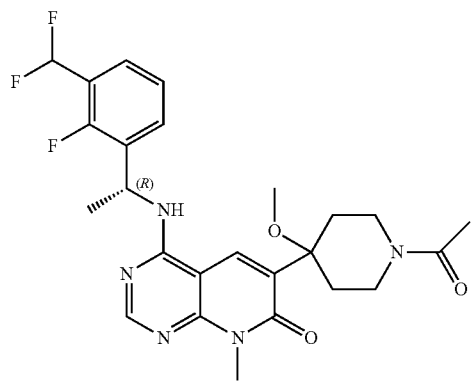 |

TABLE A-continued
| Example # | Structure |
|---|---|
| Example 63. | 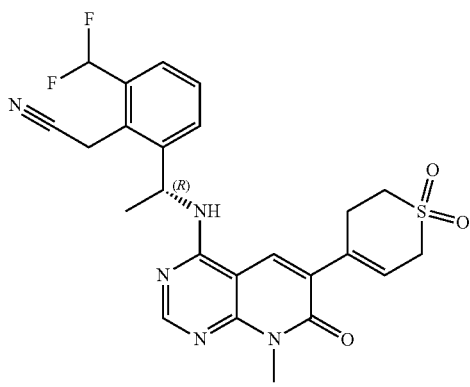 |
| Example 64. | 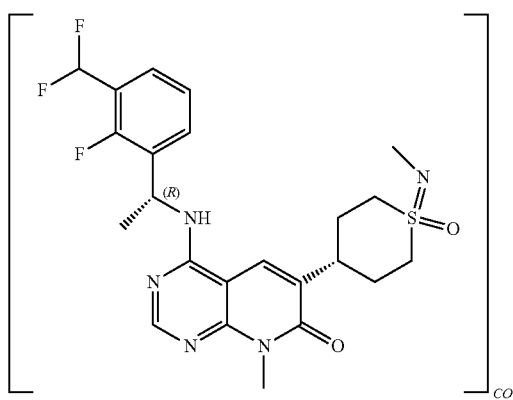 |
| Example 64-1. | 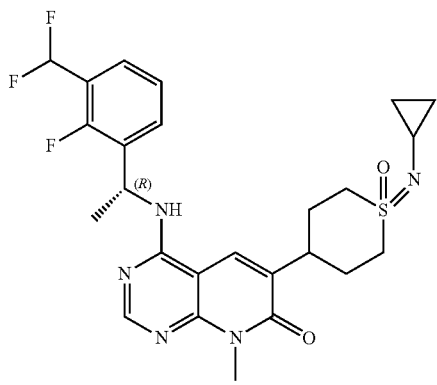 |
| Example 64-2. | 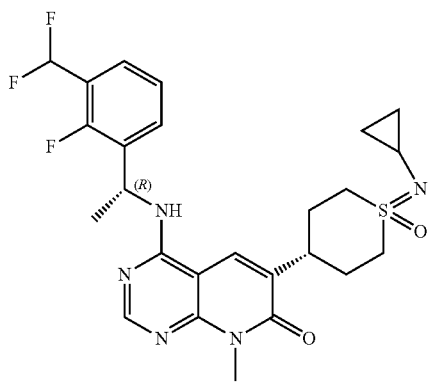 |

TABLE A-continued
| Example # | Structure |
|---|---|
| Example 64-3. | 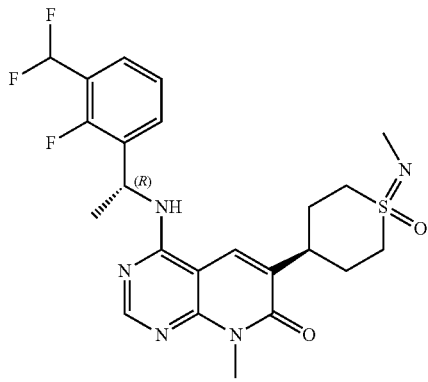 |
| Example 65. | 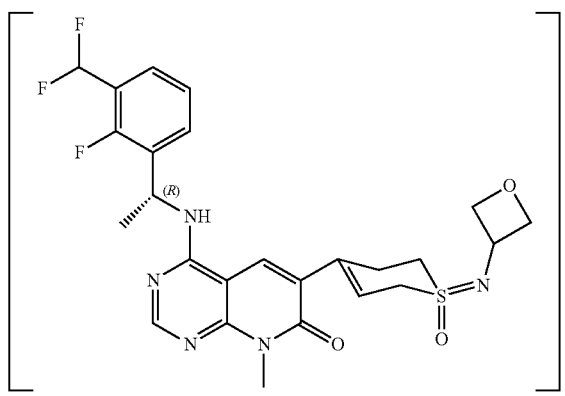 |
| Example 66. | 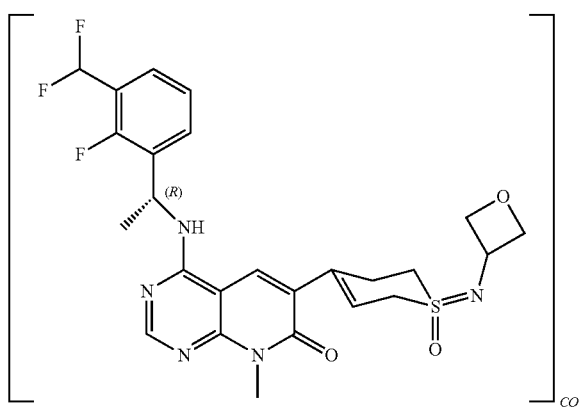 |
| Example 67. | 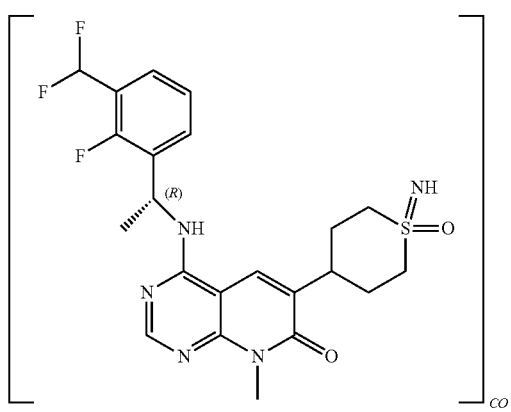 |

TABLE A-continued
| Example # | Structure |
|---|---|
| Example 68. | 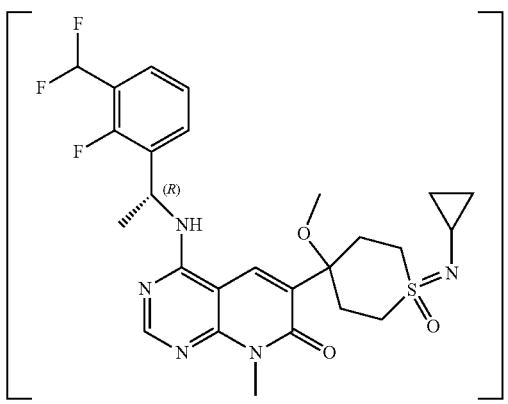 |
| Example 68-1. | 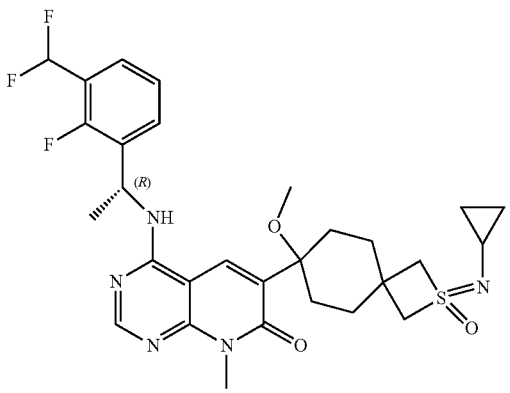 |
| Example 68-2. | 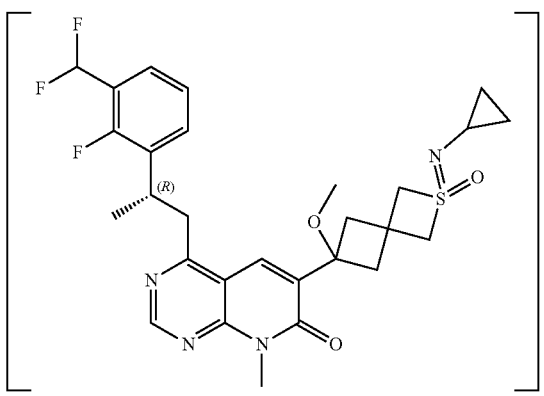 |
| Example 68-3. | 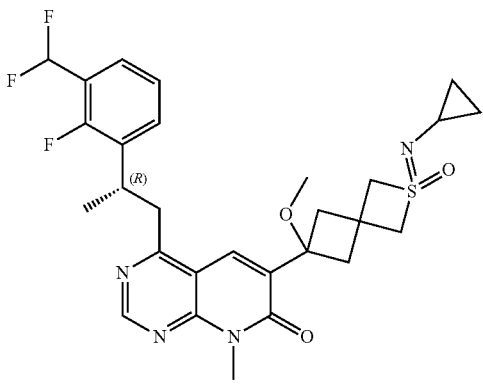 |

TABLE A-continued
| Example # | Structure |
|---|---|
| Example 69. | 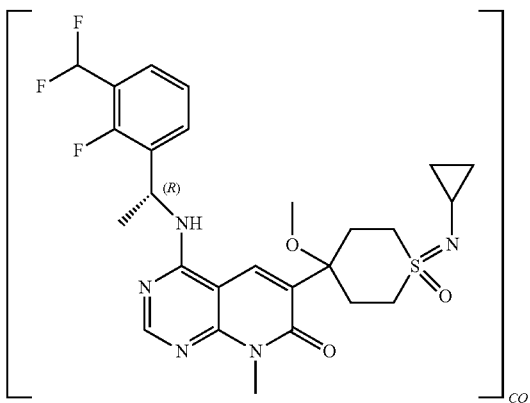 |
| Example 70. | 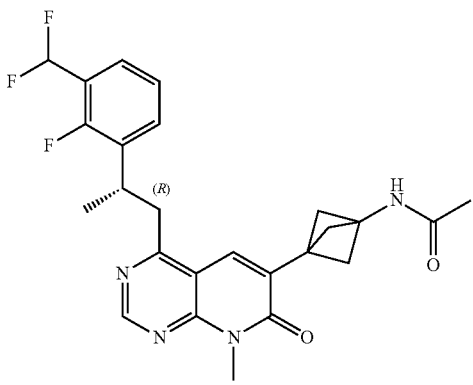 |
| Example 71. | 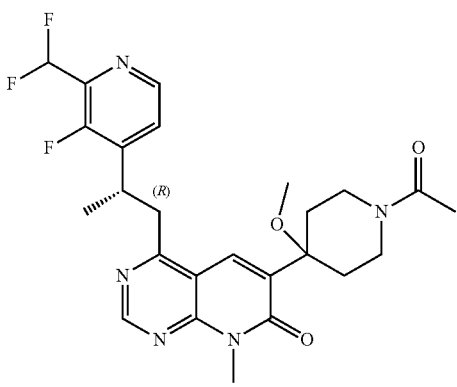 |
| Example P-1. | 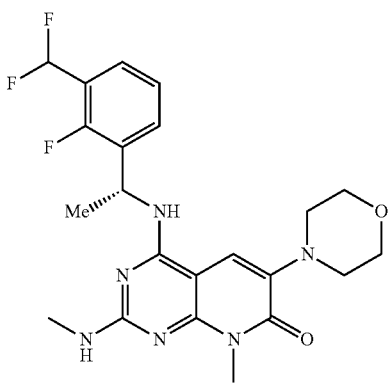 [SMILES: CNc1nc(N[C@H](C)c2cccc(C(F)F)c2F)c2cc(N3CCOCC3)c(=O)n(C)c2n1] |

TABLE A-continued
| Example # | Structure |
|---|---|
| Example P-2. | 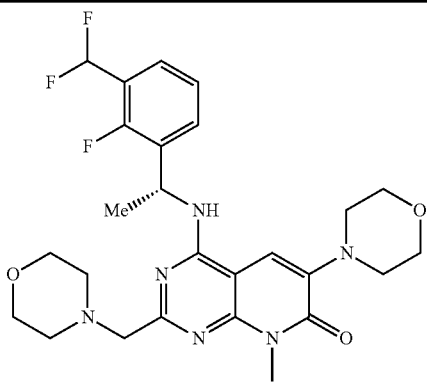 |
| Example P-3. | 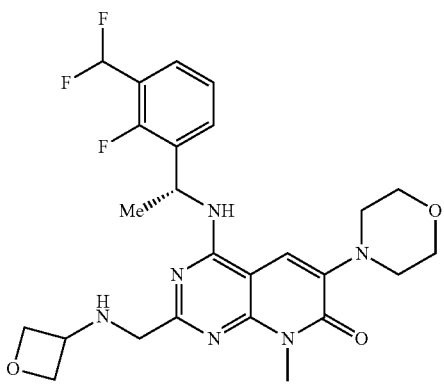 [SMILES: C[C@@H](Nc1nc(CNC2COC2)nc2c1cc(N1CCOCC1)c(=O)n2C)c1cccc(C(F)F)c1F] |
| Example P-4. | 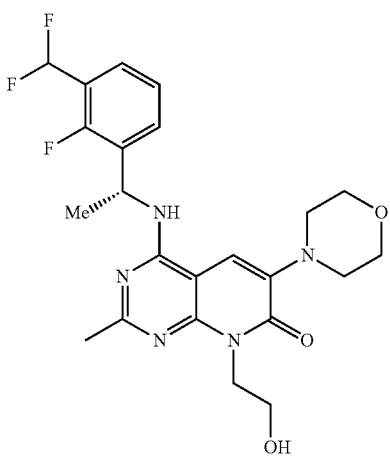 [SMILES: Cc1nc(N[C@H](C)c2cccc(C(F)F)c2F)c2cc(N3CCOCC3)c(=O)n(CCO)c2n1] |
| Example P-5. | 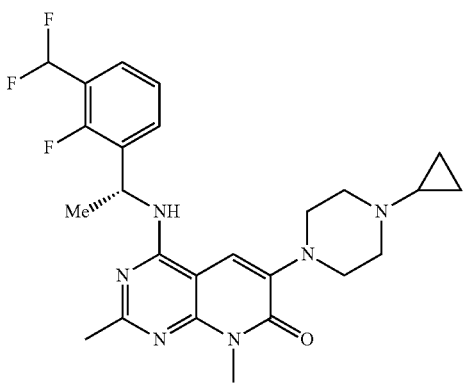 [SMILES: Cc1nc(N[C@H](C)c2cccc(C(F)F)c2F)c2cc(N3CCN(C4CC4)CC3)c(=O)n(C)c2n1] |

TABLE A-continued

| Example # | Structure |
|---|---|
| Example P-6. | (structure) |
| Example P-7. | (structure) |
| Example P-8. | (structure) |
| Example P-9. | (structure) |

TABLE A-continued
| Example # | Structure |
|---|---|
| Example P-10. | 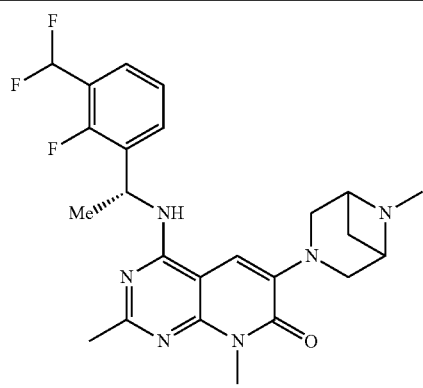 |
| Example P-11. | 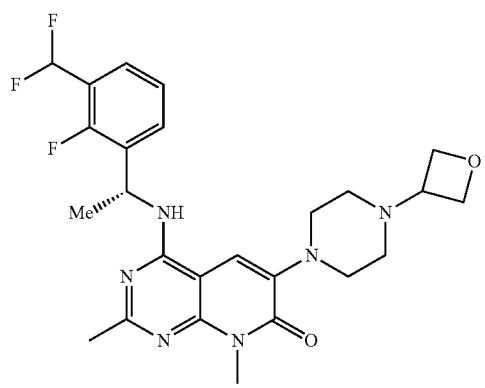 [SMILES: Cc1nc(N[C@H](C)c2cccc(C(F)F)c2F)c2cc(N3CCN(C4COC4)CC3)c(=O)n(C)c2n1] |
| Example P-12. | 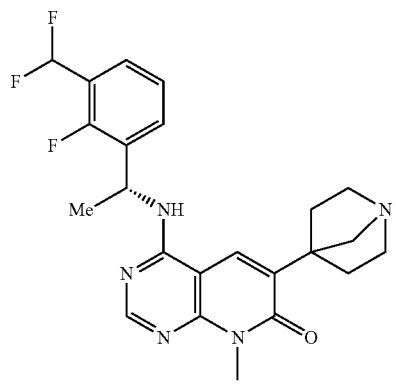 [SMILES: C[C@@H](Nc1ncnc2c1cc(C13CCN(CC1)C3)c(=O)n2C)c1cccc(C(F)F)c1F] |
| Example P-13. | 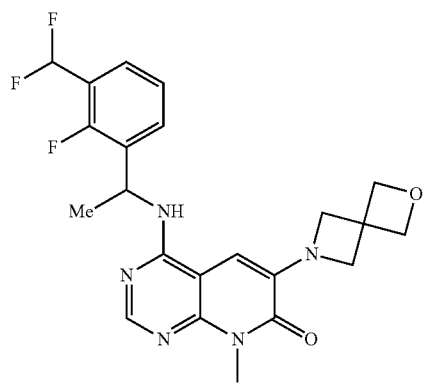 [SMILES: CC(Nc1ncnc2c1cc(N1CC3(COC3)C1)c(=O)n2C)c1cccc(C(F)F)c1F] |

TABLE A-continued
| Example # | Structure |
|---|---|
| Example P-14. | 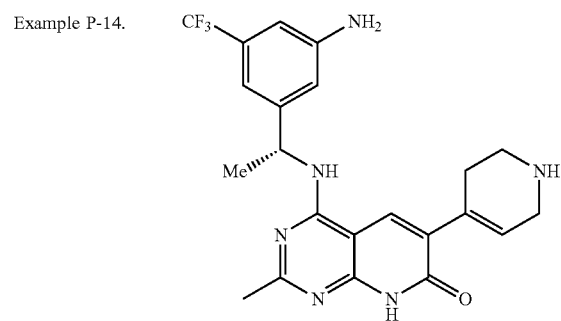 |
| Example P-15. | 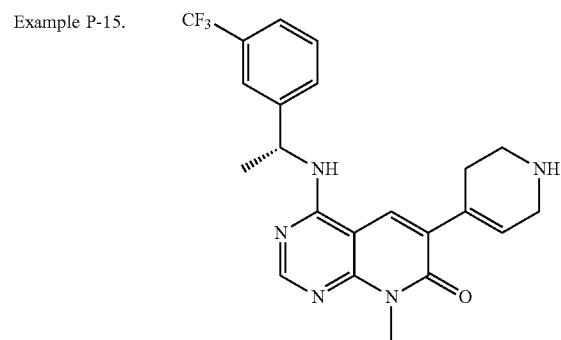 |
| Example P-16. | 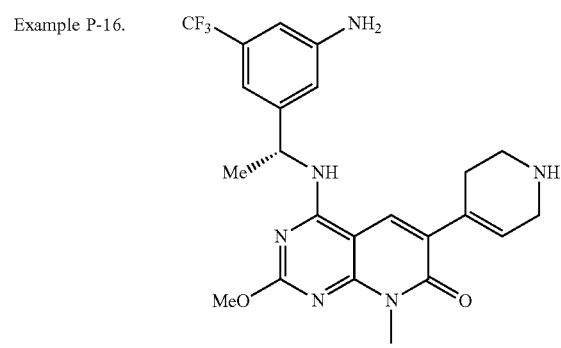 |
| Example P-17. | 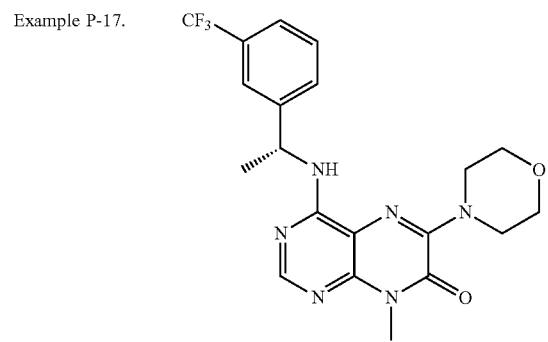 |

TABLE A-continued
| Example # | Structure |
|---|---|
| Example P-18. | 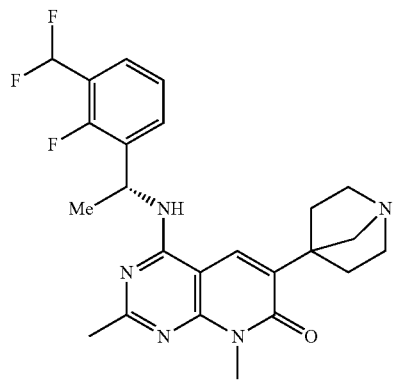 [SMILES: Cc1nc(N[C@H](C)c2cccc(C(F)F)c2F)c2cc(C34CCN(CC3)C4)c(=O)n(C)c2n1] |
| Example P-19. | 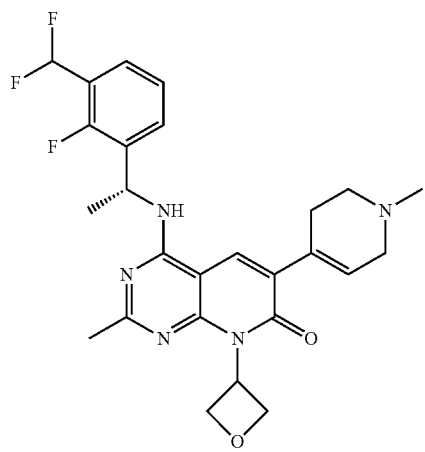 [SMILES: Cc1nc(N[C@H](C)c2cccc(C(F)F)c2F)c2cc(C3=CCN(C)CC3)c(=O)n(C3COC3)c2n1] |
| Example P-20. | 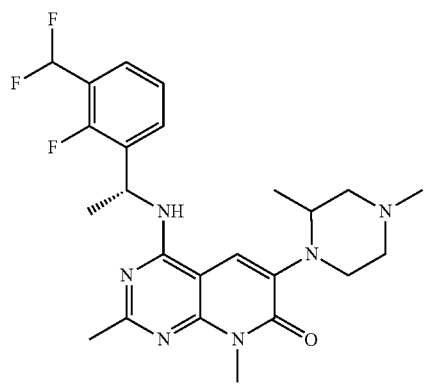 [SMILES: Cc1nc(N[C@H](C)c2cccc(C(F)F)c2F)c2cc(N3CCN(C)CC3C)c(=O)n(C)c2n1] |

TABLE A-continued

| Example # | Structure |
|---|---|
| Example P-21. | 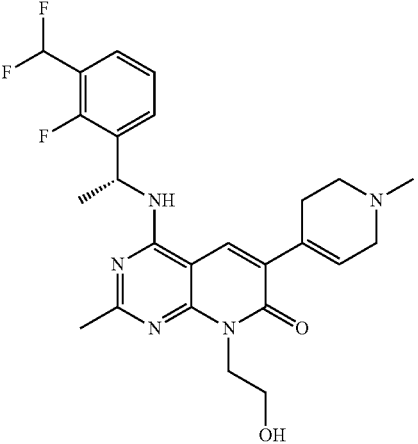 [SMILES: Cc1nc(N[C@H](C)c2cccc(C(F)F)c2F)c2cc(C3=CCN(C)CC3)c(=O)n(CCO)c2n1] |

Note:
any compound shown in brackets in Table A above and anywhere herein indicates that the compound is a diastereomer, and the absolute stereochemistry of such diastereomer may not be known.

The present disclosure provides a compound, and pharmaceutically acceptable salts, solvates, stereoisomers, and tautomers thereof, selected from the group consisting of compounds of Collection 1:

Collection 1: Certain Compounds of the Present Invention

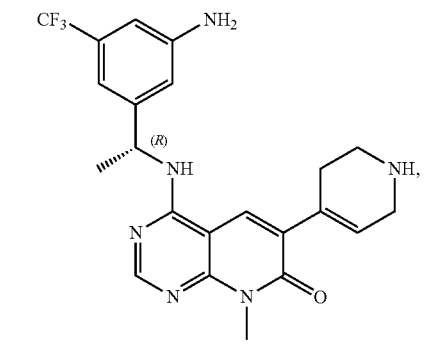

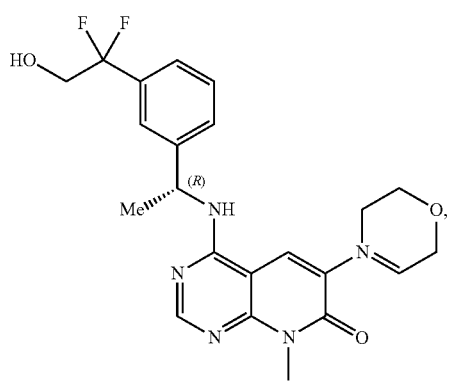

-continued

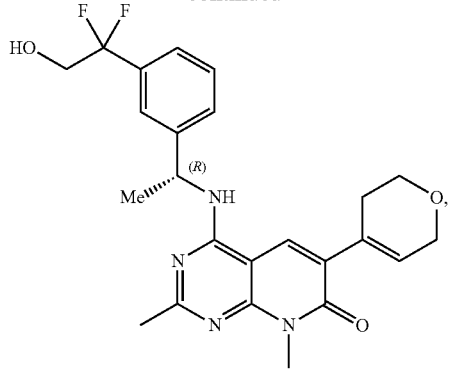

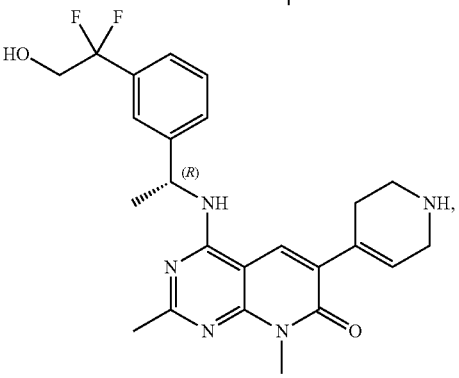

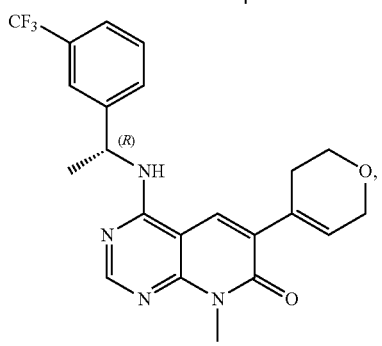

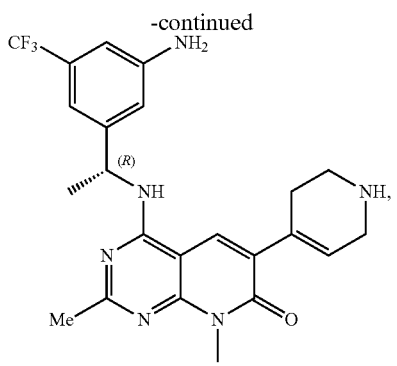
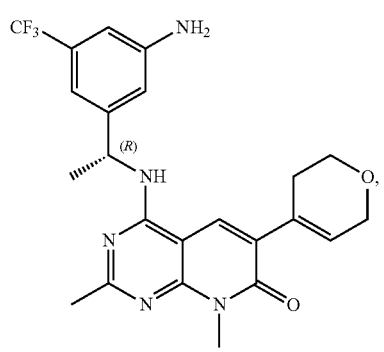
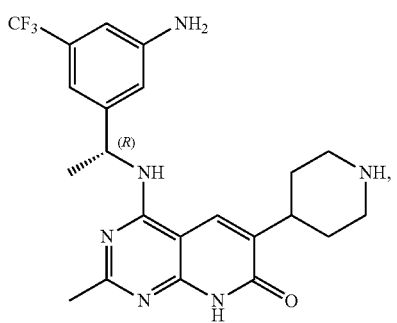
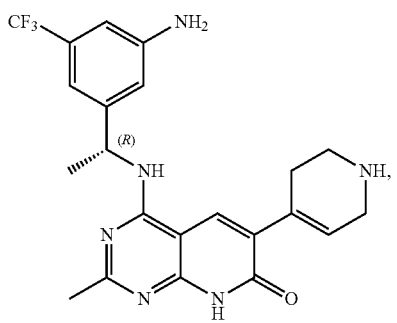
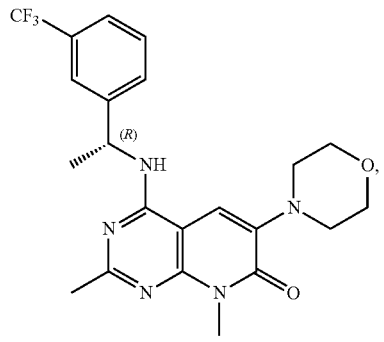
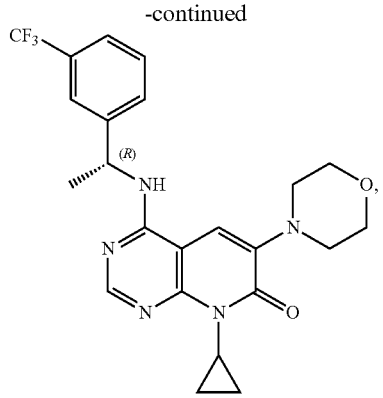
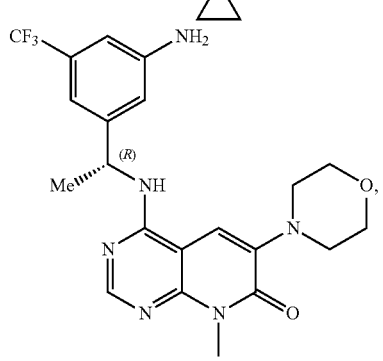
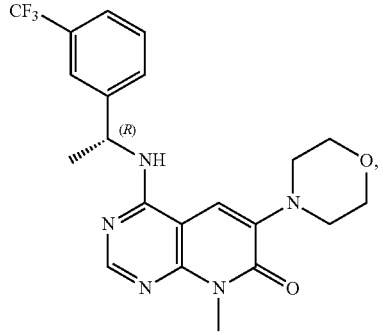
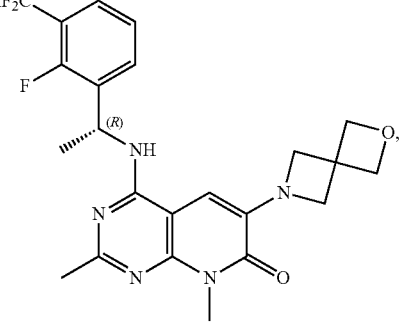
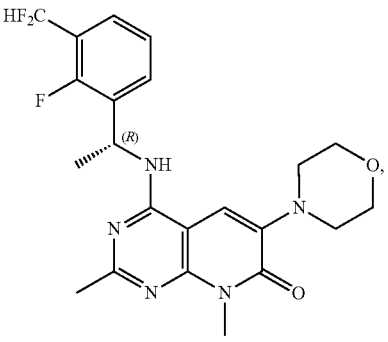

275
-continued
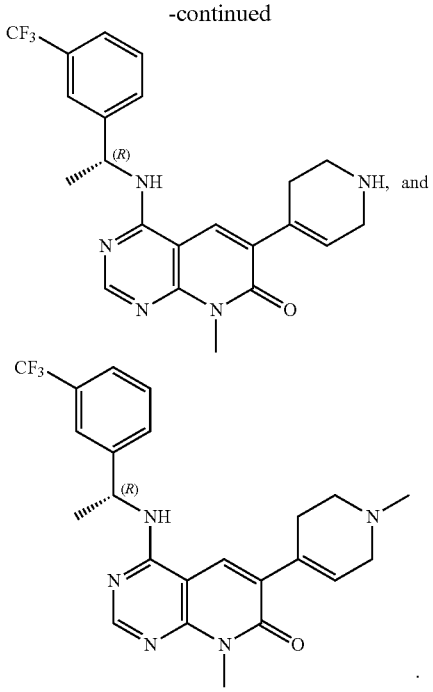
The present disclosure provides a compound, and pharmaceutically acceptable salts, solvates, stereoisomers, and tautomers thereof, selected from the group consisting of compounds of Collection 2:
Collection 2: Certain Compounds of the Present Invention
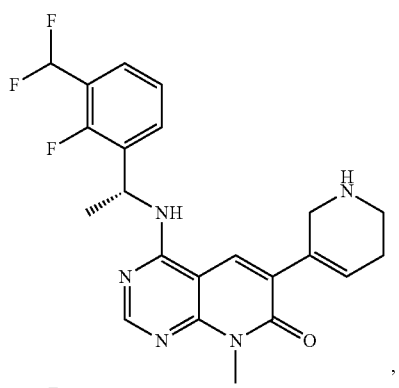
,
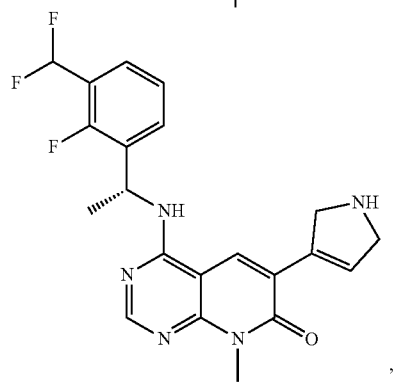
,
276
-continued
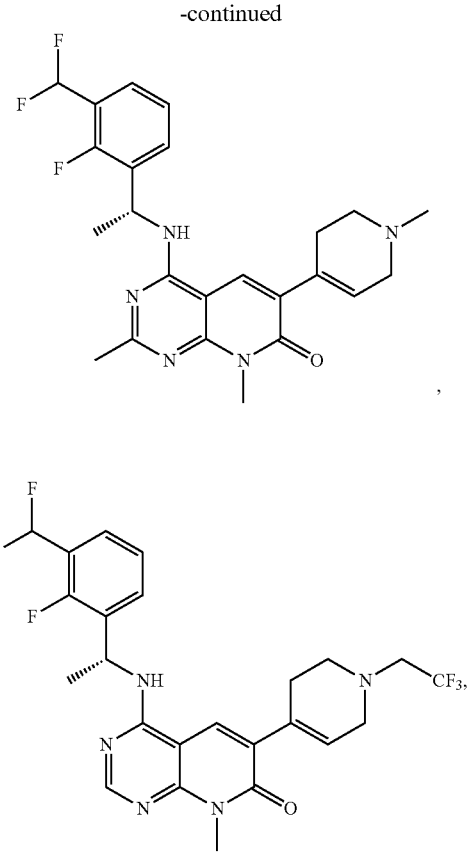
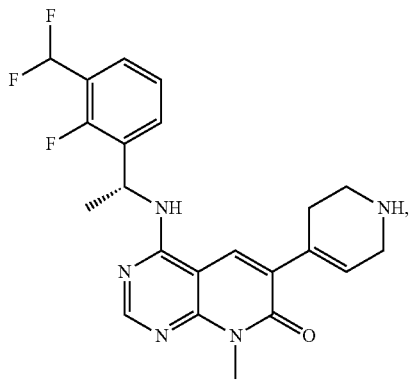
,
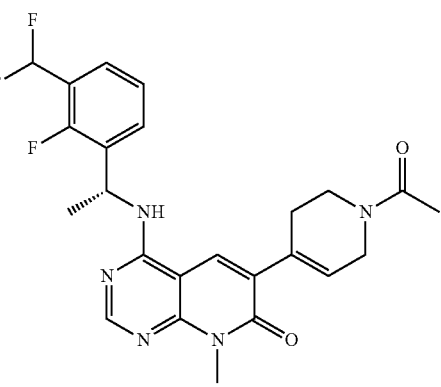
, 277
-continued
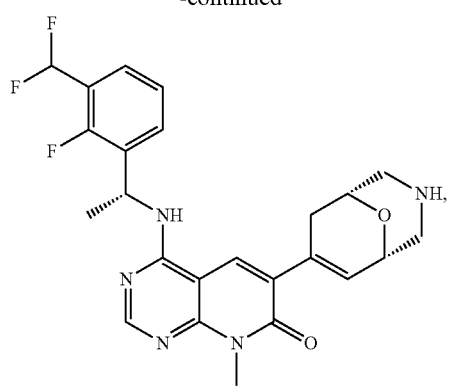
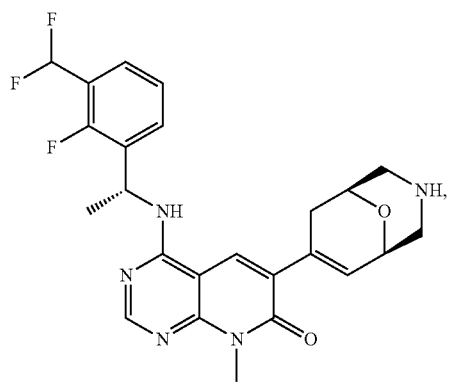
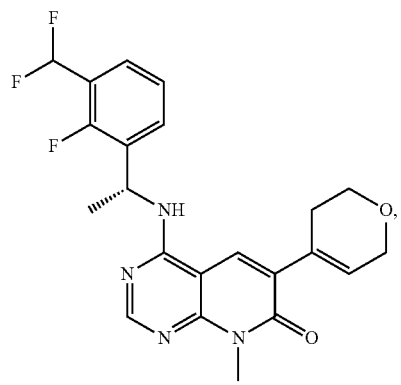
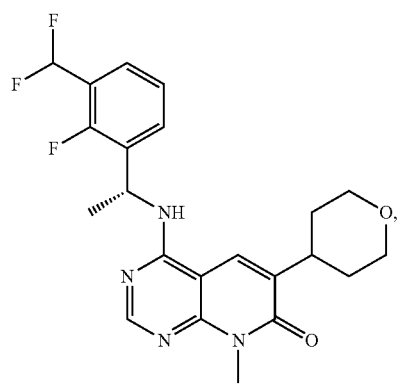
278
-continued
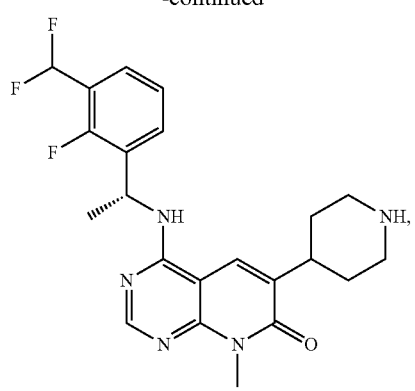
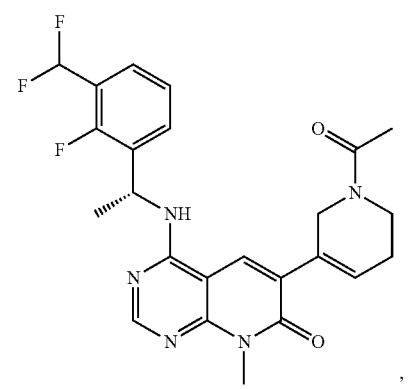
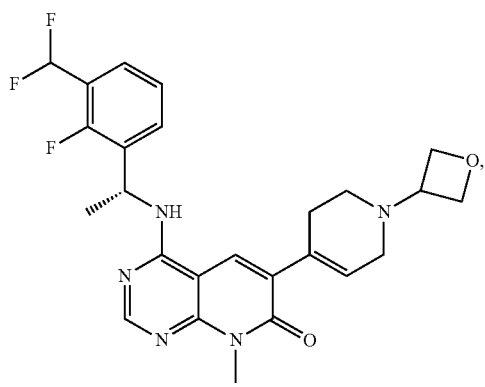
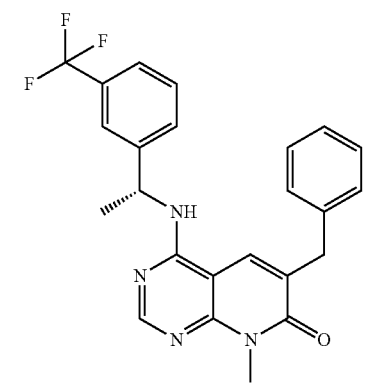

279
-continued
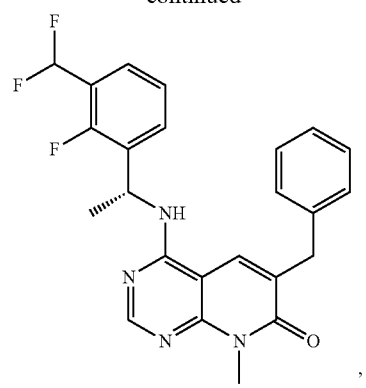
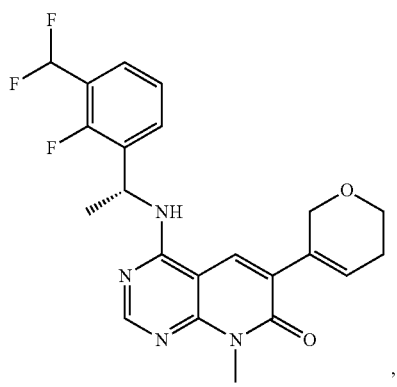
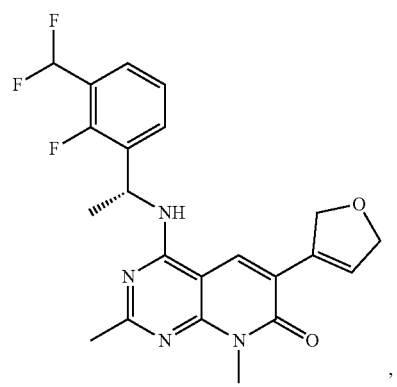
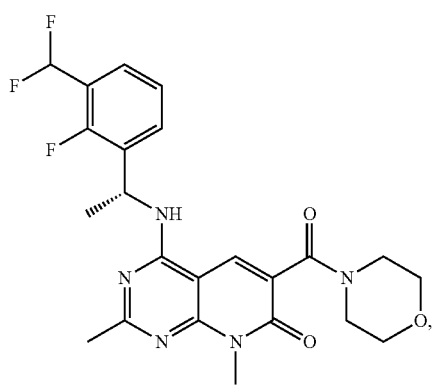
280
-continued
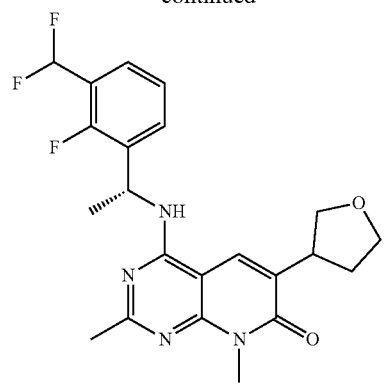
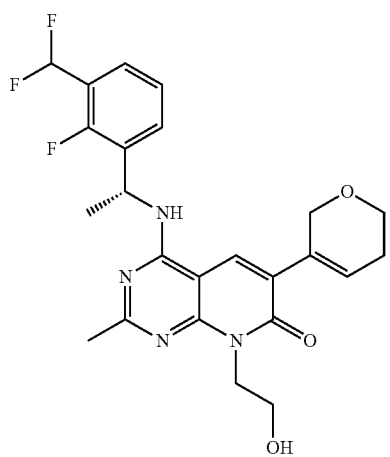
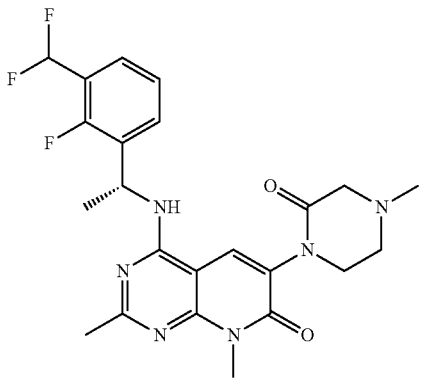
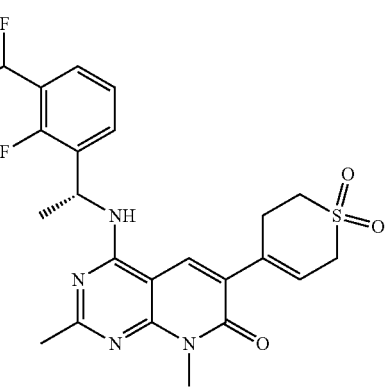

281
-continued
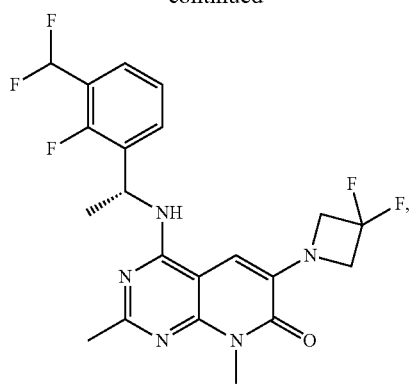
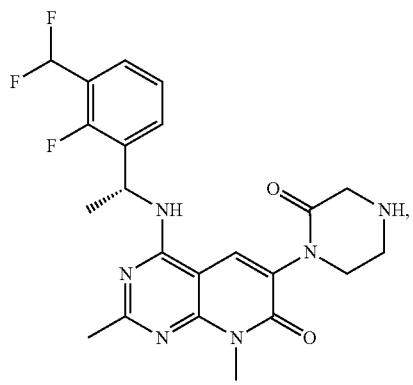
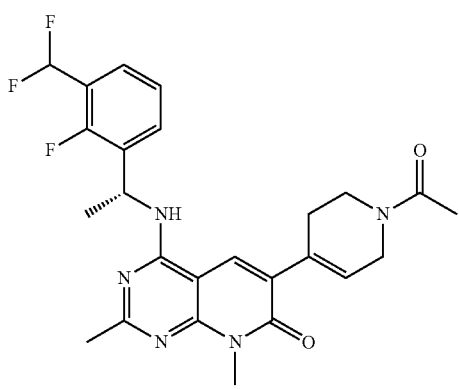
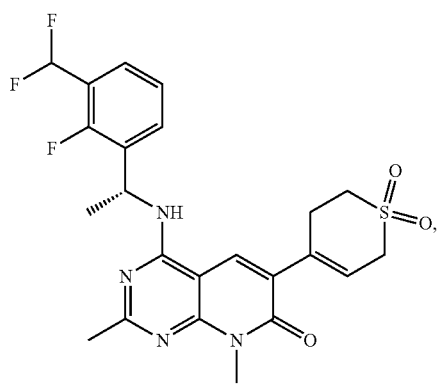
282
-continued
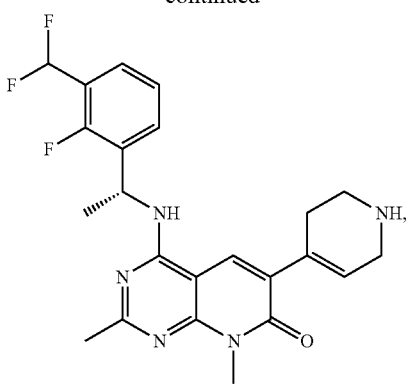
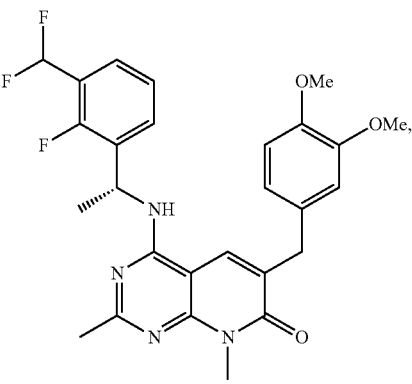
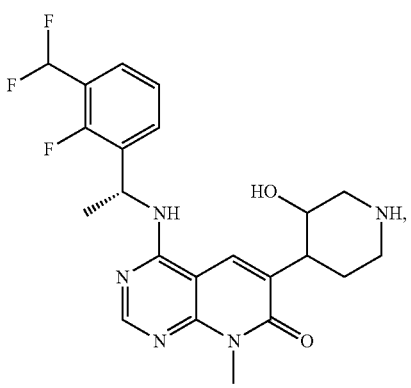
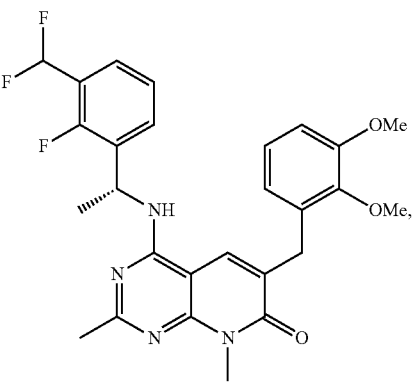

283
-continued
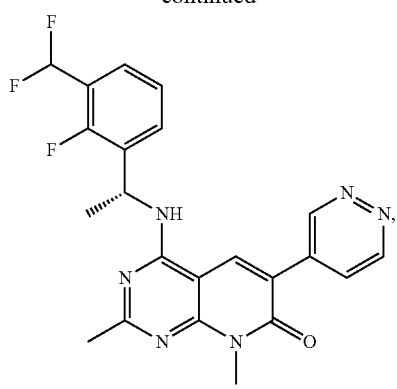
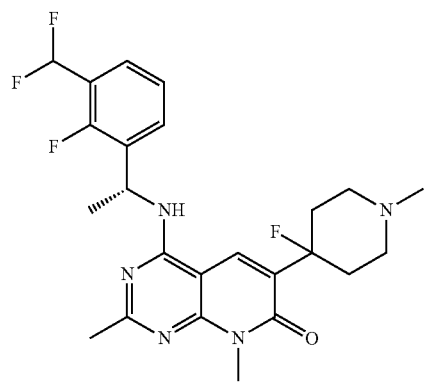
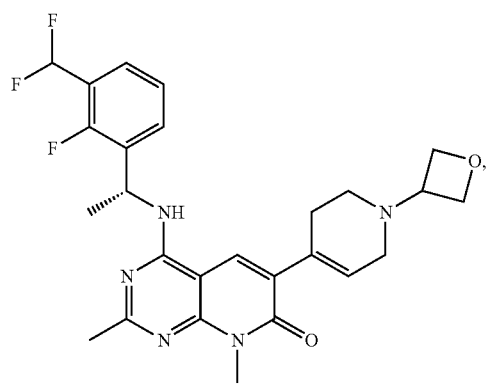
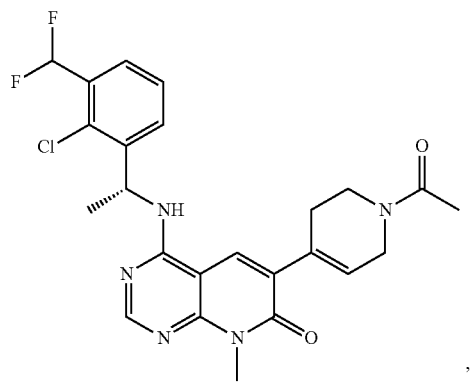
284
-continued
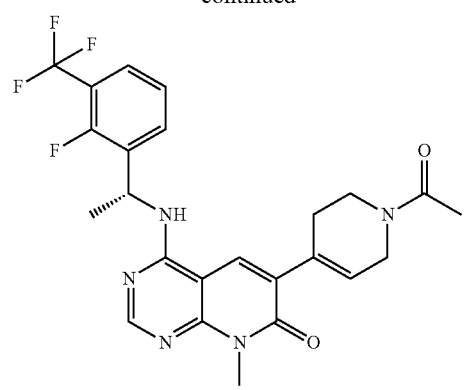
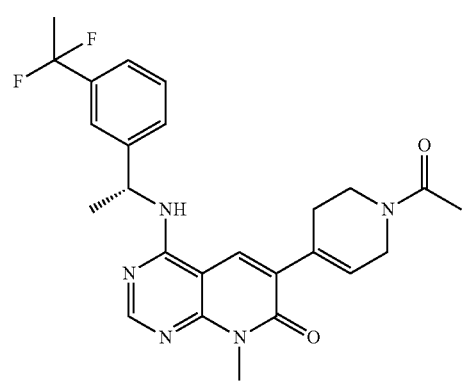
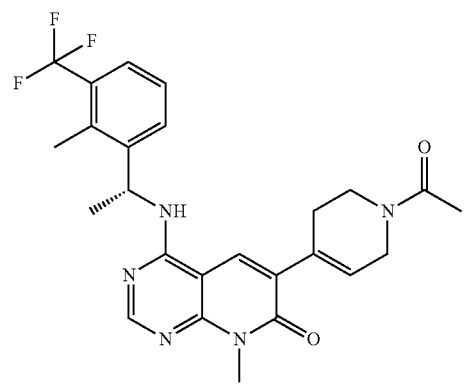
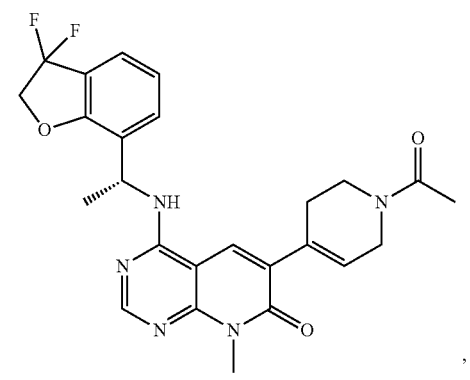

285
-continued
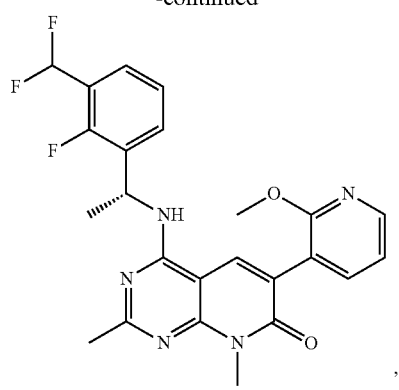
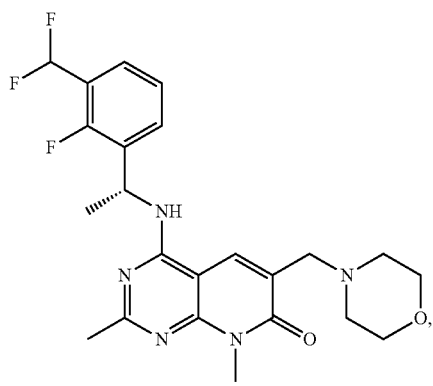
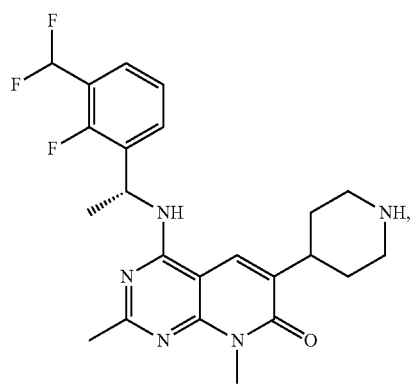
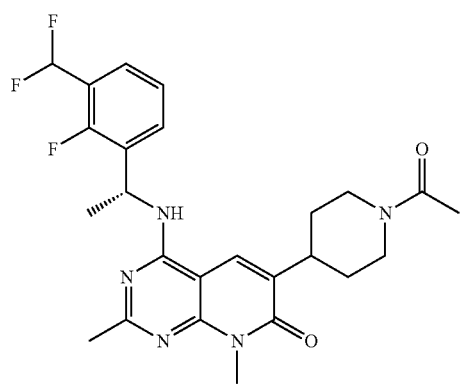
286
-continued
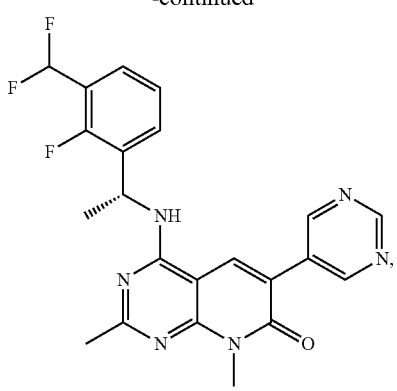
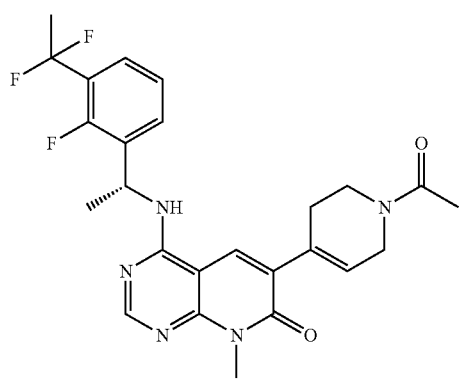
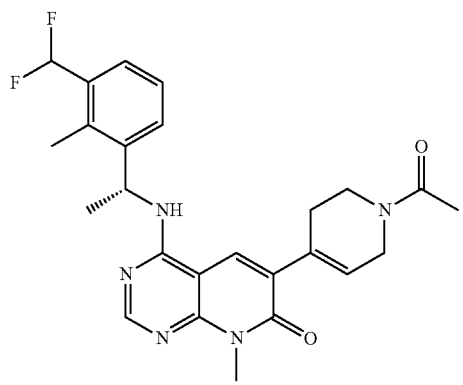
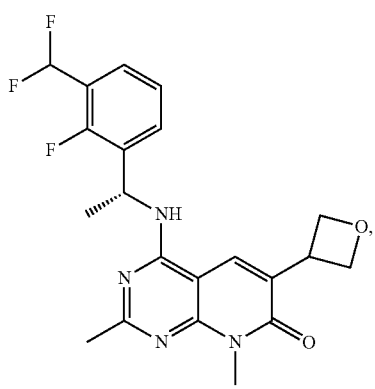

287
-continued
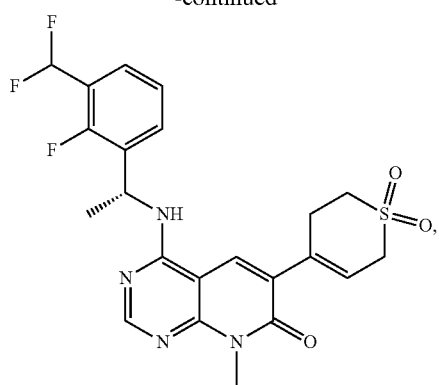
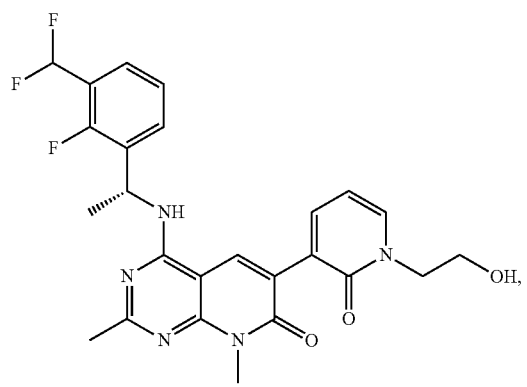
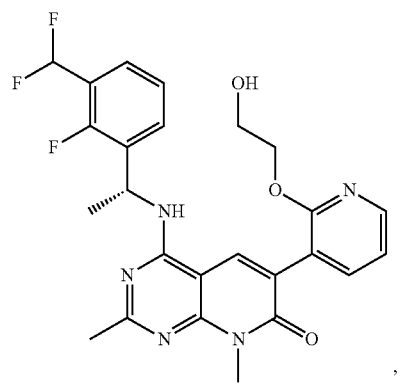
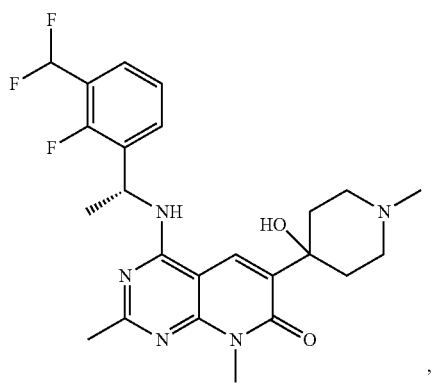
288
-continued
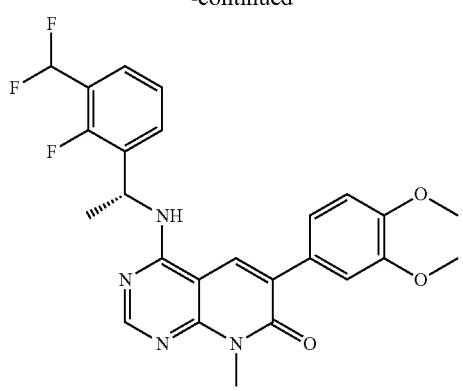
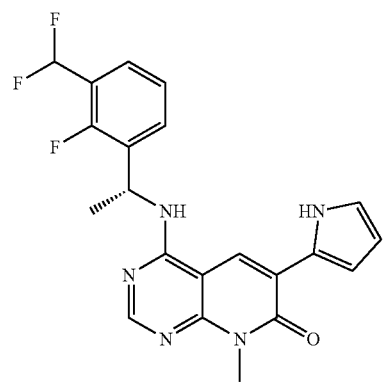
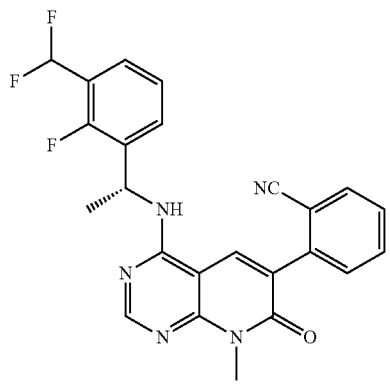
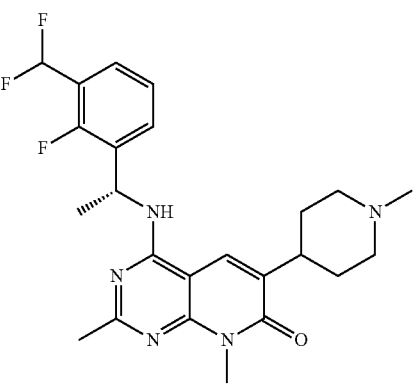

289
-continued
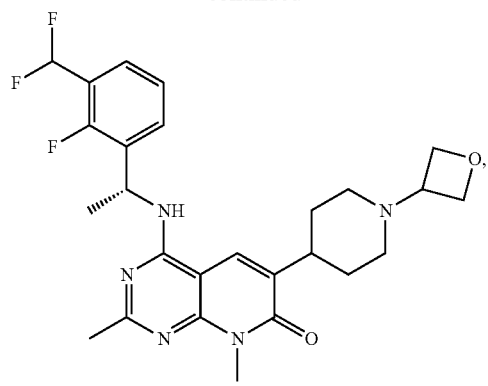
290
-continued
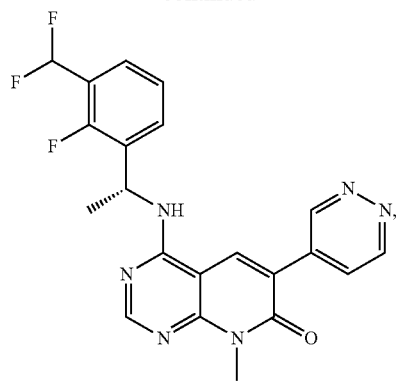
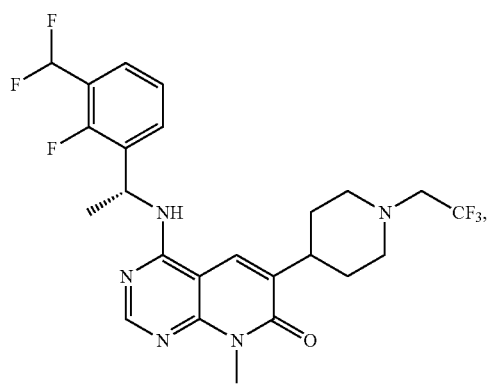
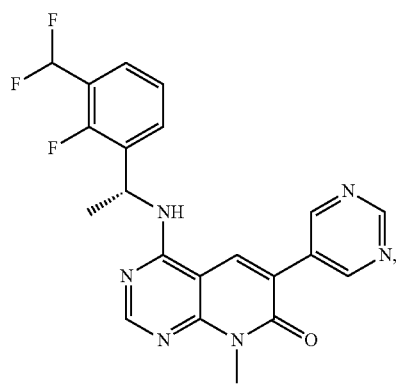
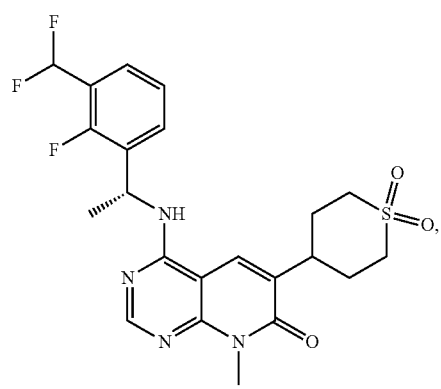
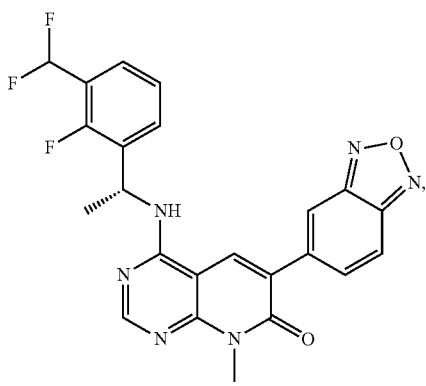
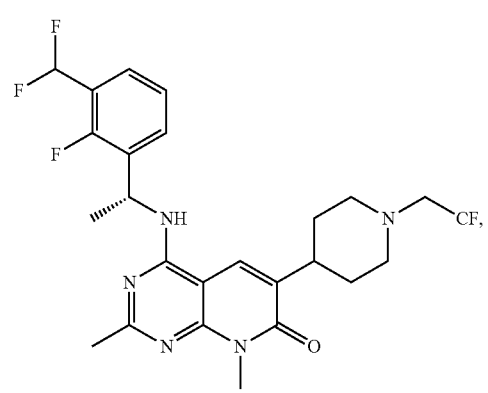
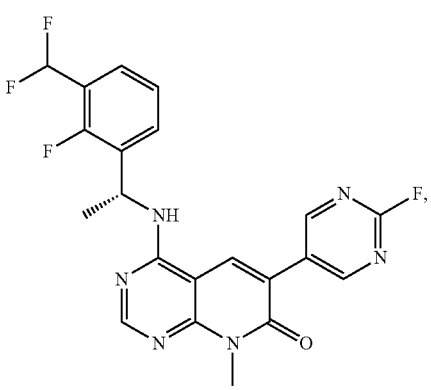

291
-continued
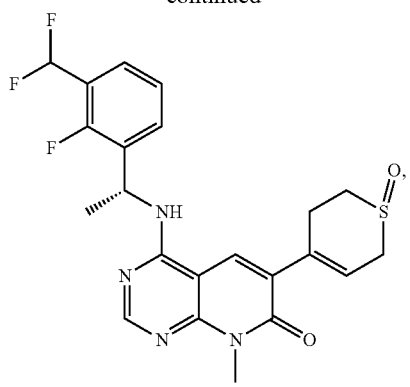
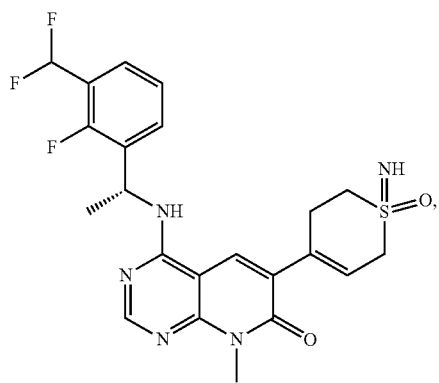
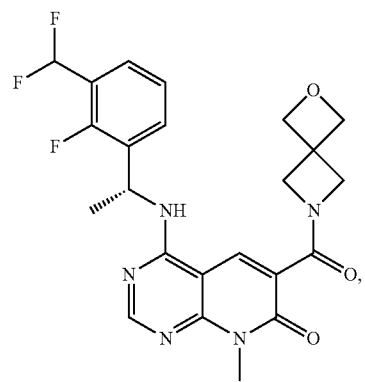
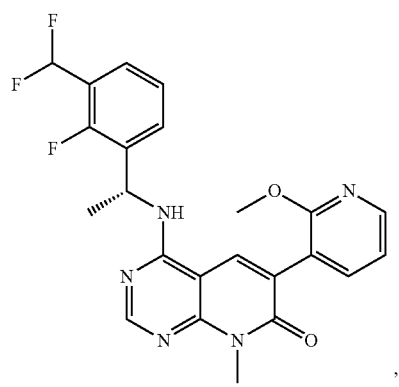
292
-continued
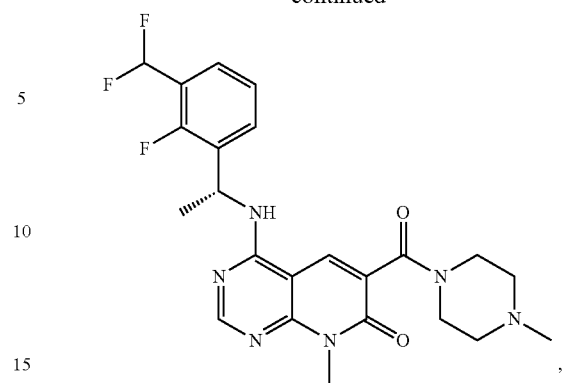
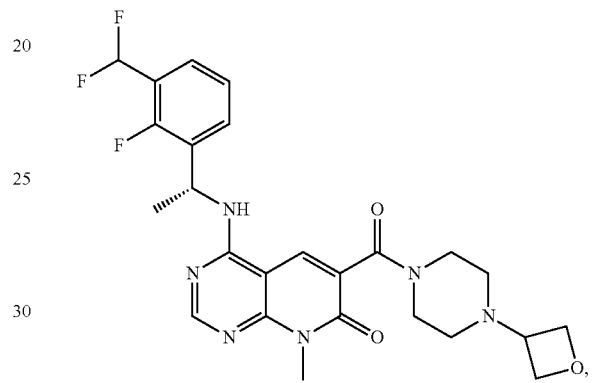
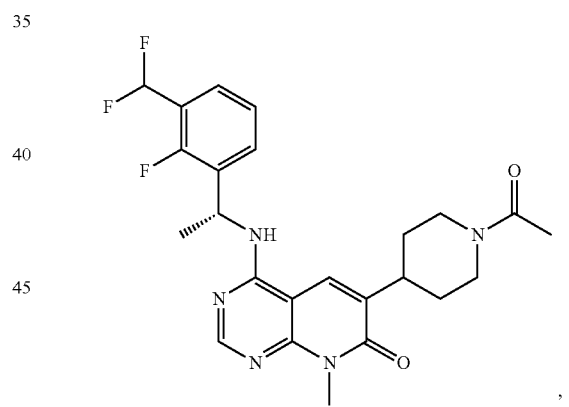
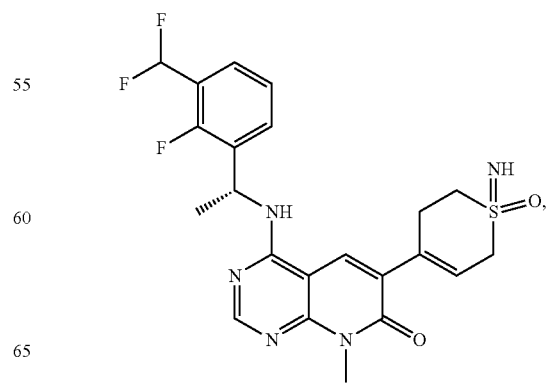

293
-continued
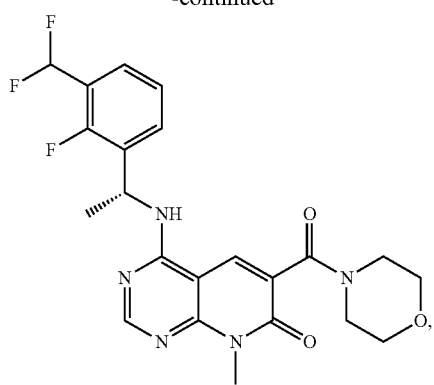
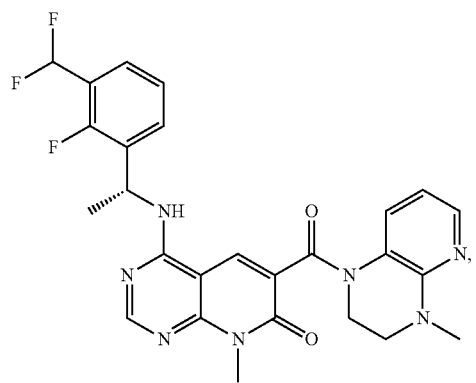
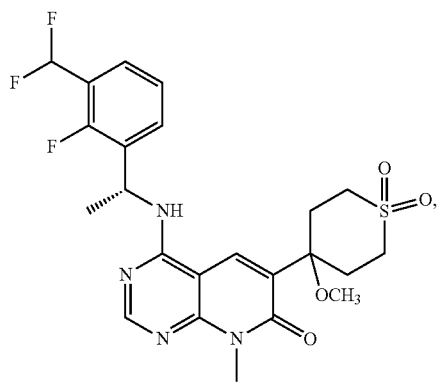
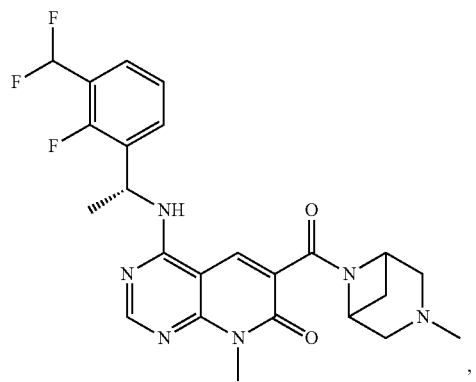
294
-continued
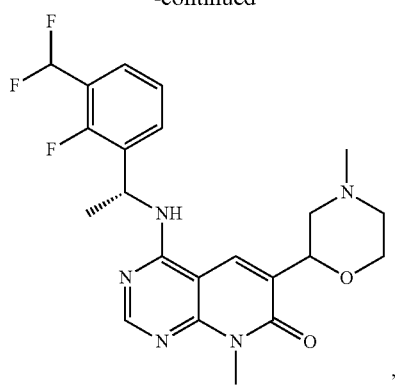
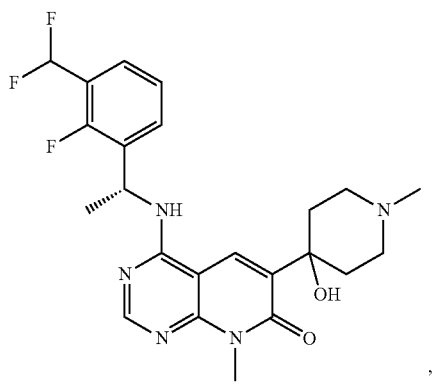 [SMILES: C[C@@H](Nc1ncnc2c1cc(C1(O)CCN(C)CC1)c(=O)n2C)c1cccc(C(F)F)c1F]
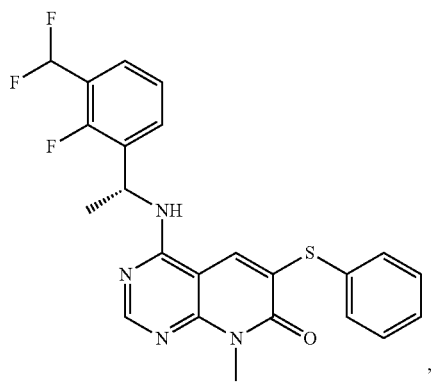
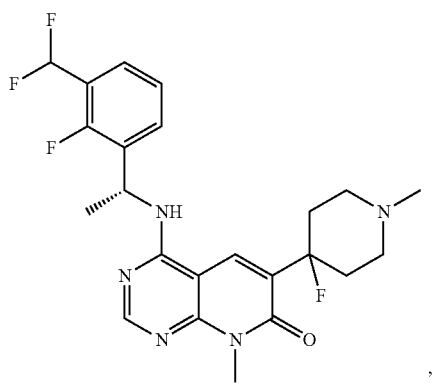

295
-continued
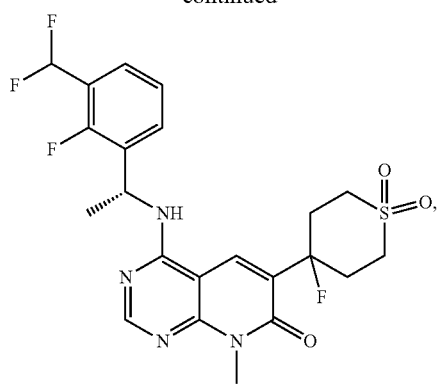
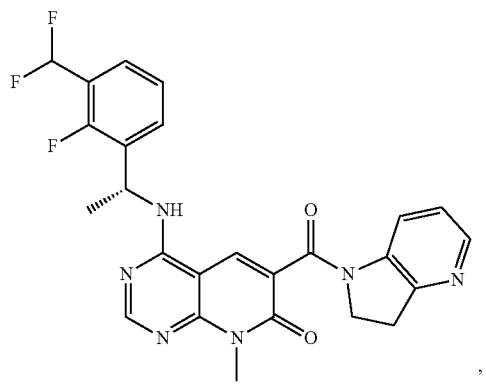
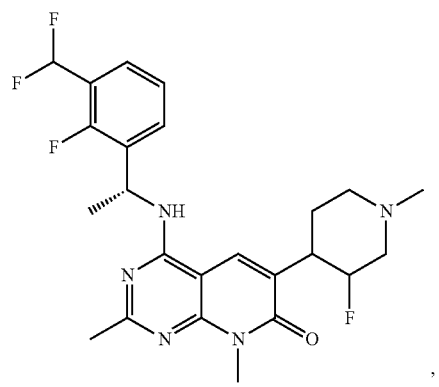
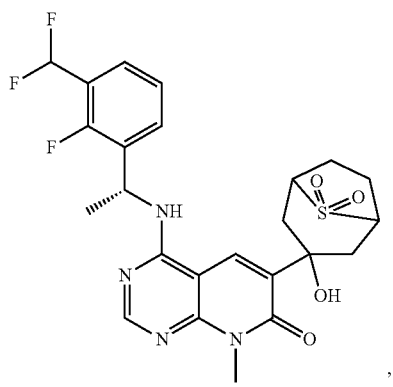
296
-continued
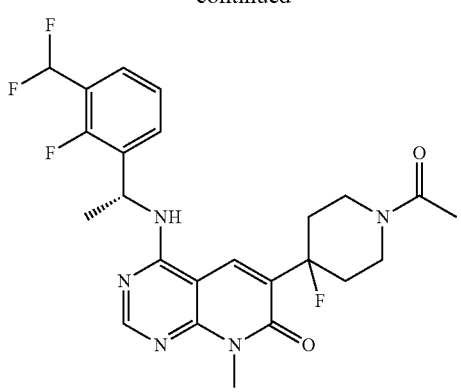
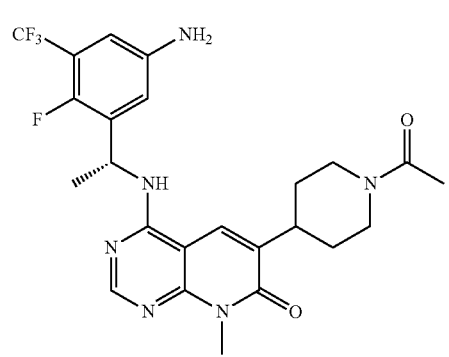
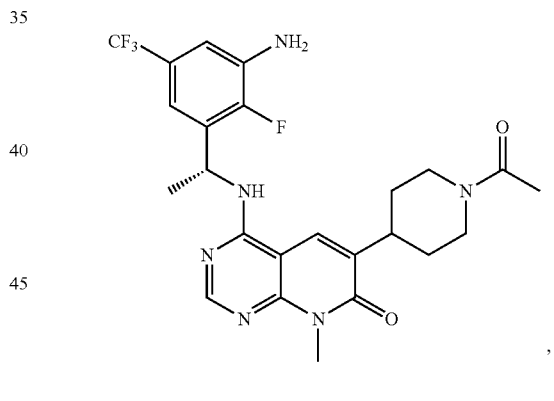
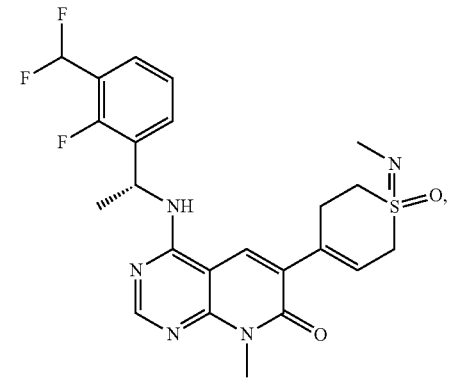

297
-continued
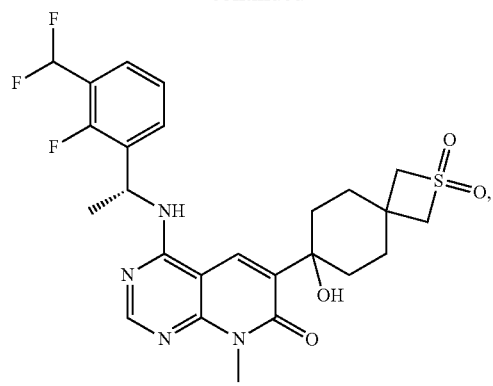
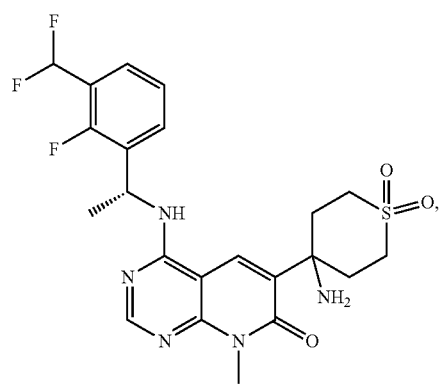
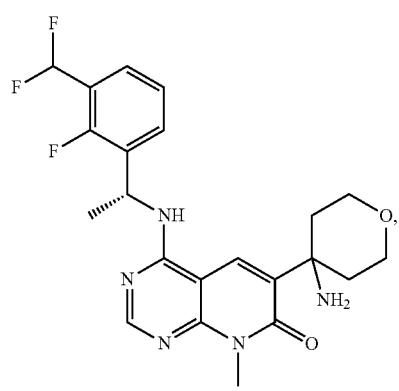
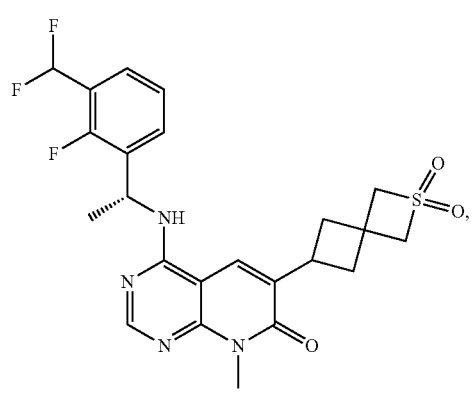
298
-continued
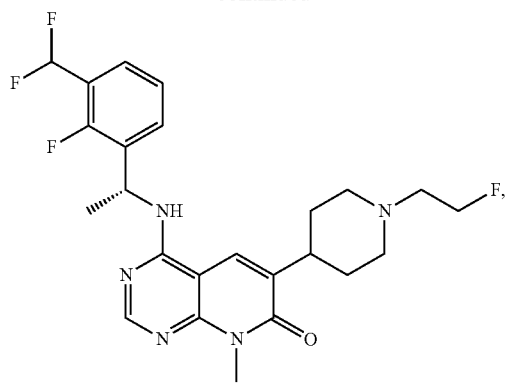
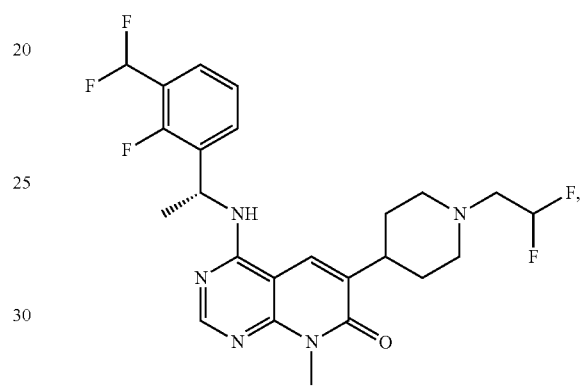
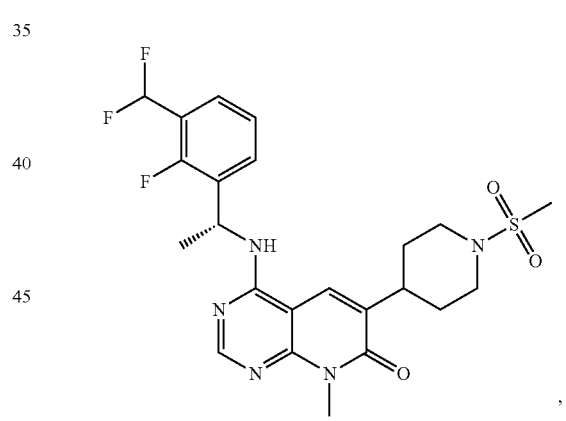
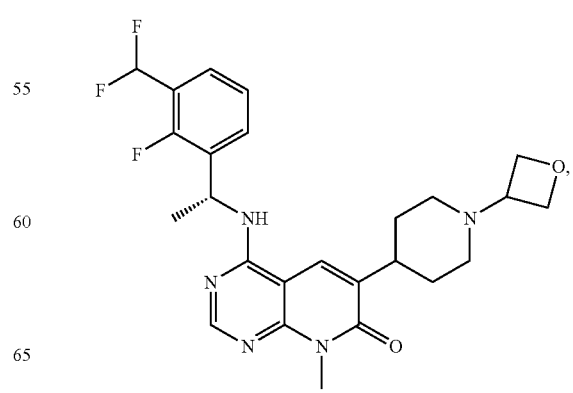

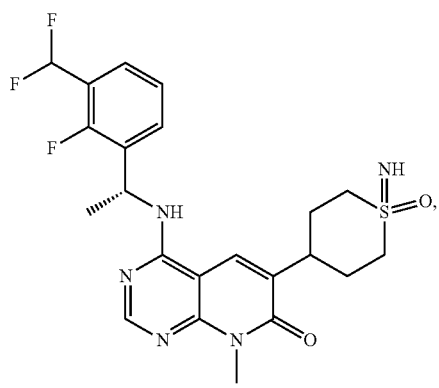
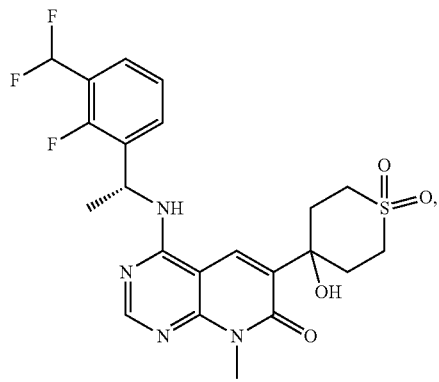
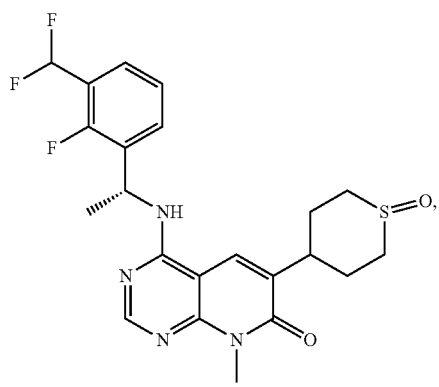
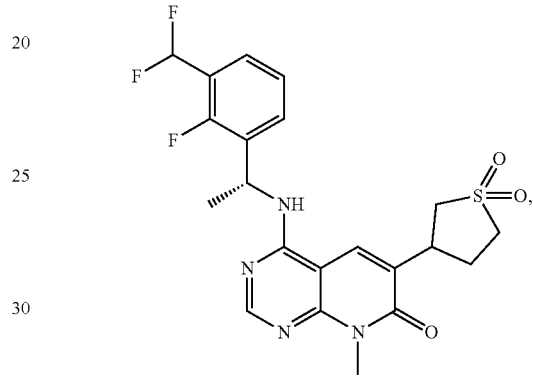
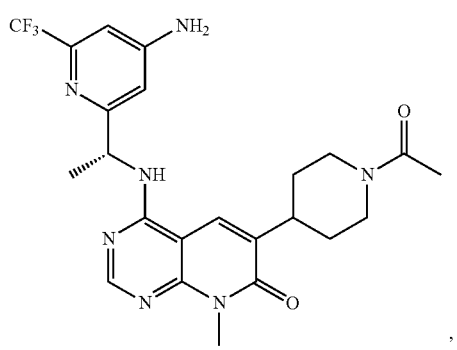
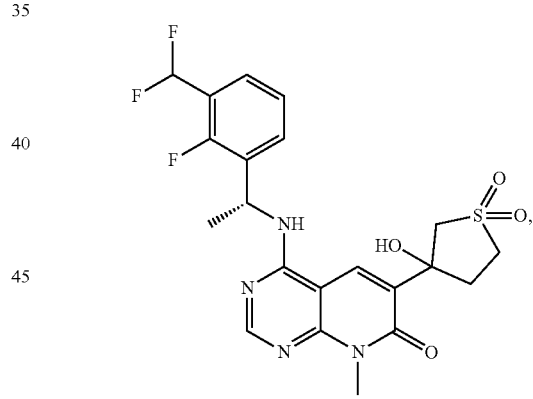
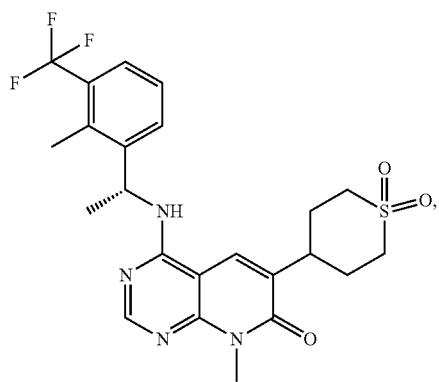
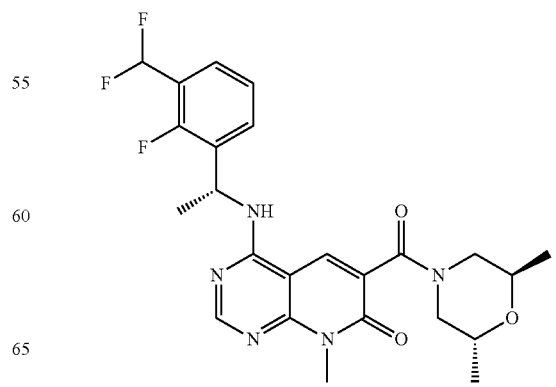

US 11,168,102 B1
301
-continued
302
-continued
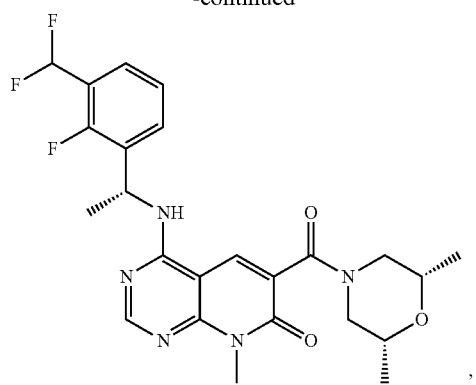
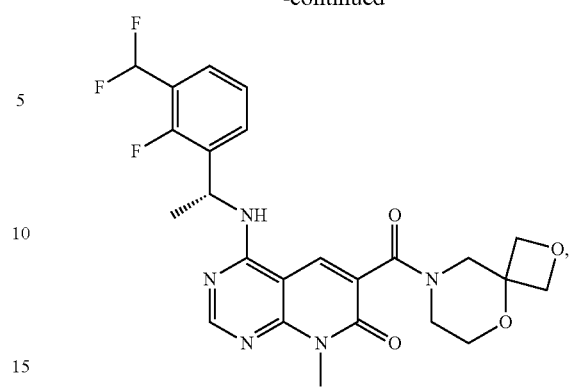
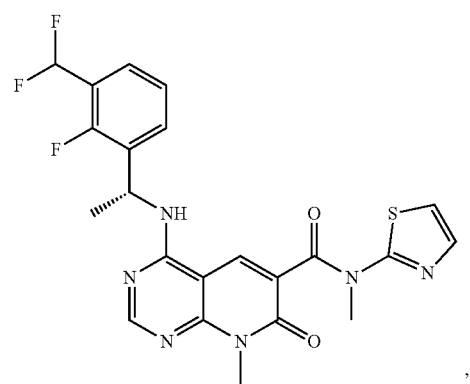
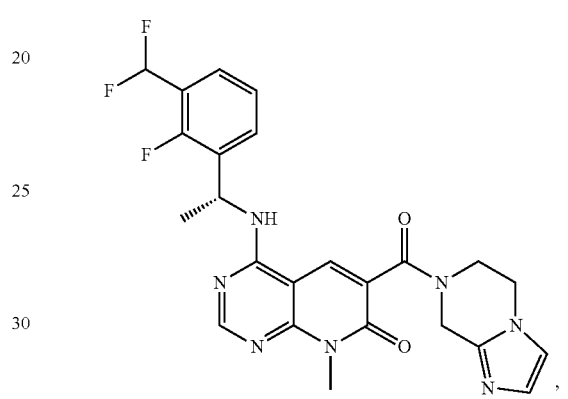
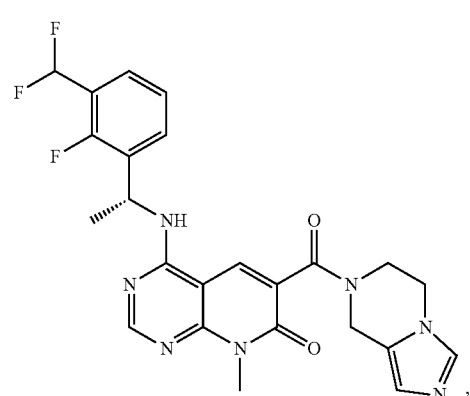

303
-continued
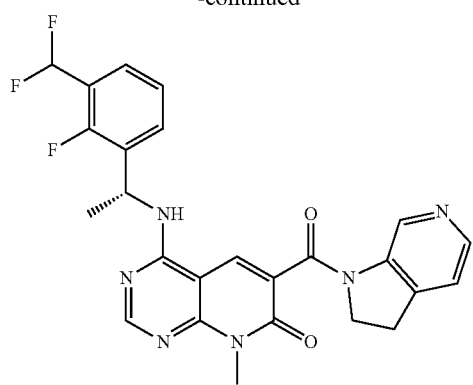
,
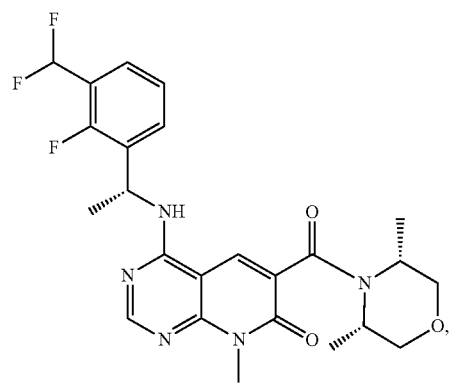
,
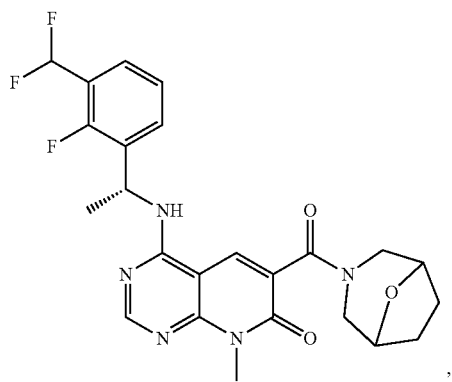
,
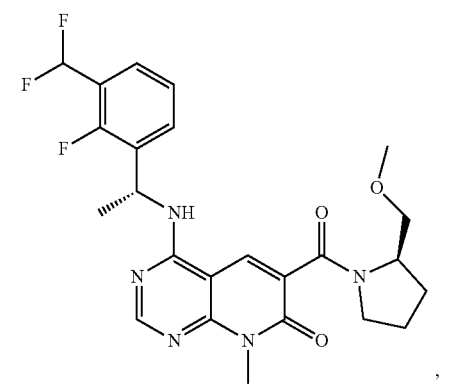
,
304
-continued
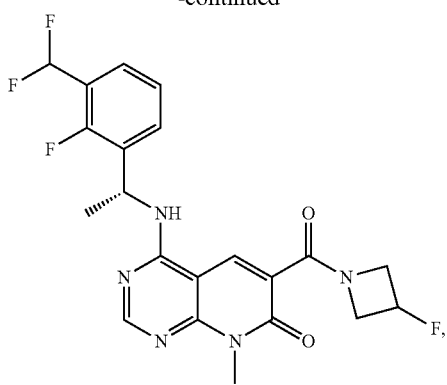
,
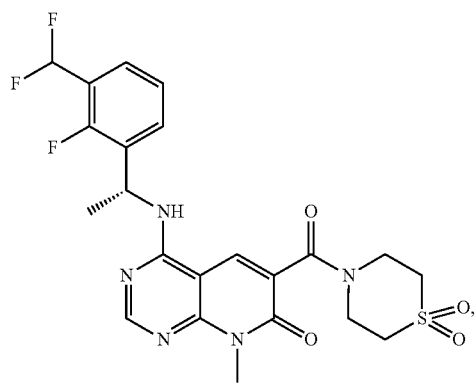
,
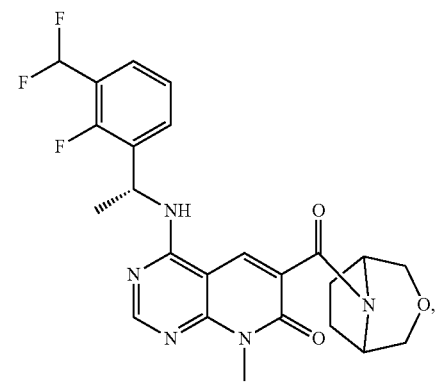
,
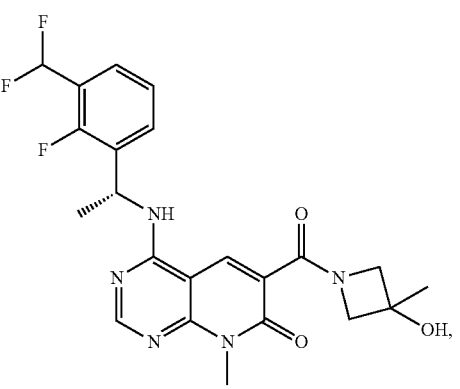

305
-continued
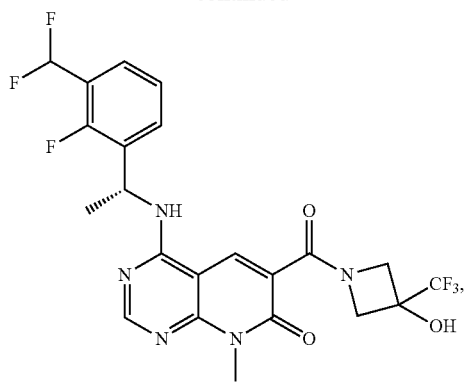
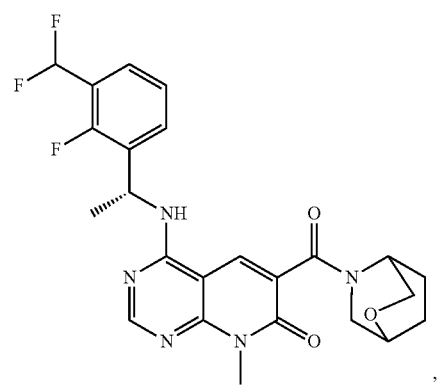
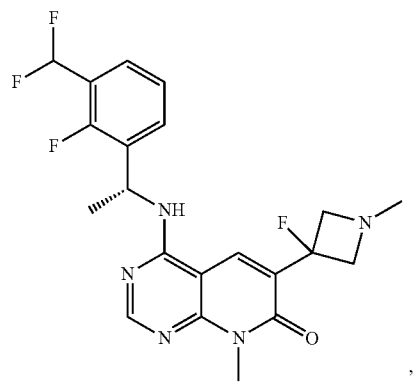
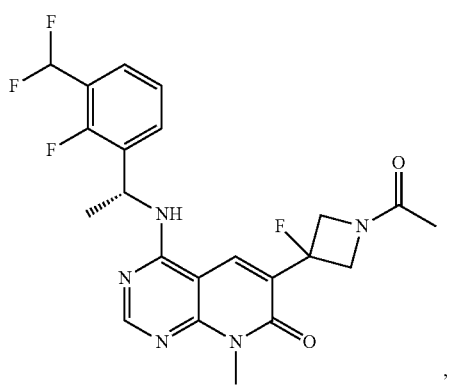
306
-continued
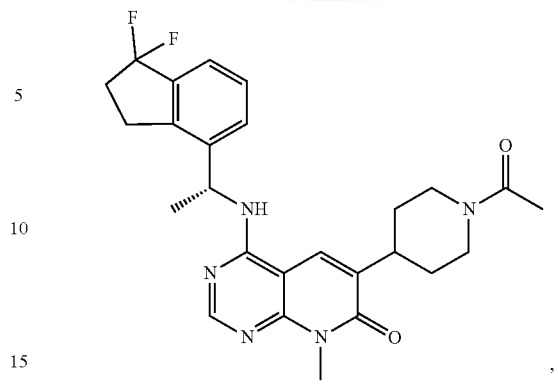

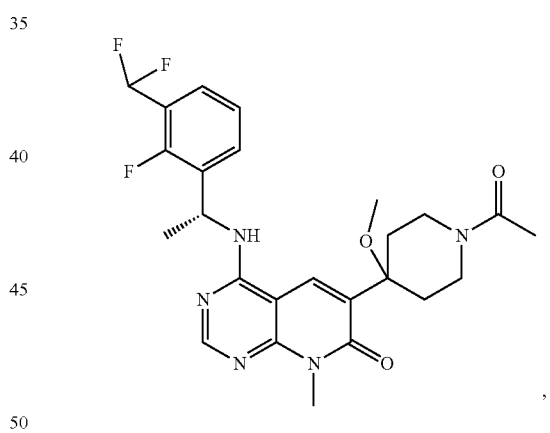
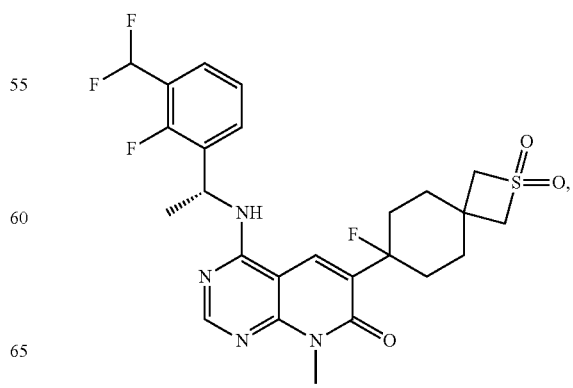

307
-continued
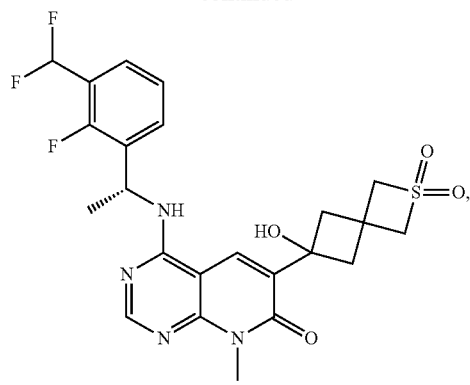
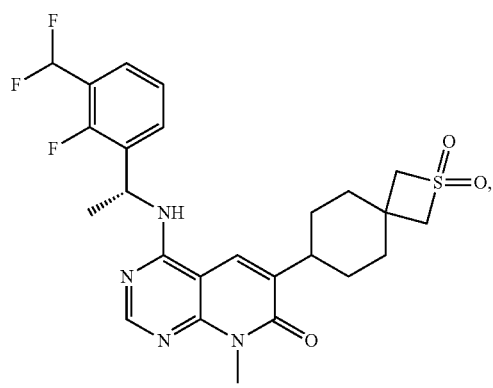
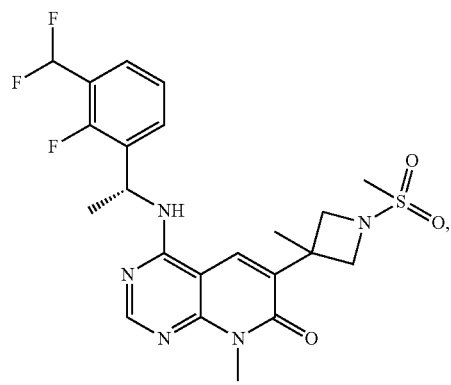
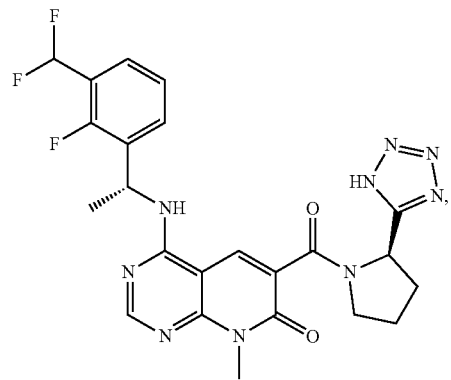
308
-continued
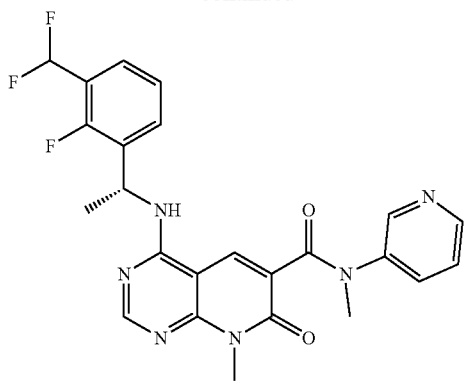
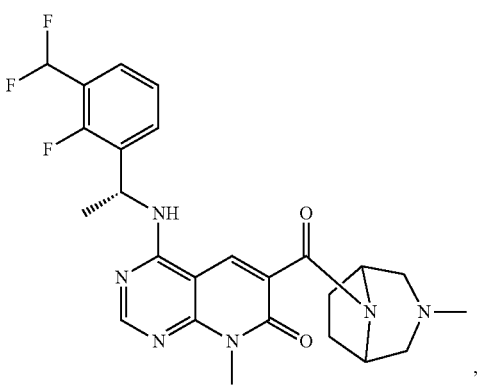
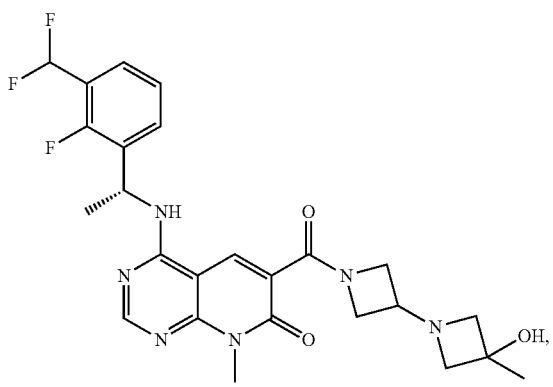
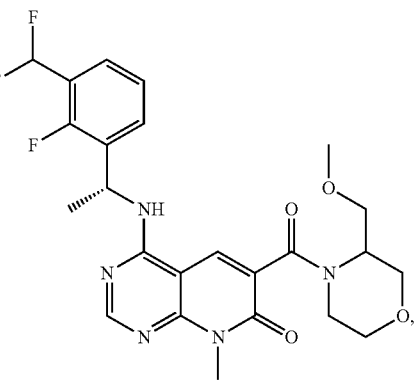

309
-continued
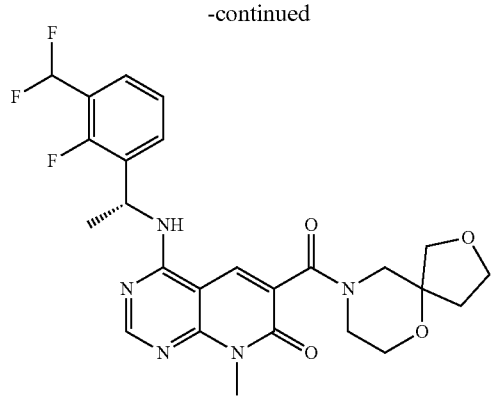
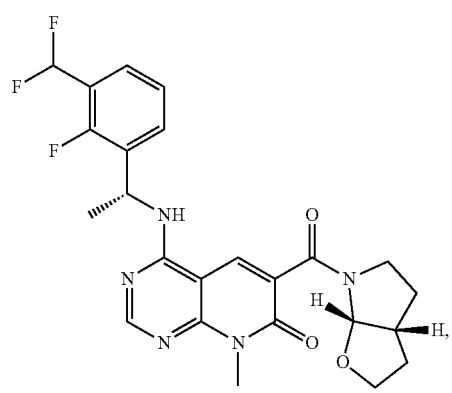
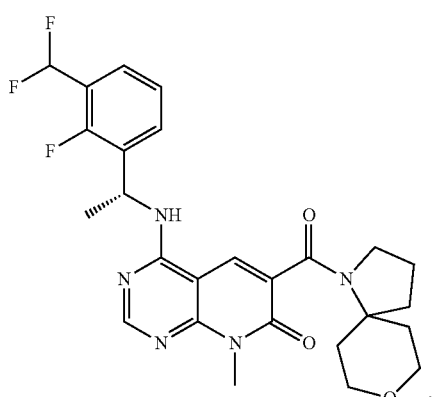
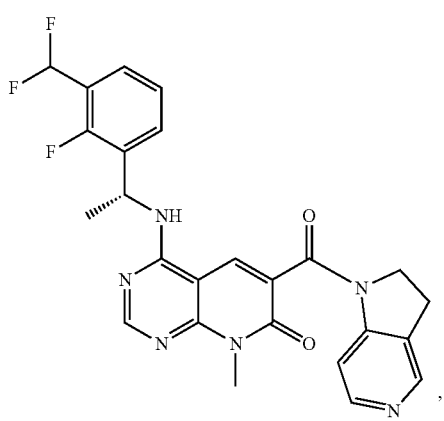
310
-continued
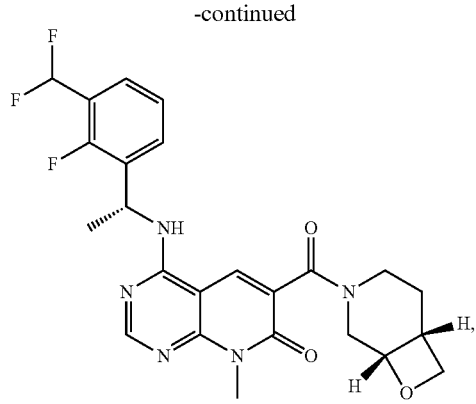
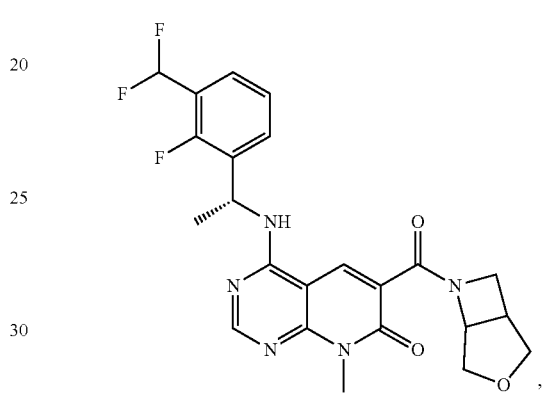
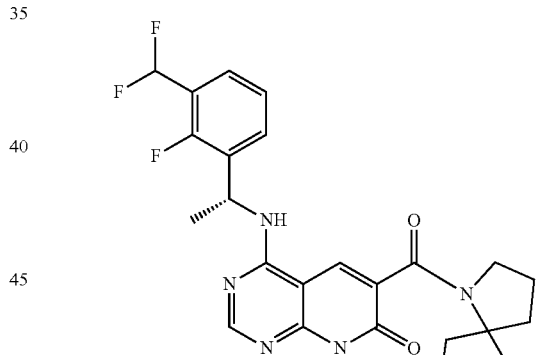
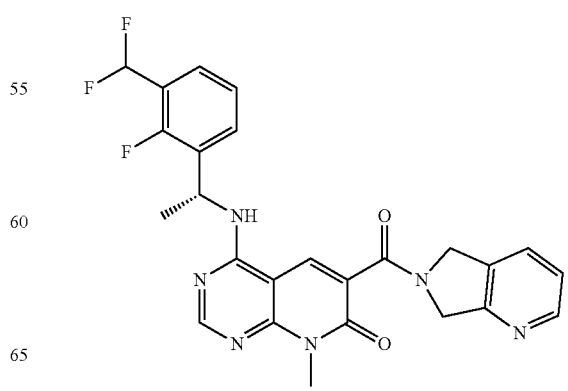

311
-continued
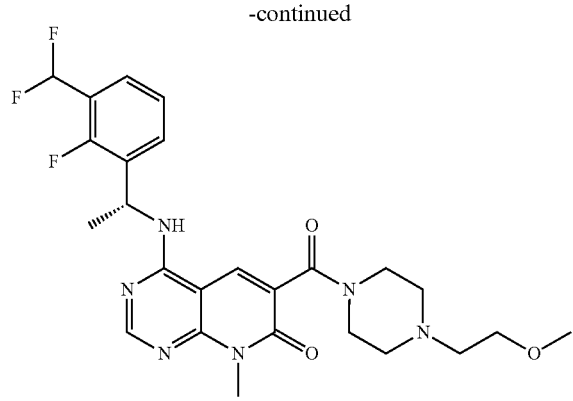
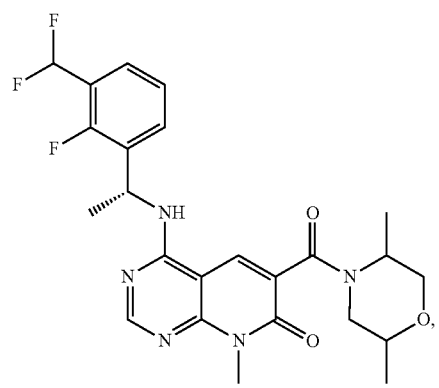
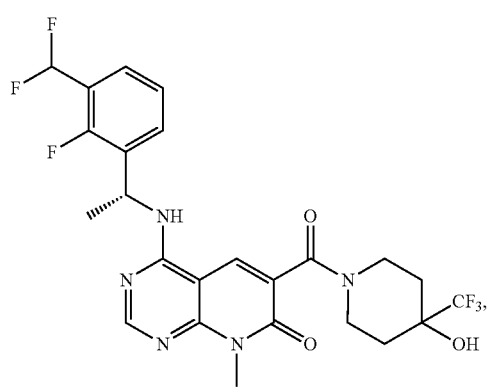
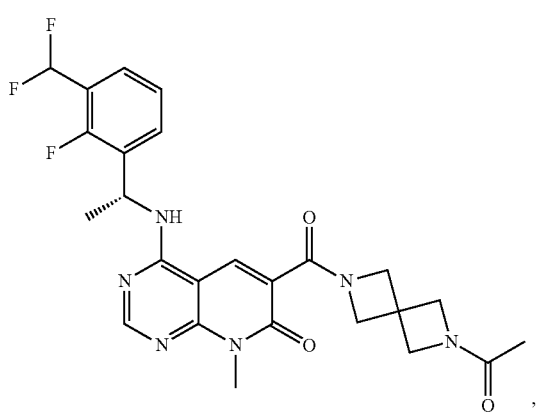
312
-continued
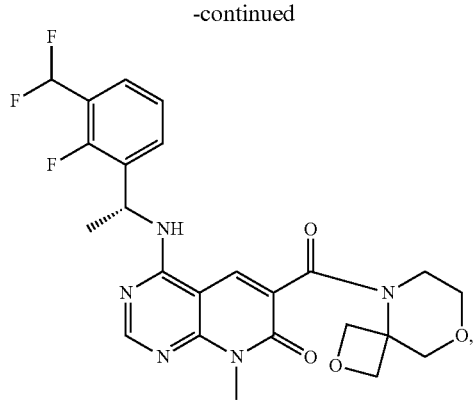
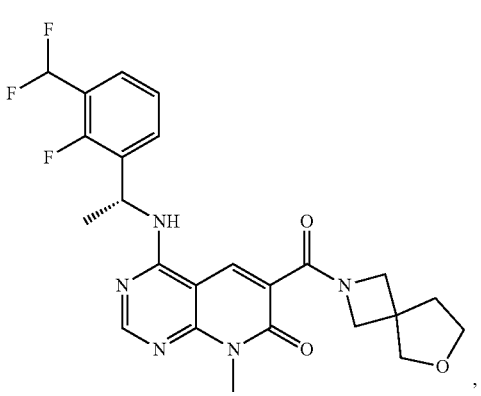
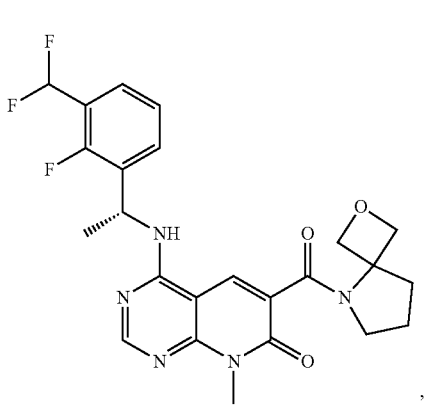
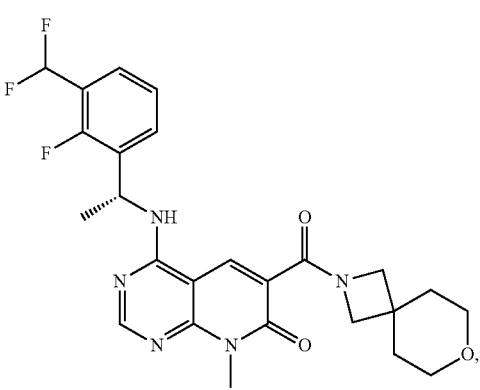

313
-continued
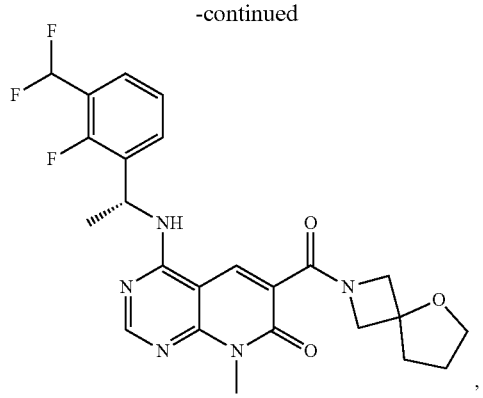
,
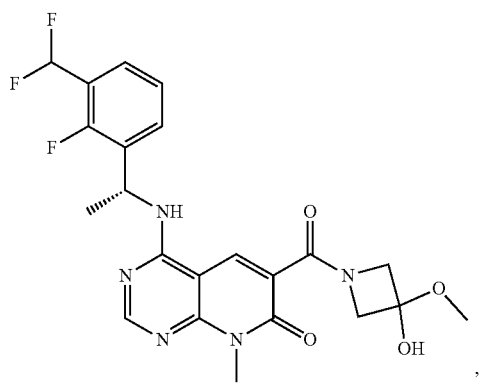
,
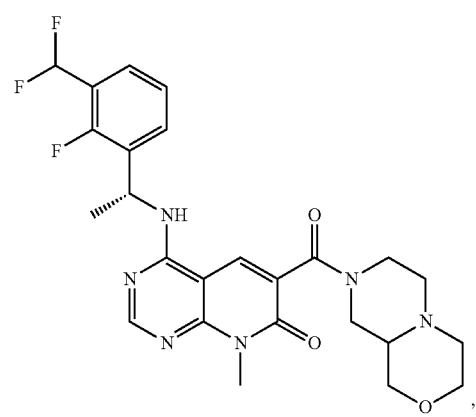
,
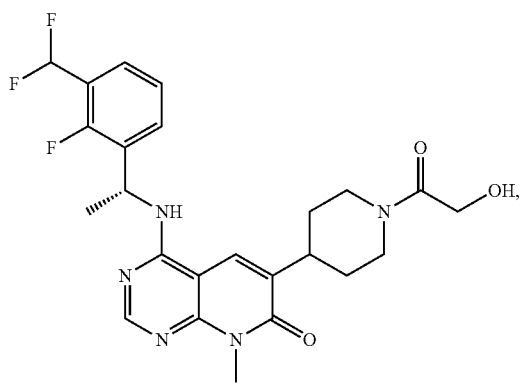
,
314
-continued
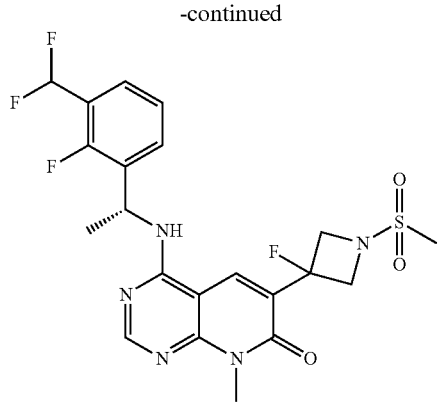
,
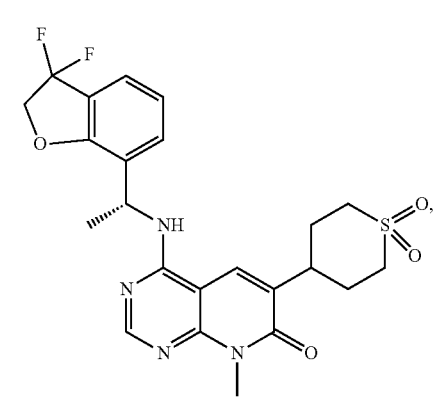
,
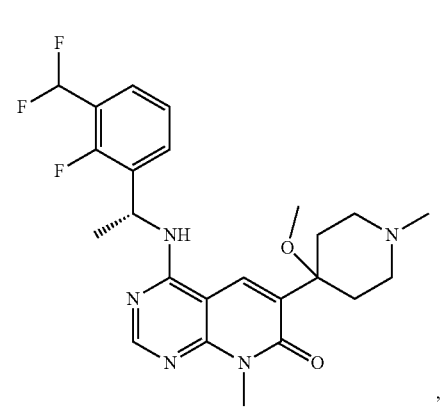
,
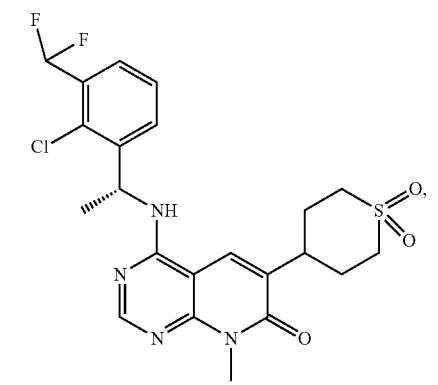
, 315
-continued
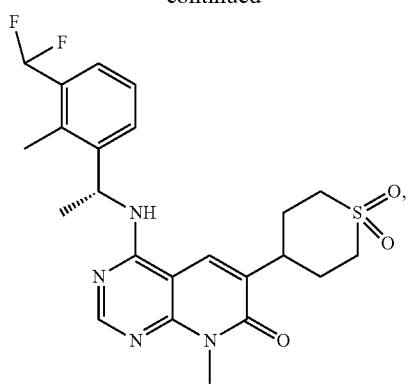
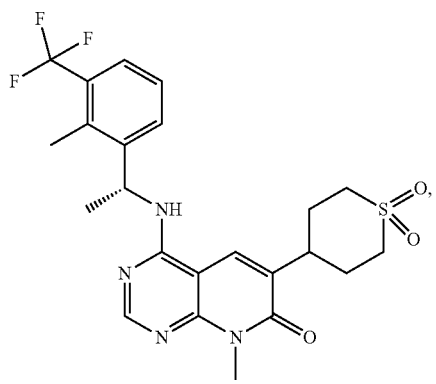
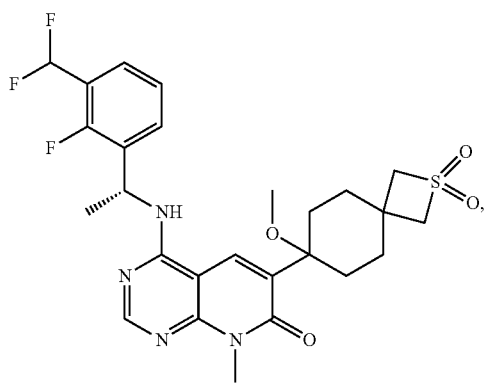
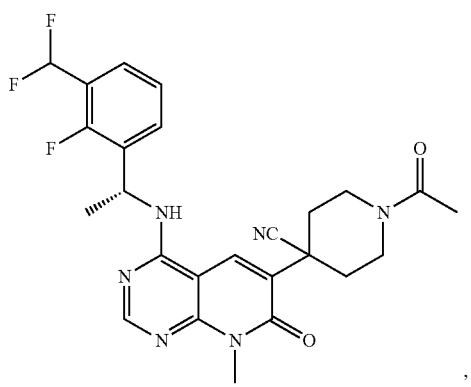
316
-continued
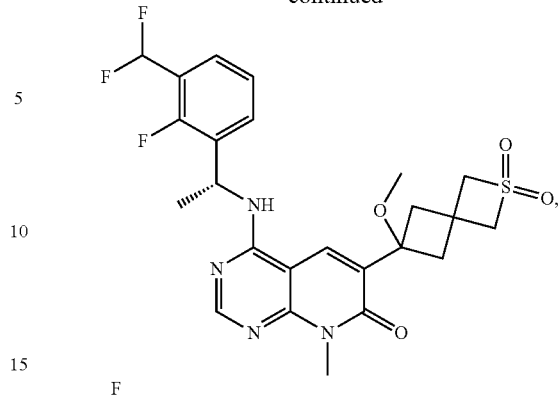
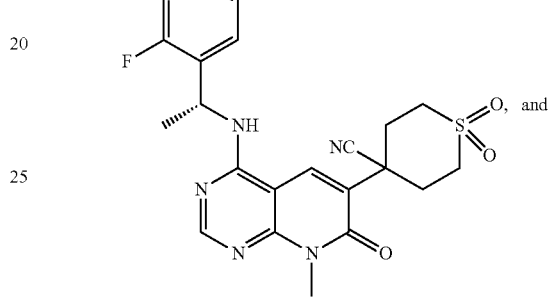
, and
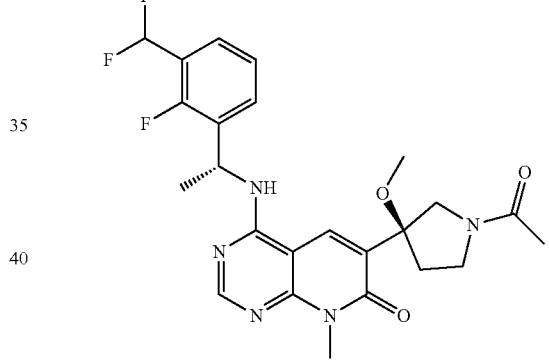
.
The present disclosure provides a compound, and pharmaceutically acceptable salts, solvates, stereoisomers, and tautomers thereof, selected from the group consisting of compounds of Collection 3:
Collection 3: Certain Compounds of the Present Invention
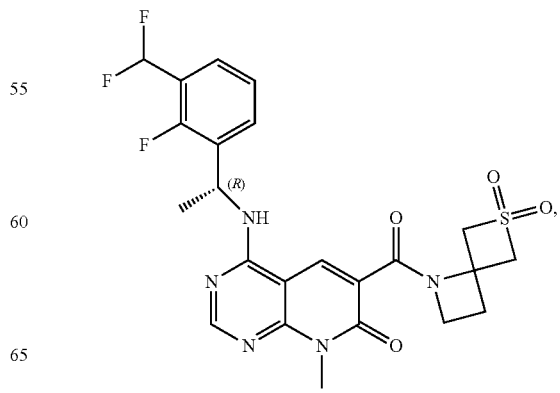

317
-continued
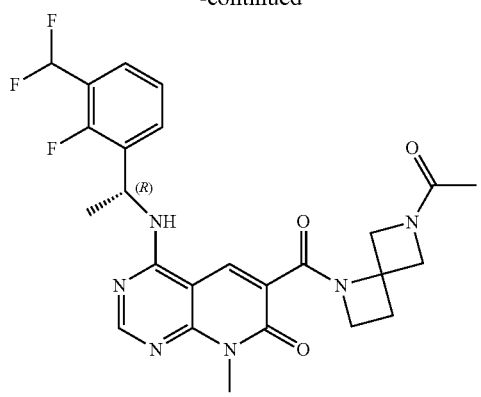
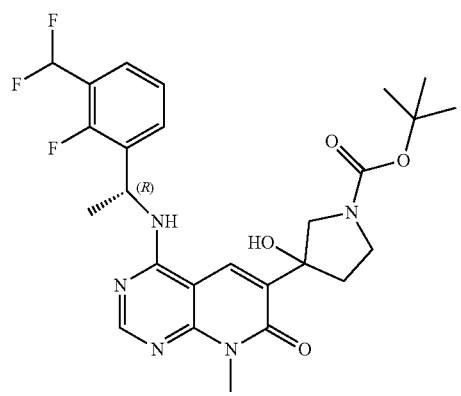
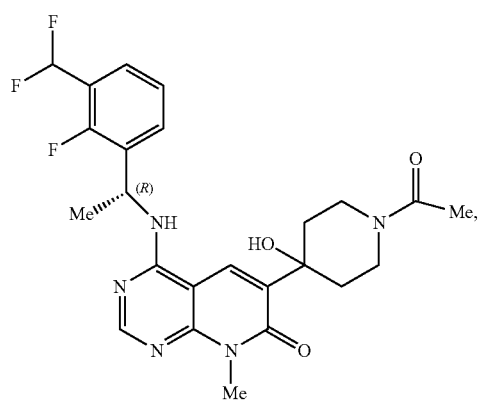
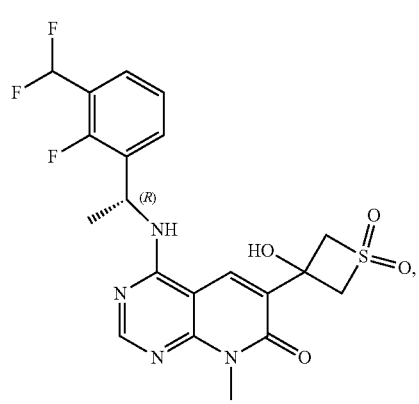
318
-continued
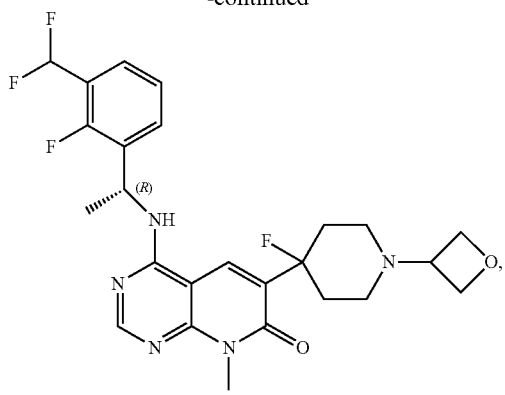
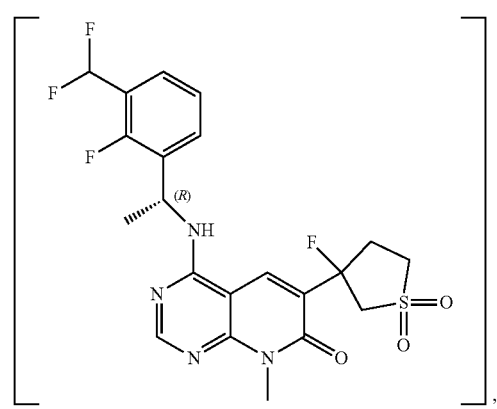
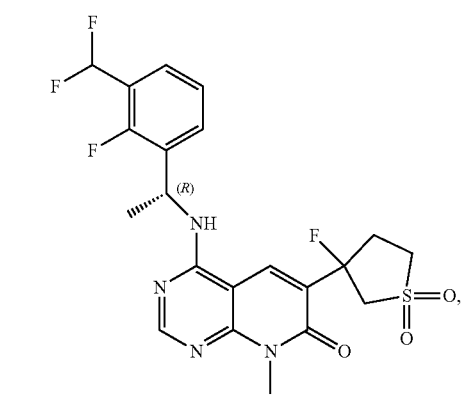
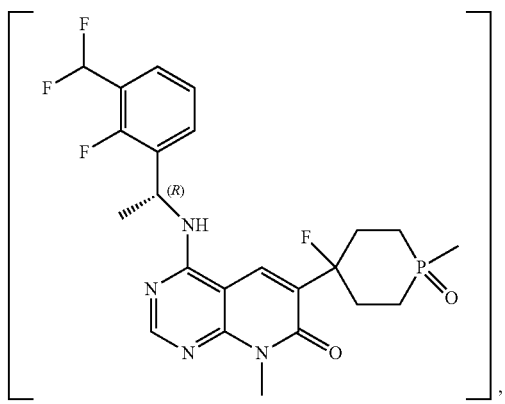

319
-continued
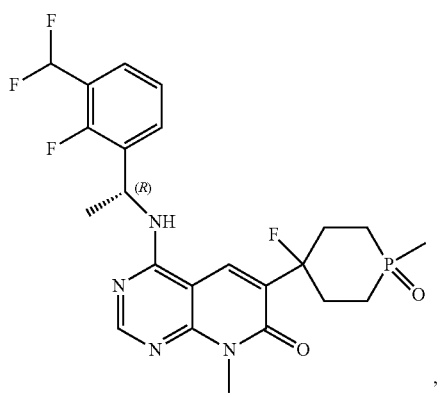
320
-continued
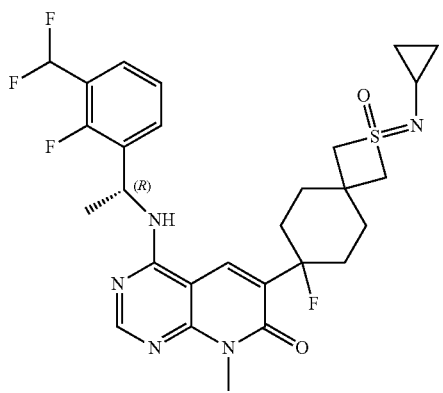
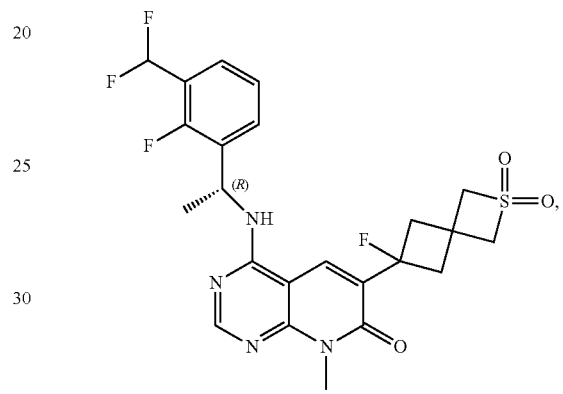
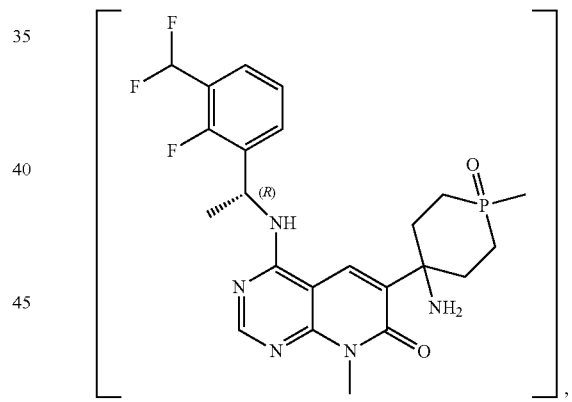
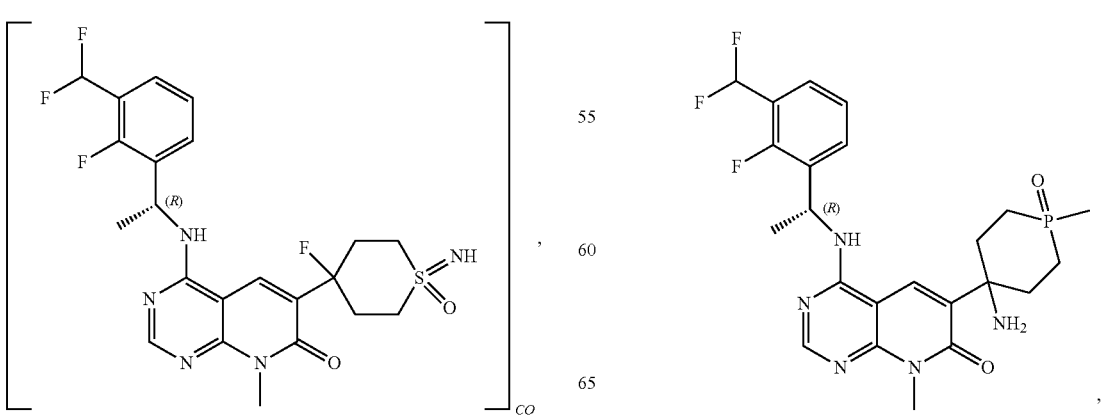

321
-continued
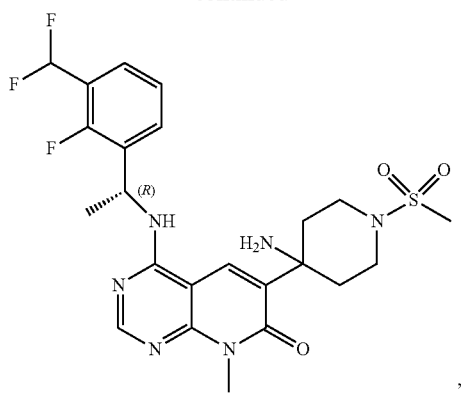
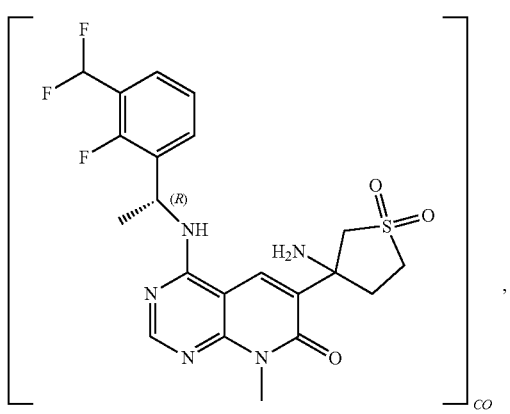
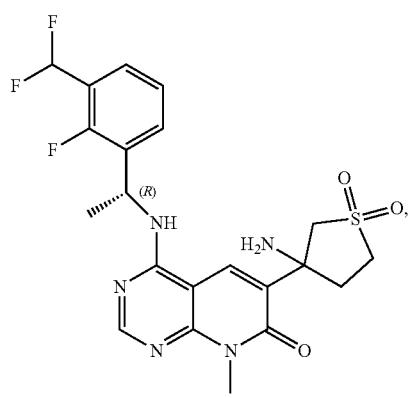
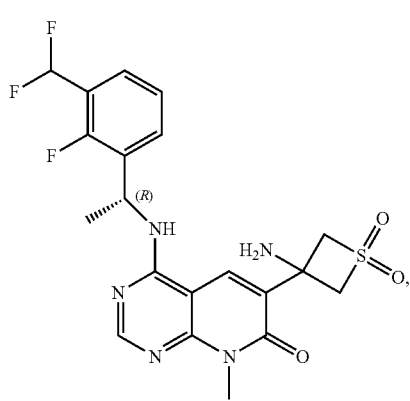
322
-continued
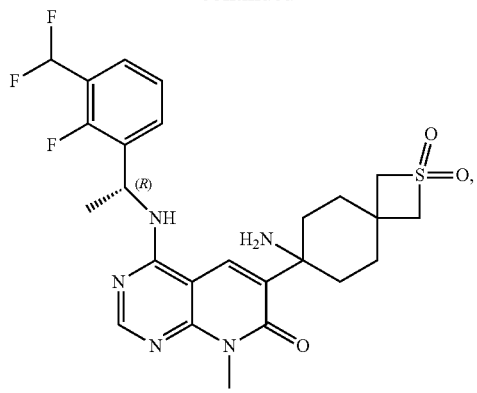
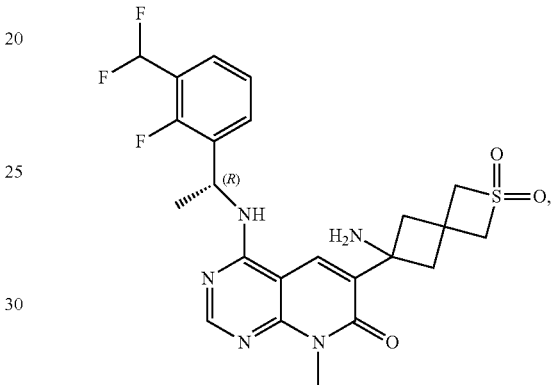
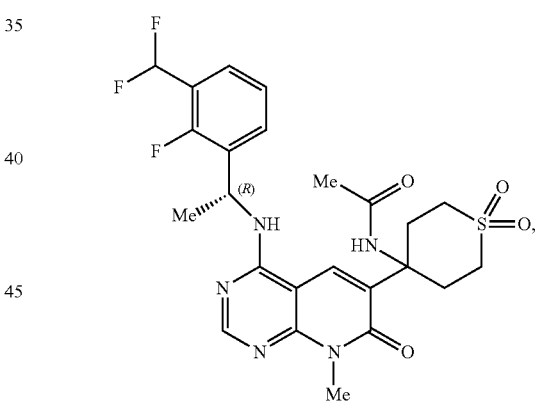
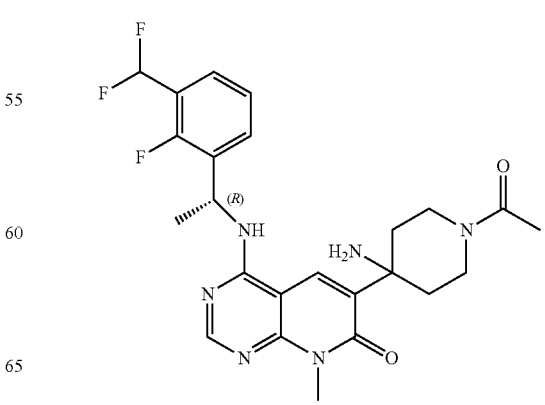

323
-continued
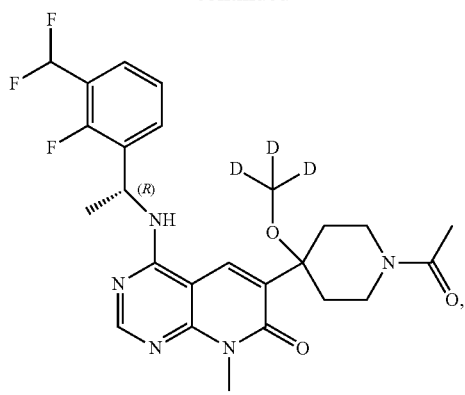
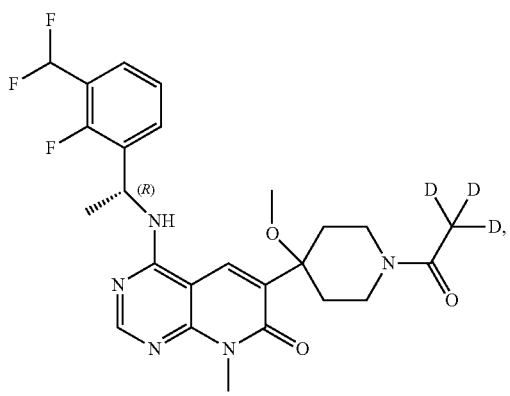
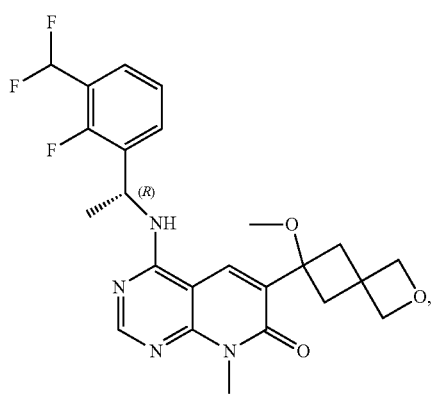
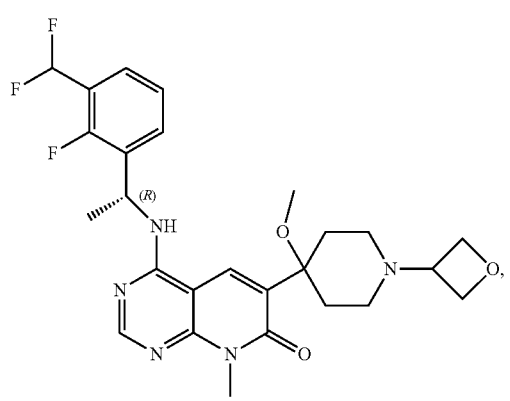
324
-continued
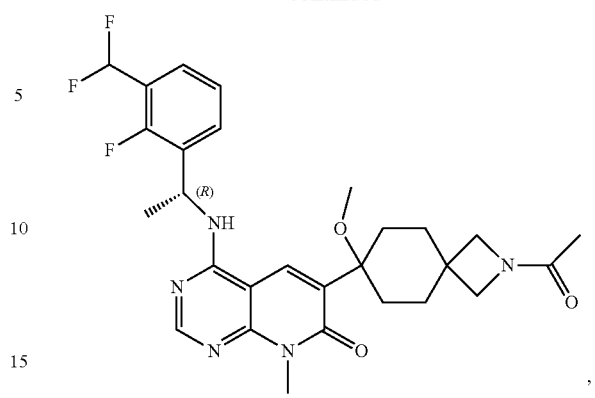
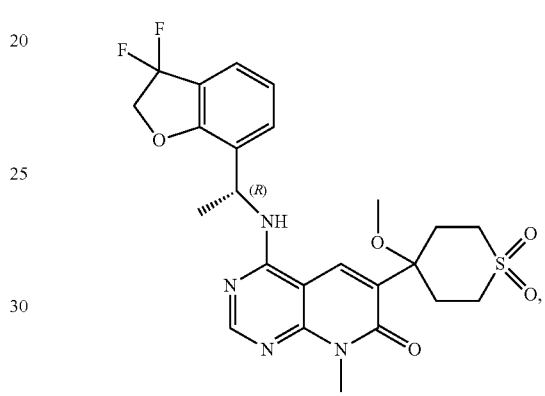
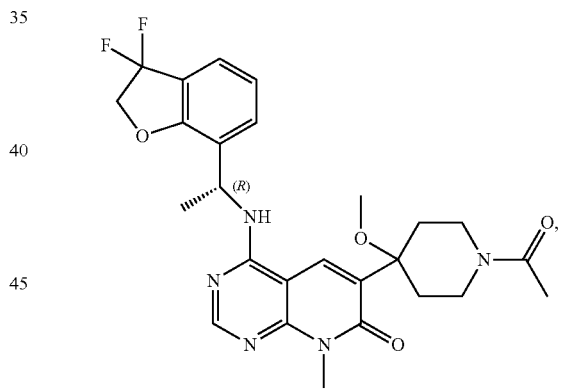
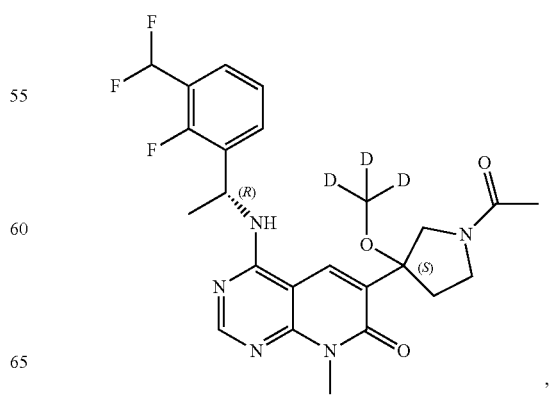

325
-continued
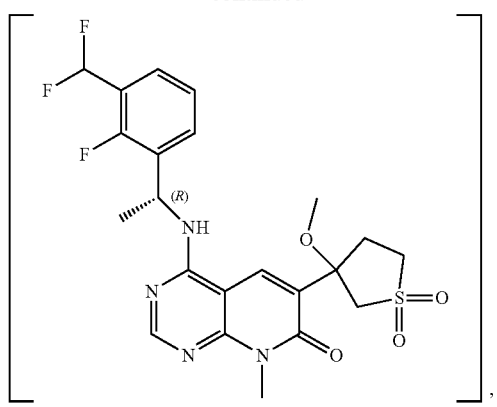
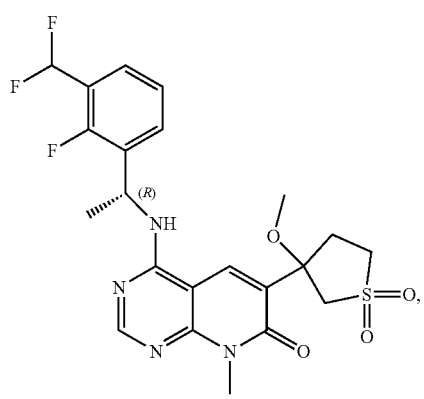
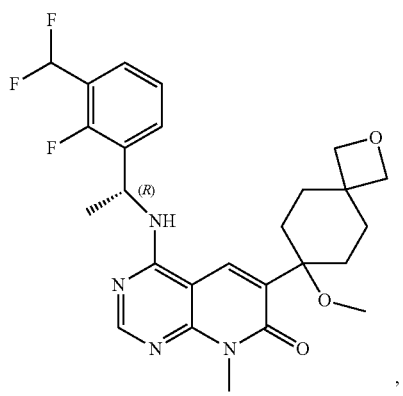
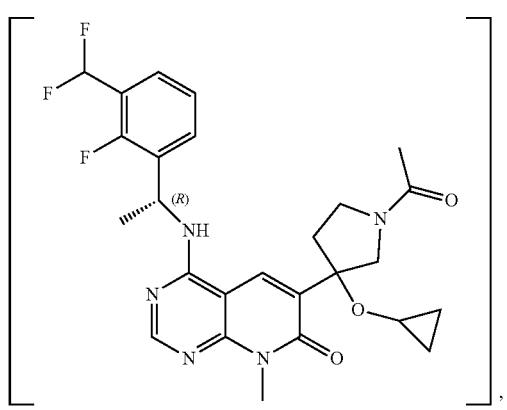
326
-continued
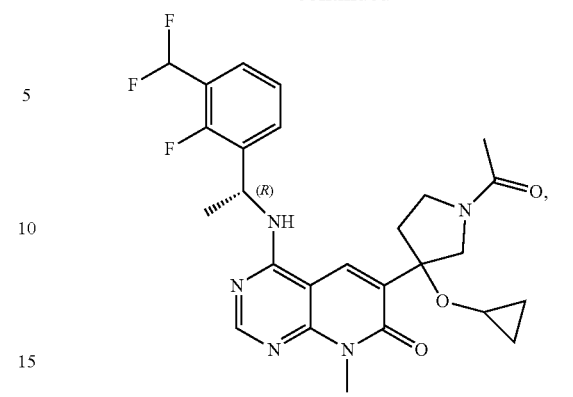
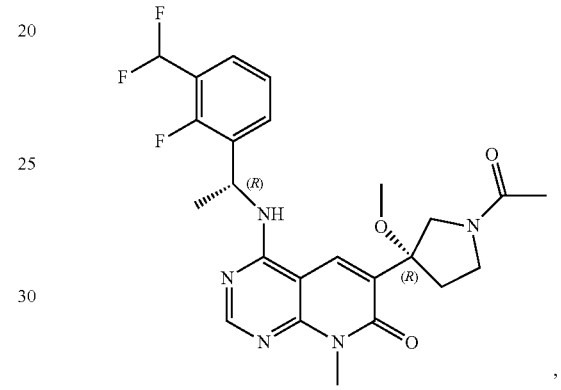
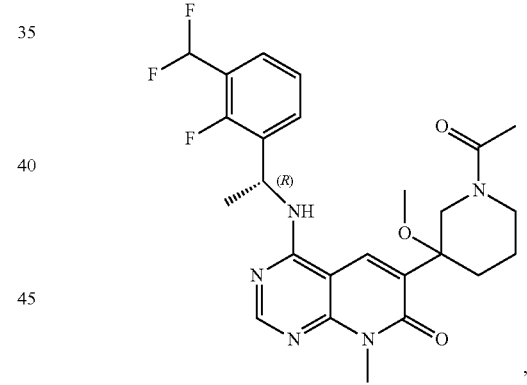
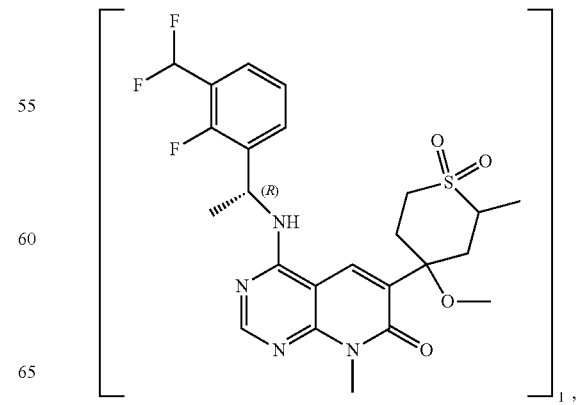

327
-continued
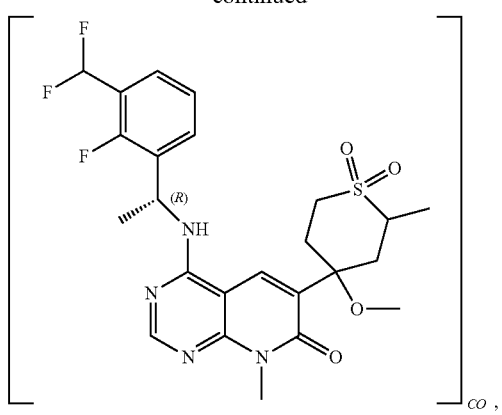
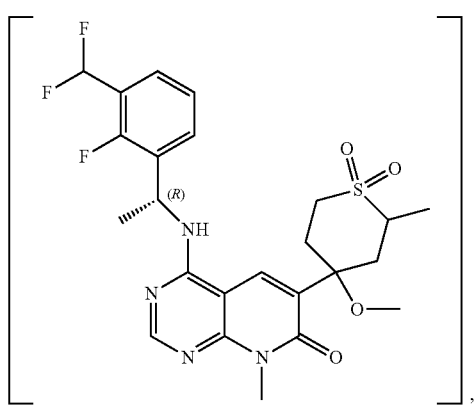
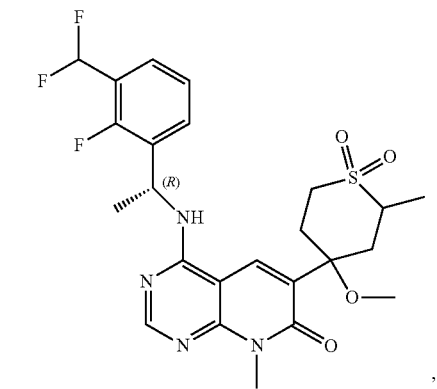
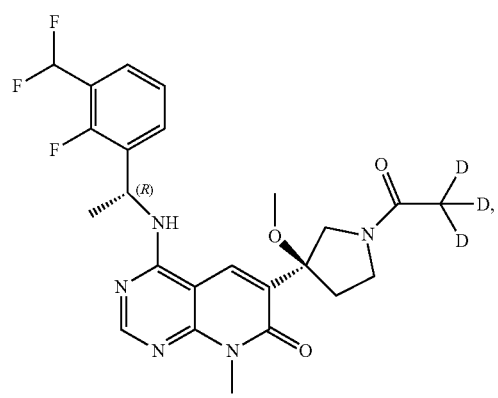
328
-continued
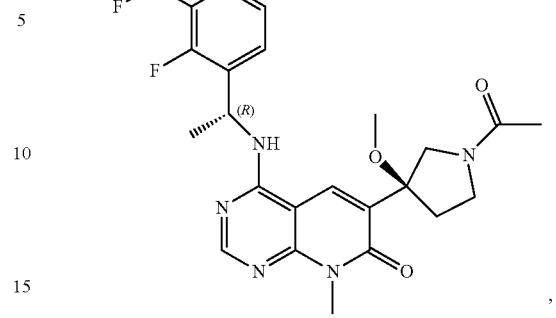
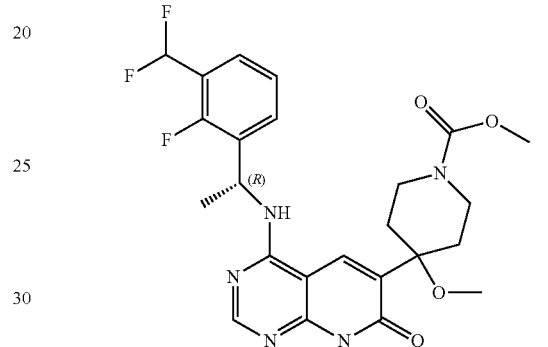
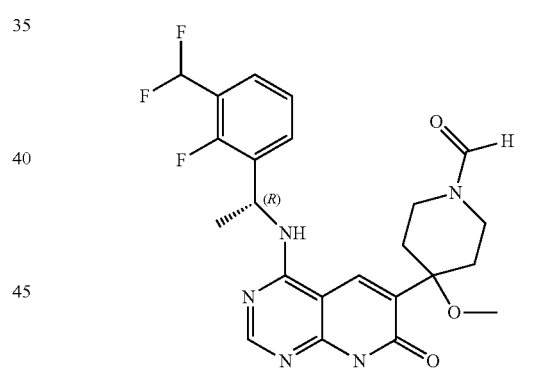
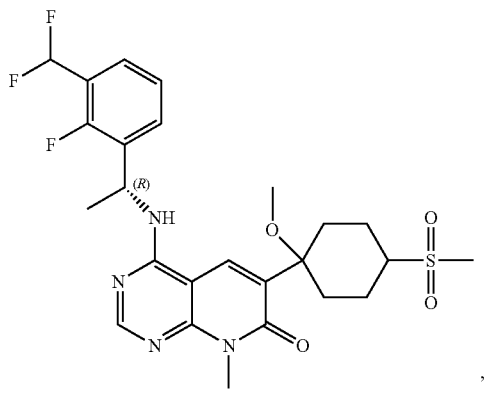

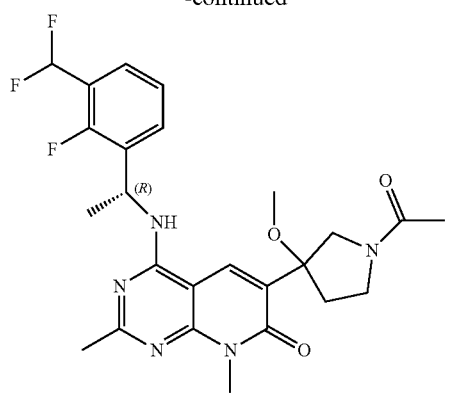
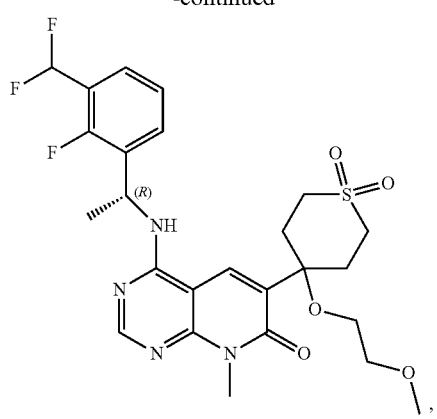
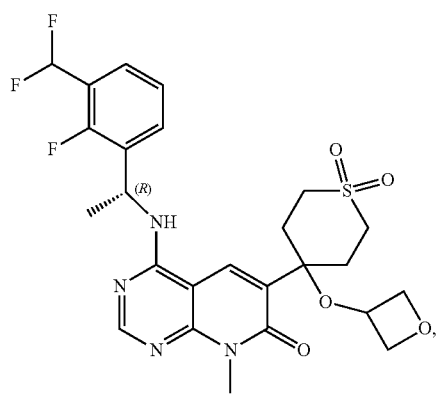
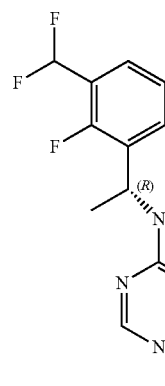
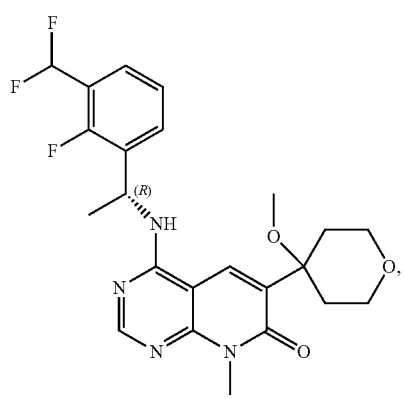
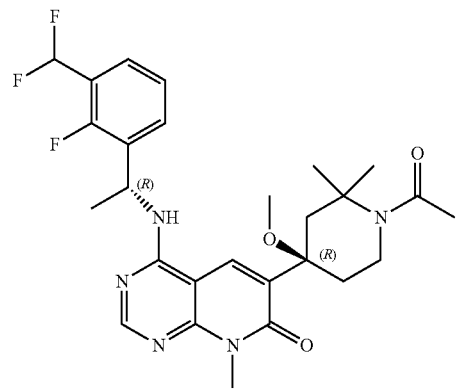
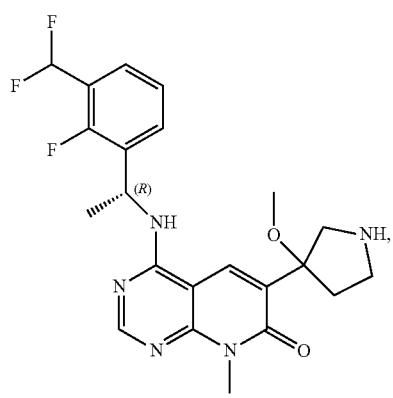
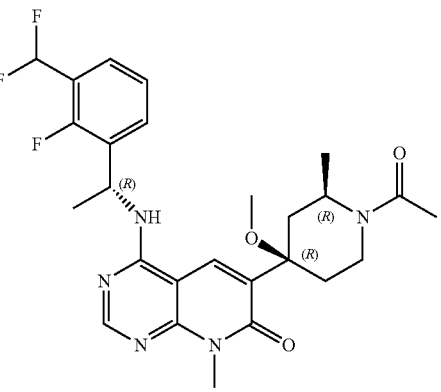

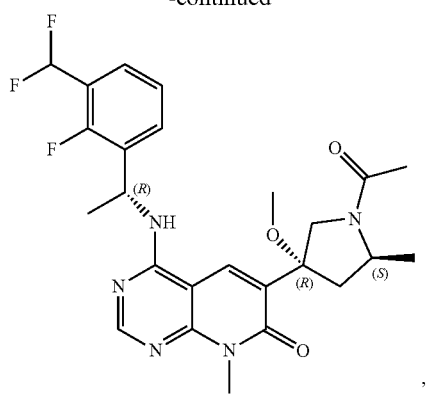
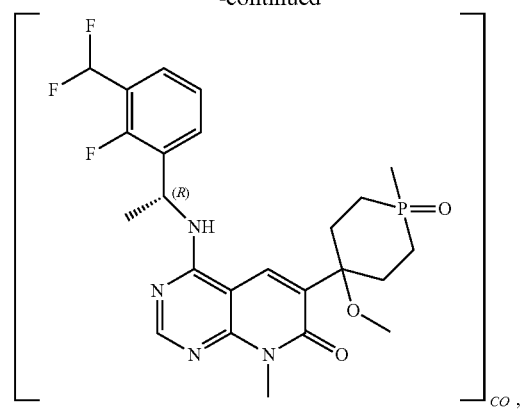
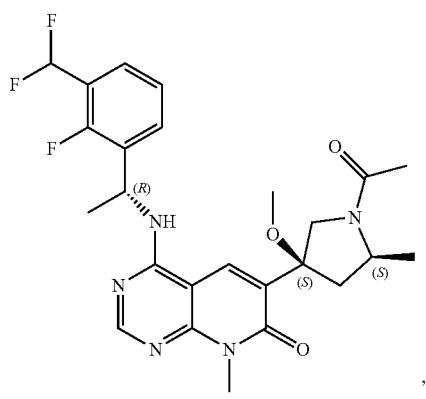
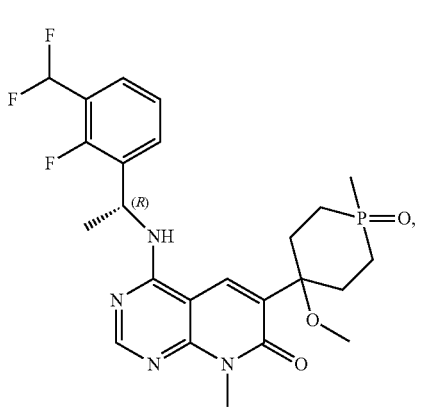
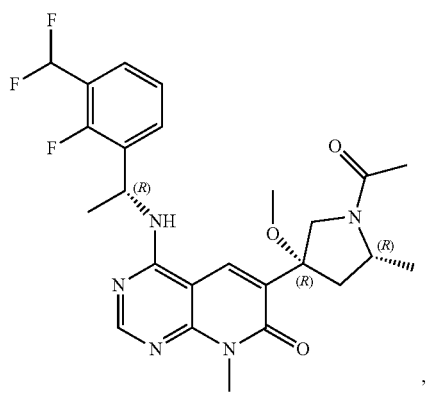
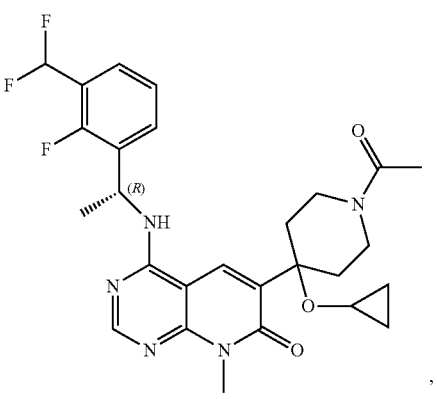
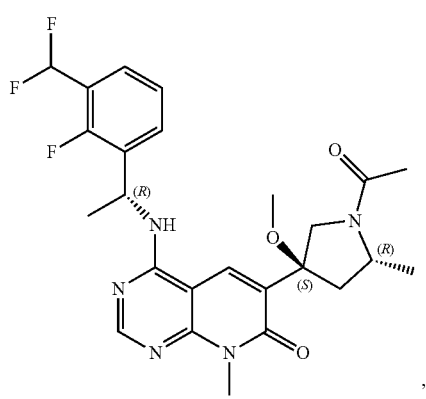
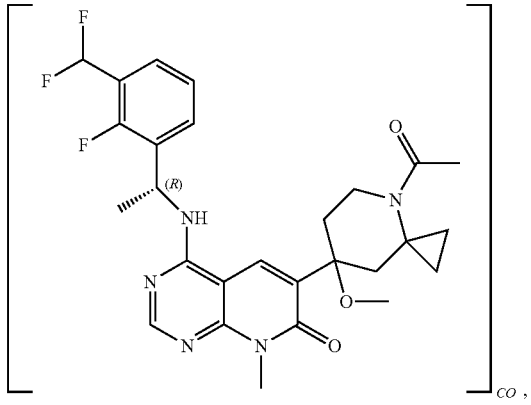

333
-continued
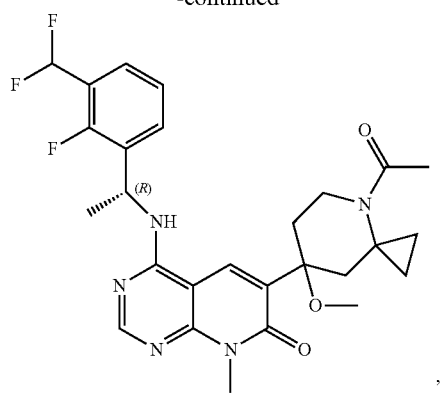
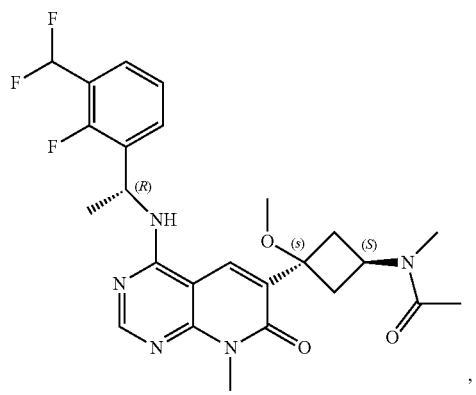
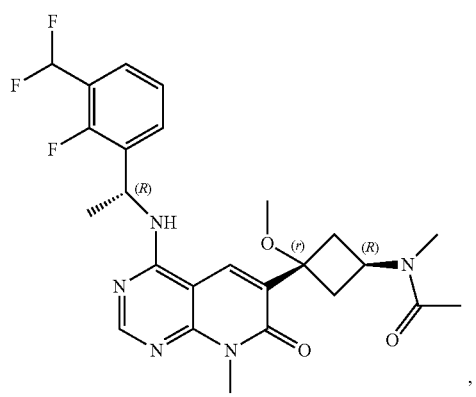
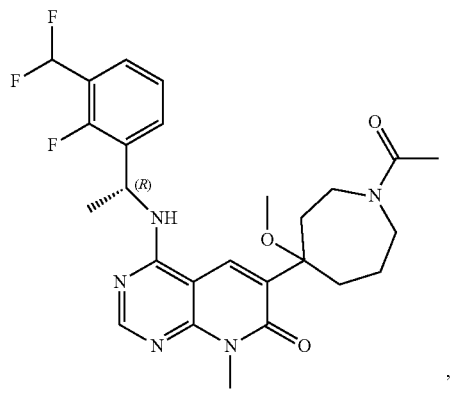
334
-continued
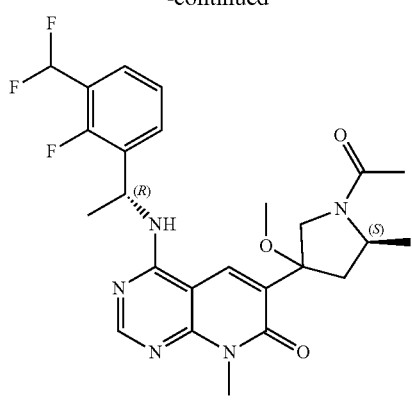
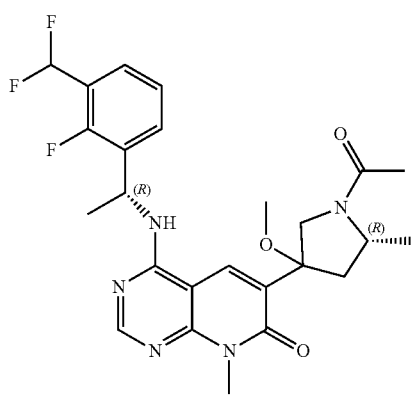
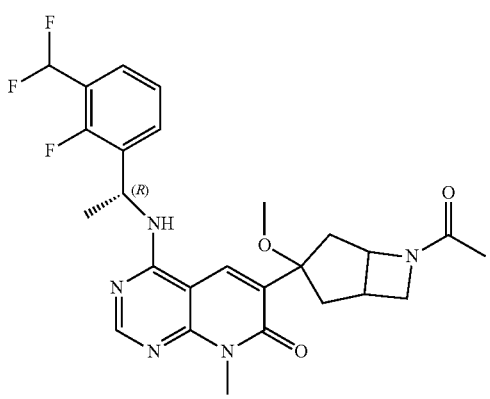
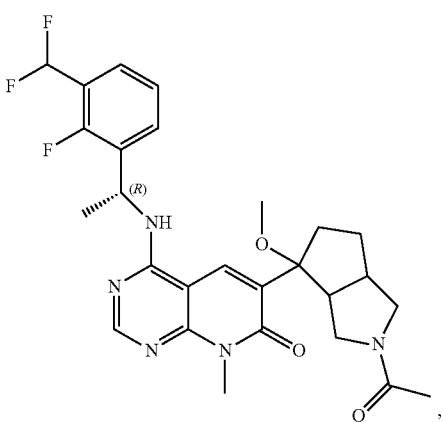

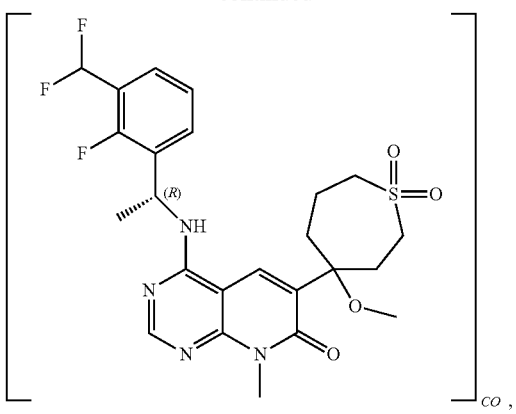
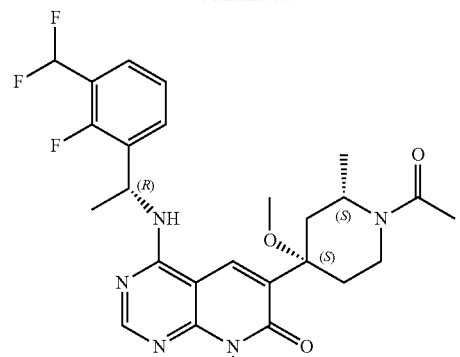
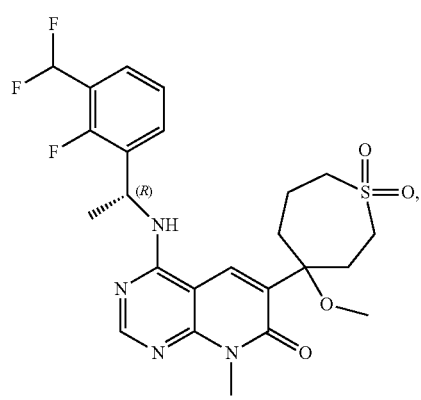
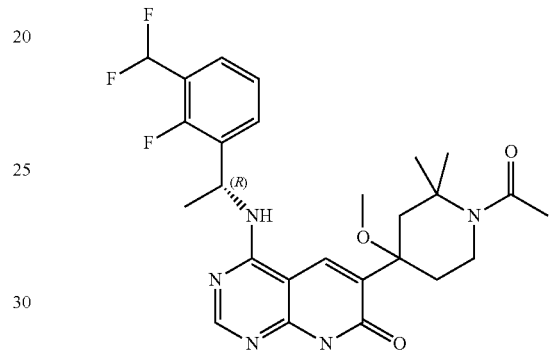
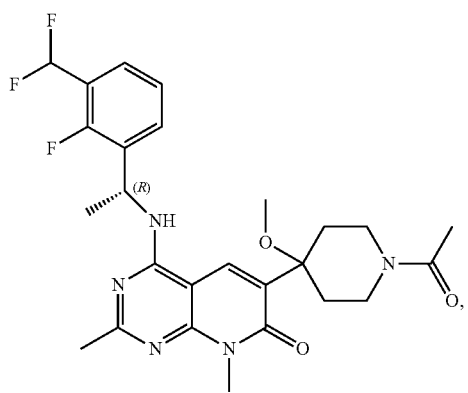
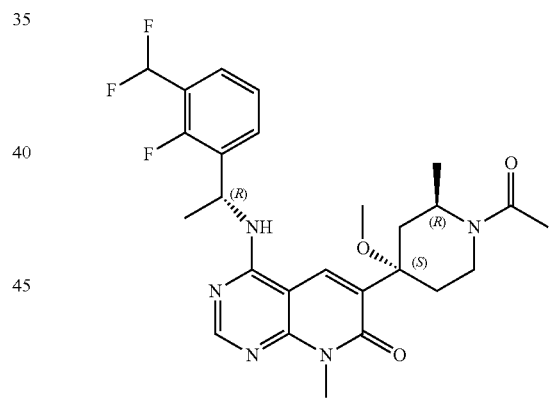
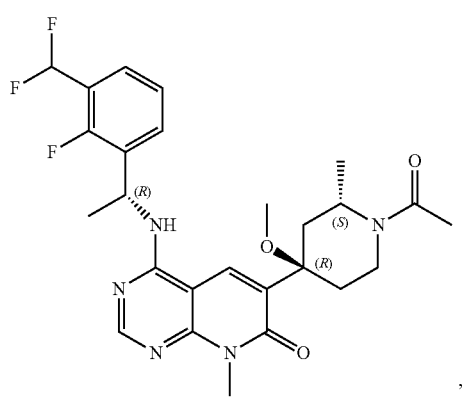
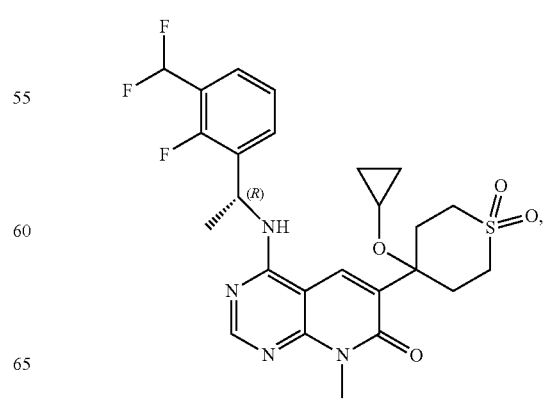

337
-continued
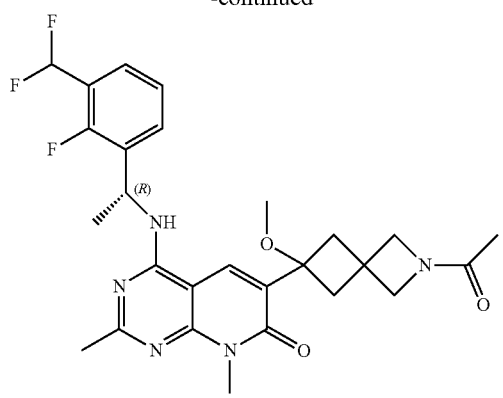
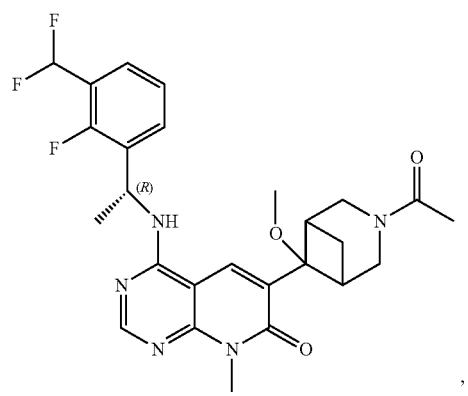
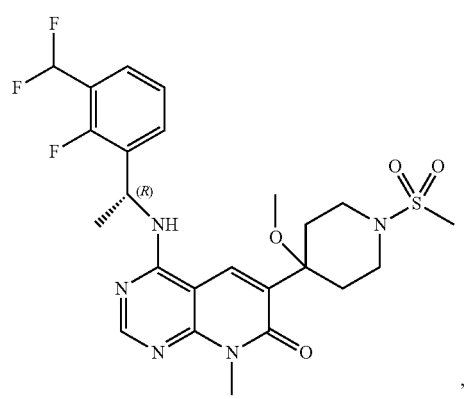
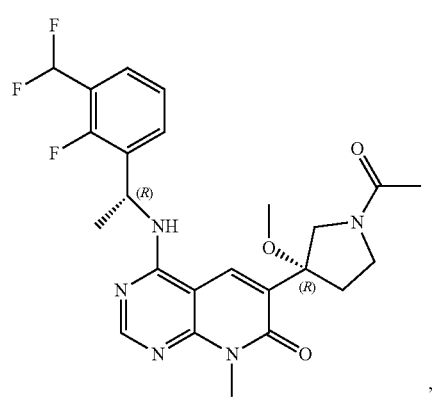
338
-continued
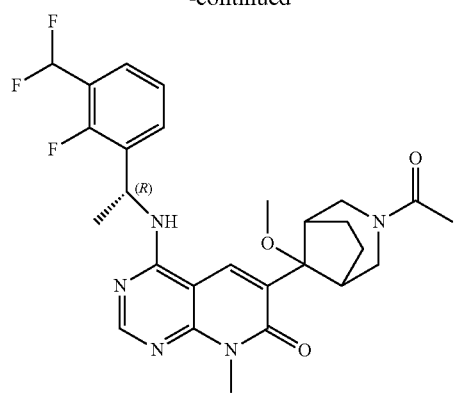
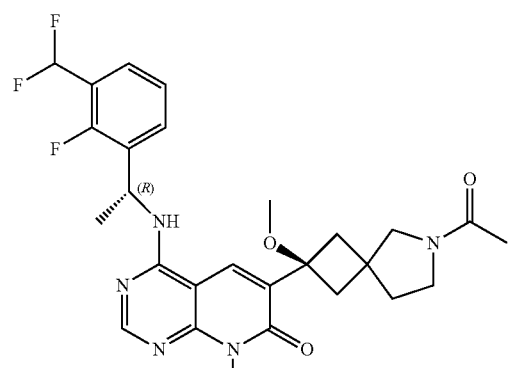
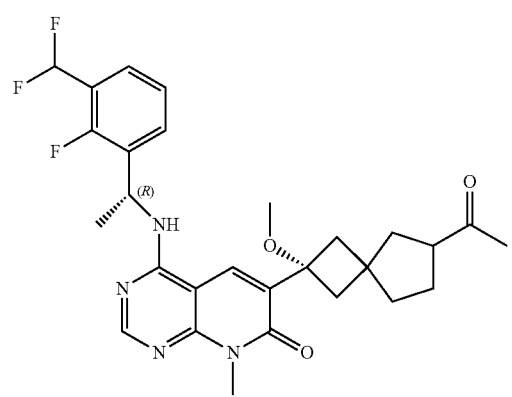
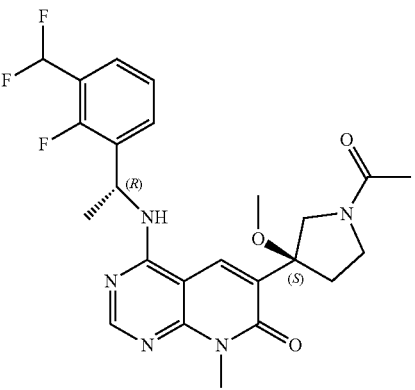

339
-continued
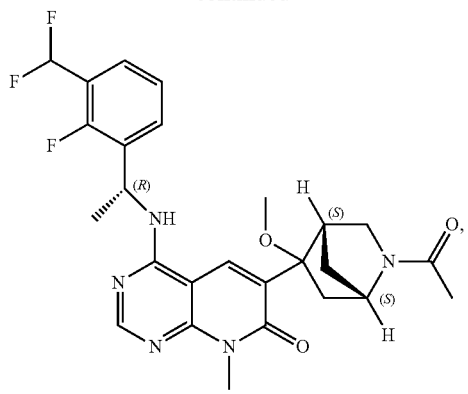
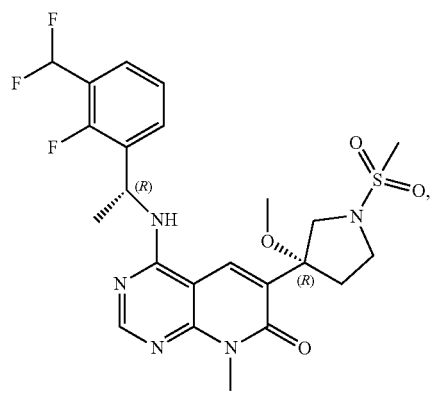
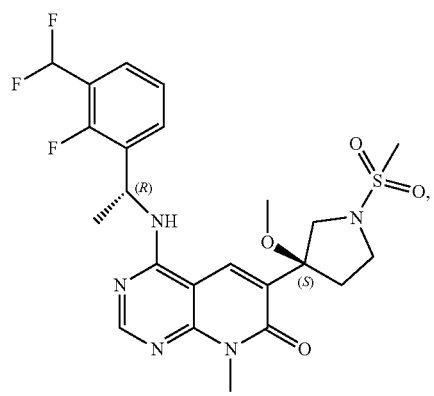
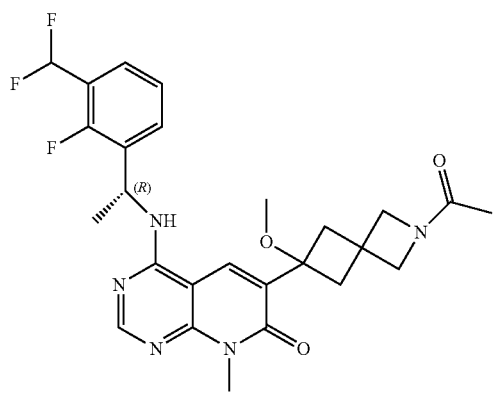
340
-continued
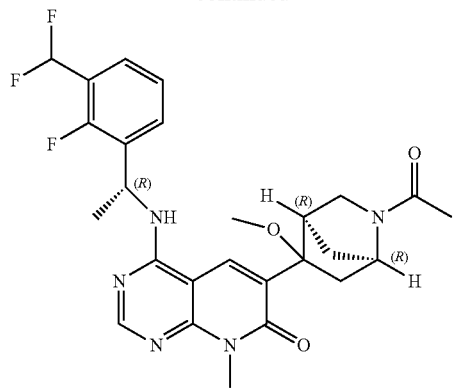
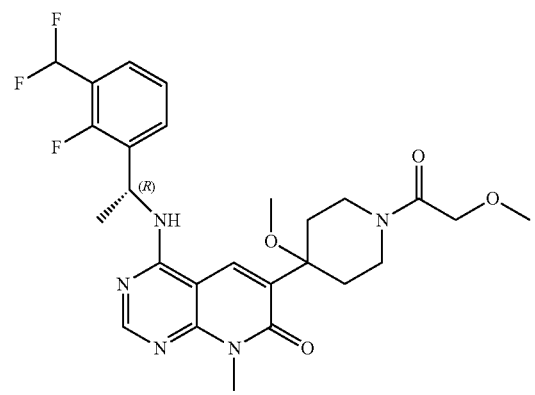
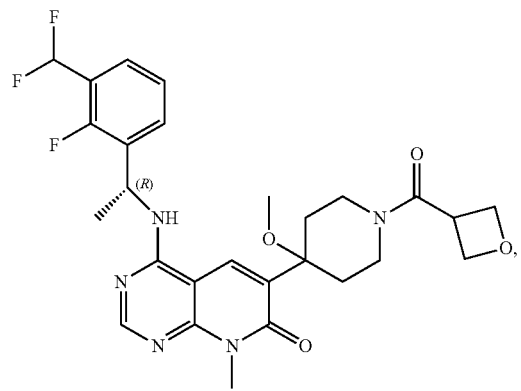
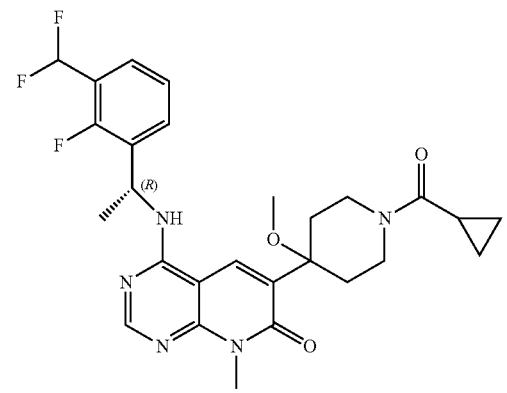

341
-continued
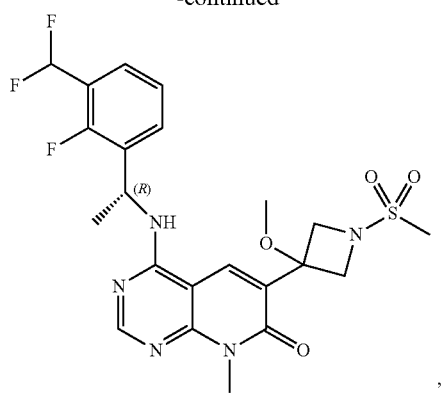
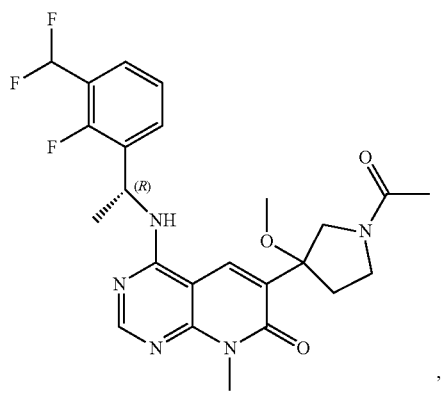
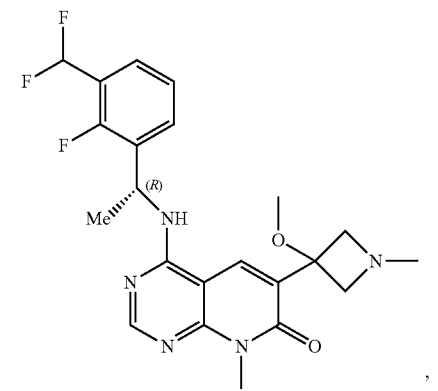
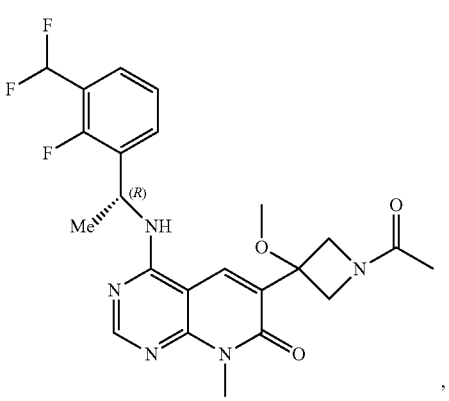
342
-continued
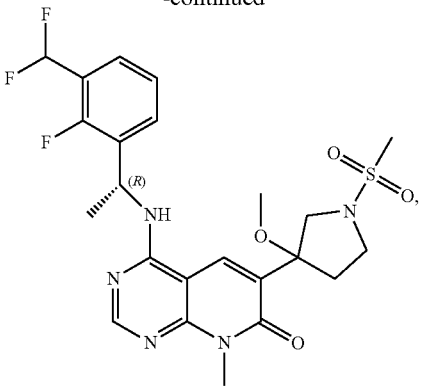
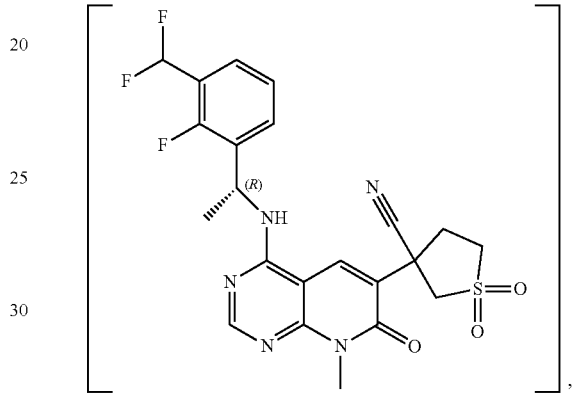
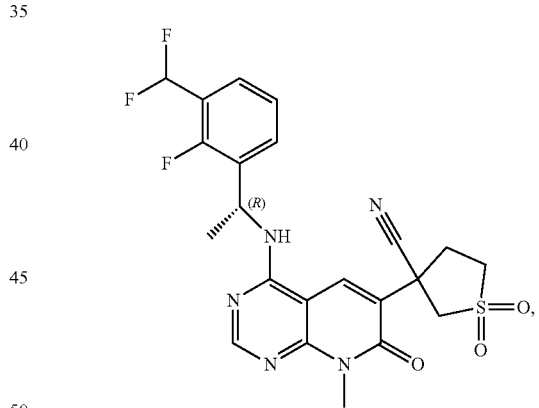
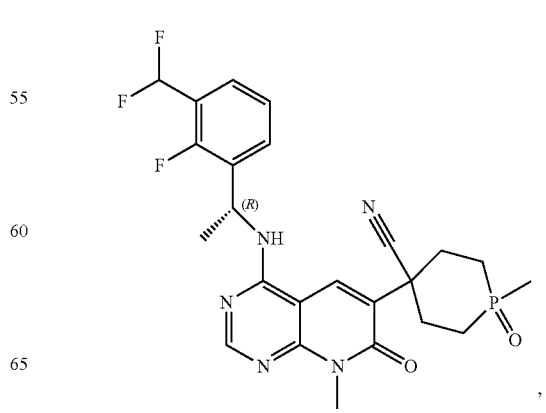

343
-continued
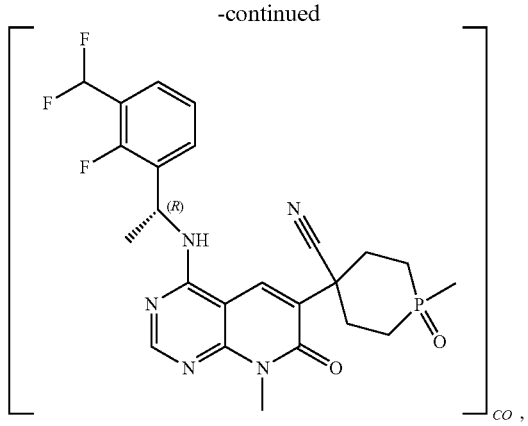
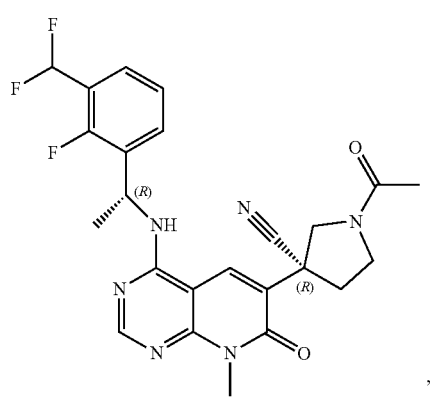
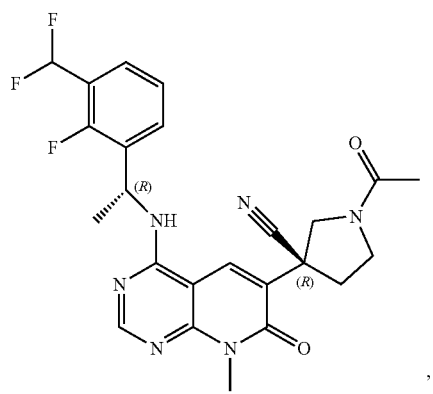
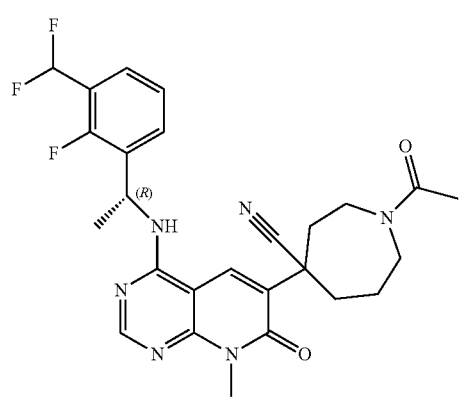
344
-continued
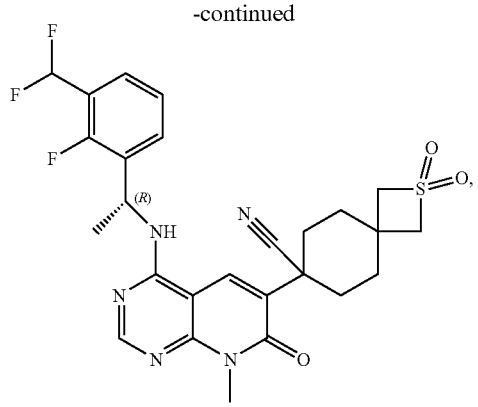
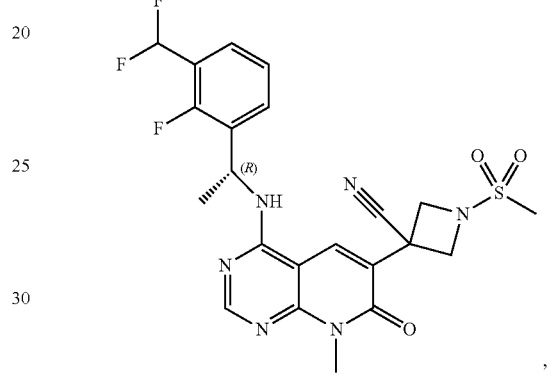
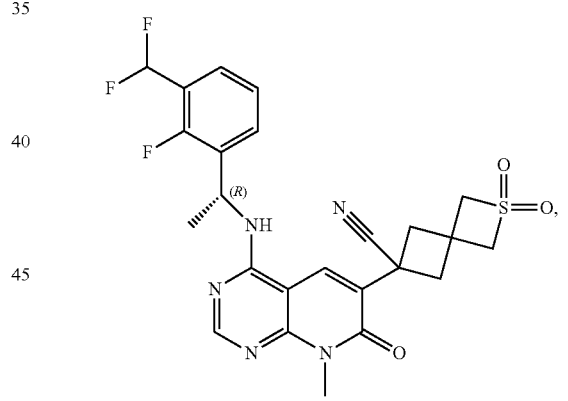
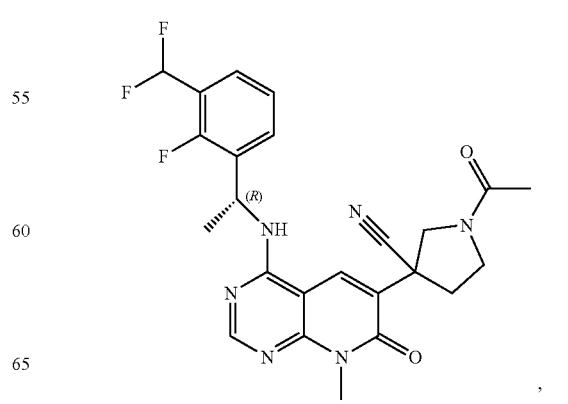

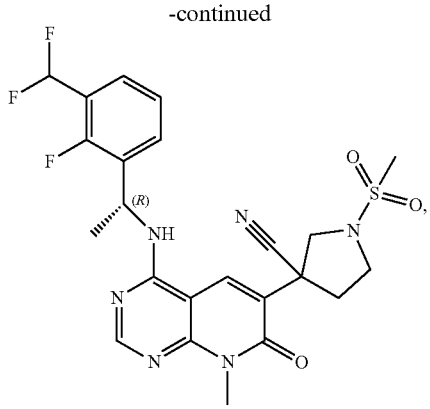
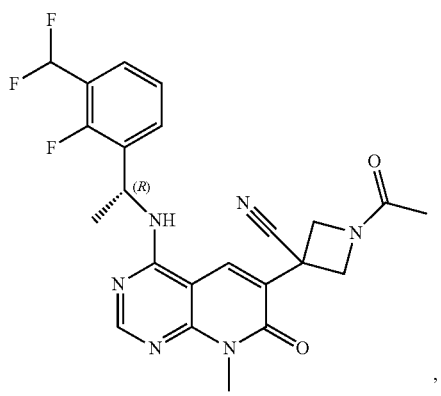
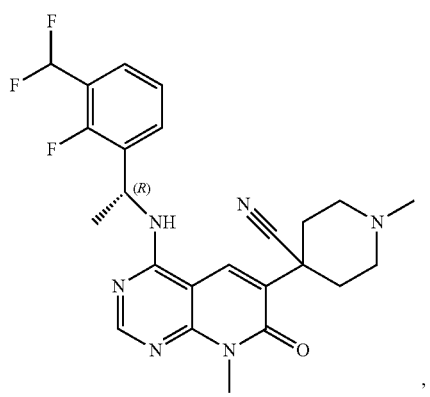
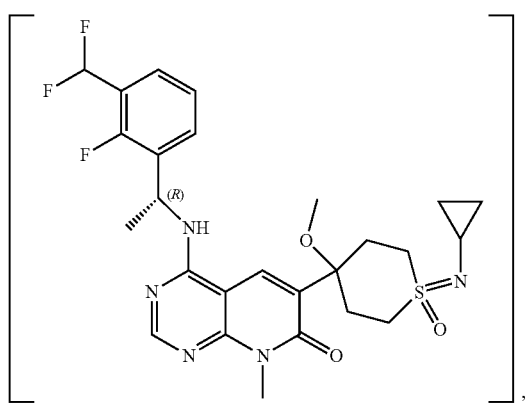
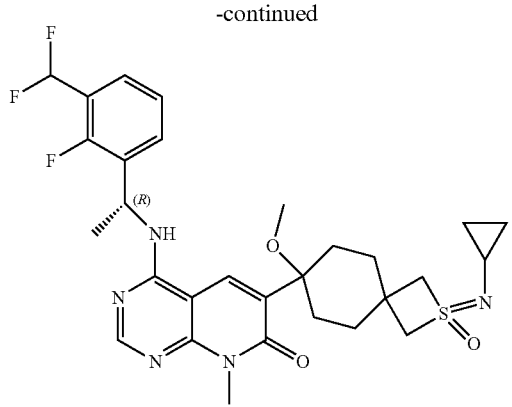
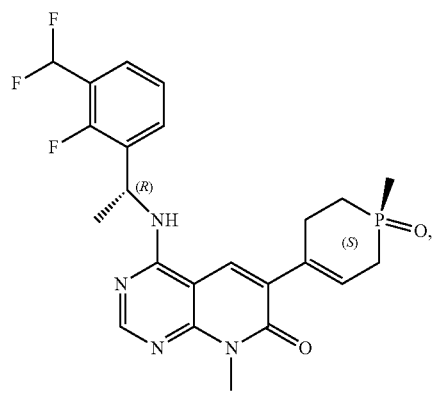
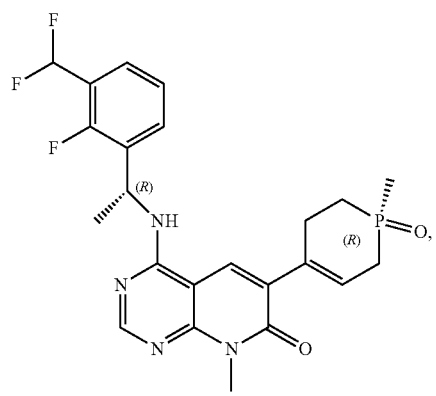
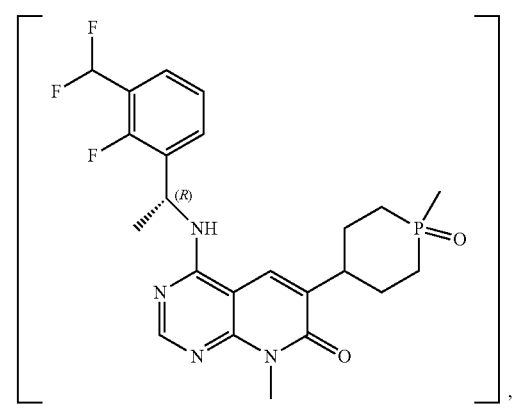

347
-continued
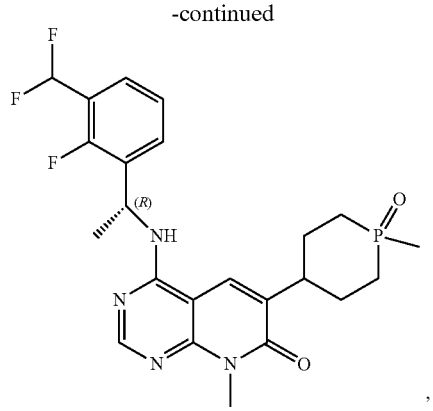
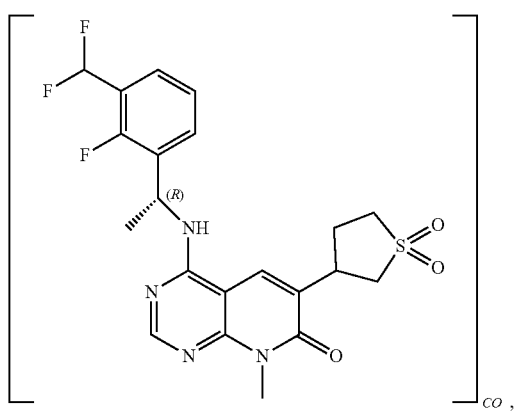
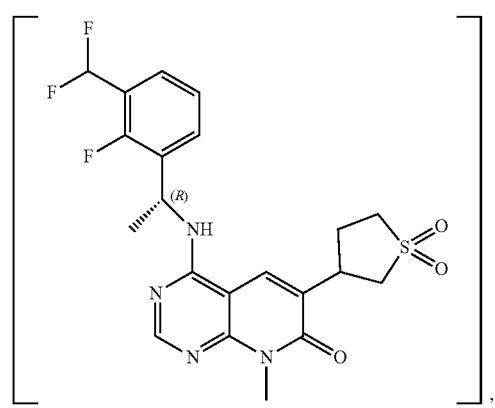
348
-continued
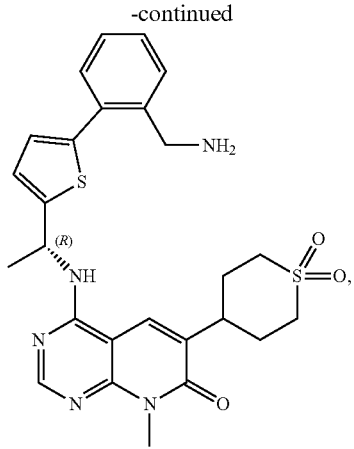
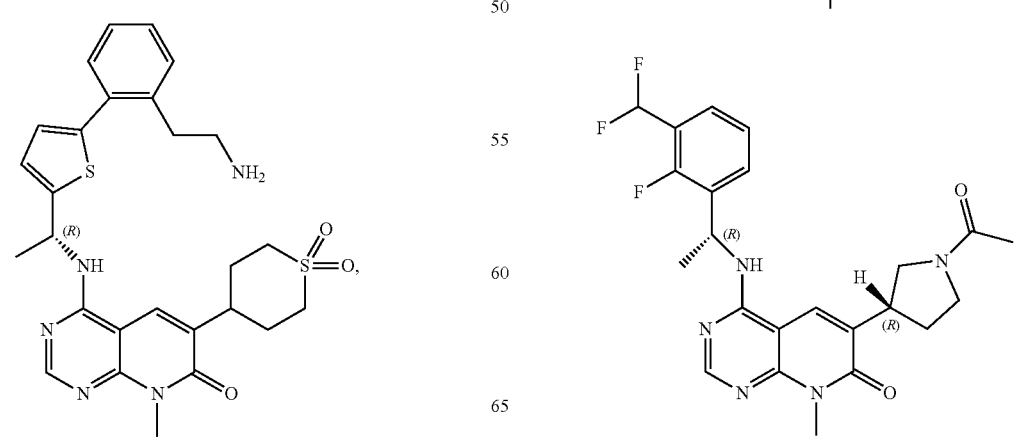

349
-continued
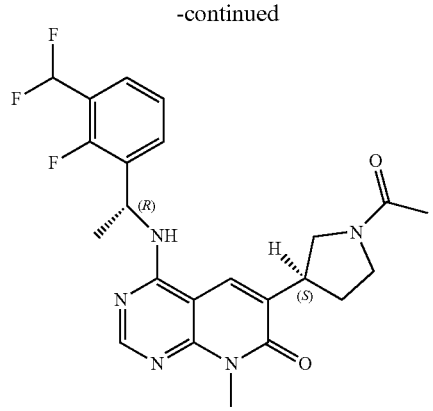
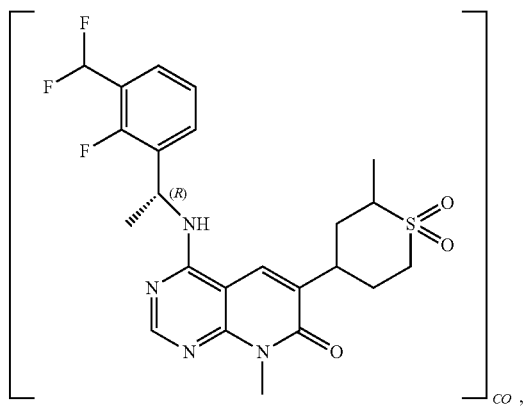
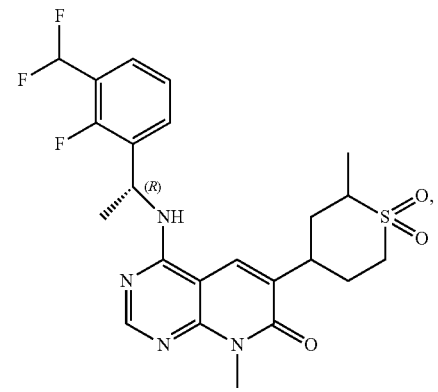
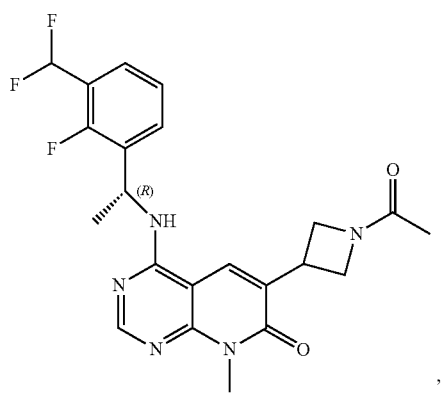
350
-continued
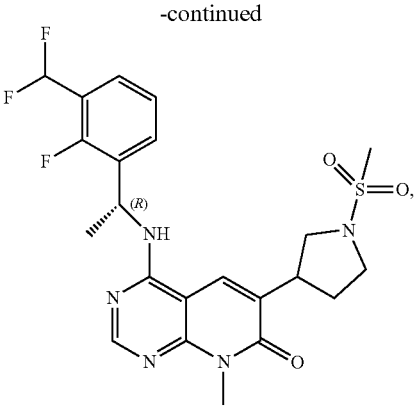
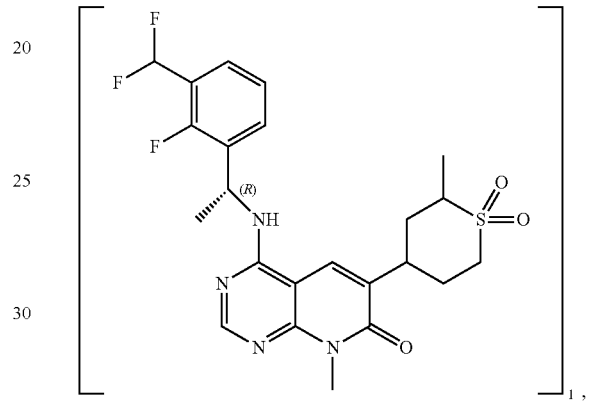
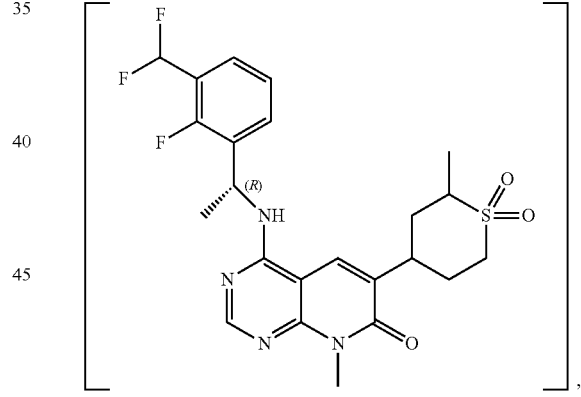
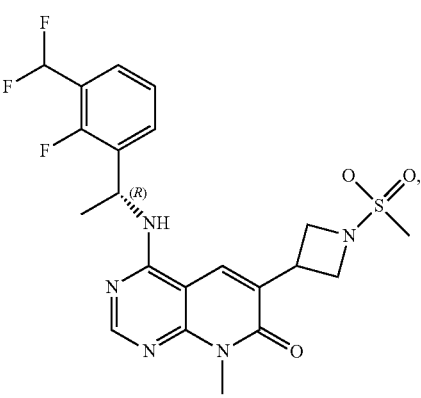

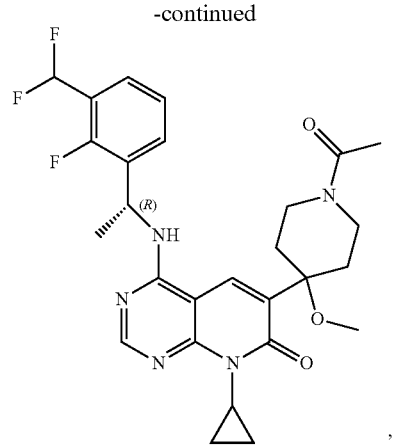
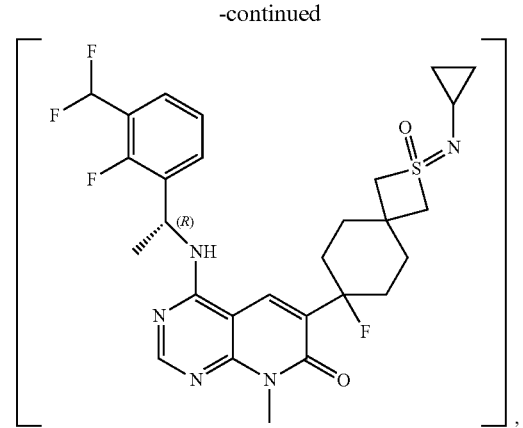
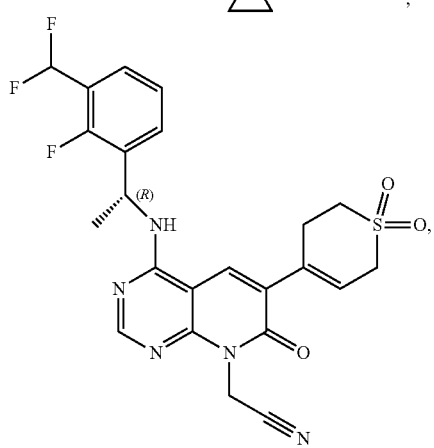
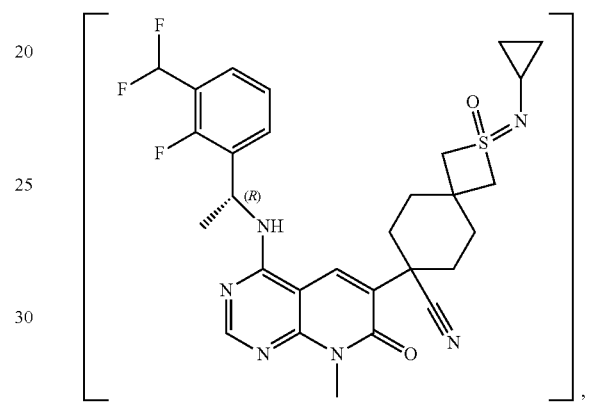
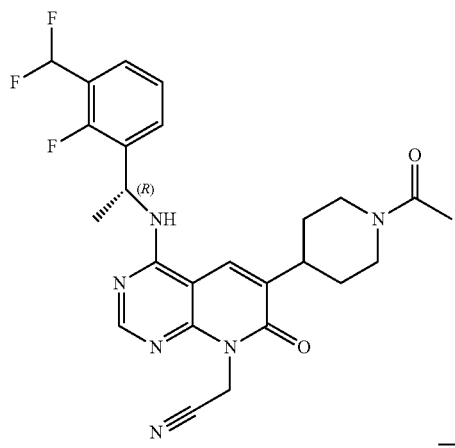
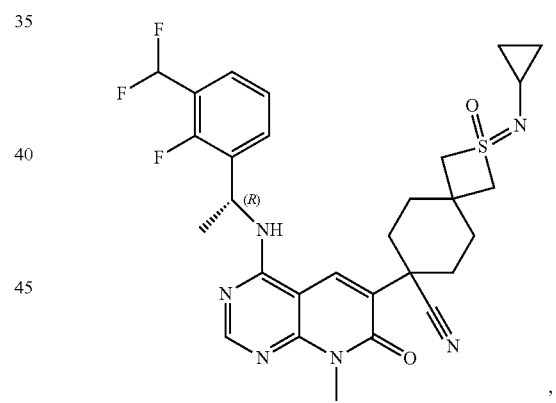
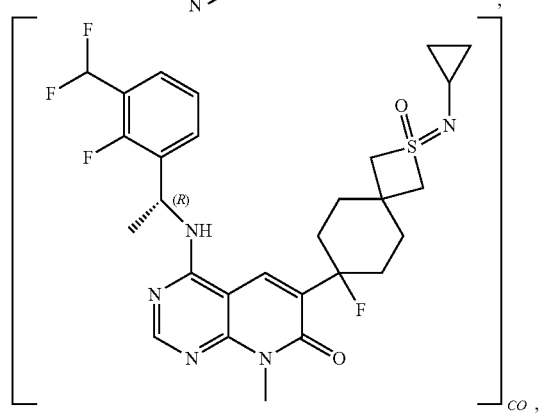
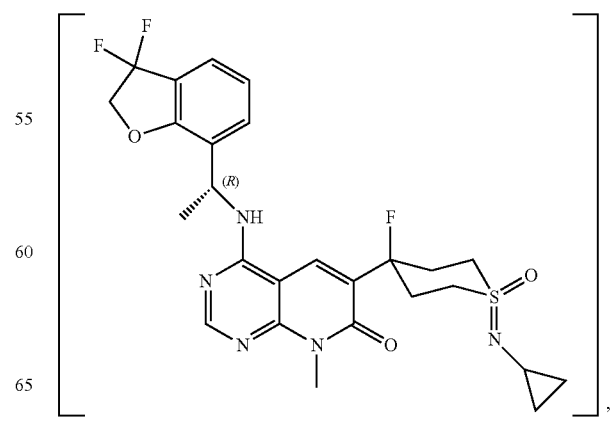

353
-continued
354
-continued
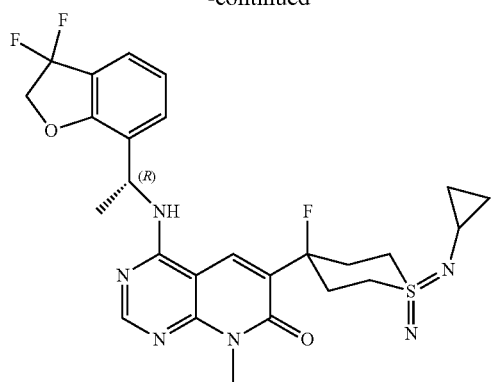
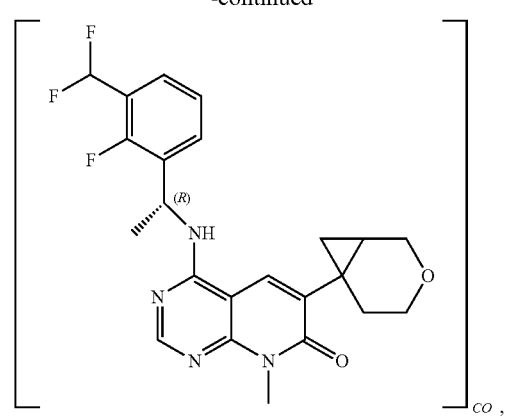
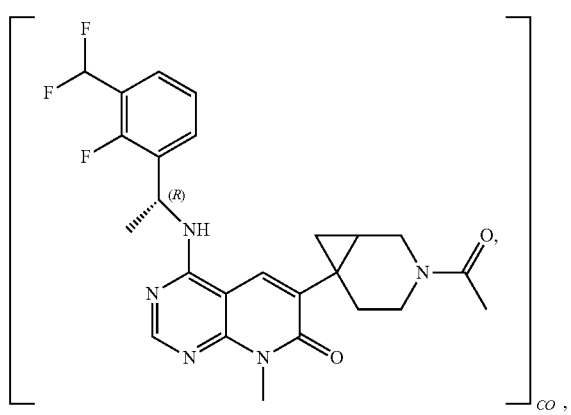
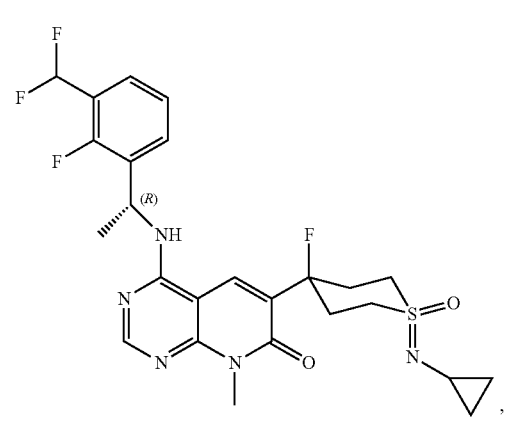
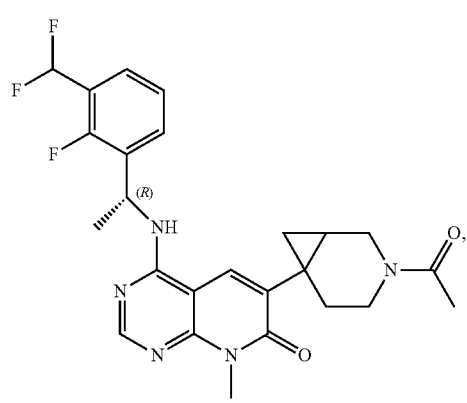
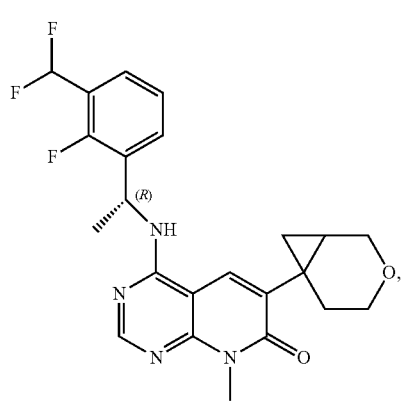

355
-continued
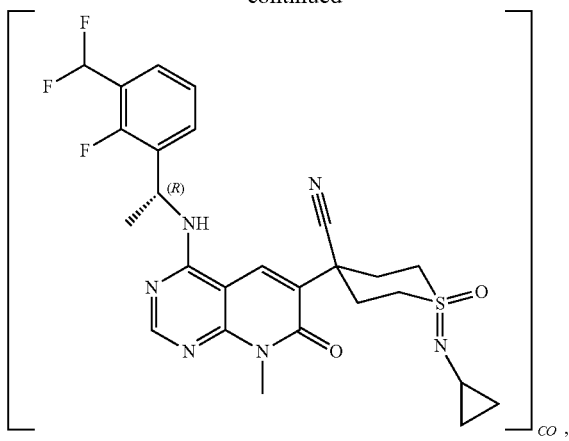
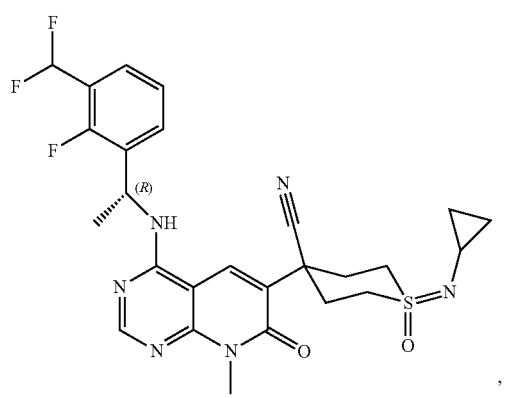
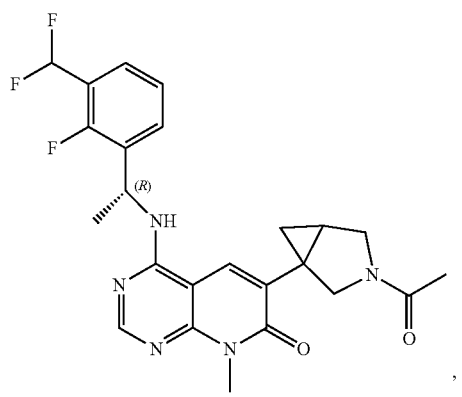
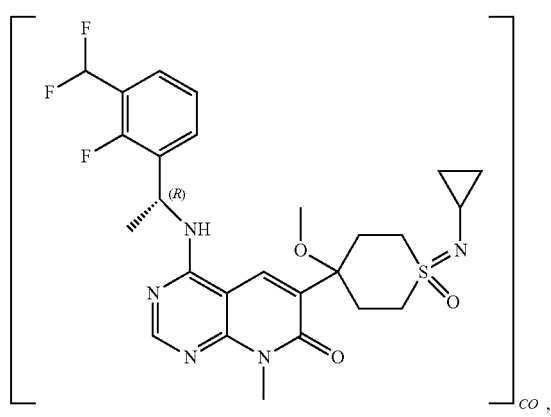
356
-continued
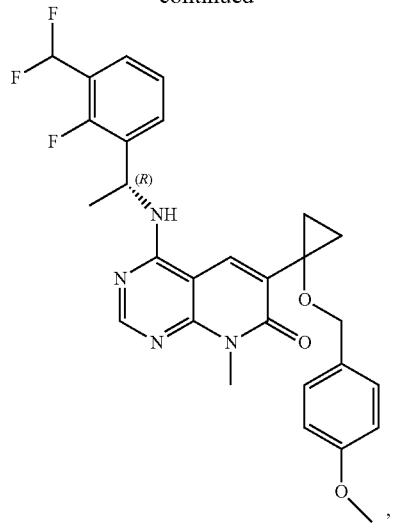
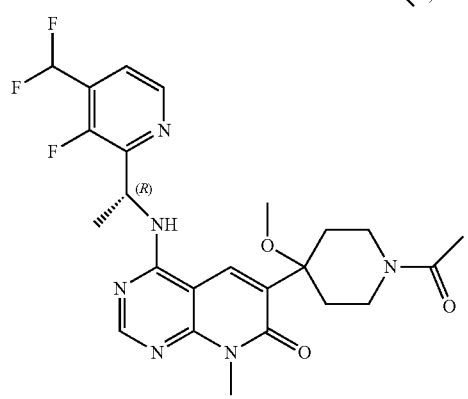
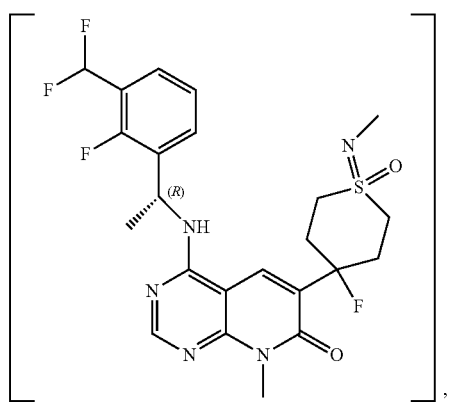
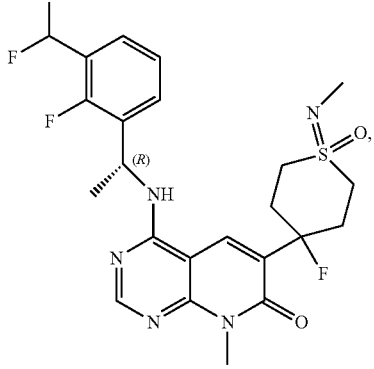

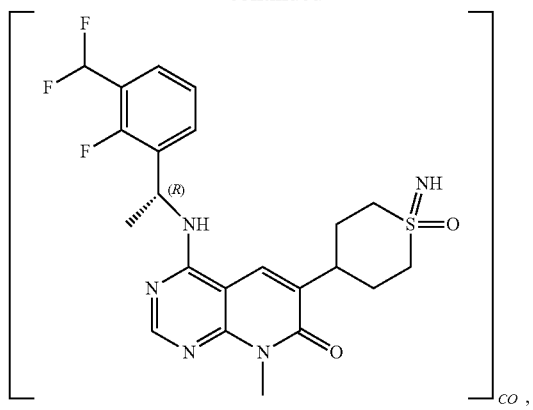
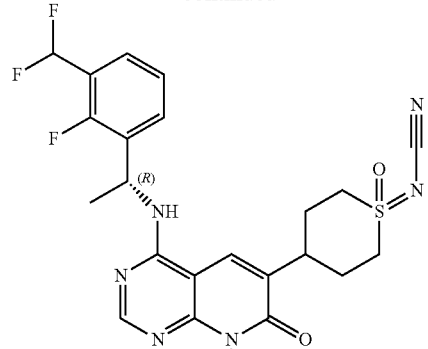
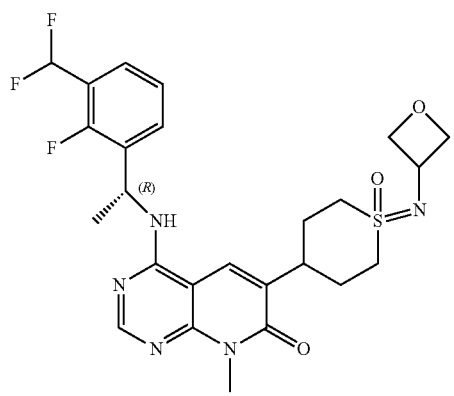
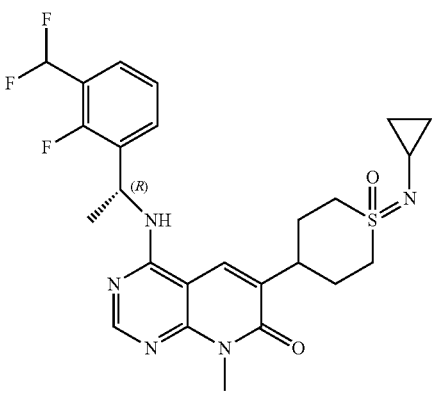
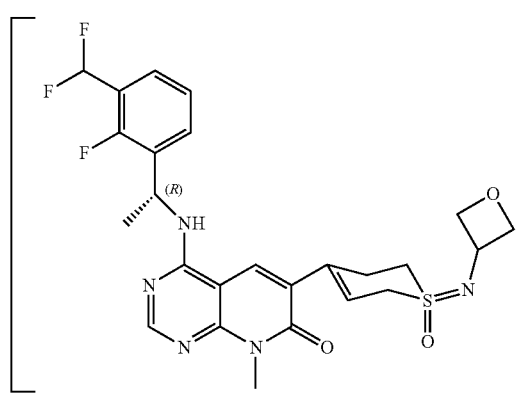
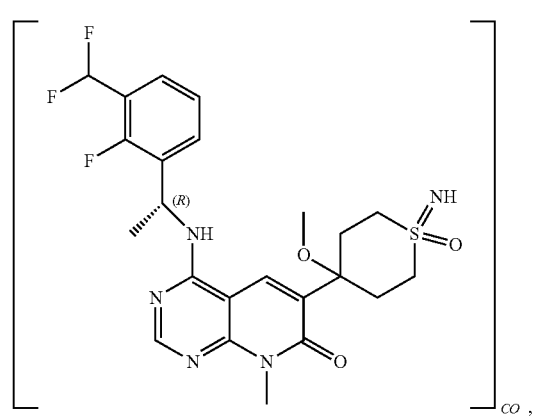
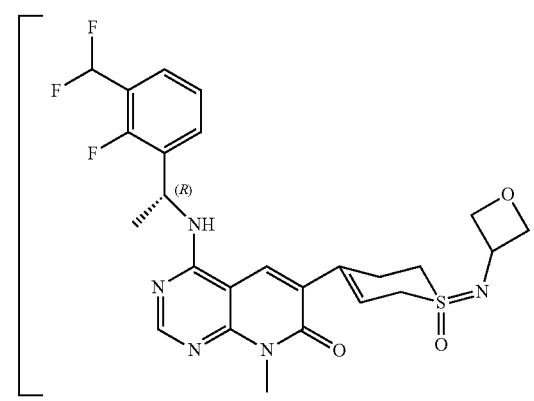
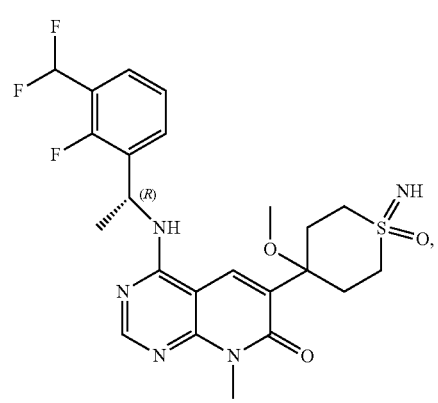

359
-continued
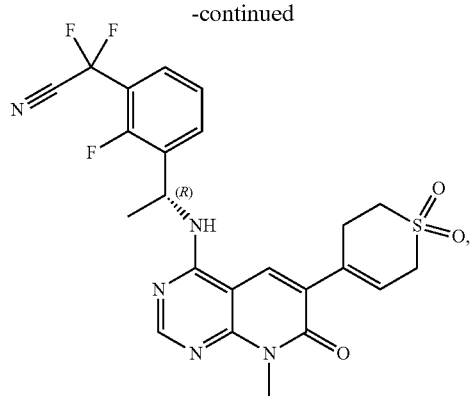
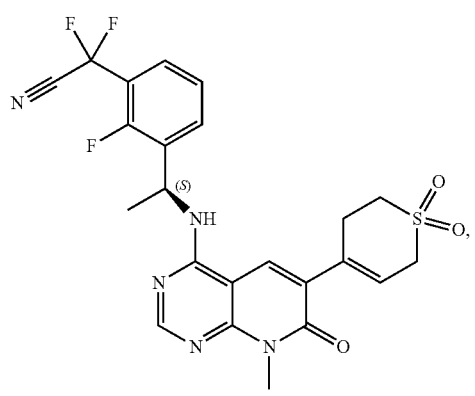
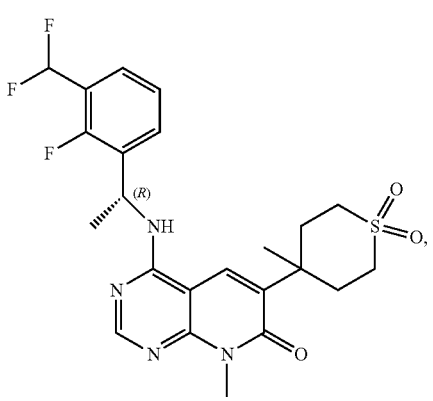
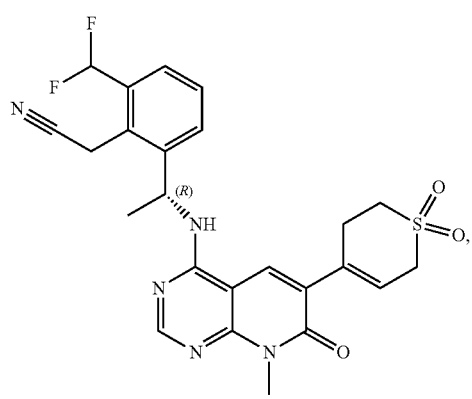
360
-continued
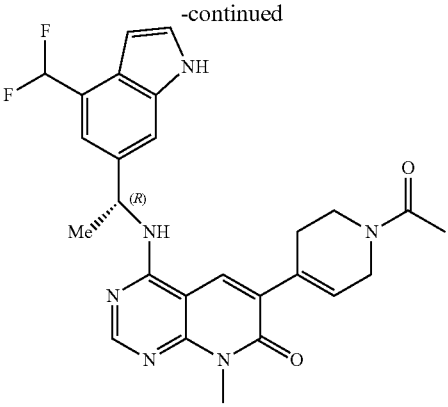
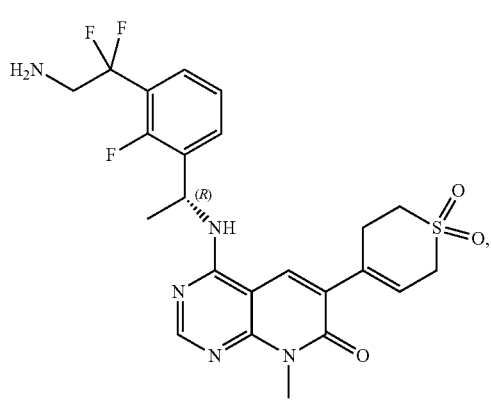
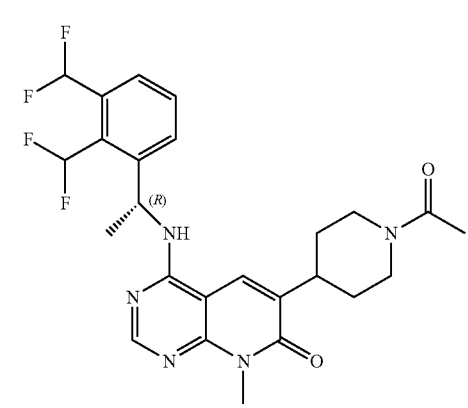
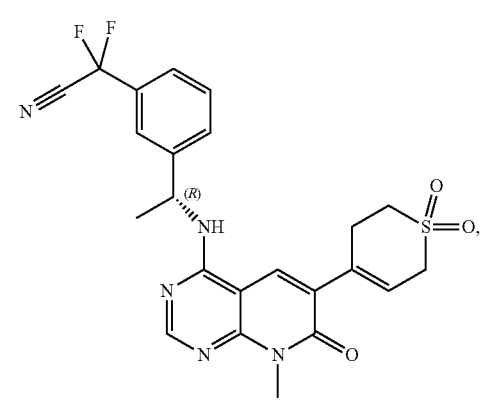

361
-continued
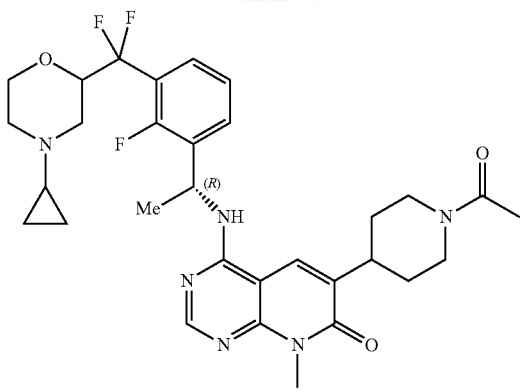
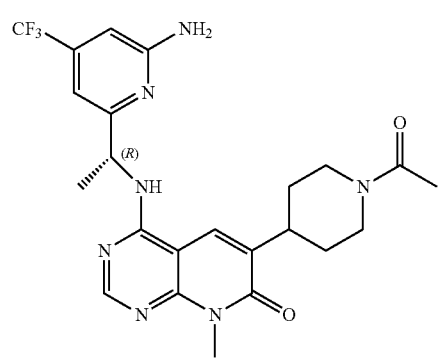
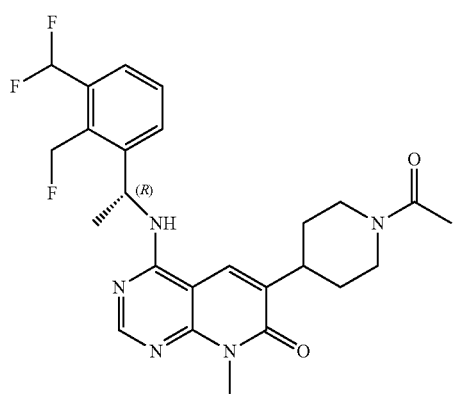
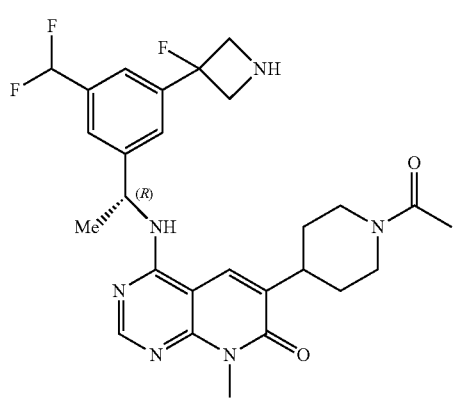
362
-continued
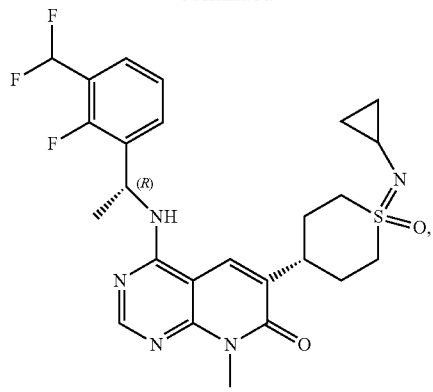
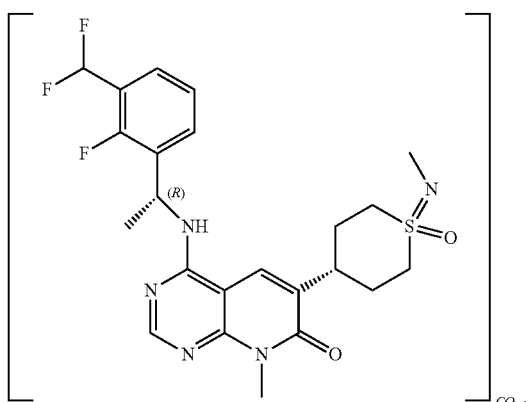
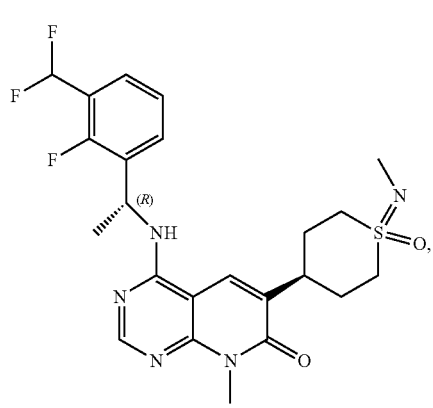
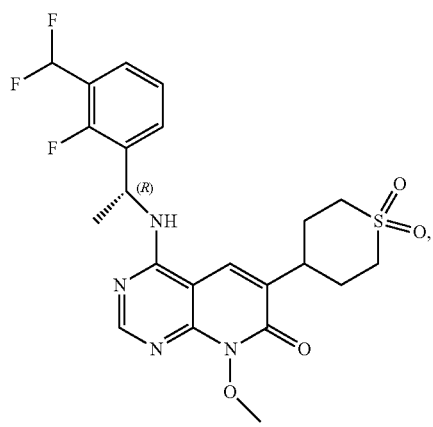

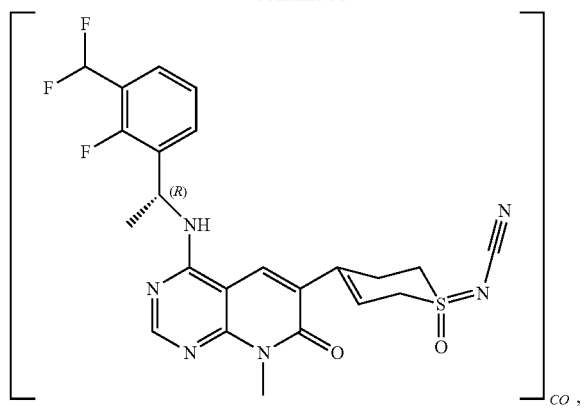
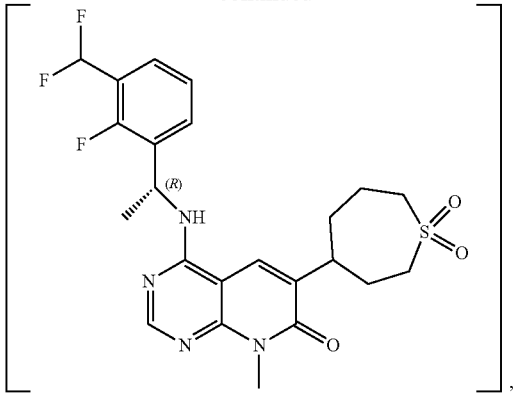
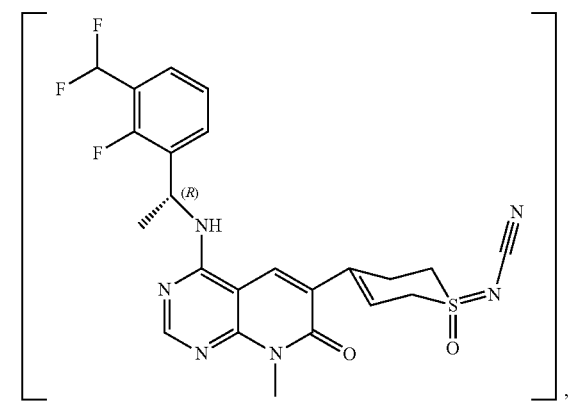
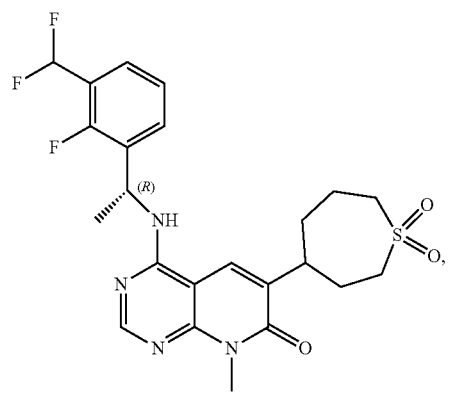
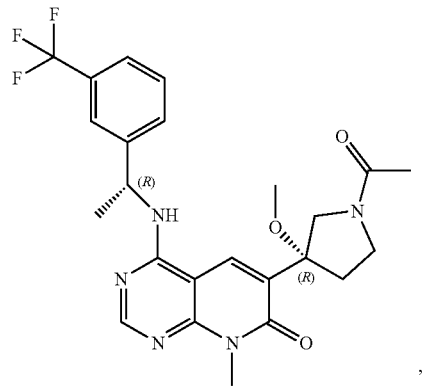
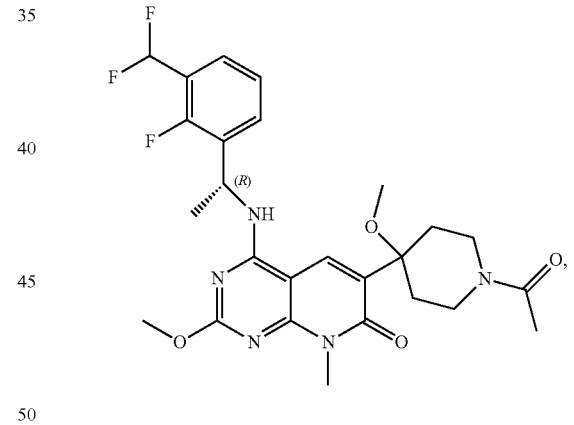
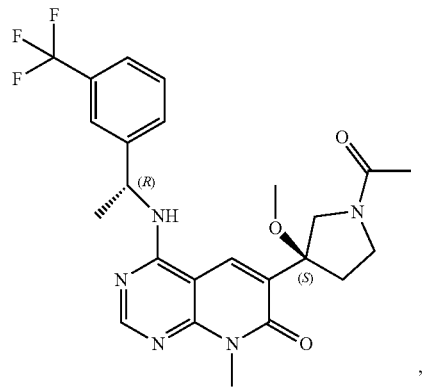
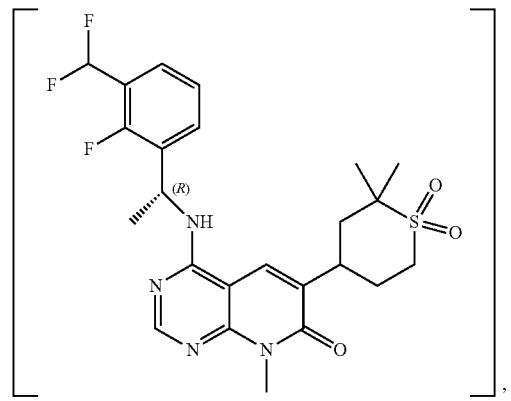

365
-continued
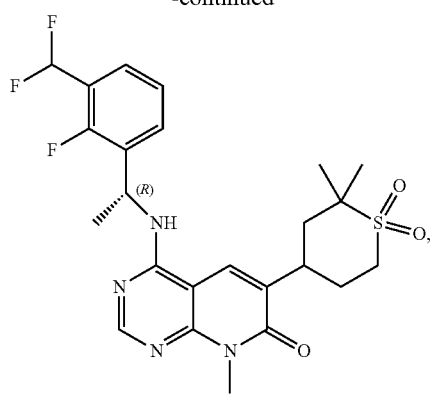
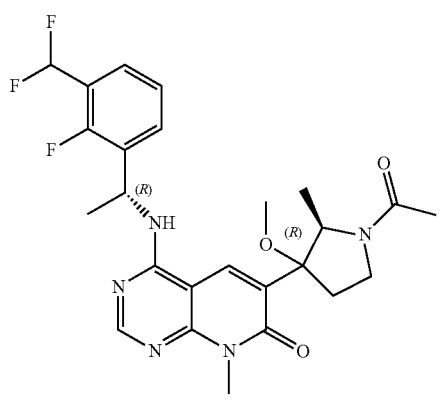
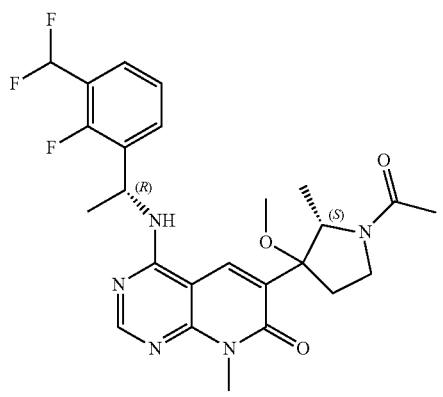
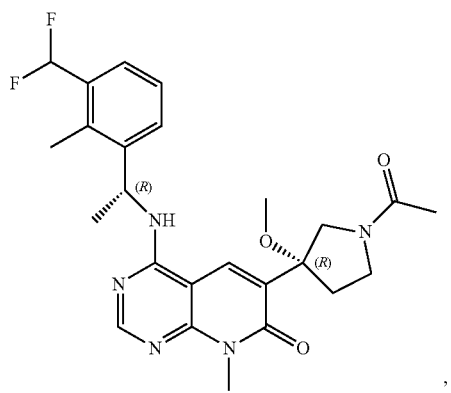
366
-continued
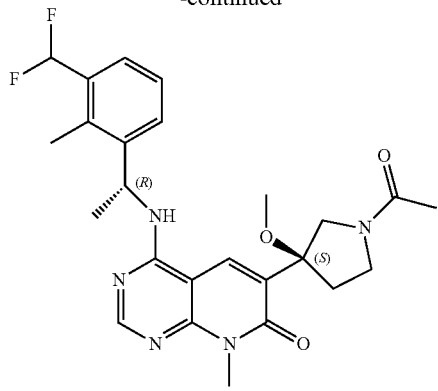
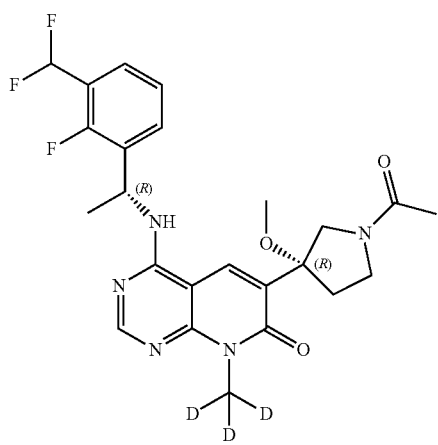
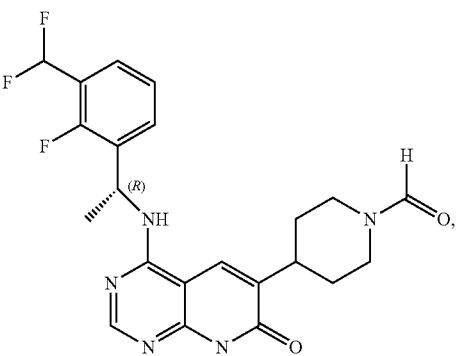
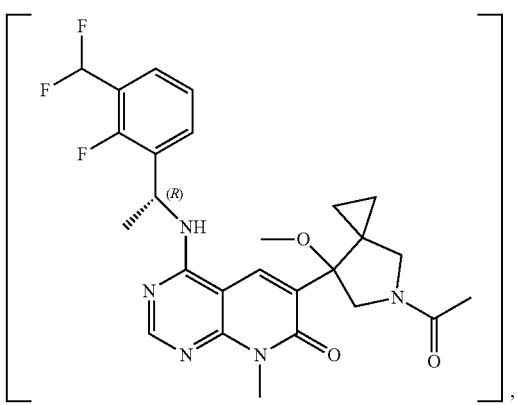

367
-continued
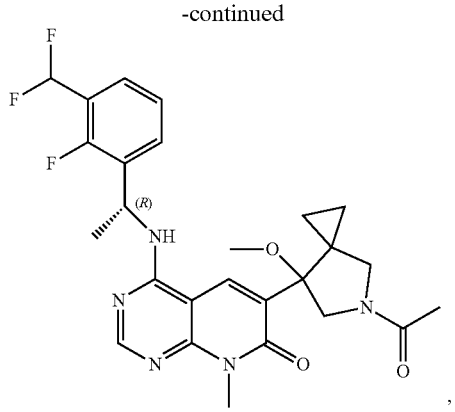
,
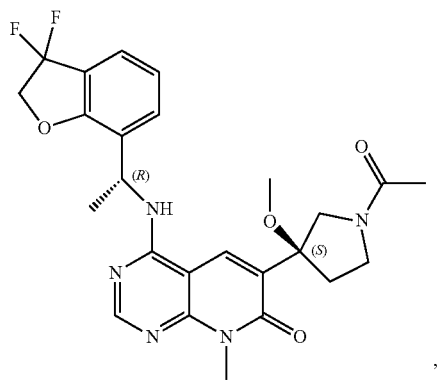
,
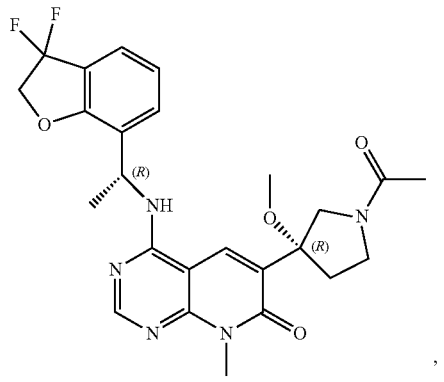
,

,
368
-continued
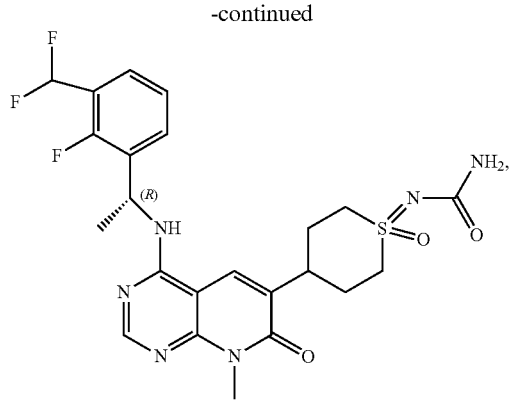
,
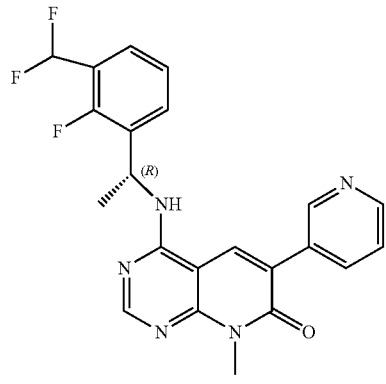
,
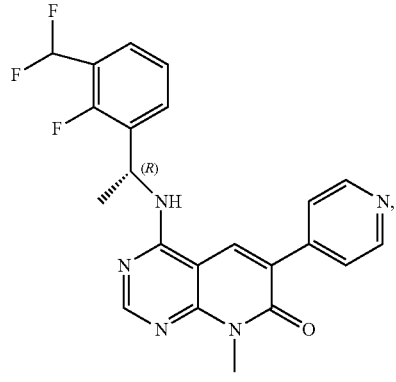
,
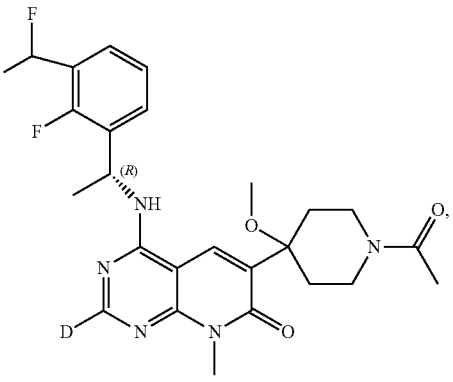
, 369
-continued
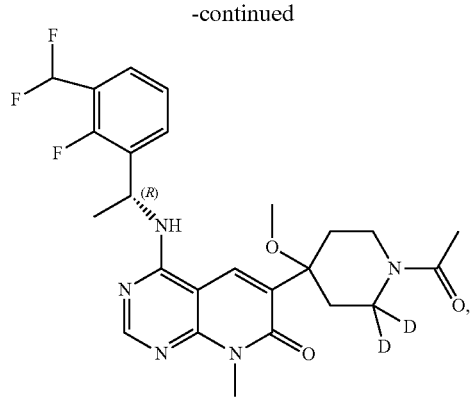
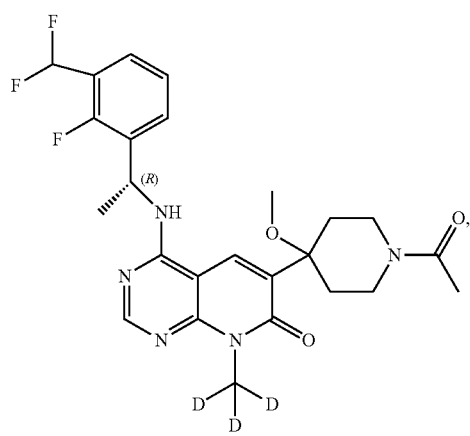
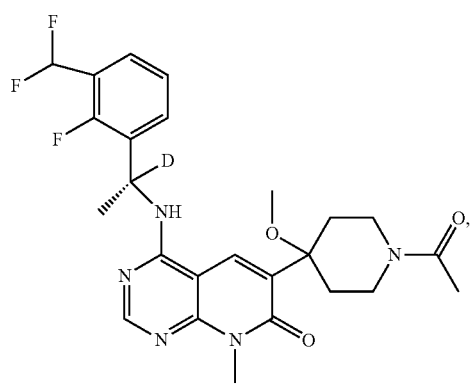
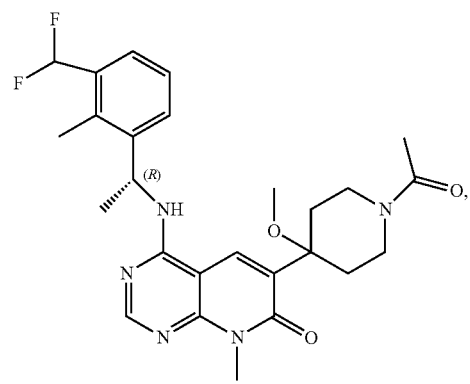
370
-continued
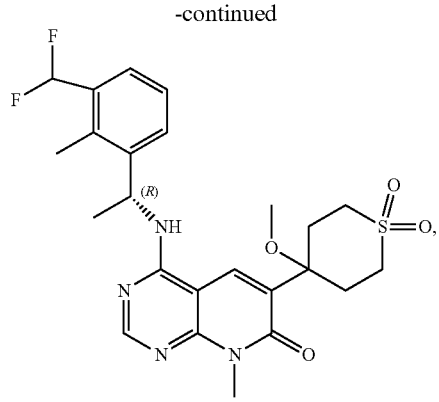
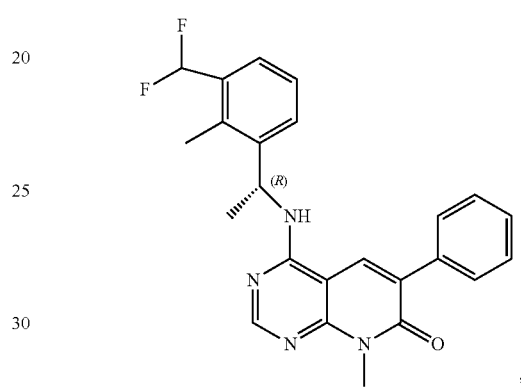
[
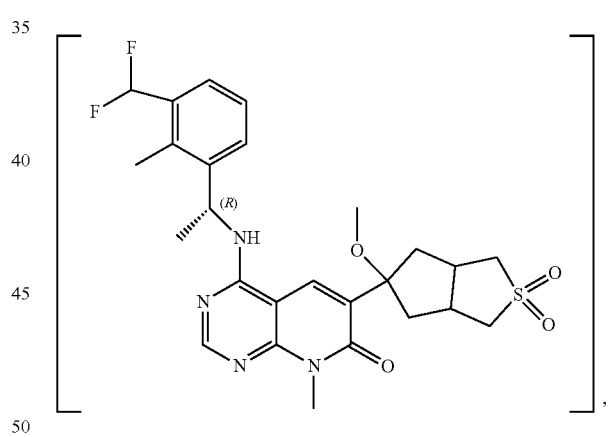
],
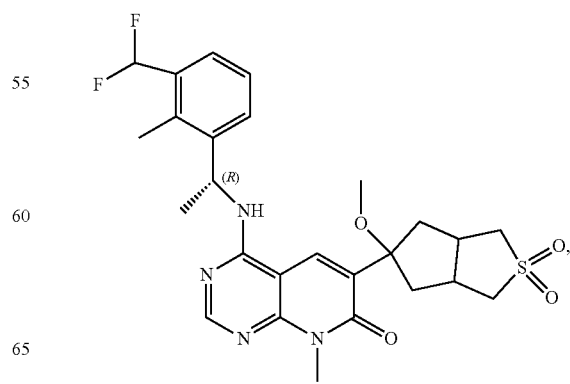

371
-continued
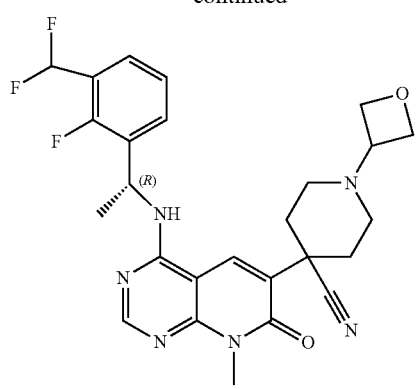
, and
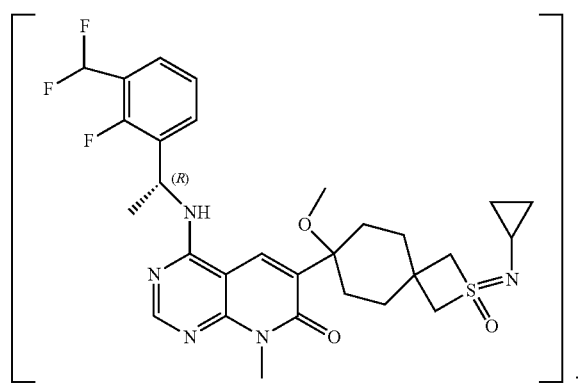
The present disclosure provides a compound, and pharmaceutically acceptable salts, solvates, stereoisomers, and tautomers thereof, selected from the group consisting of compounds of Collection 4:
Collection 4: Certain Compounds of the Present Invention
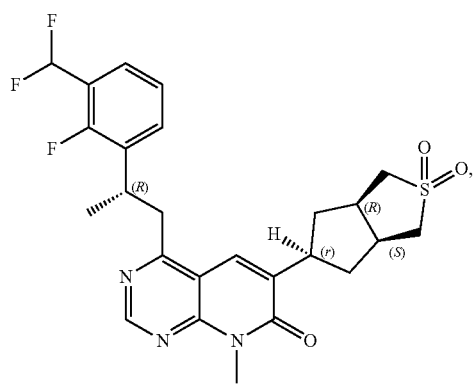
372
-continued
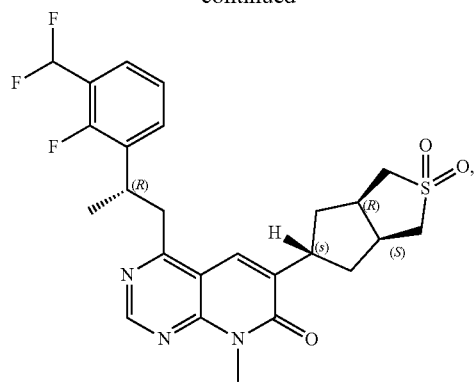
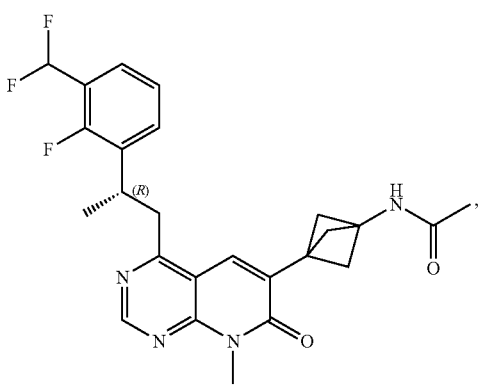
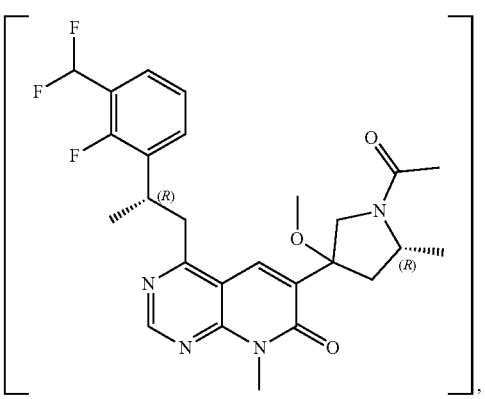
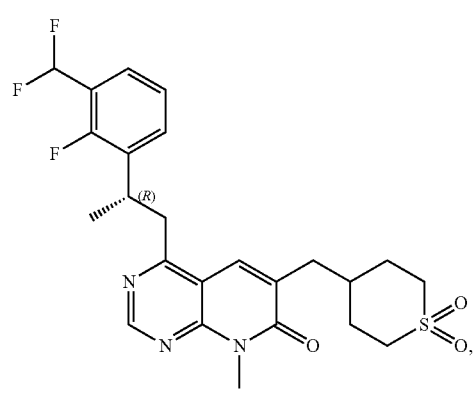

373
-continued
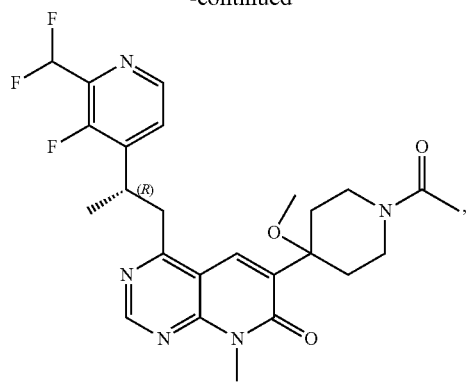
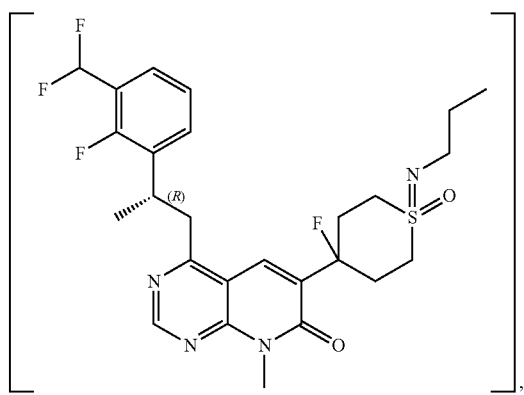
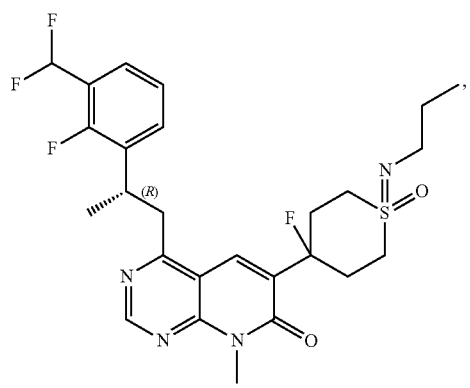
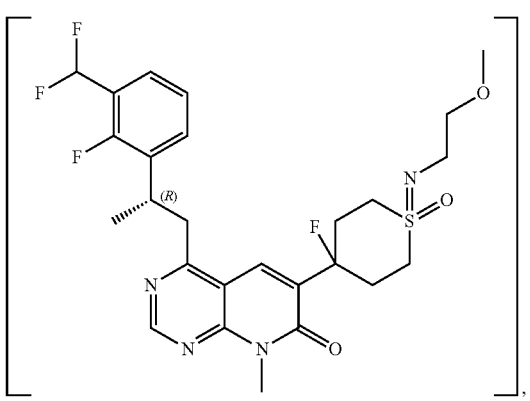
374
-continued
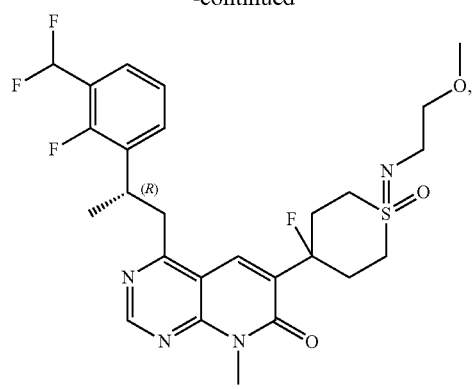
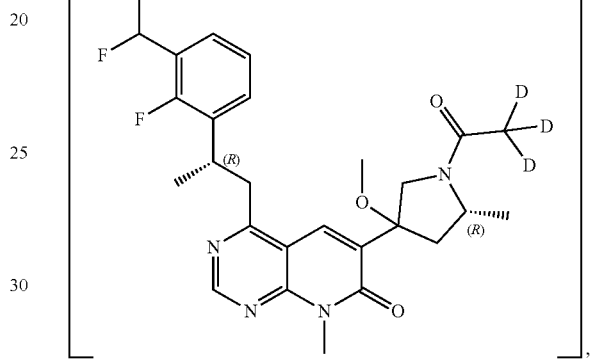
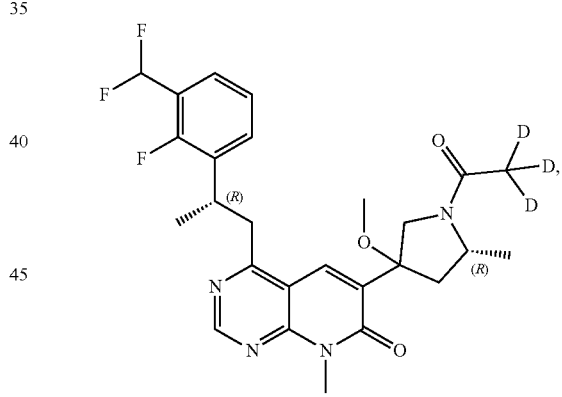
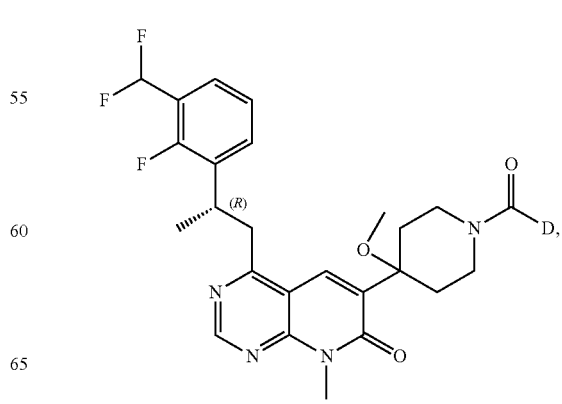

375
-continued
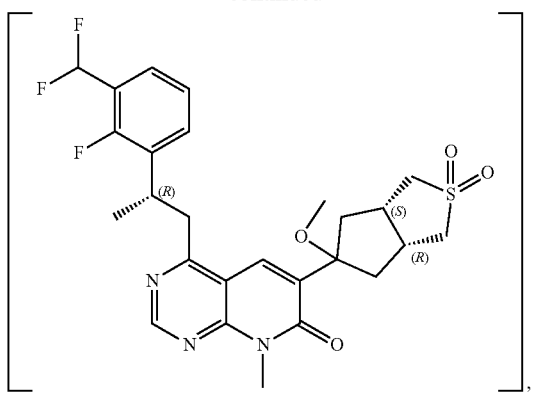
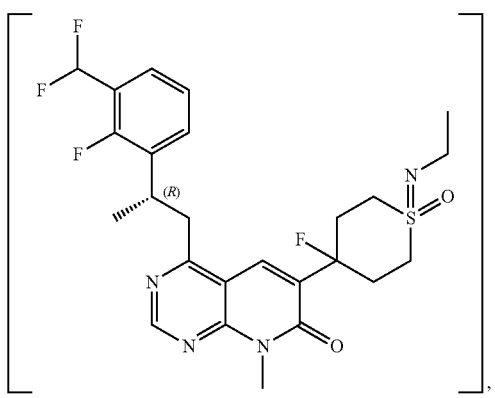
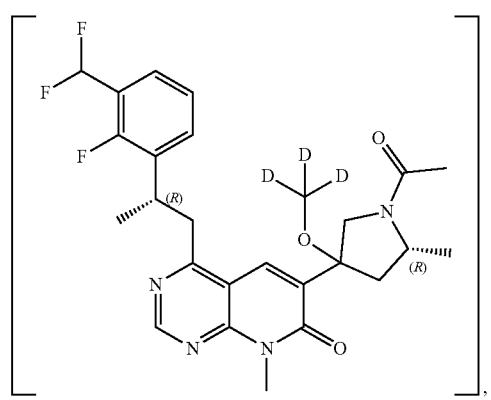
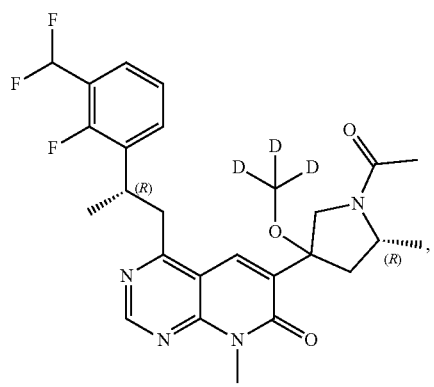
376
-continued
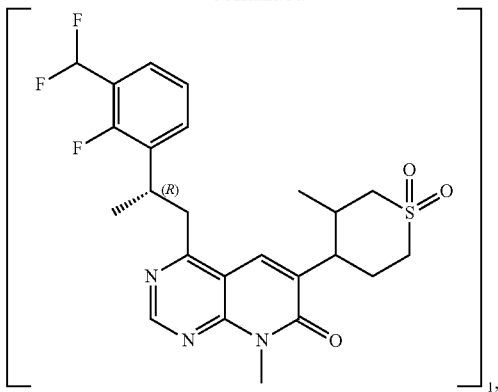
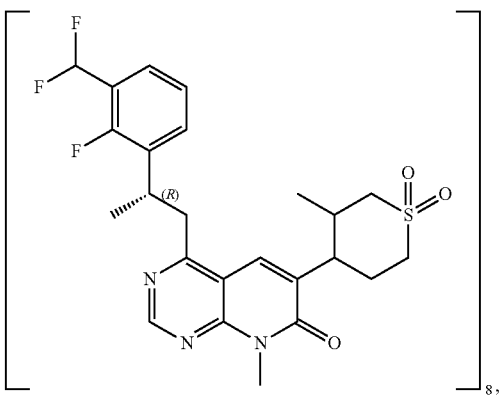
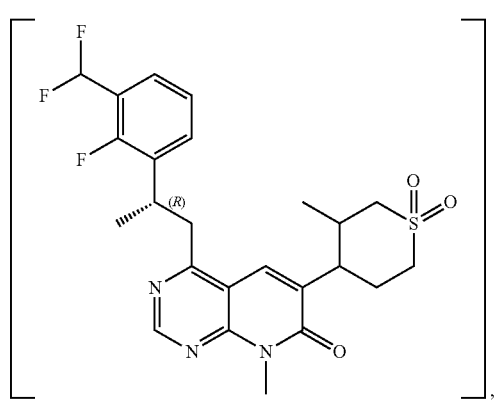
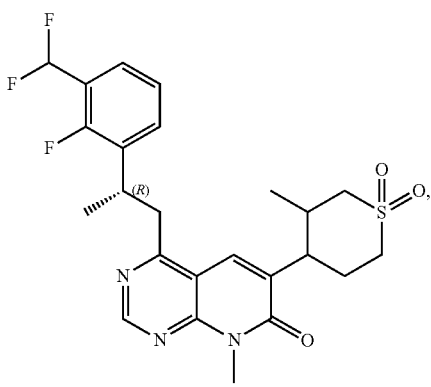

377
-continued
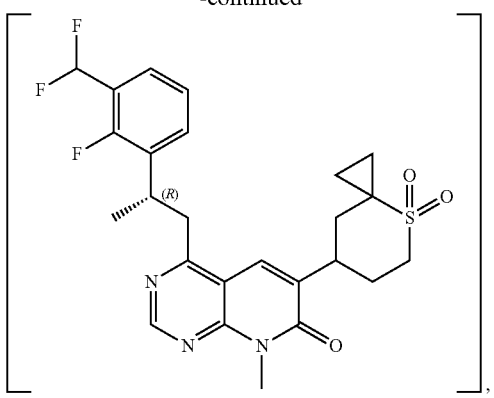
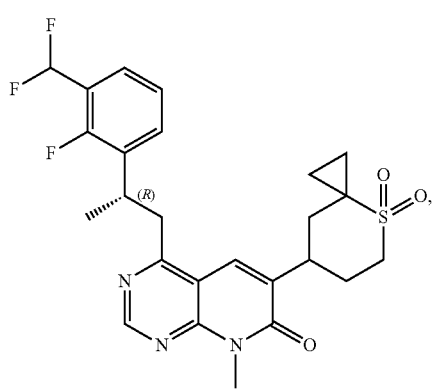
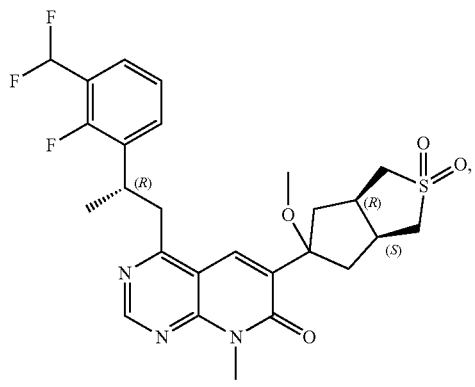
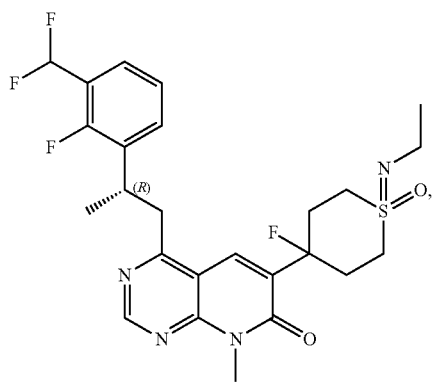
378
-continued
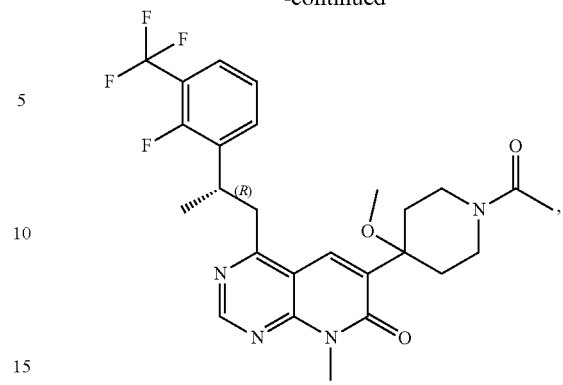
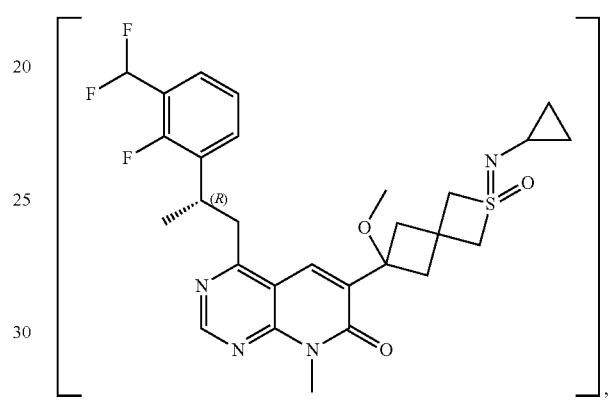
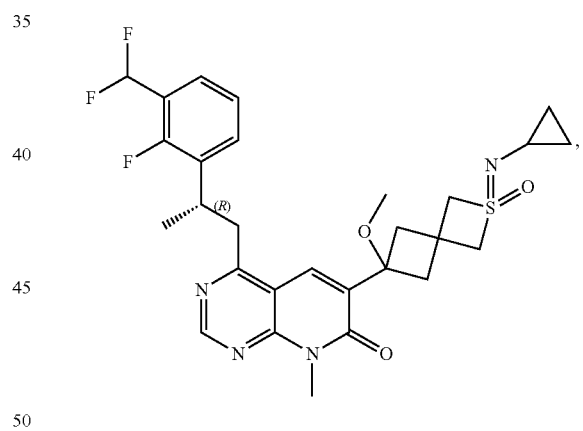
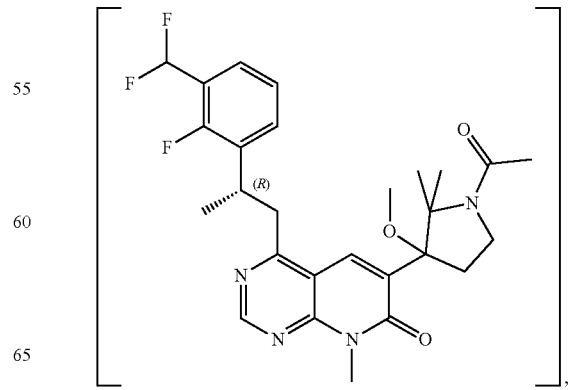

379
-continued

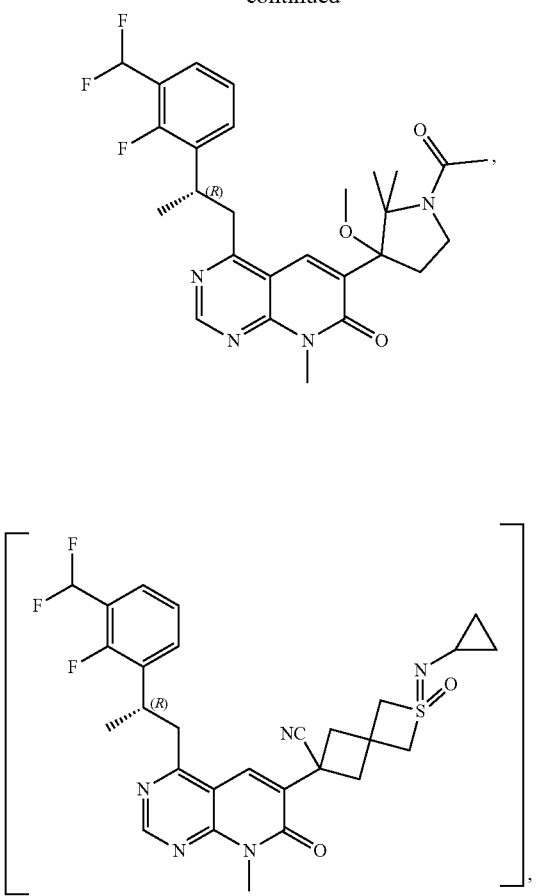

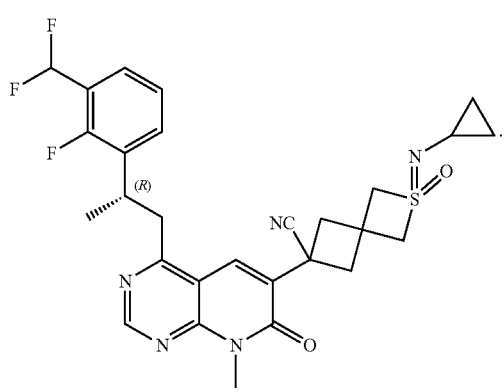

Collection 5: Certain Compounds of the Present Invention

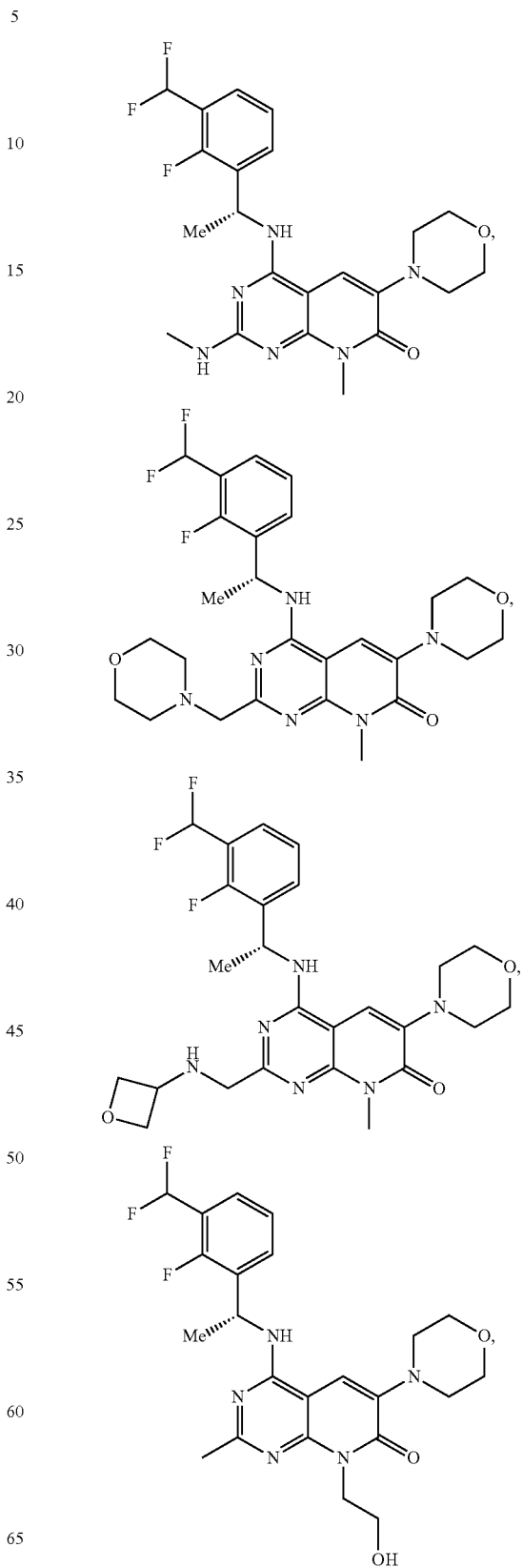

The present disclosure provides a compound, and pharmaceutically acceptable salts, solvates, stereoisomers, and tautomers thereof, selected from the group consisting of compounds of Collection 5. A person of skill in the art may prepare these using conventional methods, including adaptations of synthetic methods disclosed herein.

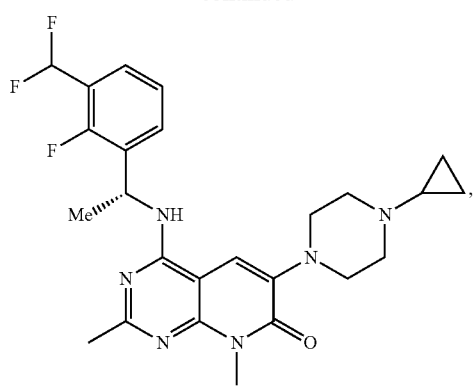
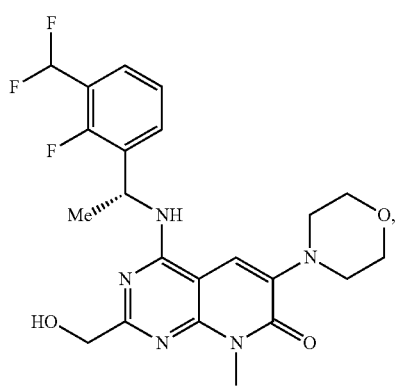
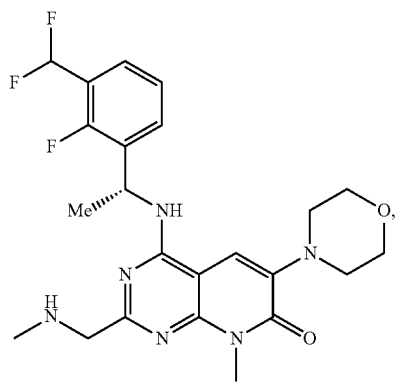
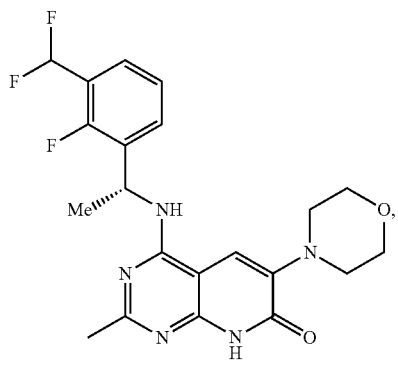
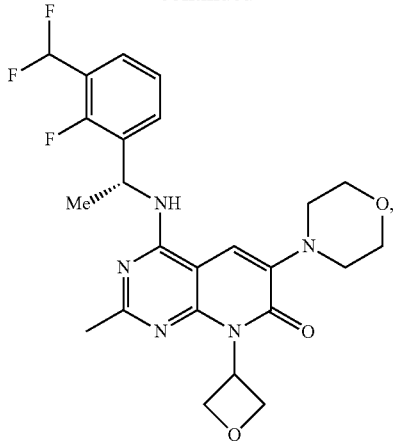
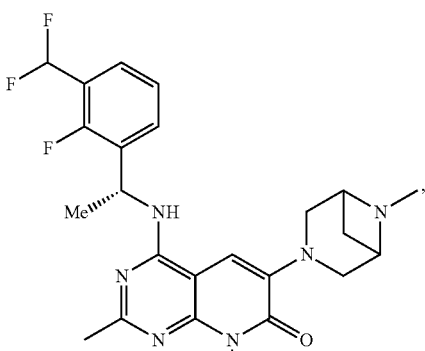
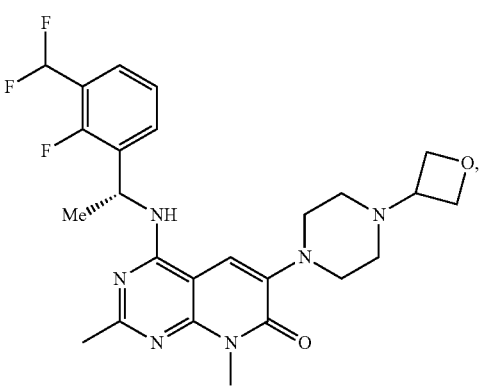
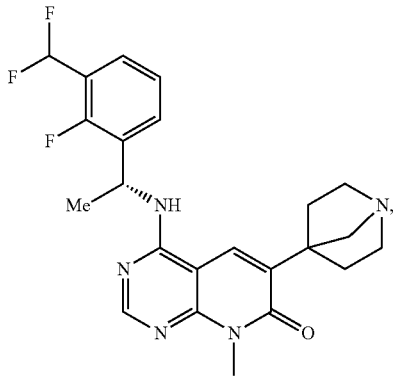

383
-continued
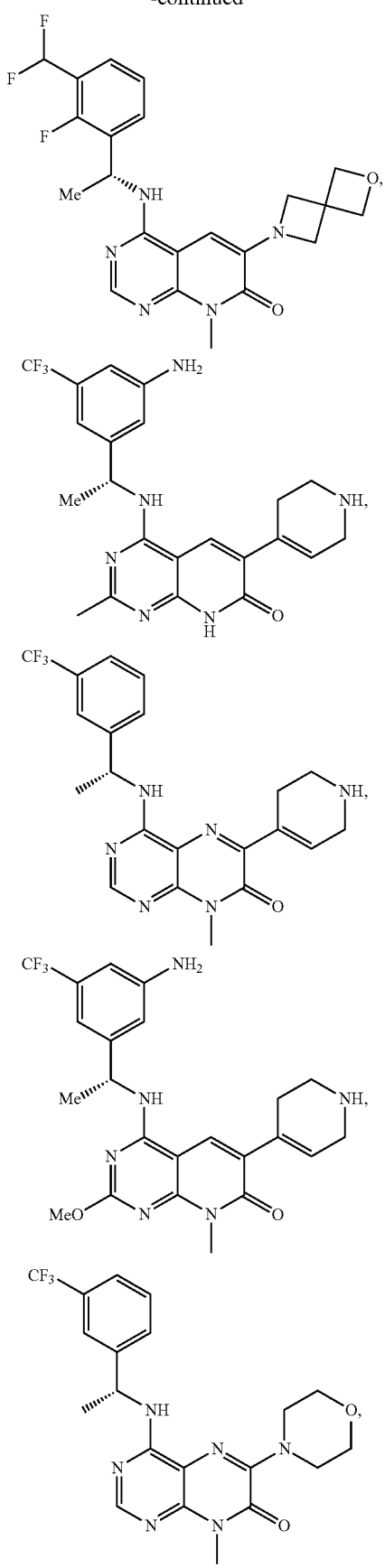
384
-continued
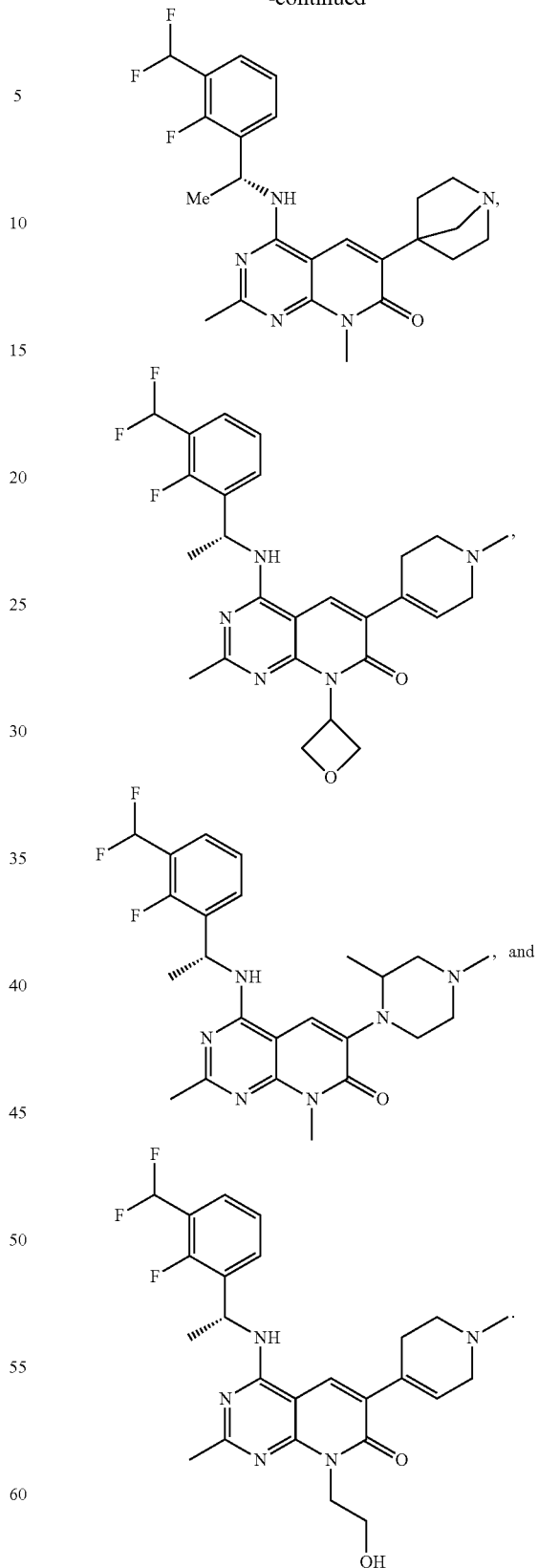
Methods of Synthesizing the Disclosed Compounds
The compounds of the present invention may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of any formula disclosed herein.

Those skilled in the art will recognize if a stereocenter exists in any of the compounds of the present disclosure. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the disclosure can be synthesized using the methods described below, together with synthetic methods known in the art of synthetic organic chemistry, or variations thereon as appreciated by those skilled in the art. These methods include but are not limited to those methods described below.

A general synthesis of substituted (4-aminopyrido[2,3-d]pyrimidin-7(8H)-one or analogous heterocycles is outlined in Scheme 1.

6-bromo-4-chloropyrido[2,3-d]pyrimidin-7(8H)-one (I-1) can undergo a nucleophilic aromatic substitution with an appropriately substituted benzyl amine (G-1). The bromide substituent in the resulting intermediate I-2 can be used for cross coupling reactions with appropriately substituted alcohols, amines, amides, alkyls, olefins, aromatics or heteroaromatics.

Scheme 1

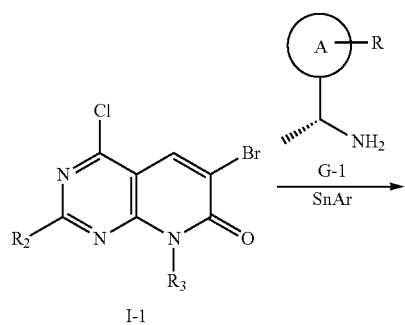

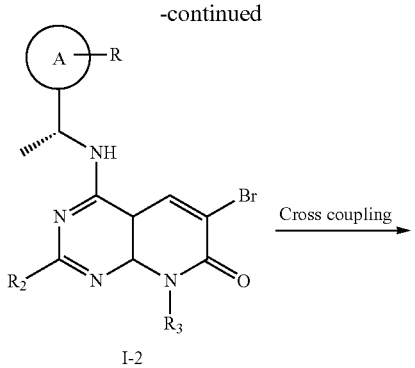

I-2

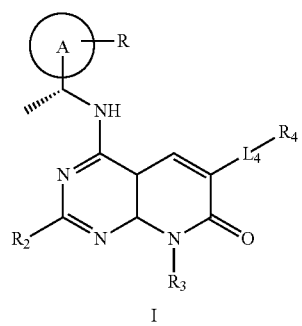

I

Alternatively final compounds with a nitrogen substituent in position 6 (bromo) can be prepared from 6-amino-4-chloropyrido[2,3-d]pyrimidin-7(8H)-one by alkylation or acylation to give intermediates if type I-5, which can undergo nucleophilic aromatic substitution with an appropriately substituted benzyl amine (G-1) to furnish final analogs I according to Scheme 2.

Scheme 2

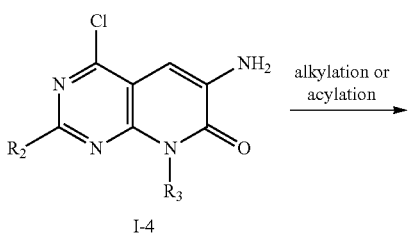

I-4

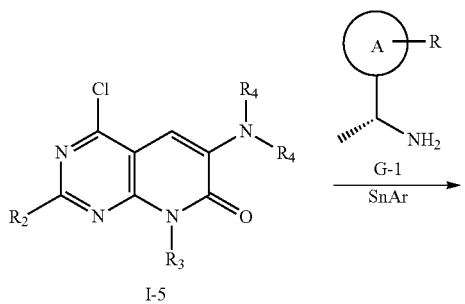

I-5

-continued

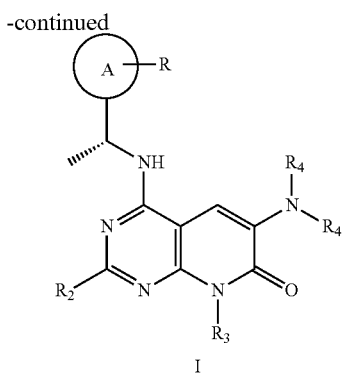

Building block G-1 can be prepared as outlined in scheme 3. Appropriately substituted aryl or heteroaryl bromides G-2 can be transformed into the correspond acetyl hetero)aryls G-3 by metal halogen exchange, followed by addition of an acylating agent. The ketone functionality can be stereoselectively transformed into the chiral amine using Ellman's method.

Scheme 3

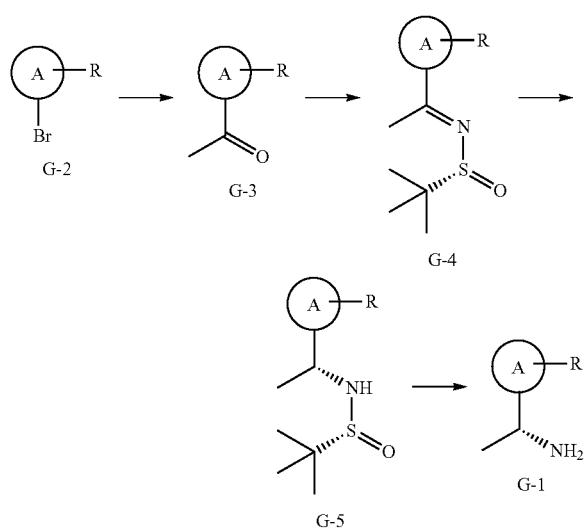

Therapeutic Use

Due to their biological properties the compounds of the present disclosure, their tautomers, racemates, enantiomers, diastereomers, mixtures thereof and the salts of all the above-mentioned forms may be suitable for treating diseases characterized by excessive or abnormal cell proliferation such as cancer.

For example, the following cancers, tumors and other proliferative diseases may be treated with compounds of the present disclosure, without being restricted thereto:

cancers/tumors/carcinomas of the head and neck: e.g., tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands); intraocular cancers (e.g., uveal melanoma), and orbital and adnexal cancers;

cancers/tumors/carcinomas of the lung: e.g., non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g., neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma), astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g., acoustic), spinal axis tumors;

cancers/tumors/carcinomas of the gastrointestinal (GI) tract: e.g., tumors/carcinomas/cancers of the esophagus, stomach (gastric cancer), pancreas, liver and biliary tree (including hepatocellular carcinoma (HCC), e.g., childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g., renal pelvis, renal cell carcinoma (RCC), nephroblastoma (Wilms tumor), hypernephroma, Grawitz tumor; ureter; urinary bladder, e.g., urachal cancer, urothelial cancer; urethra, e.g., distal, bulbomembranous, prostatic; prostate (androgen dependent, androgen independent, castration resistant, hormone independent, hormone refractory), penis);

cancers/tumors/carcinomas of the testis: e.g., seminomas, non-seminomas;

gynecologic cancers/tumors/carcinomas: e.g., tumors/carcinomas/cancers of the ovary, fallopian tube, peritoneum, cervix, vulva, vagina, uterine body (including endometrium, fundus);

cancers/tumors/carcinomas of the breast: e.g., mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), HER2 positive breast cancer, triple negative breast cancer, Paget's disease of the breast;

cancers/tumors/carcinomas of the endocrine system: e.g., tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/ tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g., fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewings sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g., myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Pagets sarcoma), Ewings tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g., pleural mesothelioma, peritoneal mesothelioma;

cancers of the skin: e.g., basal cell carcinoma, squamous cell carcinoma, Merkels cell carcinoma, melanoma (including cutaneous, superficial spreading, lentigo maligna, acral lentiginous, nodular, intraocular melanoma), actinic keratosis, eyelid cancer;

neoplasms of the peripheral and central nervous system and brain: e.g., astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g., acoustic), spinal axis tumors, neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

lymphomas and leukemias: e.g., B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), Burkitt leukemia, T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkins disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML), JMML (juvenile myelomonocytic leukemia), acute leukemia of ambiguous lineage, myeloproliferative neoplasms, blastic plasmacytoid dendritic cell neoplasm, early T-cell precursor leukemia, natural killer cell leukemia/lymphoma, myeloid/lymphoid neoplasms with eosinophilia, myeloid sarcoma, transient abnormal myelopoiesis; and cancers of unknown primary site (CUP).

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

epithelial cancers, e.g., squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma; and nonepithelial and mesenchymal cancers, e.g., sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas.

The compounds of the present disclosure may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery and/or other compounds.

Of course, the above also includes the use of the compounds of the present disclosure in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Additional Methods of Using the Disclosed Compounds

One aspect of the present disclosure relates to a method of inhibiting SOS1 in a subject in need thereof, comprising administering to the subject a SOS1 inhibitor of the present invention, or a pharmaceutically acceptable salt, solvate, hydrate, tautomer, or isomer thereof.

Another aspect of the present disclosure relates to a method of treating or preventing a disease that is effected or characterized by modification of the interaction of SOS1 and a RAS-family protein and/or RAC1 in a subject in need thereof. The method involves administering to a patient in need of treatment for diseases or disorders associated with SOS1 modulation an effective amount of a compound of any formula disclosed herein, or a pharmaceutically acceptable salt, solvate, isomer, prodrug, or tautomer thereof.

In certain embodiments, a method is provided of inhibiting the interaction of SOS1 and a RAS-family protein in a cell or inhibiting the interaction of SOS1 and RAC1 in a cell, comprising administering to the cell a compound of any formula disclosed herein, or a pharmaceutically acceptable salt, solvate, hydrate, tautomer, or isomer thereof, and a pharmaceutically acceptable carrier.

In certain embodiments, a method is provided of treating or preventing cancer in a subject in need thereof, comprising administering to the subject an effective amount of a compound of any formula disclosed herein, or a pharmaceutically acceptable salt, solvate, hydrate, tautomer, or isomer thereof.

In certain embodiments, the disease can be, but is not limited to, cancer. In certain embodiments, the disease or cancer is selected from the group consisting of pancreatic cancer, lung cancer, colorectal cancer, cholangiocarcinoma, multiple myeloma, melanoma, uterine cancer, endometrial cancer, thyroid cancer, acute myeloid leukemia, JMLL (juvenile rnyelomonocytic leukemia), acute lymphoblastic leukemia/lymphoma, lymphomas, tumors of the central and peripheral nervous system, epithelial and nonepithelial tumors and mesenchymal tumor, bladder cancer, urothelial cancer, gastric cancer, cervical cancer, head and neck squamous cell carcinoma, diffuse large B cell lymphoma, esophageal cancer, chronic lymphocytic leukemia, hepatocellular cancer, breast cancer, ovarian cancer, prostate cancer, glioblastoma, renal cancer and sarcomas. In some embodiments, the cancer is colorectal cancer or pancreatic cancer.

In certain embodiments, the disease can be, but is not limited to, cancer. In certain embodiments, the disease or cancer is selected from the group consisting of pancreatic cancer, lung cancer, colorectal cancer, cholangiocarcinoma, multiple myeloma, melanoma, uterine cancer, endometrial cancer, thyroid cancer, acute myeloid leukemia, ladder cancer, urothelial cancer, gastric cancer, cervical cancer, head and neck squamous cell carcinoma, diffuse large B cell lymphoma, esophageal cancer, chronic lymphocytic leukemia, hepatocellular cancer, breast cancer, ovarian cancer, prostate cancer, glioblastoma, renal cancer and sarcomas.

In certain embodiments, the disease can be, but is not limited to, a RASopathy. In certain embodiments, the RASopathy is selected from the group consisting of Neurofibromatosis type 1 (NF1), Noonan Syndrome (NS), Noonan Syndrome with Multiple Lentigines (NSML), Capillary Malformation-Arteriovenous Malformation Syndrome (CM-AVM), Costello Syndrome (CS), Cardio-Facio-Cutaneous Syndrome (CFC), Legius Syndrome, and Hereditary gingival fibromatosis.

Another aspect of the present disclosure is directed to a method of inhibiting SOS1. The method involves administering to a patient in need thereof an effective amount of a compound of any formula disclosed herein, or a pharmaceutically acceptable salt, solvate, isomer, prodrug, or tautomer thereof.

The present disclosure relates to compositions capable of modulating the activity of (e.g., inhibiting) SOS1. The present disclosure also relates to the therapeutic use of such compounds.

The disclosed compound can be administered in effective amounts to treat or prevent a disorder and/or prevent the development thereof in subjects.

Another aspect of the present disclosure relates to a compound of any formula disclosed herein, or a pharmaceutically acceptable salt, hydrate, solvate, prodrug, stereoisomer, or tautomer thereof, for use in treating or preventing a disease that is affected by modification of the interaction of SOS1 and a RAS-family protein and/or RAC1. Another aspect of the present disclosure relates to a compound of any formula disclosed herein, or a pharmaceutically acceptable salt, hydrate, solvate, prodrug, stereoisomer, or tautomer thereof, for use in treating or preventing a disease that is characterized by inhibition of the interaction of SOS1 with a RAS-family protein or the interaction of SOS1 with RAC1.

Another aspect of the present disclosure relates to a compound of any formula disclosed herein, or a pharmaceutically acceptable salt, hydrate, solvate, prodrug, stereoisomer, or tautomer thereof, for use in treating or preventing a disease, wherein the treating or preventing is effected or characterized by inhibition of the interaction of SOS1 and a RAS-family protein or by inhibition of the interaction of SOS1 and RA.

Another aspect of the present disclosure relates to a compound of any formula disclosed herein, or a pharmaceutically acceptable salt, hydrate, solvate, prodrug, stereoisomer, or tautomer thereof, for use inhibiting the binding of hSOS1 to H- or N- or K-RAS including their clinically known mutations and which inhibits the nucleotide exchange reaction catalyzed by hSOS1 in the presence of a concentration of 2 µM or lower, but which are substantially inactive against EGFR-kinase at concentrations of 2 µM or lower for the preparation of a medicament for the treatment or prophylaxis of a hyperproliferative disorder.

Another aspect of the present disclosure relates to a compound of any formula disclosed herein, or a pharmaceutically acceptable salt, hydrate, solvate, prodrug, stereoisomer, or tautomer thereof, for the manufacture of a medicament for use inhibiting the binding of hSOS1 specifically to K-RAS G12C protein or another Ras mutant, as described herein, and which inhibits the nucleotide exchange reaction catalyzed by hSOS1 in the presence of a concentration of 2 µM or lower, but which are substantially inactive against EGFR-kinase at concentrations of 2 µM or lower for the preparation of a medicament for the treatment or prophylaxis of a hyperproliferative disorder.

In another aspect, the present disclosure relates to the use of a compound of any formula disclosed herein, or a pharmaceutically acceptable salt, hydrate, solvate, prodrug, stereoisomer, or tautomer thereof, in the manufacture of a medicament for treating or preventing a disease.

Administration of the disclosed compounds can be accomplished via any mode of administration for therapeutic agents. These modes include systemic or local administration such as oral, nasal, parenteral, intravenous, transdermal, subcutaneous, vaginal, buccal, rectal or topical administration modes. Likewise, they can also be administered in intravenous (both bolus and infusion), intraperitoneal, subcutaneous or intramuscular form, and all using forms well known to those skilled in the pharmaceutical arts.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the present disclosure relates to a pharmaceutical composition comprising a compound of the present disclosure and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Combination Therapy

The methods of the invention may include a compound of the invention used alone or in combination with one or more additional therapies (e.g., non-drug treatments or therapeutic agents). Combination therapy may, for example, combine two therapies or may combine three therapies (e.g., a triple therapy of three therapeutic agents), or more. The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment. For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such cells. Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDIO680, BMS936559, MED14736, MPDL3280A, MSB0010718C, BMS986016, IMP321, lirilumab, IPH2101, 1-7F9, and KW-6002.

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., Proc. Am. Soc. Cin. Oncol. 18:233a (1999), and Douillard et al., Lancet 355(9209):1041-1047 (2000).

Other non-limiting examples of anti-cancer agents include Gleevec® (Imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammaII and calicheamicin omegaII (see, e.g., Agnew, Chem. Intl. Ed Engl. 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoles; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as *vinca* alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK 4/6 inhibitor such as ribociclib, abemaciclib, or palbociclib), seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP(Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), KK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HU-MAX-CD38), anti-CS1 (e.g., elotuzumab), HSP90 inhibitors (e.g., 17 AAG and KOS 953), PI3K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, RLY-1971), another SOS1 inhibitor (e.g., BI-1701963), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312. In some embodiments, an anti-cancer agent is a Ras inhibitor (e.g., AMG 510, MRTX1257, LY349946, MRTX849, ARS-3248 (JNJ-74699157), MRTX1133 or ARS-1620), or a Ras vaccine, or another therapeutic modality designed to directly or indirectly decrease the oncogenic activity of Ras.

In some embodiments, the Ras protein is wild-type. Accordingly, in some embodiments, a compound of the present invention is employed in a method of treating a patient having a cancer comprising a Ras$^{WT}$ (e.g., K-Ras$^{WT}$, H-Ras$^{WT}$ or N-Ras$^{WT}$). In some embodiments, the Ras protein is Ras amplification (e.g., K-Ras$^{amp}$). Accordingly, in some embodiments, a compound of the present invention is employed in a method of treating a patient having a cancer comprising a Ras$^{amp}$ (K-Ras$^{amp}$p, H-Ras$^{amp}$p or N-Ras$^{amp}$). In some embodiments, the cancer comprises a Ras mutation (Ras$^{MUT}$). In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof, (b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof, and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof, or a combination of any of the foregoing (e.g., both K-Ras G12C and K-Ras G13C). In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V.

In some embodiments, a cancer comprises an NF1$^{LOF}$ mutation. In some embodiments of methods herein, the cancer comprises a Ras$^{MUT}$ and a compound of the present invention is administered to, e.g., a patient in need thereof, in combination with an additional therapeutic agent, e.g., a MEK inhibitor, such as a MEK inhibitor described herein. In some embodiments of methods herein, the cancer is colorectal cancer and a compound of the present invention is administered to, e.g., a patient in need thereof, in combination with an additional therapeutic agent, such as a topoisomerase I inhibitor (e.g., irinotecan). In some embodiments of methods herein, the cancer is non-small cell lung cancer and a compound of the present invention is administered to, e.g., a patient in need thereof, in combination with an additional therapeutic agent, e.g., a MEK inhibitor, such as a MEK inhibitor described herein (e.g., trametinib). In some embodiments of methods herein, the cancer is non-small cell lung cancer or colorectal cancer, and a compound of the present invention is administered to, e.g., a patient in need thereof, in combination with a Ras inhibitor, such as a Ras inhibitor described herein (e.g., MRTX849, MRTX1133 or AMG-510).

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (Neo-Pharm), ISIS 5132; vemurafenib, pimasertib, TAK733, RO4987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000).

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab $C_{225}$ (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676): 1497-500. Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747, 498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/

35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is osimertinib.

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran-4-one (available from Axon Medchem); PI 103 hydrochloride (3-[4-(4-morpholinylpyrido-[3',2':4,5]furo[3,2-d]pyrimidin-2-yl] phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[1-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a]pyrindin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Akt1) (Barnett et al., Biochem. J. 2005, 385 (Pt. 2): 399-408); Akt-1-1,2 (inhibits Ak1 and 2) (Barnett et al., Biochem. J. 2005, 385 (Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 34935-3498); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g., AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies, and may form the basis of a triple combination inhibitor with a SOS1 inhibitor.

Non-limiting examples of such SHP2 inhibitors that are known in the art, include: Chen et al. Mol Pharmacol. 2006, 70, 562; Sarver et al., J Med. Chem. 2017, 62, 1793; Xie et al., J. Med. Chem. 2017, 60, 10205; and Igbe et al., Oncotarget, 2017, 8, 113734; and PCT applications: WO2005094314; WO2007117699; WO2008124815; WO2009049098; WO2009135000; WO2010011666; WO2010121212; WO2011022440; WO2012041524; WO2014113584; WO2014176488; WO2015003094 WO2015107493; WO2015107494; WO2015107495; WO2016191328; WO2016196591; WO2016203404; WO2016203405; WO2016203406; WO2017078499; WO2017079723; WO2017100279; WO2017156397; WO2017210134; WO2017211303; WO2018013597; WO2018057884; WO2018081091; WO2018129402; WO2018130928; WO2018136264; WO2018136265; WO2018160731; WO2018172984; WO2018218133; WO2019051469; WO2019051084; WO2019067843; WO2019152454; WO2019158019; WO2019165073; WO2019167000; WO2019182960; WO2019183364; WO2019183367; WO2019213318; WO2019233810; WO2020022323; WO2020033286; WO2020033828; WO2020061101; WO2020061103; WO2020063760; WO2020072656; WO2020073945; WO2020073949; WO2020081848; US20110281942; US20160030594 and U.S. Pat. No. 8,637,684, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RCM-4630. In some embodiments, the SHP2 inhibitor is JAB-3068.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAGl, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloproteinase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/

0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Children's Hospital, USA); ATN 161 (Attenuon, USA); 2-methoxyestradiol (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Children's Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

In some embodiments, an additional compound used in combination therapy with a compound of the present invention is selected from the group consisting of a CDK4/6 inhibitor (e.g., abemaciclib, palbociclib, or ribociclib), a KRAS:GDP G12C inhibitor (e.g., AMG 510, MRTX 1257) or other mutant Ras:GDP inhibitor, a KRAS:GTP G12C inhibitor or other mutant Ras:GTP inhibitor, a MEK inhibitor (e.g., refametinib, selumetinib, trametinib, or cobimetinib), a SHP2 inhibitor (e.g., TNO155, RMC-4630), an ERK inhibitor, and an RTK inhibitor (e.g., an EGFR inhibitor). In some embodiments, a SOS1 inhibitor may be used in combination with a Ras inhibitor, a SHP2 inhibitor, or a MK inhibitor. In some embodiments, a combination therapy includes a SOS1 inhibitor, a RAS inhibitor and a EK inhibitor.

In some embodiments, an additional compound used in combination therapy with a compound of the present invention is selected from the group consisting of ABT-737, AT-7519, carfilzomib, cobimetinib, danusertib, dasatinib, doxorubicin, GSK-343, JQ1, MLN-7243, NVP-ADW742, paclitaxel, palbociclib and volasertib. In some embodiments, an additional compound used in combination therapy with a compound of the present invention is selected from the group consisting of neratinib, acetinib and reversine.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments, a combination therapeutic regimen employs two therapeutic agents, one compound of the present invention and a second selected from the therapeutic agents described herein. In some embodiments, a combination therapeutic regimen employs three therapeutic agents, one compound of the present invention and two selected from the therapeutic agents described herein. In some embodiments, a combination therapeutic regimen employs four or more therapeutic agents, one compound of the present invention and three selected from the therapeutic agents described herein.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

In this Combination Therapy section, all references are incorporated by reference for the agents described, whether explicitly stated as such or not.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:
BOP (benzotriazole-1-yl)tris(dimethylamino)phosphonium
$CH_2Cl_2$, DCM Methylene chloride, Dichloromethane
ACN, $CH_3CN$, Acetonitrile
MeCN
DAST Diethylaminosulfur trifluoride
DBU Diazabicycloundecene
DCE 1,2-dichloroethane
DDQ 2,3-dichloro-5,6-dicyano-1,4-benzoquinone
DIEA N,N-diisopropylethylamine
DIPEA Diisopropylethylamine
DMA Dimethylacetamide
DMAP 4-Dimethylaminopyridine
DME Dimethylether
DMF N,N-Dimethylformamide
DMSO Dimethyl Sulfoxide
EDCI 1-Ethyl-3-(3-dimethylaminopropyl)carbodiimide
EtOAc Ethyl acetate
h Hour
HATU O-(7-Azabenzotriazol-1-yl)-N,N,N',N'-tetramethyluronium hexafluorophosphate
$H_2O$ Water
HOBt Hydroxybenzotriazole
HCl Hydrochloric acid
$K_3PO_4$ Potassium phosphate (tribasic)
LHMDS Lithium bis(trimethylsilyl)amide
mCPBA meta-Chloroperoxybenzoic acid
MeOH Methanol
MsCl Methanesulfonyl chloride
MTBE Methyl tert-butyl ether
$Na_2SO_4$ Sodium sulfate
NBS N-bromosuccinimide
NIS N-iodosuccinimide
NMP N-methyl pyrrolidone
rt Room temperature
$SmI_2$ Samarium(II)iodide
TEA Triethylamine
TES Triethylsilane
TFA Trifluroacetic acid
THF Tetrahydrofuran
TMSCl Chlorotrimethylsilane
XPhos 2-Dicyclohexylphosphino-2',4',6'-triisopropylbiphenyl

Example 1: Synthesis of (R)-4-((1-(3-amino-5-(trifluoromethyl)phenyl)ethyl)amino)-8-methyl-6-(1,2,3,6-tetrahydropyridin-4-yl)pyrido[2,3-d]pyrimidin-7(8H)-one

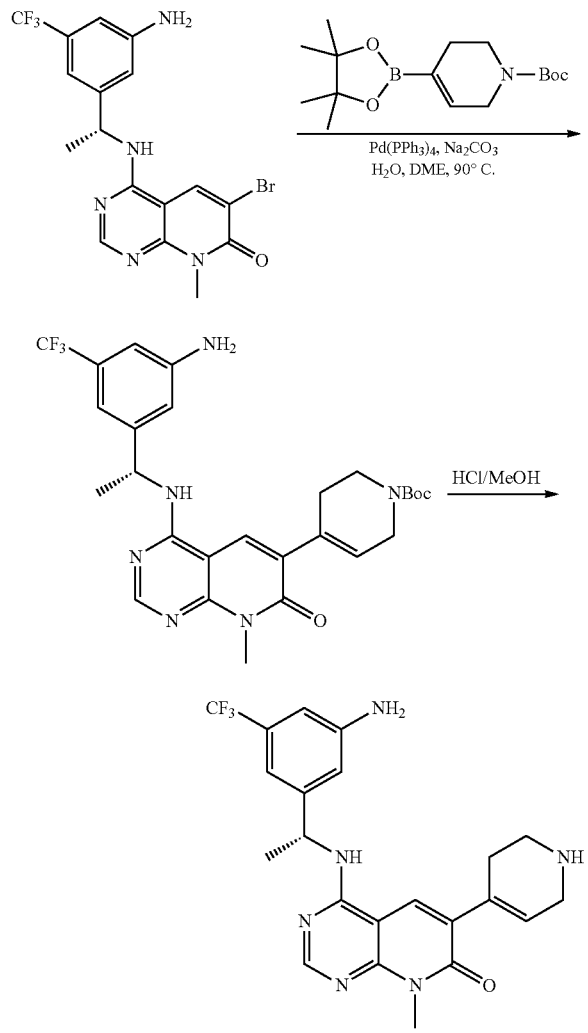

Step 1

To a mixture of 4-[[(1R)-1-[3-amino-5-(trifluoromethyl)phenyl]ethyl]amino]-6-bromo-8-methyl-pyrido[2,3-d]pyrimidin-7-one (50 mg, 113 µmol) in dioxane (1 ml) and H$_2$O (0.2 ml) was added K$_2$CO$_3$ (47 mg, 339 µmol), tert-butyl 4-(4,4,5,5-tetramethyl-1,3,2-dioxaborolan-2-yl)-3,6-dihydro-2H-pyridine-1-carboxylate (38 mg, 124 µmol) and Pd(PPh$_3$)$_4$ (Tetrakis(triphenylphosphine)palladium(0), 13 mg, 11 µmol). The mixture was heated at 100° C. for 3 h under N$_2$. After cooling to rt the mixture was filtered and the solvent was removed reduced pressure to give tert-butyl 4-[4-[[(1R)-1-[3-amino-5-(trifluoromethyl)phenyl]ethyl]amino]-8-methyl-7-oxo-pyrido[2,3-d]pyrimidin-6-yl]-3,6-dihydro-2H-pyridine-1-carboxylate (50 mg, 81% yield). LCMS (ESI): m/z: [M+H] calculated for C$_{27}$H$_{32}$F$_3$N$_6$O$_3$: 545.2; found 545.2.

Step 2

To a mixture of tert-butyl 4-[4-[[(1R)-1-[3-amino-5-(trifluoromethyl)phenyl]ethyl]amino]-8-methyl-7-oxo-pyrido[2,3-d]pyrimidin-6-yl]-3,6-dihydro-2H-pyridine-1-carboxylate (50 mg, 92 µmol) in MeOH (1 ml) was added HCl/MeOH (4 M, 23 µl). The mixture was stirred at rt for 1 h. The solvent removed under reduced pressure and the residue was purified by prep-HPLC to give 4-[[(1R)-1-[3-amino-5-(trifluoromethyl)phenyl]ethyl]amino]-8-methyl-6-(1,2,3,6-tetrahydropyridin-4-yl)pyrido[2,3-d]pyrimidin-7-one (38 mg, 91% yield). LCMS (ESI): m/z: [M+H] calculated for C$_{22}$H$_{24}$F$_3$N$_6$O: 445.2; found 445.2; $^1$H NMR (400 MHz, methanol-d$_4$) δ=8.53 (s, 1H), 8.35 (s, 1H), 8.25 (s, 1H), 6.92 (s, 2H), 6.79 (s, 1H), 6.42 (s, 1H), 5.50 (q, J=6.8 Hz, 1H), 3.82 (d, J=2.6 Hz, 2H), 3.70 (s, 3H), 3.40 (t, J=6.0 Hz, 2H), 2.81 (s, 2H), 1.60 (d, J=7.1 Hz, 3H).

The following examples 1-1 to 1-33 shown in Table 1 were synthesized in the manner similar to Example 1.

TABLE 1

| Examples 1-1 to 1-33 | | |
|---|---|---|
| Example # | Structure | Mass Found |
| 1-1 | | 416.5 |

TABLE 1-continued

Examples 1-1 to 1-33

| Example # | Structure | Mass Found |
|---|---|---|
| 1-2 | 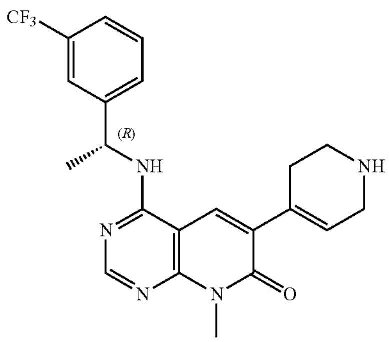 | 430.2 |
| 1-3 | 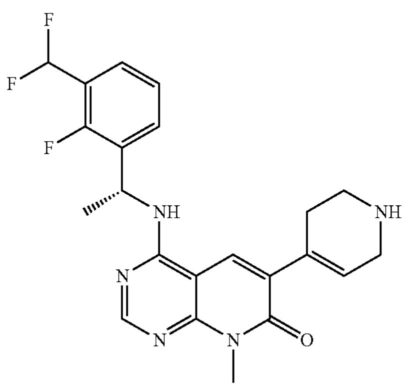 [SMILES: C[C@@H](Nc1ncnc2c1cc(C1=CCNCC1)c(=O)n2C)c1cccc(C(F)F)c1F] | 430.5 |
| 1-4 | 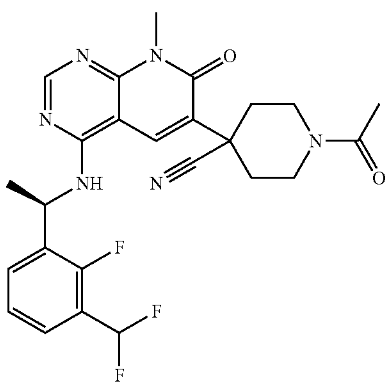 [SMILES: CC(=O)N1CCC(C#N)(c2cc3c(N[C@H](C)c4cccc(C(F)F)c4F)ncnc3n(C)c2=O)CC1] | 430.7 |
| 1-5 | 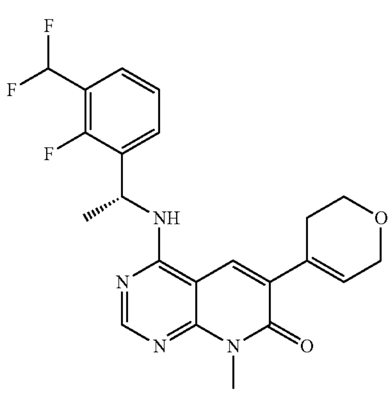 | 431.4 |

TABLE 1-continued
Examples 1-1 to 1-33
| Example # | Structure | Mass Found |
|---|---|---|
| 1-6 | 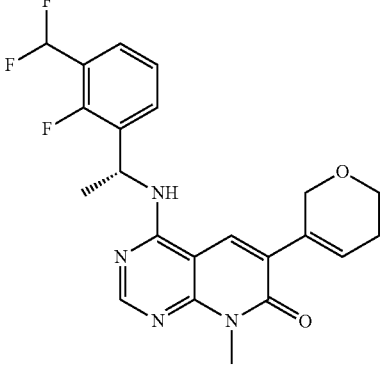 | 431.5 |
| 1-7 | 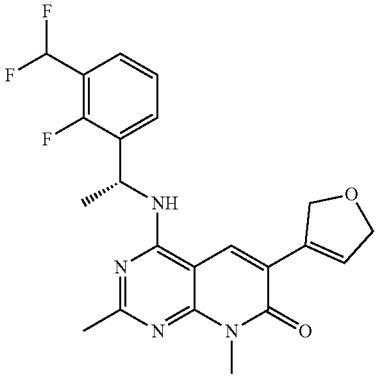 | 431.6 |
| 1-8 | 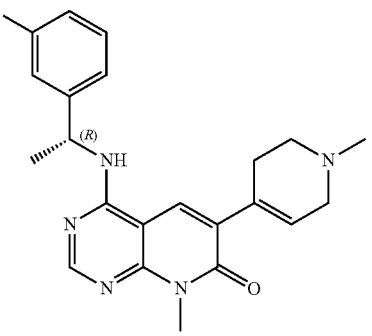 | 444.2 |
| 1-9 | 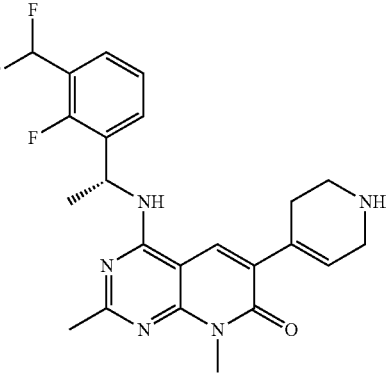 | 444.4 |

TABLE 1-continued

Examples 1-1 to 1-33

| Example # | Structure | Mass Found |
|---|---|---|
| 1-10 | 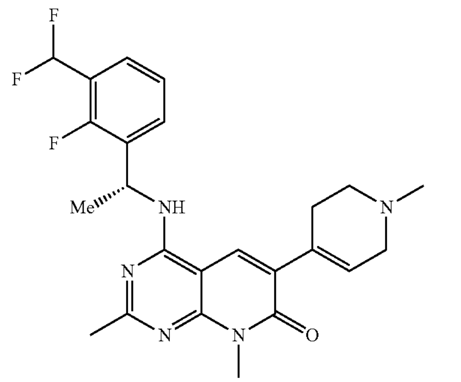 [SMILES: Cc1nc(N[C@H](C)c2cccc(C(F)F)c2F)c2cc(C3=CCN(C)CC3)c(=O)n(C)c2n1] | 458.2 |
| 1-11 | 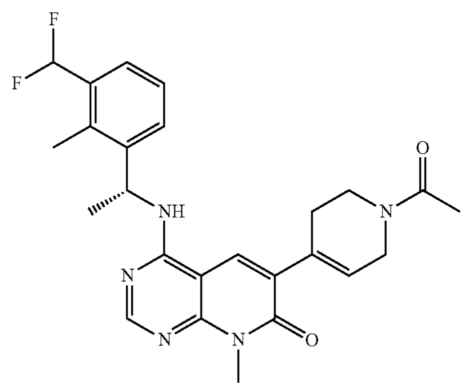 | 468.2 |
| 1-12 | 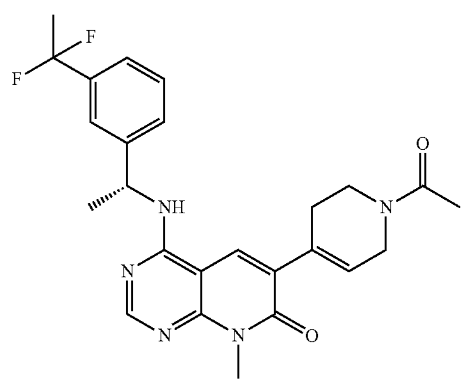 [SMILES: CC(=O)N1CC=C(c2cc3c(N[C@H](C)c4cccc(C(C)(F)F)c4)ncnc3n(C)c2=O)CC1] | 468.2 |
| 1-13 | 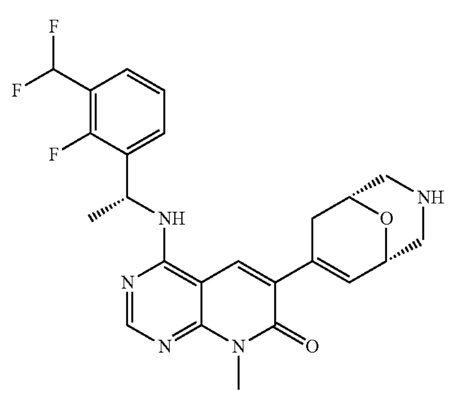 [SMILES: C[C@@H](Nc1ncnc2c1cc(C1=C[C@H]3CNC[C@@H](C1)O3)c(=O)n2C)c1cccc(C(F)F)c1F] | 472.4 |

TABLE 1-continued

Examples 1-1 to 1-33

| Example # | Structure | Mass Found |
|---|---|---|
| 1-14 | 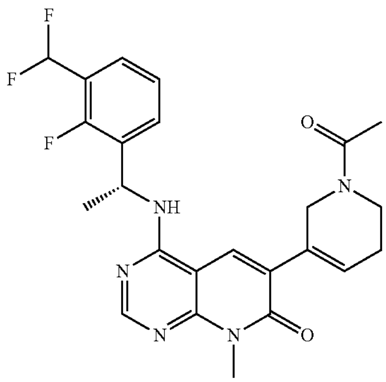 [SMILES: CC(=O)N1CCC=C(c2cc3c(N[C@H](C)c4cccc(C(F)F)c4F)ncnc3n(C)c2=O)C1] | 472.5 |
| 1-15 | 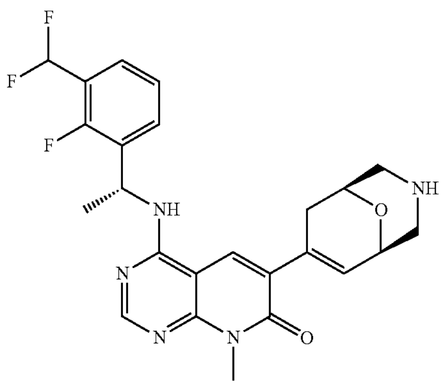 [SMILES: C[C@@H](Nc1ncnc2c1cc(C1=C[C@@H]3CNC[C@H](C1)O3)c(=O)n2C)c1cccc(C(F)F)c1F] | 472.5 |
| 1-16 | 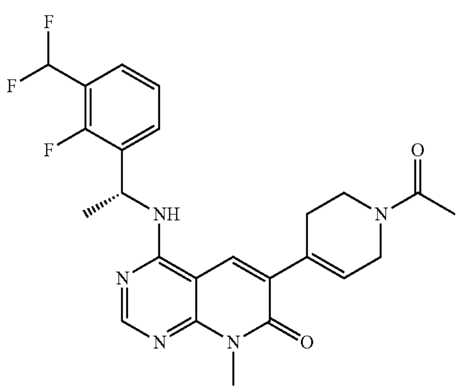 | 472.5 |
| 1-17 | 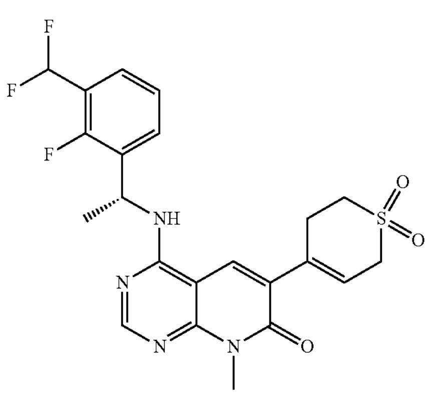 [SMILES: C[C@@H](Nc1ncnc2c1cc(C1=CCS(=O)(=O)CC1)c(=O)n2C)c1cccc(C(F)F)c1F] | 479.0 |

TABLE 1-continued

Examples 1-1 to 1-33

| Example # | Structure | Mass Found |
|---|---|---|
| 1-18 | 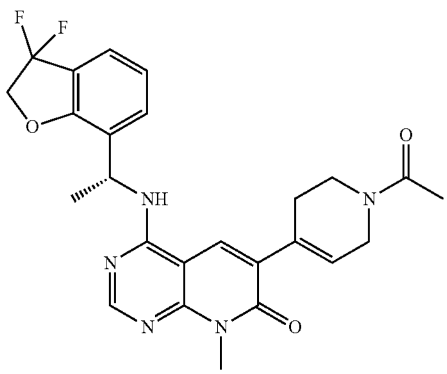 [SMILES: CC(=O)N1CC=C(c2cc3c(N[C@H](C)c4cccc5c4OCC5(F)F)ncnc3n(C)c2=O)CC1] | 482.2 |
| 1-19 | 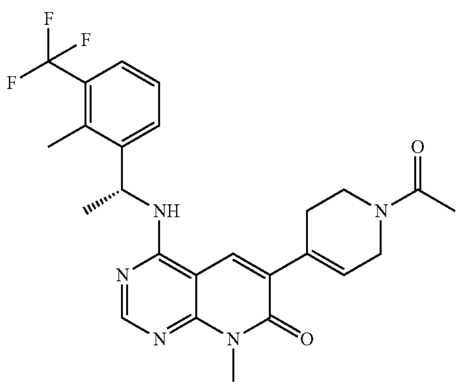 [SMILES: CC(=O)N1CC=C(c2cc3c(N[C@H](C)c4cccc(C(F)(F)F)c4C)ncnc3n(C)c2=O)CC1] | 486.2 |
| 1-20 | 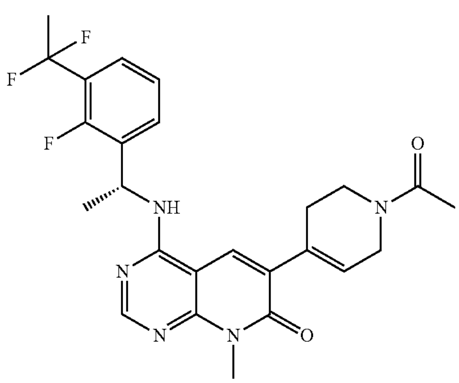 [SMILES: CC(=O)N1CC=C(c2cc3c(N[C@H](C)c4cccc(C(C)(F)F)c4F)ncnc3n(C)c2=O)CC1] | 486.3 |
| 1-21 | 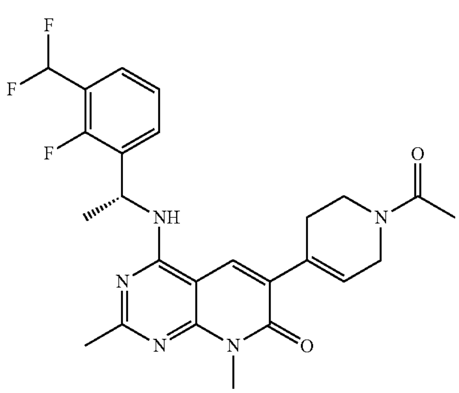 [SMILES: CC(=O)N1CC=C(c2cc3c(N[C@H](C)c4cccc(C(F)F)c4F)nc(C)nc3n(C)c2=O)CC1] | 486.5 |

TABLE 1-continued

Examples 1-1 to 1-33

| Example # | Structure | Mass Found |
|---|---|---|
| 1-22 | 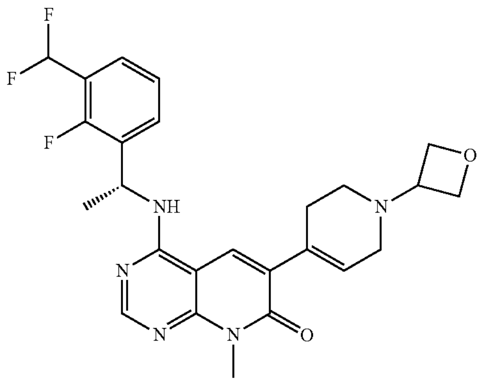 [SMILES: C[C@@H](Nc1ncnc2c1cc(C1=CCN(C3COC3)CC1)c(=O)n2C)c1cccc(C(F)F)c1F] | 486.5 |
| 1-23 | 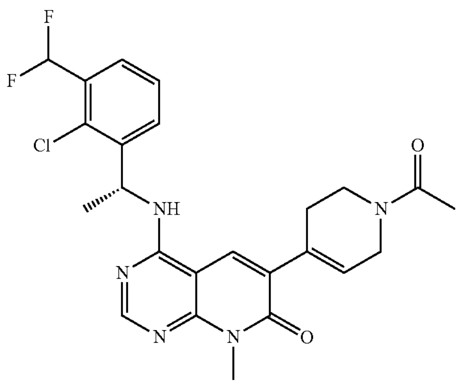 [SMILES: CC(=O)N1CC=C(c2cc3c(N[C@H](C)c4cccc(C(F)F)c4Cl)ncnc3n(C)c2=O)CC1] | 488.2 |
| 1-24 | 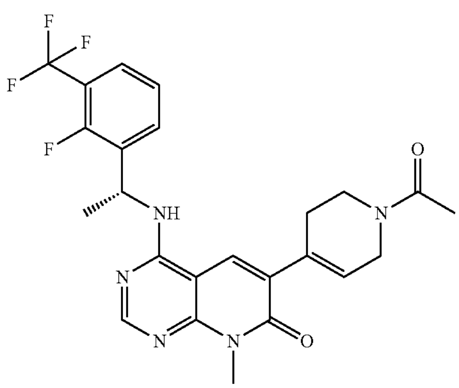 [SMILES: CC(=O)N1CC=C(c2cc3c(N[C@H](C)c4cccc(C(F)(F)F)c4F)ncnc3n(C)c2=O)CC1] | 490.2 |
| 1-25 | 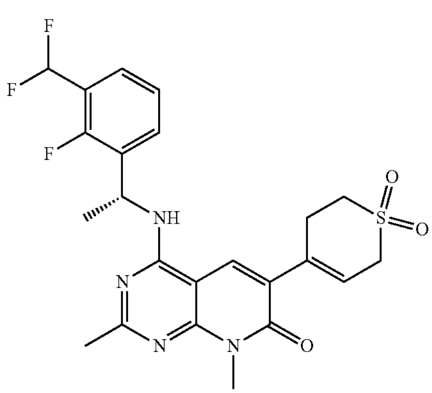 [SMILES: Cc1nc(N[C@H](C)c2cccc(C(F)F)c2F)c2cc(C3=CCS(=O)(=O)CC3)c(=O)n(C)c2n1] | 493.5 |

TABLE 1-continued

Examples 1-1 to 1-33

| Example # | Structure | Mass Found |
|---|---|---|
| 1-26 | 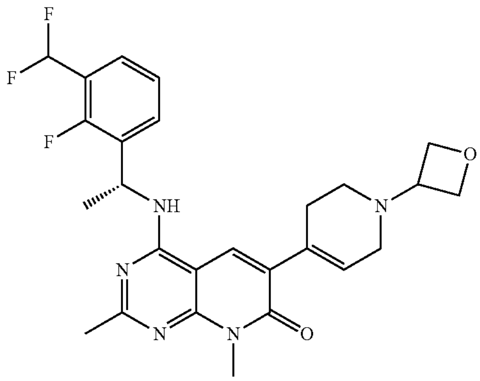 [SMILES: Cc1nc(N[C@H](C)c2cccc(C(F)F)c2F)c2cc(C3=CCN(C4COC4)CC3)c(=O)n(C)c2n1] | 500.3 |
| 1-27 | 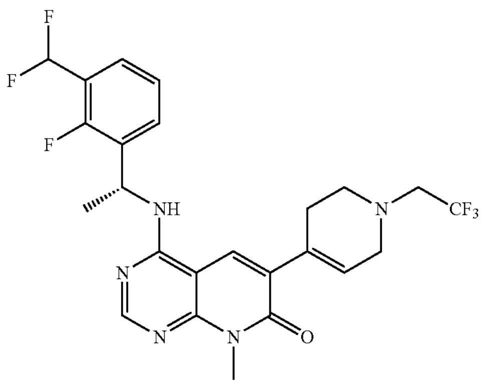 [SMILES: C[C@@H](Nc1ncnc2c1cc(C1=CCN(CC(F)(F)F)CC1)c(=O)n2C)c1cccc(C(F)F)c1F] | 512.6 |
| 1-28 | 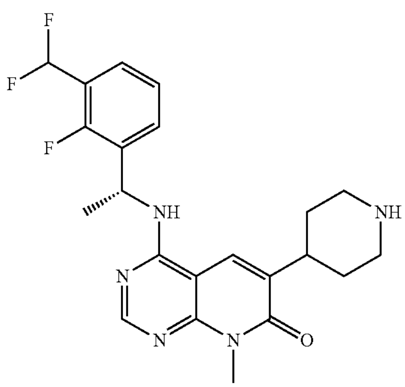 [SMILES: C[C@@H](Nc1ncnc2c1cc(C1CCNCC1)c(=O)n2C)c1cccc(C(F)F)c1F] | 432.4 |
| 1-29 | 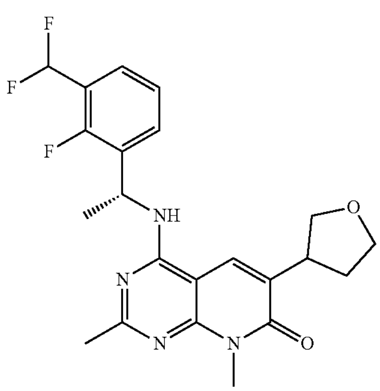 [SMILES: Cc1nc(N[C@H](C)c2cccc(C(F)F)c2F)c2cc(C3CCOC3)c(=O)n(C)c2n1] | 433.5 |

TABLE 1-continued

Examples 1-1 to 1-33

| Example # | Structure | Mass Found |
|---|---|---|
| 1-30 | 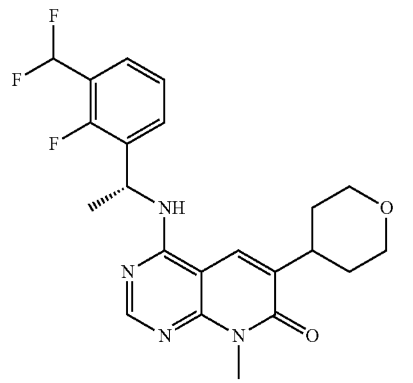 [SMILES: C[C@@H](Nc1ncnc2c1cc(C1CCOCC1)c(=O)n2C)c1cccc(C(F)F)c1F] | 433.5 |
| 1-31 | 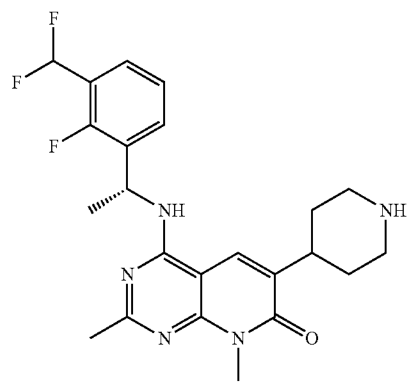 [SMILES: Cc1nc(N[C@H](C)c2cccc(C(F)F)c2F)c2cc(C3CCNCC3)c(=O)n(C)c2n1] | 446.7 |
| 1-32 | 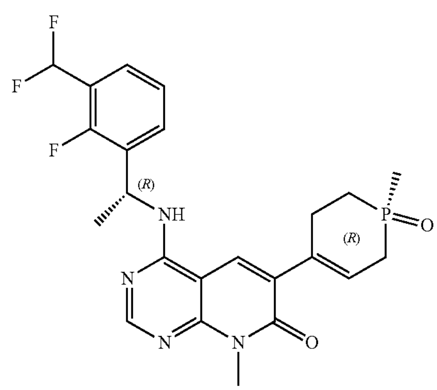 | 477.3 |
| 1-33 | 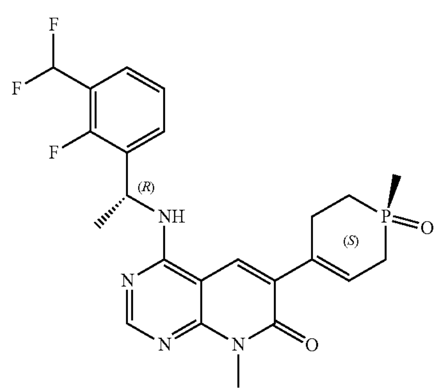 | 477.1 |

Example 2: Synthesis of (R)-4-((1-(3-(1,1-difluoro-2-hydroxyethyl)phenyl)ethyl)amino)-8-methyl-6-morpholinopyrido[2,3-d]pyrimidin-7(8H)-one

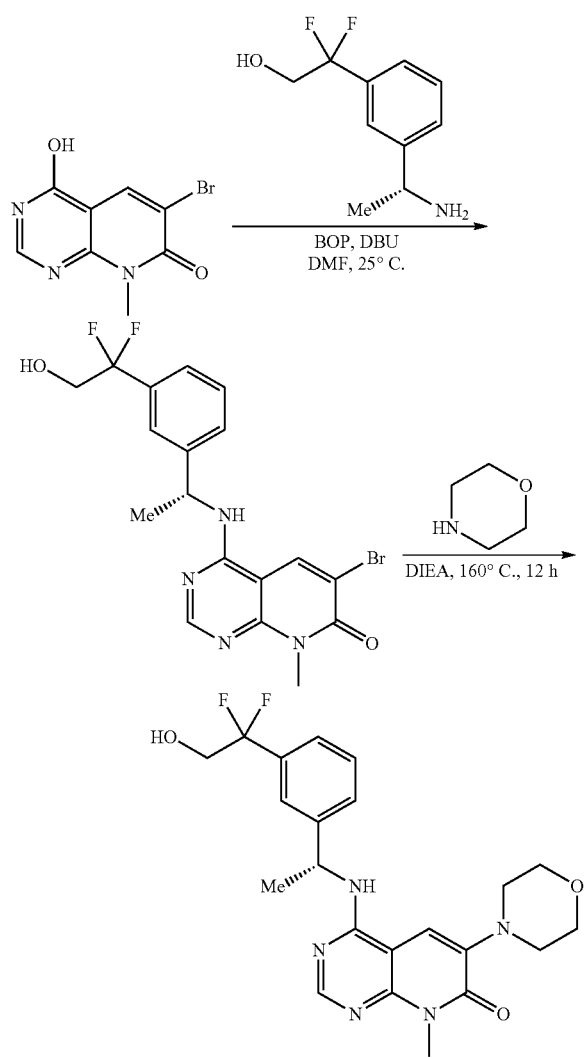

Step 1

To a solution of 6-bromo-4-hydroxy-8-methyl-pyrido[2,3-d]pyrimidin-7-one (430 mg, 1.68 mmol) and 2-[3-[(1R)-1-aminoethyl]phenyl]-2,2-difluoro-ethanol (507 mg, 2.52 mmol) in DMF (10 ml) were added BOP (1.11 g, 2.52 mmol) and DBU (760 μl, 5.04 mmol). The mixture was stirred at 25° C. for 16 h. Water was added and the mixture was extracted with EtOAc. The combined organic layers were washed with brine and dried over $Na_2SO_4$. The solvent was removed under reduced pressure and the residue was purified by column chromatography to give 6-bromo-4-[[(1R)-1-[3-(1,1-difluoro-2-hydroxy-ethyl)phenyl]ethyl]amino]-8-methyl-pyrido[2,3-d]pyrimidin-7-one (190 mg, 26% yield). LCMS (ESI): m/z: [M+H] calculated for $C_{18}H_{17}BrF_2N_4O_2$: 439.1; found 439.2.

Step 2

A mixture of 6-bromo-4-[[(1R)-1-[3-(1,1-difluoro-2-hydroxy-ethyl)phenyl]ethyl]amino]-8-methyl-pyrido[2,3-d]pyrimidin-7-one (200 mg, 455 μmol), morpholine (2.89 ml, 33 mmol) and DIEA (2.86 ml, 16.4 mmol) was stirred under nitrogen at 160° C. for 12 h. The solvent was removed under reduced pressure and the crude residue was purified by prep-HPLC to give 4-[[(1R)-1-[3-(1,1-difluoro-2-hydroxy-ethyl)phenyl]ethyl]amino]-8-methyl-6-morpholino-pyrido[2,3-d]pyrimidin-7-one (16 mg, 8% yield). LCMS (ESI): m/z: [M+H] calculated for $C_{22}H_{26}F_2N_5O_3$: 446.2; found 446.3; $^1H$ NMR (400 MHz, chloroform-d) δ ppm 8.25 (s, 1H) 7.59 (s, 1H) 7.54 (d, J=8 Hz, 2H) 7.4 (m, 2H) 5.59 (m, 1H) 3.88 (m, 6H) 3.73 (s, 3H) 3.2 (d, J=2.08 Hz, 4H) 1.66 (d, J=7.09 Hz, 3H).

The following examples 2-1 to 2-5 shown in Table 2 were synthesized in the manner similar to Example 2.

TABLE 2

Examples 2-1 to 2-5

| Example # | Structure | Mass Found |
|---|---|---|
| 2-1 | (R)-4-[[1-(2-fluoro-3-(difluoromethyl)phenyl)ethyl]amino]-2-methyl-6-morpholino-pyrido[2,3-d]pyrimidin-7(8H)-one | 448.0 |
| 2-2 | (R)-4-[[1-(2-fluoro-3-(difluoromethyl)phenyl)ethyl]amino]-6-(3,3-difluoroazetidin-1-yl)-2-methyl-pyrido[2,3-d]pyrimidin-7(8H)-one | 454.2 |
| 2-3 | (R)-4-[[1-(2-fluoro-3-(difluoromethyl)phenyl)ethyl]amino]-2-methyl-6-(2-oxa-6-azaspiro[3.3]heptan-6-yl)-pyrido[2,3-d]pyrimidin-7(8H)-one | 460.2 |

TABLE 2-continued

Examples 2-1 to 2-5

| Example # | Structure | Mass Found |
|---|---|---|
| 2-4 | 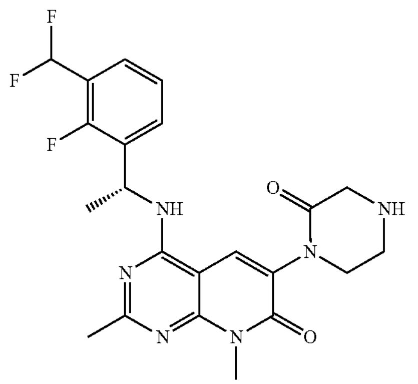 [SMILES: Cc1nc(N[C@H](C)c2cccc(C(F)F)c2F)c2cc(N3CCNCC3=O)c(=O)n(C)c2n1] | 461.0 |
| 2-5 | 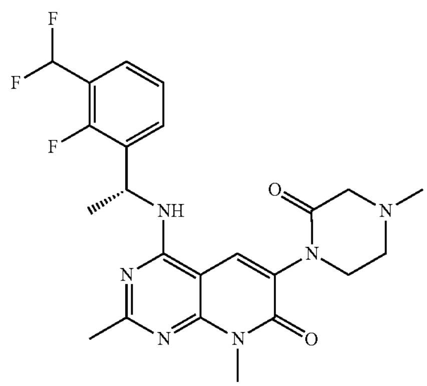 [SMILES: Cc1nc(N[C@H](C)c2cccc(C(F)F)c2F)c2cc(N3CCN(C)CC3=O)c(=O)n(C)c2n1] | 475.0 |

Example 3: Synthesis of (R)-4-((1-(3-(1,1-difluoro-2-hydroxyethyl)phenyl)ethyl)amino)-6-(3,6-dihydro-2H-pyran-4-yl)-2,8-dimethylpyrido[2,3-d]pyrimidin-7(8H)-one

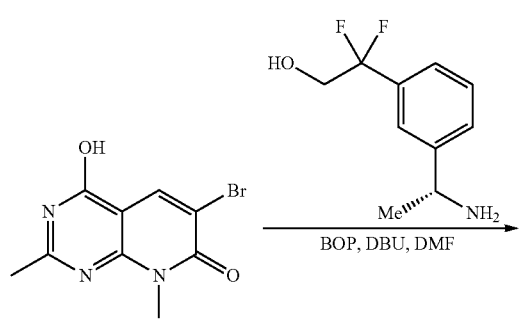

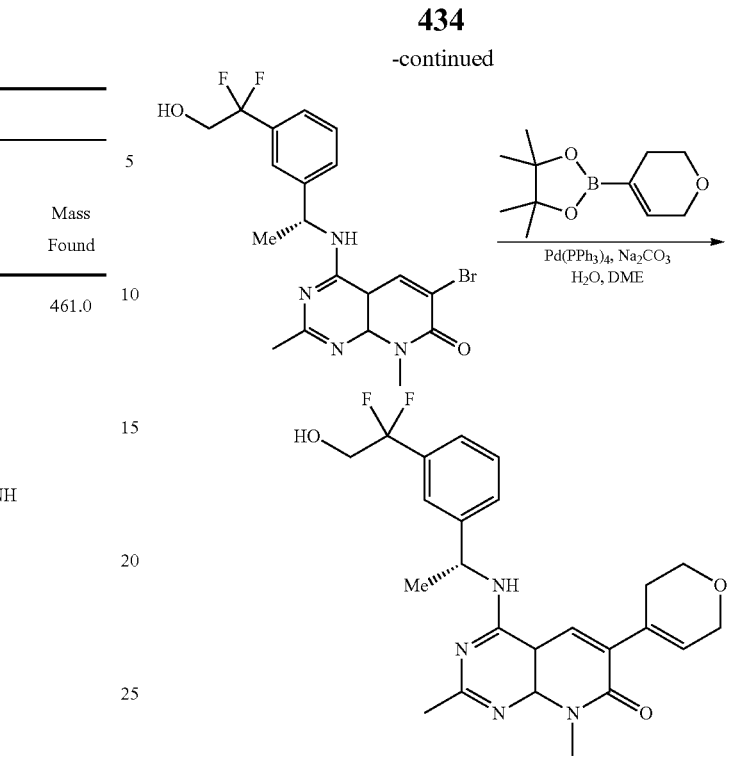

Step 1

To a solution of 6-bromo-4-hydroxy-2,8-dimethyl-pyrido[2,3-d]pyrimidin-7-one (1.1 g, 4.07 mmol) in DMF (10 ml) was added BOP (2.81 g, 6.35 mmol), 2-[3-[(1R)-1-amino-ethyl]phenyl]-2,2-difluoro-ethanol (1.64 g, 8.15 mmol) and DBU (1.84 ml, 12.22 mmol). The reaction was stirred at 20° C. for 12 h. Water was added and the mixture was extracted with ethyl acetate. The combined organic phase was washed with brine, dried with anhydrous $Na_2SO_4$ and the solvent was removed under reduced pressure. The crude residue was purified by silica gel chromatography to give 6-bromo-4-[[(1R)-1-[3-(1,1-difluoro-2-hydroxy-ethyl)phenyl]ethyl]amino]-2,8-dimethyl-pyrido[2, 3-d]pyrimidin-7-one (1.4 g, 76% yield). $^1$H NMR (400 MHz, methanol-d4) δ ppm 8.71 (s, 1H) 7.61 (s, 1H) 7.53 (d, J=8 Hz, 1H) 7.43-7.36 (m, 2H) 5.60-5.55 (m, 1H) 3.91-3.84 (m, 2H) 3.68 (s, 3H) 2.41 (s, 3H) 1.62 (d, J=8 Hz, 3H).

Step 2

To a solution of 6-bromo-4-[[(1R)-1-[3-(1,1-difluoro-2-hydroxy-ethyl) phenyl]ethyl]amino]-2,8-dimethyl-pyrido[2, 3-d]pyrimidin-7-one (0.2 g, 441 μmol) in DME (2 ml) was added 2-(3,6-dihydro-2H-pyran-4-yl)-4,4,5,5-tetramethyl-1, 3,2-dioxaborolane (139 mg, 662 μmol), $H_2O$ (0.4 ml), $Na_2CO_3$ (94 mg, 882 μmol) and $Pd(PPh_3)_4$ (Tetrakis(triphenylphosphine)paladium(0), 51 mg, 44 μmol)under $N_2$. The mixture was stirred at 90° C. for 2 h. Water was added and the mixture was extracted with ethyl acetate. The combined organic phase was washed with brine, dried with anhydrous $Na_2SO_4$ and the solvent was removed under reduced pressure. The crude residue was purified by prep-HPLC to give 4-[[(1R)-1-[3-(1,1-difluoro-2-hydroxy-ethyl)phenyl]ethyl]amino]-6-(3,6-dihydro-2H-pyran-4-yl)-2,8-dimethyl-pyrido[2,3-d]pyrimidin-7-one (0.03 g, 15% yield). LCMS (ESI): m/z: [M+H] calculated for $C_{24}H_{27}F_2N_4O_3$: 457.2; found 457.3; $^1$H NMR (400 MHz, methanol-$d_4$) δ ppm 8.16 (s, 1H) 7.62 (s, 1H) 7.54 (d, J=8 Hz, 1H) 7.43-7.37 (m, 2H) 6.46 (s, 1H) 5.68-5.62 (m, 1H) 4.33-4.29 (m, 2H) 3.94-3.83 (m, 4H) 3.69 (s, 3H) 2.59-2.53 (m, 2H) 2.44 (s, 3H) 1.63 (d, J=4 Hz, 3H).

Example 4: Synthesis of (R)-4-((1-(3-(1,1-difluoro-2-hydroxyethyl)phenyl)ethyl)amino)-2,8-dimethyl-6-(1,2,3,6-tetrahydropyridin-4-yl)pyrido[2,3-d]pyrimidin-7(8H)-one

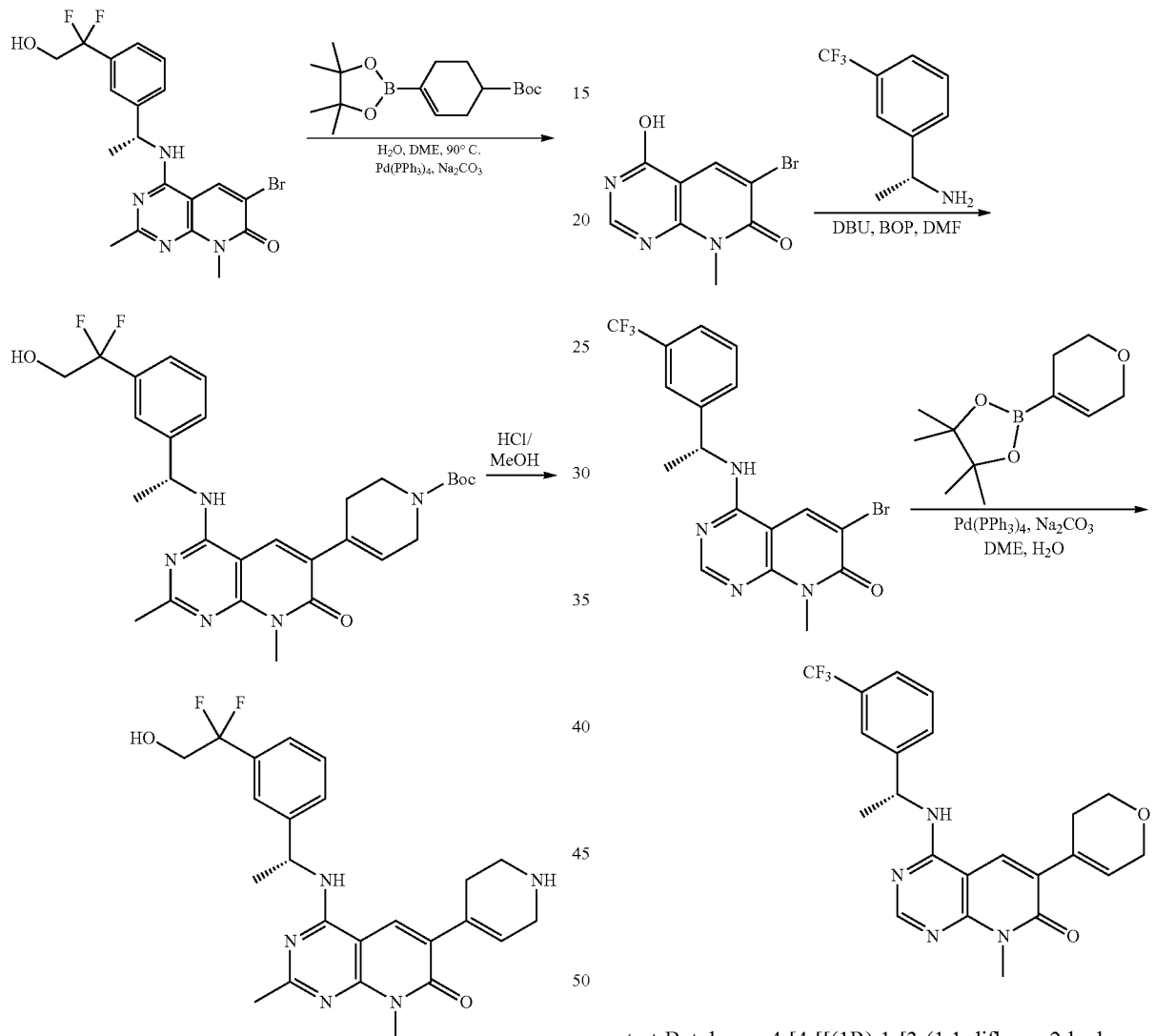

Step 1

To a solution of 6-bromo-4-[[(1R)-1-[3-(1,1-difluoro-2-hydroxy-ethyl)phenyl]ethyl]amino]-2,8-dimethyl-pyrido[2,3-d]pyrimidin-7-one (0.2 g, 441 μmol) in DME (2 ml) was added tert-butyl 4-(4,4,5,5-tetramethyl-1,3,2-dioxaborolan-2-yl)-3,6-dihydro-2H-pyridine-1-carboxylate (205 mg, 662 μmol), H$_2$O (0.4 ml), Na$_2$CO$_3$ (94 mg, 882 μmol) and Pd(PPh$_3$)$_4$ (Tetrakis(triphenylphosphine)palladium(0), 51 mg, 44 μmol) at 25° C. under N$_2$. The reaction was stirred at 90° C. for 2 h. Water was added and the mixture was extracted with ethyl acetate. The combined organic phase was washed with brine and dried with anhydrous Na$_2$SO$_4$. The solvent was removed under reduced pressure and the crude residue was purified by silica gel chromatography to give tert-butyl 4-[4-[[(1R)-1-[3-(1,1-difluoro-2-hydroxyethyl)phenyl]ethyl]amino]-2,8-dimethyl-7-oxo-pyrido[2,3-d]pyrimidin-6-yl]-3,6-dihydro-2H-pyridine-1-carboxylate (0.2 g, 82% yield). $^1$H NMR (400 MHz, methanol-d$_4$) δ ppm 8.14 (s, 1H) 7.62 (s, 1H) 7.54 (d, J=8 Hz, 2H) 7.43-7.37 (m, 2H) 6.27 (s, 1H) 5.67-5.57 (m, 1H) 4.08 (d, J=8 Hz, 2H) 3.93-3.80 (m, 2H) 3.66 (s, 3H) 3.64-3.58 (m, 2H) 2.57-2.51 (m, 2H) 2.43 (s, 3H) 1.63 (d, J=8 Hz, 3H) 1.49 (s, 9H).

Step 2 tert-Butyl 4-[4-[[(1R)-1-[3-(1,1-difluoro-2-hydroxy-ethyl)phenyl]ethyl]amino]-2,8-dimethyl-7-oxo-pyrido[2,3-d]pyrimidin-6-yl]-3,6-dihydro-2H-pyridine-1-carboxylate (0.1 g, 180 μmol) was dissolved in HCl/MeOH (5 ml) at 20° C. and reaction was stirred at 20° C. for 0.5 h. The solvent was removed under reduced pressure and the residue was purified by prep-HPLC to give 4-[[(1R)-1-[3-(1,1-difluoro-2-hydroxy-ethyl)phenyl]ethyl]amino]-2,8-dimethyl-6-(1,2,3,6-tetrahydropyridin-4-yl)pyrido[2,3-d]pyrimidin-7-one (30 mg, 35% yield). LCMS (ESI): m/z: [M+H] calculated for C$_{24}$H$_{28}$F$_2$N$_5$O$_2$: 456.2; found 456.2; $^1$H NMR (400 MHz, methanol-d$_4$) δ ppm 8.54 (s, 1H) 8.21 (s, 1H) 7.63 (s, 1H) 7.55 (d, J=8 Hz, 1H) 7.47-7.36 (m, 2H) 6.41 (s, 1H) 5.72-5.60 (m, 1H) 3.92-3.80 (m, 4H) 3.70 (s, 3H) 3.38-3.46 (m, 2H) 2.77-2.87 (m, 2H) 2.45 (s, 3H) 1.64 (d, J=4 Hz, 3H).

Example 5: Synthesis of (R)-6-(3,6-dihydro-2H-pyran-4-yl)-8-methyl-4-((1-(3-(trifluoromethyl)phenyl)ethyl)amino)pyrido[2,3-d]pyrimidin-7(8H)-one

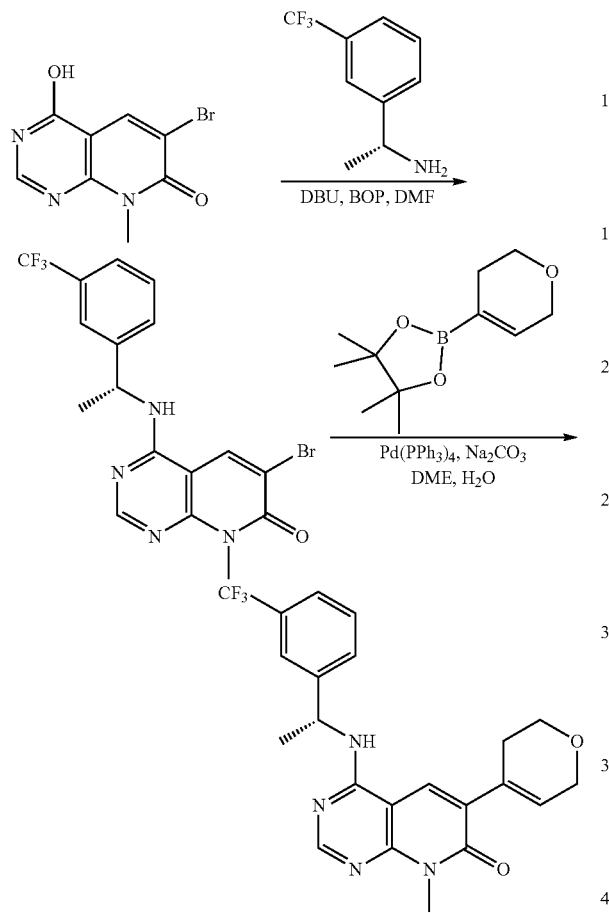

Step 1

To a solution of 6-bromo-4-hydroxy-8-methyl-pyrido[2,3-d]pyrimidin-7-one (987 mg, 3.86 mmol), (1R)-1-[3-(trifluoromethyl)phenyl]ethanamine (663 mg, 3.50 mmol) in DMF (9.6 ml) was added DBU (2.11 ml, 14.02 mmol) and BOP (2.33 g, 5.26 mmol). The mixture was stirred at 25° C. for 0.5 h. Water was added and the mixture was extracted with ethyl acetate. The combined organic layers were washed with brine and dried with $Na_2SO_4$. The solvent was removed under reduced pressure and the crude residue was purified by column chromatography to give 6-bromo-8-methyl-4-[[(1R)-1-[3-(trifluoromethyl)phenyl]ethyl]amino]pyrido[2,3-d]pyrimidin-7-one (107 mg, 7% yield). $^1$H NMR (400 MHz, methanol-$d_4$) δ=8.82 (s, 1H) 8.37 (s, 1H) 7.63-7.73 (m, 2H) 7.48-7.54 (m, 2H) 5.58 (q, 1H) 3.75 (s, 3H) 1.64 (d, J=4.00 Hz, 3H).

Step 2

To a mixture of 6-bromo-8-methyl-4-[[(1R)-1-[3-(trifluoromethyl)phenyl]ethyl]amino]pyrido[2,3-d]pyrimidin-7-one (38 mg, 89 μmol) and 2-(3,6-dihydro-2H-pyran-4-yl)-4,4,5,5-tetramethyl-1,3,2-dioxaborolane (28 mg, 133 μmol) in DME (0.7 ml) and water (0.13 ml) was added Pd(PPh$_3$)$_4$ (Tetrakis(triphenylphosphine)palladium(0), 21 mg, 17.79 μmol), Na$_2$CO$_3$ (28 mg, 266 μmol). The mixture was stirred at 85° C. for 1 h. After cooling to rt the reaction mixture was filtered and purified by prep-HPLC to give 6-(3,6-dihydro-2H-pyran-4-yl)-8-methyl-4-[[(1R)-1-[3-(trifluoromethyl)phenyl]ethyl]amino]pyrido[2,3-d]pyrimidin-7-one (25.4 mg, 23% yield). LCMS (ESI): m/z: [M+H] calculated for $C_{22}H_{22}F_3N_4O_2$: 431.2; found; 431.2; $^1$H NMR (400 MHz, methanol-$d_4$) δ=8.32 (s, 1H) 8.21 (s, 1H) 7.65-7.72 (m, 2H) 7.47-7.56 (m, 2H) 6.52 (s, 1H) 5.58-5.64 (m, 1H) 4.32-4.34 (q, 2H) 3.92-3.94 (t, J=8.00 Hz, 2H) 3.71 (s, 3H) 2.52-2.62 (dd, 2H) 1.65 (d, J=8.00 Hz, 3H).

Example 6: Synthesis of 4-[[(1R)-1-[3-amino-5-(trifluoromethyl)phenyl]ethyl]amino]-2,8-dimethyl-6-(1,2,3,6-tetrahydropyridin-4-yl)pyrido[2,3-d]pyrimidin-7-one

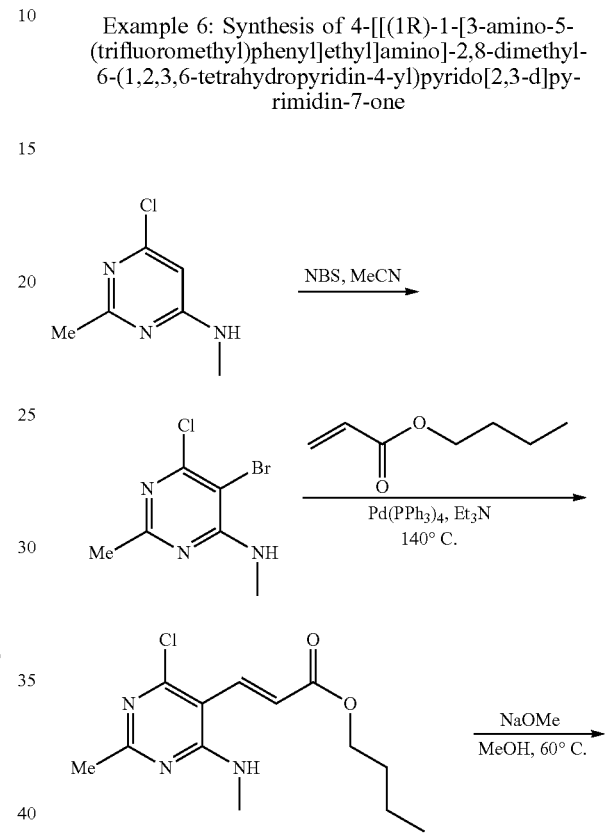

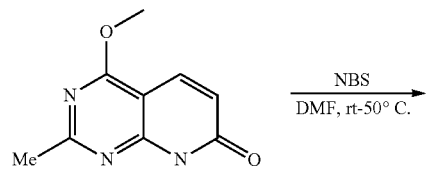

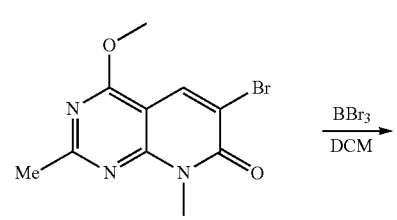

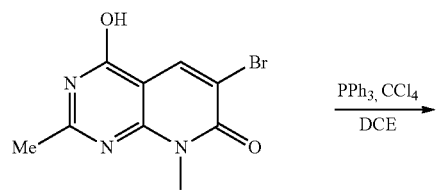

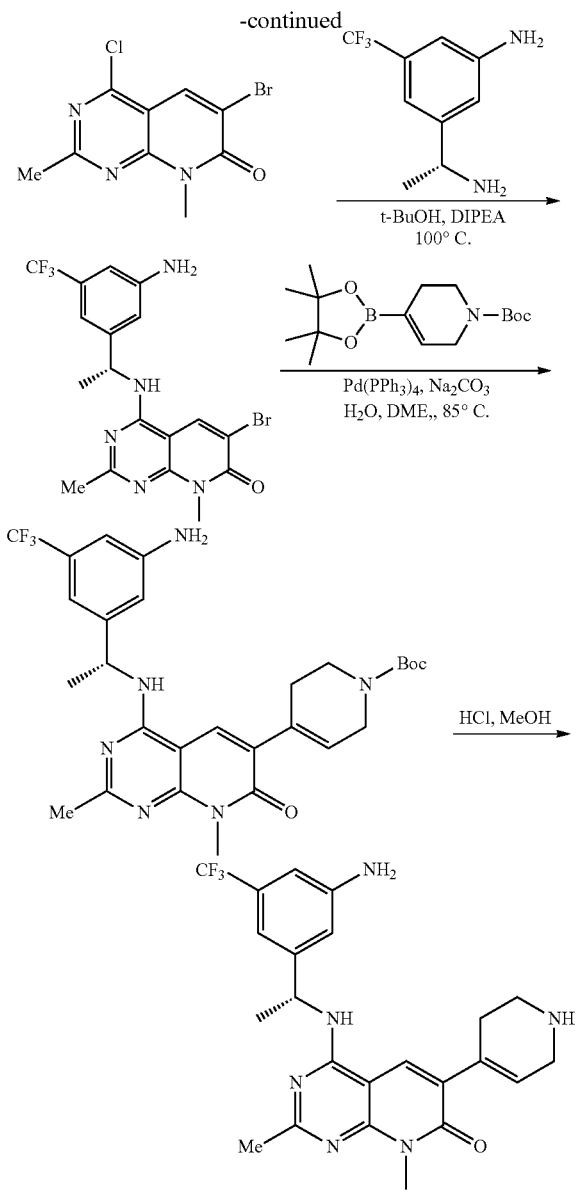

Step 1

To a mixture of 6-chloro-N2-dimethyl-pyrimidin-4-amine (6.0 g, 38 mmol) in DMF (60 ml) at rt was added NBS (8.13 g, 45.7 mmol). The mixture was stirred at rt for 2 h, then diluted with H$_2$O and extracted with EtOAc. The combined organic layers were washed with brine, dried with anhydrous Na$_2$SO$_4$, and filtered. The solvent was removed under reduced pressure and the residue was purified by column chromatography to give 5-bromo-6-chloro-N2-dimethyl-pyrimidin-4-amine (7 g, 78% yield). $^1$H NMR (400 MHz, DMSO-d$_6$) δ ppm 7.44 (d, J=4.0 Hz, 1H), 2.87 (d, J=4.0 Hz, 3H), 2.34 (s, 3H).

Step 2

A mixture of 5-bromo-6-chloro-N2-dimethyl-pyrimidin-4-amine (4.0 g, 16.9 mmol), TEA (5.9 ml, 42.3 mmol), butyl prop-2-enoate (24.1 ml, 169.1 mmol) and Pd(PPh$_3$)$_4$ (Tetrakis(triphenylphosphine)palladium(0), 1.95 g, 1.69 mmol) were combined and heated to 140° C. for 36 h. H$_2$O was added and the mixture was extracted with EtOAc. The combined organic layers were washed with brine, dried with anhydrous Na$_2$SO$_4$, and filtered. The solvent was removed under reduced pressure and the residue was purified by prep-HPLC to give (E)-3-[4-chloro-2-methyl-6-(methylamino)pyrimidin-5-yl]prop-2-enoate (0.35 g, 7% yield). LCMS (ESI): m/z: [M+H] calculated for C$_{13}$H$_{19}$ClN$_3$O$_2$: 284.1; found 284.1; $^1$H NMR (400 MHz, methanol-d$_4$) δ ppm 7.58 (d, J=16.0 Hz, 1H), 6.46 (d, J=16.0 Hz, 1H), 4.21 (t, J=12.0 Hz, 2H), 2.97 (s, 3H), 2.42 (s, 3H), 1.75-1.63 (m, 2H), 1.53-1.35 (m, 2H), 0.97 (t, J=16.0 Hz, 3H).

Step 3

To a mixture of butyl (E)-3-[4-chloro-2-methyl-6-(methylamino)pyrimidin-5-yl]prop-2-enoate (0.35 g, 1.23 mmol) in MeOH (5 ml) was added NaOMe (200 mg, 3.7 mmol). The mixture was heated to 60° C. and stirred for 2 h. Aqueous NH$_4$Cl was added, the solvent was removed under reduced pressure and the crude residue was purified by prep-TLC to give 4-methoxy-2,8-dimethyl-pyrido[2,3-d]pyrimidin-7-one (0.15 g, 59% yield). $^1$H NMR (400 MHz, DMSO-d$_6$) δ ppm 7.92 (d, J=8.0 Hz, 1H), 6.58 (d, J=12.0 Hz, 1H), 4.05 (s, 3H), 3.59 (s, 3H), 2.59 (s, 3H).

Step 4

To a mixture of 4-methoxy-2,8-dimethyl-pyrido[2,3-d]pyrimidin-7-one (0.15 g, 0.73 mmol) in DMF (1 ml) at rt was added NBS (130 mg, 0.73 mmol). The mixture was heated to 50° C. for and stirred for 2 h. The mixture was poured into cold H$_2$O and stirred for 5 min, the emerging precipitate was filtered and the filter cake was dried under vacuum to give 6-bromo-4-methoxy-2,8-dimethyl-pyrido[2,3-d]pyrimidin-7-one (0.12 g, 58% yield). LCMS (ESI): m/z: [M+H] calculated for C$_{10}$H$_{11}$BrN$_3$O$_2$: 284.0; found 284.0; $^1$H NMR (400 MHz, DMSO-d$_6$) δ ppm 8.43 (s, 1H), 4.06 (s, 3H), 3.67 (s, 3H), 2.59 (s, 3H).

Step 5

To a mixture of 6-bromo-4-methoxy-2,8-dimethyl-pyrido[2,3-d]pyrimidin-7-one (120 mg, 0.42 mmol) in DCM (1 ml) at 0° C. was added BBr$_3$ (204 μl, 2.11 mmol). The mixture was warmed to rt and stirred for 12 h, then poured into aqueous cooled (0° C.) Na$_2$CO$_3$ and the emerging precipitate filtered to give 6-bromo-4-hydroxy-2,8-dimethyl-pyrido[2,3-d]pyrimidin-7-one (0.14 g). $^1$H NMR (400 MHz, methanol-d$_4$) δ ppm 8.41 (s, 1H), 3.77 (s, 3H), 2.45 (s, 3H).

Step 6

A mixture of 6-bromo-4-hydroxy-2,8-dimethyl-pyrido[2,3-d]pyrimidin-7-one (0.2 g, 0.74 mmol) and Ph$_3$P (583 mg, 2.22 mmol) in DCE (5 ml) was stirred until the mixture became clear, then CCl$_4$ (285 μl, 2.96 mmol) was added. The mixture was heated to 70° C. and stirred for 2.5 h, then the solvent was concentrated under reduced pressure and the crude residue was purified by column chromatography to give 6-bromo-4-chloro-2,8-dimethyl-pyrido[2,3-d]pyrimidin-7-one (50 mg, 23% yield). $^1$H NMR (400 MHz, methanol-d$_4$) δ ppm 8.55 (s, 1H), 3.82 (s, 3H), 2.71 (s, 3H).

Step 7

To a mixture of 6-bromo-4-chloro-2,8-dimethyl-pyrido[2,3-d]pyrimidin-7-one (0.05 g, 0.17 mmol) in t-BuOH (0.5 ml) was added DIPEA (302 μl, 1.73 mmol) and 3-[(1R)-1-aminoethyl]-5-(trifluoromethyl)aniline (43 mg, 0.21 mmol). The mixture was heated to 100° C. in a crimped vial and stirred for 2 h, then the solvent was concentrated under reduced pressure and the crude residue was purified by prep-TLC to give 4-[[(1R)-1-[3-amino-5-(trifluoromethyl)phenyl]ethyl]amino]-6-bromo-2-methyl-8H-pyrido[2,3-d]pyrimidin-7-one (0.03 g, 39% yield). $^1$H NMR (400 MHz, methanol-d$_4$) δ ppm 8.77 (s, 1H), 6.96 (s, 1H), 6.93 (s, 1H), 6.80 (s, 1H), 5.54-5.48 (m, 1H), 3.76 (s, 3H), 2.44 (s, 3H), 1.58 (d, J=8.0 Hz, 3H).

441

Step 8

To a mixture of tert-butyl 4-(4,4,5,5-tetramethyl-1,3,2-dioxaborolan-2-yl)-3,6-dihydro-2H-pyridine-1-carboxylate (31 mg, 1.0 mmol) in DME (0.5 ml) under an atmosphere of N₂ was added 4-[[(1R)-1-[3-amino-5-(trifluoromethyl)phenyl]ethyl]amino]-6-bromo-2,8-dimethyl-pyrido[2,3-d]pyrimidin-7-one (0.03 g, 66 μmol), Na₂CO₃ (14 mg, 0.13 mmol), H₂O (0.1 ml) and Pd(PPh₃)₄ (Tetrakis(triphenylphosphine)palladium(0), 7.6 mg, 6.6 μmol). The mixture was heated to 85° C. and stirred for 2 h, then the solvent was concentrated under reduced pressure and the residue was purified by prep-TLC to give tert-butyl 4-[4-[[(1R)-1-[3-amino-5-(trifluoromethyl)phenyl]ethyl]amino]-2,8-dimethyl-7-oxo-pyrido[2,3-d]pyrimidin-6-yl]-3,6-dihydro-2H-pyridine-1-carboxylate (40 mg). ¹H NMR (400 MHz, methanol-d₄) δ ppm 8.16 (s, 1H), 6.96 (s, 1H), 6.94 (s, 1H), 6.79 (s, 1H), 6.26 (s, 1H), 5.58-5.49 (m, 1H), 4.11-4.03 (m, 2H), 3.69 (s, 3H), 3.62 (s, 2H), 2.55 (s, 2H), 2.44 (s, 3H), 1.58 (d, J=4.0 Hz, 3H), 1.49 (s, 9H).

Step 9

A mixture of tert-butyl 4-[4-[[(1R)-1-[3-amino-5-(trifluoromethyl)phenyl]ethyl]amino]-2,8-dimethyl-7-oxo-pyrido[2,3-d]pyrimidin-6-yl]-3,6-dihydro-2H-pyridine-1-carboxylate (30 mg, 54 μmol) in 4M HCl in MeOH (3 ml) was degassed, then at rt for 15 min. The solvent was concentrated under reduced pressure and the residue was purified by prep-HPLC to give 4-[[(1R)-1-[3-amino-5-(trifluoromethyl)phenyl]ethyl]amino]-2,8-dimethyl-6-(1,2,3,6-tetrahydropyridin-4-yl)pyrido[2,3-d]pyrimidin-7-one as a formic acid salt (8 mg, 30% yield). LCMS (ESI): m/z: [M+H] calculated for C₂₃H₂₆F₃N₆O: 459.2; found 459.2; ¹H NMR (400 MHz, methanol-d4) δ ppm 8.52 (s, 1H), 8.22 (s, 1H), 6.95 (s, 2H), 6.80 (s, 1H), 6.40 (s, 1H), 5.59-5.53 (m, 1H), 3.85 (s, 2H), 3.70 (s, 3H), 3.45-3.42 (m, 2H) 2.83 (s, 2H), 2.45 (s, 3H), 1.60 (d, J=8.0 Hz, 3H).

Example 7: Synthesis of (R)-4-((1-(3-amino-5-(trifluoromethyl)phenyl)ethyl)amino)-6-(3,6-dihydro-2H-pyran-4-yl)-2,8-dimethylpyrido[2,3-d]pyrimidin-7(8H)-one

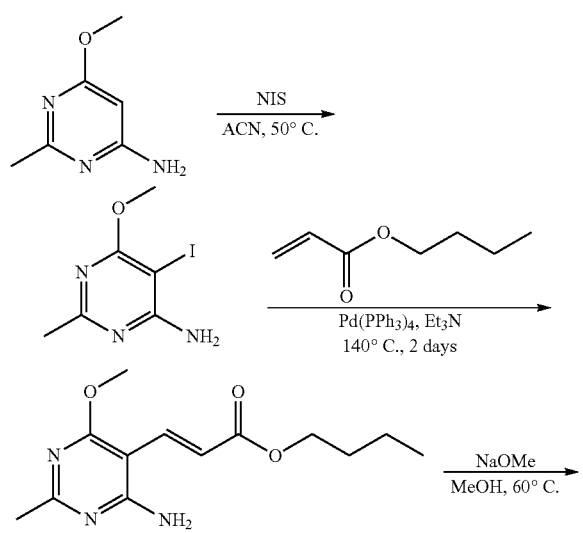

442

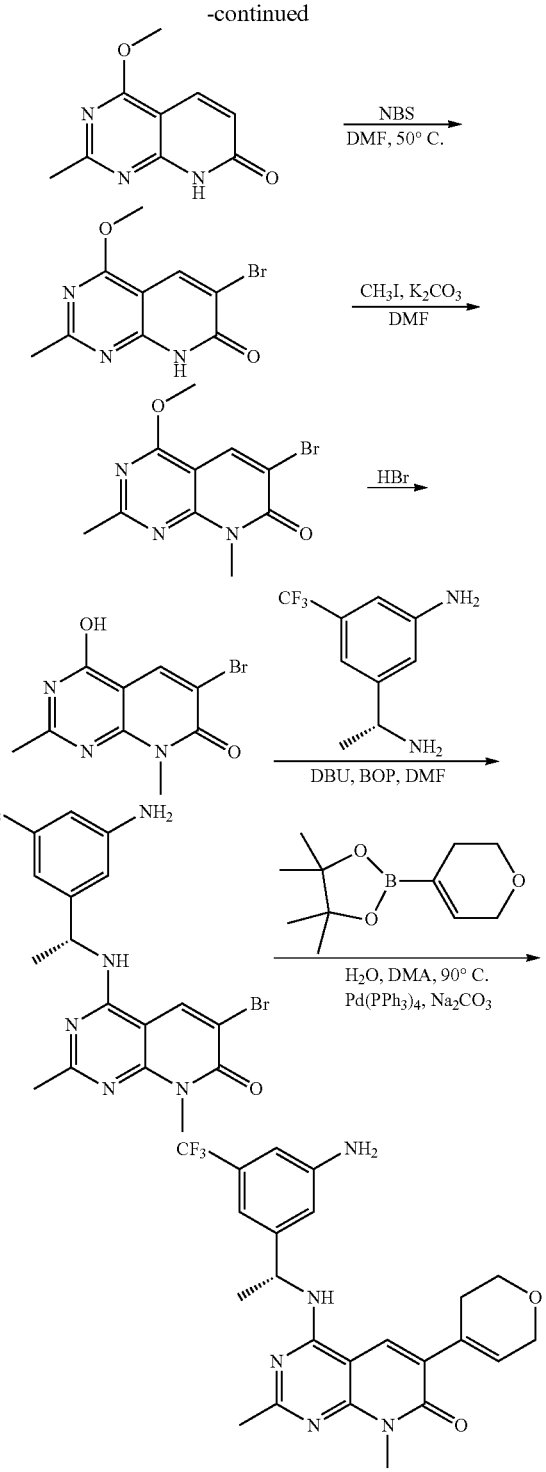

Step 1

To a mixture of 6-methoxy-2-methyl-pyrimidin-4-amine (15 g, 108 mmol) in ACN (150 ml) was added NIS (24 g, 108 mmol). The mixture was stirred at 50° C. for 2 h. After cooling to rt excess aqueous Na₂SO₃ was added and the mixture was extracted with EtOAc. The combined organic phases were washed with brine and dried over Na₂SO₄. The solvent was removed under reduced pressure and the crude residue was purified by column chromatography to give 5-iodo-6-methoxy-2-methyl-pyrimidin-4-amine (22 g, 77% yield). LCMS (ESI): m/z: [M+H] calculated for $C_6H_8IN_3O$: 265.0; found 266.2.

Step 2

To a mixture of 5-iodo-6-methoxy-2-methyl-pyrimidin-4-amine (20 g, 75 mmol) and butyl prop-2-enoate (21.5 ml, 151 mmol) in DMA (80 ml) was added tris-o-tolylphosphane (4.6 g, 15 mmol), TEA (42 ml, 302 mmol) and Pd(OAc)$_2$ (3.4 g, 15 mmol). The mixture was heated to 100° C. and stirred for 10 h under N$_2$. After cooling to rt the reaction was filtered through a plug of silica. The solvent was removed under reduced pressure. The residue was dissolved in EtOA and washed with 10% aqueous LiCl, followed by water and brine. The aqueous phase was extracted with EtOAc and the combined organic phases were washed with brine and dried over Na$_2$SO$_4$. The solvent was removed under reduced pressure and the crude residue was purified by column chromatography to give butyl (E)-3-(4-amino-6-methoxy-2-methyl-pyrimidin-5-yl)prop-2-enoate (15 g, 75% yield). LCMS (ESI): m/z: [M+H] calculated for $C_{13}H_{19}N_3O_3$: 265.1; found 266.3.

Step 3

To a mixture of butyl (E)-3-(4-amino-6-methoxy-2-methyl-pyrimidin-5-yl) prop-2-enoate (15 g, 57 mmol) in MeOH (20 ml) was added NaOMe (30.5 g, 170 mmol). The mixture was heated to 90° C. for 1 h. After cooling to rt aqueous NH$_4$Cl was added and the mixture was concentrated under reduced pressure to remove most of the solvent. The precipitate was collected by filtration, washed with EtOAc and dried under vacuum to give 4-methoxy-2-methyl-8H-pyrido [2, 3-d]pyrimidin-7-one (9 g, 83% yield). $^1$H NMR (400 MHz, DMSO-d$_6$) δ ppm 7.84 (d, J=8 Hz, 1H) 6.41 (d, J=8 Hz, 1H) 4.01 (s, 3H) 2.50 (s, 3H).

Step 4

To a mixture of 4-methoxy-2-methyl-8H-pyrido [2,3-d]pyrimidin-7-one (9 g, 47 mmol) in DMF (80 ml) was added NBS (8.4 g, 47 mmol). The mixture was heated to 50° C. for 2 h. After cooling to rt H$_2$O was added and the mixture was extracted with EtOAc. The combined organic layers were washed with brine, dried with Na$_2$SO$_4$ and the solvent was removed under reduced pressure. The crude residue was purified by column chromatography to give 6-bromo-4-methoxy-2-methyl-8H-pyrido [2, 3-d]pyrimidin-7-one (9 g, 71% yield). $^1$H NMR (400 MHz, DMSO-d$_6$) δ ppm 12.83 (s, 1H) 8.28 (s, 1H) 4.03 (s, 3H) 2.52 (s, 3H).

Step 5

To a mixture of 6-bromo-4-methoxy-2-methyl-8H-pyrido [2,3-d]pyrimidin-7-one (1 g, 3.7 mmol) in DMF (10 ml) was added K$_2$CO$_3$ (1 g, 7.4 mmol) and CH$_3$I (0.46 ml, 7.4 mmol). The mixture was stirred at rt for 2 h. H$_2$O was added and the mixture was extracted with EtOAc. The combined organic layers were washed with brine and dried with Na$_2$SO$_4$. The solvent was removed under reduced pressure and the crude residue was purified by column chromatography to give 6-bromo-4-methoxy-2,8-dimethyl-pyrido[2,3-d]pyrimidin-7-one (0.6 g, 57% yield). H NMR (400 MHz, DMSO-d$_6$) δ ppm 8.32 (s, 1H) 4.06 (s, 3H) 3.65 (s, 3H) 2.59 (s, 3H).

Step 6

A mixture of 6-bromo-4-methoxy-2,8-dimethyl-pyrido[2,3-d]pyrimidin-7-one (0.6 g, 2.1 mmol) in HBr (6 ml, 33% in AcOH) was heated to 100° C. for 2 h. After cooling to rt the mixture was concentrated under reduced pressure and the precipitate was collected by filtration. After recrystallization from EtOAc 6-bromo-4-hydroxy-2,8-dimethyl-pyrido[2,3-d]pyrimidin-7-one (0.5 g, crude) was obtained. $^1$H NMR (400 MHz, DMSO-d$_6$) δ ppm 12.80 (s, 1H) 8.23 (s, 1H) 3.62 (s, 3H) 2.39 (s, 3H).

Step 7

To a mixture of 6-bromo-4-hydroxy-2,8-dimethyl-pyrido [2,3-d]pyrimidin-7-one (0.1 g, 0.37 mmol) and 3-[(1R)-1-aminoethyl]-5-(trifluoromethyl)aniline (151 mg, 0.74 mmol) in DMF (1 ml) was added benzotriazol-1-yloxy-tris (dimethylamino)phosphonium; hexafluorophosphate (255 mg, 0.58 mmol) and 2,3,4,6,7,8,9,10-octahydropyrimido[1,2-a]azepine (167 µl, 1.1 mmol). The mixture was stirred at rt for 3 h. Water was added and the mixture was extracted with EtOAc. The combined organic phases were washed with brine and dried over Na$_2$SO$_4$. The solvent was removed under reduce pressure and the residue was purified by prep-TLC to give 4-[[(1R)-1-[3-amino-5-(trifluoromethyl) phenyl]ethyl]amino]-6-bromo-2,8-dimethyl-pyrido[2,3-d] pyrimidin-7-one (0.15 g, 89% yield). $^1$H NMR (400 MHz, DMSO-d$_6$) δ ppm 8.91 (s, 1H) 8.26 (d, J=8 Hz, 1H) 6.85 (s, 1H) 6.81 (s, 1H) 6.70 (s, 1H) 5.54 (s, 2H) 5.50-5.39 (m, 1H) 3.60 (s, 3H) 2.38 (s, 3H) 1.50 (d, J=8 Hz, 3H).

Step 8

To a mixture of 2-(3,6-dihydro-2H-pyran-4-yl)-4,4,5,5-tetramethyl-1,3,2-dioxaborolane (104 mg, 0.49 mmol) in DMA (1.5 ml) was added 4-[[(1R)-1-[3-amino-5-(trifluoromethyl)phenyl]ethyl]amino]-6-bromo-2,8-dimethyl-pyrido[2,3-d]pyrimidin-7-one (0.15 g, 0.33 mmol), Na$_2$CO$_3$ (69 mg, 0.66 mmol), H$_2$O (0.3 ml) and Pd(PPh$_3$)$_4$ (Tetrakis (triphenylphosphine)palladium(0), 38 mg, 33 µmol). The mixture was stirred under N$_2$ at 90° C. for 2 h. After cooling to rt water was added and the mixture was extracted with EtOAc. The combined organic phases were washed with brine and dried with Na$_2$SO$_4$. The solvent was removed under reduced pressure and the residue was purified by prep-HPLC to give 4-[[(1R)-1-[3-amino-5-(trifluoromethyl) phenyl]ethyl]amino]-6-(3,6-dihydro-2H-pyran-4-yl)-2,8-dimethyl-pyrido[2,3-d]pyrimidin-7-one (30 mg, 20% yield). LCMS (ESI): m/z: [M+H] calculated for $C_{23}H_{25}F_3N_5O_2$: 460.2; found 460.2; $^1$H NMR (400 MHz, methanol-d$_4$) δ ppm 8.15 (s, 1H) 6.97 (s, 1H) 6.94 (s, 1H) 6.79 (s, 1H) 6.46 (s, 1H) 5.57-5.52 (m, 1H) 4.34-4.29 (m, 2H) 3.93-3.90 (m, 2H) 3.69 (s, 3H) 2.59-2.52 (m, 2H) 2.44 (s, 3H) 1.59 (d, J=8 Hz, 3H).

Example 8: Synthesis of (R)-4-((1-(3-amino-5-(trifluoromethyl)phenyl)ethyl)amino)-2-methyl-6-(piperidin-4-yl)pyrido[2,3-d]pyrimidin-7(8H)-one

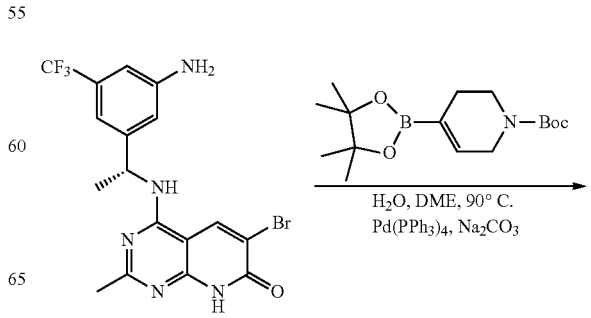

-continued

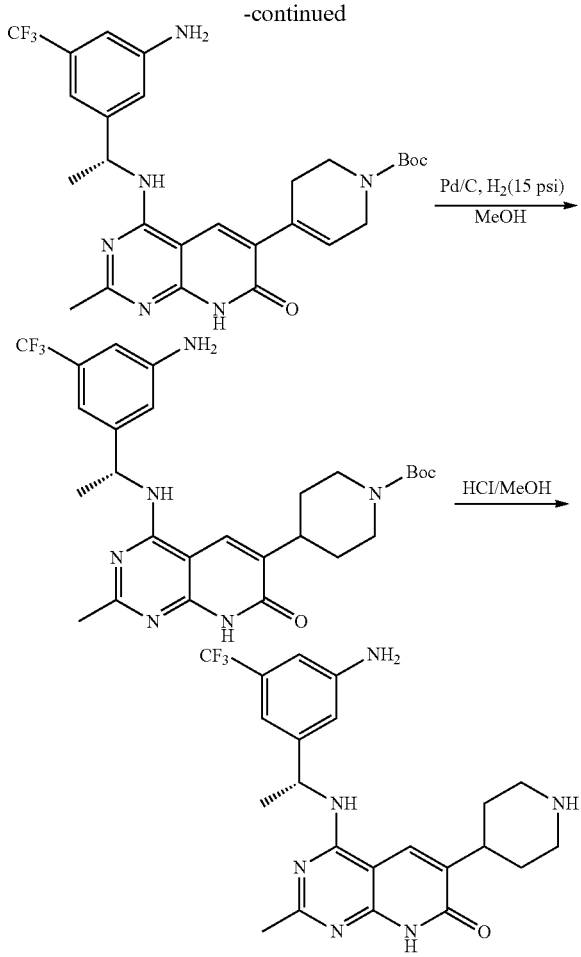

Step 1

To a mixture of tert-butyl 4-(4,4,5,5-tetramethyl-1,3,2-dioxaborolan-2-yl)-3,6-dihydro-2H-pyridine-1-carboxylate (73 mg, 0.25 mmol) in DME (1 ml) was added 4-[[(1R)-1-[3-amino-5-(trifluoromethyl)phenyl]ethyl]amino]-6-bromo-2-methyl-8H-pyrido[2,3-d]pyrimidin-7-one (0.07 g, 0.16 mmol), Na$_2$CO$_3$ (34 mg, 0.32 mmol), H$_2$O (0.2 ml) and Pd(PPh$_3$)$_4$ (Tetrakis(triphenylphosphine)palladium(0), 18 mg, 16 μmol). The mixture was stirred under N$_2$ at 90° C. for 2 h. After cooling to rt H$_2$O was added and the mixture was extracted with EtOAc. The combined organic layers were washed with brine and dried with Na$_2$SO$_4$. The solvent was removed under reduced pressure and the crude residue was purified by column chromatography to give tert-butyl 4-[4-[[(1R)-1-[3-amino-5-(trifluoromethyl)phenyl]ethyl]amino]-2-methyl-7-oxo-8H-pyrido[2, 3-d] pyrimidin-6-yl]-3,6-dihydro-2H-pyridine-1-carboxylate (30 mg 35% yield). $^1$H NMR (400 MHz, methanol-d$_4$) δ ppm 8.17 (s, 1H) 6.96 (s, 1H) 6.93 (s, 1H) 6.80 (s, 1H) 6.44-6.38 (m, 1H) 5.56-5.51 (m, 1H) 4.12-4.05 (m, 2H) 3.64-3.59 (m, 2H) 2.58-2.52 (m, 2H) 2.39 (s, 3H) 1.58 (d, J=4 Hz, 3H) 1.48 (d, J=4 Hz, 9H).

Step 2

To a mixture of tert-butyl 4-[4-[[(1R)-1-[3-amino-5-(trifluoromethyl)phenyl]ethyl]amino]-2-methyl-7-oxo-8H-pyrido[2,3-d]pyrimidin-6-yl]-3,6-dihydro-2H-pyridine-1-carboxylate (30 mg, 55 μmol) in MeOH (2 ml) was added Pd/C (0.01 g). The mixture was stirred at rt for 1 h under H$_2$ (15 psi). The reaction mixture was filtered and the solvent was removed under reduced pressure to give tert-butyl 4-[4-[[(1R)-1-[3-amino-5-(trifluoromethyl)phenyl]ethyl]amino]-2-methyl-7-oxo-8H-pyrido[2,3-d]pyrimidin-6-yl]piperidine-1-carboxylate (20 mg, 66% yield). LCMS (ESI): m/z: [M+H] calculated for C$_{27}$H$_{34}$F$_3$N$_6$O$_3$: 547.3; found 547.3.

Step 3

A mixture of tert-butyl 4-[4-[[(1R)-1-[3-amino-5-(trifluoromethyl)phenyl]ethyl]amino]-2-methyl-7-oxo-8H-pyrido[2,3-d]pyrimidin-6-yl]piperidine-1-carboxylate (30 mg, 55 μmol) in HCl/MeOH (2 ml) was stirred at rt for 20 min. The solvent was removed under reduced pressure and the residue was purified by prep-HPLC to give 4-[[(1R)-1-[3-amino-5-(trifluoromethyl)phenyl]ethyl]amino]-2-methyl-6-(4-piperidyl)-8H-pyrido[2,3-d]pyrimidin-7-one (9 mg, 37% yield). LCMS (ESI): m/z: [M+H] calculated for C$_{22}$H$_{26}$F$_3$N$_6$O: 447.2; found 447.2; $^1$H NMR (400 MHz, methanol-d$_4$) δ ppm 8.51 (s, 1H) 8.07 (s, 1H) 6.97-6.95 (m, 2H) 6.81 (s, 1H) 5.60-5.54 (m, 1H) 3.52 (d, J=12 Hz, 2H) 3.21-3.12 (m, 2H) 3.10-3.01 (m, 1H) 2.40 (s, 3H) 2.18 (d, J=12 Hz, 2H) 1.99-1.84 (m, 2H) 1.61 (d, J=8 Hz, 3H).

The following examples 8-1 to 8-17 and 1-28 to 1-31 shown in Table 3 were synthesized in the manner similar to Example 8.

TABLE 3

| Examples 8-1 to 8-17 and 1-28 to 1-31 | | |
|---|---|---|
| Example # | Structure | Mass Found |
| 8-1 | | 448.4 |

TABLE 3-continued

| Examples 8-1 to 8-17 and 1-28 to 1-31 | | |
|---|---|---|
| Example # | Structure | Mass Found |
| 8-2 | | 460.6 |
| 8-3 | | 474.5 |
| 8-4 | | 478.4 |
| 8-5 | | 481.4 |

TABLE 3-continued

Examples 8-1 to 8-17 and 1-28 to 1-31

| Example # | Structure | Mass Found |
|---|---|---|
| 8-6 | 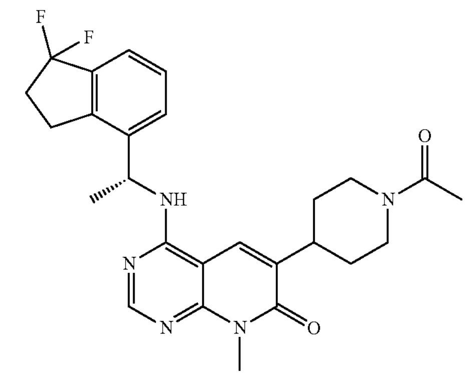 [SMILES: CC(=O)N1CCC(c2cc3c(N[C@H](C)c4cccc5c4CCC5(F)F)ncnc3n(C)c2=O)CC1] | 482.3 |
| 8-7 | 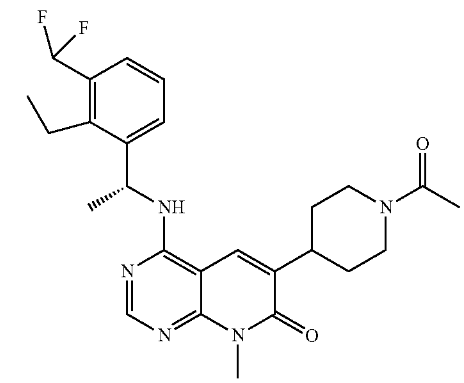 [SMILES: CCc1c(C(F)F)cccc1[C@@H](C)Nc1ncnc2c1cc(C1CCN(C(C)=O)CC1)c(=O)n2C] | 484.3 |
| 8-8 | 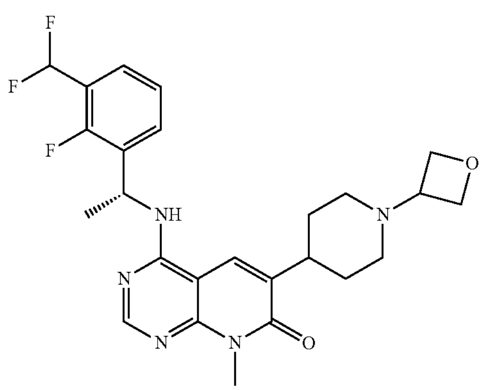 [SMILES: C[C@@H](Nc1ncnc2c1cc(C1CCN(C3COC3)CC1)c(=O)n2C)c1cccc(C(F)F)c1F] | 488.5 |
| 8-9 | 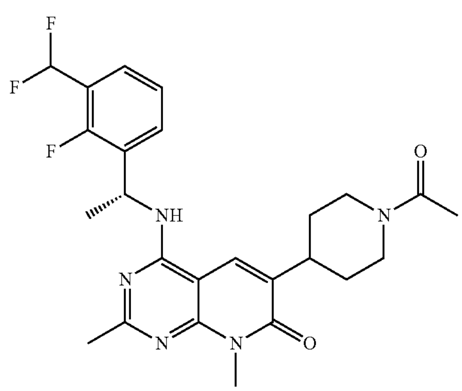 | 488.5 |

TABLE 3-continued

Examples 8-1 to 8-17 and 1-28 to 1-31

| Example # | Structure | Mass Found |
|---|---|---|
| 8-10 | 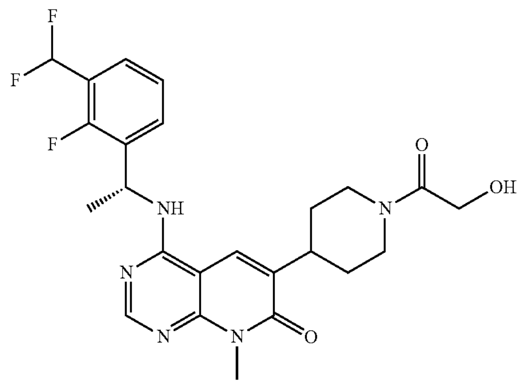 | 490.5 |
| 8-11 | 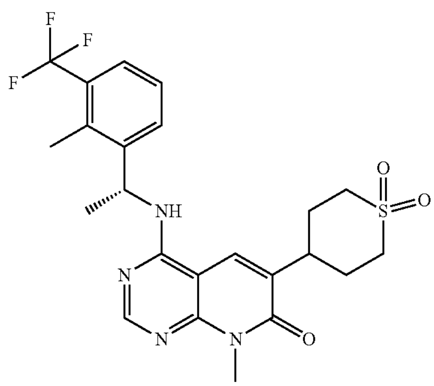 [SMILES: Cc1c([C@@H](C)Nc2ncnc3c2cc(C2CCS(=O)(=O)CC2)c(=O)n3C)cccc1C(F)(F)F] | 495.1 |
| 8-12 | 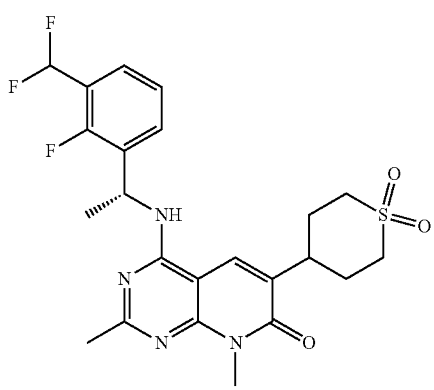 [SMILES: Cc1nc(N[C@H](C)c2cccc(C(F)F)c2F)c2cc(C3CCS(=O)(=O)CC3)c(=O)n(C)c2n1] | 495.4 |
| 8-13 | 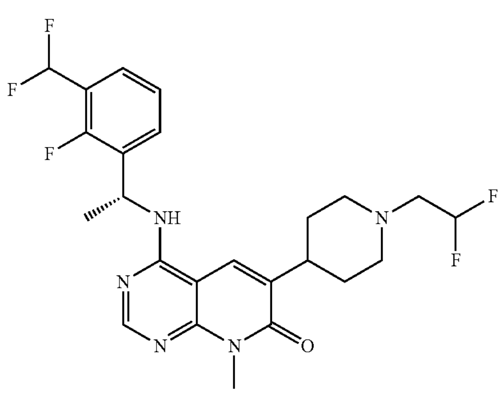 [SMILES: C[C@@H](Nc1ncnc2c1cc(C1CCN(CC(F)F)CC1)c(=O)n2C)c1cccc(C(F)F)c1F] | 496.6 |

TABLE 3-continued

Examples 8-1 to 8-17 and 1-28 to 1-31

| Example # | Structure | Mass Found |
|---|---|---|
| 8-14 | 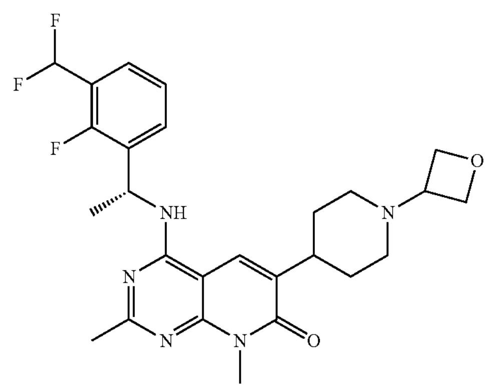 [SMILES: Cc1nc(N[C@H](C)c2cccc(C(F)F)c2F)c2cc(C3CCN(C4COC4)CC3)c(=O)n(C)c2n1] | 502.5 |
| 8-15 | 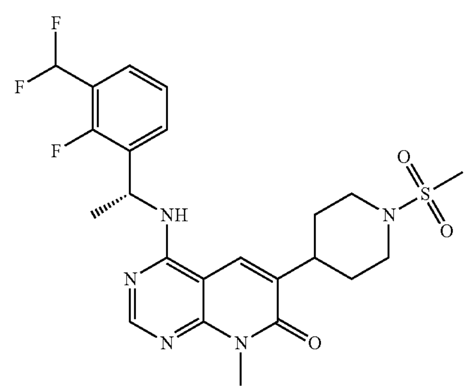 [SMILES: C[C@@H](Nc1ncnc2c1cc(C1CCN(S(C)(=O)=O)CC1)c(=O)n2C)c1cccc(C(F)F)c1F] | 510.5 |
| 8-16 | 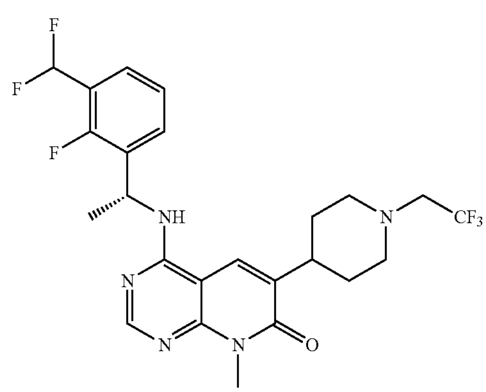 [SMILES: C[C@@H](Nc1ncnc2c1cc(C1CCN(CC(F)(F)F)CC1)c(=O)n2C)c1cccc(C(F)F)c1F] | 514.5 |
| 8-17 | 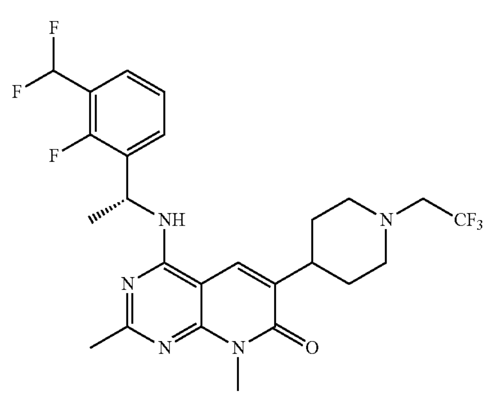 [SMILES: Cc1nc(N[C@H](C)c2cccc(C(F)F)c2F)c2cc(C3CCN(CC(F)(F)F)CC3)c(=O)n(C)c2n1] | 528.5 |

TABLE 3-continued

Examples 8-1 to 8-17 and 1-28 to 1-31

| Example # | Structure | Mass Found |
|---|---|---|
| 1-28 | 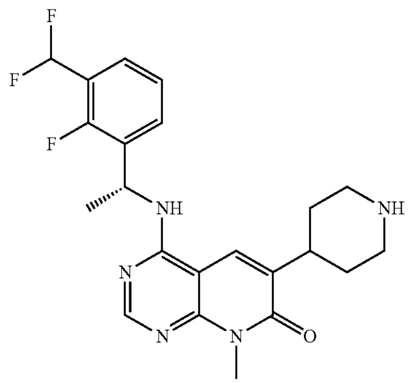 | 432.4 |
| 1-29 | 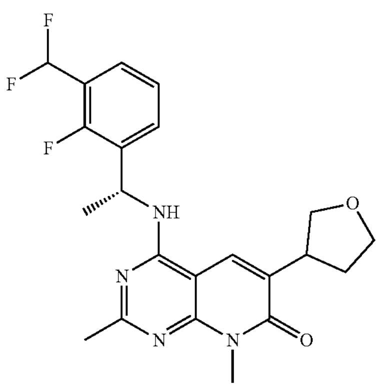 | 433.5 |
| 1-30 | 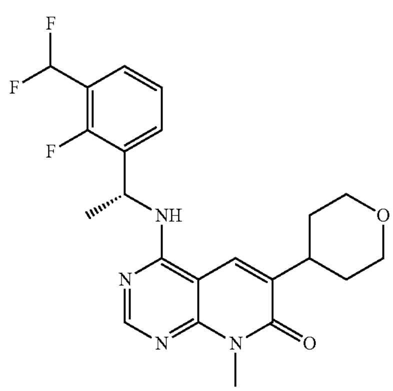 [SMILES: C[C@@H](Nc1ncnc2c1cc(C1CCOCC1)c(=O)n2C)c1cccc(C(F)F)c1F] | 433.5 |
| 1-31 | 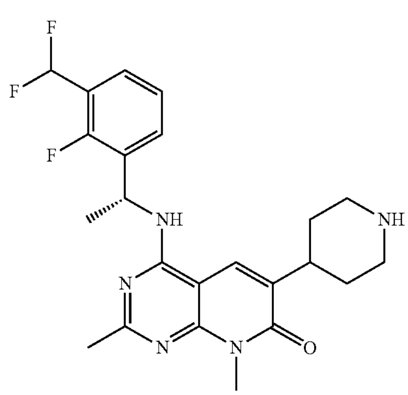 | 446.7 |

Example 9: Synthesis of (R)-4-((1-(3-amino-5-(trifluoromethyl)phenyl)ethyl)amino)-2-methyl-6-(1,2,3,6-tetrahydropyridin-4-yl)pyrido[2,3-d]pyrimidin-7(8H)-one

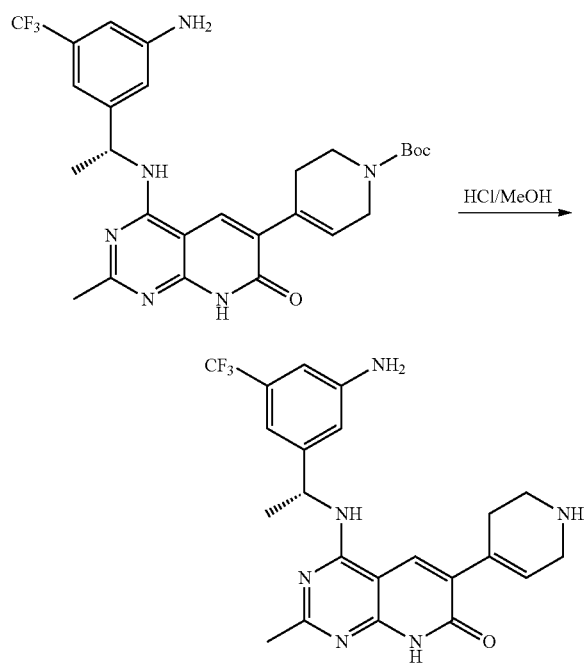

Step 1

A mixture of tert-butyl 4-[4-[[(1R)-1-[3-amino-5-(trifluoromethyl)phenyl]ethyl]amino]-2-methyl-7-oxo-8H-pyrido[2,3-d]pyrimidin-6-yl]-3,6-dihydro-2H-pyridine-1-carboxylate (0.15 g, 0.28 mmol) in HCl/MeOH (5 ml) was stirred at rt for 0.5 h. The solvent was removed under reduced pressure and the crude residue was purified by prep-HPLC to give 4-[[(1R)-1-[3-amino-5-(trifluoromethyl)phenyl]ethyl]amino]-2-methyl-6-(1,2,3,6-tetrahydropyridin-4-yl)-8H-pyrido[2, 3-d]pyrimidin-7-one (20 mg, 15% yield). LCMS (ESI): m/z: [M+H] calculated for $C_{22}H_{24}F_3N_6O$: 445.2; found 445.2; $^1$H NMR (400 MHz, methanol-$d_4$) δ ppm 8.53 (S, 1H) 8.22 (s, 1H) 6.94 (d, J=4 Hz, 2H) 6.80 (s, 1H) 6.55 (s, 1H) 5.59-5.53 (m, 1H) 3.83 (s, 2H) 3.45-3.39 (m, 2H) 2.86-2.78 (m, 2H) 2.41 (s, 3H) 1.60 (d, J=8 Hz, 3H).

Example 10: Synthesis of 2,8-dimethyl-6-(morpolin-4-yl)-4-[[(1R)-1-[3-(trifluoromethyl)phenyl]ethyl]amino]-7H,8H-pyrido[2,3-d]pyrimidin-7-one

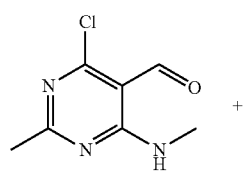 +

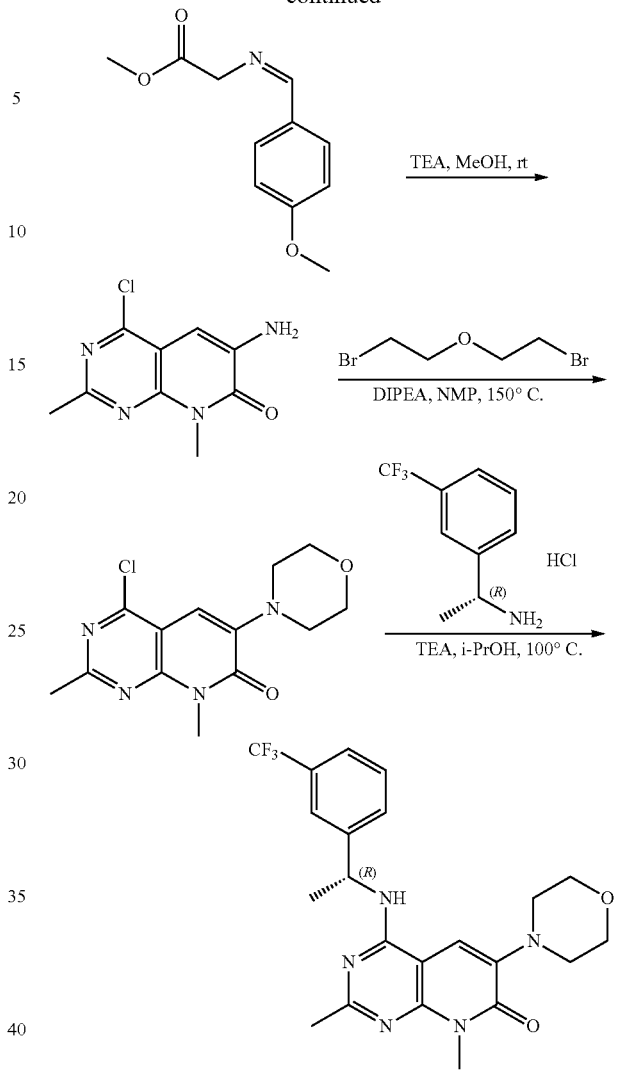

Step 1

To a stirred solution of 2-[(4-methoxyphenyl)methylidene]amino acetate (2.1 g, 10.35 mmol) and triethylamine (2.16 ml, 15.53 mmol) in methanol (43 ml), 4-chloro-2-methyl-6-(methylamino)pyrimidine-5-carbaldehyde (1.9 g, 10.40 mmol) was added and the mixture was stirred for 48 h at room temperature. Acetic acid (2.96 ml, 51.80 mmol) was added and the mixture was stirred for 30 minutes at 50° C. After cooling to room temperature, the solvent was removed under reduced pressure. The residue was diluted with EtOAc, extracted with water, and dried with $Na_2SO_4$. The solvent was removed under reduced pressure and the crude product was purified by flash column chromatography to give 6-amino-4-chloro-2,8-dimethyl-7H,8H-pyrido[2,3-d]pyrimidin-7-one (1.50 g, 65% yield). LCMS (ESI): m/z: [M+H] calculated for $C_9H_{10}ClN_4$: 225.1; found 225.1.

Step 2

To a solution of 6-amino-4-chloro-2,8-dimethyl-7H,8H-pyrido[2,3-d]pyrimidin-7-one (500 mg, 2.23 mmol) in NMP (15.0 ml) was added 2-bromoethyl ether (560 µl, 4.50 mmol) and DIPEA (1.94 ml, 11.13 mmol). The reaction was stirred for 18 h at 150° C. in a sealed tube. After cooling to rt brine was added and the mixture was extracted with EtOAc. The combined organic phases were dried over $Na_2SO_4$ and the solvent was removed under reduced pressure. The resulting residue was purified by flash column chromatography to give 4-chloro-2,8-dimethyl-6-(morpholin-4-yl)-7H,8H-pyrido[2,3-d]pyrimidin-7-one (285 mg, 43% yield). ¹H NMR (300 MHz, DMSO-$d_6$): δ 6.97 (s, 1H), 3.76 (m, 4H), 3.67 (s, 3H), 3.25 (m, 4H), 2.64 (s, 3H).

Step 3

4-chloro-2,8-dimethyl-6-(morpholin-4-yl)-7H,8H-pyrido[2,3-d]pyrimidin-7-one (287 mg, 0.98 mmol) and (1R)-1-[3-(trifluoromethyl)phenyl]ethan-1-amine hydrochloride (220 mg, 0.98 mmol) were suspended in propan-2-ol (11 ml). Triethylamine (408 µl, 2.90 mmol) was added and the mixture was heated to 100° C. for 16 h. After cooling to rt the solvent was removed under reduced pressure. The residue was diluted with EtOAc, washed with water and brine, dried over $Na_2SO_4$ and the solvent was removed under reduced pressure. The resulting residue was purified by preparative HPLC to give 2,8-dimethyl-6-(morpholin-4-yl)-4-{[(1R)-1-[3-(trifluoromethyl)phenyl]ethyl]amino}-7H,8H-pyrido[2,3-d]pyrimidin-7-one (150 mg, 34% yield). LCMS (ESI): m/z: [M+H] calculated for $C_{22}H_{25}F_3N_5O$: 448.2; found 447.9; ¹H NMR (300 MHz, DMSO-$d_6$): δ 8.07 (d, J=7.7 Hz, 1H), 7.79 (s, 1H), 7.74 (d, J=6.4 Hz, 1H), 7.66-7.54 (m, 2H), 7.45 (s, 1H), 5.63 (q, J=7.3 Hz, 1H), 3.77 (t, J=4.6 Hz, 4H), 3.58 (s, 3H), 3.15 (t, J=4.8 Hz, 4H), 2.35 (s, 3H), 1.61 (d, J=7.1 Hz, 3H).

Example 11: Synthesis of 8-cyclopropyl-6-(morpholin-4-yl)-4-{[(1R)-1-[3-(trifluoromethyl)phenyl]ethyl]amino}-7H,8H-pyrido[2,3-d]pyrimidin-7-one

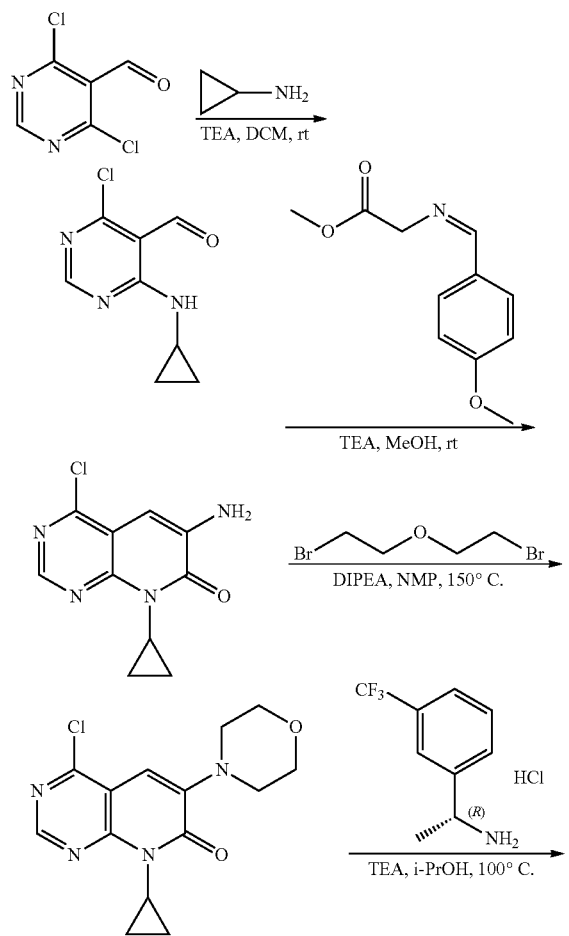

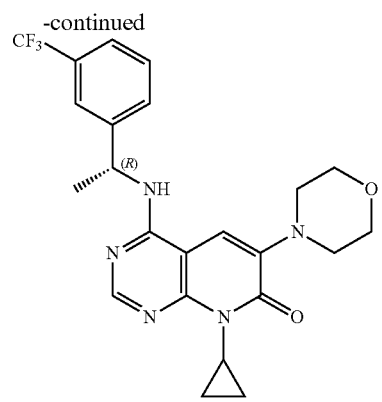

Step 1

To a solution of 4,6-dichloropyrimidine-5-carbaldehyde (3.0 g, 16.95 mmol) in DCM (170 ml) under argon atmosphere, cyclopropylamine (1.29 ml, 18.65 mmol) and triethylamine (3.54 ml, 25.40 mmol) were added. The resulting mixture was stirred for 2 h at room temperature. The reaction mixture was diluted with DCM and washed with water and brine, dried over $Na_2SO_4$ and solvent was removed under reduced pressure to give 4-chloro-6-(cyclopropylamino)pyrimidine-5-carbaldehyde (3.90 g, 100% yield), which was used in the next step without further purification. LCMS (ESI): m/z: [M+H] calculated for $C_8H_9ClN_3O$: 198.1; found 198.1.

Step 2

To a stirred solution of 2-[(Z)-[(4-methoxyphenyl)methylidene]amino]acetate (2.5 g, 12.06 mmol) and triethylamine (2.52 ml, 18.10 mmol) in MeOH (50.0 ml) was added 4-chloro-6-(cyclopropylamino)pyrimidine-5-carbaldehyde (2.4 g, 12.10 mmol). The mixture was stirred for 48 h at room temperature. Acetic acid (3.45 ml, 60.30 mmol) was added and mixture was stirred for 30 minutes at 50° C. After cooling to room temperature, the solvent was removed under reduced pressure. The residue was diluted with EtOAc and washed with water, dried with $Na_2SO_4$ and the solvent was removed under reduced pressure. The crude residue was purified by flash column chromatography to give 6-amino-4-chloro-8-cyclopropyl-7H,8H-pyrido[2,3-d]pyrimidin-7-one (1.44 g, 50% yield). LCMS (ESI): m/z: [M+H] calculated for $C_9H_{10}ClN_4O$: 237.1; found 237.1.

Step 3

To a solution of 6-amino-4-chloro-8-cyclopropyl-7H,8H-pyrido[2,3-d]pyrimidin-7-one (500 mg, 2.11 mmol) in NMP (15.0 ml) was added 2-bromoethyl ether (530 µl, 4.20 mmol) and DIPEA (1.84 ml, 10.56 mmol). The reaction mixture was stirred for 18 h at 150° C. in a sealed tube. After cooling to rt brine was added and the mixture was extracted with EtOAc. The organic phases were dried with $Na_2SO_4$ and the solvent was removed under reduced pressure. The crude residue was purified by flash column chromatography to give 4-chloro-8-cyclopropyl-6-(morpholin-4-yl)-7H,8H-pyrido[2,3-d]pyrimidin-7-one (157 mg, 24% yield). LCMS (ESI): m/z: [M+H] calculated for $C_{14}H_{16}ClN_4O_2$: 307.1; found 306.9.

Step 4

4-chloro-8-cyclopropyl-6-(morpholin-4-yl)-7H,8H-pyrido[2,3-d]pyrimidin-7-one (156 mg, 0.51 mmol), (1R)-

1-[3-(trifluoromethyl)phenyl]ethan-1-amine hydrochloride (115 mg, 0.51 mmol) and triethylamine (213 µl, 1.50 mmol) were dissolved in propan-2-ol (5.8 ml). The mixture was heated to 100° C. for 48 h. After cooling to room temperature, the solvent was removed under reduced pressure. The residue was diluted with EtOAc, washed with water and brine, dried over $Na_2SO_4$, and the solvent was removed under reduced pressure. The crude product was purified by preparative HPLC to give 8-cyclopropyl-6-(morpholin-4-yl)-4-{[(1R)-1-[3-(trifluoromethyl)phenyl]ethyl]amino}-7H,8H-pyrido[2,3-d]pyrimidin-7-one (95 mg, 41% yield). LCMS (ESI): m/z: [M+H] calculated for $C_{23}H_{25}F_3N_5O_2$: 460.2; found 459.9; $^1$H NMR (300 MHz, DMSO-$d_6$): δ 8.25 (s, 1H), 8.07 (d, J=7.6 Hz, 1H), 7.75 (s, 1H), 7.73-7.68 (m, 1H), 7.66-7.54 (m, 2H), 7.39 (s, 1H), 5.59 (q, J=7.1 Hz, 1H), 3.78 (t, J=4.5 Hz, 4H), 3.22-3.07 (m, 4H), 2.96-2.80 (m, 1H), 1.58 (d, 3H), 1.21-1.02 (m, 2H), 0.84-0.50 (m, 2H).

The following examples 11-1 to 11-4 shown in Table 4 were synthesized in the manner similar to Example 11.

TABLE 4

Examples 11-1 to 11-4

| Example # | Structure | Mass Found |
|---|---|---|
| 11-1 | 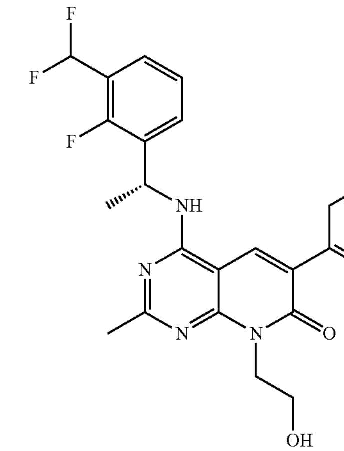 | 475.0 |
| 11-2 | 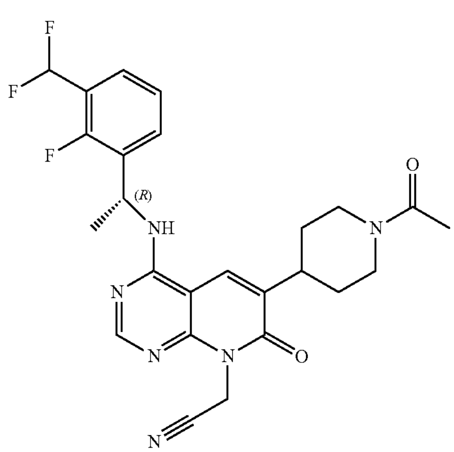 | 498.8 |
| 11-3 | | 504 |
| 11-4 | | 530.1 |

Example 12: Synthesis of 4-{[(1R)-1-[3-amino-5-(trifluoromethyl)phenyl]ethyl]amino}-8-methyl-6-(morpholin-4-yl)-7H,8H-pyrido[2,3-d]pyrimidin-7-one

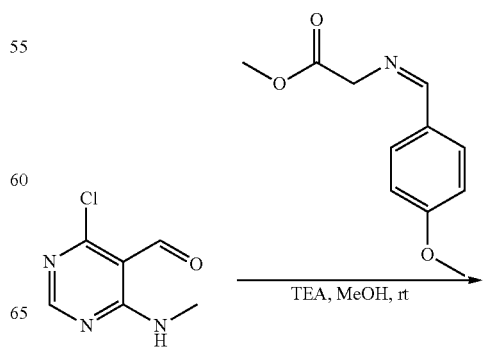

-continued

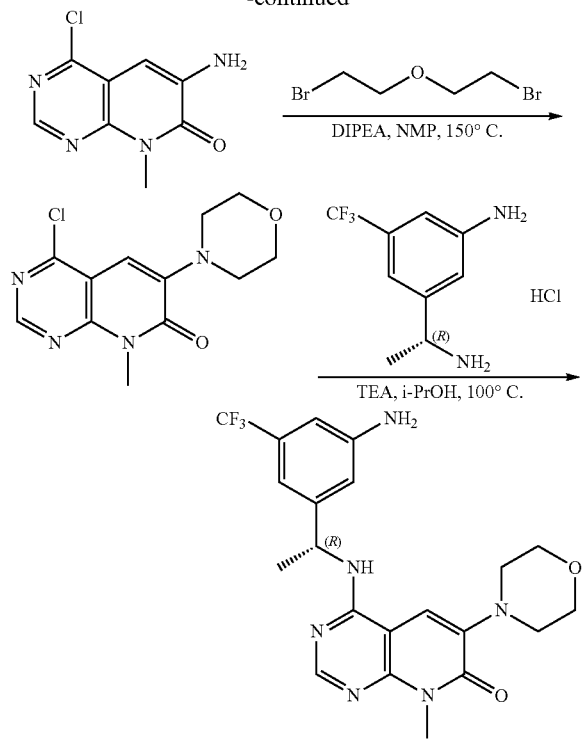

Step 1

Triethylamine (3.02 ml, 21.72 mmol), 2-[(Z)-[(4-methoxyphenyl)methylidene]amino]acetate (3.0 g, 14.48 mmol) and 4-chloro-6-(methylamino)pyrimidine-5-carbaldehyde (2.5 g, 14.50 mmol) were dissolved in MeOH (60 ml). The mixture was stirred for 48 h at room temperature. Acetic acid (4.14 ml, 72.40 mmol) was added and the mixture was stirred for 30 min at 50° C. After cooling to room temperature, the solvent was removed under reduced pressure. The residue was diluted with EtOAc, washed with water and dried with $Na_2SO_4$. The solvent was removed under reduced pressure and the crude product was purified by flash column chromatography to give 6-amino-4-chloro-8-methyl-7H,8H-pyrido[2,3-d]pyrimidin-7-one (1.84 g, 60% yield). $^1$H NMR (300 MHz, DMSO-$d_6$) δ 8.60 (s, 1H), 6.79 (s, 1H), 6.41 (s, 2H), 3.71 (s, 3H).

Step 2

DIPEA (2.48 ml, 14.24 mmol), 2-bromoethyl ether (0.72 ml, 5.70 mmol) and 6-amino-4-chloro-8-methyl-7H,8H-pyrido[2,3-d]pyrimidin-7-one (600 mg, 2.85 mmol) were dissolved in NMP (18.0 ml). The mixture was stirred for 18 h at 150° C. in a sealed tube. After cooling to rt brine was added and the mixture was extracted with EtOAc. The combined organic phases were dried over $Na_2SO_4$ and the solvent was removed under reduced pressure. The crude residue was purified by flash column chromatography to give 4-chloro-8-methyl-6-(morpholin-4-yl)-7H,8H-pyrido[2,3-d]pyrimidin-7-one (356 mg, 45% yield). $^1$H NMR (300 MHz, DMSO-$d_6$) δ 8.77 (s, 1H), 6.99 (s, 1H), 3.77-3.75 (m, 4H), 3.69 (s, 3H), 3.31-3.20 (m, 4H).

Step 3

4-Chloro-8-methyl-6-(morpholin-4-yl)-7H,8H-pyrido[2,3-d]pyrimidin-7-one (350 mg, 1.25 mmol), 3-[(1R)-1-aminoethyl]-5-(trifluoromethyl)aniline hydrochloride (300 mg, 1.25 mmol) and triethylamine (521 μl, 3.74 mmol) were dissolved in propan-2-ol (15 ml). The mixture was heated to 100° C. for 16 h. After cooling to room temperature the solvent was removed under reduced pressure. The residue was diluted with EtOAc, washed with water and brine and dried over $Na_2SO_4$. The solvent was removed under reduced pressure and the resulting residue was purified by preparative HPLC to give 4-{[(1R)-1-[3-amino-5-(trifluoromethyl)phenyl]ethyl]amino}-8-methyl-6-(morpholin-4-yl)-7H,8H-pyrido[2,3-d]pyrimidin-7-one (74 mg, 54% yield). LCMS (ESI): m/z: [M+H] calculated for $C_{21}H_{24}F_3N_6O_2$: 449.2; found 449.1; $^1$H NMR (300 MHz, DMSO-$d_6$): δ 8.27 (s, 1H), 8.09 (d, J=7.7 Hz, 1H), 7.48 (s, 1H), 6.83-6.78 (m, 2H), 6.72-6.67 (m, 1H), 5.60-5.52 (m, 2H), 5.46 (q, J=7.1 Hz, 1H), 3.78 (t, J=4.6 Hz, 4H), 3.61 (s, 3H), 3.22-3.12 (m, 4H), 1.54 (d, J=7.1 Hz, 3H).

Example 13: Synthesis of 8-methyl-6-(morpholin-4-yl)-4-{[(1R)-1-[3-(trifluoromethyl)phenyl]-ethyl]amino}-7H,8H-pyrido[2,3-d]pyrimidin-7-one

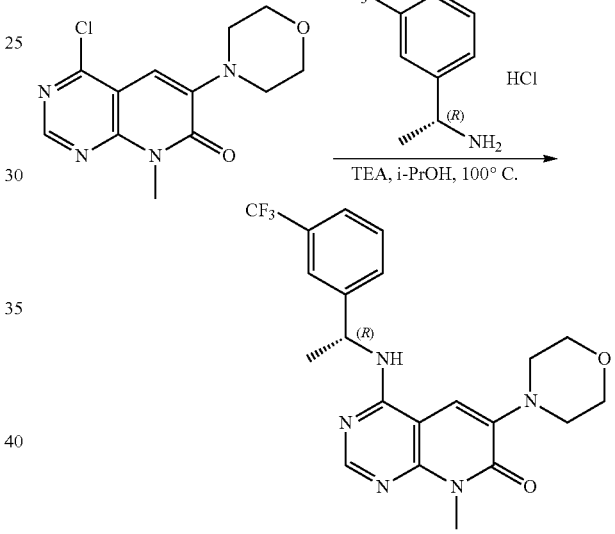

Step 1

4-Chloro-8-methyl-6-(morpholin-4-yl)-7H,8H-pyrido[2,3-d]pyrimidin-7-one (187 mg, 0.66 mmol), triethylamine (278 μl, 1.99 mmol) and (1R)-1-[3-(trifluoromethyl)phenyl]ethan-1-amine hydrochloride (150 mg, 0.66 mmol) were suspended in propan-2-ol (7.5 ml). The mixture was heated to 100° C. for 16 h. After cooling to room temperature the solvent was removed under reduced pressure. The residue was diluted with EtOAc, washed with water and brine, dried over $Na_2SO_4$ and the solvent was removed under reduced pressure. The resulting residue was purified by preparative HPLC to give 8-methyl-6-(morpholin-4-yl)-4-{[(1R)-1-[3-(trifluoromethyl)phenyl]-ethyl]amino}-7H,8H-pyrido[2,3-d]pyrimidin-7-one (46 mg, 16% yield). LCMS (ESI): m/z: [M+H] calculated for $C_{21}H_{23}F_3N_5O_2$: 434.2; found 433.7; $^1$H NMR (300 MHz, DMSO-$d_6$): δ 8.26 (s, 1H), 8.17 (d, J=7.6 Hz, 1H), 7.76 (s, 1H), 7.72 (d, J=7.4 Hz, 1H), 7.64-7.55 (m, 2H), 7.48 (s, 1H), 5.61 (q, J=7.2 Hz, 1H), 3.78 (t, J=4.6 Hz, 4H), 3.61 (s, 3H), 3.19 (t, J=4.7 Hz, 4H), 1.61 (d, J=7.1 Hz, 3H).

Example 14: Synthesis of 4-{[(1R)-1-[3-(difluoromethyl)-2-fluorophenyl]ethyl]amino}-6-(1-methanesulfonyl-3-methylazetidin-3-yl)-8-methyl-7H,8H-pyrido[2,3-d]pyrimidin-7-one

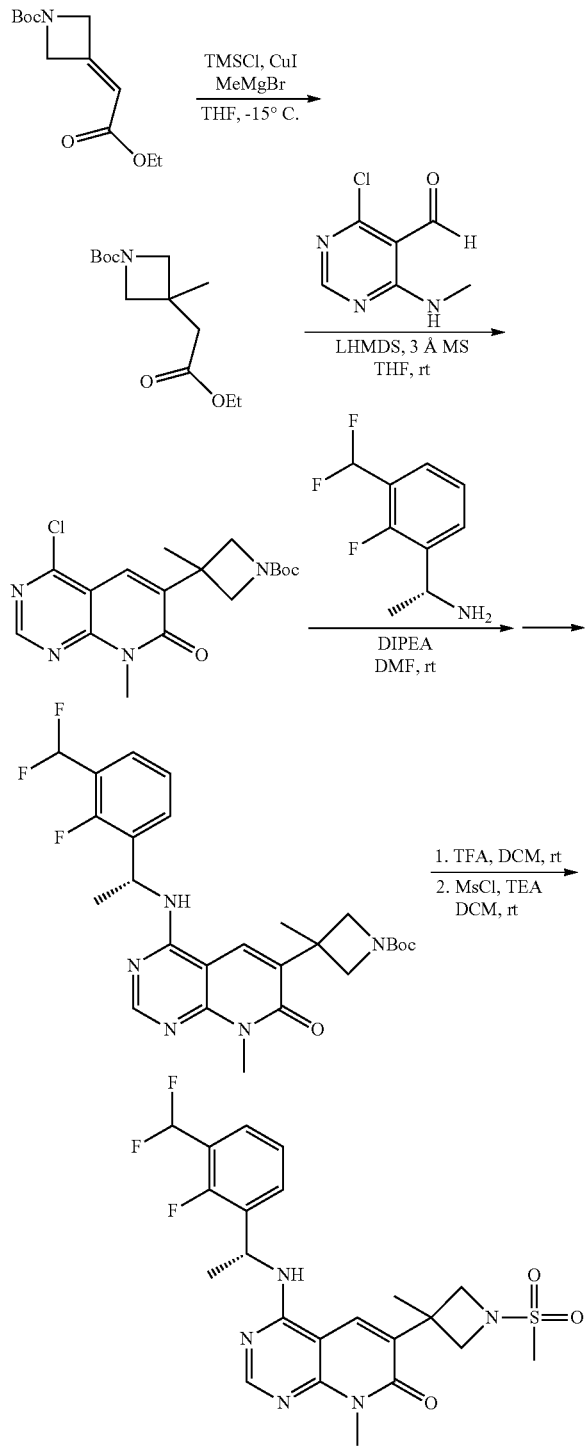

Step 1

To a solution of tert-butyl 3-(2-ethoxy-2-oxoethylidene)azetidine-1-carboxylate (1 g, 4.14 mmol) and copper (I) iodide (78.8 mg, 414 μmol) in 5 mL THF, under an atmosphere of $N_2$, was added chlorotrimethylsilane (8.28 mL, 8.28 mmol). After stirring for 10 min at rt, the mixture was cooled to −15° C., then a solution of methyl magnesium bromide (2.89 mL, 8.69 mmol) was added dropwise over 30 min. The resulting solution was stirred at rt for another 2 h and then quenched with saturated aqueous $NH_4Cl$ solution. The mixture was diluted with MTBE. The organic layer was separated, and the aqueous layer was extracted with MTBE. The combined organic layers were washed with brine and dried over anhydrous $Na_2SO_4$. The solvent was removed under reduced pressure and the crude residue was purified by column chromatography to give tert-butyl 3-(2-ethoxy-2-oxoethyl)-3-methylazetidine-1-carboxylate (782.3 mg, 73.7%). LCMS (ESI) m/z: [M+H] calculated for $C_{13}H_{23}NO_4$: 257.2; found 257.4.

Step 2 tert-Butyl 3-(2-ethoxy-2-oxoethyl)-3-methylazetidine-1-carboxylate (500 mg, 1.94 mmol), LHMDS (324 mg, 1.94 mmol) and 3 Å mol sieves were added to THF and stirred for 10 min. 4-chloro-6-(methylamino)pyrimidine-5-carbaldehyde (221 mg, 1.29 mmol) was dissolved in a minimal amount of DMF and added dropwise. The reaction was stirred at rt for 3 h. The reaction was quenched with $NH_4Cl$ and extracted with MTBE. The organic layers were combined and washed with water and brine and then dried over $Na_2SO_4$. The solvent was removed under reduced pressure and the crude residue was purified by column chromatography to give tert-butyl 3-(4-chloro-8-methyl-7-oxo-7,8-dihydropyrido[2,3-d]pyrimidin-6-yl)-3-methylazetidine-1-carboxylate (76.8 mg, 16%). LCMS (ESI) m/z: [M+H] calculated for $C_{17}H_{21}ClN_4O_3$: 364.1; found 364.4.

Step 3

(1R)-1-[3-(difluoromethyl)-2-fluorophenyl]ethan-1-amine (59.5 mg, 315 μmol) and tert-butyl 3-{4-chloro-8-methyl-7-oxo-7H,8H-pyrido[2,3-d]pyrimidin-6-yl}-3-methylazetidine-1-carboxylate (76.8 mg, 210 μmol) were suspended in DMF (3 mL). DIPEA (109 μL, 630 μmol) was added. The reaction was stirred at rt overnight. The reaction mixture was diluted with $H_2O$ and washed with EtOAc. The organic layers were combined and washed with water and brine, and the solvent was removed under reduced pressure. The crude material was purified by column chromatography to give tert-butyl (R)-3-(4-((1-(3-(difluoromethyl)-2-fluorophenyl)ethyl)amino)-8-methyl-7-oxo-7,8-dihydropyrido[2,3-d]pyrimidin-6-yl)-3-methylazetidine-1-carboxylate (20.8 mg, 19%). LCMS (ESI) m/z: [M+H] calculated for $C_{26}H_{30}F_3N_5O_3$: 518.2; found 518.6.

Step 4 tert-Butyl 3-(4-{[(1R)-1-[3-(difluoromethyl)-2-fluorophenyl]ethyl]amino}-8-methyl-7-oxo-7H,8H-pyrido[2,3-d]pyrimidin-6-yl)-3-methylazetidine-1-carboxylate (20.8 mg, 40.1 μmol) was dissolved in DCM (3 mL) followed by the addition of TFA (15.3 μL, 200 μmol), the reaction was stirred overnight at rt. The solvent was removed under reduced pressure and the crude product was used without further purification. LCMS (ESI) m/z: [M+H] calculated for $C_{21}H_{22}F_3N_5O$: 417.2; found 418.5.

Step 5

4-{[(1R)-1-[3-(difluoromethyl)-2-fluorophenyl]ethyl]amino}-8-methyl-6-(3-methylazetidin-3-yl)-7H,8H-pyrido[2,3-d]pyrimidin-7-one; trifluoroacetic acid (21.3 mg, 40.0 μmol) was dissolved in DCM (2 mL) followed by the addition of TEA (16.6 μL, 120 μmol) and mesyl chloride (3.70 μL, 48.0 μmol). The reaction was stirred at rt for 4 h. The mixture was washed with water and brine, then dried over $Na_2SO_4$ and the solvent was removed under reduced pressure. The crude residue was purified by prep-HPLC to give 4-{[(1R)-1-[3-(difluoromethyl)-2-fluorophenyl]ethyl]amino}-6-(1-methanesulfonyl-3-methylazetidin-3-yl)-8-methyl-7H,8H-pyrido[2,3-d]pyrimidin-7-one (6.90 mg, 34.8%). LCMS (ESI) m/z: [M+H] calculated for $C_{22}H_{24}F_3N_5O_3S$: 496.2; found 496.5. $^1$H NMR (500 MHz, Chloroform-d) δ 8.47 (s, 1H), 7.55 (q, J=6.9 Hz, 2H), 7.25 (t, J=7.7 Hz, 1H), 5.78 (p, J=7.0 Hz, 1H), 5.67 (t, J=7.5 Hz, 1H), 4.32 (t, J=7.7 Hz, 2H), 3.96-3.91 (m, 2H), 3.74 (s, 3H), 2.93 (s, 3H), 1.77 (s, 3H), 1.73 (d, J=6.9 Hz, 3H).

Example 15: Synthesis of 6-(1-acetyl-4-piperidyl)-4-[[(1R)-1-[3-amino-2-fluoro-5-(trifluoromethyl)phenyl]ethyl]amino]-8-methyl-pyrido[2,3-d]pyrimidin-7-one

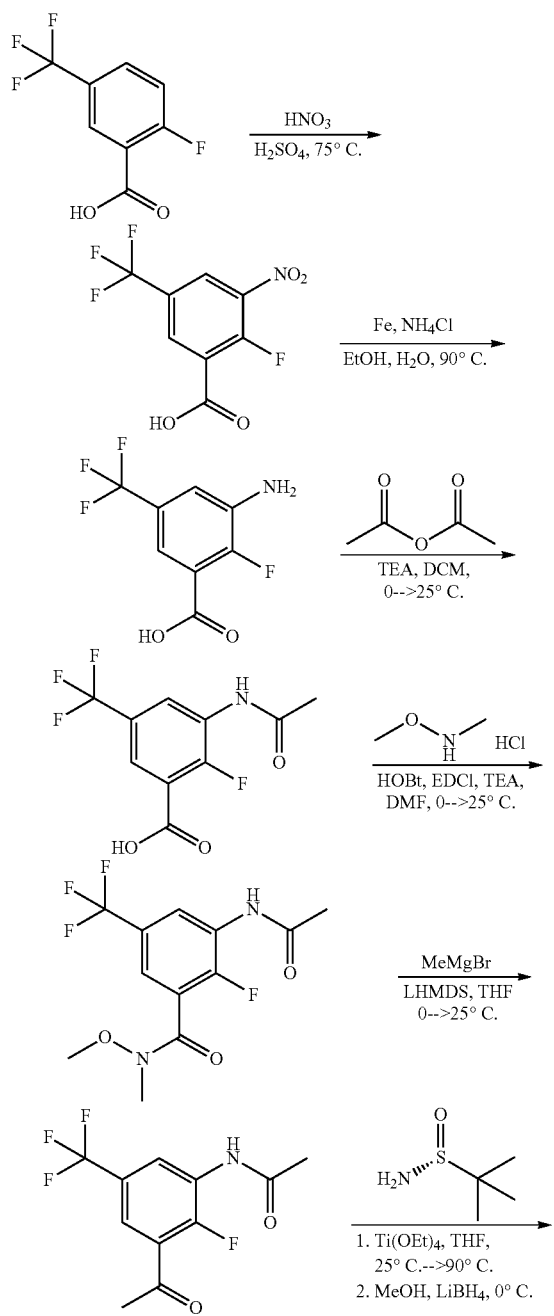

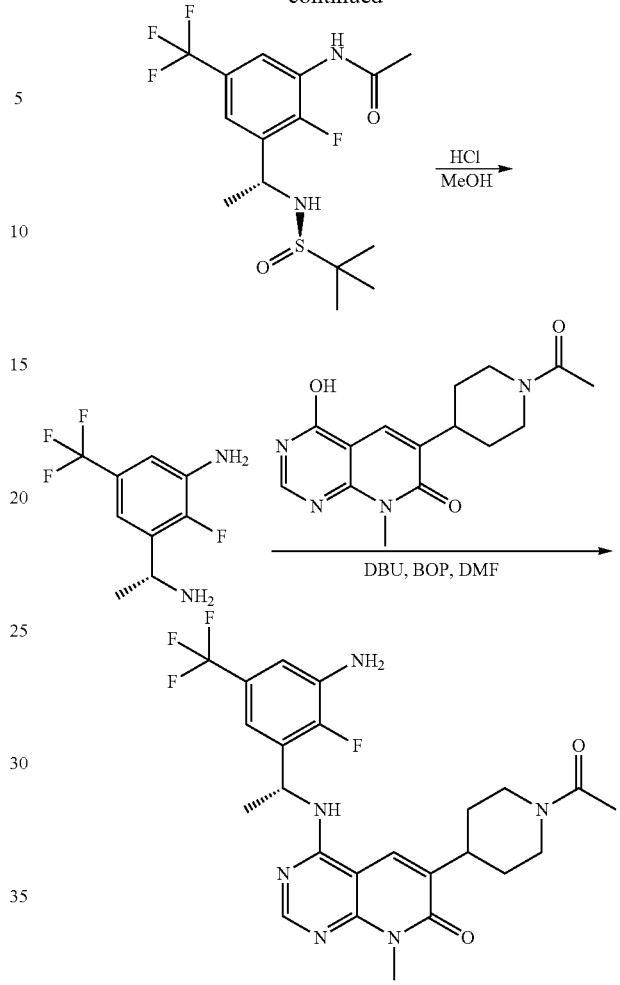

Step 1

To a mixture of 2-fluoro-5-(trifluoromethyl) benzoic acid (2 g, 9.61 mmol) and $HNO_3$ (10 mL) was added $H_2SO_4$ (2.5 mL) at 25° C. The mixture was stirred at 75° C. for 1 h and then added to ice water and stirred for 10 min. EtOAc was added and the pH was adjusted to 2-3 by adding $NaHCO_3$. The aqueous layer was extracted with EtOAc. The combined organic layers were washed with brine, dried with anhydrous $Na_2SO_4$, and the solvent was removed under reduced pressure to give 2-fluoro-3-nitro-5-(trifluoromethyl)benzoic acid (2.3 g, 94.56% yield). $^1$H NMR (DMSO-d$_6$, 400 MHz) δ ppm 14.28 (s, 1H), 8.71 (dd, J=5.8, 2.2 Hz, 1H), 8.46 (dd, J=5.4, 2.2 Hz, 1H).

Step 2

To a solution of 2-fluoro-3-nitro-5-(trifluoromethyl)benzoic acid (2 g, 7.90 mmol) in EtOH (9.6 mL) and $H_2O$ (4.8 mL) was added iron powder (1.32 g, 23.71 mmol) and $NH_4Cl$ (211.34 mg, 3.95 mmol). The mixture was stirred at 90° C. for 1 h and then poured into ice water. After filtration the filtrate was extracted with EtOAc, washed with brine, dried with anhydrous $Na_2SO_4$, and the solvent was removed under reduced pressure to give 3-amino-2-fluoro-5-(trifluoromethyl)benzoic acid (2 g, crude). The material was used without further purification. LCMS (ESI): m/z: [M+H] calculated for $C_8H_5F_4NO_2$: 224.0; found 224.1.

Step 3

To a solution of 3-amino-2-fluoro-5-(trifluoromethyl)benzoic acid (1.76 g, 7.89 mmol) in DCM (20 mL) at 0° C. was added TEA (1.10 mL, 7.89 mmol) and acetyl acetate (2.59 mL, 27.61 mmol). The reaction mixture was warmed to 25° C. and stirred for 3 h. The reaction was diluted with water, extracted with EtOAc, washed with brine, dried with anhydrous Na$_2$SO$_4$, and the solvent was removed under reduced pressure to give 3-acetamido-2-fluoro-5-(trifluoromethyl) benzoic acid (2.2 g, crude). LCMS (ESI): m/z: [M+H] calculated for C$_{10}$H$_7$F$_4$NO$_3$: 266.0; found 266.1.

Step 4

To a solution of 3-acetamido-2-fluoro-5-(trifluoromethyl) benzoic acid (1.2 g, 4.53 mmol) in DMF (10 mL) at 0° C. were added N-methoxymethanamine hydrochloride (485.58 mg, 4.98 mmol), HOBt (733.81 mg, 5.43 mmol), EDCI (1.04 g, 5.43 mmol) and TEA (1.89 mL, 13.58 mmol). The mixture was warmed to 25° C. and stirred for 2 h. The reaction mixture was diluted with ice water and filtered. The filtrate was extracted with EtOAc, dried with anhydrous Na$_2$SO$_4$, and the solvent was removed under reduced pressure. The residue was purified by column chromatography to give 3-acetamido-2-fluoro-N-methoxy-N-methyl-5-(trifluoromethyl)benzamide (785 mg, 56.28% yield). $^1$H NMR (methanol-d$_4$, 400 MHz) δ ppm=8.55 (d, J=5.6 Hz, 1H), 7.53 (d, J=3.6 Hz, 1H), 3.56 (s, 3H), 3.37 (s, 3H), 2.21 (s, 3H).

Step 5

To a solution of 3-acetamido-2-fluoro-N-methoxy-N-methyl-5-(trifluoromethyl)benzamide (785 mg, 2.55 mmol) in THF (8 mL) at 0° C. was added LHMDS (1M in THF, 2.55 mL, 2.55 mmol). The reaction mixture was stirred at 0° C. for 30 min, and then 3M MeMgBr in THF (2.55 mL, 7.65 mmol) was added. The reaction mixture was warmed to 25° C. and stirred for 30 min. The reaction was quenched with H$_2$O, extracted with EtOAc, washed with brine, dried over Na$_2$SO$_4$, and the solvent was removed under reduced pressure. The residue was purified by column chromatography to give N-[3-acetyl-2-fluoro-5-(trifluoromethyl)phenyl]acetamide (510 mg, 76.09% yield). $^1$H NMR (methanol-d$_4$, 400 MHz) δ ppm=8.62 (dd, J=6.4, 2.0 Hz, 1H), 7.84 (dd, J=6.0, 2.0 Hz, 1H), 2.66 (d, J=4.4 Hz, 3H), 2.23 (s, 3H).

Step 6

To a solution of N-[3-acetyl-2-fluoro-5-(trifluoromethyl)phenyl]acetamide (510 mg, 1.94 mmol) and (R)-2-methylpropane-2-sulfinamide (281.83 mg, 2.33 mmol) in THF (6 mL) was added Ti(OEt)$_4$ (1.21 mL, 5.81 mmol). The mixture was stirred at 90° C. for 3 h. The reaction was cooled to 0° C. and then MeOH (78.42 μL, 1.94 mmol) and LiBH$_4$ (42.21 mg, 1.94 mmol) were added to the solution. The reaction stirred at 0° C. for 1 h and then diluted with ice water and filtered. The filtrate was extracted with EtOAc, dried over Na$_2$SO$_4$ and the solvent was removed under reduced pressure. The residue was purified by column chromatography to give N-[3-[(1R)-1-[[(R)-tert-butylsulfinyl]amino]ethyl]-2-fluoro-5-(trifluoromethyl) phenyl]acetamide (150 mg, 20.17% yield). LCMS (ESI): m/z: [M+H] calculated for C$_{15}$H$_{21}$F$_4$N$_2$O$_2$S: 369.1; found 369.1. $^1$H NMR (methanol-d$_4$, 400 MHz) δ ppm=8.29-8.38 (m, 1H), 7.62 (d, J=4.4 Hz, 1H), 4.2 (m, 1H), 2.20 (s, 3H), 1.53 (d, J=6.8 Hz, 3H), 1.23 (s, 9H).

Step 7

To a solution of N-[3-[(1R)-1-[[(R)-tert-butylsulfinyl]amino]ethyl]-2-fluoro-5-(trifluoromethyl) phenyl]acetamide (150 mg, 407 μmol) in MeOH (2 mL) was added 4M HCl in MeOH (1.63 mL, 6.52 mmol). The solution was stirred at 25° C. for 2 h. The pH was then adjusted to ~8 using a NaOH/MeOH solution and the mixture was filtered. The solvent was removed under reduced pressure and the residue was washed with DCM/MeOH (10:1), filtered, and the solvent was removed under reduced pressure to give 3-[(1R)-1-aminoethyl]-2-fluoro-5-(trifluoromethyl)aniline (110 mg, crude). LCMS (ESI): m/z: [M+H] calculated for C$_9$H$_{11}$F$_4$N$_2$: 223.1; found 223.0.

Step 8

To a solution of 3-[(1R)-1-aminoethyl]-2-fluoro-5-(trifluoromethyl)aniline (110 mg, 495.09 μmol) in DMF (1.5 mL) was added 6-(1-acetyl-4-piperidyl)-4-hydroxy-8-methyl-pyrido[2,3-d]pyrimidin-7-one (149.68 mg, 495.09 μmol), BOP (350.35 mg, 792.14 μmol), and DBU (223.87 μL, 1.49 mmol). Then the mixture was stirred at 25° C. for 3 h. The reaction was diluted with sat. NaHCO$_3$, extracted with EtOAc, washed with brine, dried over anhydrous Na$_2$SO$_4$, filtered, and the solvent was removed under reduced pressure. The residue was purified by prep-HPLC to give 6-(1-acetyl-4-piperidyl)-4-[[(1R)-1-[3-amino-2-fluoro-5-(trifluoromethyl)phenyl]ethyl]amino]-8-methyl-pyrido[2,3-d]pyrimidin-7-one (24.5 mg, 9.47% yield). LCMS (ESI): m/z: [M+H] calculated for C$_{24}$H$_{27}$F$_4$N$_6$O$_2$: 507.2; found 507.3. $^1$H NMR (methanol-d$_4$, 400 MHz) δ ppm=8.33 (s, 1H), 8.16 (s, 1H), 6.98 (dd, J=7.6, 2.0 Hz, 1H), 6.90 (d, J=5.6 Hz, 1H), 5.71-5.80 (m, 1H), 4.67-4.78 (m, 1H), 4.07 (d, J=13.2 Hz, 1H), 3.72 (s, 3H), 3.13-3.28 (m, 2H), 2.67-2.83 (m, 1H), 2.15 (s, 3H), 1.92-2.06 (m, 1H), 1.90-1.96 (m, 1H), 1.60-1.70 (m, 5H).

Example 16: Synthesis of 4-[[(1R)-1-[3-(difluoromethyl)-2-fluoro-phenyl]ethyl]amino]-2,8-dimethyl-6-(oxetan-3-yl)pyrido[2,3-d]pyrimidin-7-one

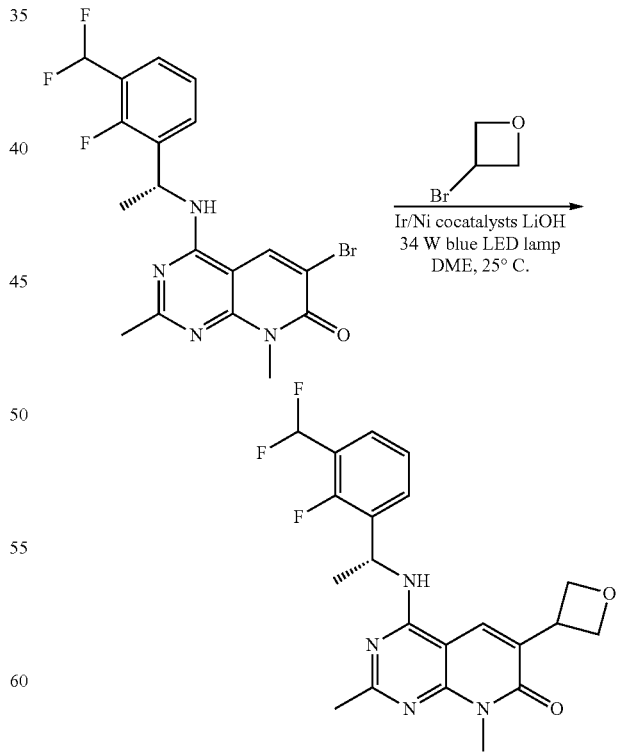

Step 1

To a solution of (Ir(dF(CF$_3$)ppy)$_2$(dtbbpy))PF$_6$ (1.27 mg, 1.13 μmol), 6-bromo-4-[[(1R)-1-[3-(difluoromethyl)-2- fluoro-phenyl]ethyl]amino]-2,8-dimethyl-pyrido[2,3-d]pyrimidin-7-one (50 mg, 113.32 µmol), 3-bromooxetane (23.28 mg, 169.97 µmol), 4-tert-butyl-2-(4-tert-butyl-2-pyridyl)pyridine (304.14 ug, 1.13 µmol) and bis(trimethylsilyl)silyl-trimethyl-silane (34.96 µL, 113.32 µmol) in DME (2 mL) was added lithium hydroxide (5.43 mg, 226.63 µmol) and dichloronickel 1,2-dimethoxyethane (248.98 µg, 1.13 µmol). The solution was degassed by sparging with nitrogen for 10 min. The reaction was stirred and irradiated with a 34 W blue LED lamp for 16 h. The solvent was removed under reduced pressure concentrated and purified by prep-HPLC to give 4-[[(1R)-1-[3-(difluoromethyl)-2-fluoro-phenyl]ethyl]amino]-2,8-dimethyl-6-(oxetan-3-yl)pyrido[2,3-d]pyrimidin-7-one (2 mg, 4.08% yield). LCMS (ESI): m/z: [M+H] calculated for $C_{21}H_{22}F_3N_4O_2$: 419.16; found 419.2. $^1$H NMR (400 MHz, methanol-d4) δ ppm 8.32 (s, 1H) 7.59 (t, J=8.0 Hz, 1H) 7.47 (t, J=6.0 Hz, 1H) 7.23 (t, J=6.0 Hz, 1H) 7.02 (t, J=54 Hz, 1H) 5.83-5.77 (m, 1H) 5.08-5.04 (m, 2H) 4.88 (d, J=8 Hz, 2H) 4.47-4.39 (m, 1H) 3.68 (s, 3H) 2.40 (s, 3H) 1.66 (d, J=8.0 Hz 3H).

Example 17: Synthesis of 6-(1-acetyl-4-piperidyl)-4-[[(1R)-1-[4-amino-6-(trifluoromethyl)-2-pyridyl]ethyl]amino]-8-methyl-pyrido[2,3-d]pyrimidin-7-one

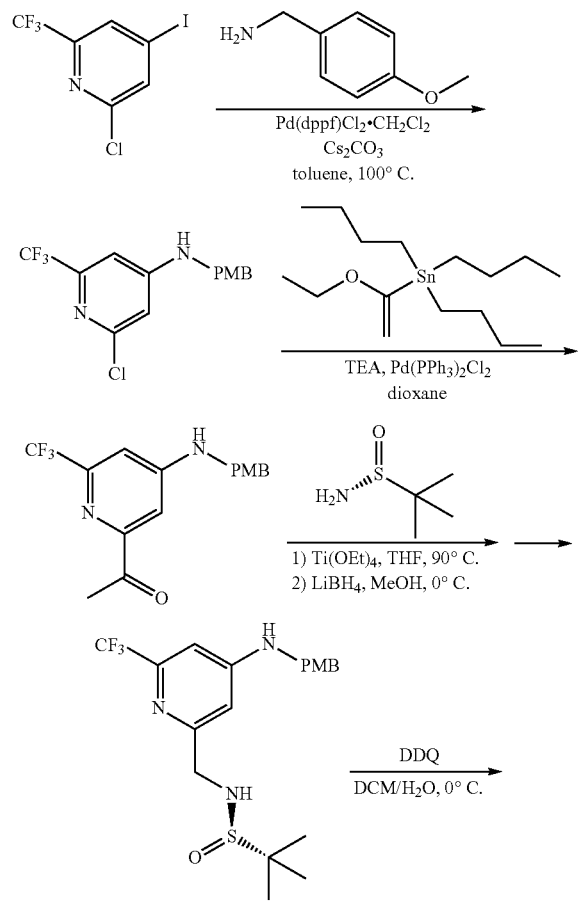

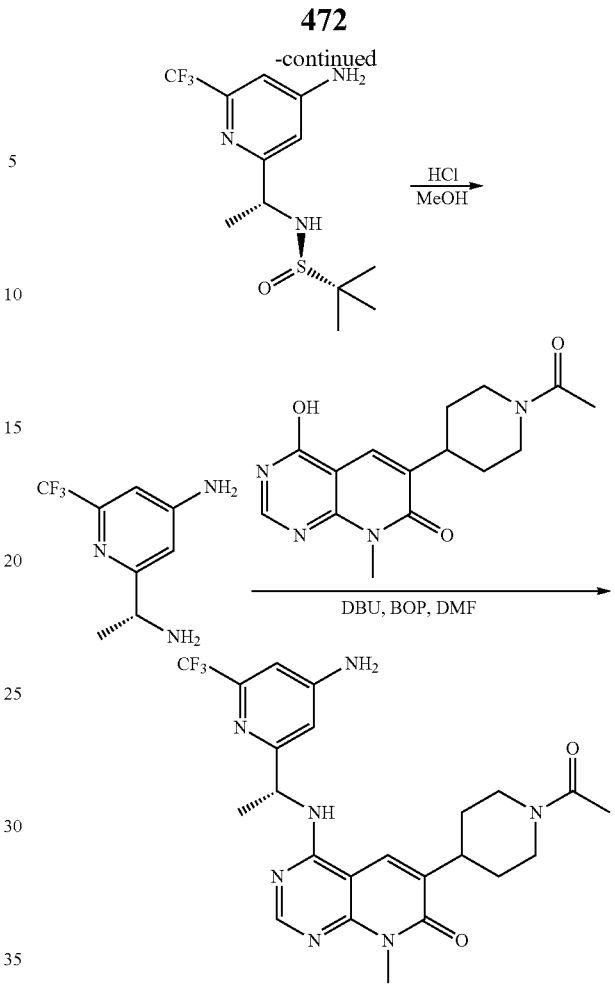

Step 1

To a solution of 2-chloro-4-iodo-6-(trifluoromethyl)pyridine (2 g, 6.51 mmol) and (4-methoxyphenyl)methanamine (841.89 µL, 6.51 mmol) in toluene (10 mL) was added $Cs_2CO_3$ (4.24 g, 13.01 mmol) and Pd(dppf)Cl$_2$.DCM (265.63 mg, 325.27 µmol). The mixture was stirred under nitrogen at 100° C. for 3 h. The reaction mixture was diluted with water, extracted with EtOAc, washed with brine, dried with Na$_2$SO$_4$, and the solvent was removed under reduced pressure. The residue was purified by column chromatography to give 2-chloro-N-[(4-methoxyphenyl)methyl]-6-(trifluoromethyl)pyridin-4-amine (1.7 g, 82.51% yield). LCMS (ESI): m/z: [M+H] calculated for $C_{14}H_{13}ClF_3N_2O$: 317.1; found 317.1. $^1$H NMR (400 MHz, methanol-d$_4$) δ ppm 7.26 (d, J=8.60 Hz, 2H) 6.93-6.88 (m, 3H) 6.65 (s, 1H) 4.32 (s, 2H) 3.78 (s, 3H).

Step 2

To a solution of 2-chloro-N-[(4-methoxyphenyl)methyl]-6-(trifluoromethyl)pyridin-4-amine (1.1 g, 3.47 mmol) and tributyl(1-ethoxyvinyl)stannane (5.28 mL, 15.63 mmol) in dioxane (10 mL) was added TEA (2.42 mL, 17.37 mmol) and Pd(PPh$_3$)$_2$Cl$_2$ (487.58 mg, 694.65 µmol). The mixture was stirred under nitrogen at 100° C. for 18 h. The reaction was diluted with 1 M HCl (10 mL) and stirred for 16 h. The mixture was filtered, and the filtrate was extracted with EtOAc. The combined organic layers were washed with aq. KF and stirred for 20 min. The mixture was filtered. The organic layer was washed with brine, dried with anhydrous Na$_2$SO$_4$, filtered, and the solvent was removed under reduced pressure. The crude product was purified by column chromatography to give 1-[4-[(4-methoxyphenyl) methyl-amino]-6-(trifluoromethyl)-2-pyridyl] ethanone (980 mg, 87.02% yield). $^1$H NMR (400 MHz, methanol-d$_4$) δ ppm 7.30-7.24 (m, 3H) 7.02 (d, J=0.88 Hz, 1H) 6.91-6.87 (m, 2H) 4.36 (d, J=5.51 Hz, 2H) 3.77 (s, 3H) 2.59 (s, 3H).

Step 3

To a solution of 1-[4-[(4-methoxyphenyl)methylamino]-6-(trifluoromethyl)-2-pyridyl]ethanone (980 mg, 3.02 mmol), 2-methylpropane-2-sulfinamide (476.14 mg, 3.93 mmol) in THF (2 mL) was added tetraethoxytitanium (3.13 mL, 15.11 mmol). The reaction mixture was stirred at 90° C. for 16 h. Then LiBH$_4$ (78.98 mg, 3.63 mmol) and MeOH (122.28 μL, 3.02 mmol) were added to the mixture at 0° C. and the reaction was stirred at 0° C. for 30 min. The reaction mixture was diluted with water, extracted with EtOAc, washed with brine, dried with anhydrous Na$_2$SO$_4$, filtered, and the solvent was removed under reduced pressure. The residue was purified by column chromatography give (R)—N-[(1R)-1-[4-[(4-methoxyphenyl)methylamino]-6-(trifluoromethyl)-2-pyridyl]ethyl]-2-methyl-propane-2-sulfinamide (800 mg, 59.79% yield). LCMS (ESI): m/z: [M+H] calculated for C$_{20}$H$_{27}$F$_3$N$_3$O$_2$S: 430.2; found 430.1; $^1$H NMR (400 MHz, methanol-d$_4$) δ ppm 7.29 (d, J=8.50 Hz, 2H) 6.92 (d, J=8.63 Hz, 2H) 6.82 (d, J=11.26 Hz, 2H) 4.44-4.40 (m, 1H) 4.37 (s, 2H) 3.79 (s, 3H) 1.46 (d, J=6.88 Hz, 3H) 1.24 (s, 9H).

Step 4

To a solution of (R)—N-[(1R)-1-[4-[(4-methoxyphenyl) methylamino]-6-(trifluoromethyl)-2-pyridyl]ethyl]-2-methyl-propane-2-sulfinamide (200 mg, 465.66 μmol) in DCM (5 mL) and H$_2$O (0.25 mL) at 0° C. was added DDQ (158.56 mg, 698.49 μmol). The mixture was warmed to 25° C. and stirred for 3 h. The reaction mixture was diluted with water, extracted with EtOAc, washed with brine, dried with anhydrous Na$_2$SO$_4$, and the solvent was removed under reduced pressure. The residue was purified by prep-TLC to give (R)—N-[(1R)-1-[4-amino-6-(trifluoromethyl)-2-pyridyl]ethyl]-2-methyl-propane-2-sulfinamide (60 mg, 41.65% yield). LCMS (ESI): m/z: [M+H] calculated for C$_{12}$H$_{19}$F$_3$N$_3$OS: 310.1; found 310.1.

Step 5

(R)—N-[(1R)-1-[4-amino-6-(trifluoromethyl)-2-pyridyl] ethyl]-2-methyl-propane-2-sulfinamide (60 mg, 193.95 μmol) was added to 4M HCl in MeOH and stirred for 1 h. The mixture was neutralized with aq. NaOH. The solvent was removed under reduced pressure. The residue was dissolved in DCM, filtered and concentrated under reduced pressure to give 2-[(1R)-1-aminoethyl]-6-(trifluoromethyl) pyridin-4-amine (39 mg, crude). LCMS (ESI): m/z: [M+H] calculated for C$_8$H$_{11}$F$_3$N$_3$:206.1; found 206.1.

Step 6

To a solution of 2-[(1R)-1-aminoethyl]-6-(trifluoromethyl)pyridin-4-amine (39.8 mg, 193.98 μmol) and 6-(1-acetyl-4-piperidyl)-4-hydroxy-8-methyl-pyrido[2,3-d]pyrimidin-7-one (64.51 mg, 213.37 μmol) in DMF (1 mL) was added BOP (137.22 mg, 310.36 μmol) and DBU (87.71 μL, 581.93 μmol). The mixture was stirred for 16 h. The mixture was diluted with sat. NaHCO$_3$ and water, extracted with EtOAc, washed with brine, dried with anhydrous Na$_2$SO$_4$, and the solvent was removed under reduced pressure. The residue was purified by prep-HPLC to give 6-(1-acetyl-4-piperidyl)-4-[[(1R)-1-[4-amino-6-(trifluoromethyl)-2-pyridyl]ethyl]amino]-8-methyl-pyrido[2,3-d]pyrimidin-7-one (20 mg, 20.85% yield). LCMS (ESI): m/z: [M+H] calculated for C$_{23}$H$_{27}$F$_3$N$_7$2: 490.2; found 490.3. $^1$H NMR (400 MHz, methanol-d$_4$) δ ppm 8.32 (s, 1H) 8.12 (d, J=1.2 Hz, 1H) 6.78 (s, 1H) 6.69 (t, J=2.21 Hz, 1H) 5.39-5.36 (m, 1H) 4.76-4.67 (m, 1H) 4.10-4.03 (m, 1H) 3.71 (s, 3H) 3.29-3.26 (m, 1H) 3.25-3.14 (m, 1H) 2.80-2.71 (m, 1H) 2.14 (s, 3H) 2.06-1.90 (m, 2H) 1.68-1.61 (m, 1H) 1.59 (d, J=7.06 Hz, 3H).

Example 18: Synthesis of 4-[[(1R)-1-[3-(difluoromethyl)-2-fluoro-phenyl]ethyl]amino]-6-(3-fluoro-1-methyl-4-piperidyl)-2,8-dimethyl-pyrido[2,3-d]pyrimidin-7-one

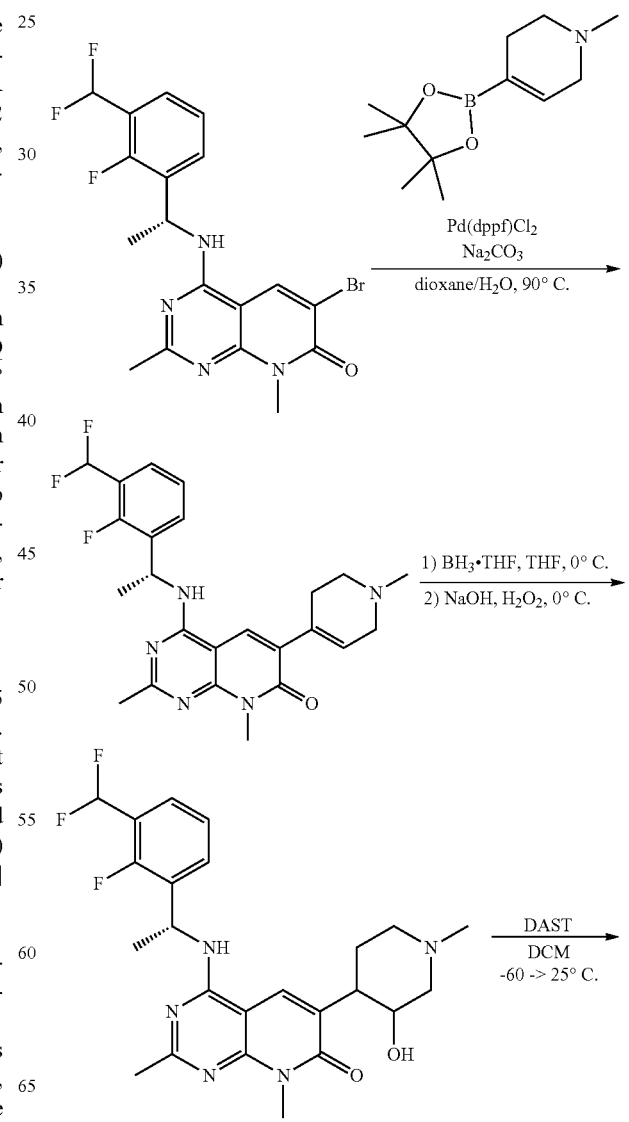

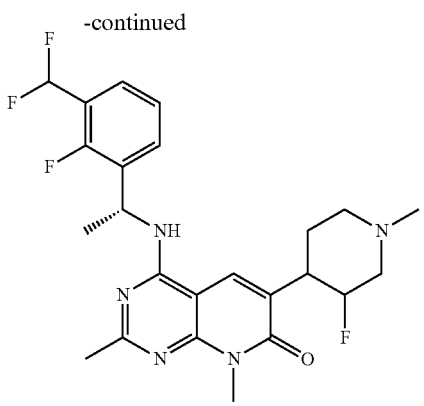

Step 1

To a solution of 6-bromo-4-[[(1R)-1-[3-(difluoromethyl)-2-fluoro-phenyl]ethyl]amino]-2,8-dimethyl-pyrido[2,3-d]pyrimidin-7-one (1.8 g, 4.08 mmol) in dioxane (18 mL) was added 1-methyl-4-(4,4,5,5-tetramethyl-1,3,2-dioxaborolan-2-yl)-3,6-dihydro-2H-pyridine (1.37 g, 6.12 mmol), Pd(dppf)Cl$_2$ (298.49 mg, 407.94 mol), H$_2$ (3.8 mL) and Na$_2$CO$_3$ (864.74 mg, 8.16 mmol). The mixture was stirred under nitrogen at 90° C. for 2 h. The reaction was diluted with water, extracted with EtOAc, washed with brine, dried with anhydrous Na$_2$SO$_4$, filtered, and the solvent was removed under reduced pressure. The residue was purified by column chromatography to give 4-[[(1R)-1-[3-(difluoromethyl)-2-fluoro-phenyl]ethyl] amino]-2,8-dimethyl-6-(1-methyl-3,6-dihydro-2H-pyridin-4-yl)pyrido[2,3-d]pyrimidin-7-one (1.9 g, crude). $^1$H NMR (400 MHz, methanol-d$_4$) δ ppm 8.17 (s, 1H) 7.59-7.55 (i, 1H) 7.47-7.44 (m, 1H) 7.23-7.20 (m, 1H) 7.00 (t, J=54.8 Hz, 1H) 6.42 (s, 1H) 5.80-5.75 (m, 1H) 3.65 (s, 3H) 3.26 (s, 2H) 2.84-2.81 (m, 2H) 2.70 (s, 2H) 2.48 (s, 3H) 2.37 (s, 3H) 1.64 (d, J=8 Hz, 3H)

Step 2

To a solution of 4-[[(1R)-1-[3-(difluoromethyl)-2-fluoro-phenyl]ethyl]amino]-2,8-dimethyl-6-(1-methyl-3,6-dihydro-2H-pyridin-4-yl)pyrido[2,3-d]pyrimidin-7-one (1 g, 2.19 mmol) in THE (30 mL) under nitrogen at 0° C. was added 1M BH$_3$ in THE (13.12 mL, 13.14 mmol). The mixture was stirred at 20° C. for 12 h. The reaction was cooled to 0° C. and aq. 2M NaOH (3.28 mL, 6.56 mmol) was added, followed by 30% H$_2$O$_2$ (2.10 mL, 21.86 mmol), keeping the internal temperature below 5° C. The reaction mixture was warmed to 30° C. and stirred for 1 h. The reaction mixture was poured into 10% aq. Na$_2$S$_2$O$_3$ and stirred for 15 min. The organic layer was separated, and the aqueous layer was extracted with EtOAc. The combined organic layers were washed with brine, dried with anhydrous Na$_2$SO$_4$, filtered, and the solvent was removed under reduced pressure. The residue was purified by prep-HPLC to give 4-[[(1R)-1-[3-(difluoromethyl)-2-fluoro-phenyl]ethyl]amino]-6-(3-hydroxy-1-methyl-4-piperidyl)-2,8-dimethyl-pyrido[2,3-d]pyrimidin-7-one (100 mg, 9.62% yield). LCMS (ESI): m/z: [M+H] calculated for C$_{24}$H$_{29}$F$_3$N$_5$O$_2$: 476.2; found 476.3.

Step 3

To a solution of 4-[[(1R)-1-[3-(difluoromethyl)-2-fluoro-phenyl]ethyl]amino]-6-(3-hydroxy-1-methyl-4-piperidyl)-2,8-dimethyl-pyrido[2,3-d]pyrimidin-7-one (0.07 g, 147.21 μmol) in DCM (5 mL) at −60° C. was added N-ethyl-N-(trifluoro-sulfanyl)ethanamine (38.90 μL, 294.42 μmol). The mixture was warmed to 25° C. and stirred for 12 h. The reaction mixture was gradually poured into NaHCO$_3$ and stirred for 15 min. The organic layer was separated and the aqueous layer was extracted with DCM. The combined organic layers were washed with brine, dried with anhydrous Na$_2$SO$_4$, filtered, and the solvent was removed under reduced pressure. The residue was purified by prep-HPLC to give 4-[[(1R)-1-[3-(difluoromethyl)-2-fluoro-phenyl]ethyl]amino]-6-(3-fluoro-1-methyl-4-piperidyl)-2,8-dimethyl-pyrido[2,3-d]pyrimidin-7-one (8 mg, 10.47% yield). LCMS (ESI): m/z: [M+H] calculated for C$_{24}$H$_{28}$F$_4$N$_5$O: 478.2; found 478.1. $^1$H NMR (400 MHz, methanol-d$_4$) δ ppm 8.47 (s, 1H) 7.58 (t, J=8 Hz, 1H) 7.47 (t, J=8 Hz, 1H) 7.22 (t, J=8 Hz, 1H) 6.99 (t, J=54.8 Hz, 1H) 5.83-5.77 (m, 1H) 3.68 (s, 3H) 3.15-2.81 (m, 5H) 2.62 (s, 3H) 2.39 (s, 3H) 1.91 (t, J=12 Hz, 2H) 1.64 (d, J=8 Hz, 3H).

Example 19: Synthesis of 6-(1-acetyl-4-piperidyl)-4-[[(1R)-1-[5-amino-2-fluoro-3-(trifluoromethyl)phenyl]ethyl]amino]-8-methyl-pyrido[2,3-d]pyrimidin-7-one

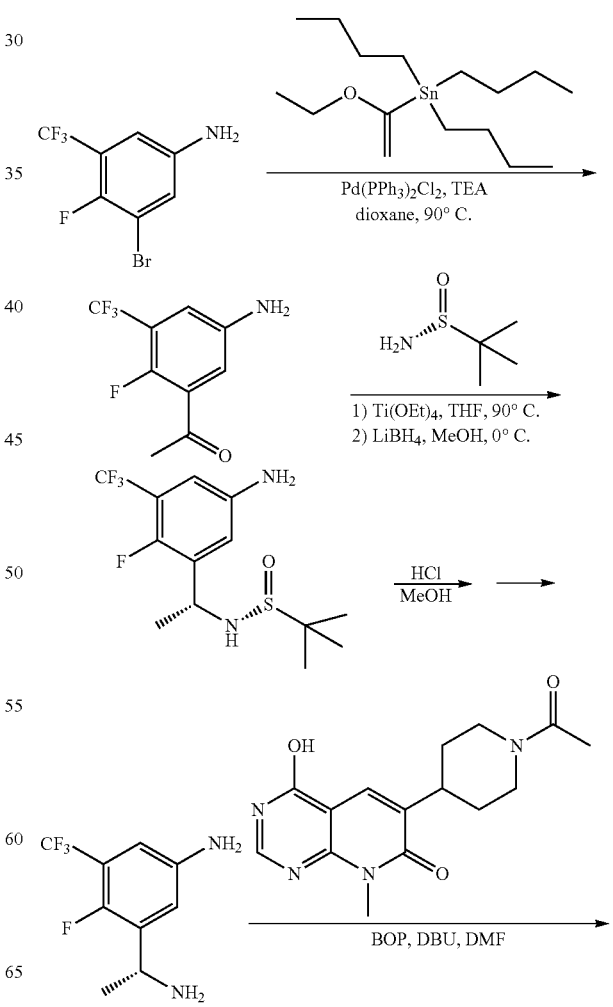

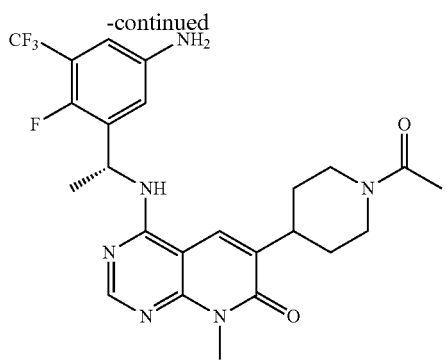

Step 1

To a solution of 3-bromo-4-fluoro-5-(trifluoromethyl)aniline (1 g, 3.88 mmol) and tributyl(1-ethoxyvinyl)stannane (1.96 mL, 5.81 mmol) in dioxane (10 mL) was added TEA (1.35 mL, 9.69 mmol) and Pd(PPh$_3$)$_2$Cl$_2$ (272.04 mg, 387.58 µmol). The mixture was stirred under nitrogen at 90° C. for 3 h. The reaction was adjusted to pH=2 using 1M HCl and stirred for 16 h. The mixture was filtered, and the filtrate was extracted with EtOAc. The organic layer was poured into aq. KF and stirred for 20 min. The mixture was filtered, washed with brine, dried with anhydrous Na$_2$SO$_4$, and the solvent was removed under reduced pressure. The residue was purified by column chromatography to give 1-[5-amino-2-fluoro-3-(trifluoromethyl)phenyl]ethanone (440 mg, 51.33% yield). $^1$H NMR (400 MHz, methanol-d4) δ ppm 7.25 (d, J=4 Hz, 1H) 7.11 (d, J=4 Hz, 1H) 2.58 (d, J=4.63 Hz, 3H).

Step 2

To a solution of 1-[5-amino-2-fluoro-3-(trifluoromethyl)phenyl]ethanone (440 mg, 1.99 mmol) and 2-methylpropane-2-sulfinamide (313.48 mg, 2.59 mmol) in THF (5 mL) was added tetraethoxytitanium (1.24 mL, 5.97 mmol). The reaction mixture was stirred at 90° C. for 3 h. Then the reaction was cooled to 0° C. and LiBH$_4$ (47.67 mg, 2.19 mmol) and MeOH (80.51 µL, 1.99 mmol) were added. The reaction mixture was stirred at 0° C. for 30 min. The reaction mixture was diluted with water, filtered and the solvent was removed under reduced pressure. The residue was purified by prep-HPLC to give N-[(1R)-1-[5-amino-2-fluoro-3-(trifluoromethyl)phenyl]ethyl]-2-methyl-propane-2-sulfinamide (350 mg, 53.90% yield). LCMS (ESI): m/z: [M+H] calculated for C$_{13}$H$_{19}$F$_4$N$_2$OS:327.1; found 327.05.

Step 3

To a solution of N-[(1R)-1-[5-amino-2-fluoro-3-(trifluoromethyl)phenyl]ethyl]-2-methyl-propane-2-sulfinamide (350 mg, 1.07 mmol) in MeOH (4 mL) was added 4 M HCl in MeOH (1.07 mL, 4.28 mmol). The mixture was stirred at 25° C. for 3 h. The reaction was adjusted to pH=8 using aq. NaOH and the solvent was removed under reduced pressure. The residue was dissolved in DCM/MeOH (10:1), filtered and the solvent was removed under reduced pressure to give 3-[(1R)-1-aminoethyl]-4-fluoro-5-(trifluoromethyl) aniline (200 mg, crude). LCMS (ESI): m/z: [M+H] calculated for C$_9$H$_{11}$F$_4$N$_2$:223.1; found 223.1.

Step 4

To a solution of 3-[(1R)-1-aminoethyl]-4-fluoro-5-(trifluoromethyl)aniline (100 mg, 450.08 µmol) and 6-(1-acetyl-4-piperidyl)-4-hydroxy-8-methyl-pyrido[2,3-d]pyrimidin-7-one (136.07 mg, 450.08 µmol) in DMF (2 mL) was added BOP (318.50 mg, 720.13 µmol) and DBU (203.5 µL, 1.35 mmol). The mixture was stirred at 25° C. for 16 h. The reaction mixture was diluted with water, extracted with EtOAc, washed with brine, dried with anhydrous Na$_2$SO$_4$, filtered, and the solvent was removed under reduced pressure. The residue was purified by prep-HPLC to give 6-(1-acetyl-4-piperidyl)-4-[[(1R)-1-[5-amino-2-fluoro-3-(trifluoromethyl)phenyl]ethyl]amino]-8-methyl-pyrido[2,3-d]pyrimidin-7-one (20 mg, 8.60% yield). LCMS (ESI): m/z: [M+H] calculated for C$_{24}$H$_{27}$F$_4$N$_6$O$_2$:507.2; found 507.2. $^1$H NMR (400 MHz, methanol-d4) δ ppm 8.31 (s, 1H) 8.19 (s, 1H) 6.90-6.85 (m, 1H) 6.80-6.76 (m, 1H) 5.68-5.60 (m, 1H) 4.74-4.67 (m, 1H) 4.12-4.01 (m, 1H) 3.71 (s, 3H) 3.26-3.14 (m, 1H) 2.79-2.72 (m, 1H) 2.14 (d, J=1.32 Hz, 3H) 2.07-1.90 (m, 2H) 1.70-1.62 (m, 2H) 1.60 (d, J=7.06 Hz, 3H).

Example 20: Synthesis of (R)-4-((1-(3-(difluoromethyl)-2-fluorophenyl)ethyl)amino)-6-(2,3-dimethoxybenzyl)-2-methylpyrido[2,3-d]pyrimidin-7(8H)-one

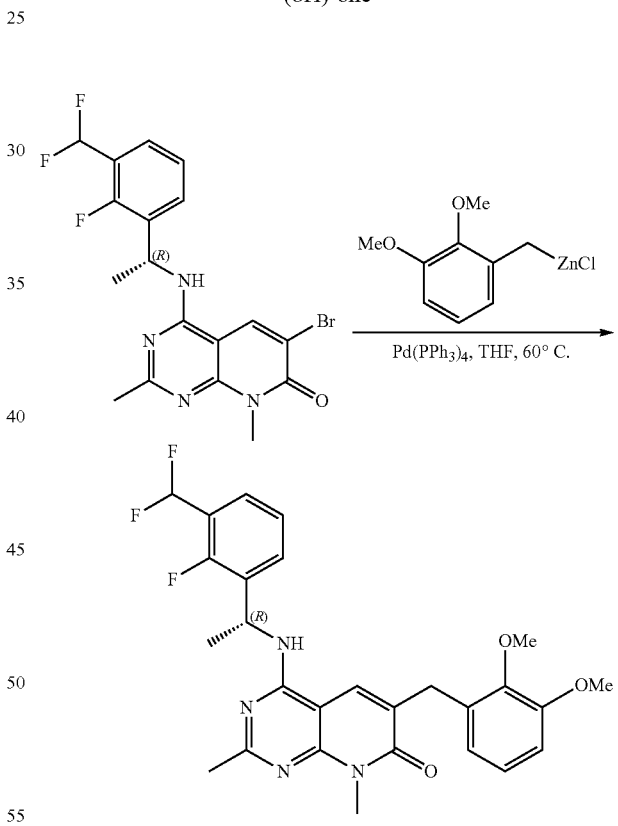

Step 1

To a solution of 6-bromo-4-{[(1R)-1-[3-(difluoromethyl)-2-fluorophenyl]ethyl]amino}-2,8-dimethyl-7H,8H-pyrido[2,3-d]pyrimidin-7-one (81.3 mg, 184 µmol) and Pd(PPh$_3$)$_4$ (21.2 mg, 18.3 µmol) in THF (2.0 mL) was added a solution of 3,4-dimethoxybenzylzinc chloride (0.5 M in THF, 1.0 mL, 0.50 mmol) at 25° C. under N$_2$. The mixture was warmed to 60° C. and stirred for 30 min. The mixture was quenched with water, extracted with EtOAc, dried over MgSO$_4$, filtered, and concentrated under reduced pressure.

The crude residue was purified by prep-HPLC to give (R)-4-((1-(3-(difluoromethyl)-2-fluorophenyl)ethyl)amino)-6-(2,3-dimethoxybenzyl)-2-methylpyrido[2,3-d]pyrimidin-7(8H)-one (9.7 mg, 10% yield). LCMS (ESI): m/z: [M+H] calculated for $C_{21}H_{28}N_5O_3$: 513.2; found: 513.5; $^1$H NMR (500 MHz, METHANOL-d4) δ ppm 8.07 (s, 1H), 7.55 (t, J=7.5 Hz, 1H), 7.47 (t, J=7.1 Hz, 1H), 7.22 (t, J=7.7 Hz, 1H), 7.15-6.88 (m, 3H), 6.81 (d, J=7.1 Hz, 1H), 5.77 (q, J=7.1 Hz, 1H), 4.01-3.92 (m, 2H), 3.87 (s, 3H), 3.83 (s, 3H), 3.70 (s, 3H), 2.39 (s, 3H), 1.61 (d, J=7.1 Hz, 3H).

The following examples 20-1 to 20-4 shown in Table 5 were synthesized in the manner similar to Example 20.

TABLE 5

| Example # | Structure | Mass Found |
|---|---|---|
| 20-1 | 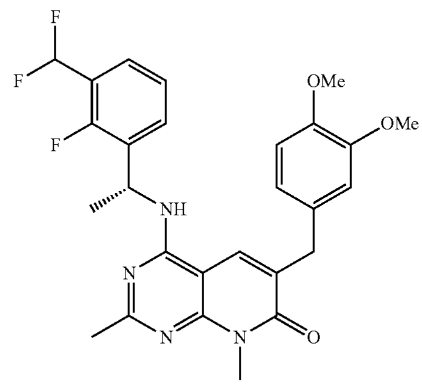 [SMILES: COc1ccc(Cc2cc3c(N[C@H](C)c4cccc(C(F)F)c4F)nc(C)nc3n(C)c2=O)cc1OC] | 513.5 |
| 20-2 | 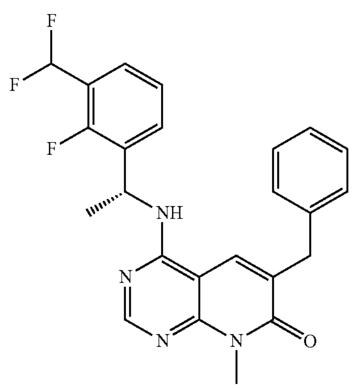 [SMILES: C[C@@H](Nc1ncnc2c1cc(Cc1ccccc1)c(=O)n2C)c1cccc(C(F)F)c1F] | 439.4 |
| 20-3 | 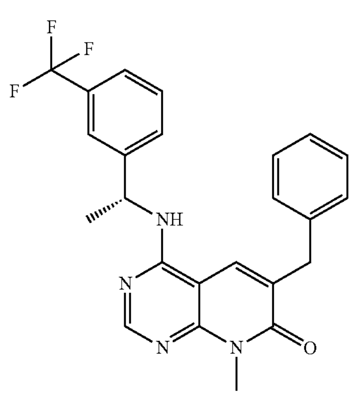 [SMILES: C[C@@H](Nc1ncnc2c1cc(Cc1ccccc1)c(=O)n2C)c1cccc(C(F)(F)F)c1] | 439.6 |
| 20-4 | | 495.1 |

Example 21: Synthesis of (R)-4-((1-(3-(difluoromethyl)-2-fluorophenyl)ethyl)amino)-8-methyl-6-(pyridazin-4-yl)pyrido[2,3-d]pyrimidin-7(8H)-one

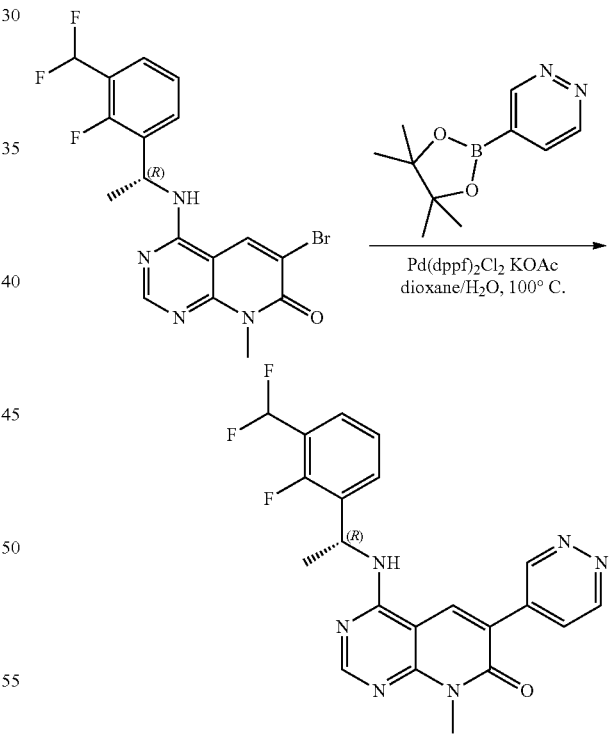

Step 1

A mixture of 6-bromo-4-{[(1R)-1-[3-(difluoromethyl)-2-fluorophenyl]ethyl]amino}-8-methyl-7H,8H-pyrido[2,3-d]pyrimidin-7-one (43.6 mg, 102 μmol), pyridazine-4-boronic acid pinacol ester (33.1 mg, 160 μmol) and KOAc (32.0 mg, 326 μmol) in dioxane (2.0 mL) and water (0.5 mL) was sparged with N$_2$ for 10 min. To this mixture was added Pd(dppf)$_2$Cl$_2$ dichloromethane complex (8.3 mg, 10 μmol)

at 25° C. under N₂. The mixture was warmed to 100° C. and stirred for 30 min. The mixture was quenched with water, extracted with EtOAc, dried over MgSO₄, filtered, and concentrated under reduced pressure. The crude residue was purified by prep-HPLC to give (R)-4-((1-(3-(difluoromethyl)-2-fluorophenyl)ethyl)amino)-8-methyl-6-(pyridazin-4-yl)pyrido[2,3-d]pyrimidin-7(8H)-one (16.5 mg, 38% yield). LCMS (ESI): m/z: [M+H] calculated for C₂₁H₁₈F₃N₆O: 427.1; found: 427.3; ¹H NMR (500 MHz, METHANOL-d₄) δ ppm 9.69 (dd, J=2.4, 1.2 Hz, 1H), 9.25 (dd, J=5.5, 1.3 Hz, 1H), 8.89 (s, 1H), 8.40 (s, 1H), 8.27 (dd, J=5.5, 2.4 Hz, 1H), 7.63 (t, J=7.5 Hz, 1H), 7.51 (t, J=7.2 Hz, 1H), 7.26 (t, J=7.8 Hz, 1H), 7.02 (t, J=54.9 Hz, 1H), 5.82 (q, J=7.1 Hz, 1H), 3.77 (s, 3H), 1.69 (d, J=7.0 Hz, 3H).

The following examples 21-1 to 21-15 shown in Table 6 were synthesized in the manner similar to Example 21.

TABLE 6

Examples 21-1 to 21-15

| Example # | Structure | Mass Found |
|---|---|---|
| 21-1 | 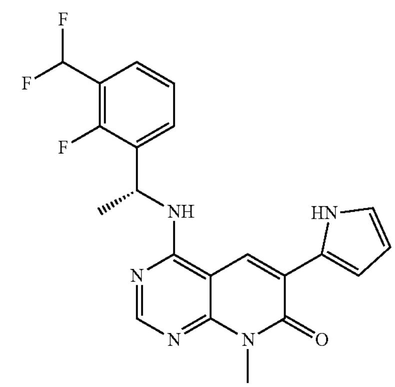 [SMILES: C[C@@H](Nc1ncnc2c1cc(-c1ccc[nH]1)c(=O)n2C)c1cccc(C(F)F)c1F] | 414.5 |
| 21-2 | 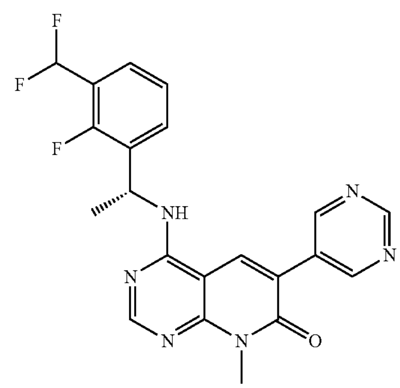 [SMILES: C[C@@H](Nc1ncnc2c1cc(-c1cncnc1)c(=O)n2C)c1cccc(C(F)F)c1F] | 427.5 |
| 21-3 | 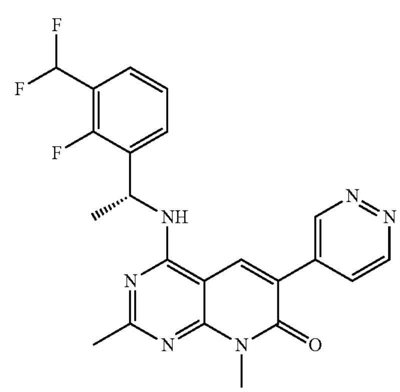 [SMILES: Cc1nc(N[C@H](C)c2cccc(C(F)F)c2F)c2cc(-c3ccnnc3)c(=O)n(C)c2n1] | 441.3 |

TABLE 6-continued
Examples 21-1 to 21-15
| Example # | Structure | Mass Found |
|---|---|---|
| 21-4 | 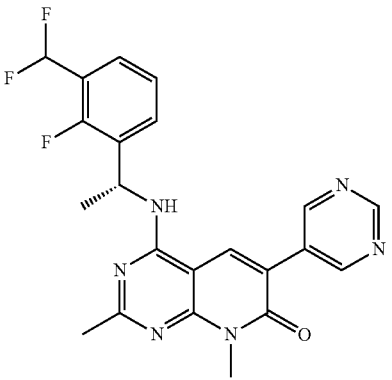 [SMILES: Cc1nc(N[C@H](C)c2cccc(C(F)F)c2F)c2cc(-c3cncnc3)c(=O)n(C)c2n1] | 441.4 |
| 21-5 | 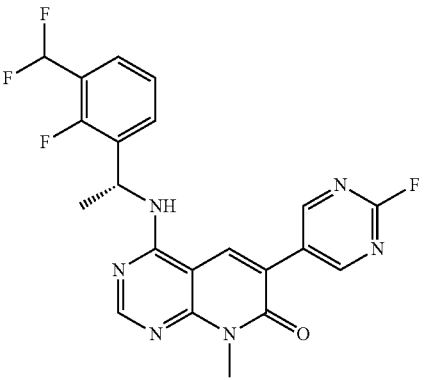 [SMILES: C[C@@H](Nc1ncnc2c1cc(-c1cnc(F)nc1)c(=O)n2C)c1cccc(C(F)F)c1F] | 445.4 |
| 21-6 | 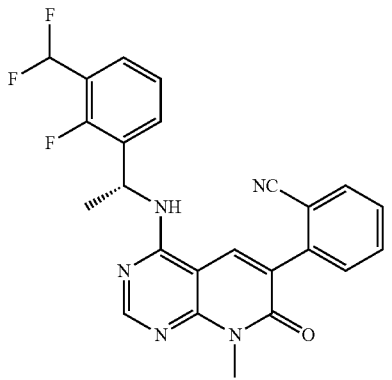 [SMILES: C[C@@H](Nc1ncnc2c1cc(-c1ccccc1C#N)c(=O)n2C)c1cccc(C(F)F)c1F] | 450.4 |
| 21-7 | 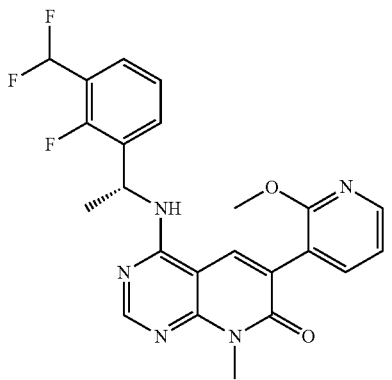 [SMILES: COc1ncccc1-c1cc2c(N[C@H](C)c3cccc(C(F)F)c3F)ncnc2n(C)c1=O] | 456.0 |

TABLE 6-continued

Examples 21-1 to 21-15

| Example # | Structure | Mass Found |
|---|---|---|
| 21-8 | 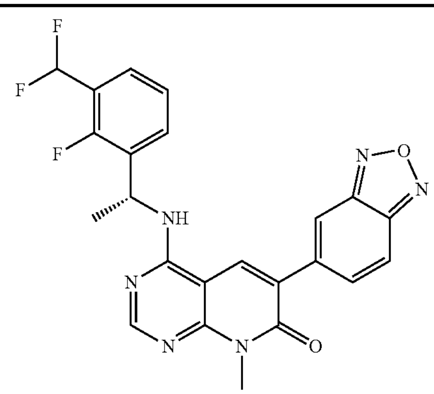 | 467.5 |
| 21-9 | 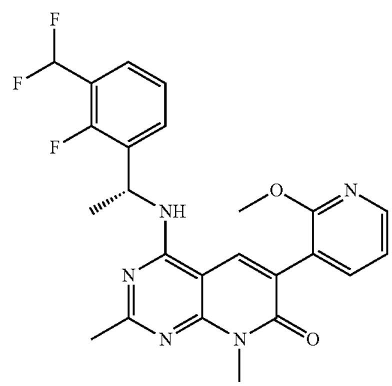 [SMILES: COc1ncccc1-c1cc2c(N[C@H](C)c3cccc(C(F)F)c3F)nc(C)nc2n(C)c1=O] | 470.1 |
| 21-10 | 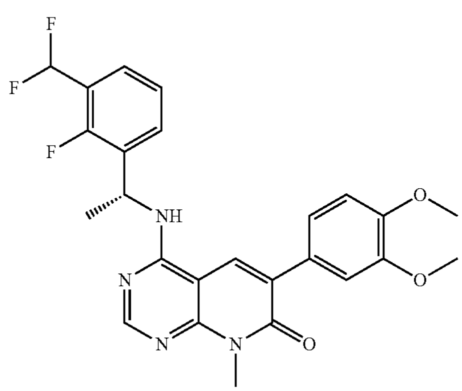 [SMILES: COc1ccc(-c2cc3c(N[C@H](C)c4cccc(C(F)F)c4F)ncnc3n(C)c2=O)cc1OC] | 485.4 |
| 21-11 | 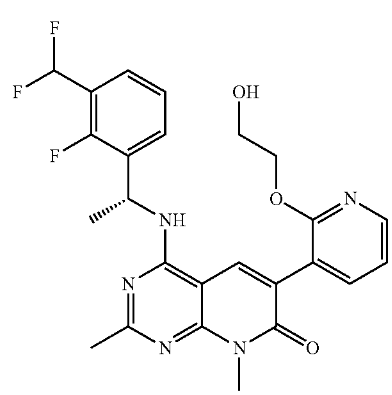 [SMILES: Cc1nc(N[C@H](C)c2cccc(C(F)F)c2F)c2cc(-c3cccnc3OCCO)c(=O)n(C)c2n1] | 500.0 |

TABLE 6-continued

Examples 21-1 to 21-15

| Example # | Structure | Mass Found |
|---|---|---|
| 21-12 | 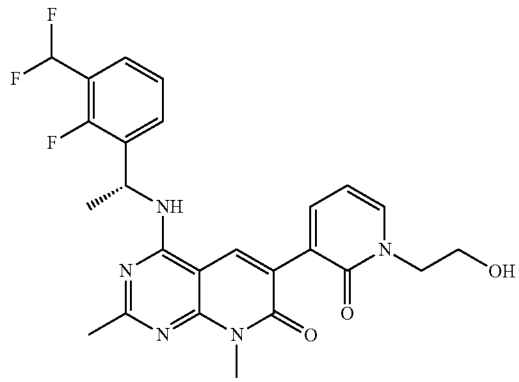 [SMILES: Cc1nc(N[C@H](C)c2cccc(C(F)F)c2F)c2cc(-c3cccn(CCO)c3=O)c(=O)n(C)c2n1] | 500.0 |
| 21-13 | 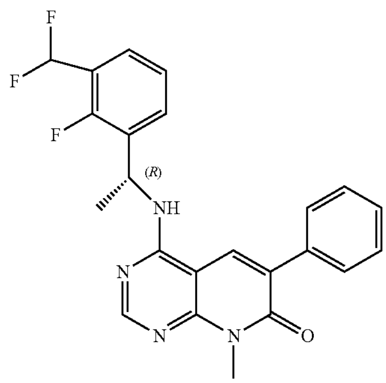 | 425.4 |
| 21-14 | 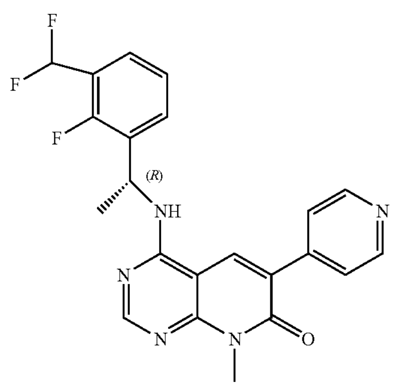 | 426.07 |
| 21-15 | 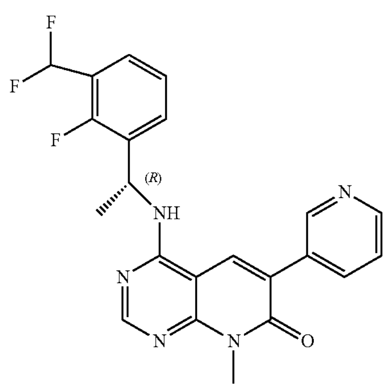 | 426.07 |

Example 22: Synthesis of 4-(((R)-1-(3-(difluoromethyl)-2-fluorophenyl)ethyl)amino)-8-methyl-6-(1-oxido-3,6-dihydro-2H-thiopyran-4-yl)pyrido[2,3-d]pyrimidin-7(8H)-one

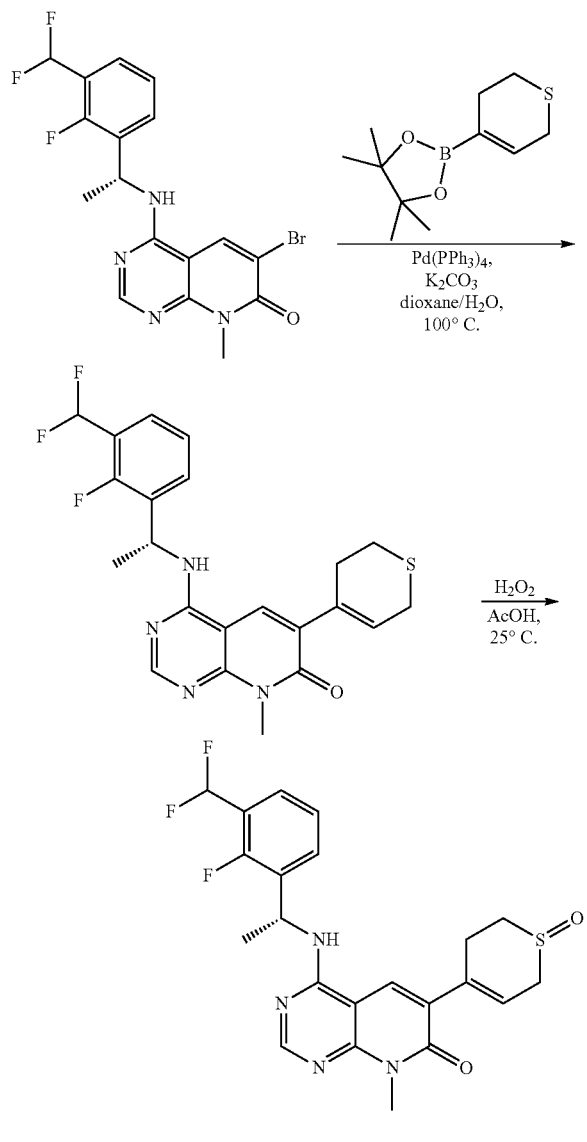

Step 1

A mixture of 6-bromo-4-{[(1R)-1-[3-(difluoromethyl)-2-fluorophenyl]ethyl]amino}-8-methyl-7H,8H-pyrido[2,3-d]pyrimidin-7-one (1.52 g, 3.55 mmol), 3,6-dihydro-2 h-thiopyran-4-yl boronic acid pinacol ester (2.07 g, 9.15 mmol), Pd(PPh$_3$)$_4$ (627 mg, 542 μmol), and K$_2$CO$_3$ (1.52 g, 10.9 mmol) in dioxane (50 mL) and H$_2$O (20 mL) was sparged with N$_2$ for 5 min. The mixture was heated to 100° C. and stirred under N$_2$ for 2 h. The reaction was quenched with water, extracted with EtOAc, dried over MgSO$_4$, filtered, and concentrated under reduced pressure. The crude residue was purified by column chromatography to give (R)-4-((1-(3-(difluoromethyl)-2-fluorophenyl)ethyl)amino)-6-(3,6-dihydro-2H-thiopyran-4-yl)-8-methylpyrido[2,3-d]pyrimidin-7(8H)-one (1.41 g, 89% yield). LCMS (ESI): m/z: [M+H] calculated for C$_{22}$H$_{22}$F$_3$N$_4$OS: 447.2; found: 447.4.

Step 2

To a mixture of (R)-4-((1-(3-(difluoromethyl)-2-fluorophenyl)ethyl)amino)-6-(3,6-dihydro-2H-thiopyran-4-yl)-8-methylpyrido[2,3-d]pyrimidin-7(8H)-one (1.41 g, 3.15 mmol) in acetic acid (30 mL) was added an aqueous solution of hydrogen peroxide (30%, 416 μL, 4.05 mmol). The mixture was stirred at 25° C. for 30 min. The reaction mixture was diluted in EtOAc (100 mL), quenched with water (200 mL), and neutralized with NaHCO$_3$. The layers were separated and the aqueous layer was extracted with EtOAc. The combined organic layers were dried over MgSO$_4$, filtered, and concentrated under reduced pressure to give 4-(((R)-1-(3-(difluoromethyl)-2-fluorophenyl)ethyl)amino)-8-methyl-6-(1-oxido-3,6-dihydro-2H-thiopyran-4-yl)pyrido[2,3-d]pyrimidin-7(8H)-one (1.43 g, 99% yield). LCMS (ESI): m/z: [M+H] calculated for C$_{22}$H$_{22}$F$_3$N$_4$O$_2$S: 463.1; found: 463.4; $^1$H NMR (500 MHz, Methanol-d$_4$) δ 8.32 (s, 1H), 8.28 (s, 1H), 7.58 (t, J=7.5 Hz, 1H), 7.49 (t, J=7.3 Hz, 1H), 7.24 (t, J=7.8 Hz, 1H), 7.02 (t, J=54.9 Hz, 1H), 6.12-6.06 (m, 1H), 5.83-5.74 (m, 1H), 3.77 (d, J=17.7 Hz, 1H), 3.70 (s, 3H), 3.49 (dd, J=17.9, 4.7 Hz, 1H), 3.30-3.21 (m, 1H), 3.16-3.06 (m, 1H), 3.05-2.89 (m, 2H), 1.66 (d, J=7.0 Hz, 3H).

Example 23: Synthesis of 4-(((R)-1-(3-(difluoromethyl)-2-fluorophenyl)ethyl)amino)-6-(1-imino-1-oxido-1,2,3,6-tetrahydro-1λ$^6$-thiopyran-4-yl)-8-methylpyrido[2,3-d]pyrimidin-7(8H)-one

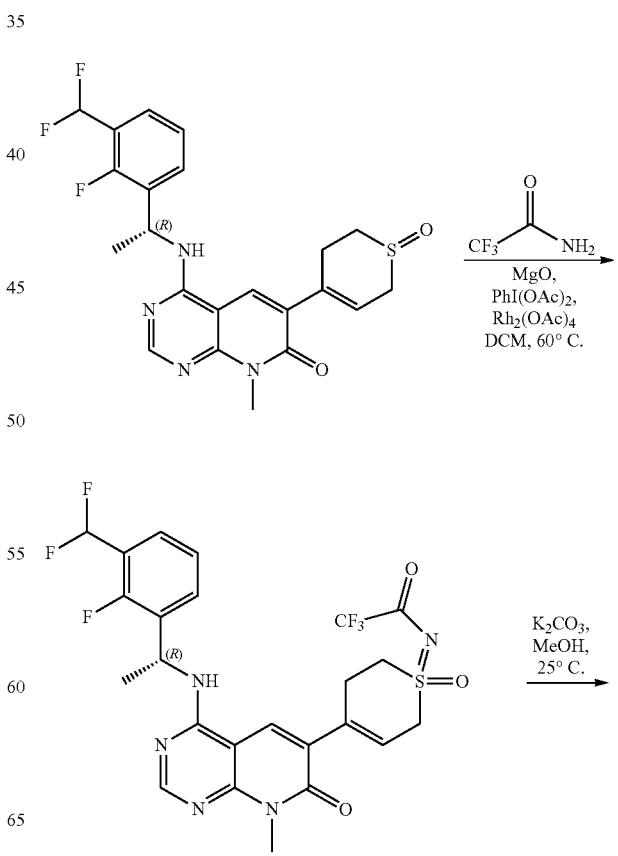

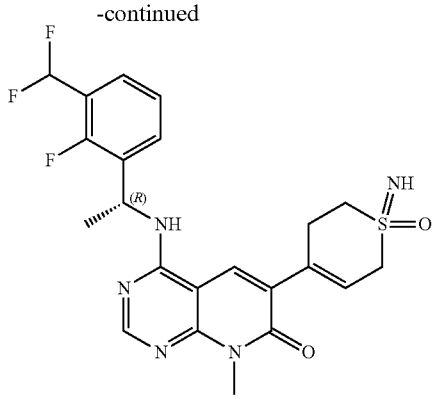

Step 1

To a mixture of magnesium oxide (407 mg, 10.1 mmol), PhI(OAc)₂ (1.48 g, 4.59 mmol), trifluoroacetamide (516 mg, 4.56 mmol), and Rh₂(OAc)₄ (135 mg, 305 μmol) was added a solution of 4-(((R)-1-(3-(difluoromethyl)-2-fluorophenyl)ethyl)amino)-8-methyl-6-(1-oxido-3,6-dihydro-2H-thiopyran-4-yl)pyrido[2,3-d]pyrimidin-7(8H)-one (711 mg, 1.53 mmol) in DCM (15 mL). The mixture was heated to 60° C. and stirred for 90 min. The reaction mixture was filtered through Celite® and concentrated under reduced pressure. The crude residue was purified by column chromatography to give N-(4-(4-(((R)-1-(3-(difluoromethyl)-2-fluorophenyl)ethyl)amino)-8-methyl-7-oxo-7,8-dihydropyrido[2,3-d]pyrimidin-6-yl)-1-oxido-3,6-dihydro-2H-1λ⁶-thiopyran-1-ylidene)-2,2,2-trifluoroacetamide (741 mg, 72% yield). LCMS (ESI): m/z: [M+H] calculated for $C_{24}H_{22}F_6N_5O_3S$: 574.1; found: 574.2.

Step 2

To a solution of N-(4-(4-(((R)-1-(3-(difluoromethyl)-2-fluorophenyl)ethyl)amino)-8-methyl-7-oxo-7,8-dihydropyrido[2,3-d]pyrimidin-6-yl)-1-oxido-3,6-dihydro-2H-1λ⁶-thiopyran-1-ylidene)-2,2,2-trifluoroacetamide (213 mg, 371 μmol) in MeOH (6.0 mL) was added K₂CO₃ (102 mg, 738 μmol). The mixture was stirred at 25° C. for 5 min. The reaction mixture was concentrated under reduced pressure, quenched with water, extracted with EtOAc, dried over MgSO₄, filtered, and concentrated under reduced pressure. The crude residue was purified by prep-HPLC to give 4-(((R)-1-(3-(difluoromethyl)-2-fluorophenyl)ethyl)amino)-6-(1-imino-1-oxido-1,2,3,6-tetrahydro-1λ⁶-thiopyran-4-yl)-8-methylpyrido[2,3-d]pyrimidin-7(8H)-one (26.7 mg, 16% yield). LCMS (ESI): m/z: [M+H] calculated for $C_{22}H_{23}F_3N_5O_2S$: 478.1; found: 478.1. H NMR (500 MHz, METHANOL-d₄) δ ppm 8.32 (s, 1H), 8.29 (s, 1H), 7.58 (t, J=7.5 Hz, 1H), 7.49 (t, J=6.9 Hz, 1H), 7.24 (t, J=7.7 Hz, 1H), 7.02 (t, J=54.9 Hz, 1H), 6.07-6.03 (m, 1H), 5.78 (q, J=7.1 Hz, 1H), 4.01-3.89 (m, 2H), 3.70 (s, 3H), 3.48-3.35 (m, 2H), 3.21-3.05 (m, 2H), 1.66 (d, J=7.1 Hz, 3H).

The following example 23-1 shown in Table 7 was synthesized in the manner similar to Example 23.

TABLE 7

Example 23-1

| Example # | Structure | Mass Found |
|---|---|---|
| Example 23-1 | 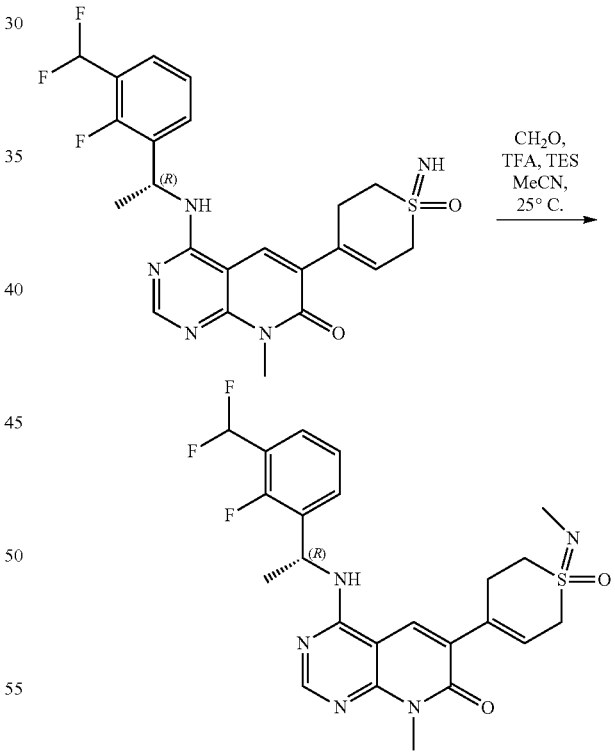 | 492.3 |

Example 24: Synthesis of 4-(((R)-1-(3-(difluoromethyl)-2-fluorophenyl)ethyl)amino)-8-methyl-6-(1-(methylimino)-1-oxido-1,2,3,6-tetrahydro-1λ⁶-thiopyran-4-yl)pyrido[2,3-d]pyrimidin-7(8H)-one Step 1

To a mixture of 4-(((R)-1-(3-(difluoromethyl)-2-fluorophenyl)ethyl)amino)-6-(1-imino-1-oxido-1,2,3,6-tetrahydro-1λ⁶-thiopyran-4-yl)-8-methylpyrido[2,3-d]pyrimidin-7(8H)-one (85.6 mg, 179 μmol) in MeCN (4.0 mL) were added an aqueous solution of formaldehyde (37%, 53.2 μL, 712 μmol) and trifluoroacetic acid (54.4 μL, 710 μmol). The solution was stirred at 25° C. for 30 min. Triethylsilane (114 μL, 712 μmol) was added and the mixture was stirred at 25° C. for 4 h. The mixture was concentrated under reduced pressure, partitioned between water and DCM, and neutralized by the addition of NaHCO₃. The aqueous layer was extracted with DCM and the combined organic layers were dried over MgSO₄, filtered, and concentrated under reduced pressure. The crude residue was purified by prep-HPLC to give 4-(((R)-1-(3-(difluoromethyl)-2-fluorophenyl)ethyl)amino)-8-methyl-6-(1-(methylimino)-1-oxido-1,2,3,6-tetrahydro-1-thiopyran-4-yl)pyrido[2,3-d]pyrimidin-7(8H)-one (26.8 mg, 30% yield). LCMS (ESI): m/z: [M+H] calculated for $C_{23}H_{25}F_3N_5O_2S$: 492.2; found: 492.4. ¹H NMR (500 MHz, METHANOL-d₄) δ ppm 8.33 (s, 1H), 8.29 (s, 1H), 7.58 (t, J=7.5 Hz, 1H), 7.49 (t, J=7.1 Hz, 1H), 7.25 (t, J=7.7 Hz, 1H), 7.02 (t, J=54.9 Hz, 1H), 6.08-6.01 (m, 1H), 5.78 (q, J=7.1 Hz, 1H), 4.08-4.00 (m, 1H), 3.94-3.87 (m, 1H), 3.70 (s, 3H), 3.51-3.41 (m, 2H), 3.16-3.00 (m, 2H), 2.86 (s, 3H), 1.66 (d, J=7.0 Hz, 3H).

Example 25: Synthesis of (R)-4-((1-(3-(difluoromethyl)-2-fluorophenyl)ethyl)amino)-8-methyl-6-(1-oxidotetrahydro-2H-thiopyran-4-yl)pyrido[2,3-d]pyrimidin-7(8H)-one

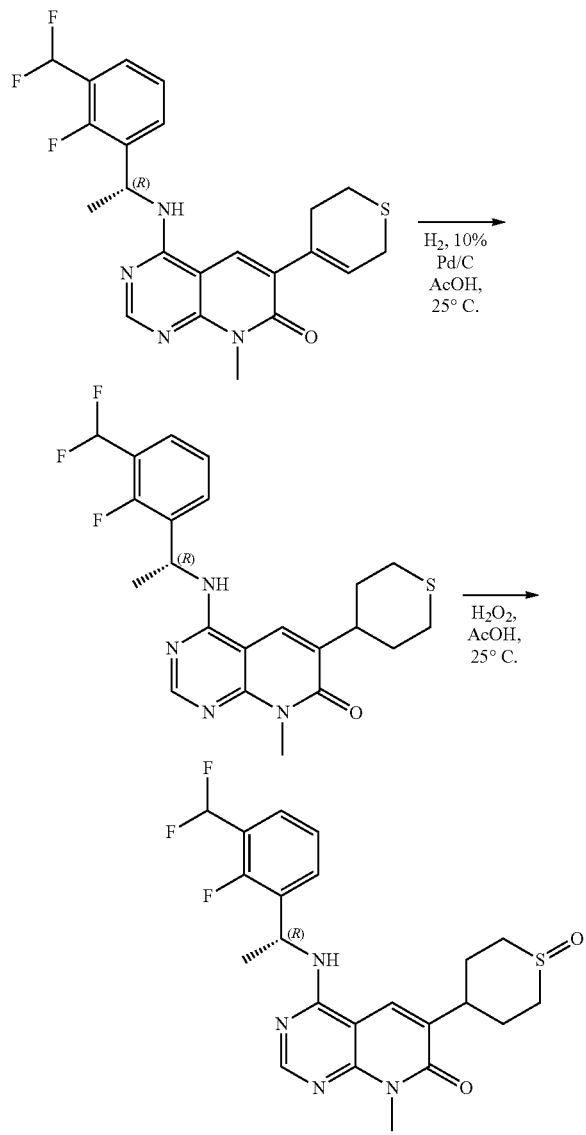

Step 1

To a solution of (R)-4-((1-(3-(difluoromethyl)-2-fluorophenyl)ethyl)amino)-6-(3,6-dihydro-2H-thiopyran-4-yl)-8-methylpyrido[2,3-d]pyrimidin-7(8H)-one (450 mg; 1.00 mmol) in AcOH (5.0 mL) under N₂, 10% wt. Pd/C (462 mg, 0.434 mmol) was added. The mixture was placed under a hydrogen balloon (1 atm) and stirred at 25° C. for 2 h. The mixture was filtered through Celite® and concentrated under reduced pressure. The crude residue was purified by column chromatography to give (R)-4-((1-(3-(difluoromethyl)-2-fluorophenyl)ethyl)amino)-8-methyl-6-(tetrahydro-2H-thiopyran-4-yl)pyrido[2,3-d]pyrimidin-7(8H)-one (247 mg, 55% yield). LCMS (ESI): m/z: [M+H] calculated for $C_{22}H_{24}F_3N_4OS$: 449.2; found: 449.2.

Step 2

To a solution of (R)-4-((1-(3-(difluoromethyl)-2-fluorophenyl)ethyl)amino)-8-methyl-6-(tetrahydro-2H-thiopyran-4-yl)pyrido[2,3-d]pyrimidin-7(8H)-one (106 mg, 236 μmol) in AcOH (3.0 mL) was added was added an aqueous solution of hydrogen peroxide (30%, 48.0 μL, 467 μmol). The mixture was stirred at 25° C. for 30 min. The reaction was diluted with EtOAc and water, then was treated with NaHCO₃ to pH=7. The phases were separated and the aqueous solution was extracted with EtOAc. The combined organic extracts were concentrated and the crude residue was purified by prep-HPLC to give (R)-4-((1-(3-(difluoromethyl)-2-fluorophenyl)ethyl)amino)-8-methyl-6-(1-oxidotetrahydro-2H-thiopyran-4-yl)pyrido[2,3-d]pyrimidin-7(8H)-one (31.3 mg, 29% yield). LCMS (ESI): m/z: [M+H] calculated for $C_{22}H_{24}F_3N_4O_2S$: 465.2; found: 465.3. ¹H NMR (500 MHz, METHANOL-d₄) δ ppm 8.31-8.20 (m, 2H), 7.61-7.56 (m, 1H), 7.51-7.48 (m, 1H), 7.26-7.23 (m, 1H), 7.13-6.91 (m, 1H), 5.82-5.76 (m, 1H), 3.72-3.70 (m, 3H), 3.61-3.14 (m, 2H), 2.98-2.90 (m, 1H), 2.50-2.28 (m, 1H), 2.06-1.96 (m, 1H), 1.69-1.66 (m, 3H).

Example 26: Synthesis of 4-{[(1R)-1-[3-(difluoromethyl)-2-fluorophenyl]ethyl]amino}-2,8-dimethyl-6-(morpholine-4-carbonyl)-7H,8H-pyrido[2,3-d]pyrimidin-7-one

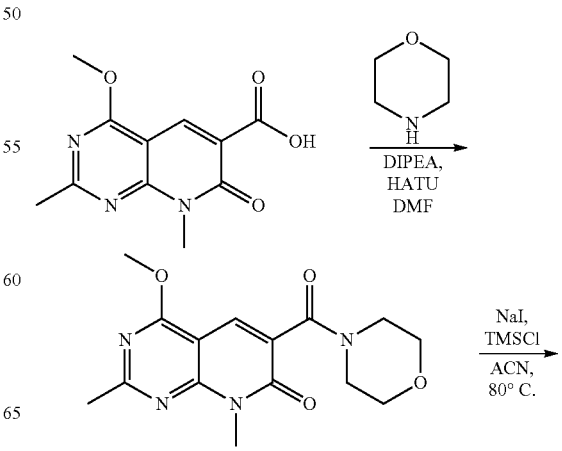

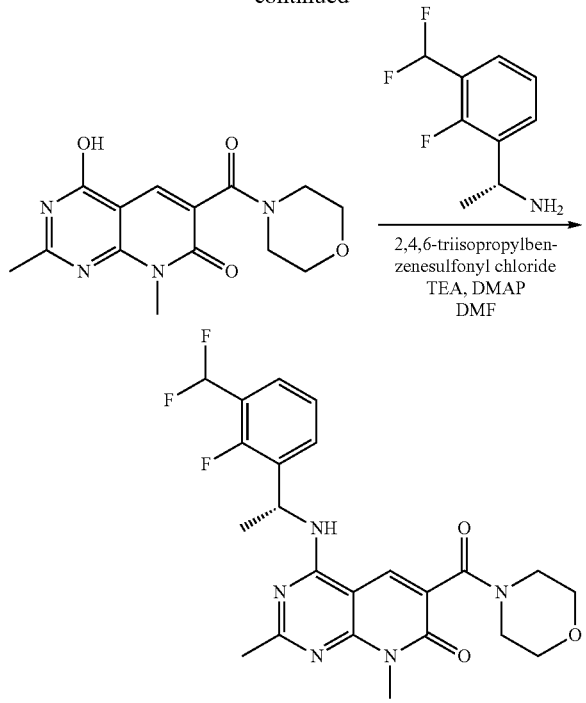

Step 1
To a solution of morpholine (169 µl, 1.93 mmol) and 4-methoxy-2,8-dimethyl-7-oxo-7H,8H-pyrido[2,3-d]pyrimidine-6-carboxylic acid (400 mg, 1.61 mmol) in DMF (8 mL) was added DIPEA (839 µL, 4.82 mmol). After 5 min of stirring HATU (749 mg, 2.09 mmol) was added and the resulting mixture was stirred at rt overnight. The mixture was diluted with EtOAc, washed with sat. aq. NaHCO$_3$, the solids were filtered off, and the layers were separated. The organic layer was washed with brine, dried with Na$_2$SO$_4$, filtered, and the solvent was removed under reduced pressure. The residue was combined with the filtered solid and triturated with water to give 4-methoxy-2,8-dimethyl-6-(morpholine-4-carbonyl)-7H,8H-pyrido[2,3-d]pyrimidin-7-one (356 mg, 71% yield). LCMS (ESI): m/z: [M+H] calculated for $C_{15}H_{19}N_4O_4$: 319.1; found 319.0. $^1$H NMR (300 MHz, methanol-d$_4$) δ ppm 7.30 (s, 1H), 3.32 (s, 3H), 2.95 (d, J=1.4 Hz, 7H), 2.87-2.79 (m, 2H), 2.59-2.53 (m, 2H), 1.85 (s, 3H).

Step 2
Sodium iodide (1.02 g, 6.8 mmol) was added to a suspension of 4-methoxy-2,8-dimethyl-6-(morpholine-4-carbonyl)-7H,8H-pyrido[2,3-d]pyrimidin-7-one (360 mg, 1.13 mmol) in MeCN (14.4 mL). Chlorotrimethylsilane (861 µL, 6.79 mmol) was added and the mixture was heated in a sealed tube at 80° C. for 2 h and then cooled to rt. The solvent was removed under reduced pressure. The residue was suspended in water and sat. aq. sodium thiosulphate was added until the dark color faded. The solution was extracted with EtOAc, and the solvent was removed under reduced pressure to give 4-hydroxy-2,8-dimethyl-6-(morpholine-4-carbonyl)-7H,8H-pyrido[2,3-d]pyrimidin-7-one (322 mg, 94% yield). $^1$H NMR (300 MHz, DMSO-d$_6$) δ ppm 7.87 (s, 1H), 3.64-3.48 (m, 6H), 3.55 (s, 3H), 3.26-3.18 (m, 2H), 2.37 (s, 3H).

Step 3
TEA (900 µL, 4.73 mmol) was added to a suspension of 4-hydroxy-2,8-dimethyl-6-(morpholine-4-carbonyl)-7H,8H-pyrido[2,3-d]pyrimidin-7-one (320 mg, 1.05 mmol) in DMF (11.2 mL). 2,4,6-Triisopropylbenzenesulfonyl chloride (637 mg, 2.1 mmol) and DMAP (13 mg, 0.11 mmol) were added and the reaction mixture was stirred for 1 h. before (1R)-1-[3-(difluoromethyl)-2-fluorophenyl]ethan-1-amine hydrochloride (320 mg, 1.42 mmol) was added and the reaction was stirred overnight at rt. The reaction mixture was diluted with diethyl ether, washed with water and brine, dried with anhydrous Na$_2$SO$_4$, filtered, and the solvent was removed under reduced pressure. The crude product was purified by prep-HPLC to give 4-{[(1R)-1-[3-(difluoromethyl)-2-fluorophenyl]ethyl]amino}-2,8-dimethyl-6-(morpholine-4-carbonyl)-7H,8H-pyrido[2,3-d]pyrimidin-7-one (100 mg, 20% yield). LCMS (ESI): m/z: [M+H] calculated for $C_{23}H_{25}F_3N_5O_3$: 476.2; found 476.0. $^1$H NMR (300 MHz, methanol-d$_4$) δ ppm 8.44 (s, 1H), 7.59 (t, J=7.5 Hz, 1H), 7.49 (t, J=7.1 Hz, 1H), 7.24 (t, J=7.7 Hz, 1H), 7.02 (t, J=54.9 Hz, 1H), 5.80 (q, J=7.1 Hz, 1H), 3.78 (s, 4H), 3.71 (s, 3H), 3.71-3.66 (m, 2H), 3.41 (t, J=4.8 Hz, 2H), 2.43 (s, 3H), 1.64 (d, J=7.1 Hz, 3H).

The following examples 26-1 to 26-52 shown in Table 8 were synthesized in the manner similar to Example 26.

TABLE 8

Examples 26-1 to 26-52

| Example # | Structure | Mass Found |
|---|---|---|
| 26-1 | 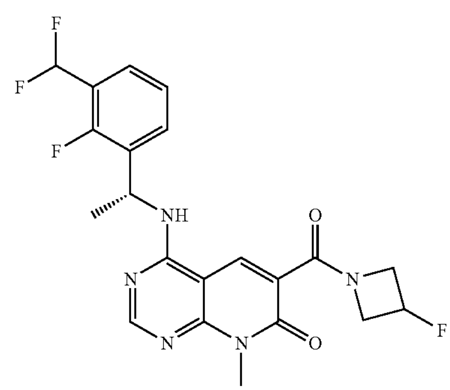 [SMILES: C[C@@H](Nc1ncnc2c1cc(C(=O)N1CC(F)C1)c(=O)n2C)c1cccc(C(F)F)c1F] | 450.6 |

TABLE 8-continued

Examples 26-1 to 26-52

| Example # | Structure | Mass Found |
|---|---|---|
| 26-2 | 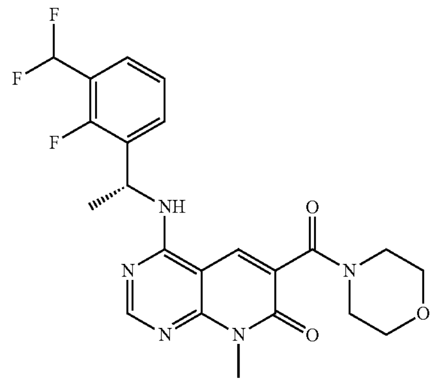 [SMILES: C[C@@H](Nc1ncnc2c1cc(C(=O)N1CCOCC1)c(=O)n2C)c1cccc(C(F)F)c1F] | 462.4 |
| 26-3 | 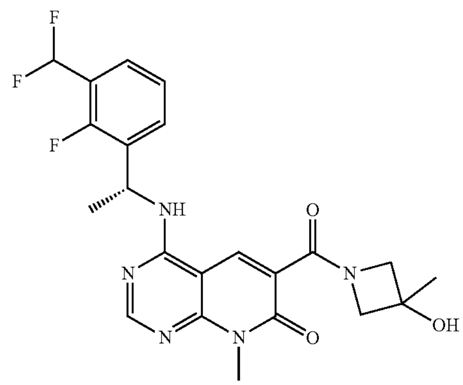 [SMILES: C[C@@H](Nc1ncnc2c1cc(C(=O)N1CC(C)(O)C1)c(=O)n2C)c1cccc(C(F)F)c1F] | 462.5 |
| 26-4 | 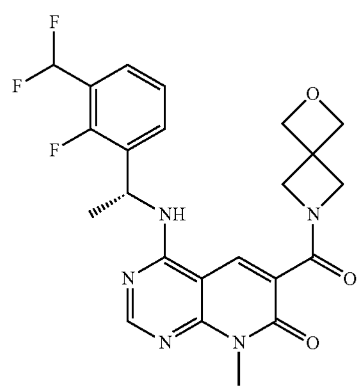 [SMILES: C[C@@H](Nc1ncnc2c1cc(C(=O)N1CC3(COC3)C1)c(=O)n2C)c1cccc(C(F)F)c1F] | 474.0 |
| 26-5 | 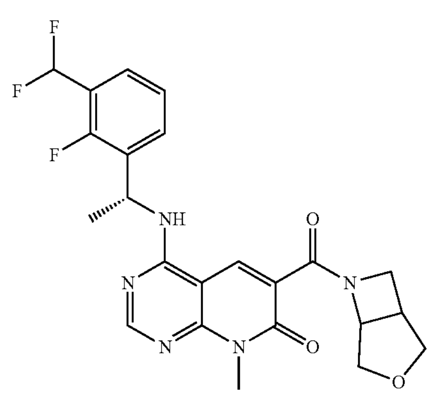 [SMILES: C[C@@H](Nc1ncnc2c1cc(C(=O)N1CC3COCC31)c(=O)n2C)c1cccc(C(F)F)c1F] | 474.4 |

TABLE 8-continued

Examples 26-1 to 26-52

| Example # | Structure | Mass Found |
|---|---|---|
| 26-6 | 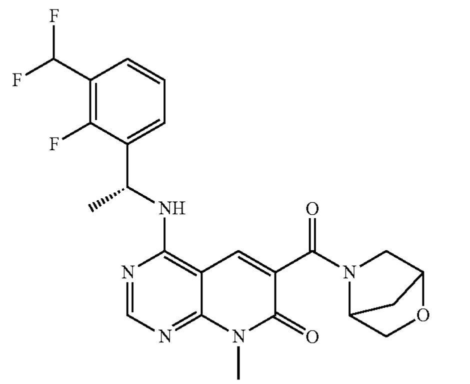 [SMILES: C[C@@H](Nc1ncnc2c1cc(C(=O)N1CC3CC1CO3)c(=O)n2C)c1cccc(C(F)F)c1F] | 474.4 |
| 26-7 | 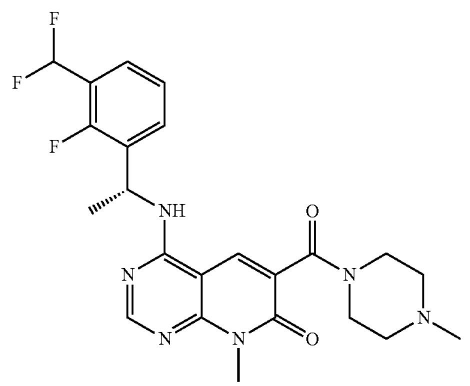 [SMILES: C[C@@H](Nc1ncnc2c1cc(C(=O)N1CCN(C)CC1)c(=O)n2C)c1cccc(C(F)F)c1F] | 475.0 |
| 26-8 | 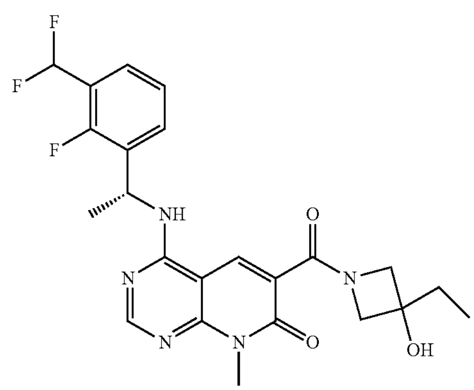 [SMILES: CCC1(O)CN(C(=O)c2cc3c(N[C@H](C)c4cccc(C(F)F)c4F)ncnc3n(C)c2=O)C1] | 476.5 |
| 26-9 | 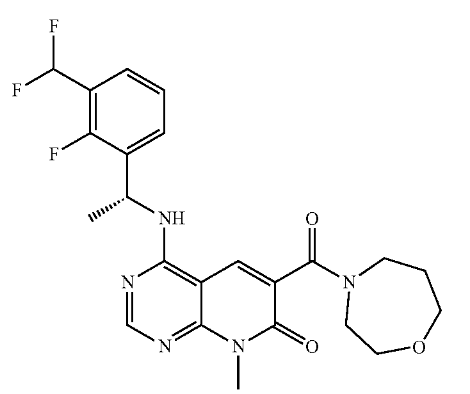 [SMILES: C[C@@H](Nc1ncnc2c1cc(C(=O)N1CCCOCC1)c(=O)n2C)c1cccc(C(F)F)c1F] | 476.6 |

TABLE 8-continued

Examples 26-1 to 26-52

| Example # | Structure | Mass Found |
|---|---|---|
| 26-10 | 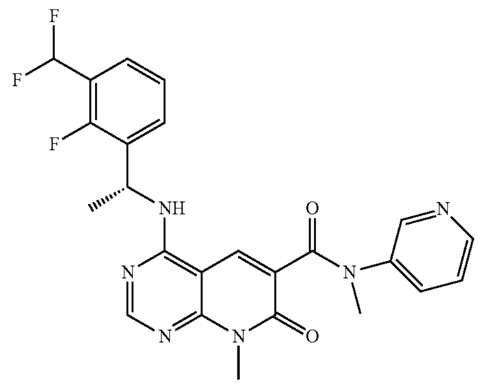 [SMILES: C[C@@H](Nc1ncnc2c1cc(C(=O)N(C)c1cccnc1)c(=O)n2C)c1cccc(C(F)F)c1F] | 483.6 |
| 26-11 | 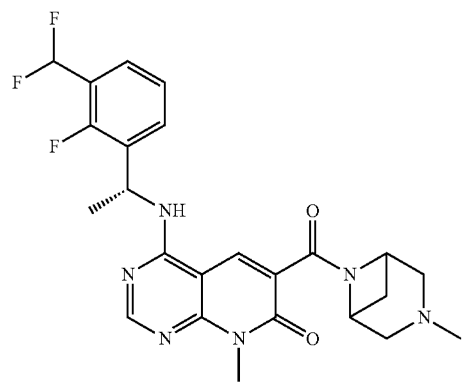 [SMILES: C[C@@H](Nc1ncnc2c1cc(C(=O)N1C3CC1CN(C)C3)c(=O)n2C)c1cccc(C(F)F)c1F] | 487.2 |
| 26-12 | 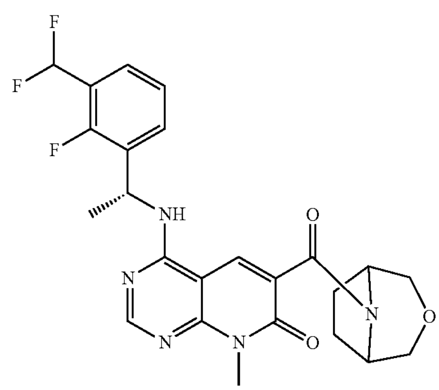 [SMILES: C[C@@H](Nc1ncnc2c1cc(C(=O)N1C3CCC1COC3)c(=O)n2C)c1cccc(C(F)F)c1F] | 488.4 |
| 26-13 | 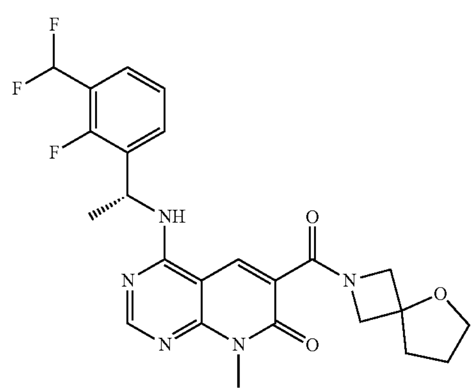 [SMILES: C[C@@H](Nc1ncnc2c1cc(C(=O)N1CC3(CCCO3)C1)c(=O)n2C)c1cccc(C(F)F)c1F] | 488.5 |

TABLE 8-continued

Examples 26-1 to 26-52

| Example # | Structure | Mass Found |
|---|---|---|
| 26-14 | 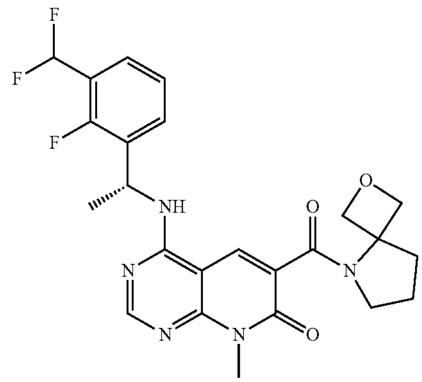 [SMILES: C[C@@H](Nc1ncnc2c1cc(C(=O)N1CCCC13COC3)c(=O)n2C)c1cccc(C(F)F)c1F] | 488.5 |
| 26-15 | 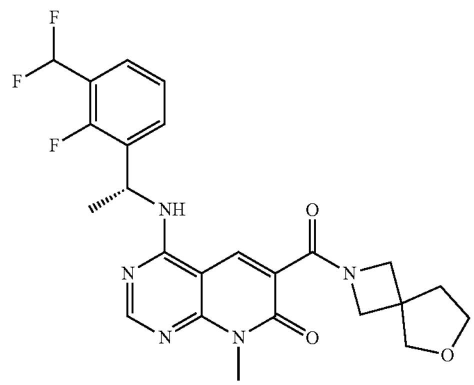 [SMILES: C[C@@H](Nc1ncnc2c1cc(C(=O)N1CC3(CCOC3)C1)c(=O)n2C)c1cccc(C(F)F)c1F] | 488.5 |
| 26-16 | 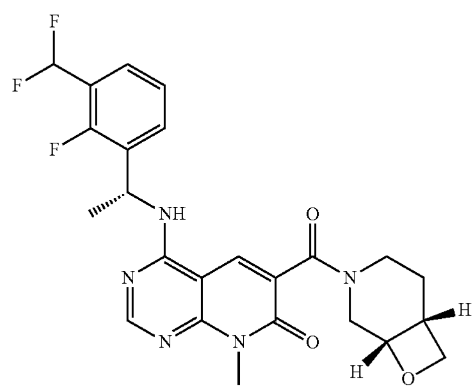 [SMILES: C[C@@H](Nc1ncnc2c1cc(C(=O)N1CC[C@@H]3CO[C@@H]3C1)c(=O)n2C)c1cccc(C(F)F)c1F] | 488.5 |
| 26-17 | 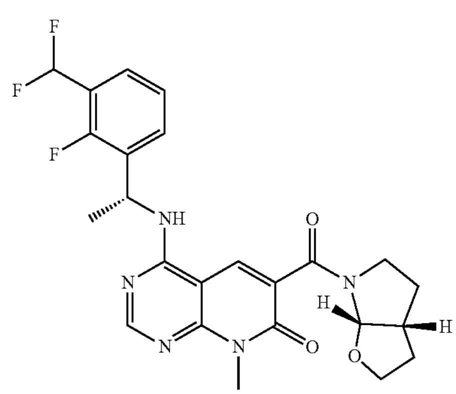 [SMILES: C[C@@H](Nc1ncnc2c1cc(C(=O)N1CC[C@@H]3CCO[C@@H]31)c(=O)n2C)c1cccc(C(F)F)c1F] | 488.5 |

TABLE 8-continued

Examples 26-1 to 26-52

| Example # | Structure | Mass Found |
|---|---|---|
| 26-18 | 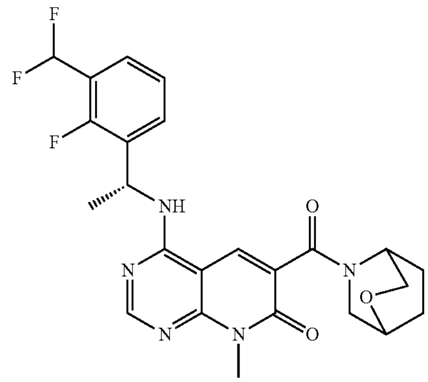 [SMILES: C[C@@H](Nc1ncnc2c1cc(C(=O)N1CC3CCC1CO3)c(=O)n2C)c1cccc(C(F)F)c1F] | 488.5 |
| 26-19 | 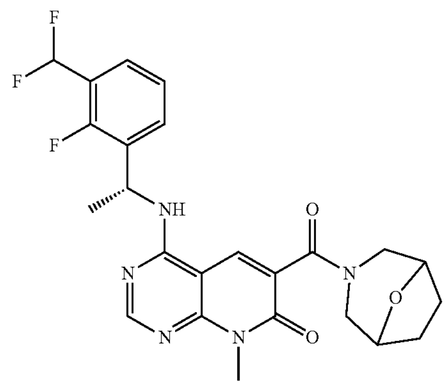 [SMILES: C[C@@H](Nc1ncnc2c1cc(C(=O)N1CC3CCC(C1)O3)c(=O)n2C)c1cccc(C(F)F)c1F] | 488.6 |
| 26-20 | 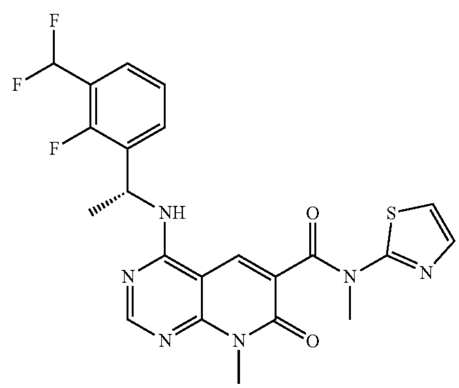 [SMILES: C[C@@H](Nc1ncnc2c1cc(C(=O)N(C)c1nccs1)c(=O)n2C)c1cccc(C(F)F)c1F] | 489.3 |
| 26-21 | 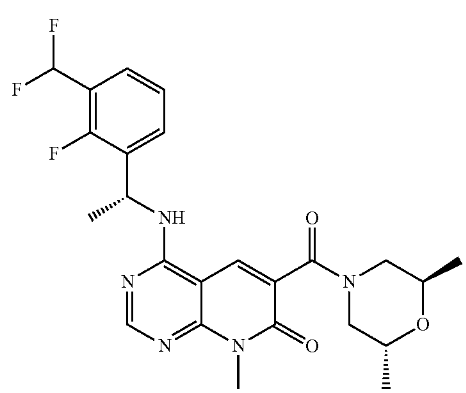 [SMILES: C[C@@H]1CN(C(=O)c2cc3c(N[C@H](C)c4cccc(C(F)F)c4F)ncnc3n(C)c2=O)C[C@@H](C)O1] | 489.8 |

TABLE 8-continued

Examples 26-1 to 26-52

| Example # | Structure | Mass Found |
|---|---|---|
| 26-22 | 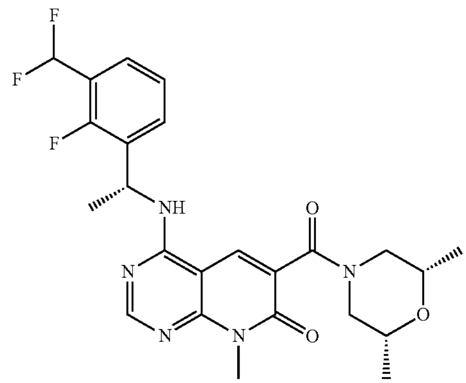 [SMILES: C[C@@H]1CN(C(=O)c2cc3c(N[C@H](C)c4cccc(C(F)F)c4F)ncnc3n(C)c2=O)C[C@H](C)O1] | 490.4 |
| 26-23 | 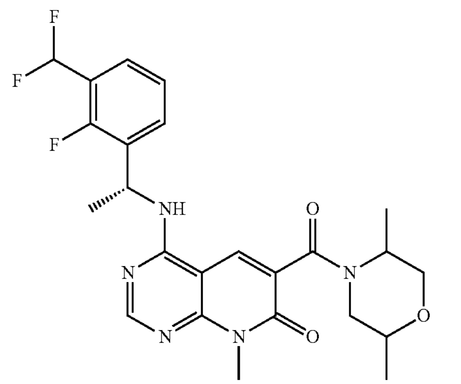 [SMILES: CC1CN(C(=O)c2cc3c(N[C@H](C)c4cccc(C(F)F)c4F)ncnc3n(C)c2=O)C(C)CO1] | 490.5 |
| 26-24 | 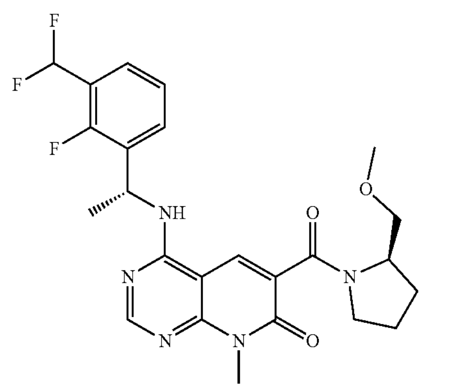 [SMILES: COC[C@H]1CCCN1C(=O)c1cc2c(N[C@H](C)c3cccc(C(F)F)c3F)ncnc2n(C)c1=O] | 490.5 |
| 26-25 | 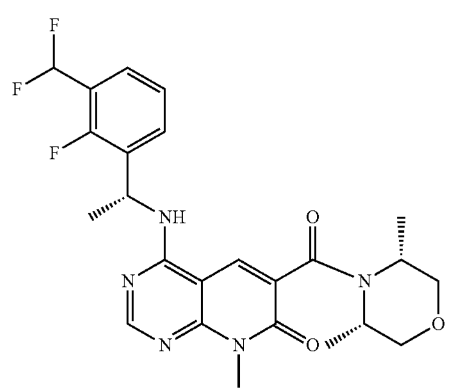 [SMILES: C[C@@H]1COC[C@H](C)N1C(=O)c1cc2c(N[C@H](C)c3cccc(C(F)F)c3F)ncnc2n(C)c1=O] | 490.5 |

TABLE 8-continued

Examples 26-1 to 26-52

| Example # | Structure | Mass Found |
|---|---|---|
| 26-26 | 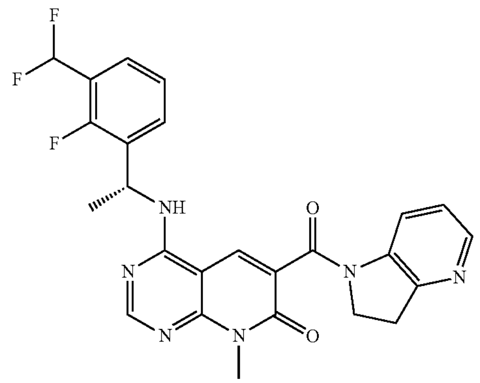 [SMILES: C[C@@H](Nc1ncnc2c1cc(C(=O)N1CCc3ncccc31)c(=O)n2C)c1cccc(C(F)F)c1F] | 495.2 |
| 26-27 | 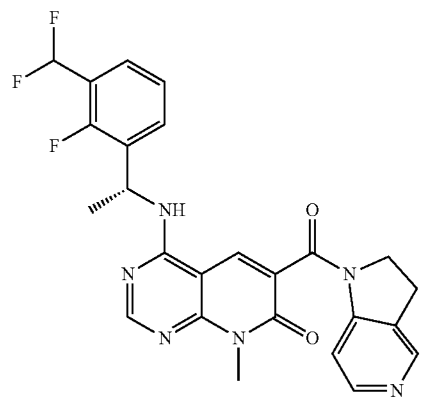 [SMILES: C[C@@H](Nc1ncnc2c1cc(C(=O)N1CCc3cnccc31)c(=O)n2C)c1cccc(C(F)F)c1F] | 495.4 |
| 26-28 | 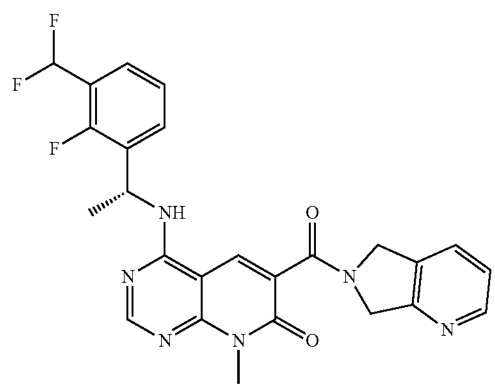 [SMILES: C[C@@H](Nc1ncnc2c1cc(C(=O)N1Cc3cccnc3C1)c(=O)n2C)c1cccc(C(F)F)c1F] | 495.5 |
| 26-29 | 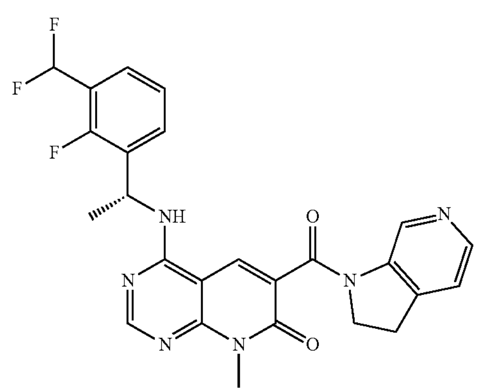 [SMILES: C[C@@H](Nc1ncnc2c1cc(C(=O)N1CCc3ccncc31)c(=O)n2C)c1cccc(C(F)F)c1F] | 495.6 |

TABLE 8-continued
Examples 26-1 to 26-52
| Example # | Structure | Mass Found |
|---|---|---|
| 26-30 | 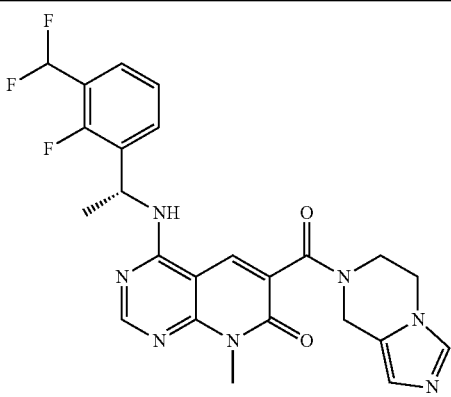 | 498.3 |
| 26-31 | 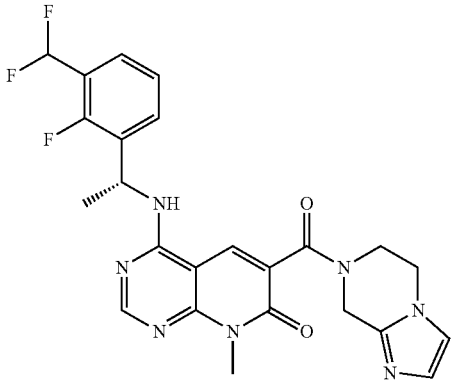 | 498.5 |
| 26-32 | 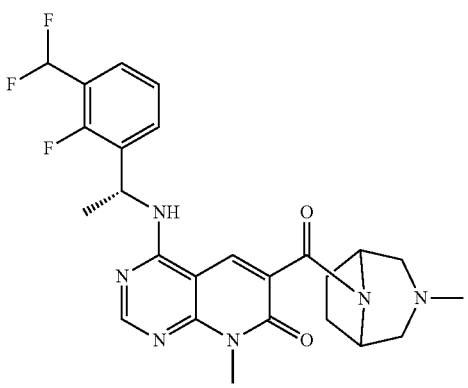 [SMILES: C[C@@H](Nc1ncnc2c1cc(C(=O)N1C3CCC1CN(C)C3)c(=O)n2C)c1cccc(C(F)F)c1F] | 501.5 |
| 26-33 | 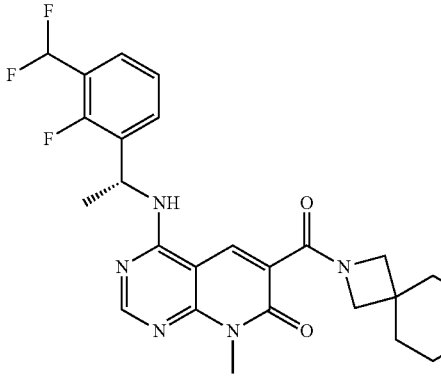 | 502.5 |

TABLE 8-continued

Examples 26-1 to 26-52

| Example # | Structure | Mass Found |
|---|---|---|
| 26-34 | 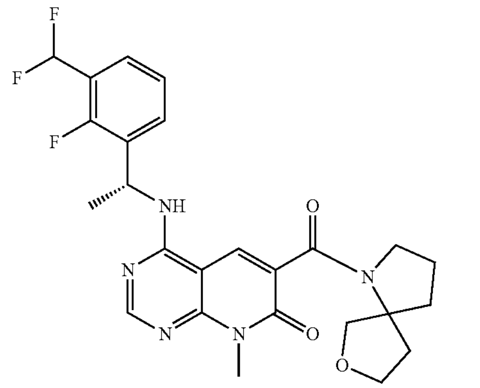 [SMILES: C[C@@H](Nc1ncnc2c1cc(C(=O)N1CCCC13CCOC3)c(=O)n2C)c1cccc(C(F)F)c1F] | 502.5 |
| 26-35 | 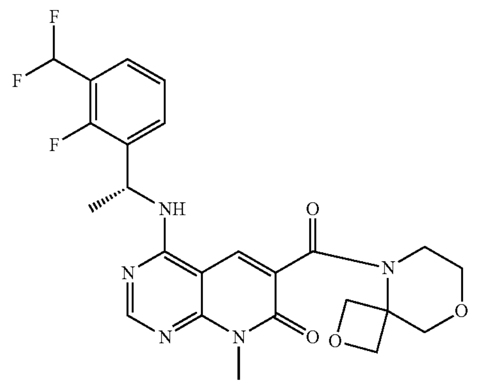 [SMILES: C[C@@H](Nc1ncnc2c1cc(C(=O)N1CCOCC13COC3)c(=O)n2C)c1cccc(C(F)F)c1F] | 504.5 |
| 26-36 | 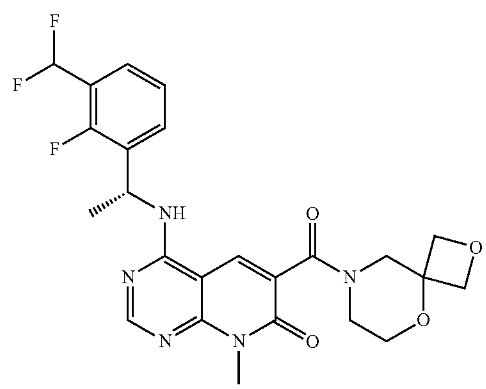 [SMILES: C[C@@H](Nc1ncnc2c1cc(C(=O)N1CCOC3(COC3)C1)c(=O)n2C)c1cccc(C(F)F)c1F] | 504.5 |
| 26-37 | 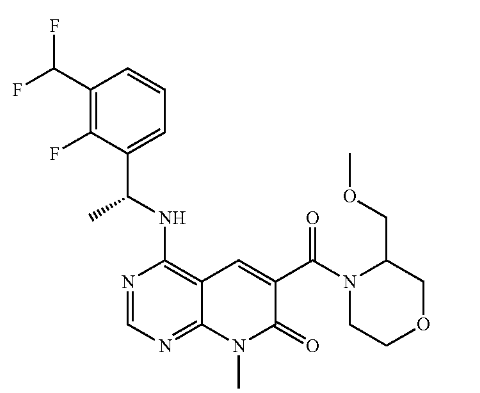 [SMILES: COCC1COCCN1C(=O)c1cc2c(N[C@H](C)c3cccc(C(F)F)c3F)ncnc2n(C)c1=O] | 506.5 |

TABLE 8-continued

Examples 26-1 to 26-52

| Example # | Structure | Mass Found |
|---|---|---|
| 26-38 | 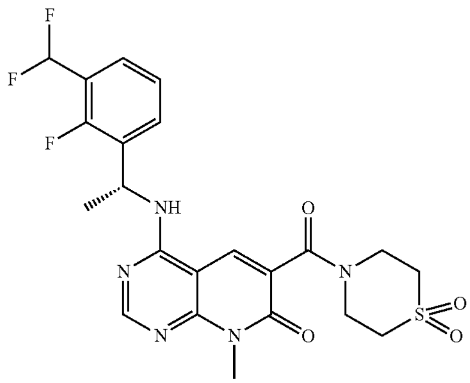 [SMILES: C[C@@H](Nc1ncnc2c1cc(C(=O)N1CCS(=O)(=O)CC1)c(=O)n2C)c1cccc(C(F)F)c1F] | 510.5 |
| 26-39 | 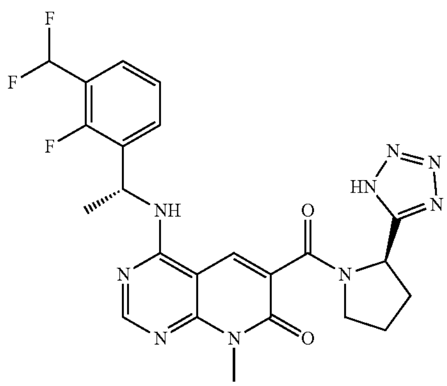 [SMILES: C[C@@H](Nc1ncnc2c1cc(C(=O)N1CCC[C@@H]1c1nnn[nH]1)c(=O)n2C)c1cccc(C(F)F)c1F] | 514.5 |
| 26-40 | 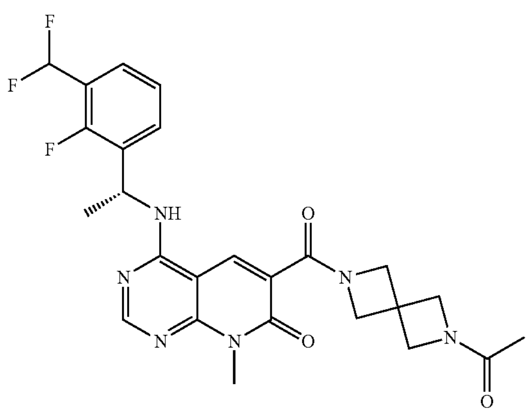 [SMILES: CC(=O)N1CC2(C1)CN(C(=O)c1cc3c(N[C@H](C)c4cccc(C(F)F)c4F)ncnc3n(C)c1=O)C2] | 515.4 |
| 26-41 | 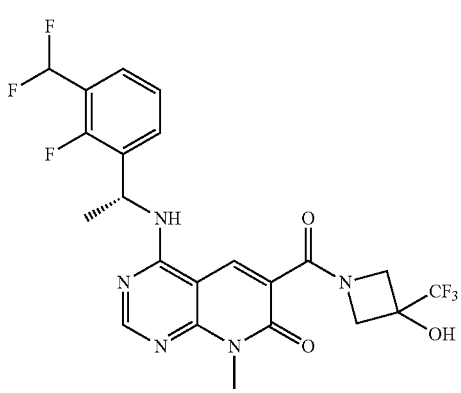 [SMILES: C[C@@H](Nc1ncnc2c1cc(C(=O)N1CC(O)(C(F)(F)F)C1)c(=O)n2C)c1cccc(C(F)F)c1F] | 516.4 |

TABLE 8-continued

Examples 26-1 to 26-52

| Example # | Structure | Mass Found |
|---|---|---|
| 26-42 | 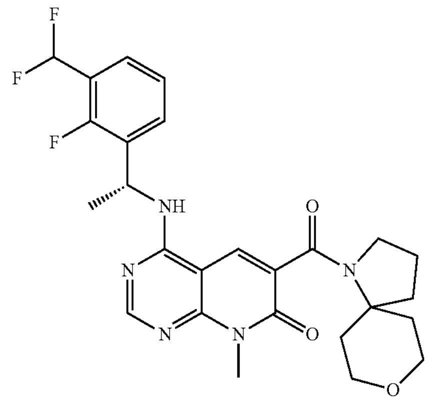 [SMILES: C[C@@H](Nc1ncnc2c1cc(C(=O)N1CCCC13CCOCC3)c(=O)n2C)c1cccc(C(F)F)c1F] | 516.5 |
| 26-43 | 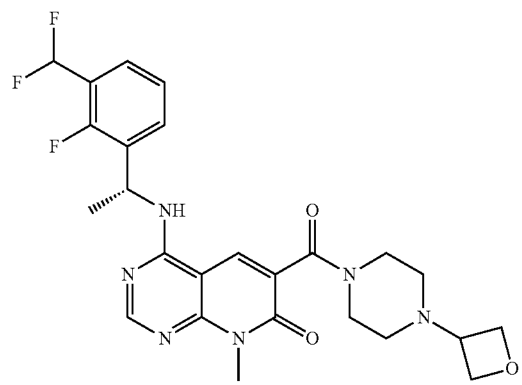 [SMILES: C[C@@H](Nc1ncnc2c1cc(C(=O)N1CCN(C3COC3)CC1)c(=O)n2C)c1cccc(C(F)F)c1F] | 517.0 |
| 26-44 | 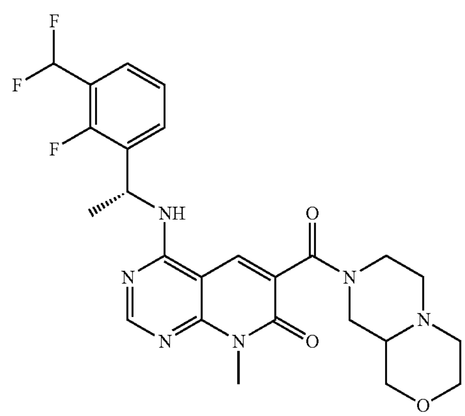 [SMILES: C[C@@H](Nc1ncnc2c1cc(C(=O)N1CCN3CCOCC3C1)c(=O)n2C)c1cccc(C(F)F)c1F] | 517.5 |
| 26-45 | 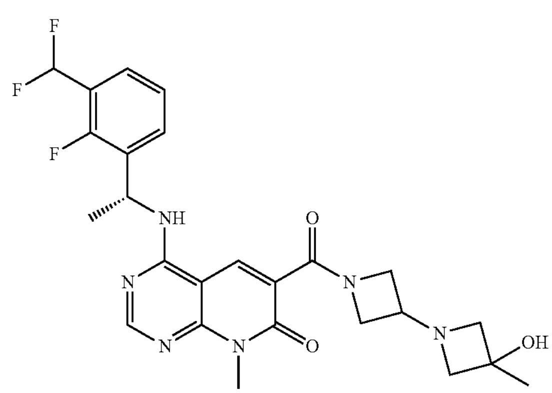 [SMILES: C[C@@H](Nc1ncnc2c1cc(C(=O)N1CC(N3CC(C)(O)C3)C1)c(=O)n2C)c1cccc(C(F)F)c1F] | 517.5 |

TABLE 8-continued

Examples 26-1 to 26-52

| Example # | Structure | Mass Found |
|---|---|---|
| 26-46 | 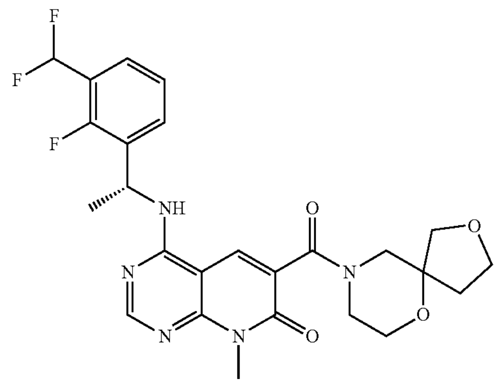 [SMILES: C[C@@H](Nc1ncnc2c1cc(C(=O)N1CCOC3(CCOC3)C1)c(=O)n2C)c1cccc(C(F)F)c1F] | 518.4 |
| 26-47 | 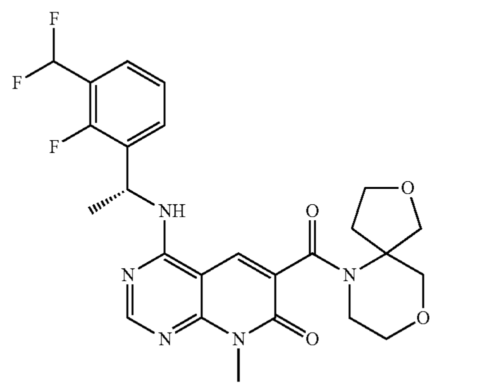 [SMILES: C[C@@H](Nc1ncnc2c1cc(C(=O)N1CCOCC13CCOC3)c(=O)n2C)c1cccc(C(F)F)c1F] | 518.5 |
| 26-48 | 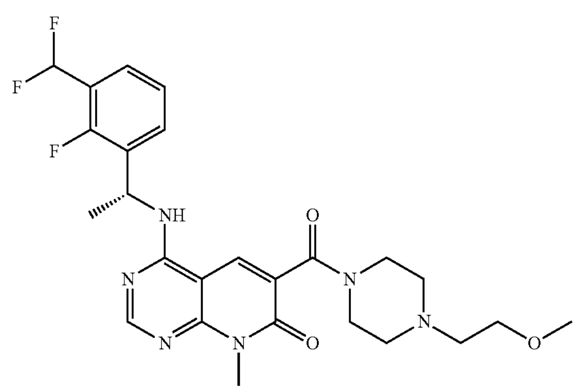 [SMILES: COCCN1CCN(C(=O)c2cc3c(N[C@H](C)c4cccc(C(F)F)c4F)ncnc3n(C)c2=O)CC1] | 519.5 |
| 26-49 | 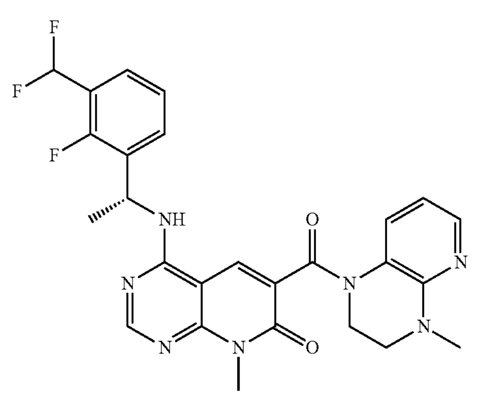 [SMILES: C[C@@H](Nc1ncnc2c1cc(C(=O)N1CCN(C)c3ncccc31)c(=O)n2C)c1cccc(C(F)F)c1F] | 524.2 |

TABLE 8-continued
Examples 26-1 to 26-52
| Example # | Structure | Mass Found |
|---|---|---|
| 26-50 | 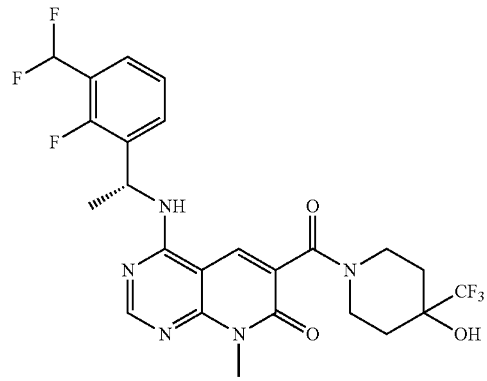 [SMILES: C[C@@H](Nc1ncnc2c1cc(C(=O)N1CCC(O)(C(F)(F)F)CC1)c(=O)n2C)c1cccc(C(F)F)c1F] | 544.4 |
| 26-51 | 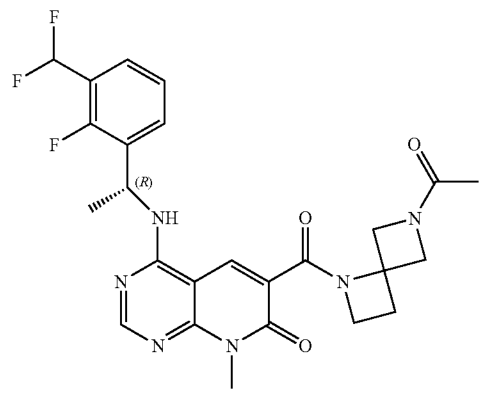 | 515.3 |
| 26-52 | 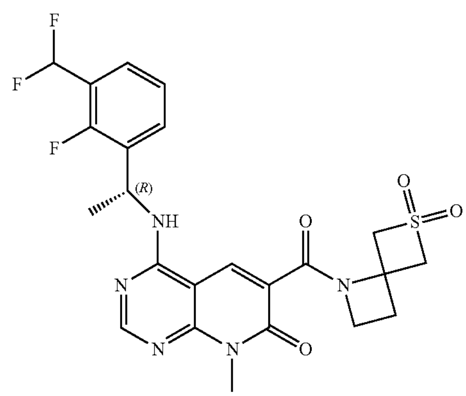 | 522.14 |
Example 27: Synthesis of 4-{[(1R)-1-[3-(difluoromethyl)-2-fluorophenyl]ethyl]amino}-2,8-dimethyl-6-[(morpholin-4-yl)meth-yl]-7H,8H-pyrido[2,3-d]pyrimidin-7-one
-continued
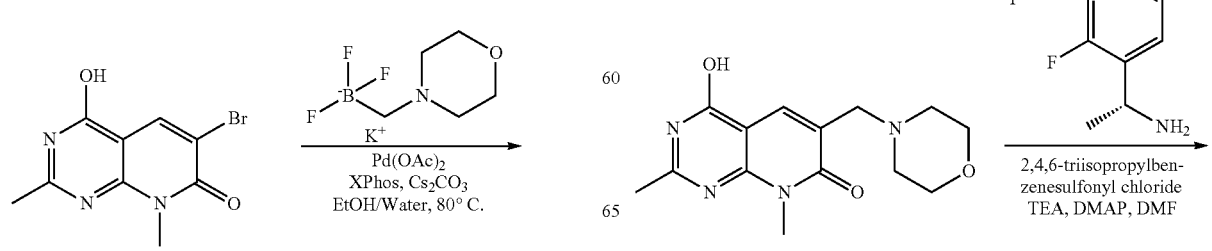

523

-continued

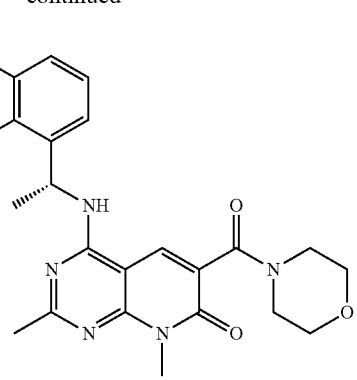

Step 1

A solution of 6-bromo-4-hydroxy-2,8-dimethyl-7H,8H-pyrido[2,3-d]pyrimidin-7-one (500 mg, 1.851 mmol) in aqueous ethanol (ethanol/water, 9:1, 20 mL) was degassed and potassium (morpholin-4-yl)methyltrifluoroborate (498 mg, 2.41 mmol), palladium(II) acetate (12 mg, 0.056 mmol), XPhos (44 mg, 0.093 mmol) and cesium carbonate (1.51 g, 4.63 mmol) were added. The mixture was stirred under inert atmosphere at 80° C. for 18 h. The mixture was filtered through a pad of Celite®, the solvent was removed under reduced pressure, and the residue was purified by column chromatography to give 4-hydroxy-2,8-dimethyl-6-[(morpholin-4-yl)methyl]-7H,8H-pyrido[2,3-d]pyrimidin-7-one (196 mg, 37% yield). LCMS (ESI): m/z: [M+H] calculated for $C_{14}H_{19}N_4O_3$: 291.1; found 291.1.

Step 2

To a solution of 4-hydroxy-2,8-dimethyl-6-[(morpholin-4-yl)methyl]-7H,8H-pyrido[2,3-d]-pyrimidin-7-one (300 mg, 1.11 mmol) in DMF (9.0 mL) 2,4,6-triisopropylbenzenesulfonyl chloride (673 mg, 2.2 mmol), TEA (952 µL, 5.00 mmol) and 4-dimethylaminopyridine (53.2 mg, 0.44 mmol) were added. The reaction mixture was stirred at rt for 1 h. (1R)-1-[3-(Difluoromethyl)-2-fluorophenyl]ethan-1-amine hydrochloride (330 mg, 1.50 mmol) was added and the mixture was stirred at rt for 18 h. The solvent was removed under reduced pressure and the crude product was purified by prep-HPLC to give 4-{[(1R)-1-[3-(difluoromethyl)-2-fluorophenyl]ethyl]amino}-2,8-dimethyl-6-[(morpholin-4-yl)meth-yl]-7H,8H-pyrido[2,3-d]pyrimidin-7-one (50 mg, 10% yield). LCMS (ESI): m/z: [M+H] calculated for $C_{23}H_{27}F_3N_5O_2$: 462.1; found 462.0. $^1$H NMR (300 MHz, methanol-$d_4$) δ ppm 8.26 (s, 1H), 7.57 (t, J=7.5 Hz, 2H), 7.45 (t, J=7.1 Hz, 1H), 7.21 (t, J=7.8 Hz, 1H), 7.00 (t, J=54.9 Hz, 1H), 5.77 (q, J=7.0 Hz, 1H), 3.71 (t, J=4.6 Hz, 4H), 3.65 (s, 3H), 3.49 (s, 2H), 2.55 (t, J=4.7 Hz, 4H), 2.37 (s, 3H), 1.64 (d, J=7.1 Hz, 3H).

524

Example 28: Synthesis of 4-(4-{[(1R)-1-[3-(difluoromethyl)-2-fluorophenyl]-ethyl]amino}-8-methyl-7-oxo-7H,8H-pyrido[2,3-d]pyrimidin-6-yl)-4-hydroxy-1λ$^6$-thiane-1,1-dione

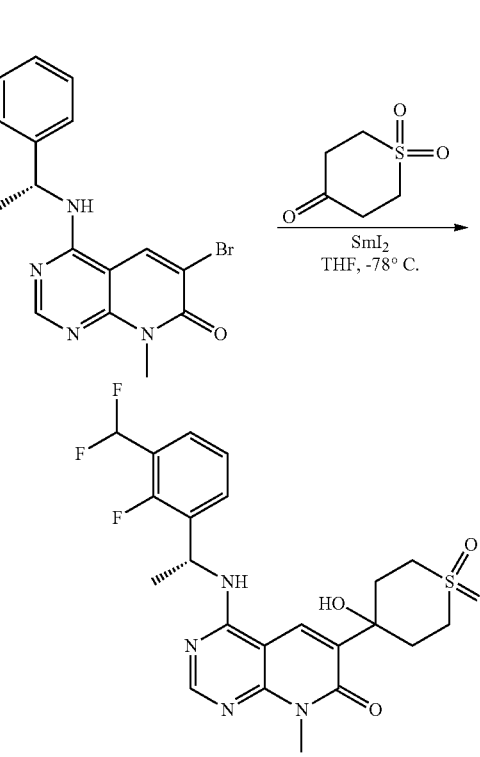

Step 1

To a solution of 6-bromo-4-{[(1R)-1-[3-(difluoromethyl)-2-fluorophenyl]ethyl]amino}-8-methyl-7H,8H-pyrido[2,3-d]pyrimidin-7-one (150 mg, 0.35 mmol) and tetrahydrothiopyran-4-one 1,1-dioxide (104 mg, 0.7 mmol) in THF (4.5 mL) at −78° C. was added a 0.1 M SmI$_2$ solution in THF (24.6 mL, 2.46 mmol). After 4 h stirring at −78° C. additional 0.1 M SmI$_2$ solution in THF (1.4 mL, 0.14 mmol) was added and the reaction mixture was stirred overnight at rt. The reaction was quenched with sat. aq. NH$_4$Cl and extracted with EtOAc. The organic layer was dried with Na$_2$SO$_4$, filtered, and the solvent was removed under reduced pressure. The residue was purified by prep-HPLC to give 4-(4-{[(1R)-1-[3-(difluoromethyl)-2-fluorophenyl]-ethyl]amino}-8-methyl-7-oxo-7H,8H-pyrido[2,3-d]pyrimidin-6-yl)-4-hydroxy-1λ$^6$-thiane-1, 1-dione (80 mg, 46% yield). LCMS (ESI): m/z: [M+H] calculated for $C_{22}H_{24}F_3N_4O_4S$: 497.1; found 497.0. $^1$H NMR (300 MHz, DMO-$d_6$) δ ppm 8.74-8.59 (m, 2H), 8.37 (s, 1H), 7.71-7.59 (m, 1H), 7.52 (t, J=7.1 Hz, 1H), 7.31 (t, J=7.7 Hz, 1H), 7.25 (t, J=54.4 Hz, 1H), 5.97 (s, 1H), 5.77 (t, J=7.0 Hz, 1H), 3.60 (s, 3H), 3.43 (d, J=13.1 Hz, 2H), 3.15-2.95 (m, 4H), 1.92 (d, J=13.9 Hz, 2H), 1.59 (d, J=7.0 Hz, 3H).

The following examples 28-1 to 28-9 shown in Table 9 were synthesized in the manner similar to Example 28.

TABLE 9
Examples 28-1 to 28-9
| Example # | Structure | Mass Found |
|---|---|---|
| 28-1 | 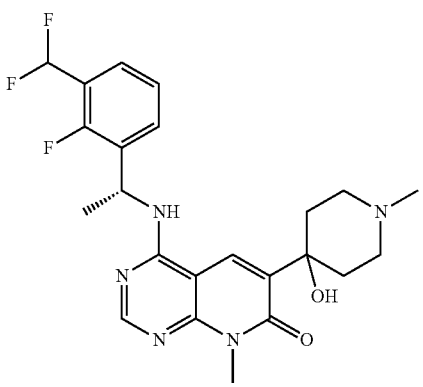 [SMILES: C[C@@H](Nc1ncnc2c1cc(C1(O)CCN(C)CC1)c(=O)n2C)c1cccc(C(F)F)c1F] | 462.2 |
| 28-2 | 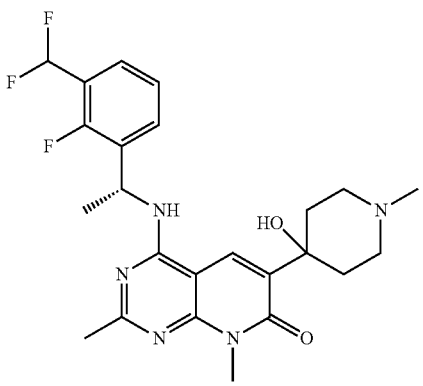 | 476.2 |
| 28-3 | 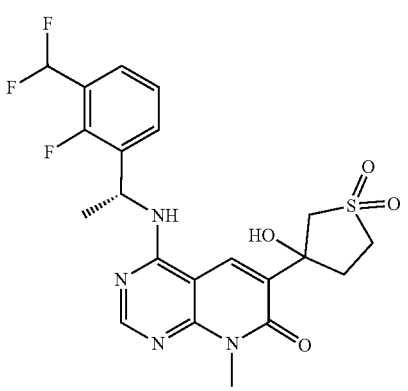 | 483.1 |
| 28-4 | 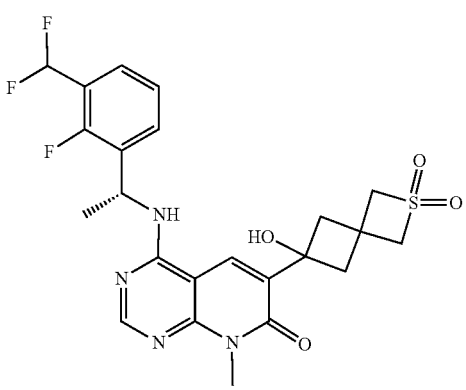 [SMILES: C[C@@H](Nc1ncnc2c1cc(C1(O)CC3(C1)CS(=O)(=O)C3)c(=O)n2C)c1cccc(C(F)F)c1F] | 507.04 |

TABLE 9-continued

Examples 28-1 to 28-9

| Example # | Structure | Mass Found |
|---|---|---|
| 28-5 | 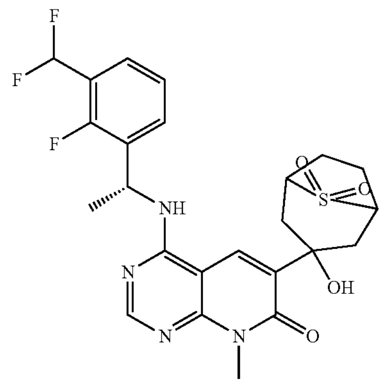 [SMILES: C[C@@H](Nc1ncnc2c1cc(C1(O)CC3CCC(C1)S3(=O)=O)c(=O)n2C)c1cccc(C(F)F)c1F] | 523.3 |
| 28-6 | 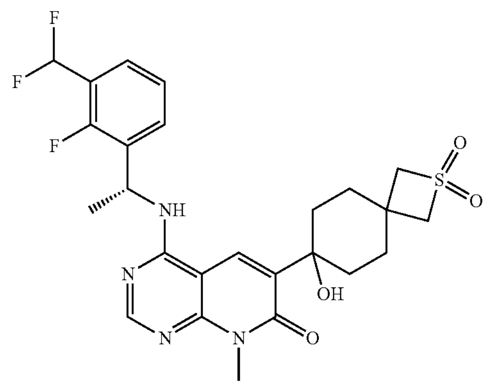 [SMILES: C[C@@H](Nc1ncnc2c1cc(C1(O)CCC3(CC1)CS(=O)(=O)C3)c(=O)n2C)c1cccc(C(F)F)c1F] | 537.0 |
| 28-7 | 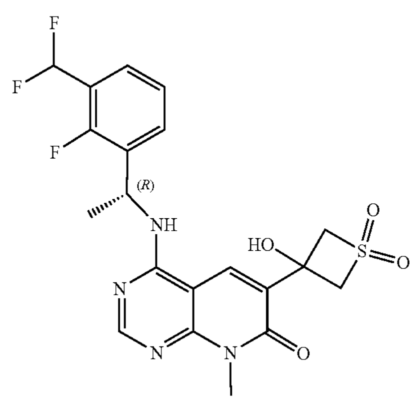 | 469.3 |
| 28-8 | 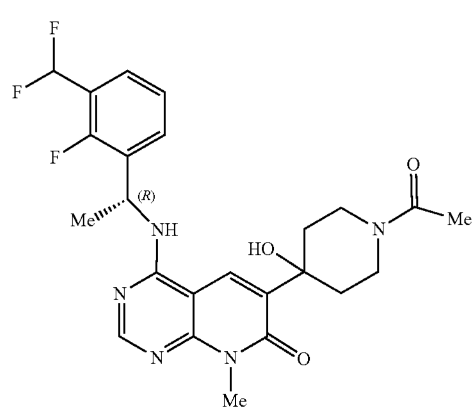 | 490.1 |

TABLE 9-continued

Examples 28-1 to 28-9

| Example # | Structure | Mass Found |
|---|---|---|
| 28-9 | 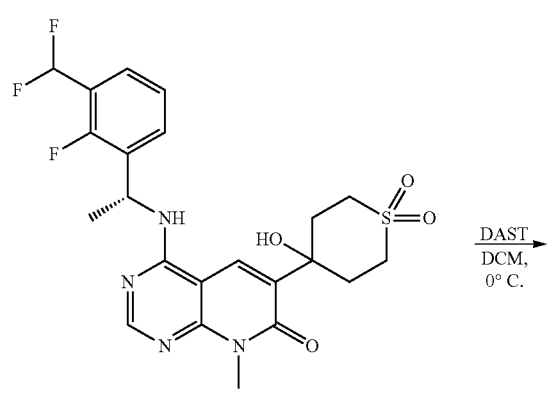 | 534.1 |

Example 29: Synthesis of 4-(4-{[(1R)-1-[3-(difluoromethyl)-2-fluorophenyl]ethyl]amino}-8-methyl-7-oxo-7H,8H-pyrido[2,3-d]-pyrimidin-6-yl)-4-fluoro-1λ⁶-thiane-1,1-dione Step 1

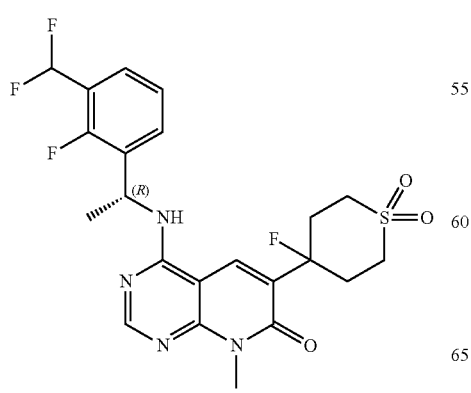

To a solution of 4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-hydroxy-1λ⁶-thiane-1,1-dione (150 mg, 0.3 mmol) in DCM (4.5 mL) at 0° C. under N₂ DAST (60 μL, 0.45 mmol) was added. The reaction mixture was stirred for 2 h at rt. Sat. aq. NaHCO₃ was added and the mixture was extracted with DCM. The organic layer was dried with Na₂SO₄, filtered, and the solvent was removed under reduced pressure. The crude product was purified by prep-HPLC to give 4-(4-{[(1R)-1-[3-(difluoromethyl)-2-fluorophenyl]ethyl]amino}-8-methyl-7-oxo-7H,8H-pyrido[2,3-d]-pyrimidin-6-yl)-4-fluoro-1λ⁶-thiane-1,1-dione (76 mg, 50% yield). LCMS (ESI): m/z: [M+H] calculated for $C_{22}H_{23}F_4N_4O_3S$: 499.1; found 499.1. ¹H NMR (300 MHz, DMSO-d₆) δ ppm 8.71 (d, J=7.2 Hz, 1H), 8.62 (s, 1H), 8.39 (s, 1H), 7.64 (t, J=7.6 Hz, 1H), 7.52 (t, J=7.1 Hz, 1H), 7.31 (t, J=7.7 Hz, 1H), 7.25 (t, J=54.4 Hz, 1H), 5.75 (p, J=7.0 Hz, 1H), 3.59 (s, 3H), 3.49-3.36 (m, 3H), 3.27-3.07 (m, 3H), 2.24-2.12 (m, 2H), 1.58 (d, J=7.0 Hz, 3H).

The following examples 29-1 to 29-15 shown in Table 10 were synthesized in the manner similar to Example 29.

TABLE 10

Examples 29-1 to 29-15

| Example # | Structure | Mass Found |
|---|---|---|
| 29-1 | 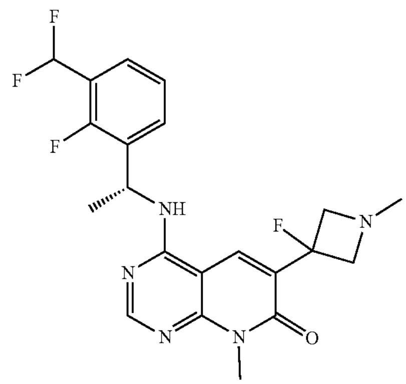 [SMILES: C[C@@H](Nc1ncnc2c1cc(C1(F)CN(C)C1)c(=O)n2C)c1cccc(C(F)F)c1F] | 436.1 |
| 29-2 | 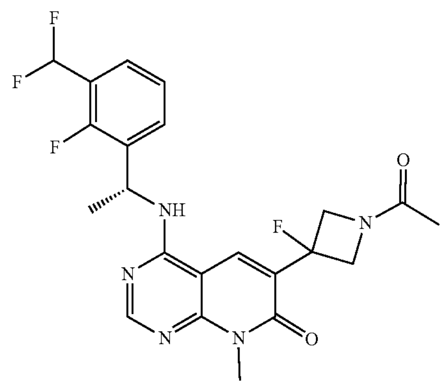 [SMILES: CC(=O)N1CC(F)(c2cc3c(N[C@H](C)c4cccc(C(F)F)c4F)ncnc3n(C)c2=O)C1] | 464.1 |
| 29-3 | 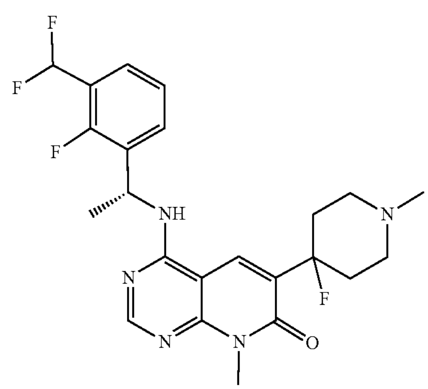 [SMILES: C[C@@H](Nc1ncnc2c1cc(C1(F)CCN(C)CC1)c(=O)n2C)c1cccc(C(F)F)c1F] | 464.2 |
| 29-4 | 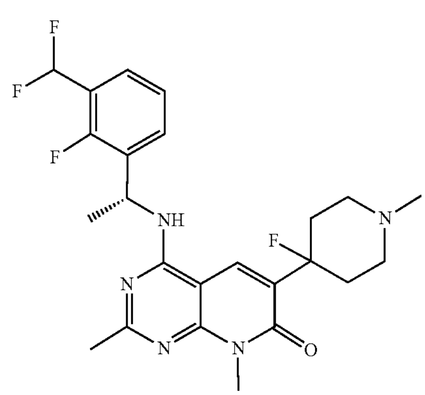 [SMILES: Cc1nc(N[C@H](C)c2cccc(C(F)F)c2F)c2cc(C3(F)CCN(C)CC3)c(=O)n(C)c2n1] | 478.2 |

TABLE 10-continued

Examples 29-1 to 29-15

| Example # | Structure | Mass Found |
|---|---|---|
| 29-5 | 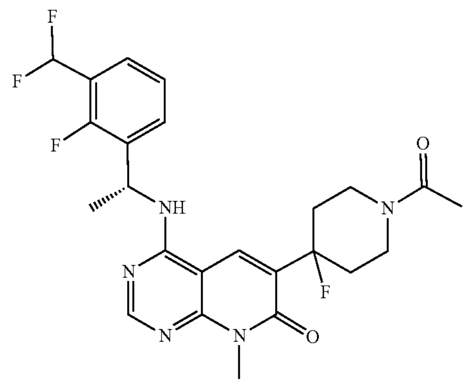 [SMILES: CC(=O)N1CCC(F)(c2cc3c(N[C@H](C)c4cccc(C(F)F)c4F)ncnc3n(C)c2=O)CC1] | 492.4 |
| 29-6 | 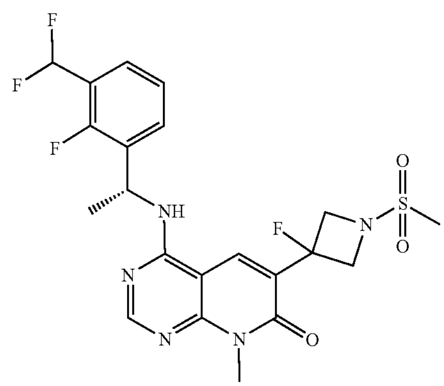 [SMILES: C[C@@H](Nc1ncnc2c1cc(C1(F)CN(S(C)(=O)=O)C1)c(=O)n2C)c1cccc(C(F)F)c1F] | 500.4 |
| 29-7 | 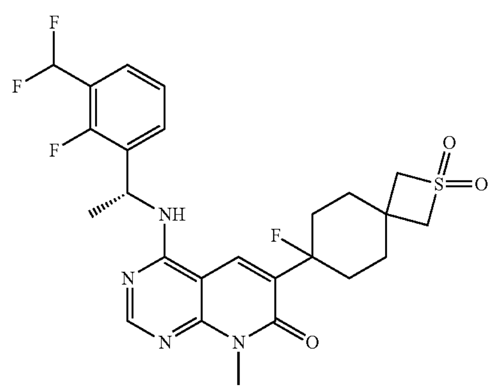 [SMILES: C[C@@H](Nc1ncnc2c1cc(C1(F)CCC3(CC1)CS(=O)(=O)C3)c(=O)n2C)c1cccc(C(F)F)c1F] | 539.11 |
| 29-8 | 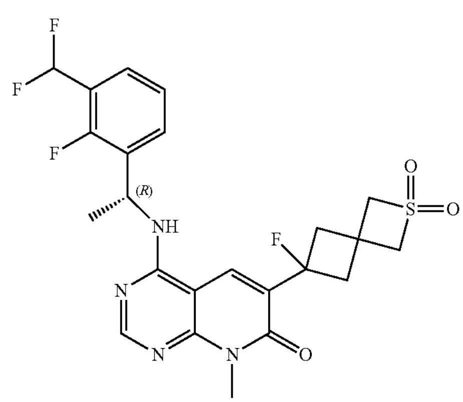 | 511.08 |

TABLE 10-continued
Examples 29-1 to 29-15
| Example # | Structure | Mass Found |
|---|---|---|
| 29-9 | 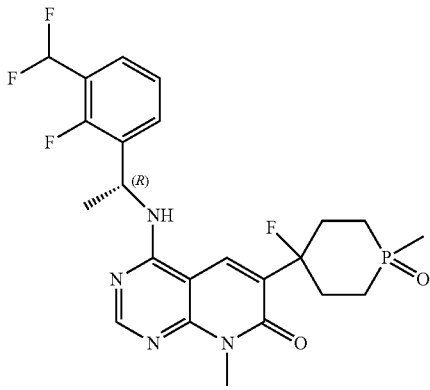 | 497.2 |
| 29-10 | 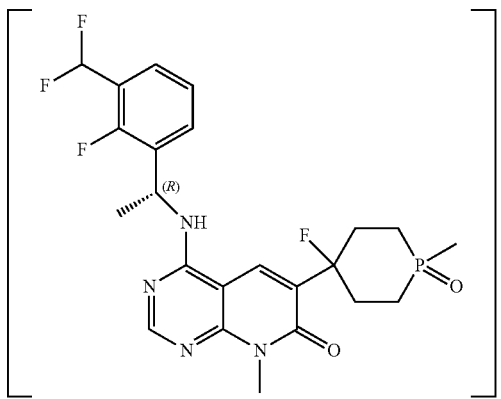 | 497.4 |
| 29-11 | 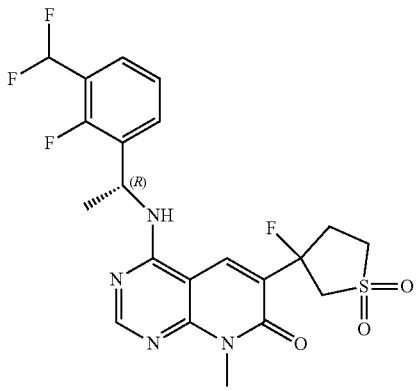 | 485.1 |

TABLE 10-continued
Examples 29-1 to 29-15
| Example # | Structure | Mass Found |
|---|---|---|
| 29-12 | 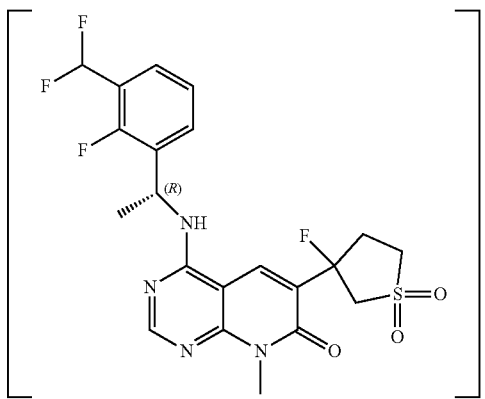 | 485.2 |
| 29-13 | 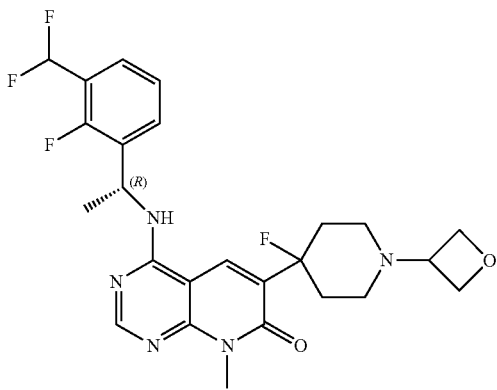 | 506.14 |
| 29-14 | 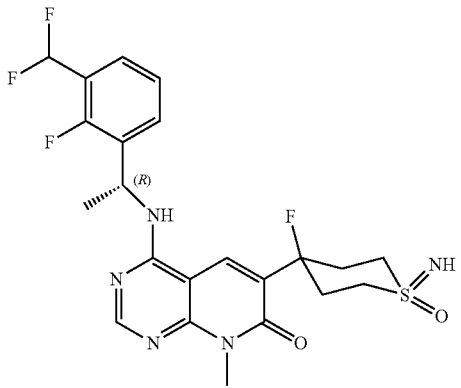 | 498.1 |

TABLE 10-continued

Examples 29-1 to 29-15

| Example # | Structure | Mass Found |
|---|---|---|
| 29-15 | 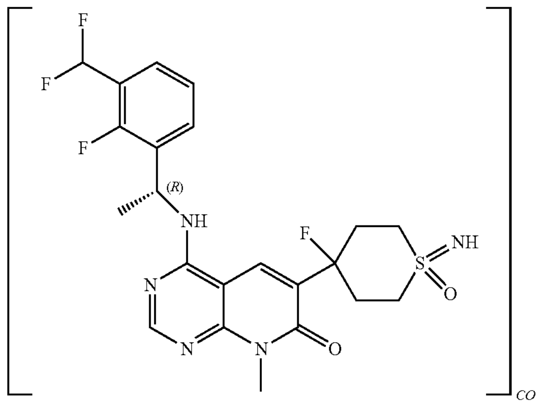 | 498.5 |

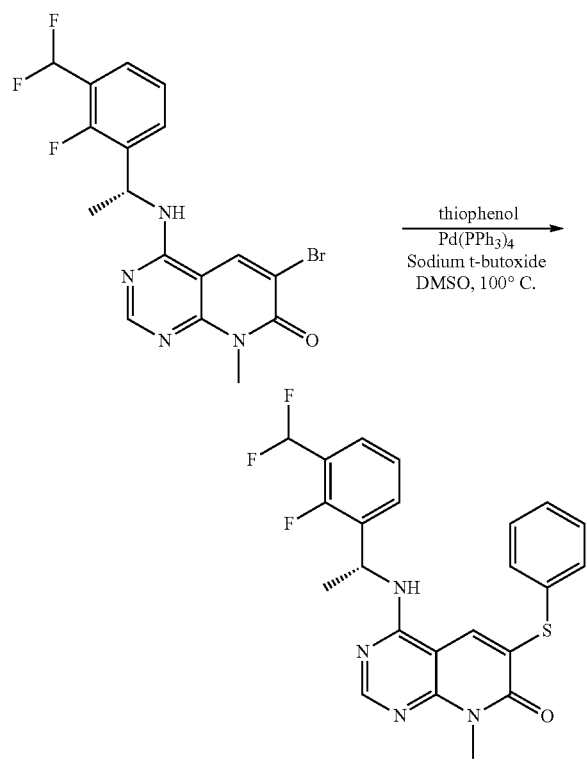

Example 30: Synthesis of 4-{[(1R)-1-[3-(difluoromethyl)-2-fluorophenyl]ethyl]amino}-8-methyl-6-(phenylsulfanyl)-7H,8H-pyrido[2,3-d]pyrimidin-7-one

Step 1

A solution of 6-bromo-4-{[(1R)-1-[3-(difluoromethyl)-2-fluorophenyl]ethyl]amino}-8-methyl-7H,8H-pyrido[2,3-d]pyrimidin-7-one (200 mg, 0.47 mmol) in DMSO (1.2 mL) was purged with argon for 15 min. Pd(PPh$_3$)$_4$ (43 mg, 0.037 mmol) was added and the reaction was stirred at 100° C. for 1 h. Then a solution of thiophenol (48 µL, 0.47 mmol) and sodium t-butoxide (90 mg, 0.94 mmol) in DMSO (5.0 mL) was added dropwise. The reaction mixture was stirred under N$_2$ overnight at 100° C. The mixture was filtered through a pad of Celite®, diluted with sat. aq. NaHCO$_3$, extracted with EtOAc, dried with anhydrous Na$_2$SO$_4$, filtered, and the solvent was removed under reduced pressure. The crude product was purified by prep-HPLC to give 4-{[(1R)-1-[3-(difluoromethyl)-2-fluorophenyl]ethyl]amino}-8-methyl-6-(phenylsulfanyl)-7H,8H-pyrido[2,3-d]pyrimidin-7-one (64 mg, 30% yield). LCMS (ESI): m/z: [M+H] calculated for C$_{23}$H$_2$F$_3$N$_4$OS: 457.1; found 457.1. $^1$H NMR (300 MHz, DMSO-d$_6$) δ ppm 8.85 (s, 1H), 8.53 (d, J=7.2 Hz, 1H), 8.38 (s, 1H), 7.61 (t, J=7.4 Hz, 1H), 7.51 (t, J=7.1 Hz, 1H), 7.39-7.17 (m, 6H), 7.24 (t, J=54.5 Hz, 1H), 5.79-5.62 (m, 1H), 3.57 (s, 3H), 1.54 (d, J=7.0 Hz, 3H).

Example 31: Synthesis of 6-(4-aminooxan-4-yl)-4-{[(1R)-1-[3-(difluoromethyl)-2-fluorophenyl]ethyl]amino}-8-methyl-7H,8H-pyrido-[2,3-d]pyrimidin-7-one

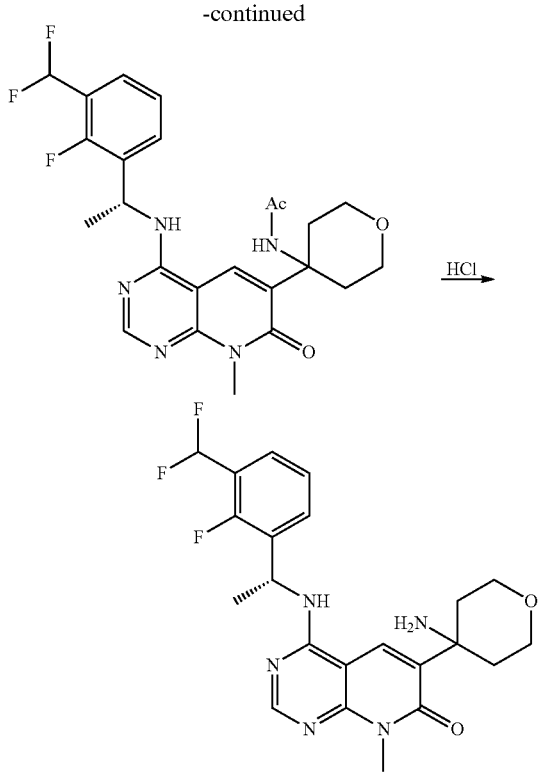

Step 1

A solution of 6-bromo-4-{[(1R)-1-[3-(difluoromethyl)-2-fluorophenyl]ethyl] amino}-8-methyl-7H,8H-pyrido[2,3-d]-pyrimidin-7-one (330 mg, 0.77 mmol) and tetrahydro-4H-pyran-4-one (140 μL, 1.54 mmol) in THF (10 mL) was cooled to −78° C. then 0.1M SmI$_2$ in THF (54 mL, 5.41 mmol) was added. The reaction mixture was stirred at −78° C. for one h then was warmed up to rt and quenched with sat. aq NH$_4$Cl, extracted with EtOAc, dried with anhydrous Na$_2$SO$_4$, filtered, and the solvent was removed under reduced pressure. The crude product was purified by column chromatography to give 4-{[(1R)-1-[3-(difluoromethyl)-2-fluorophenyl] ethyl]amino}-6-(4-hydroxyoxan-4-yl)-8-methyl-7H, 8H-pyri do[2,3-d]pyrimidin-7-one (254 mg, 73% yield). LCMS (ESI): m/z: [M+H] calculated for C$_{22}$H$_{24}$F$_3$N$_4$O$_3$: 449.2; found 449.3. $^1$H NMR (300 MHz, chloroform-d) δ ppm 8.46 (s, 1H), 7.64-7.41 (m, 3H), 7.22 (t, J=7.7 Hz, 1H), 6.92 (t, J=55.0 Hz, 1H), 5.98 (d, J=7.4 Hz, 1H), 5.76 (p, J=7.1 Hz, 1H), 5.60 (s, 1H), 4.07 (tt, J=11.3, 3.9 Hz, 2H), 3.90 (d, J=10.6 Hz, 2H), 3.76 (s, 2H), 2.20-1.95 (m, 4H), 1.71 (d, J=7.0 Hz, 3H).

Step 2

Concentrated sulfuric acid (1.5 mL, 27.4 mmol) was added dropwise to a suspension of 4-{[(1R)-1-[3-(difluoromethyl)-2-fluorophenyl]ethyl]amino}-6-(4-hydroxyoxan-4-yl)-8-methyl-7H,8H-pyrido[2,3-d]pyrimidin-7-one (225 mg, 0.5 mmol) in MeCN (4.3 mL) at 0° C. The solution was stirred at rt overnight and then poured onto ice, and the pH was adjusted to 8 with sat. aq. NaHCO$_3$. The solution was extracted with DCM, washed with brine, dried with anhydrous Na$_2$SO$_4$, filtered, and the solvent was removed under reduced pressure to give N-[4-(4-{[(1R)-1-[3-(difluoromethyl)-2-fluorophenyl]ethyl]amino}-8-methyl-7-oxo-7H, 8H-pyrido[2,3-d]pyrimidin-6-yl)oxan-4-yl]acetamide (220 mg, 98% yield). LCMS (ESI): m/z: [M+H] calculated for C$_{24}$H$_{27}$F$_3$N$_5$O$_3$: 490.2; found 490.1. $^1$H NMR (300 MHz, DMSO-d$_6$) δ ppm 8.49 (d, J=7.2 Hz, 1H), 8.33 (s, 1H), 8.19 (s, 1H), 8.01 (s, 1H), 7.63 (t, J=7.5 Hz, 1H), 7.52 (t, J=7.1 Hz, 1H), 7.32 (t, J=7.7 Hz, 1H), 7.25 (t, J=54.4 Hz, 1H), 5.79 (q, J=7.0 Hz, 1H), 3.74 (d, J=7.7 Hz, 4H), 3.55 (s, 3H), 2.72 (d, J=13.1 Hz, 2H), 2.02-1.83 (m, 2H), 1.80 (s, 3H), 1.61 (d, J=7.1 Hz, 3H).

Step 3

A solution of N-[4-(4-{[(1R)-1-[3-(difluoromethyl)-2-fluorophenyl]ethyl]amino}-8-methyl-7-oxo-7H,8H-pyrido[2,3-d]pyrimidin-6-yl)oxan-4-yl]acetamide (220 mg, 0.45 mmol) in 3.0 M aq. HCl (3.7 mL, 11.24 mmol) was heated at 100° C. overnight. The solution was poured onto ice and neutralized with sat. aq. NaHCO$_3$. The aqueous layer was extracted with DCM, dried with anhydrous Na$_2$SO$_4$, filtered, and the solvent was removed under reduced pressure. The crude product was purified by prep-HPLC to give 6-(4-aminooxan-4-yl)-4-{[(1R)-1-[3-(difluoromethyl)-2-fluorophenyl]ethyl]amino}-8-methyl-7H,8H-pyrido-[2,3-d]pyrimidin-7-one (38 mg, 18% yield). LCMS (ESI): m/z: [M+H] calculated for C$_{22}$H$_{25}$F$_3$N$_5$O$_2$: 448.2; found 448.1. $^1$H NMR (300 MHz, DMSO-d6) δ ppm 8.43 (d, J=7.3 Hz, 1H), 8.34 (s, 1H), 8.18 (s, 1H), 7.63 (t, J=7.5 Hz, 1H), 7.52 (t, J=7.3 Hz, 1H), 7.31 (t, J=7.7 Hz, 1H), 7.24 (t, J=54.4 Hz, 1H), 5.83-5.69 (m, 1H)), 3.95 (t, J=11.2 Hz, 2H), 3.71-3.64 (m, 2H), 3.59 (s, 3H), 2.13-1.96 (m, 4H), 1.87-1.73 (m, 2H), 1.60 (d, J=7.1 Hz, 3H).

The following examples 31-1 to 31-11 shown in Table 11 were synthesized in the manner similar to Example 31.

TABLE 11

Examples 31-1 to 31-11

| Example # | Structure | Mass Found |
|---|---|---|
| 31-1 | 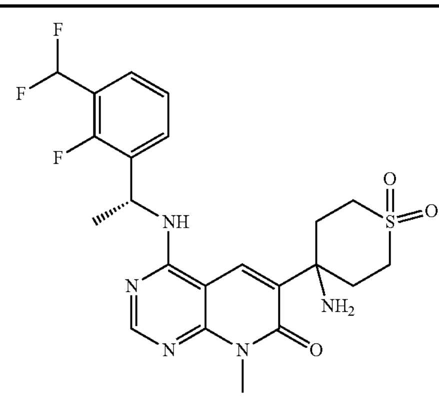 | 496.10 |

TABLE 11-continued

Examples 31-1 to 31-11

| Example # | Structure | Mass Found |
|---|---|---|
| 31-2 | 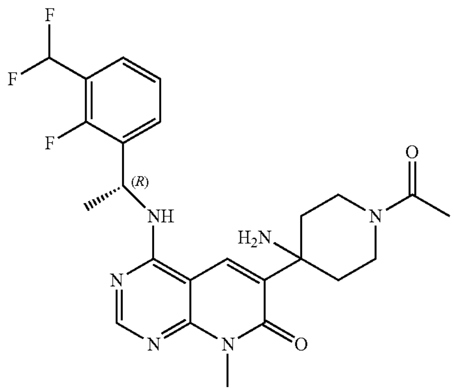 | 589.3 |
| 31-3 | 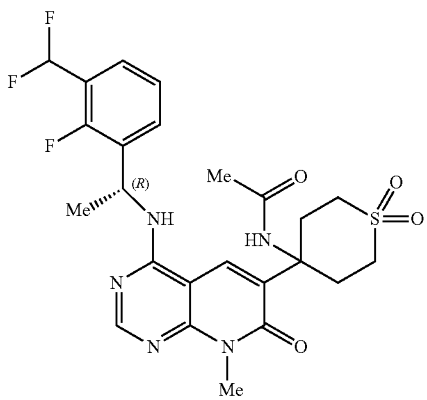 | 538.18 |
| 31-4 | 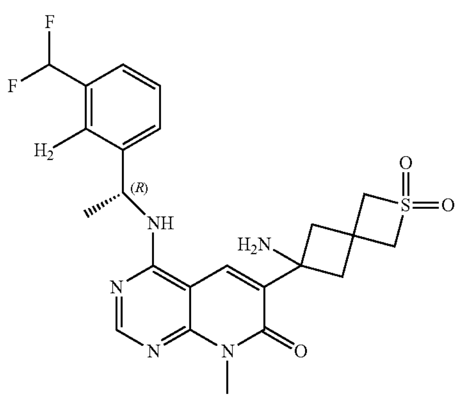 | 508.14 |
| 31-5 | 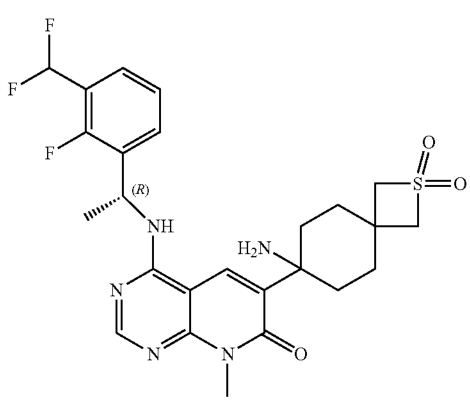 | 536.2 |

TABLE 11-continued

Examples 31-1 to 31-11

| Example # | Structure | Mass Found |
|---|---|---|
| 31-6 | 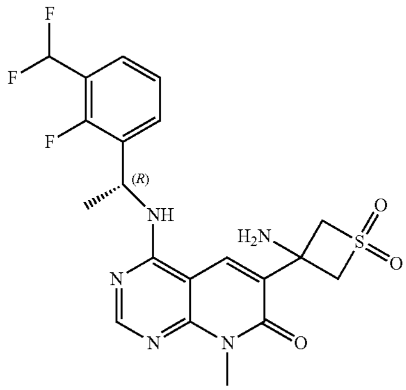 | 468.2 |
| 31-7 | 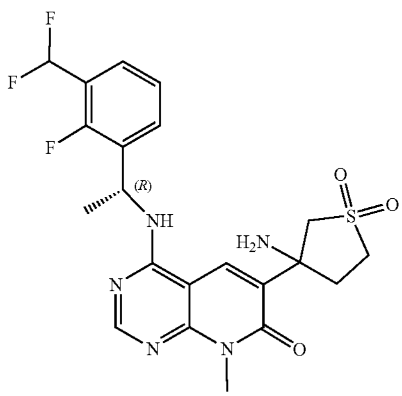 | 481.8 |
| 31-8 | 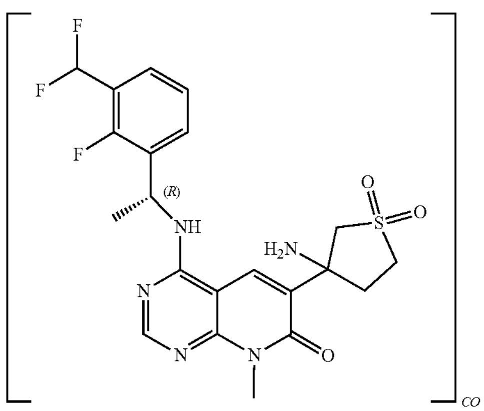 | 525.2 |
| 31-9 | 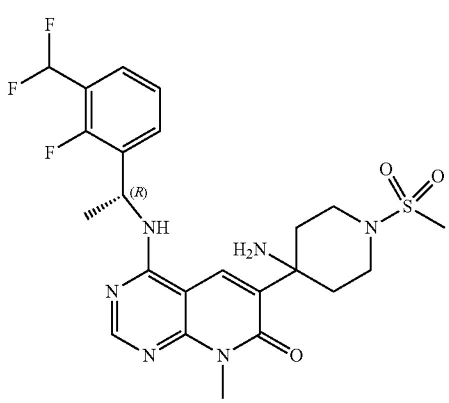 | 494.4 |

TABLE 11-continued

Examples 31-1 to 31-11

| Example # | Structure | Mass Found |
|---|---|---|
| 31-10 | 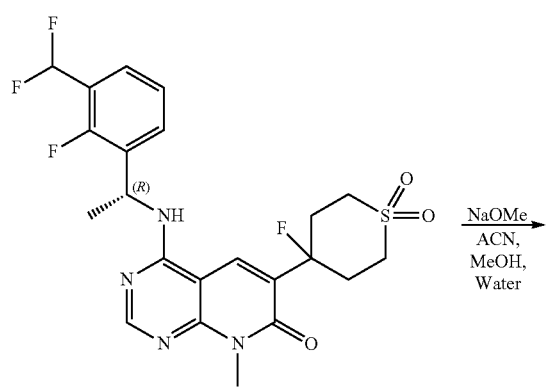 | 494.4 |
| 31-11 | 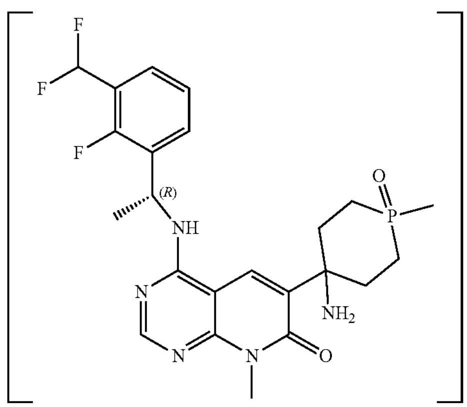 | 494.4 |

Example 32: Synthesis of 4-(4-{[(1R)-1-[3-(difluoro-methyl)-2-fluorophenyl]ethyl]amino}-8-methyl-7-oxo-7H,8H-pyrido[2,3-d]pyrimidin-6-yl)-4-methoxy-$\lambda^6$-thiane-1,1-dione

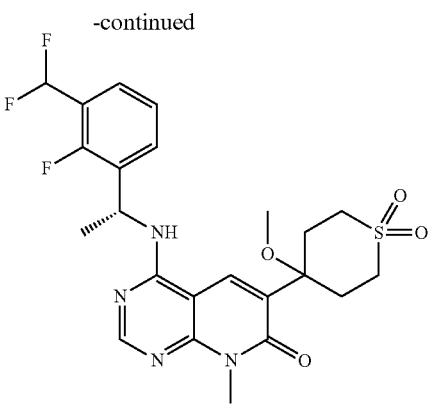

-continued

Step 1

To a solution of 4-(4-{[(R)-1-[3-(difluoromethyl)-2-fluorophenyl]ethyl]amino}-8-methyl-7-oxo-7H,8H-pyrido[2,3-d]pyrimidin-6-yl)-4-hydroxy-1$\lambda^6$-thiane-1,1-dione (190 mg, 0.38 mmol) in a mixture of ACN (4.75 mL), MeOH (2.85 mL) and water (0.95 mL) sodium methoxide (186 mg, 3.43 mmol) was added. The reaction stirred overnight. The reaction mixture was quenched with sat. aq. NH₄C₁, extracted with EtOAc, dried with anhydrous Na₂SO₄, filtered, and the solvent was removed under reduced pressure. The crude product was purified by prep-HPLC to give 4-(4-{[(R)-1-[3-(difluoro-methyl)-2-fluorophenyl]ethyl]amino}-8-methyl-7-oxo-7H,8H-pyrido[2,3-d]pyrimidin-6-yl)-4-methoxy-1λ⁶-thiane-1,1-dione (138 mg, 71% yield). LCMS (ESI): m/z: [M+H] calculated for $C_{23}H_{26}F_3N_4O_4S$: 511.2; found 511.0. 1H NMR (300 MHz, Methanol-d4) δ 8.36 (s, 1H), 8.33 (s, 1H), 7.58 (t, J=7.5 Hz, 1H), 7.48 (t, J=7.1 Hz, 1H), 7.23 (t, J=7.7 Hz, 1H), 7.00 (t, J=54.9 Hz, 1H), 5.79 (q, J=7.1 Hz, 1H), 3.69 (s, 3H), 3.53-3.38 (m, 2H), 3.21 (s, 3H), 3.07-2.77 (m, 4H), 2.77-2.58 (m, 2H), 1.66 (d, J=7.1 Hz, 3H).

The following examples 32-1 to 32-115 shown in Table 12 were synthesized in the manner similar to Example 32.

TABLE 12

| Examples 32-1 to 32-115 | | |
|---|---|---|
| Example # | Structure | Mass Found |
| 32-1 | | 504.2 |
| 32-2 | | 490.1 |
| 32-3 | | 476.2 |

TABLE 12-continued

Examples 32-1 to 32-115

| Example # | Structure | Mass Found |
|---|---|---|
| 32-4 | 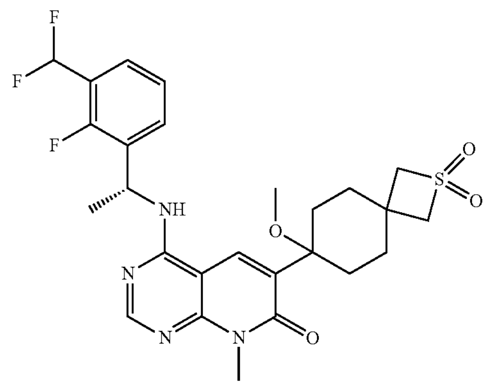 [SMILES: COC1(c2cc3c(N[C@H](C)c4cccc(C(F)F)c4F)ncnc3n(C)c2=O)CCC2(CC1)CS(=O)(=O)C2] | 551.2 |
| 32-5 | 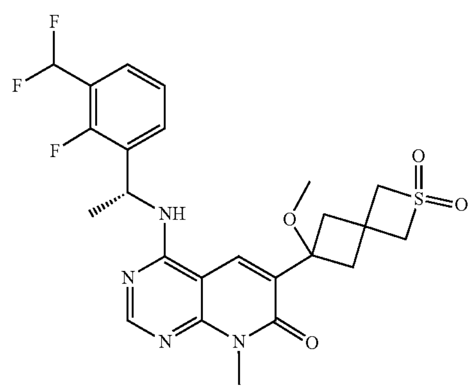 [SMILES: COC1(c2cc3c(N[C@H](C)c4cccc(C(F)F)c4F)ncnc3n(C)c2=O)CC2(C1)CS(=O)(=O)C2] | 523.2 |
| 32-6 | 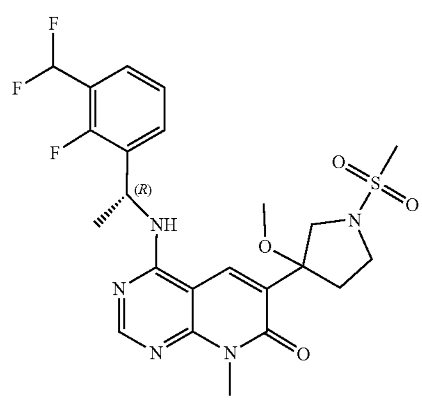 | 526.2 |
| 32-7 | 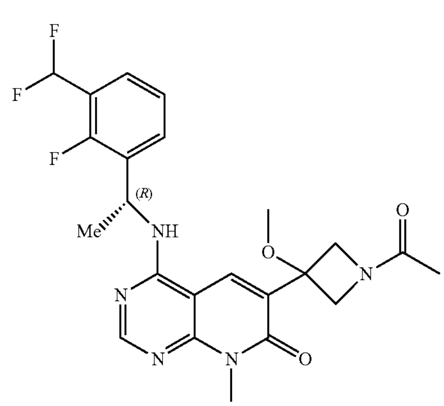 | 476.2 |

TABLE 12-continued

Examples 32-1 to 32-115

| Example # | Structure | Mass Found |
| --- | --- | --- |
| 32-8 | 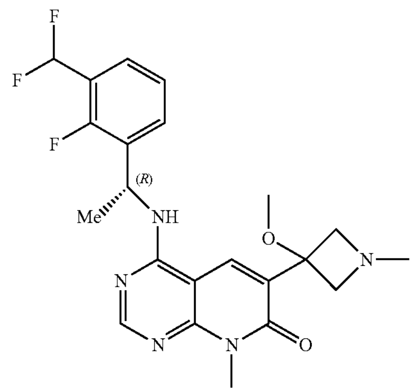 | 448.2 |
| 32-9 | 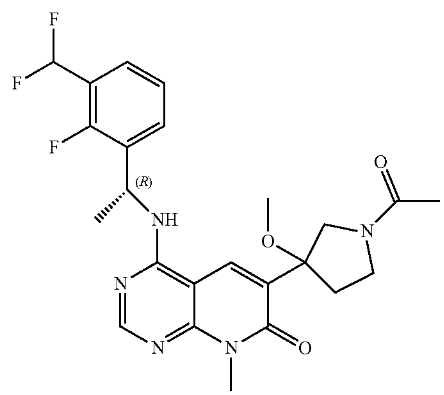 | 490.3 |
| 32-10 | 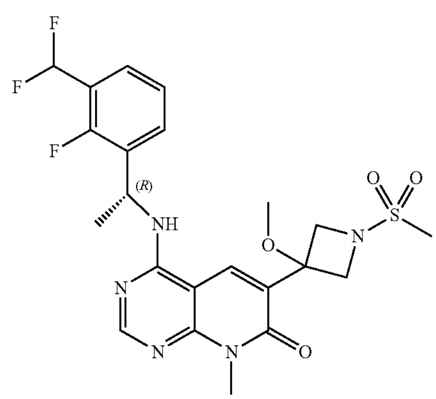 | 512.1 |
| 32-11 | 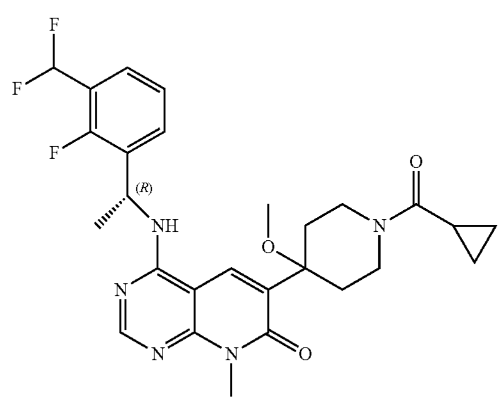 | 530 |

TABLE 12-continued

Examples 32-1 to 32-115

| Example # | Structure | Mass Found |
|---|---|---|
| 32-12 | 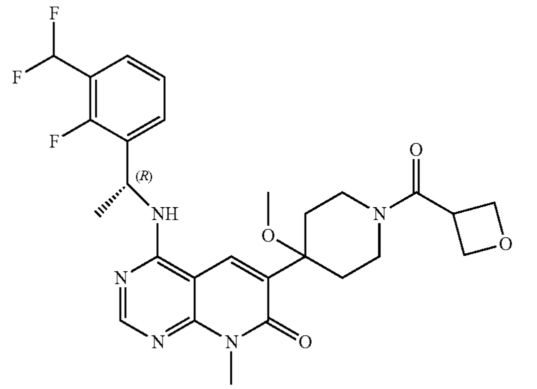 | 546.0 |
| 32-13 | 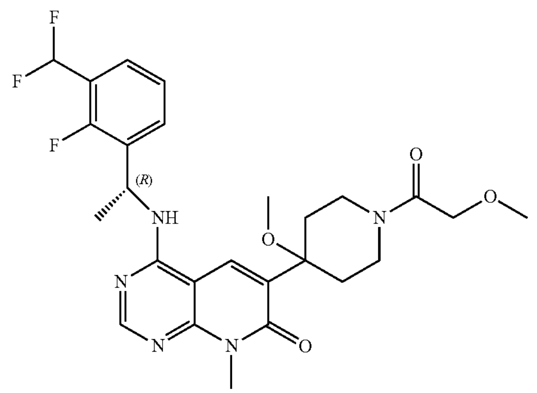 | 534.2 |
| 32-14 | 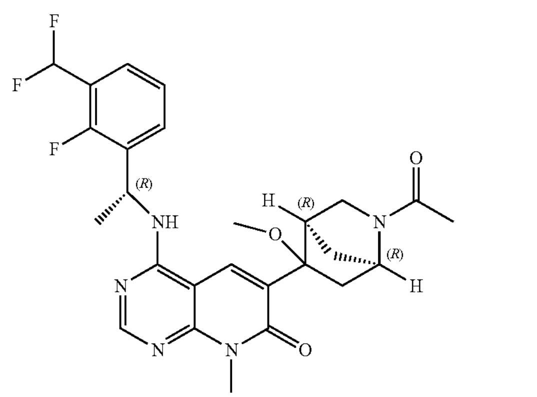 | 516.1 |
| 32-15 | 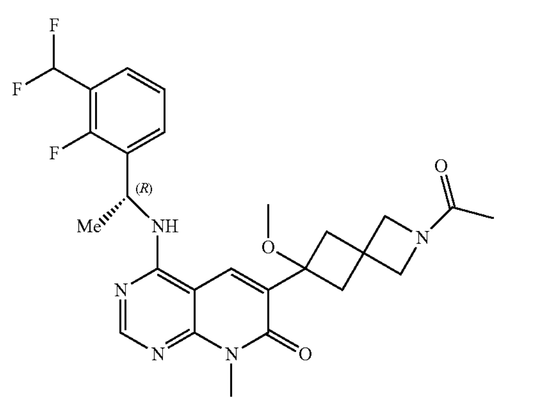 | 516.1 |

TABLE 12-continued

Examples 32-1 to 32-115

| Example # | Structure | Mass Found |
|---|---|---|
| 32-16 | 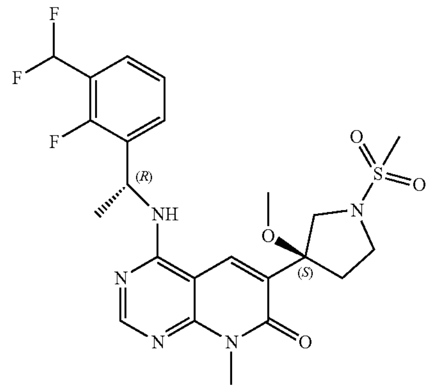 | 526.3 |
| 32-17 | 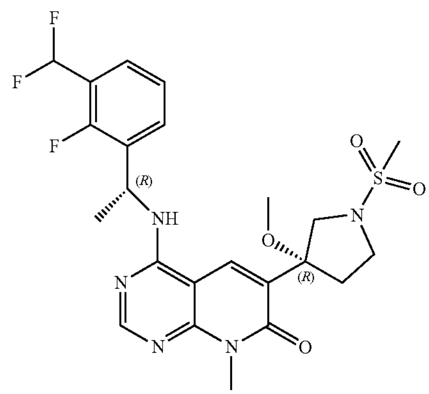 | 526.4 |
| 32-18 | 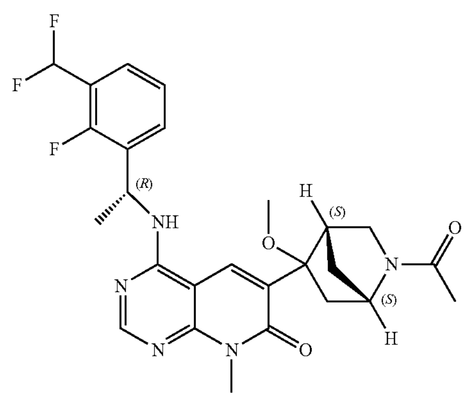 | 516.1 |
| 32-19 | 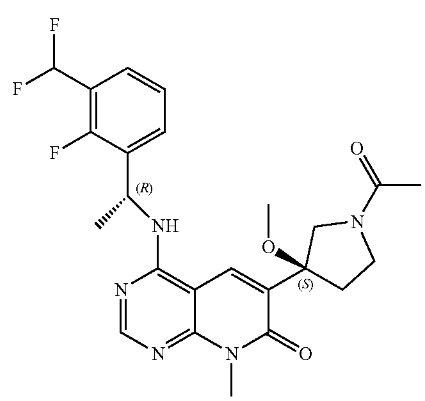 | 490.1 |

TABLE 12-continued

Examples 32-1 to 32-115

| Example # | Structure | Mass Found |
|---|---|---|
| 32-20 | 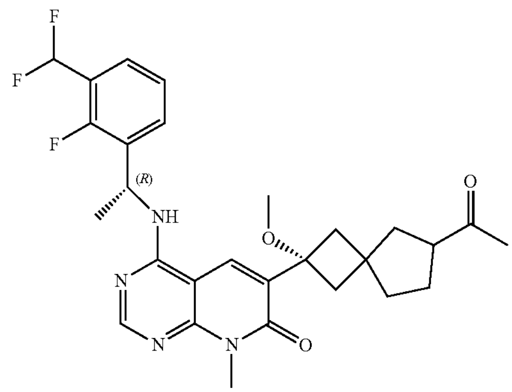 | 530.2 |
| 32-21 | 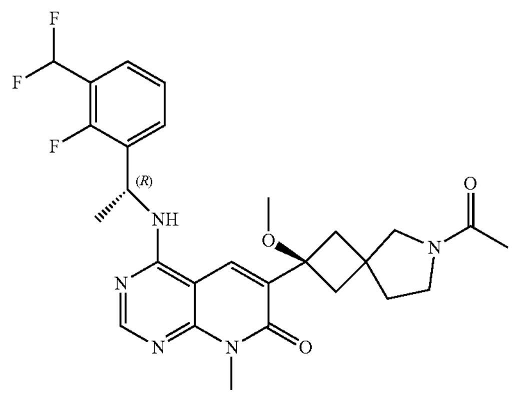 | 530.2 |
| 32-22 | 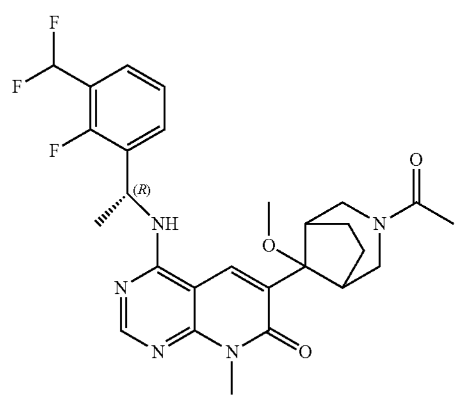 | 530.2 |
| 32-23 | 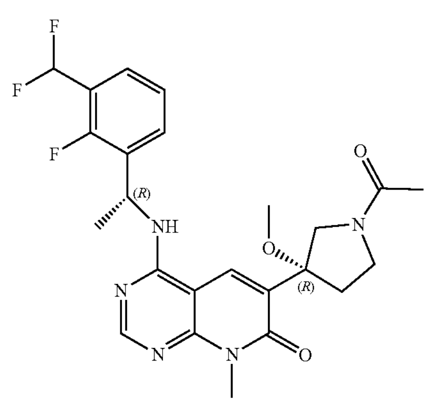 | 490.1 |

TABLE 12-continued

Examples 32-1 to 32-115

| Example # | Structure | Mass Found |
|---|---|---|
| 32-24 | 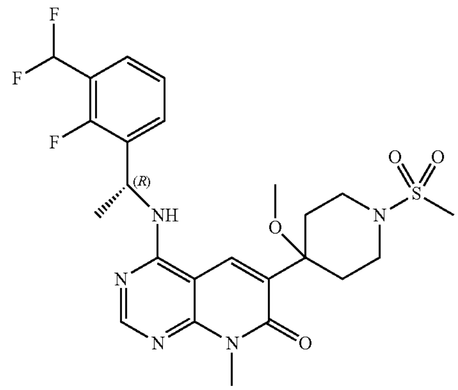 | 540.1 |
| 32-25 | 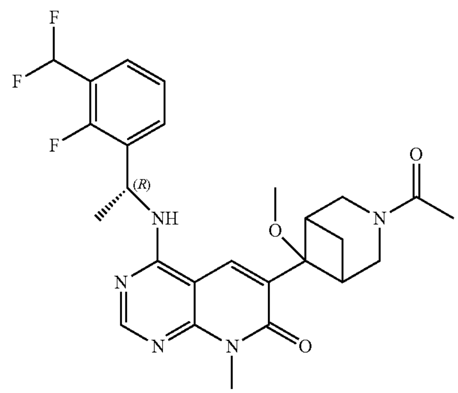 | 516.1 |
| 32-26 | 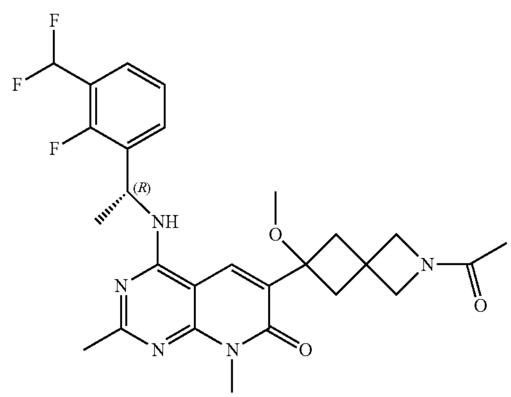 | 530.1 |
| 32-27 | 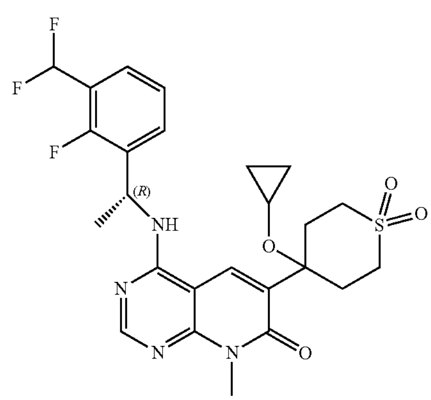 | 537.17 |

TABLE 12-continued

Examples 32-1 to 32-115

| Example # | Structure | Mass Found |
|---|---|---|
| 32-28 | 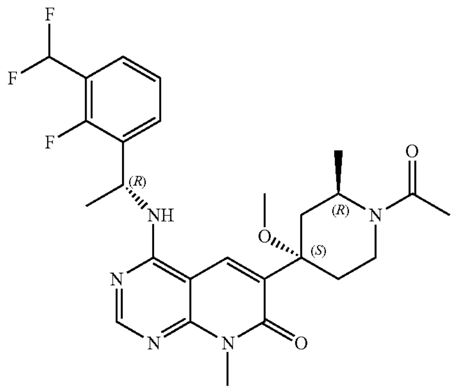 | 518.1 |
| 32-29 | 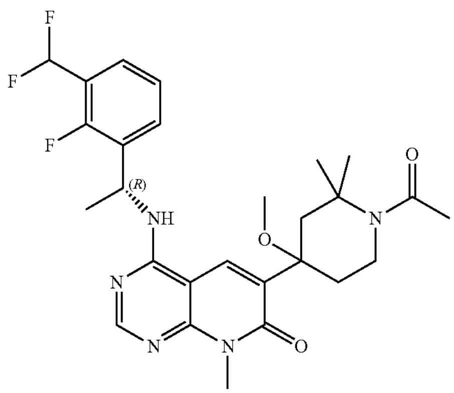 | 532.1 |
| 32-30 | 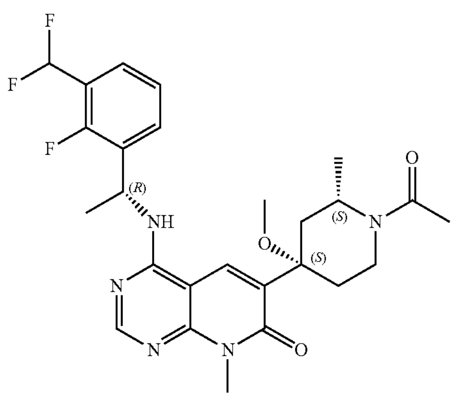 | 518.1 |
| 32-31 | 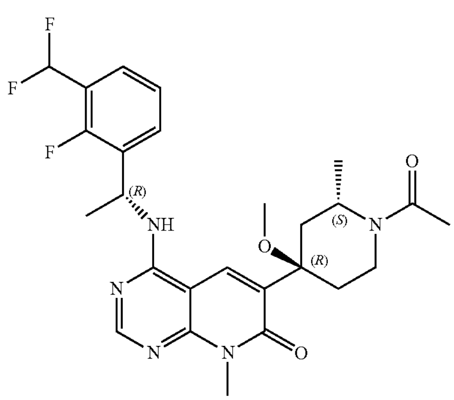 | 518.1 |

TABLE 12-continued
Examples 32-1 to 32-115
| Example # | Structure | Mass Found |
|---|---|---|
| 32-32 | 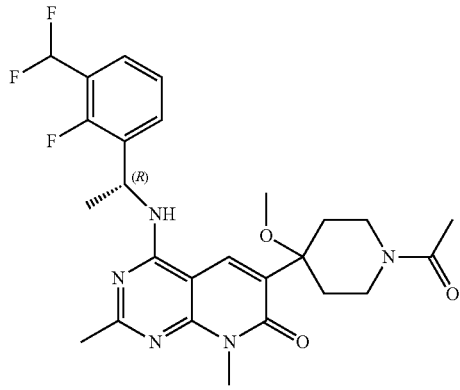 | 518.2 |
| 32-33 | 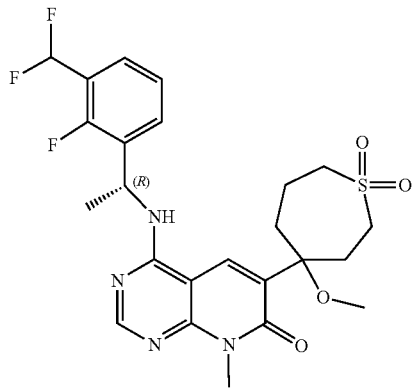 | 525.2 |
| 32-34 | 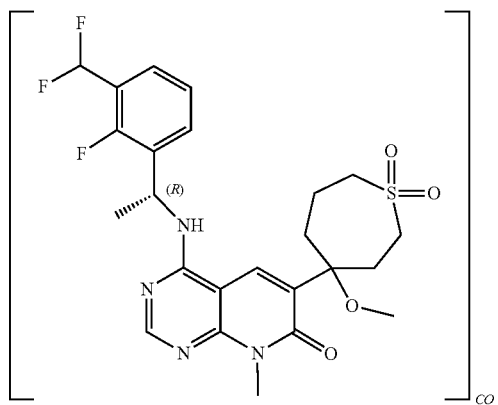 | 525.2 |

TABLE 12-continued

Examples 32-1 to 32-115

| Example # | Structure | Mass Found |
|---|---|---|
| 32-35 | 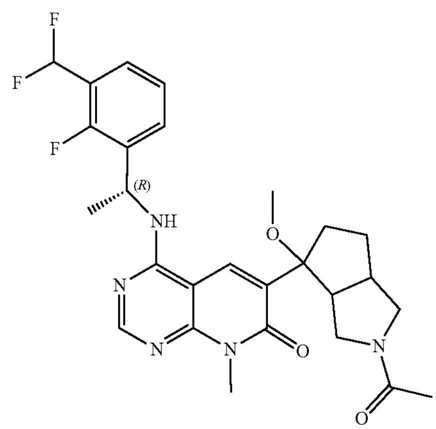 | 530.1 |
| 32-36 | 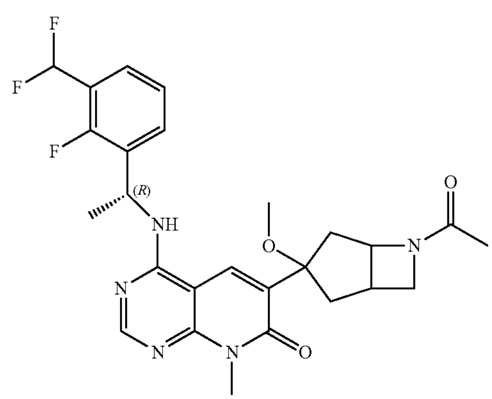 | 516.1 |
| 32-37 | 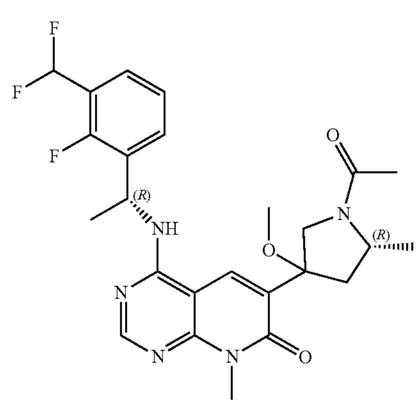 | 504.1 |

TABLE 12-continued
Examples 32-1 to 32-115
| Example # | Structure | Mass Found |
|---|---|---|
| 32-38 | 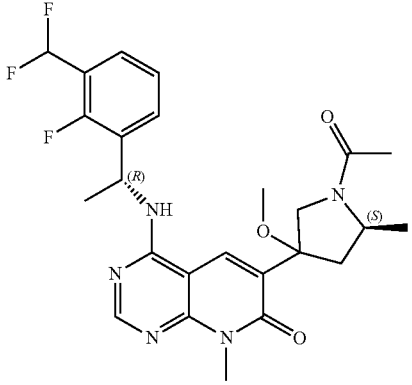 | 504.1 |
| 32-39 | 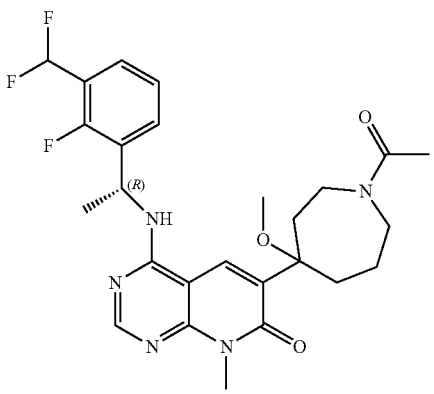 | 518.2 |
| 32-40 | 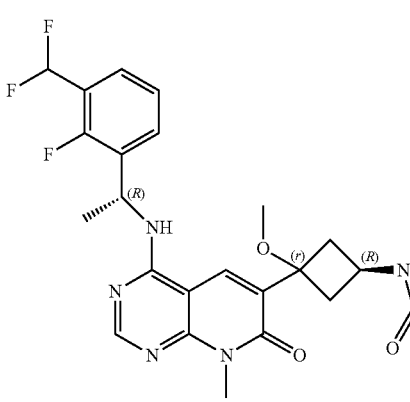 | 504.1 |
| 32-41 | 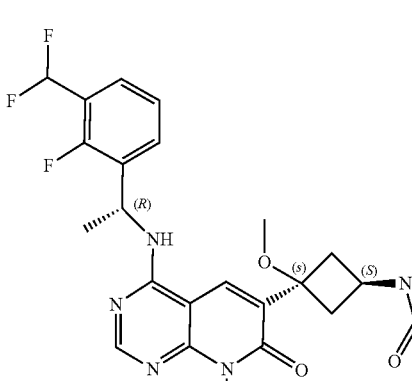 | 504.1 |

TABLE 12-continued

Examples 32-1 to 32-115

| Example # | Structure | Mass Found |
|---|---|---|
| 32-42 | 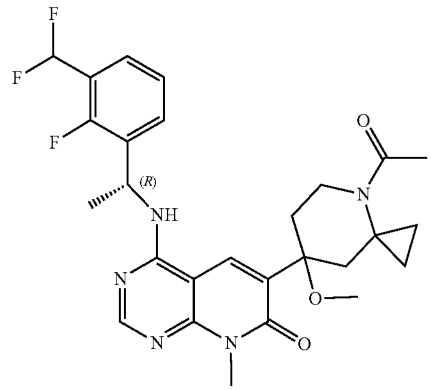 | 530.1 |
| 32-43 | 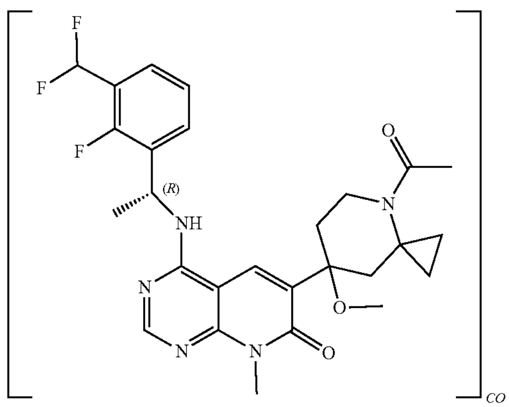 | 530.1 |
| 32-44 | 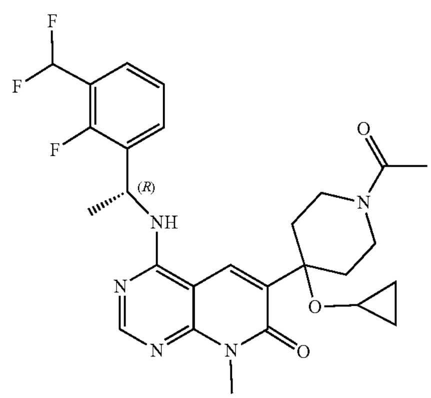 | 530 |
| 32-45 | 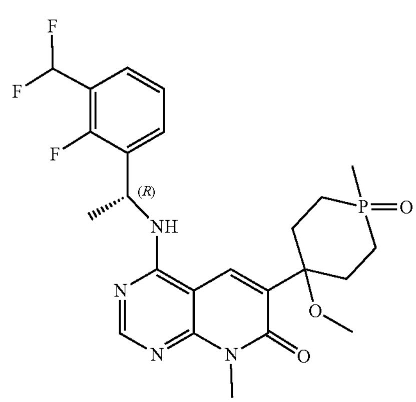 | 509.2 |

TABLE 12-continued

Examples 32-1 to 32-115

| Example # | Structure | Mass Found |
|---|---|---|
| 32-46 | 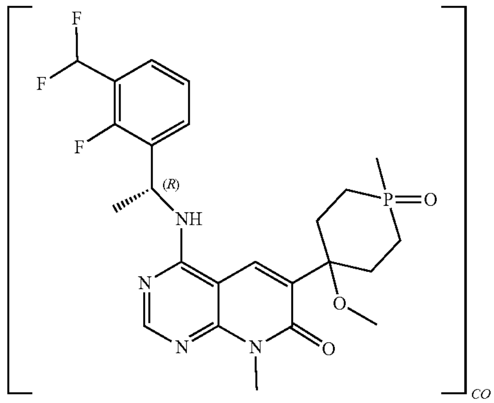 | 509.1 |
| 32-47 | 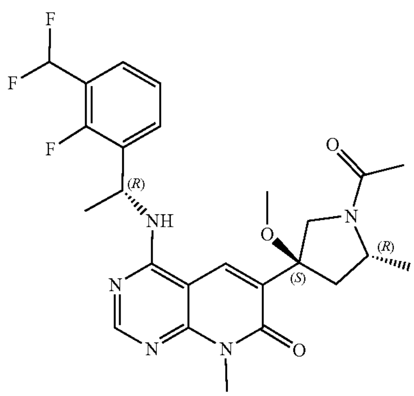 | 504.1 |
| 32-48 | 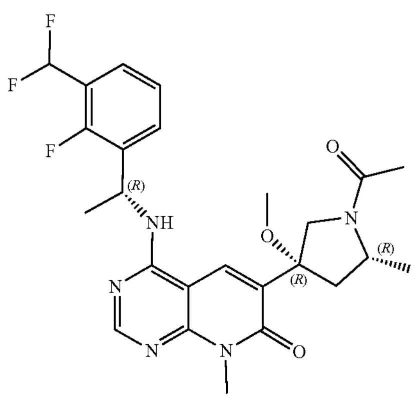 | 504.1 |
| 32-49 | 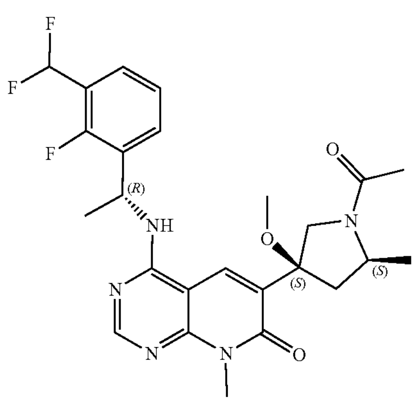 | 504.1 |

TABLE 12-continued

Examples 32-1 to 32-115

| Example # | Structure | Mass Found |
|---|---|---|
| 32-50 | 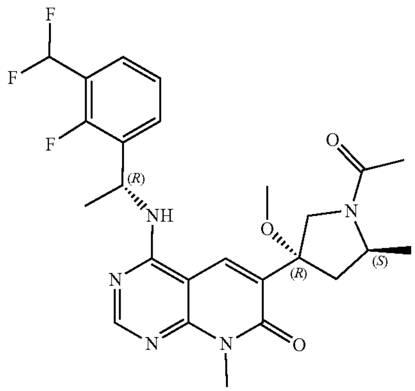 | 504.1 |
| 32-51 | 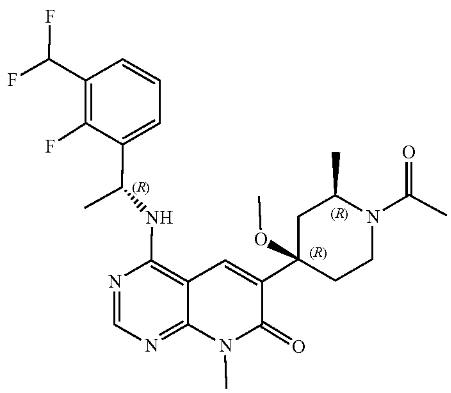 | 518.1 |
| 32-52 | 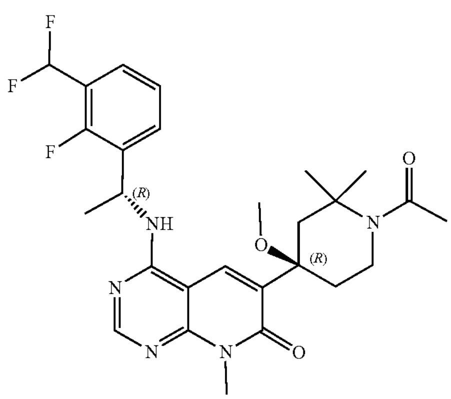 | 532.1 |
| 32-53 | 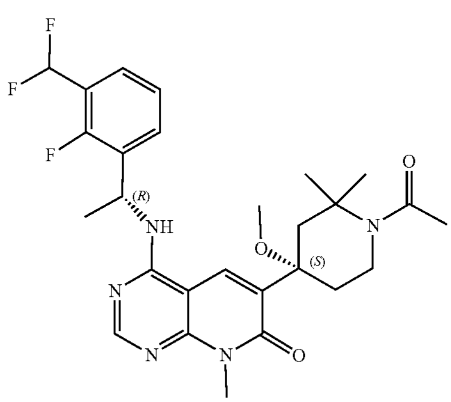 | 532.1 |

TABLE 12-continued

Examples 32-1 to 32-115

| Example # | Structure | Mass Found |
|---|---|---|
| 32-54 | 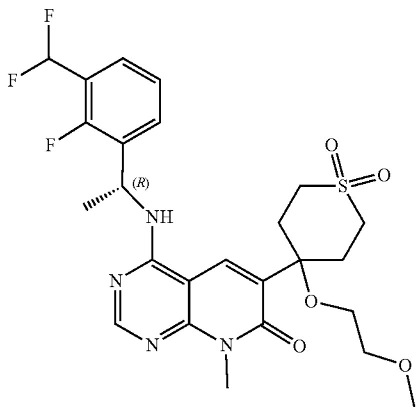 | 555.2 |
| 32-55 | 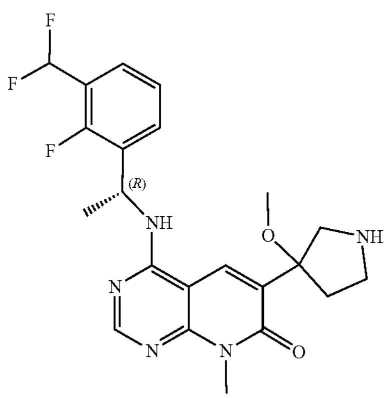 | 448.1 |
| 32-56 | 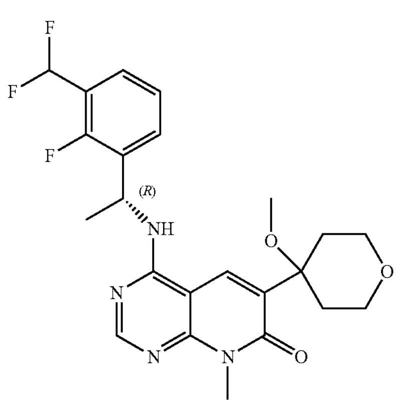 | 463.1 |

TABLE 12-continued

Examples 32-1 to 32-115

| Example # | Structure | Mass Found |
|---|---|---|
| 32-57 | 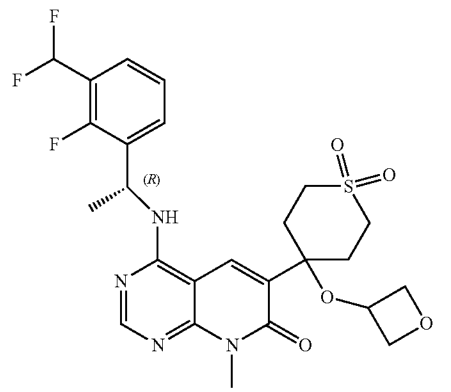 | 553.17 |
| 32-58 | 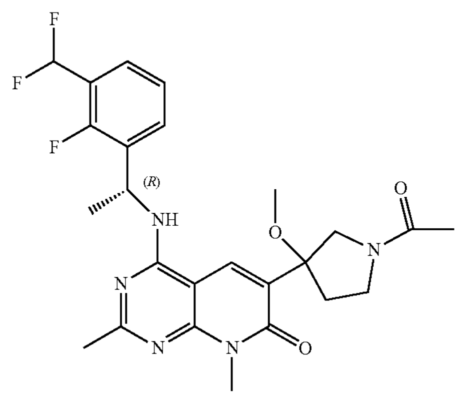 | 504.1 |
| 32-59 | 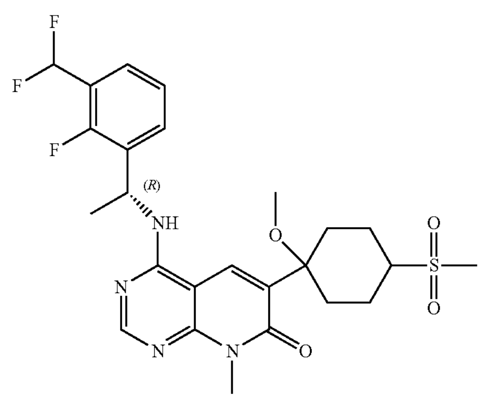 | 539.1 |
| 32-60 | 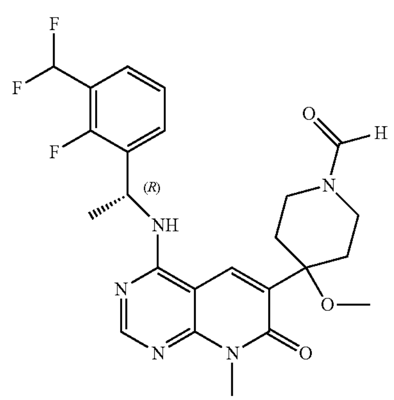 | 490.2 |

TABLE 12-continued

Examples 32-1 to 32-115

| Example # | Structure | Mass Found |
|---|---|---|
| 32-61 | 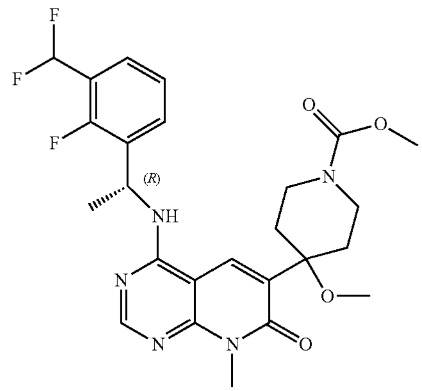 | 520.2 |
| 32-62 | 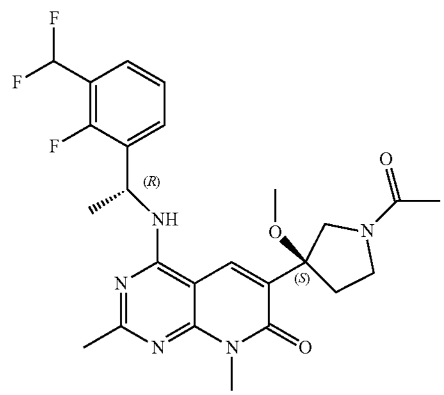 | 504.1 |
| 32-63 | 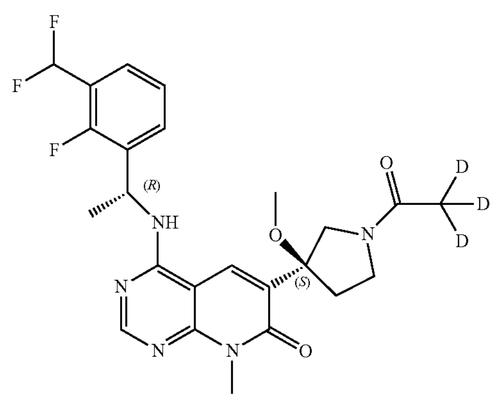 | 493.1 |
| 32-64 | 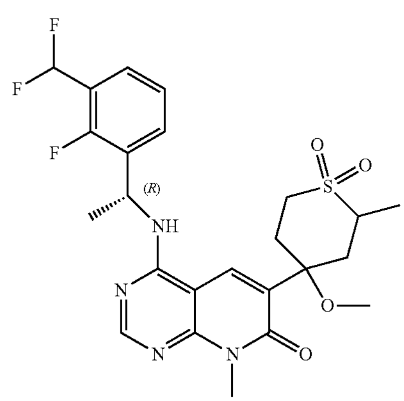 | 525.2 |

TABLE 12-continued

Examples 32-1 to 32-115

| Example # | Structure | Mass Found |
|---|---|---|
| 32-65 | 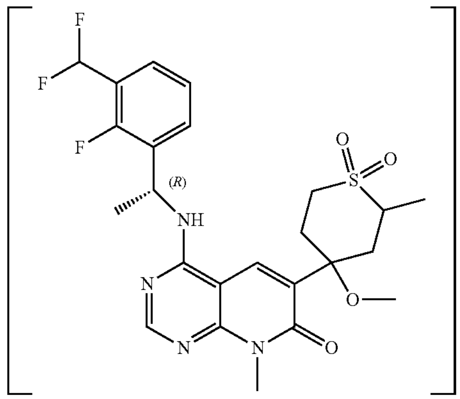 | 525.31 |
| 32-66 | 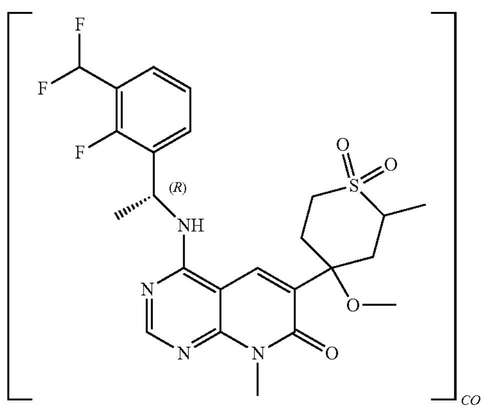 | 525.05 |
| 32-67 | 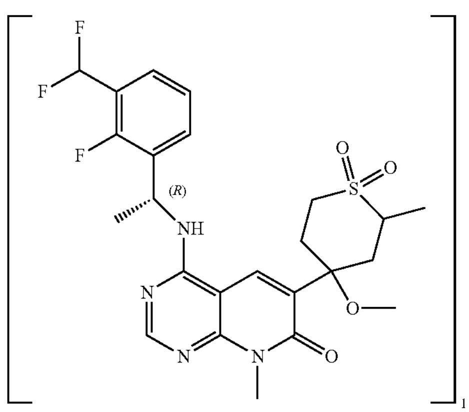 | 525.32 |

TABLE 12-continued

Examples 32-1 to 32-115

| Example # | Structure | Mass Found |
|---|---|---|
| 32-68 | 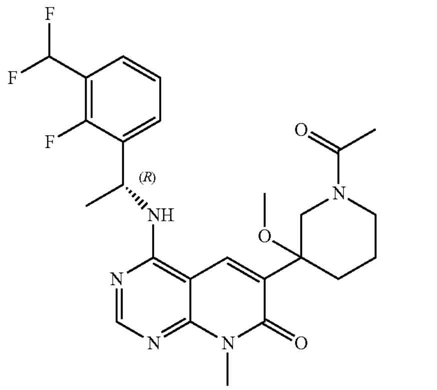 | 504.1 |
| 32-69 | 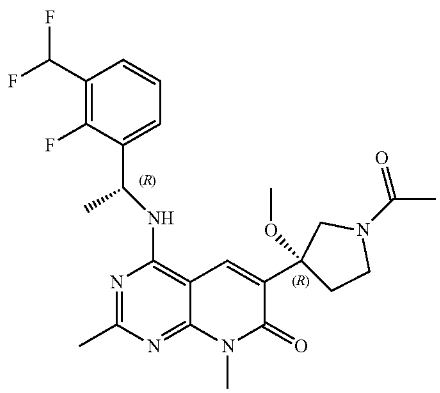 | 504.1 |
| 32-70 | 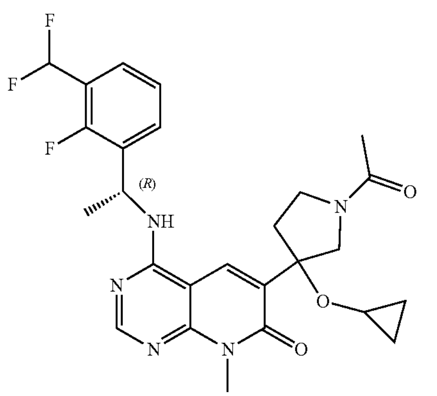 | 516.2 |
| 32-71 | 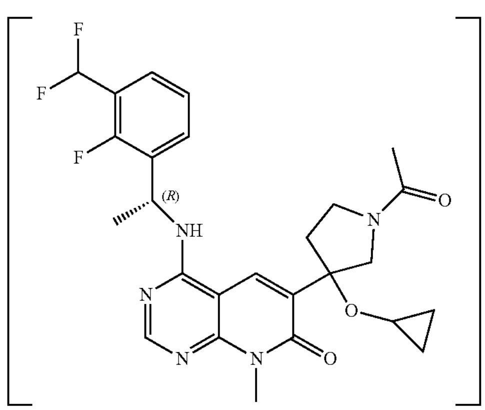 | 516.2 |

TABLE 12-continued

Examples 32-1 to 32-115

| Example # | Structure | Mass Found |
|---|---|---|
| 32-72 | 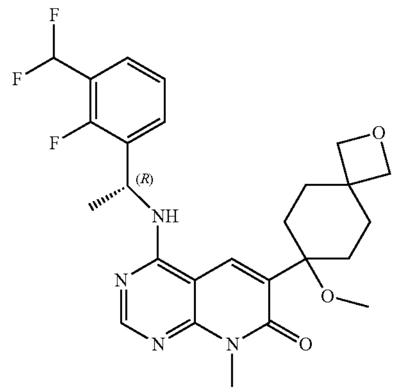 | 503.19 |
| 32-73 | 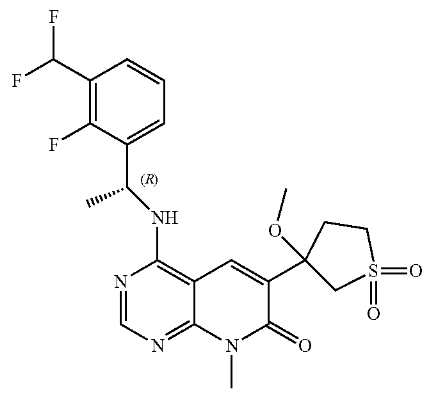 | 497.2 |
| 32-74 | 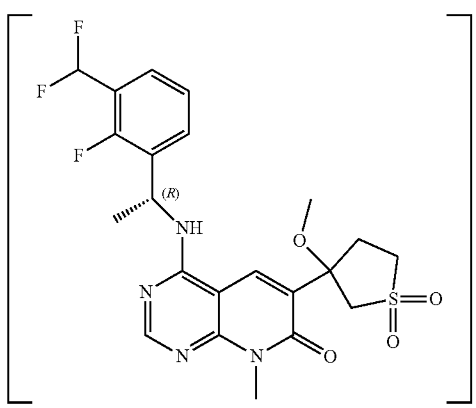 | 497.2 |
| 32-75 | 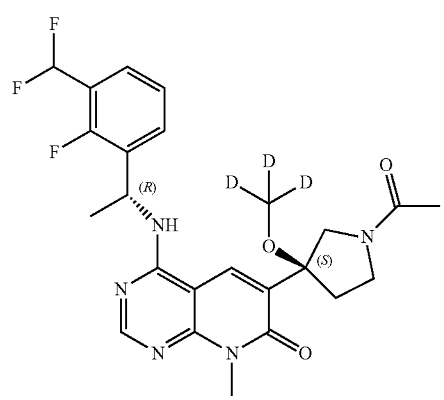 | 493.1 |

TABLE 12-continued

Examples 32-1 to 32-115

| Example # | Structure | Mass Found |
|---|---|---|
| 32-76 | 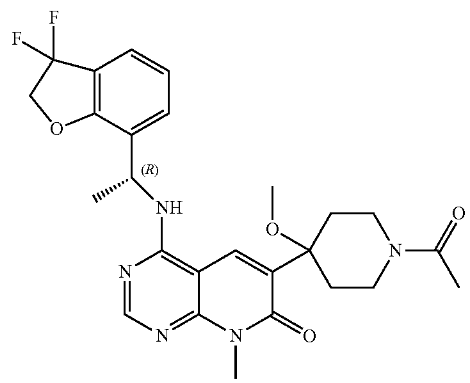 | 514.1 |
| 32-77 | 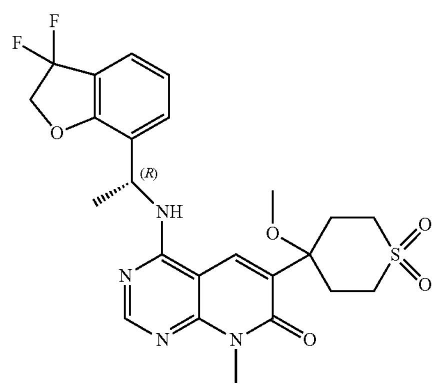 | 521.1 |
| 32-78 | 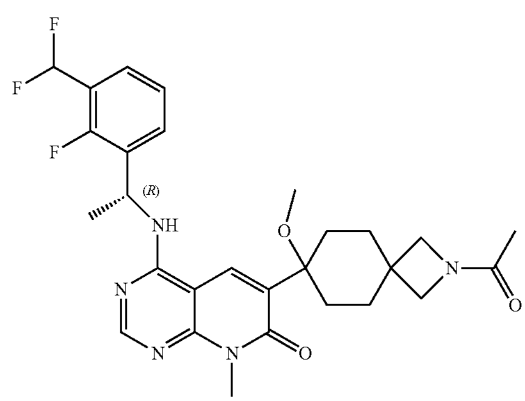 | 544.2 |
| 32-79 | 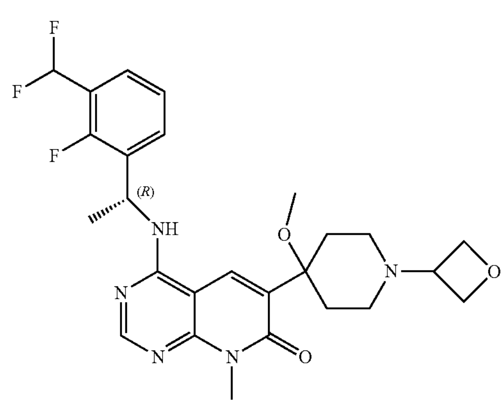 | 518.18 |

TABLE 12-continued

Examples 32-1 to 32-115

| Example # | Structure | Mass Found |
|---|---|---|
| 32-80 | 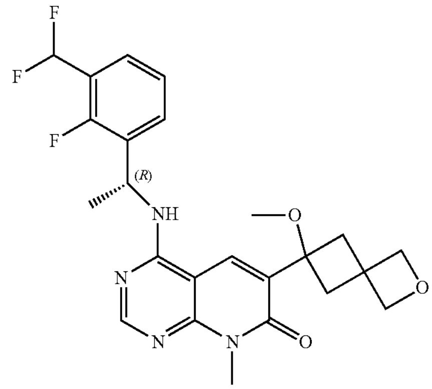 | 475.1 |
| 32-81 | 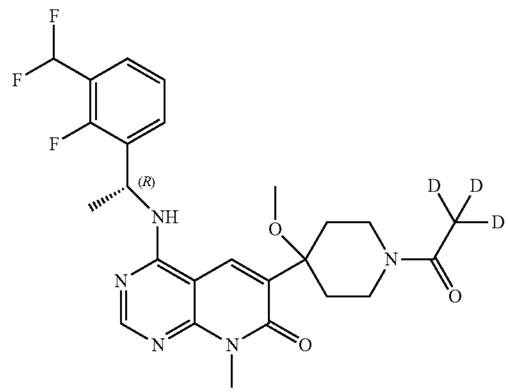 | 507.1 |
| 32-82 | 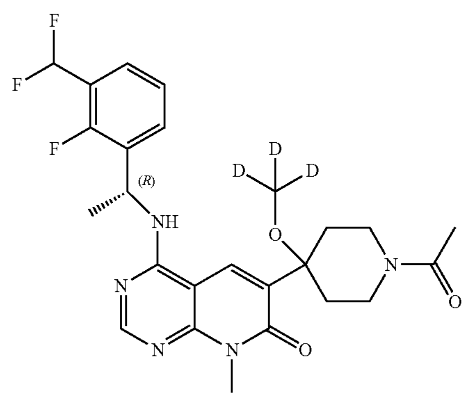 | 507.2 |
| 32-83 | 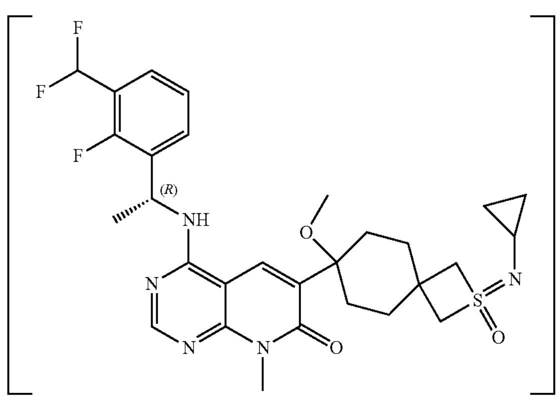 | 590.18 |

TABLE 12-continued

Examples 32-1 to 32-115

| Example # | Structure | Mass Found |
|---|---|---|
| 32-84 | 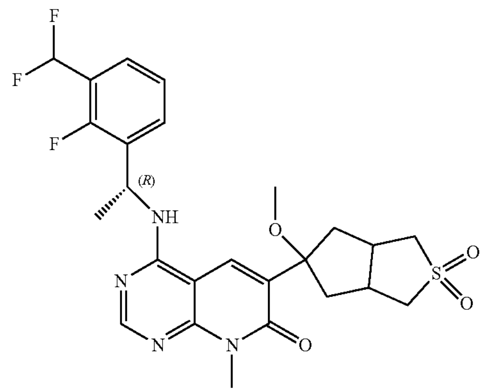 | 537.4 |
| 32-85 | 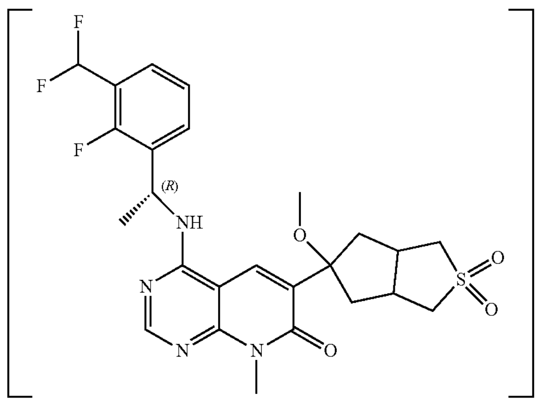 | 537.4 |
| 32-86 | 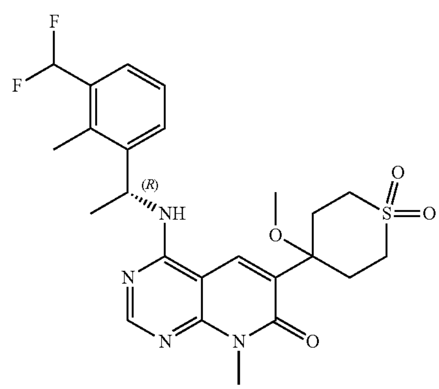 | 507.1 |
| 32-87 | 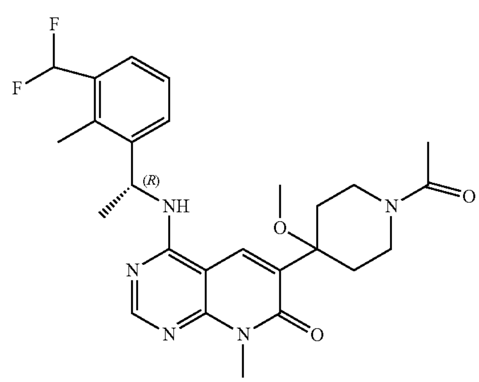 | 500.1 |

TABLE 12-continued

Examples 32-1 to 32-115

| Example # | Structure | Mass Found |
|---|---|---|
| 32-88 | 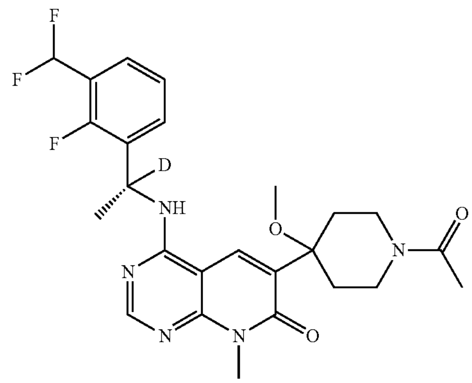 [SMILES: [2H][C@@](C)(Nc1ncnc2c1cc(C1(OC)CCN(C(C)=O)CC1)c(=O)n2C)c1cccc(C(F)F)c1F] | 505.2 |
| 32-89 | 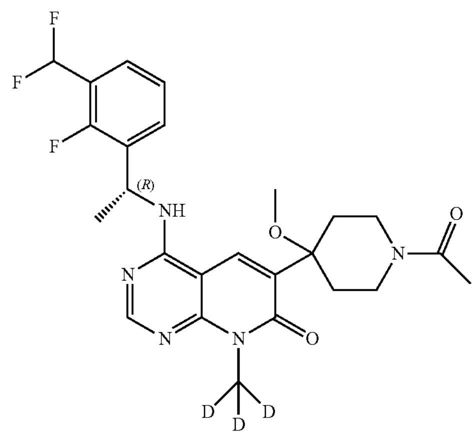 | 507.1 |
| 32-90 | 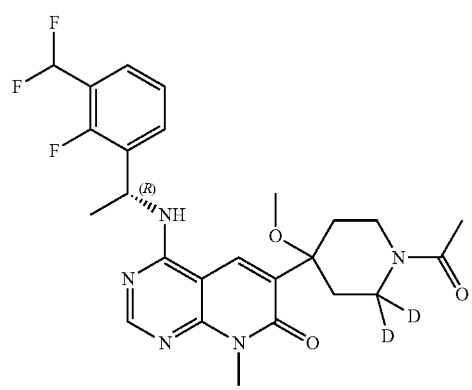 | 506.1 |
| 32-91 | 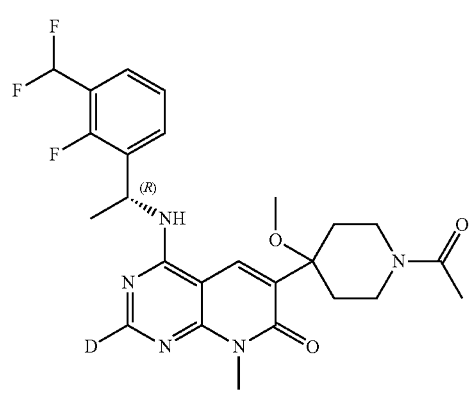 | 505.1 |

TABLE 12-continued

Examples 32-1 to 32-115

| Example # | Structure | Mass Found |
|---|---|---|
| 32-92 | 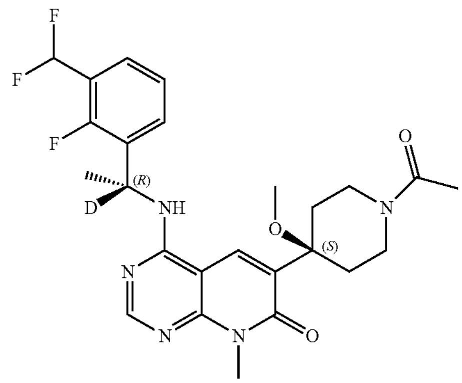 | 491.1 |
| 32-93 | 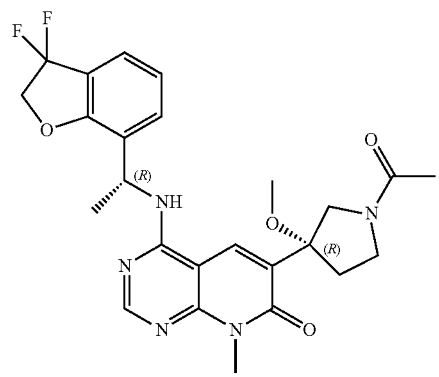 | 500.1 |
| 32-94 | 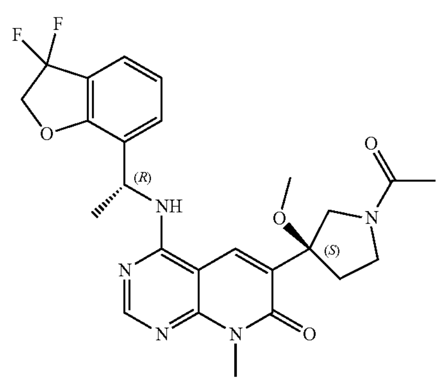 | 500.1 |
| 32-95 | 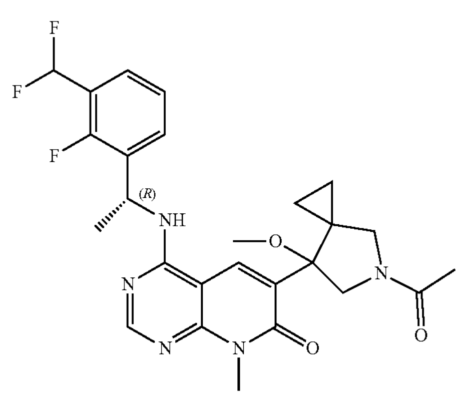 | 516.1 |

TABLE 12-continued

Examples 32-1 to 32-115

| Example # | Structure | Mass Found |
|---|---|---|
| 32-96 | 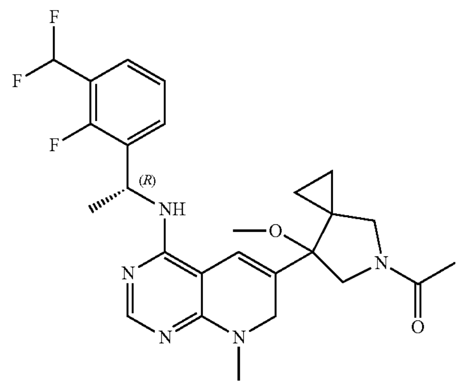 | 516.2 |
| 32-97 | 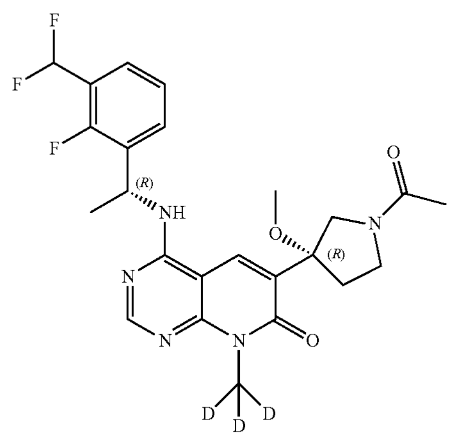 | 493 |
| 32-98 | 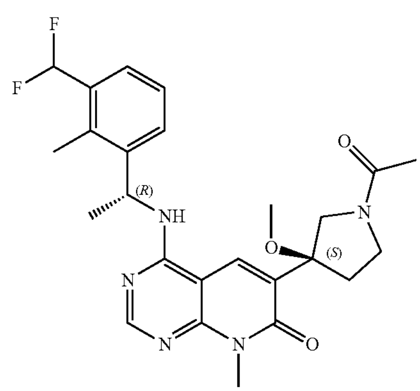 | 486.1 |
| 32-99 | 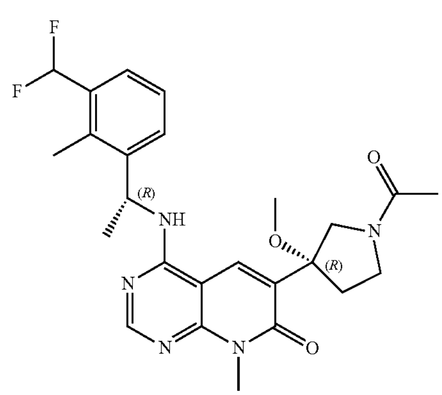 | 486.1 |

TABLE 12-continued

Examples 32-1 to 32-115

| Example # | Structure | Mass Found |
|---|---|---|
| 32-100 | 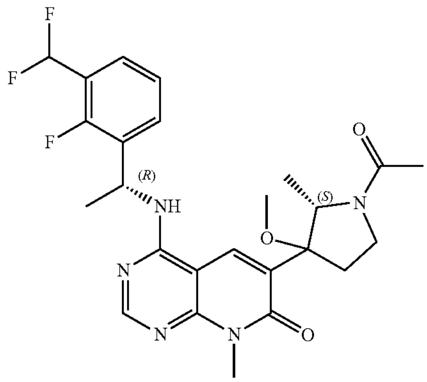 | 504.1 |
| 32-101 | 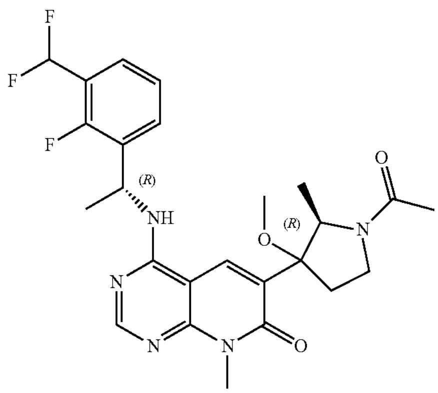 | 504.1 |
| 32-102 | 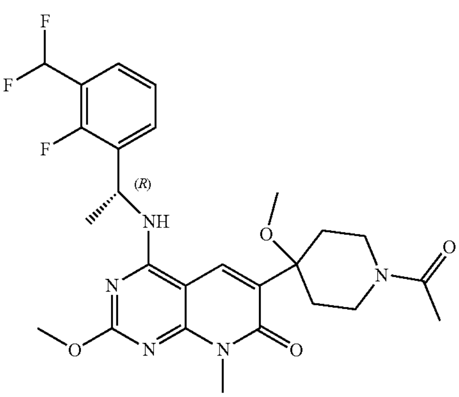 | 534.14 |
| 32-103 | 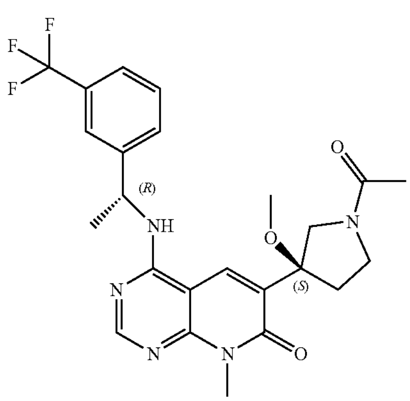 | 490.1 |

TABLE 12-continued
Examples 32-1 to 32-115
| Example # | Structure | Mass Found |
|---|---|---|
| 32-104 | 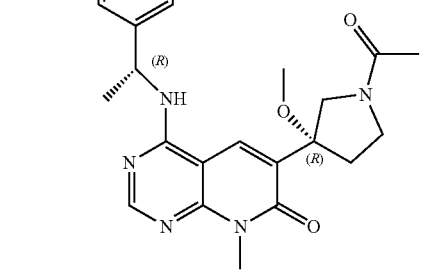 | 490.1 |
| 32-105 | 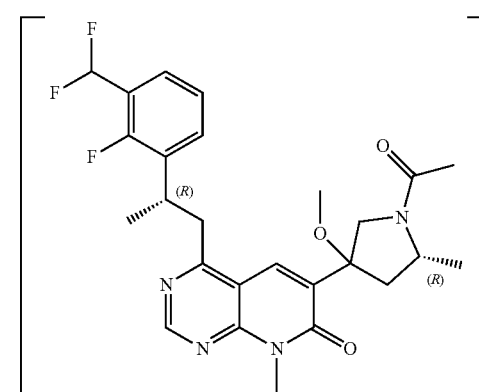 | 504.1 |
| 32-106 | 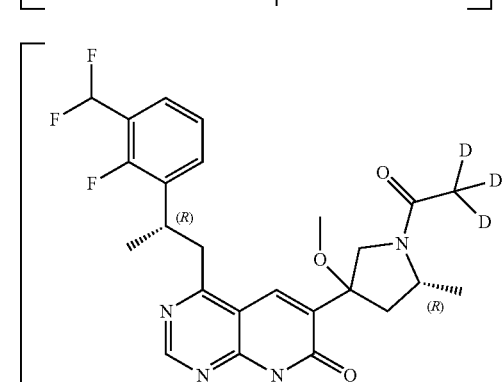 | 507.2 |
| 32-107 | 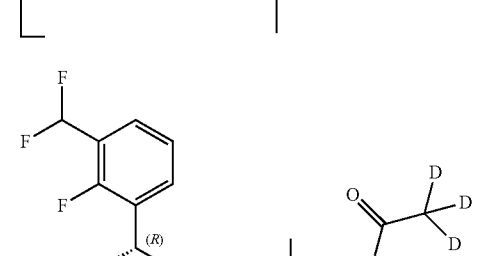 | 507.4 |

TABLE 12-continued

Examples 32-1 to 32-115

| Example # | Structure | Mass Found |
|---|---|---|
| 32-108 | 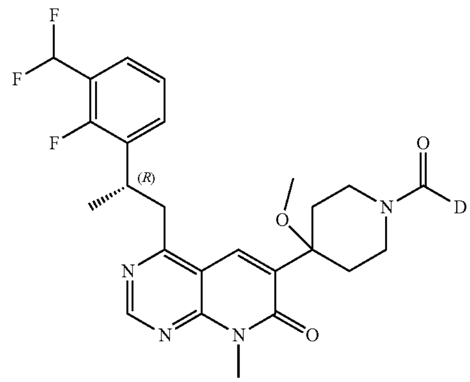 | 490.7 |
| 32-109 | 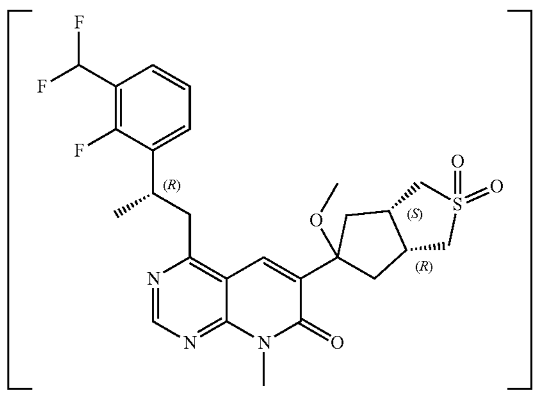 | 537.4 |
| 32-110 | 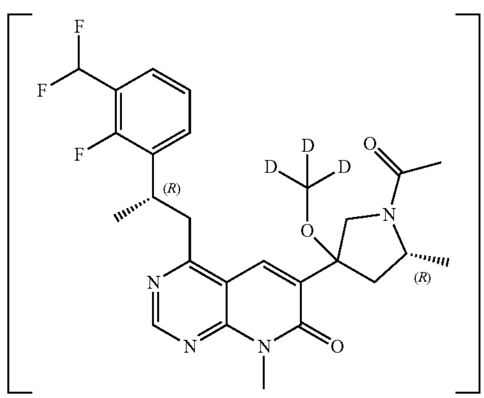 | 507.2 |
| 32-111 | 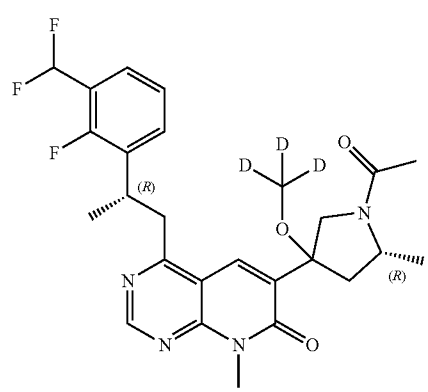 | 507.1 |

TABLE 12-continued

Examples 32-1 to 32-115

| Example # | Structure | Mass Found |
|---|---|---|
| 32-112 | 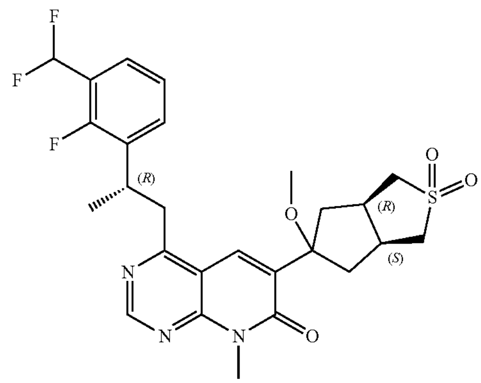 | 537.3 |
| 32-113 | 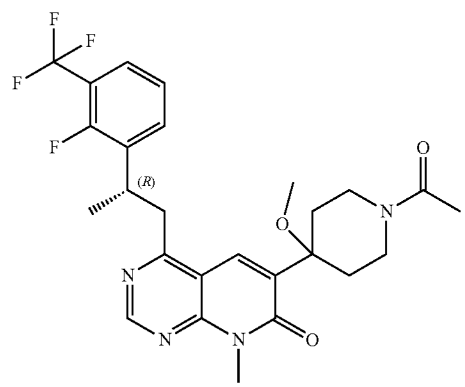 | 522.1 |
| 32-114 | 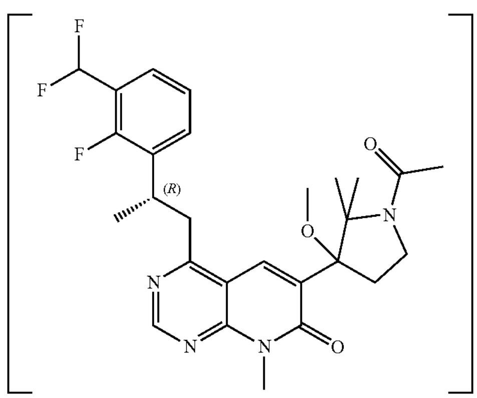 | 518.1 |
| 32-115 | 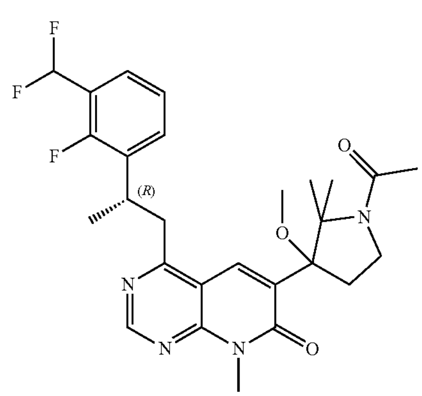 | 518.1 |

Example 33: Synthesis of 6-(4-{[(1R)-1-[3-(difluoromethyl)-2-fluorophenyl]ethyl]amino}-8-methyl-7-oxo-7H,8H-pyrido[2,3-d]pyrimidin-6-yl)-2λ⁶-thiaspiro[3.3]heptane-2,2-dione

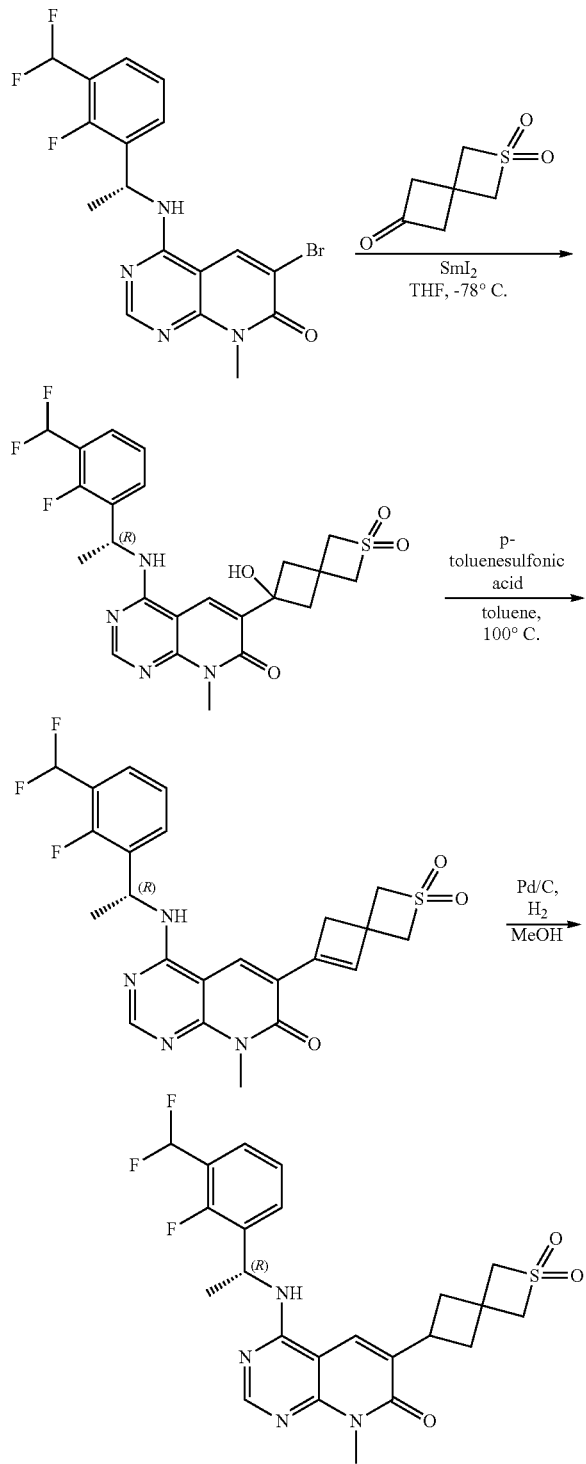

Step 1
To a solution of 2-thiaspiro[3.3]heptan-6-one 2,2-dioxide (300 mg, 1.87 mmol) in THF (10.0 mL) at −78° C. a 0.1M SmI$_2$ in THF solution (93.6 mL, 9.36 mmol) was added. Then a solution of 6-bromo-4-{[(1R)-1-[3-(difluoromethyl)-2-fluorophenyl]ethyl]amino}-8-methyl-7H,8H-pyrido[2,3-d]pyrimidin-7-one (400 mg, 0.94 mmol) in THF (10.0 mL) was added, and reaction mixture was stirred at −78° C. for 6 h. The reaction was quenched with sat. aq. NH$_4$Cl, extracted with EtOAc dried with Na$_2$SO$_4$, filtered, and the solvent was removed under reduced pressure. The crude product was purified by column chromatography to give 6-(4-{[(1R)-1-[3-(difluoromethyl)-2-fluorophenyl]ethyl]amino}-8-methyl-7-oxo-7H,8H-pyrido[2,3-d]pyrimidin-6-yl)-6-hydroxy-2λ⁶-thiaspiro[3.3]heptane-2,2-dione (225 mg, 47% yield). LCMS (ESI): m/z: [M+H] calculated for C$_{23}$H$_{24}$F$_3$N$_4$O$_4$S: 509.1; found 509.3. ¹H NMR (300 MHz, methanol-d$_4$) δ ppm 8.36 (s, 1H), 8.34 (s, 1H), 7.58 (t, J=7.5 Hz, 1H), 7.50 (t, J=7.1 Hz, 1H), 7.25 (t, J=7.7 Hz, 1H), 7.02 (t, J=109.8 Hz, 1H), 5.80 (q, J=7.2 Hz, 1H), 4.39 (s, 2H), 4.21 (s, 2H), 3.71 (s, 3H), 3.23-3.10 (m, 2H), 2.70-2.56 (m, 2H), 1.68 (d, J=7.1 Hz, 3H).

Step 2
To a solution of 6-(4-{[(1R)-1-[3-(difluoromethyl)-2-fluorophenyl]ethyl]amino}-8-methyl-7-oxo-7H,8H-pyrido[2,3-d]pyrimidin-6-yl)-6-hydroxy-2λ⁶-thiaspiro[3.3]heptane-2,2-dione (225 mg, 0.44 mmol) in toluene (7.0 mL), p-toluenesulfonic acid monohydrate (152 mg, 0.88 mmol) was added, and reaction mixture was refluxed for one h. The reaction mixture was diluted with sat. aq. NaHCO$_3$, extracted with EtOAc, dried with Na$_2$SO$_4$, filtered, and the solvent was removed under reduced pressure to give 6-(4-{[(1R)-1-[3-(difluoromethyl)-2-fluorophenyl]ethyl]amino}-8-methyl-7-oxo-7H,8H-pyrido[2,3-d]pyrimi-din-6-yl)-2λ⁶-thiaspiro[3.3]hept-5-ene-2,2-dione (195 mg, 90% yield). LCMS (ESI): m/z: [M+H] calculated for C$_{23}$H$_{22}$F$_3$N$_4$O$_3$S: 491.1; found 491.1.

Step 3
6-(4-{[(1R)-1-[3-(difluoromethyl)-2-fluorophenyl]ethyl]amino}-8-methyl-7-oxo-7H,8H-pyrido[2,3-d]pyrimidin-6-yl)-2λ⁶-thiaspiro[3.3]hept-5-ene-2,2-dione (173 mg, 0.35 mmol) was dissolved in MeOH (11.0 mL). Then Pd/C (30 wt %, 35 mg) was added under argon atmosphere. Argon was evacuated from the reaction mixture, and a H$_2$ (balloon) was attached to the flask. The reaction stirred overnight. The reaction mixture was filtered through pad of Celite®, and the solvent was removed under reduced pressure. The crude product was purified by prep-HPLC to give 6-(4-{[(1R)-1-[3-(difluoromethyl)-2-fluorophenyl]ethyl]amino}-8-methyl-7-oxo-7H,8H-pyrido[2,3-d]pyrimidin-6-yl)-2λ⁶-thiaspiro[3.3]heptane-2,2-dione (60 mg, 34% yield). LCMS (ESI): m/z: [M+H] calculated for C$_{23}$H$_{24}$F$_3$N$_4$O$_3$S: 493.1; found 493.1. ¹H NMR (300 MHz, methanol-d4) δ ppm 8.32 (s, 1H), 8.21 (d, J=1.3 Hz, 1H), 7.59 (t, J=7.5 Hz, 1H), 7.50 (t, J=7.1 Hz, 1H), 7.25 (t, J=7.7 Hz, 1H), 7.02 (t, J=54.9 Hz, 1H), 5.79 (q, J=7.1 Hz, 1H), 4.37 (s, 2H), 4.15 (s, 2H), 3.75-3.60 (m, 4H), 2.82-2.71 (m, 2H), 2.65-2.53 (n, 2H), 1.68 (d, J=7.1 Hz, 3H).

The following examples 33-1 to 33-37 shown in Table 13 were synthesized in the manner similar to Example 33.

TABLE 13

Examples 33-1 to 33-37

| Example # | Structure | Mass Found |
|---|---|---|
| 33-1 | 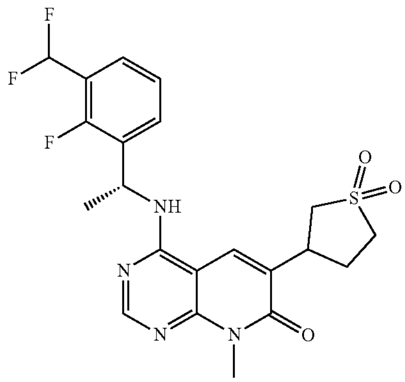 [SMILES: C[C@@H](Nc1ncnc2c1cc(C1CCS(=O)(=O)C1)c(=O)n2C)c1cccc(C(F)F)c1F] | 467.0 |
| 33-2 | 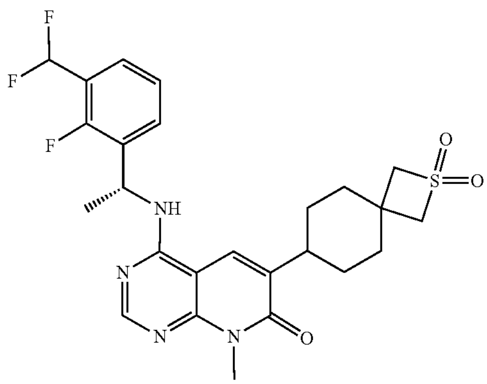 [SMILES: C[C@@H](Nc1ncnc2c1cc(C1CCC3(CC1)CS(=O)(=O)C3)c(=O)n2C)c1cccc(C(F)F)c1F] | 521.15 |
| 33-3 | 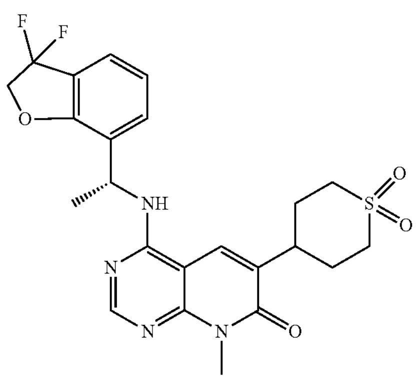 [SMILES: C[C@@H](Nc1ncnc2c1cc(C1CCS(=O)(=O)CC1)c(=O)n2C)c1cccc2c1OCC2(F)F] | 491.1 |
| 33-4 | 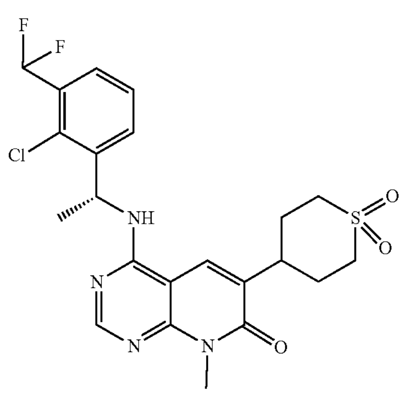 [SMILES: C[C@@H](Nc1ncnc2c1cc(C1CCS(=O)(=O)CC1)c(=O)n2C)c1cccc(C(F)F)c1Cl] | 497.1 |

TABLE 13-continued

Examples 33-1 to 33-37

| Example # | Structure | Mass Found |
|---|---|---|
| 33-5 | 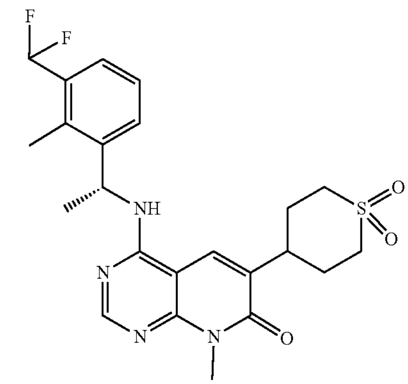 [SMILES: Cc1c(C(F)F)cccc1[C@@H](C)Nc1ncnc2c1cc(C1CCS(=O)(=O)CC1)c(=O)n2C] | 477.1 |
| 33-6 | 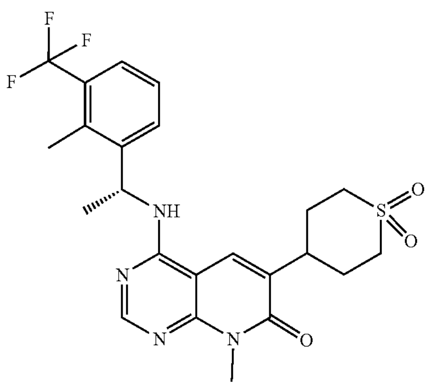 [SMILES: Cc1c([C@@H](C)Nc2ncnc3c2cc(C2CCS(=O)(=O)CC2)c(=O)n3C)cccc1C(F)(F)F] | 499.1 |
| 33-7 | 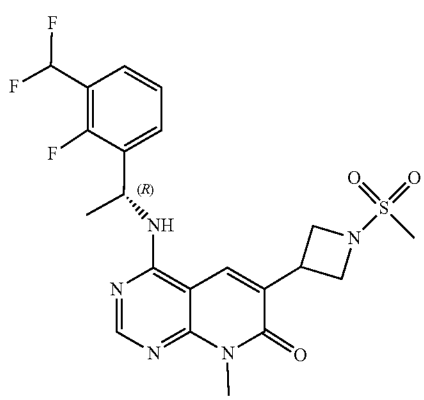 | 482.2 |
| 33-8 | 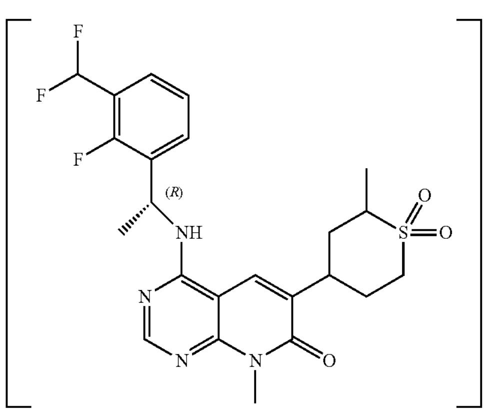 | 495.2 |

TABLE 13-continued

Examples 33-1 to 33-37

| Example # | Structure | Mass Found |
|---|---|---|
| 33-9 | 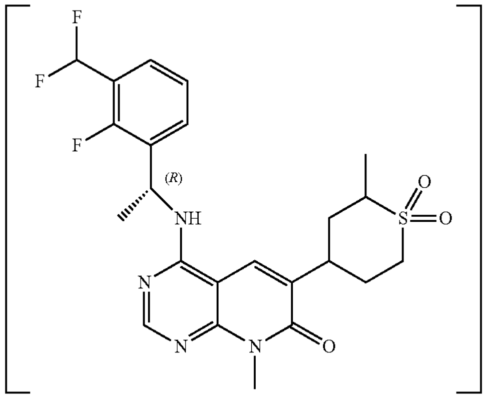 | 495.1 |
| 33-10 | 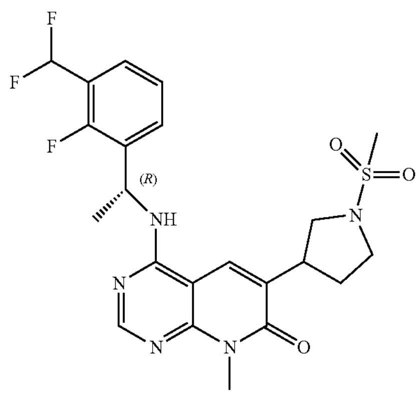 | 496 |
| 33-11 | 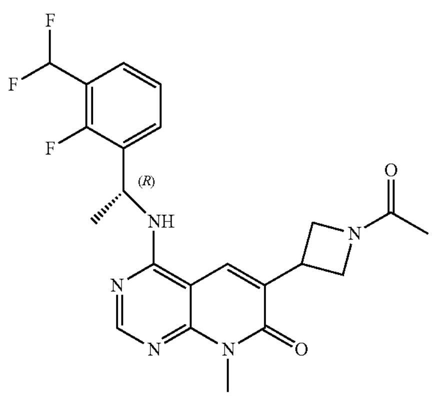 | 446.17 |
| 33-12 | 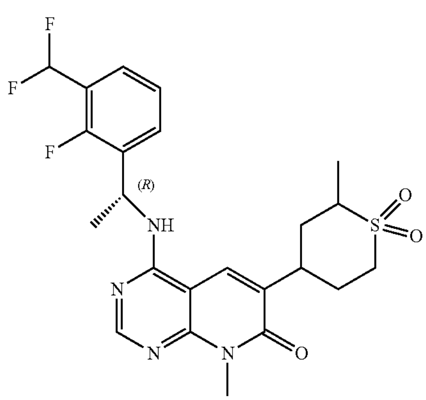 | 495.2 |

TABLE 13-continued
Examples 33-1 to 33-37
| Example # | Structure | Mass Found |
|---|---|---|
| 33-13 | 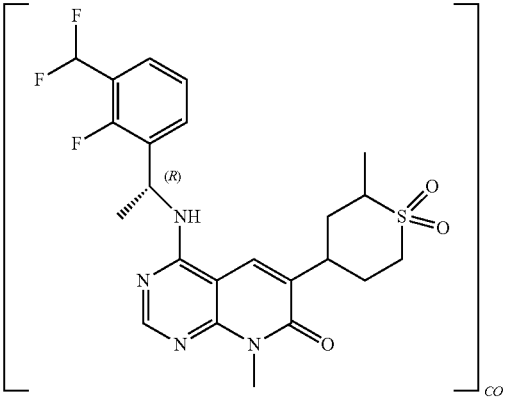 | 495.1 |
| 33-14 | 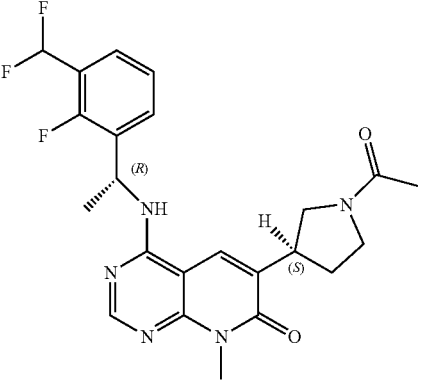 | 460.2 |
| 33-15 | 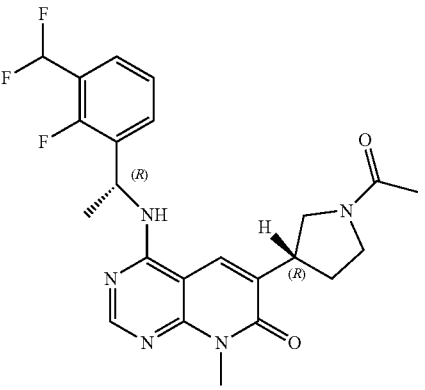 | 460.2 |
| 33-16 | 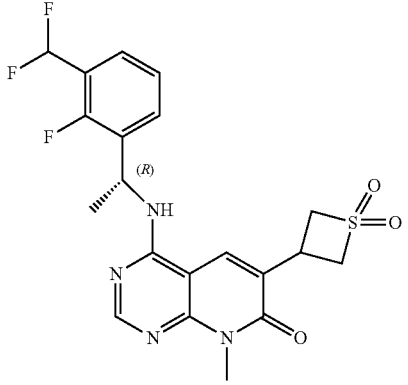 | 453.1 |

TABLE 13-continued
Examples 33-1 to 33-37
| Example # | Structure | Mass Found |
|---|---|---|
| 33-17 | 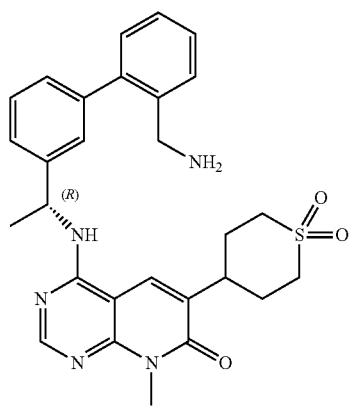 | 518.1 |
| 33-18 | 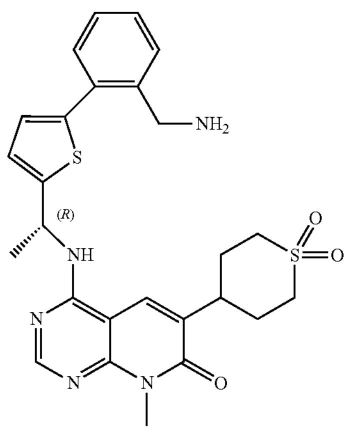 | 524.1 |
| 33-19 | 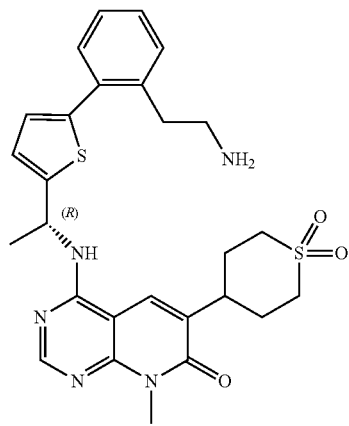 | 538.1 |

TABLE 13-continued
Examples 33-1 to 33-37
| Example # | Structure | Mass Found |
|---|---|---|
| 33-20 | 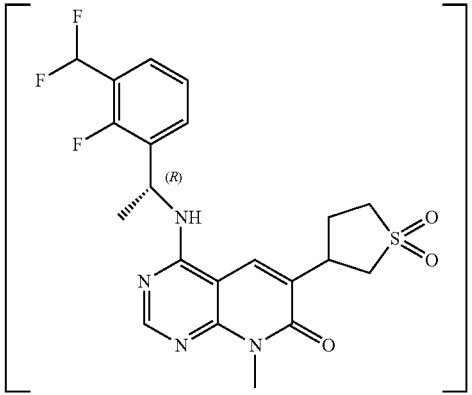 | 467.1 |
| 33-21 | 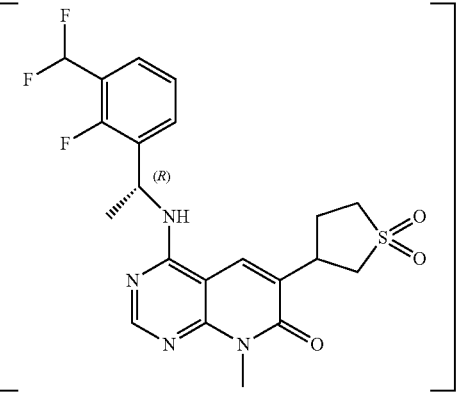 | 467.1 |
| 33-22 | 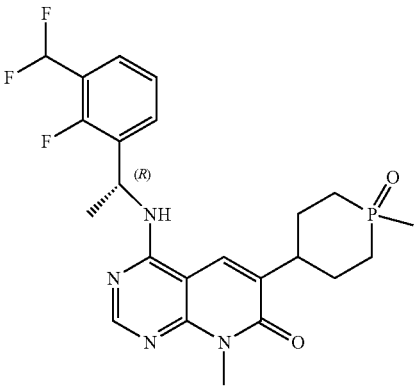 | 479.3 |

TABLE 13-continued

Examples 33-1 to 33-37

| Example # | Structure | Mass Found |
|---|---|---|
| 33-23 | 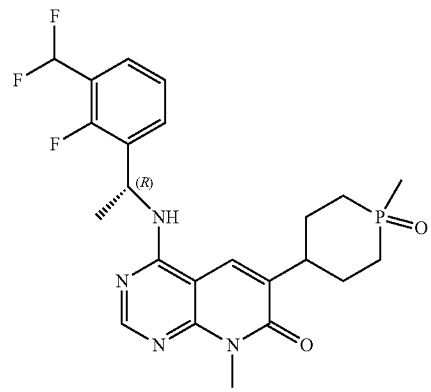 | 479.4 |
| 33-24 | 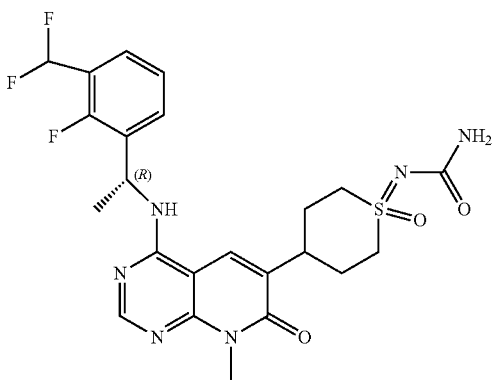 | 523.4 |
| 33-25 | 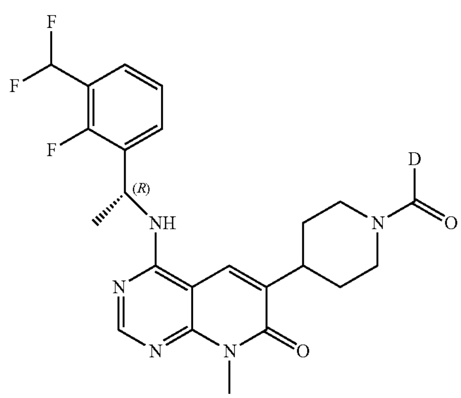 | 461.2 |
| 33-26 | 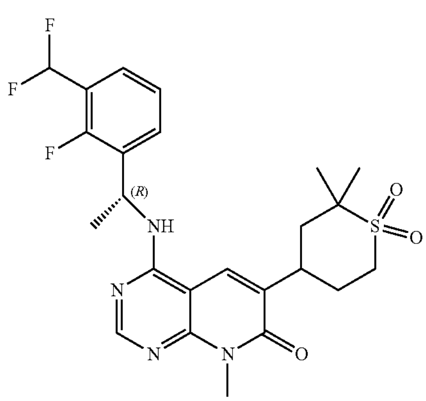 | 509.11 |

TABLE 13-continued

Examples 33-1 to 33-37

| Example # | Structure | Mass Found |
|---|---|---|
| 33-27 | 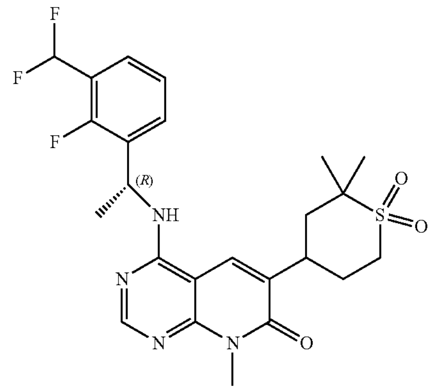 | 509.14 |
| 33-28 | 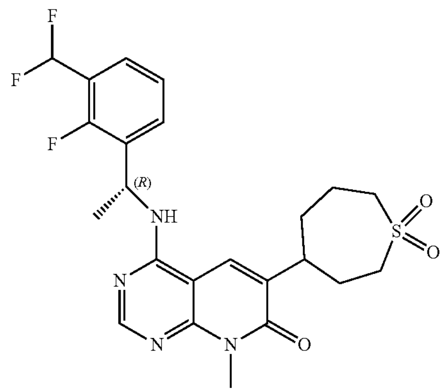 | 495.1 |
| 33-29 | 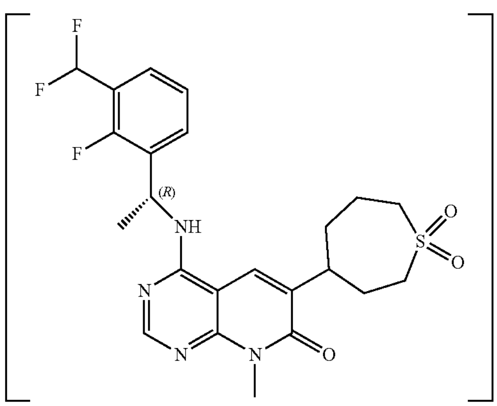 | 495.1 |
| 33-30 | 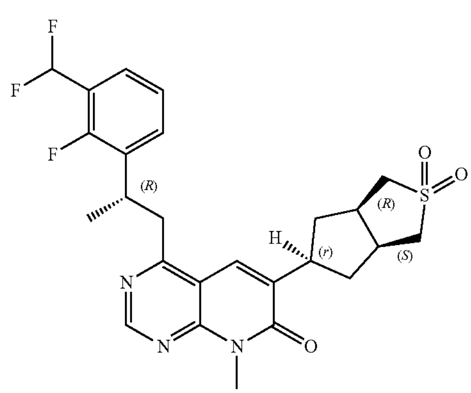 | 507.4 |

TABLE 13-continued

Examples 33-1 to 33-37

| Example # | Structure | Mass Found |
|---|---|---|
| 33-31 | 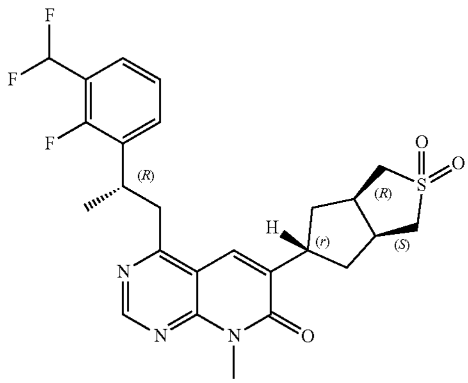 | 507.7 |
| 33-32 | 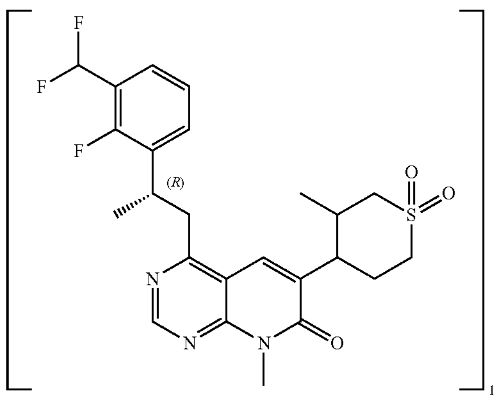 | 495.1 |
| 33-33 | 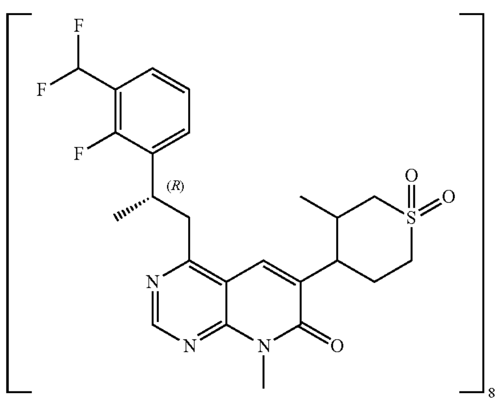 | 495.1 |
| 33-34 | 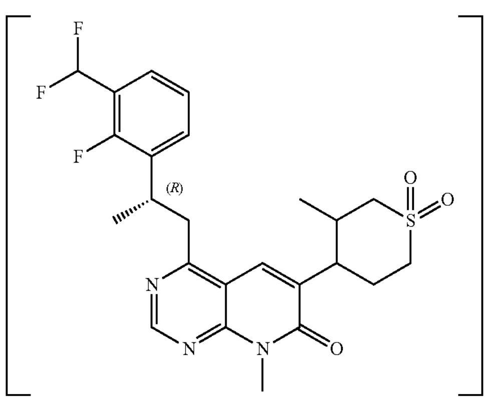 | 495.1 |

TABLE 13-continued

Examples 33-1 to 33-37

| Example # | Structure | Mass Found |
|---|---|---|
| 33-35 | 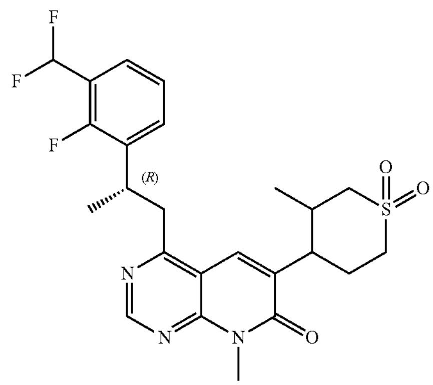 | 495.1 |
| 33-36 | 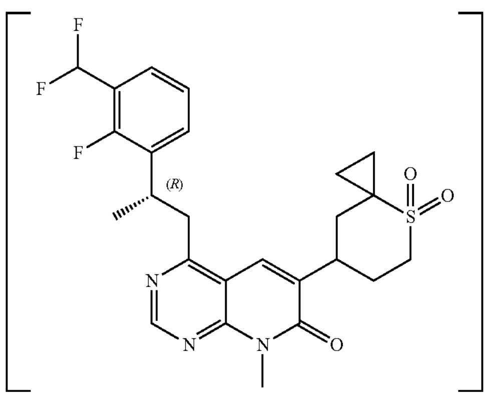 | 507.1 |
| 33-37 | 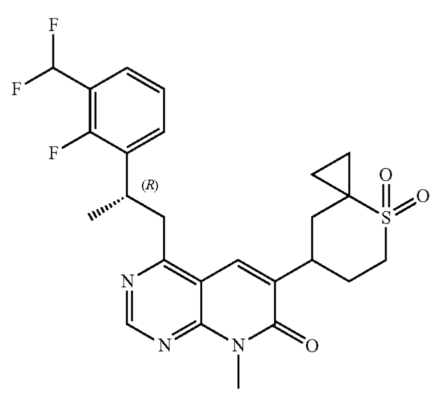 | 507.1 |

Example 34: Synthesis of 4-(((R)-1-(3-(difluoromethyl)-2-fluorophenyl)ethyl)amino)-6-(3-hydroxypiperidin-4-yl)-8-methylpyrido[2,3-d]pyrimidin-7(8H)-one

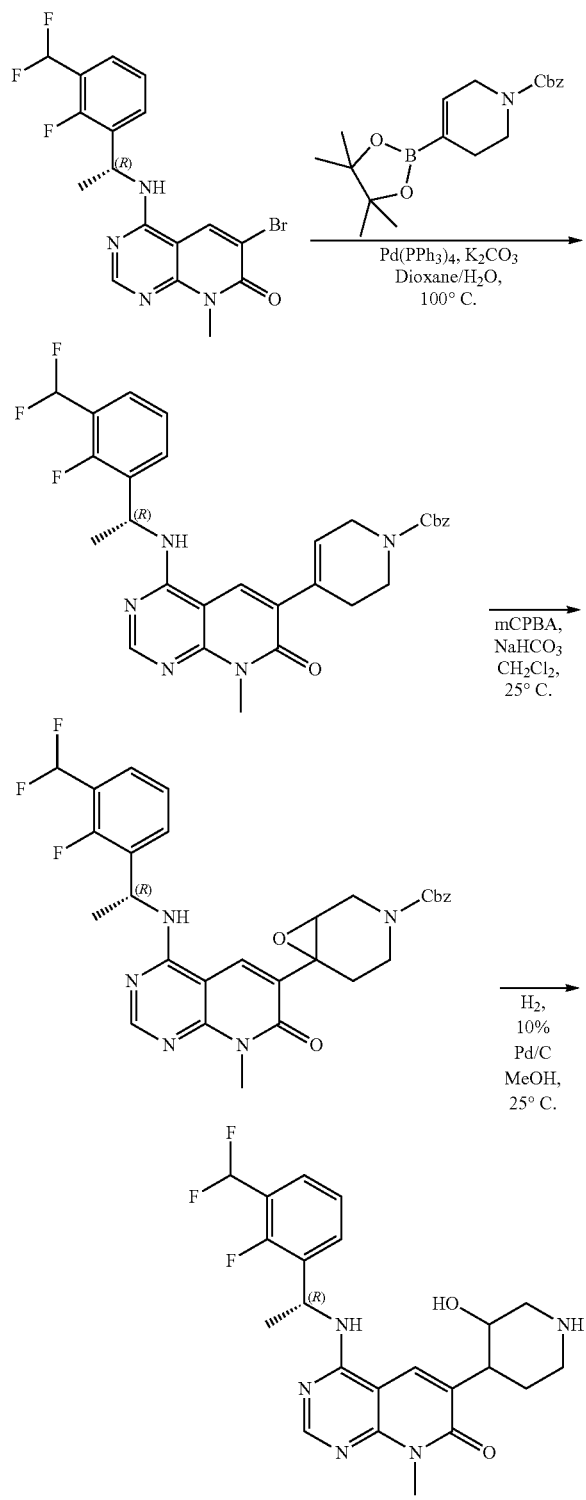

Step 1
A solution of 6-bromo-4-[[(R)-1-[3-(difluoromethyl)-2-fluorophenyl]ethyl]amino]-8-methyl-7H,8H-pyrido[2,3-d]pyrimidin-7-one (279 mg, 653 μmol), benzyl 4-(4,4,5,5-tetramethyl-1,3,2-dioxaborolan-2-yl)-1,2,3,6-tetrahydropyridine-1-carboxylate (450 mg, 1.31 mmol), $Pd(PPh_3)_4$ (75.2 mg, 65.0 μmol), and potassium carbonate (270 mg, 1.95 mmol) in dioxane (8 mL) and $H_2O$ (1.5 mL) was stirred at 100° C. for 4 h under $N_2$. The mixture was concentrated under reduced pressure, quenched with saturated aqueous $NaHCO_3$ solution, extracted with EtOAc, dried over $MgSO_4$, and concentrated under reduced pressure. The residue was run through a silica gel plug to give benzyl (R)-4-(4-((1-(3-(difluoromethyl)-2-fluorophenyl)ethyl)amino)-8-methyl-7-oxo-7,8-dihydropyrido[2,3-d]pyrimidin-6-yl)-3,6-dihydropyridine-1(2H)-carboxylate, which was taken to the next reaction without further purification. LCMS (ESI): m/z: [M+H] calculated for $C_{30}H_2F_3N_5O_3$: 564.2; found: 564.3.

Step 2
To a solution of crude benzyl (R)-4-(4-((1-(3-(difluoromethyl)-2-fluorophenyl)ethyl)amino)-8-methyl-7-oxo-7,8-dihydropyrido[2,3-d]pyrimidin-6-yl)-3,6-dihydropyridine-1(2H)-carboxylate in dry DCM were added $NaHCO_3$ (74.6 mg, 888 μmol) and mCPBA (70% wt, 219 mg, 886 μmol). The reaction mixture was stirred at 25° C. for 10 min. The mixture was diluted with $H_2O$, extracted with DCM, dried over $MgSO_4$, filtered, and concentrated under reduced pressure to give benzyl 6-(4-(((R)-1-(3-(difluoromethyl)-2-fluorophenyl)ethyl)amino)-8-methyl-7-oxo-7,8-dihydropyrido[2,3-d]pyrimidin-6-yl)-7-oxa-3-azabicyclo[4.1.0]heptane-3-carboxylate. The crude product was used in the next step without further purification. LCMS (ESI): m/z: [M+H] calculated for $C_{30}H_{28}F_3N_5O_4$: 580.2; found: 580.1.

Step 3
To a mixture of benzyl 6-(4-(((R)-1-(3-(difluoromethyl)-2-fluorophenyl)ethyl)amino)-8-methyl-7-oxo-7,8-dihydropyrido[2,3-d]pyrimidin-6-yl)-7-oxa-3-azabicyclo[4.1.0]heptane-3-carboxylate in MeOH (1.0 mL) was added 10% Pd/C (102 mg). The reaction mixture was stirred at 25° C. under a hydrogen balloon for 30 minutes. The mixture was then filtered through Celite® with additional MeOH and concentrated under reduced pressure. The crude residue was purified by reverse phase prep-HPLC to give 4-(((R)-1-(3-(difluoromethyl)-2-fluorophenyl)ethyl)amino)-6-(3-hydroxypiperidin-4-yl)-8-methylpyrido[2,3-d]pyrimidin-7(8H)-one (1.4 mg, 0.48% yield over 3 steps) as the formate salt. LCMS (ESI): m/z: [M+H] calculated for $C_{22}H_{25}F_3N_5O_2$: 448.2; found: 448.5. $^1$H NMR (500 MHz, METHANOL-$d_4$) δ ppm 8.57 (s, 1H), 8.35-8.29 (m, 1H), 8.20-8.14 (m, 1H), 7.65-7.55 (m, 1H), 7.54-7.44 (m, 1H), 7.29-7.20 (m, 1H), 7.15-6.88 (m, 1H), 5.86-5.76 (m, 1H), 4.30 (s, 1H), 3.72 (s, 3H), 3.54-3.46 (m, 1H), 3.41-3.27 (m, 3H), 3.22-3.13 (m, 1H), 2.72-2.59 (m, 1H), 1.87-1.74 (m, 1H), 1.69 (d, J=7.0 Hz, 3H).

Example 35: Synthesis of (R)-4-((1-(3-(difluoromethyl)-2-fluorophenyl)ethyl)amino)-6-(1-imino-1-oxidohexahydro-1λ⁶-thiopyran-4-yl)-8-methylpyrido[2,3-d]pyrimidin-7(8H)-one Example 36: Synthesis of 1-acetyl-4-(4-{[(1R)-1-[3-(difluoromethyl)-2-fluorophenyl]ethyl]amino}-8-methyl-7-oxo-7H,8H-pyrido[2,3-d]pyrimidin-6-yl)piperidine-4-carbonitrile

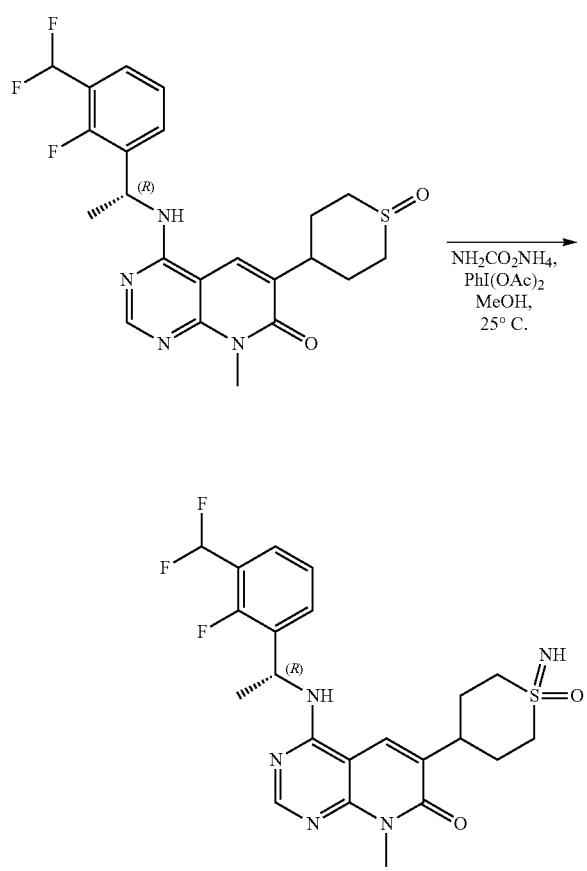

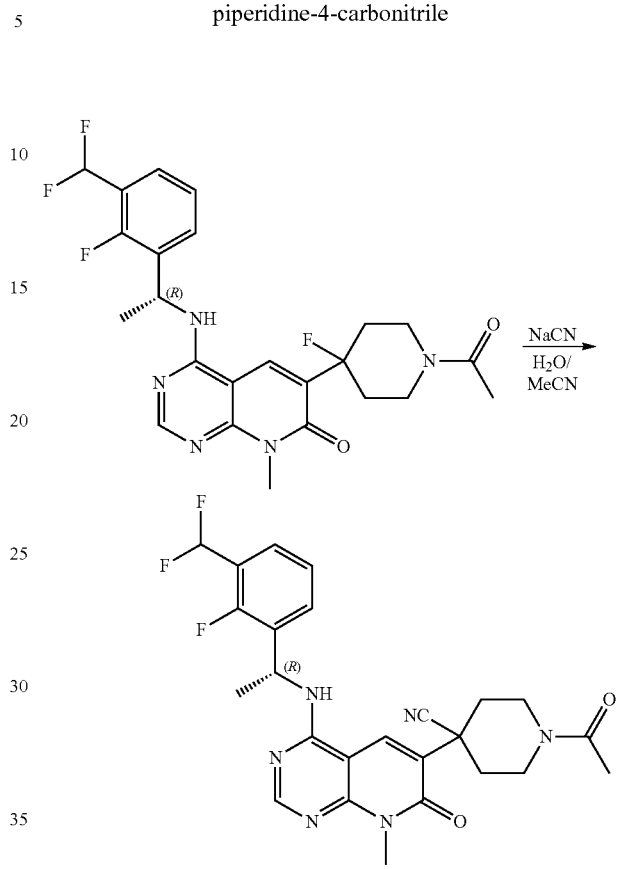

To a solution of (R)-4-((1-(3-(difluoromethyl)-2-fluorophenyl)ethyl)amino)-8-methyl-6-(1-oxidotetrahydro-2H-thiopyran-4-yl)pyrido[2,3-d]pyrimidin-7(8H)-one (320 mg, 689 µmol) in MeOH (5 mL) were added PhI(OAc)₂ (666 mg, 2.07 mmol) and ammonium carbamate (215 mg, 2.76 mmol). The reaction mixture was stirred at 25° C. for 4 h. The mixture was concentrated under reduced pressure and the residue was purified by prep-HPLC to give (R)-4-((1-(3-(difluoromethyl)-2-fluorophenyl)ethyl)amino)-6-(1-imino-1-oxidohexahydro-1λ⁶-thiopyran-4-yl)-8-methylpyrido[2,3-d]pyrimidin-7(8H)-one (206 mg, 62% yield). LCMS (ESI): m/z: [M+H] calculated for $C_{22}H_{25}F_3N_5O_2S$: 480.2; found: 480.1. ¹H NMR (400 MHz, METHANOL-d₄) δ ppm 8.30 (s, 1H), 8.28 (s, 1H), 7.57 (t, J=7.4 Hz, 1H), 7.48 (t, J=7.0 Hz, 1H), 7.23 (t, J=7.8 Hz, 1H), 7.01 (t, J=54.8 Hz, 1H), 5.77 (q, J=7.0 Hz, 1H), 3.71 (s, 3H), 3.38-3.33 (m, 2H), 3.27-3.23 (m, 3H), 2.35-2.25 (m, 4H), 1.66 (d, J=7.2 Hz, 3H).

To a solution of 6-(1-acetyl-4-fluoropiperidin-4-yl)-4-{[(1R)-1-[3-(difluoromethyl)-2-fluoro-phenyl]ethyl]amino}-8-methyl-7H,8H-pyrido[2,3-d]pyrimidin-7-one (170 mg, 0.35 mmol) in mixture of ACN (5.1 mL) and water (1.2 mL) sodium cyanide (102 mg, 2.08 mmol) was added. After stirring at rt overnight the reaction mixture was extracted with EtOAc. The combined organic phases were dried over Na₂SO₄, filtered and the solvent was removed under reduced pressure. The crude product was purified by prep-HPLC to give 1-acetyl-4-(4-{[(1R)-1-[3-(difluoromethyl)-2-fluorophenyl]-ethyl]amino}-8-methyl-7-oxo-7H,8H-pyrido[2,3-d]pyrimidin-6-yl)piperidine-4-carbonitrile (61 mg, 35% yield). LCMS (ESI): m/z: [M+H] calculated for $C_{25}H_{25}F_3N_6O_2$: 499.2; found: 499.2; ¹H NMR (300 MHz, Chloroform-d) δ 8.47 (s, 1H), 7.79 (d, J=3.2 Hz, 1H), 7.51 (q, J=7.2 Hz, 2H), 7.25-7.17 (m, 1H), 6.92 (t, J=54.9 Hz, 1H), 6.08 (t, J=6.2 Hz, 1H), 5.86-5.69 (m, 1H), 4.85 (d, J=13.9 Hz, 1H), 3.95 (d, J=14.5 Hz, 1H), 3.75 (s, 3H), 3.59 (t, J=13.3 Hz, 1H), 3.05 (t, J=13.2 Hz, 1H), 2.55-2.40 (m, 1H), 2.40-2.29 (m, 1H), 2.28-2.19 (m, 2H), 2.13 (d, J=6.1 Hz, 3H), 1.69 (d, J=7.0 Hz, 3H).

The following examples 36-1 to 36-16 shown in Table 14 were synthesized in the manner similar to Example 36.

TABLE 14
Examples 36-1 to 36-16
| Example # | Structure | Mass Found |
|---|---|---|
| 36-1 | 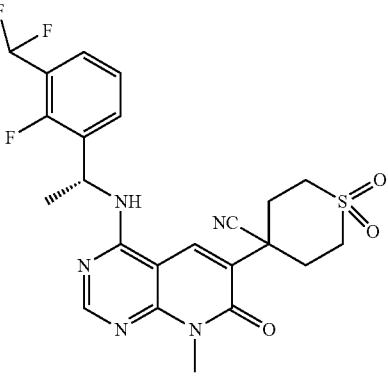 | 506.1 |
| 36-2 | 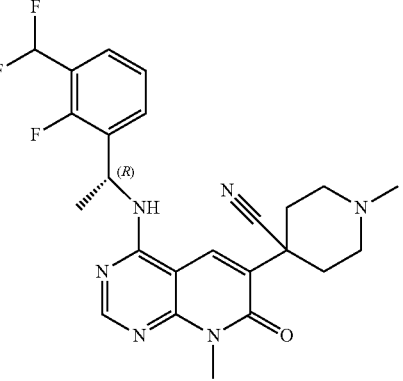 | 471.2 |
| 36-3 | 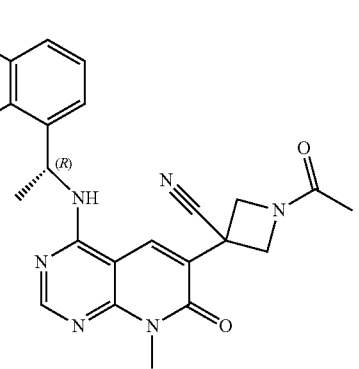 | 471.17 |
| 36-4 | 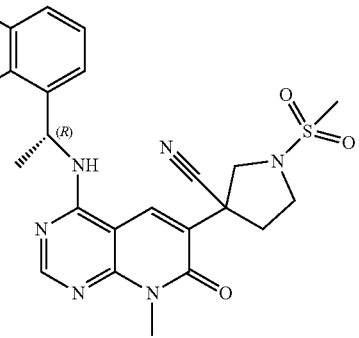 | 521.2 |

TABLE 14-continued

Examples 36-1 to 36-16

| Example # | Structure | Mass Found |
|---|---|---|
| 36-5 | 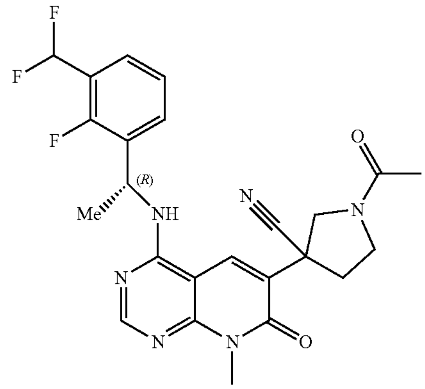 | 485.2 |
| 36-6 | 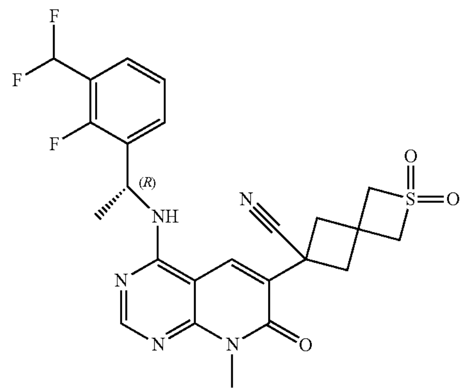 | 518.1 |
| 36-7 | 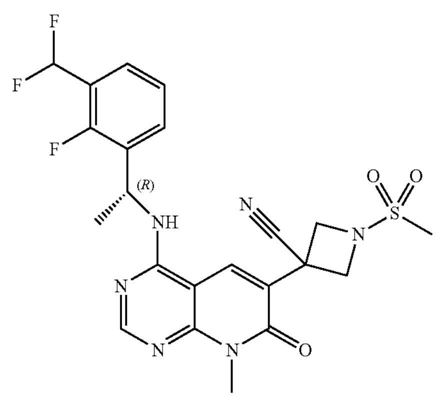 | 507.13 |
| 36-8 | 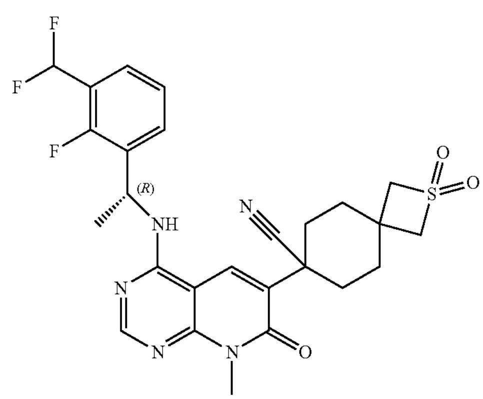 | 545.92 |

TABLE 14-continued

Examples 36-1 to 36-16

| Example # | Structure | Mass Found |
|---|---|---|
| 36-9 | 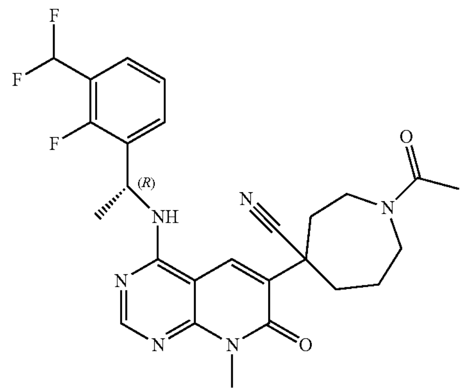 | 513.1 |
| 36-10 | 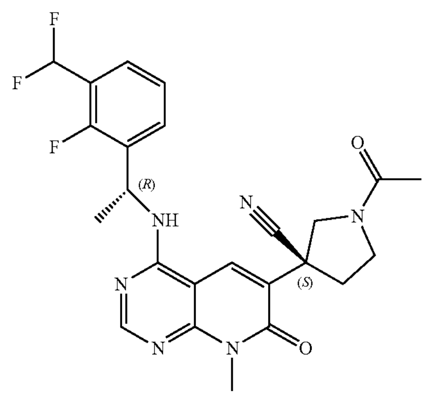 | 485.1 |
| 36-11 | 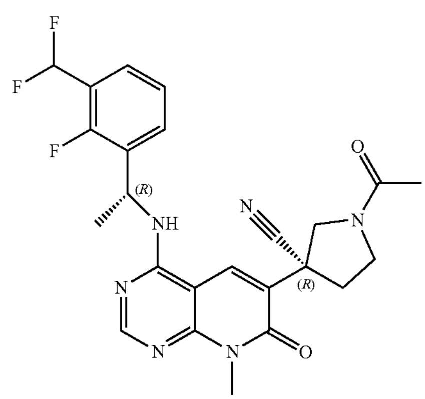 | 485.1 |
| 36-12 | 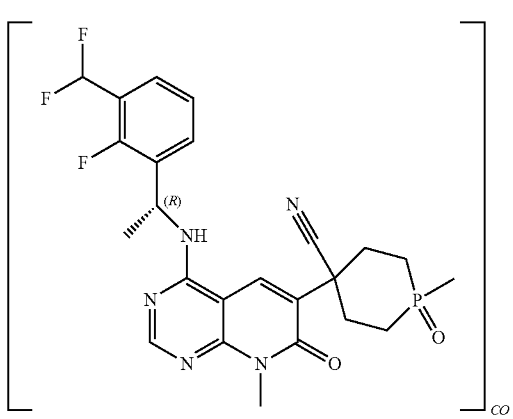 | 504.1 |

TABLE 14-continued

Examples 36-1 to 36-16

| Example # | Structure | Mass Found |
|---|---|---|
| 36-13 | 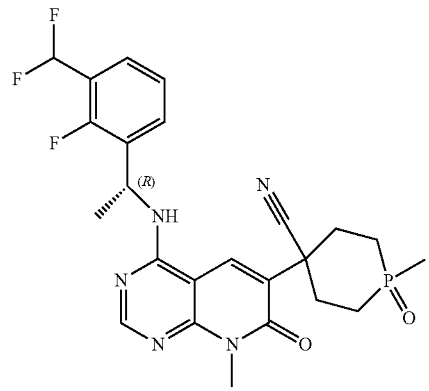 | 504.3 |
| 36-14 | 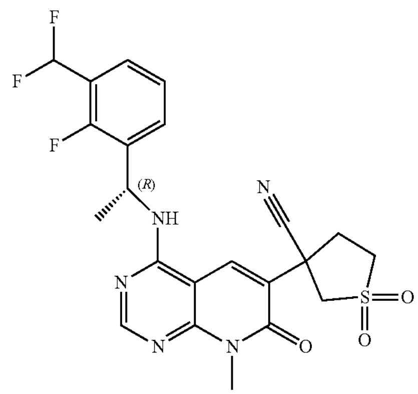 | 492.1 |
| 36-15 | 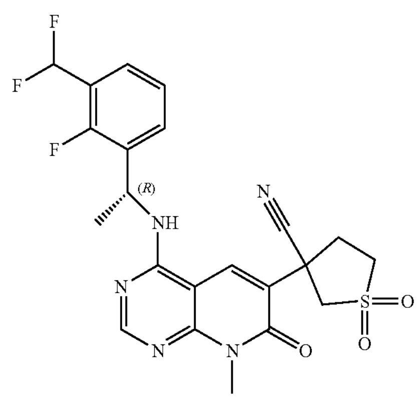 | 492.1 |
| 36-16 | 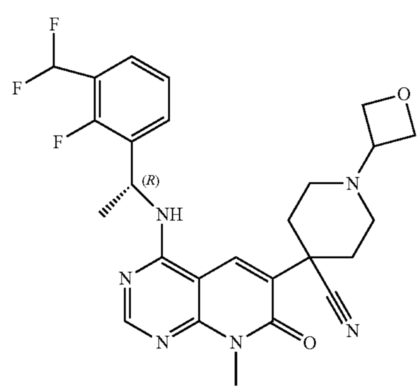 | 513.92 |

Example 37: Synthesis of 4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-methyl-1λ⁶-thiane-1,1-dione

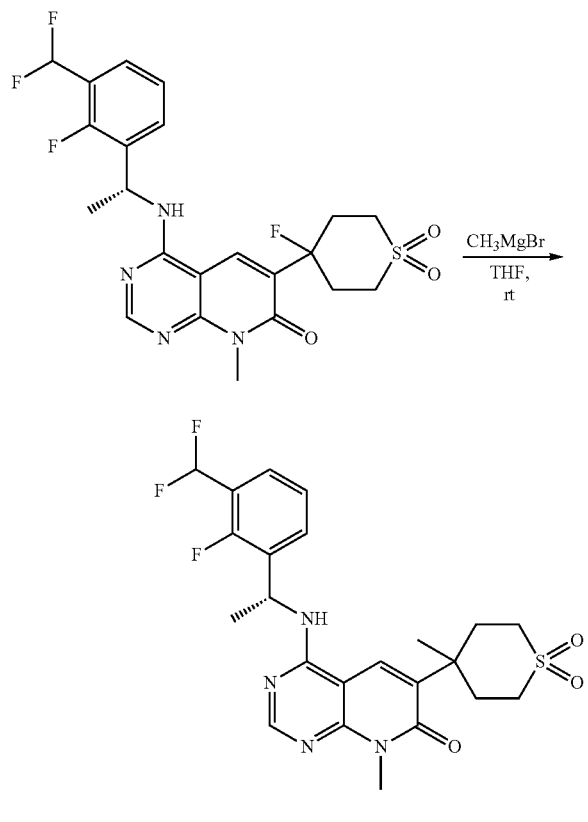

Step 1

To a solution of 4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-fluoro-1λ⁶-thiane-1,1-dione (130 mg, 0.26 mmol) in THF (5.2 mL) was added methylmagnesium bromide solution (3.0 M in diethyl ether, 1.3 mL, 3.91 mmol) at 0° C. The reaction mixture was stirred at rt for 1 h and then quenched with sat. aq NH₄Cl solution and extracted with EtOAc. The combined organic layers were dried over anhydrous Na₂SO₄ and the solvent was removed under reduced pressure. The crude product was purified by prep-HPLC to give 4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-methyl-1λ⁶-thiane-1,1-dione (53 mg, 41% yield). LCMS (ESI): exact mass for C₂₃H₂₆F₃N₄O₃S: 495.2; [M+H]+=495.2 found; ¹H NMR (300 MHz, DMSO-d₆) δ 8.46 (d, J=7.1 Hz, 1H), 8.33 (s, 1H), 8.16 (s, 1H), 7.63 (t, J=7.5 Hz, 1H), 7.51 (t, J=7.2 Hz, 1H), 7.31 (t, J=7.7 Hz, 1H), 7.24 (t, J=54.4 Hz, 1H), 5.76 (q, J=7.0 Hz, 1H), 3.57 (s, 3H), 3.21 (t, J=11.9 Hz, 2H), 3.02 (t, J=11.0 Hz, 2H), 2.88-2.67 (m, 2H), 2.39-2.15 (m, 2H), 1.60 (d, J=7.1 Hz, 3H), 1.42 (s, 3H).

Example 38: Synthesis of 6-(1-acetylpiperidin-4-yl)-4-{[(1R)-1-[2,3-bis(difluoromethyl)phenyl]ethyl]amino}-8-methyl-7H,8H-pyrido[2,3-d]pyrimidin-7-one

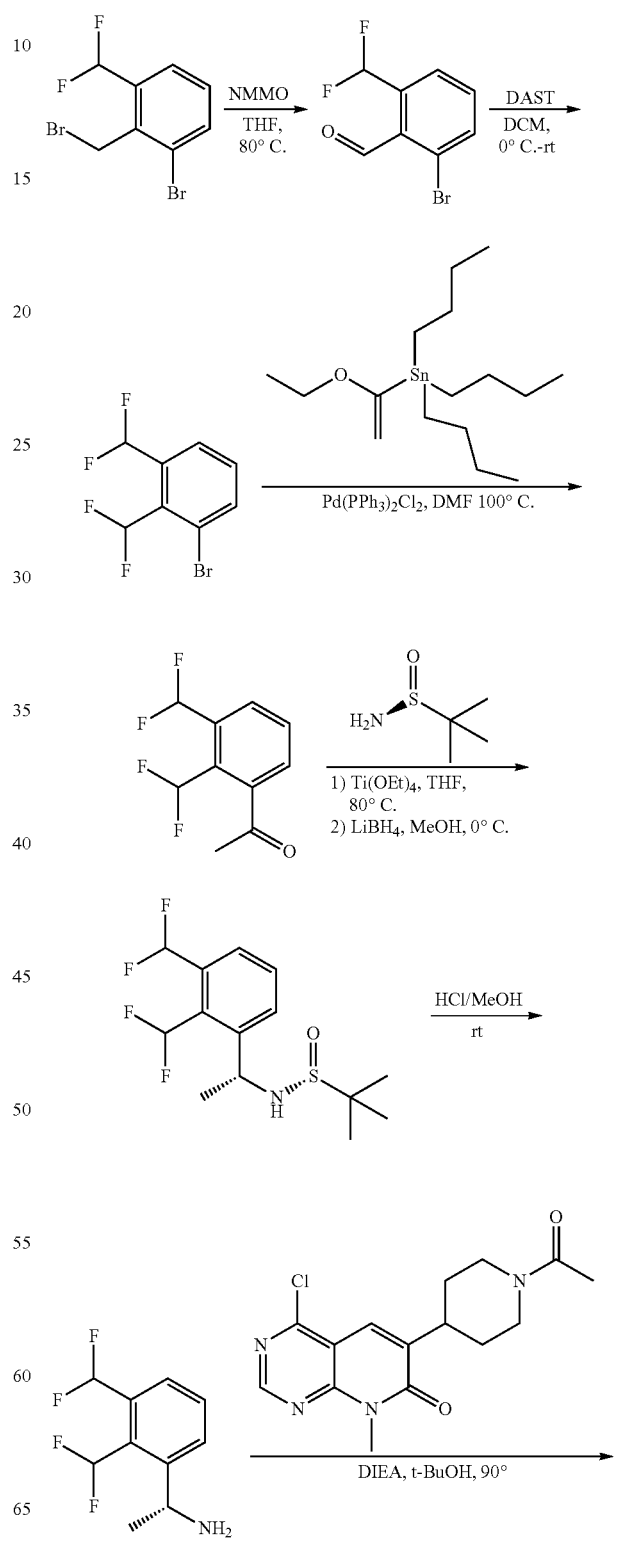

645

-continued

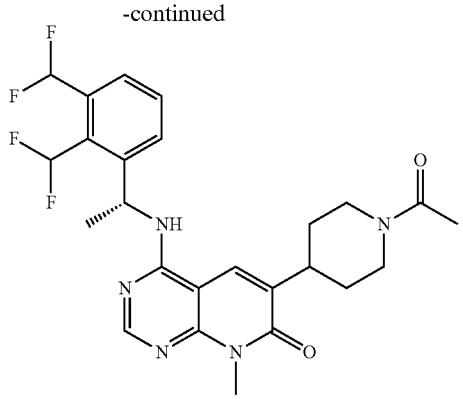

Step 1

To a solution of 1-bromo-2-(bromomethyl)-3-(difluoromethyl)benzene (1 g, 3.33 mmol) in THF (10 mL) was added 4-methyl-4-oxido-morpholin-4-ium (2.46 mL, 23 mmol). The mixture was heated to 80° C. and stirred for 16 h. The residue was diluted with H$_2$O and extracted with EtOAc. The combined organic layers were washed with brine, dried over Na$_2$SO$_4$, and the solvent was removed under reduced pressure to give 2-bromo-6-(difluoromethyl)benzaldehyde (600 mg, 77% yield). $^1$H NMR (400 MHz, CHLOROFORM-d) δ ppm 10.50 (s, 1H) 7.83 (t, J=7.6 Hz, 2H) 7.55-7.57 (m, 1H) 7.42 (t, J=56.0 Hz, 1H).

Step 2

To a solution of 2-bromo-6-(difluoromethyl)benzaldehyde (1.2 g, 5.1 mmol) in DCM (12 mL) was added DAST (2.0 mL, 15.3 mmol) at 0° C. The mixture was stirred at rt for 1 h and then diluted with H$_2$O and extracted with DCM. The combined organic layers were washed with brine, dried over Na$_2$SO$_4$, and concentrated under reduced pressure. The crude residue was purified by column chromatography to give 1-bromo-2,3-bis(difluoromethyl)benzene (1.31 g, 99% yield). $^1$H NMR (400 MHz, METHANOL-d$_4$) δ ppm 7.86 (dd, J=18.8, 7.8 Hz, 2H) 7.56-7.60 (m, 1H) 7.05-7.50 (m, 2H).

Step 3

To a solution of 1-bromo-2,3-bis(difluoromethyl)benzene (1.3 g, 5.1 mmol) and tributyl(1-ethoxyvinyl)stannane (2.1 mL, 6.1 mmol) in DMF (13 mL) was added Pd(PPh$_3$)$_2$Cl$_2$ (357 mg, 0.51 mmol) under N$_2$. The mixture was heated to 100° C. and stirred for 2 h. After cooling to rt 1M HCl was added to adjust the pH to ~2 and the mixture was stirred for 2 h, then filtered and extracted with EtOAc. The combined organic layers were poured into aq. KF and stirred for 2 h. The solids were filtered off and the organic layer was washed with brine. Ti(OEt)$_4$ (1.9 mL, 9.1 mmol) was added and the mixture heated to 80° C. and stirred for 4 h and then cooled to 0° C. MeOH (0.09 mL, 2.3 mmol) was added, followed by LiBH$_4$ (198 mg, 9.1 mmol) and the mixture was stirred at 0° C. for 1 h before water was added and the mixture was filtered. The filtrate was extracted with EtOAc and the combined organic phases were washed with brine, dried over anhydrous Na$_2$SO$_4$ and the solvent was removed under reduced pressure. The crude residue was purified by column chromatography to give (R)—N-[(1R)-1-[2,3-bis(difluoromethyl)phenyl]ethyl]-2-methyl-propane-2-sulfinamide (530 mg, 71% yield). LCMS (ESI): m/z: [M+H] calculated for C$_{14}$H$_{21}$F$_4$NOS: 326.1; found 326.2; $^1$H NMR (400 MHz, CHLOROFORM-d) δ ppm 7.57-7.71 (m, 3H) 7.19-7.46 (m, 1H) 6.88-7.17 (m, 1H) 5.04 (qd, J=6.4, 3.2 Hz, 1H) 3.55 (br s, 1H) 1.59 (d, J=6.8 Hz, 3H) 1.24 (s, 9H).

646

Step 4

To a solution of (R)—N-[(1R)-1-[2,3-bis(difluoromethyl)phenyl]ethyl]-2-methyl-propane-2-sulfinamide (500 mg, 1.54 mmol) in MeOH (5 mL) was added HCl/MeOH (4 M, 0.77 mL). The mixture was stirred at rt for 2 h. The mixture was adjusted to pH=~9-10 adjusted with sat. NaOH in MeOH and the solvent was removed under reduced pressure to give (1R)-1-[2,3-bis(difluoromethyl)phenyl]ethanamine (339 mg, crude). LCMS (ESI): m/z: [M+H] calculated for C$_{10}$H$_{13}$F$_4$N: 222.1; found 222.1; $^1$H NMR (400 MHz, METHANOL-d$_4$) δ ppm 7.95 (d, J=8.0 Hz, 1H) 7.70-7.79 (m, 2H) 7.00-7.49 (m, 2H) 4.95 (q, J=6.8 Hz, 1H) 1.58 (d, J=6.4 Hz, 3H).

Step 5

To a solution of (1R)-1-[2,3-bis(difluoromethyl)phenyl]ethanamine (58 mg, 0.26 mmol) and 6-(1-acetyl-4-piperidyl)-4-chloro-8-methyl-pyrido[2,3-d]pyrimidin-7-one (70 mg, 0.22 mmol) in t-BuOH (1 mL) was added DIEA (0.38 mL, 2.18 mmol). The mixture was heated to 90° C. and stirred for 16 h. After cooling to rt the solvent was removed under reduced pressure and the crude residue was purified by prep-HPLC to give 6-(1-acetyl-4-piperidyl)-4-[[(1R)-1-[2,3-bis(difluoromethyl)phenyl]ethyl]amino]-8-methyl-pyrido[2,3-d]pyrimidin-7-one (35 mg, 32% yield). LCMS (ESI): m/z: [M+H] calculated for C$_{25}$H$_{29}$F$_4$N$_5$O$_2$: 506.2; found 506.4; $^1$H NMR (400 MHz, METHANOL-d4) δ ppm 8.32 (d, J=2.4 Hz, 1H) 8.13 (d, J=1.2 Hz, 1H) 7.77-7.79 (m, 1H) 7.70-7.72 (m, 1H) 7.52-7.65 (m, 2H) 7.21 (t, J=54.8 Hz, 1H) 5.85 (dd, J=6.8, 4.4 Hz, 1H) 4.70-4.74 (m, 1H) 4.01-4.13 (m, 1H) 3.71 (s, 3H) 3.13-3.27 (m, 2H) 2.75 (td, J=12.8, 2.4 Hz, 1H) 2.15 (s, 3H) 1.92-2.04 (m, 2H) 1.60-1.66 (m, 5H).

Example 39: Synthesis of 6-(1-acetylpiperidin-4-yl)-4-{[(1R)-1-[3-(difluoromethyl)-2-(fluoromethyl)phenyl]ethyl]amino}-8-methyl-7H,8H-pyrido[2,3-d]pyrimidin-7-one

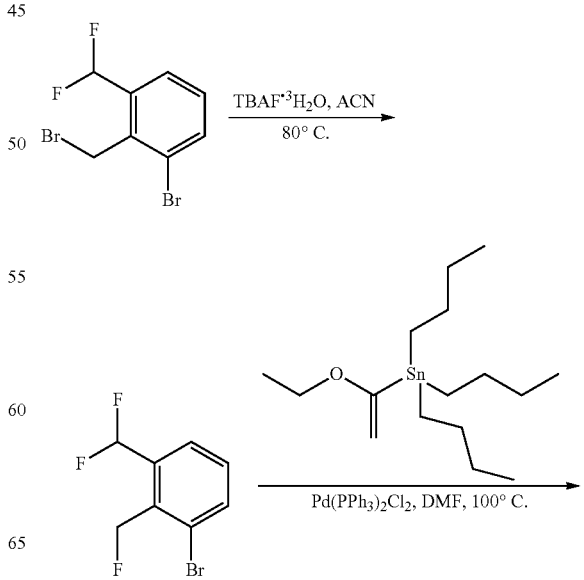

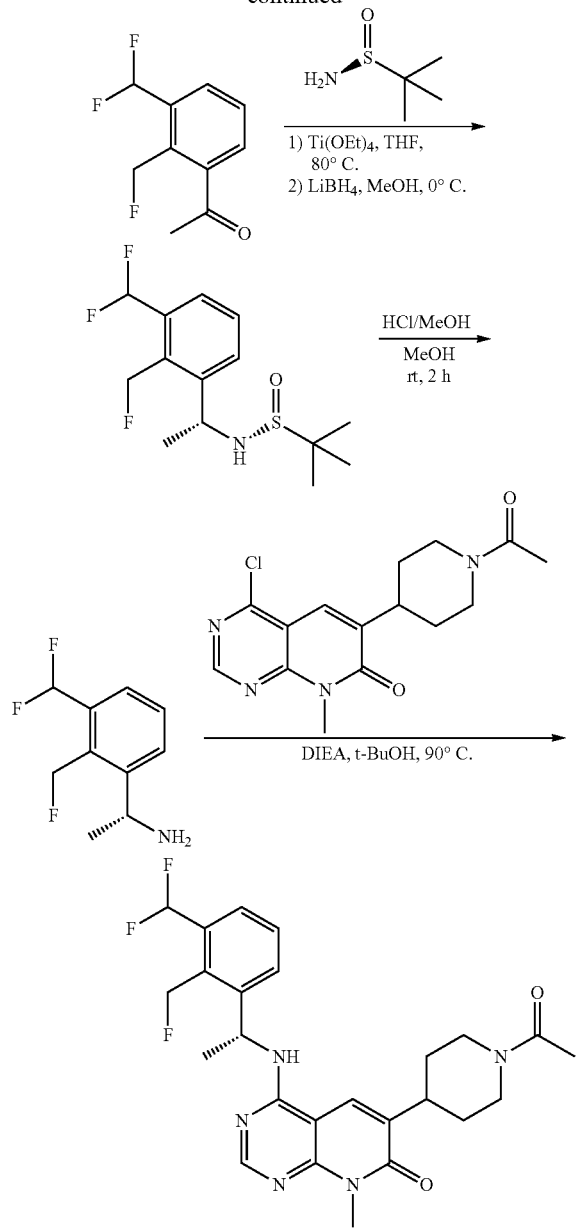

Step 1

To a solution of 1-bromo-2-(bromomethyl)-3-(difluoromethyl)benzene (600 mg, 2.0 mmol) in MeCN (1 mL) was added TBAF.3H₂O (1.26 g, 4.0 mmol). The reaction was heated to 80° C. and stirred for 16 h. After cooling to rt the mixture was diluted with H₂O and extracted with EtOAc. The combined organic layers were washed with brine, dried over Na₂SO₄, and the solvent was removed under reduced pressure to give 1-bromo-3-(difluoromethyl)-2-(fluoromethyl)benzene (450 mg, crude). ¹H NMR (400 MHz, CHLOROFORM-d) δ ppm 7.76 (d, J=8.0 Hz, 1H) 7.63 (d, J=7.8 Hz, 1H) 7.35-7.39 (m, 1H) 6.97 (t, J=54.0 Hz, 1H) 5.74 (d, J=48.0 Hz, 2H).

Step 2

To a solution of 1-bromo-3-(difluoromethyl)-2-(fluoromethyl)benzene (200 mg, 836 mmol) and tributyl(1-ethoxyvinyl)stannane (0.34 mL, 1.00 mmol) in DMF (2 mL) was added Pd(PPh₃)₂Cl₂ (29 mg, 0.04 mmol) under N₂. The mixture was heated to 100° C. and stirred for 10 h. After cooling to rt 1M HCl was added until pH ~2 and the mixture was stirred for 2 h. Solids were filtered off and the filtrate was extracted with EtOAc. The combined organic layers were poured into aq. KF and stirred for 2 h. Solids were filtered off and the phases were separated, the organic layer was washed brine, dried over Na₂SO₄ and the solvent was removed under reduced pressure. The crude residue was purified by column chromatography to give 1-[3-(difluoromethyl)-2-(fluoromethyl)phenyl]ethanone (100 mg, 59% yield). ¹H NMR (400 MHz, CHLOROFORM-d) δ ppm 7.81 (d, J=7.8 Hz, 1H) 7.75 (d, J=7.8 Hz, 1H) 7.55-7.59 (m, 1H) 7.03 (t, J=54.0 Hz, 1H) 5.77 (d, J=48.0 Hz, 2H) 2.64 (s, 3H).

Step 3

To a solution of 1-[3-(difluoromethyl)-2-(fluoromethyl)phenyl]ethanone (100 mg, 494 μmol) and 2-methylpropane-2-sulfinamide (119 mg, 0.99 mmol) in THF (1 mL) was added Ti(OEt)₄ (410 μL, 1.98 mmol). The reaction was heated to 80° C. and stirred for 4 h, then cooled to 0° C. MeOH (20 μL, 495 μmol) was added followed by LiBH₄ (43 mg, 1.98 mmol) and the mixture was stirred at 0° C. for 1 h. After adding water all solids were filtered off and the filtrate was extracted with EtOAc. The combined organic phases were washed with brine, dried with anhydrous Na₂SO₄, and the solvent was removed under reduced pressure. The crude residue was purified by column chromatography to give N-[(1R)-1-[3-(difluoromethyl)-2-(fluoromethyl)phenyl]ethyl]-2-methyl-propane-2-sulfinamide (50 mg, 33% yield). ¹H NMR (400 MHz, METHANOL-d₄) δ ppm 7.74-7.80 (m, 1H) 7.50-7.57 (m, 2H) 7.10 (t, J=54.0 Hz, 1H) 5.72 (d, J=48.0 Hz, 2H) 1.53-1.57 (m, 3H) 1.19-1.26 (m, 9H).

Step 4

To a solution of N-[(1R)-1-[3-(difluoromethyl)-2-(fluoromethyl)phenyl]ethyl]-2-methyl-propane-2-sulfinamide (50 mg, 163 μmol) in MeOH (1 mL) was added HCl/MeOH (4 M, 81 mL). The mixture was stirred at rt for 2 h and then adjusted with sat. NaOH in MeOH to pH=9~10. The solvent was removed under reduced pressure to give (1R)-1-[3-(difluoromethyl)-2-(fluoromethyl)phenyl]ethanamine (50 mg, crude). LCMS (ESI): m/z: [M+H] calculated for C₁₀H₁₄F₃N: 204.1; found 204.2.

Step 5

To a solution of (1R)-1-[3-(difluoromethyl)-2-(fluoromethyl)phenyl]ethanamine (50 mg, 246 μmol) and 6-(1-acetyl-4-piperidyl)-4-chloro-8-methyl-pyrido[2,3-d]pyrimidin-7-one (66 mg, 0.2 mmol) in t-BuOH (1 mL) was added DIEA (0.35 mL, 2.05 mmol). The mixture was heated to 90° C. and stirred for 1 h. After cooling to rt the solvent was removed under reduced pressure and the crude residue was purified by prep-HPLC to give 6-(1-acetyl-4-piperidyl)-4-[[(1R)-1-[3-(difluoromethyl)-2-(fluoromethyl)phenyl]ethyl]amino]-8-methyl-pyrido[2,3-d]pyrimidin-7-one (20 mg, 20% yield). LCMS (ESI): m/z: [M–F] calculated for C₂₅H₂₈F₂N₅O₂: 468.2; found 468.4; ¹H NMR (400 MHz, METHANOL-d₄) δ ppm 8.47 (s, 1H) 8.12-8.15 (m, 1H) 7.46-7.55 (m, 3H) 6.93 (t, J=54.0 Hz, 1H) 6.01-6.05 (m, 1H) 5.65 (d, J=14.4 Hz, 1H) 5.18 (d, J=14.4 Hz, 1H) 4.68-4.77 (m, 1H) 4.04-4.13 (m, 1H) 3.77 (s, 3H) 3.26-3.30 (m, 1H) 3.14-3.21 (m, 1H) 2.74-2.83 (m, 1H) 2.14-2.28 (m, 3H) 2.01-2.08 (m, 2H) 1.45-1.79 (m, 5H).

649

Example 40: Synthesis of 2-{3-[(1R)-1-{[6-(1,1-dioxo-3,6-dihydro-2H-1λ⁶-thiopyran-4-yl)-8-methyl-7-oxo-7H,8H-pyrido[2,3-d]pyrimidin-4-yl]amino}ethyl]phenyl}-2,2-difluoroacetonitrile

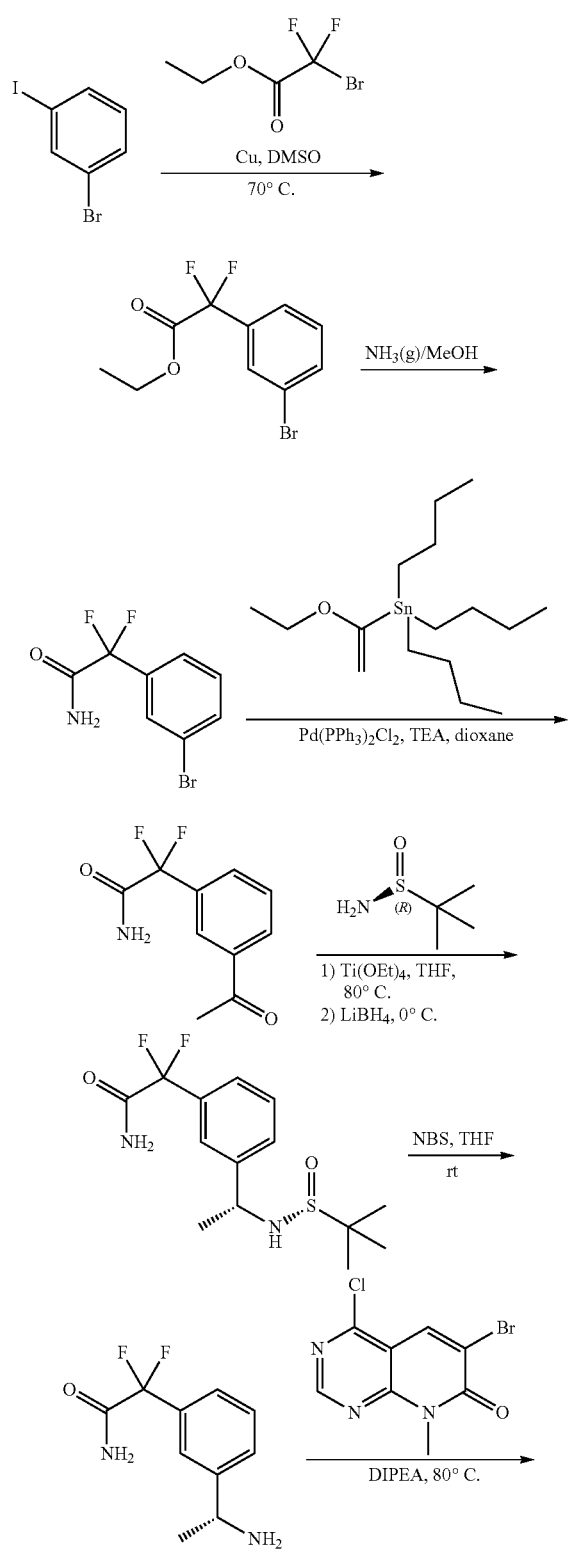

650

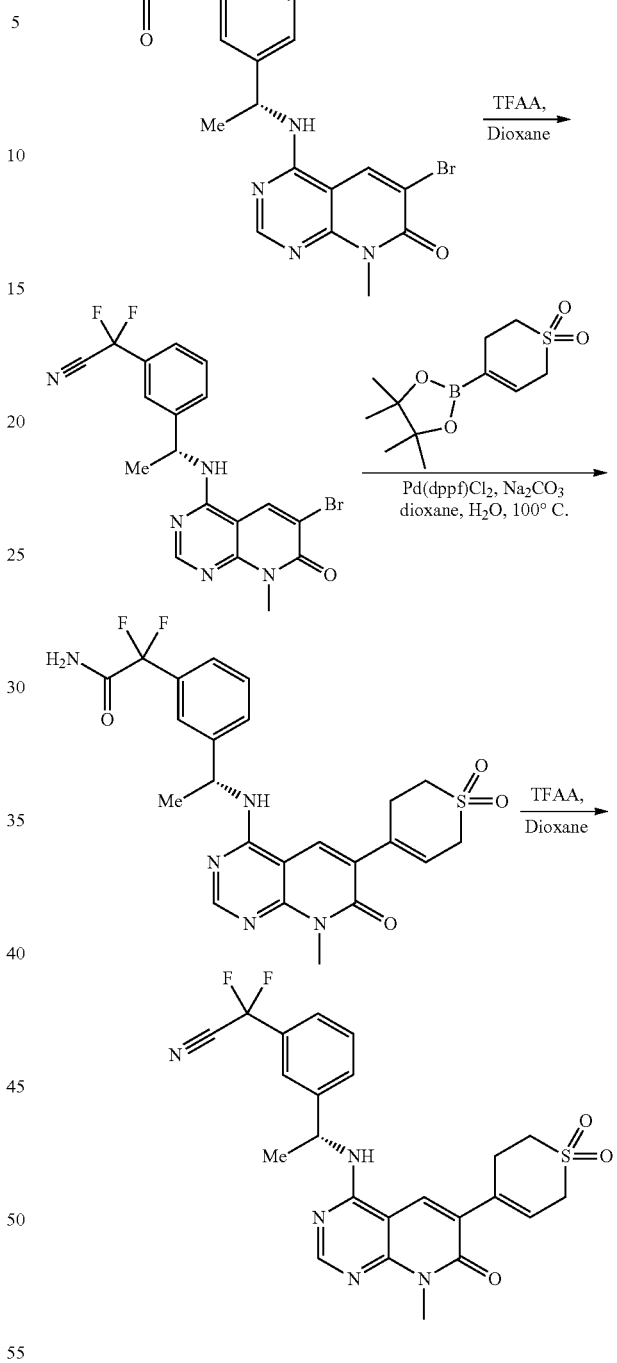

Step 1

To a solution of ethyl 2-bromo-2,2-difluoro-acetate (5.7 mL, 44 mmol) in DMSO (30 mL) was added Cu powder (3.37 g, 53.2 mmol) at rt over 1 h. Then 1-bromo-3-iodo-benzene (5 g, 17.6 mmol, 2.25 mL) was added and the mixture was heated to 70° C. for 3 h. After cooling to rt the mixture was filtered, and the filtrate was diluted with H₂O and extracted with EtOAc. The combined organic layers were washed with brine and the solvent was removed under reduced pressure to give 2-(3-bromophenyl)-2,2-difluoro-acetamide (2.5 g, crude). $^1$H NMR (400 MHz, DMSO-d$_6$) δ ppm 8.42 (br s, 1H), 8.09 (br s, 1H), 7.75-7.79 (m, 2H), 7.57-7.59 (m, 1H), 7.48-7.52 (m, 1H).

Step 2

To a mixture of 2-(3-bromophenyl)-2,2-difluoro-acetamide (1.5 g, 6.0 mmol) in DMF (15 mL) was added tributyl(1-ethoxyvinyl)stannane (2.43 mL, 7.20 mmol) and $PdCl_2(PPh_3)_2$ (211 mg, 0.30 mmol) at rt under $N_2$. Then the mixture was heated to 100° C. and stirred for 2 h. Saturated aqueous CsF (10 mL) was added and the reaction was stirred for 10 min, then filtered. The aqueous phase was extracted with EtOAc and the combined organic phases were washed with brine, dried with anhydrous $Na_2SO_4$, and the solvent was removed under reduced pressure. To the residue was added 2N HCl (20 mL) and the mixture was stirred at rt for 2 h before being extracted with EtOAc. The combined organic phases were washed with brine, dried over anhydrous $Na_2SO_4$, and the solvent was removed under reduced pressure. The crude residue was purified by column chromatography to give 2-(3-acetylphenyl)-2,2-difluoro-acetamide (1 g, 78% yield). $^1$H NMR (400 MHz, DMSO-$d_6$) δ ppm 8.46 (br s, 1H), 8.08-8.42 (m, 3H), 7.82-7.84 (m, 1H), 7.68-7.72 (m, 1H), 2.63 (s, 3H).

Step 3/4

To a solution of 2-(3-acetylphenyl)-2,2-difluoro-acetamide (1 g, 4.7 mmol) in THF (10 mL) was added Ti(OEt)$_4$ (3.89 mL, 18.76 mmol) and 2-methylpropane-2-sulfinamide (625 mg, 5.2 mmol) at rt under $N_2$. The mixture was heated to 80° C. and stirred for 2 h. After cooling to 0° C., LiBH$_4$ (102 mg, 4.7 mmol) was added and the reaction mixture was stirred for 1 h at 0° C. Water was added and the aqueous phase was extracted with EtOAc. The combined organic phases were washed with brine and NBS (184 mg, 1.04 mmol) was added to the extract. The mixture was stirred at rt for 1 h before being quenched with 2N HCl (3 mL). The aqueous phase was washed with MTBE and adjusted to pH to ~7-8 with aq NaHCO$_3$. The water was removed on the lyophilizer and the crude residue was taken up in 5:1 DCM:MeOH (5 mL), any solids were filtered off and the solvent was removed under reduced pressure to give 2-[3-[(1R)-1-aminoethyl]phenyl]-2,2-difluoro-acetamide (300 mg, crude). LCMS (ESI): m/z: [M+H] calculated for $C_{10}H_{13}F_2N_2O$: 215.1; found 215.2.

Step 5

To a solution of 2-[3-[(1R)-1-aminoethyl]phenyl]-2,2-difluoro-acetamide (0.3 g, 1.4 mmol) and 6-bromo-4-chloro-8-methyl-pyrido[2,3-d]pyrimidin-7-one (320 mg, 1.17 mmol) in n-BuOH (5 mL) was added DIEA (1 mL, 5.8 mmol). The mixture was heated to 80° C. for 2 h. After cooling to rt the mixture was washed with brine, dried with anhydrous $Na_2SO_4$, and the solvent was removed under reduced pressure. The crude residue was purified by column chromatography to give 2-[3-[(1R)-1-[(6-bromo-8-methyl-7-oxo-pyrido[2,3-d]pyrimidin-4-yl)amino]ethyl]phenyl]-2,2-difluoro-acetamide (300 mg, 57% yield). $^1$H NMR (400 MHz, DMSO-$d_6$) δ ppm 8.98 (s, 1H), 8.45-8.47 (m, 1H), 8.40 (s, 1H), 8.33 (s, 1H), 7.98 (s, 1H), 7.56-7.61 (m, 2H), 7.42-7.49 (m, 2H), 5.49-5.56 (m, 1H), 3.62 (s, 3H), 1.55 (d, J=7.2 Hz, 3H).

Step 6

To a solution of 2-[3-[(1R)-1-[(6-bromo-8-methyl-7-oxo-pyrido[2,3-d]pyrimidin-4-yl)amino] ethyl]phenyl]-2,2-difluoro-acetamide (0.25 g, 0.55 mmol) in dioxane (2.5 mL) was added pyridine (0.09 mL, 1.1 mmol), followed by the addition of TFAA (0.12 mL, 0.83 mmol) at 0° C. The mixture was stirred at rt for 1 h before water was added and the aqueous phase was extracted with EtOAc. The combined organic phases were washed with brine, dried over $Na_2SO_4$ and the solvent was removed under reduced pressure. The crude residue was purified by column chromatography to give 2-[3-[(1R)-1-[(6-bromo-8-methyl-7-oxo-pyrido[2,3-d]pyrimidin-4-yl)amino]ethyl]phenyl]-2,2-difluoro-acetonitrile (150 mg, 62% yield). $^1$H NMR (400 MHz, DMSO-$d_6$) δ ppm 8.96 (s, 1H), 8.46 (d, J=7.6 Hz, 1H), 8.39 (s, 1H), 7.78 (s, 1H), 7.49-7.68 (m, 1H), 7.66-7.74 (m, 1H), 7.59-7.63 (m, 1H), 5.45-5.59 (m, 1H), 3.61 (s, 3H), 1.57 (d, J=7.2 Hz, 3H).

Step 7

To a solution of 2-[3-[(1R)-1-[(6-bromo-8-methyl-7-oxo-pyrido[2,3-d]pyrimidin-4-yl)amino]ethyl]phenyl]-2,2-difluoro-acetonitrile (0.1 g, 0.23 mmol) and 4-(4,4,5,5-tetramethyl-1,3,2-dioxaborolan-2-yl)-3,6-dihydro-2H-thiopyran 1,1-dioxide (118 mg, 0.46 mmol) in dioxane (1.5 mL) and $H_2O$ (0.3 mL) was added $Na_2CO_3$ (48 mg, 0.46 mmol) and Pd(PPh$_3$)$_2$Cl$_2$ (16 mg, 0.023 mmol) at rt under $N_2$. The mixture was heated to 100° C. under $N_2$ and stirred for 6 h. After cooling to rt water was added and the aqueous phase was extracted with EtOAc. The combined organic phases washed with brine, dried with anhydrous $Na_2SO_4$, and the solvent was removed under reduced pressure. The residue was purified by column chromatography to give 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]phenyl]-2,2-difluoro-acetamide (80 mg, 69% yield). $^1$H NMR (400 MHz, DMSO-$d_6$) δ ppm 8.36 (s, 2H), 8.00 (s, 1H), 7.57-7.64 (m, 1H), 7.53-7.54 (m, 1H), 7.57 (br s, 1H), 7.45-7.52 (m, 1H), 7.45 (m, 1H), 6.09 (s, 1H), 5.54-5.58 (m, 1H), 3.82-3.93 (m, 3H), 3.57 (s, 3H), 3.05-3.08 (m, 3H), 1.56 (d, J=7.2 Hz, 3H).

Step 8

To a solution of 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]phenyl]-2,2-difluoro-acetamide (0.07 g, 0.139 mmol) in dioxane (1 mL) was added pyridine (22 μL, 0.28 mmol) followed by the addition of TFAA (29 μL, 0.21 mmol) at 0° C. Then the mixture was stirred at rt for 1 h before water was added and the aqueous phase was extracted with EtOAc. The combined organic phases were washed with brine, dried with anhydrous $Na_2SO_4$, and the solvent was removed under reduced pressure. The residue was purified by prep-HPLC to give 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]phenyl]-2,2-difluoro-acetonitrile (14.3 mg, 21% yield). LCMS (ESI): m/z: [M+H] calculated for $C_{23}H_{22}F_2N_5O_3S$: 486.1; found 486.3; H NMR (400 MHz, METHANOL-$d_4$) δ ppm 8.34 (s, 1H), 8.26 (s, 1H), 7.78 (s, 1H), 7.73-7.75 (m, 1H), 7.56-7.61 (m, 2H), 6.00-6.02 (m, 1H), 5.58-5.63 (m, 1H), 3.87 (s, 2H), 3.70 (s, 3H), 3.34 (s, 1H), 3.14-3.16 (m, 2H), 1.65 (d, J=7.2 Hz, 3H).

Example 41: Synthesis of 2-{3-[(1R)-1-{[6-(1,1-dioxo-3,6-dihydro-2H-1λ$^6$-thiopyran-4-yl)-8-methyl-7-oxo-7H,8H-pyrido[2,3-d]pyrimidin-4-yl]amino}ethyl]-2-fluorophenyl}-2,2-difluoroacetonitrile

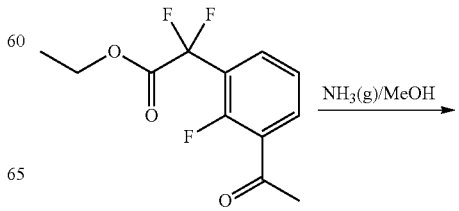

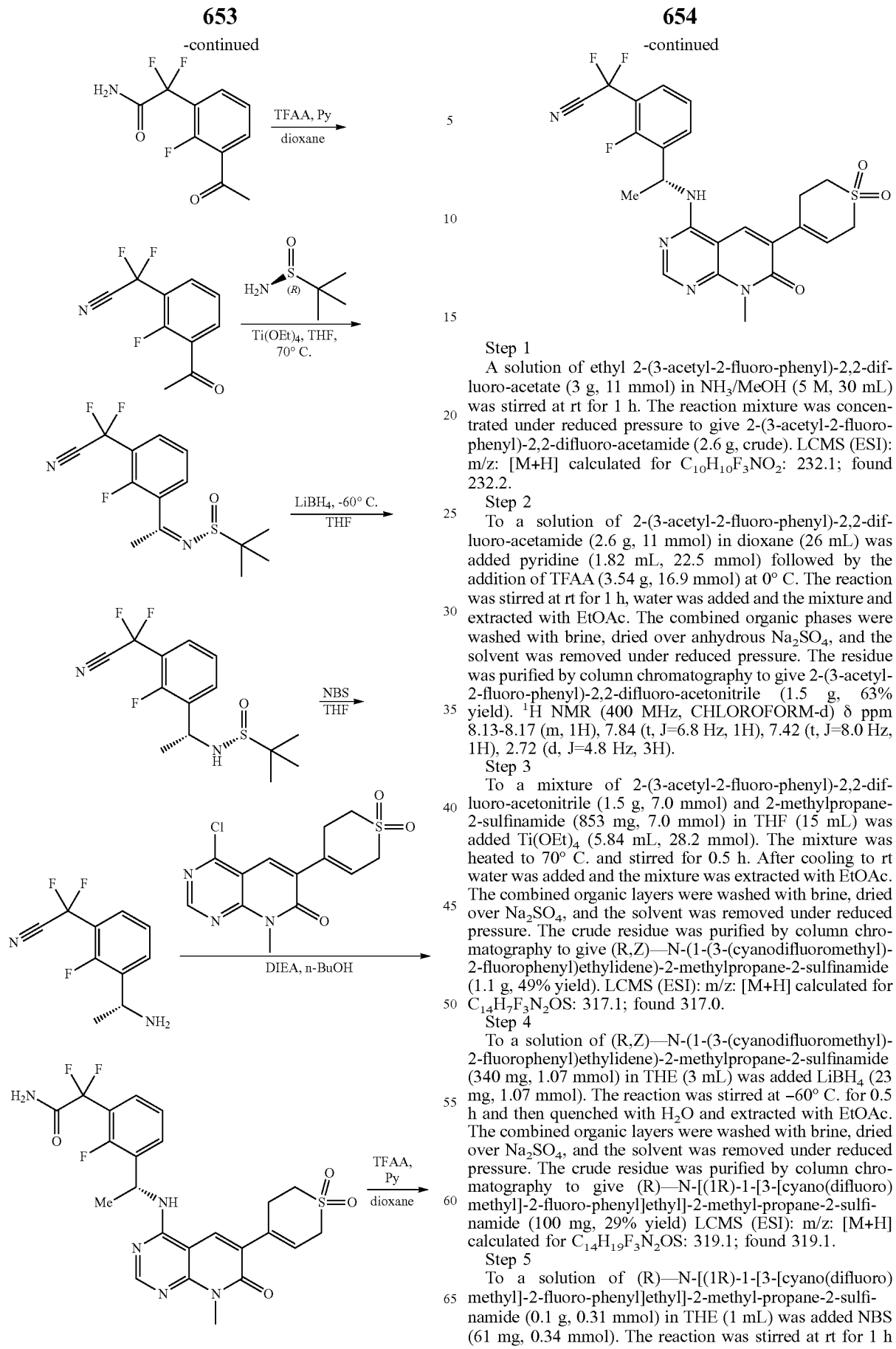

Step 1

A solution of ethyl 2-(3-acetyl-2-fluoro-phenyl)-2,2-difluoro-acetate (3 g, 11 mmol) in NH$_3$/MeOH (5 M, 30 mL) was stirred at rt for 1 h. The reaction mixture was concentrated under reduced pressure to give 2-(3-acetyl-2-fluoro-phenyl)-2,2-difluoro-acetamide (2.6 g, crude). LCMS (ESI): m/z: [M+H] calculated for $C_{10}H_{10}F_3NO_2$: 232.1; found 232.2.

Step 2

To a solution of 2-(3-acetyl-2-fluoro-phenyl)-2,2-difluoro-acetamide (2.6 g, 11 mmol) in dioxane (26 mL) was added pyridine (1.82 mL, 22.5 mmol) followed by the addition of TFAA (3.54 g, 16.9 mmol) at 0° C. The reaction was stirred at rt for 1 h, water was added and the mixture and extracted with EtOAc. The combined organic phases were washed with brine, dried over anhydrous Na$_2$SO$_4$, and the solvent was removed under reduced pressure. The residue was purified by column chromatography to give 2-(3-acetyl-2-fluoro-phenyl)-2,2-difluoro-acetonitrile (1.5 g, 63% yield). $^1$H NMR (400 MHz, CHLOROFORM-d) δ ppm 8.13-8.17 (m, 1H), 7.84 (t, J=6.8 Hz, 1H), 7.42 (t, J=8.0 Hz, 1H), 2.72 (d, J=4.8 Hz, 3H).

Step 3

To a mixture of 2-(3-acetyl-2-fluoro-phenyl)-2,2-difluoro-acetonitrile (1.5 g, 7.0 mmol) and 2-methylpropane-2-sulfinamide (853 mg, 7.0 mmol) in THF (15 mL) was added Ti(OEt)$_4$ (5.84 mL, 28.2 mmol). The mixture was heated to 70° C. and stirred for 0.5 h. After cooling to rt water was added and the mixture was extracted with EtOAc. The combined organic layers were washed with brine, dried over Na$_2$SO$_4$, and the solvent was removed under reduced pressure. The crude residue was purified by column chromatography to give (R,Z)—N-(1-(3-(cyanodifluoromethyl)-2-fluorophenyl)ethylidene)-2-methylpropane-2-sulfinamide (1.1 g, 49% yield). LCMS (ESI): m/z: [M+H] calculated for $C_{14}H_7F_3N_2OS$: 317.1; found 317.0.

Step 4

To a solution of (R,Z)—N-(1-(3-(cyanodifluoromethyl)-2-fluorophenyl)ethylidene)-2-methylpropane-2-sulfinamide (340 mg, 1.07 mmol) in THF (3 mL) was added LiBH$_4$ (23 mg, 1.07 mmol). The reaction was stirred at −60° C. for 0.5 h and then quenched with H$_2$O and extracted with EtOAc. The combined organic layers were washed with brine, dried over Na$_2$SO$_4$, and the solvent was removed under reduced pressure. The crude residue was purified by column chromatography to give (R)—N-[(1R)-1-[3-[cyano(difluoro)methyl]-2-fluoro-phenyl]ethyl]-2-methyl-propane-2-sulfinamide (100 mg, 29% yield) LCMS (ESI): m/z: [M+H] calculated for $C_{14}H_{19}F_3N_2OS$: 319.1; found 319.1.

Step 5

To a solution of (R)—N-[(1R)-1-[3-[cyano(difluoro)methyl]-2-fluoro-phenyl]ethyl]-2-methyl-propane-2-sulfinamide (0.1 g, 0.31 mmol) in THF (1 mL) was added NBS (61 mg, 0.34 mmol). The reaction was stirred at rt for 1 h before water was added and the mixture was extracted with EtOAc. The water phase was lyophilized and the dry residue was taken up in 5:1 DCM:MeOH (2 mL). Solids were filtered off and the solvent was removed under reduced pressure to give 2-[3-[(1R)-1-aminoethyl]-2-fluoro-phenyl]-2,2-difluoro-acetonitrile (70 mg, crude). LCMS (ESI): m/z: [M+H] calculated for $C_{10}H_{11}F_3N_2$: 215.1; found 215.2.

Step 6

To a solution of 2-[3-[(1R)-1-aminoethyl]-2-fluoro-phenyl]-2,2-difluoro-acetonitrile (70 mg, 0.33 mmol) and 4-chloro-6-(1,1-dioxo-3,6-dihydro-2H-thiopyran-4-yl)-8-methyl-pyrido[2,3-d]pyrimidin-7-one (85 mg, 0.26 mmol) in n-BuOH (1 mL) was added DIEA (0.28 mL, 1.63 mmol). The mixture was heated to 80° C. and stirred for 0.5 h. After cooling to rt the reaction mixture was extracted with EtOAc. The combined organic layers were washed with brine, dried over $Na_2SO_4$, and the solvent was removed under reduced pressure. The crude residue was purified by column chromatography to give 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]-2-fluoro-phenyl]-2,2-difluoro-acetamide (20 mg, 12% yield). LCMS (ESI): m/z: [M+H] calculated for $C_{23}H_{24}F_3N_5O_4S$: 522.1; found 522.4.

Step 7

To a solution of 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]-2-fluoro-phenyl]-2,2-difluoro-acetamide (20 mg, 38 μmol) in dioxane (1 mL) was added pyridine (6 μL, 77 μmol), followed by the addition of TFAA (8 μL, 58 μmol) at 0° C. The mixture was stirred at rt for 1 h, water was added, and the mixture was extracted with EtOAc. The combined organic phases were washed with brine, dried with anhydrous $Na_2SO_4$, and the solvent was removed under reduced pressure. The residue was purified by prep-HPLC to give 2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]-2-fluoro-phenyl]-2,2-difluoro-acetonitrile (5 mg, 26% yield). LCMS (ESI): m/z: [M+H] calculated for $C_{23}H_{22}F_3N_5O_3S$: 504.1; found 504.4; $^1$H NMR (400 MHz, METHANOL-$d_4$) δ ppm 8.31 (d, J=5.6 Hz, 2H), 7.74 (t, J=7.2 Hz, 1H), 7.61 (t, J=3.6 Hz, 1H), 7.34 (t, J=7.6 Hz, 1H), 6.03 (t, J=4.4 Hz, 1H), 5.76-5.78 (m, 1H), 3.88 (d, J=2.0 Hz, 2H), 3.69 (s, 3H), 3.33 (s, 2H), 3.15-3.16 (m, 2H), 1.66 (d, J=7.2 Hz, 3H).

The following example 41-1 shown in Table 15 was synthesized in the manner similar to Example 41.

Example 42: Synthesis of 4-(4-{[(1R)-1-[3-(2-amino-1,1-difluoroethyl)-2-fluorophenyl]ethyl]amino}-8-methyl-7-oxo-7H,8H-pyrido[2,3-d]pyrimidin-6-yl)-3,6-dihydro-2H-1λ$^6$-thiopyran-1,1-dione

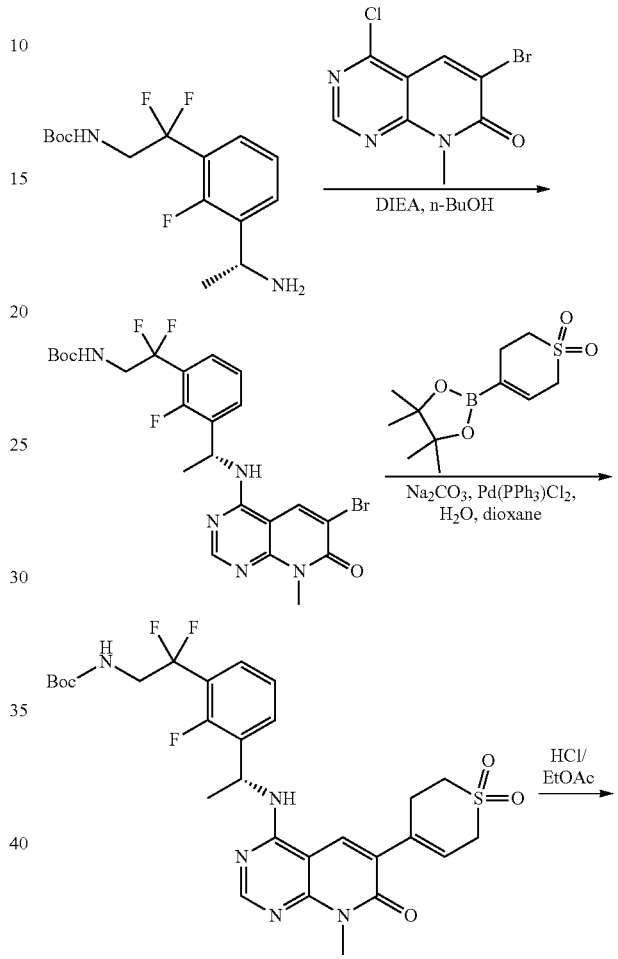

TABLE 15

Example 41-1

| Example # | Structure | Mass Found |
|---|---|---|
| 41-1 | 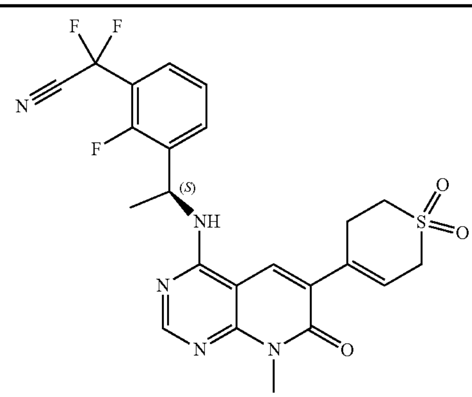 | 504 |

-continued

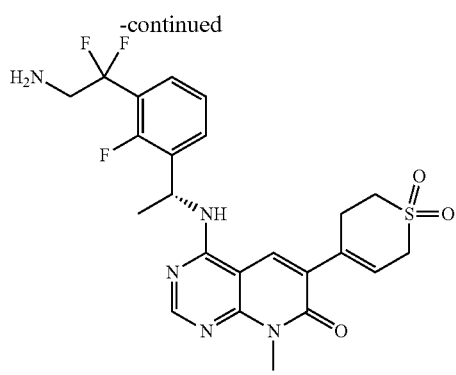

Step 1

To a solution of tert-butyl-N-[2-[3-[(1R)-1-aminoethyl]-2-fluoro-phenyl]-2,2-difluoro-ethyl]carbamate (110 mg, 0.35 mmol) in n-BuOH (0.5 mL) was added 6-bromo-4-chloro-8-methyl-pyrido[2,3-d]pyrimidin-7-one (104 mg, 0.38 mmol) and DIEA (0.3 mL, 1.73 mmol). The reaction was heated to 80° C. and stirred for 2 h. After cooling to rt water was added and the mixture was extracted with EtOAc. The combined organic layers were washed with brine, dried over $Na_2SO_4$, and the solvent was removed under reduced pressure. The crude residue was purified by column chromatography to give tert-butyl N-[2-[3-[(1R)-1-[(6-bromo-8-methyl-7-oxo-pyrido[2,3-d]pyrimidin-4-yl)amino]ethyl]-2-fluoro-phenyl]-2,2-difluoro-ethyl]carbamate (100 mg, 52% yield). $^1$H NMR (400 MHz, CHLOROFORM-d) δ ppm 8.57 (s, 1H) 8.34 (s, 1H) 7.46-7.54 (m, 2H) 7.18-7.22 (m, 1H) 6.28 (d, J=6.8 Hz, 1H) 5.60 (t, J=6.8 Hz, 1H) 4.84 (t, J=6.4 Hz, 1H) 3.85 (s, 3H) 3.79-3.82 (m, 1H) 1.76 (d, J=6.8 Hz, 3H) 1.18 (s, 9H).

Step 2

To a mixture of tert-butyl N-[2-[3-[(1R)-1-[(6-bromo-8-methyl-7-oxo-pyrido[2,3-d]pyrimidin-4-yl)amino]ethyl]-2-fluoro-phenyl]-2,2-difluoro-ethyl]carbamate (90 mg, 0.16 mmol) and 4-(4,4,5,5-tetramethyl-1,3,2-dioxaborolan-2-yl)-3,6-dihydro-2H-thiopyran 1,1-dioxide (46 mg, 0.18 mmol) in dioxane (1 mL) and $H_2O$ (0.2 mL) was added $Pd(PPh_3)_2Cl_2$ (11 mg, 16 μmol) and $Na_2CO_3$ (34 mg, 0.32 mmol) at rt under $N_2$. The mixture was heated to 100° C. under $N_2$ and stirred for 10 h. After cooling to rt the reaction was concentrated under reduced pressure and the crude residue was purified by column chromatography to give tert-butyl N-[2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]-2-fluoro-phenyl]-2,2-difluoro-ethyl]carbamate (70 mg, 71% yield). LCMS (ESI): m/z: [M+H] calculated for $C_{28}H_{33}F_3N_5O_5S$: 608.21; found 608.4.

Step 3

To a solution of tert-butyl N-[2-[3-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]-2-fluoro-phenyl]-2,2-difluoro-ethyl]carbamate (70 mg, 0.12 mmol) in EtOAc (1 mL) was added HCl (4 M in EtOAc, 58 μL, 232 μmol) at rt and the mixture was stirred for 1 h. The solvent was removed under reduced pressure and the crude residue was purified by prep-HPLC to give 4-[[(1R)-1-[3-(2-amino-1,1-difluoro-ethyl)-2-fluoro-phenyl]ethyl]amino]-6-(1,1-dioxo-3,6-dihydro-2H-thiopyran-4-yl)-8-methyl-pyrido[2,3-d]pyrimidin-7-one (20 mg, 34% yield). LCMS (ESI): m/z: [M+H] calculated for $C_{23}H_{25}F_3N_5O_3S$: 508.2; found 508.3; $^1$H NMR (400 MHz, CHLOROFORM-d) δ ppm 8.48 (s, 1H) 7.63 (s, 1H) 7.47-7.54 (m, 2H) 7.20-7.25 (m, 1H) 5.94 (s, 1H) 5.74-5.81 (m, 2H) 3.82 (s, 2H) 3.74 (s, 3H) 3.19-3.34 (m, 6H) 1.70-1.72 (m, 3H).

Example 43: Synthesis of 6-(1-acetyl-4-piperidyl)-4-[[(1R)-1-[3-(difluoromethyl)-5-(3-fluoroazetidin-3-yl)phenyl]ethyl]amino]-8-methyl-pyrido[2,3-d]pyrimidin-7-one

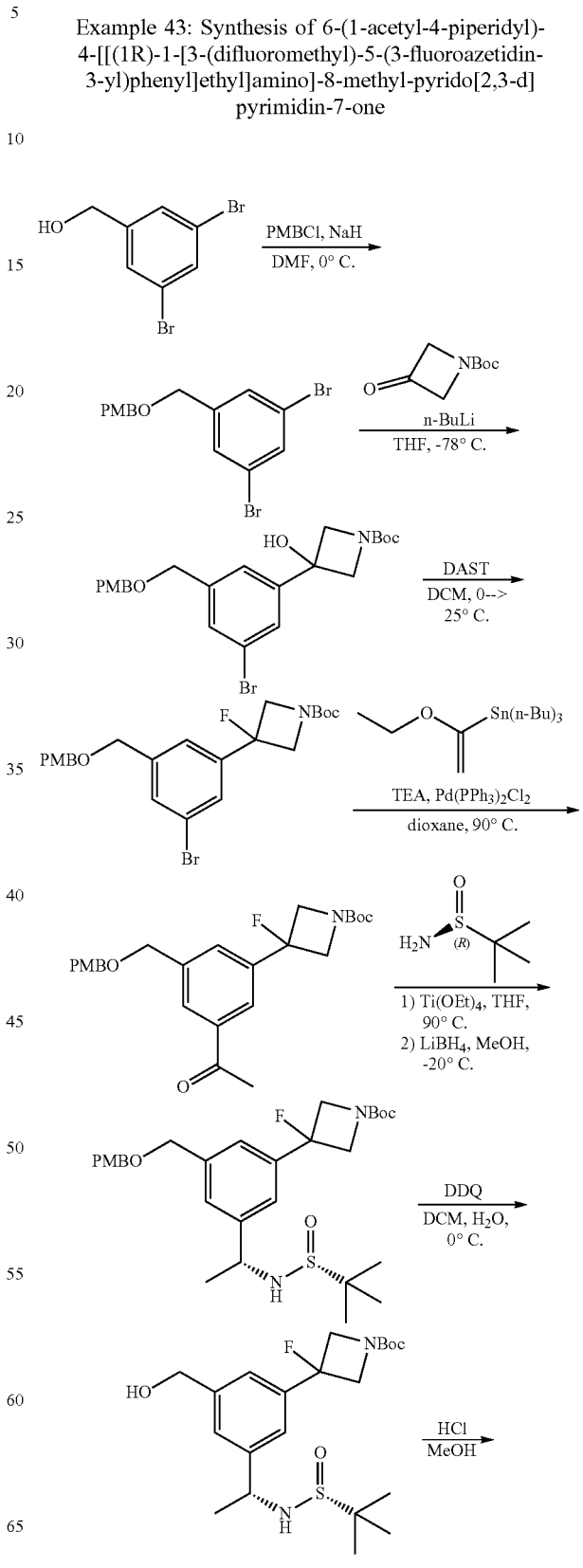

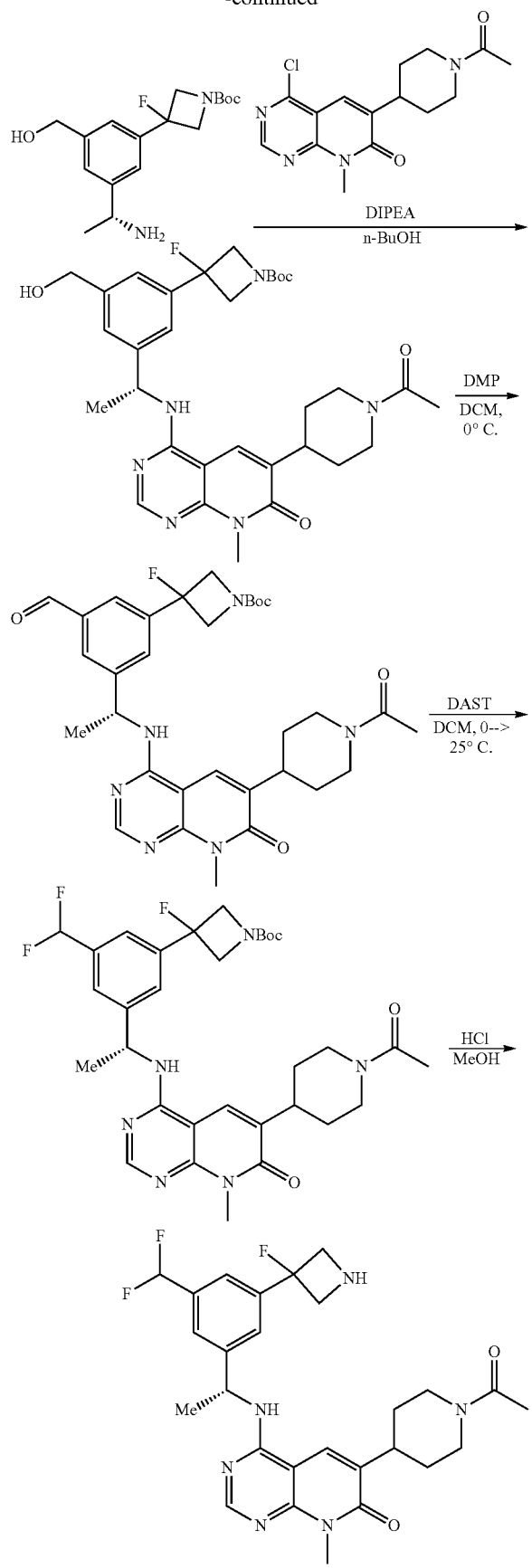

Step 1

To a solution of (3,5-dibromophenyl)methanol (10 g, 37.6 mmol) in DMF (100 mL) at 0° C. was added NaH (60 wt %, 1.80 g, 45 mmol). The reaction was stirred at 0° C. for 20 min and, then PMB-Cl (6.4 mL, 47 mmol) was added. After stirring for another 1 h the reaction was quenched with $H_2O$, extracted with EtOAc, washed with brine, dried with $Na_2SO_4$, and the solvent was removed under reduced pressure. The crude residue was purified by column chromatography to give 1,3-dibromo-5-[(4-methoxyphenyl)methoxymethyl]benzene (13 g, 90% yield). $^1$H NMR (400 MHz, chloroform-d) δ ppm 7.59-7.53 (m, 1H), 7.43 (d, J=1.10 Hz, 2H), 7.30-7.26 (m, 2H), 6.93-6.87 (m, 2H), 4.50 (s, 2H), 4.45 (s, 2H), 3.82 (s, 3H).

Step 2

To a solution of 1,3-dibromo-5-[(4-methoxyphenyl)methoxymethyl]benzene (7.5 g, 19 mmol) in THF (75 mL) under $N_2$ at −78° C. was added 2.5M n-BuLi (7 mL, 17.5 mmol). The reaction mixture stirred at −78° C. for 1 h and, then tert-butyl 3-oxoazetidine-1-carboxylate (3 g, 17 mmol) in THF (7 mL) was added. After an additional 1 h at −78° C. sat. aq. $NH_4Cl$ was added and the mixture was extracted with EtOAc, dried with $Na_2SO_4$, filtered, and the solvent was removed under reduced pressure. The residue was purified by column chromatography to give tert-butyl 3-[3-bromo-5-[(4-methoxyphenyl)methoxymethyl]phenyl]-3-hydroxy-azetidine-1-carboxylate (7.8 g, 84% yield). $^1$H NMR (400 MHz, chloroform-d) δ ppm 7.53-7.49 (m, 1H), 7.40-7.37 (m, 1H), 7.35-7.31 (m, 1H), 7.24-7.19 (m, 2H), 6.85-6.80 (m, 2H), 4.46-4.38 (m, 4H), 4.15-4.04 (m, 5H), 1.40 (s, 9H).

Step 3

To a solution of tert-butyl 3-[3-bromo-5-[(4-methoxyphenyl)methoxymethyl]phenyl]-3-hydroxy-azetidine-1-carboxylate (7.8 g, 16 mmol) in DCM (80 mL) at 0° C. was added DAST (4.31 mL, 33 mmol). The reaction mixture was stirred at for 1 h. The solvent was removed under reduced pressure and the crude residue was purified by column chromatography to give tert-butyl 3-[3-bromo-5-[(4-methoxyphenyl)methoxymethyl]phenyl]-3-fluoro-azetidine-1-carboxylate (5.4 g, 69% yield). LCMS (ESI): m/z: [M+Na] calculated for $C_{23}H_{28}BrFNO_4Na$: 502.1; found 502.0.

Step 4

To a solution of tert-butyl 3-[3-bromo-5-[(4-methoxyphenyl)methoxymethyl]phenyl]-3-fluoro-azetidine-1-carboxylate (5.4 g, 11 mmol) and tributyl(1-ethoxyvinyl)stannane (5.69 mL, 16.86 mmol) in dioxane (60 mL) under $N_2$ was added TEA (3.91 mL, 28.1 mmol), and $Pd(PPh_3)_2Cl_2$ (395 mg, 0.56 mmol). The reaction stirred at 90° C. for 1 h. After cooling to rt the mixture was acidified to pH 2 using 2M HCl and stirred for 1 h. Solids were filtered off and the filtrate was extracted with EtOAc. The organic layer was poured into aq. KF and stirred for 20 min. The mixture was filtered again and the organic layer was washed with brine, dried with $Na_2SO_4$, and the solvent was removed under reduced pressure. The residue was purified by column chromatography to give tert-butyl 3-[3-acetyl-5-[(4-methoxyphenyl)methoxymethyl]phenyl]-3-fluoro-azetidine-1-carboxylate (4.1 g, 82% yield). H NMR (400 MHz, chloroform-d) δ ppm 7.94 (d, J=18.08 Hz, 2H), 7.65 (s, 1H), 7.30 (d, J=8.38 Hz, 2H), 6.91 (d, J=8.38 Hz, 2H), 4.57 (d, J=13.89 Hz, 4H), 4.47-4.39 (m, 2H), 4.30-4.22 (m, 2H), 3.82 (s, 3H), 2.63 (s, 3H), 1.49 (s, 9H).

Step 5

To a solution of tert-butyl 3-[3-acetyl-5-[(4-methoxyphenyl)methoxymethyl]phenyl]-3-fluoro-azetidine-1-carboxylate (4.1 g, 9.2 mmol) in THF (45 mL) was added 2-methylpropane-2-sulfinamide (1.68 g, 13.9 mmol) and Ti(OEt)$_4$ (3.8 mL, 18.5 mmol). The reaction mixture was stirred at 90° C. for 2 h and then cooled to −20° C. Methanol (0.37 mL, 9.2 mmol) and LiBH$_4$ (1.0 g, 46 mmol) were added. The reaction mixture was stirred for 1 h and then quenched with H$_2$O, extracted with THF, and the solvent was removed under reduced pressure. The crude residue was purified by column chromatography to give tert-butyl 3-[3-[(1R)-1-[[(R)-tert-butylsulfinyl]amino]ethyl]-5-[(4-methoxyphenyl)methoxymethyl]phenyl]-3-fluoro-azetidine-1-carboxylate (2.6 g, 47% yield). $^1$H NMR (400 MHz, chloroform-d) δ ppm 7.32-7.20 (m, 5H), 6.87-6.80 (m, 2H), 4.53-4.48 (m, 1H), 4.46 (s, 3H), 4.37-4.27 (m, 2H), 4.22-4.12 (m, 2H), 3.75 (s, 3H), 1.47-1.39 (m, 12H), 1.16 (s, 9H).

Step 6

To a solution of tert-butyl 3-[3-[(1R)-1-[[(R)-tert-butylsulfinyl]amino]ethyl]-5-[(4-methoxyphenyl)methoxymethyl]phenyl]-3-fluoro-azetidine-1-carboxylate (2.6 g, 4.7 mmol) in DCM (26 mL) and H$_2$O (1.3 mL) at 0° C. was added DDQ (1.3 g, 5.9 mmol). The reaction was stirred for 2 h before sat. aq. NaHCO$_3$ was added and the mixture was extracted with DCM, washed with brine, dried with Na$_2$SO$_4$, and the solvent was removed under reduced pressure. The crude residue was purified by column chromatography to give tert-butyl 3-[3-[(1R)-1-[[(R)-tert-butylsulfinyl]amino]ethyl]-5-(hydroxymethyl)phenyl]-3-fluoro-azetidine-1-carboxylate (2 g, 98% yield). LCMS (ESI): m/z: [M+H] calculated for C$_{21}$H$_{34}$FN$_2$O$_4$S: 429.2; found 429.1.

Step 7

To a solution of tert-butyl 3-(3-((R)-1-((R)-1,1-dimethylethylsulfinamido)ethyl)-5-(hydroxymethyl)phenyl)-3-fluoroazetidine-1-carboxylate (400 mg, 0.93 mmol) in MeOH (5 mL) was added 4M HCl in dioxane (0.93 mL, 3.73 mmol). The reaction was stirred at rt for 1 h before NaOH in MeOH was added to adjust the pH to ~7. The solvent was removed under reduced pressure and the crude residue was purified by prep-TLC to give (R)-tert-butyl 3-(3-(1-aminoethyl)-5-(hydroxymethyl)phenyl)-3-fluoroazetidine-1-carboxylate (303 mg, crude). LCMS (ESI): m/z: [M+H] calculated for C$_{17}$H$_{26}$FN$_2$O$_3$:325.2; found 325.2.

Step 8

To a solution of tert-butyl 3-[3-[(1R)-1-aminoethyl]-5-(hydroxymethyl)phenyl]-3-fluoro-azetidine-1-carboxylate (303 mg, 0.93 mmol) in n-BuOH (6 mL) was added 6-(1-acetyl-4-piperidyl)-4-chloro-8-methyl-pyrido[2,3-d]pyrimidin-7-one (330 mg, 1.03 mmol) and DIPEA (0.49 mL, 2.8 mmol). The reaction was stirred at 90° C. for 1 h. After cooling to rt the solvent was removed under reduced pressure and the crude residue was purified by column chromatography to give tert-butyl 3-[3-[(1R)-1-[[6-(1-acetyl-4-piperidyl)-8-methyl-7-oxo-pyrido[2,3-d]pyrimidin-4-yl]amino]ethyl]-5-(hydroxymethyl)phenyl]-3-fluoro-azetidine-1-carboxylate (280 mg, 49% yield). LCMS (ESI): m/z: [M+H] calculated for C$_{32}$H$_{42}$FN$_6$O$_5$:609.3; found 609.3.

Step 9

To a solution of tert-butyl 3-[3-[(1R)-1-[[6-(1-acetyl-4-piperidyl)-8-methyl-7-oxo-pyrido [2,3-d]pyrimidin-4-yl]amino]ethyl]-5-(hydroxymethyl)phenyl]-3-fluoro-azetidine-1-carboxylate (190 mg, 0.31 mmol) in DCM (3.8 mL) at 0° C. was added Dess-Martin reagent (0.14 mL, 0.47 mmol). The reaction was stirred for 1 h before H$_2$O was added and the mixture was extracted with DCM. The combined organic phases were washed with brine, dried with Na$_2$SO$_4$, and the solvent was removed under reduced pressure. The crude residue was purified by column chromatography to give tert-butyl 3-[3-[(1R)-1-[[6-(1-acetyl-4-piperidyl)-8-methyl-7-oxo-pyrido[2,3-d] pyrimidin-4-yl]amino]ethyl]-5-formyl-phenyl]-3-fluoro-azetidine-1-carboxylate (100 mg, 53% yield). LCMS (ESI): m/z: [M+H] calculated for C$_{32}$H$_{40}$FN$_6$O$_5$:607.3; found 607.3.

Step 10

To a solution of tert-butyl 3-[3-[(1R)-1-[[6-(1-acetyl-4-piperidyl)-8-methyl-7-oxo-pyrido [2,3-d]pyrimidin-4-yl]amino]ethyl]-5-formyl-phenyl]-3-fluoro-azetidine-1-carboxylate (90 mg, 0.15 mmol) in DCM (2 mL) at 0° C. was added DAST (0.1 mL, 0.74 mmol). The reaction was stirred at rt for 1 h before aq. sat. NaHCO$_3$ was added and the mixture was extracted with DCM. The combined organic phases were washed with brine, dried with Na$_2$SO$_4$, and the solvent was removed under reduced pressure. The crude residue was purified by column chromatography to give tert-butyl 3-[3-[(1R)-1-[[6-(1-acetyl-4-piperidyl)-8-methyl-7-oxo-pyrido [2,3-d]pyrimidin-4-yl]amino]ethyl]-5-(difluoromethyl)phenyl]-3-fluoro-azetidine-1-carboxylate (63 mg, 68% yield). LCMS (ESI): m/z: [M+H] calculated for C$_{32}$H$_{40}$F$_3$N$_6$O$_4$:629.3; found 629.2.

Step 11 tert-Butyl 3-[3-[(1R)-1-[[6-(1-acetyl-4-piperidyl)-8-methyl-7-oxo-pyrido [2,3-d]pyrimidin-4-yl]amino]ethyl]-5-(difluoromethyl)phenyl]-3-fluoro-azetidine-1-carboxylate (40 mg, 64 μmol) was dissolved in HCl (3 N in MeOH, 2 mL) After stirring at rt for 1 h the reaction was adjusted to pH 7 using NaOH in MeOH and the solvent was removed under reduced pressure. The residue was purified by prep-HPLC to give 6-(1-acetyl-4-piperidyl)-4-[[(1R)-1-[3-(difluoromethyl)-5-(3-fluoroazetidin-3-yl)phenyl]ethyl]amino]-8-methyl-pyrido[2,3-d]pyrimidin-7-one (7 mg, 20% yield). LCMS (ESI): m/z: [M+H] calculated for C$_{27}$H$_{32}$F$_3$N$_6$O$_2$: 529.2; found 529.3; $^1$H NMR (400 MHz, methanol-d$_4$) δ ppm 8.51-8.44 (m, 1H), 8.30 (s, 1H), 8.14 (s, 1H), 7.80-7.74 (m, 1H), 7.67 (s, 1H), 7.62 (s, 1H), 6.81 (t, J=56 Hz, 1H), 5.64-5.55 (m, 1H), 4.76-4.67 (m, 1H), 4.51-4.32 (m, 4H), 4.11-4.02 (m, 1H), 3.71 (s, 3H), 3.26-3.10 (m, 2H), 2.81-2.71 (m, 1H), 2.14 (d, J=4 Hz, 3H), 2.08-1.94 (m, 2H), 1.66 (d, J=4 Hz, 3H), 1.63-1.51 (m, 1H).

Example 44: Synthesis of 6-(1-acetyl-4-piperidyl)-4-[1-[6-amino-4-(trifluoromethyl)-2-pyridyl]ethylamino]-8-methyl-pyrido[2,3-d]pyrimidin-7-one

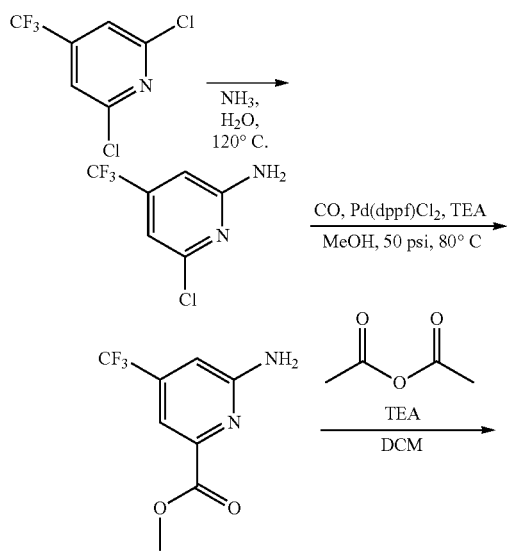

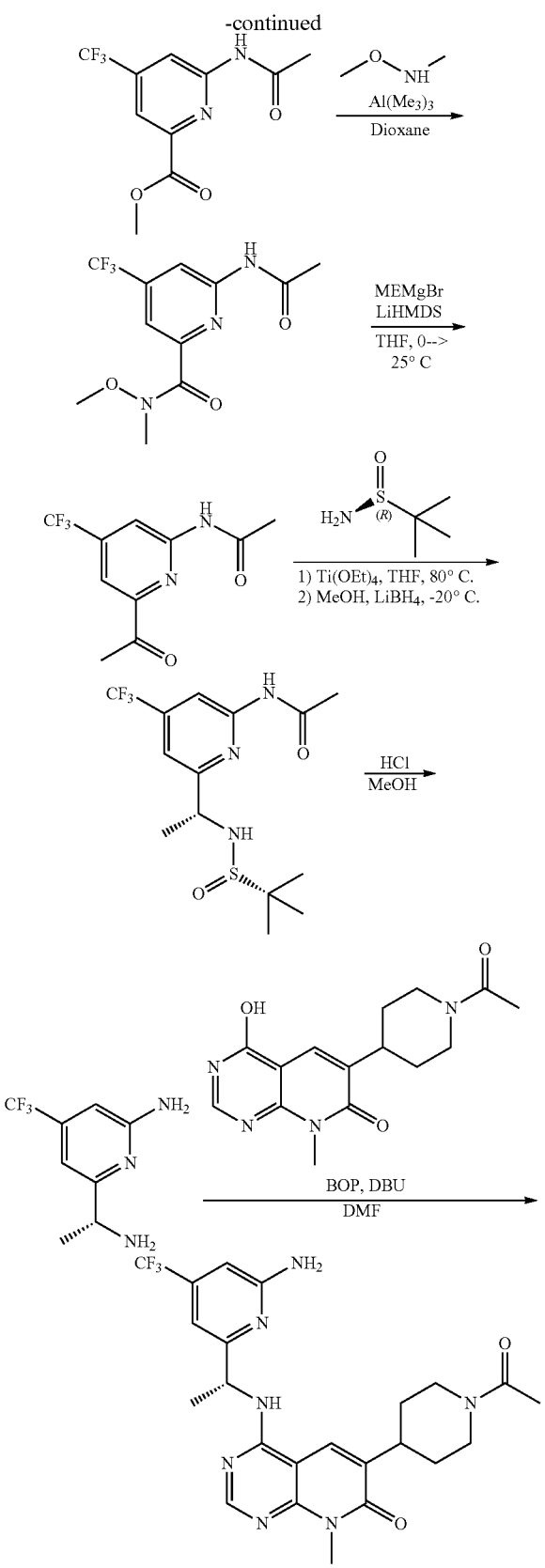

Step 1
A solution of 2, 6-dichloro-4-(trifluoromethyl)pyridine (1 g, 4.6 mmol) in NH₃ (30% aq., 17.5 mL, 137 mmol) was stirred at 120° C. for 24 h. After cooling to rt solvent was removed under reduced pressure and the crude residue was purified by column chromatography to give 6-chloro-4-(trifluoromethyl)pyridin-2-amine (583 mg, 64% yield). $^1$H NMR (400 MHz, DMSO-d6) δ ppm 7.01 (s, 2H) 6.80 (s, 1H) 6.65 (s, 1H).

Step 2
To a solution of 6-chloro-4-(trifluoromethyl)pyridin-2-amine (500 mg, 2.54 mmol) in MeOH (5 mL) under CO atmosphere was added Pd(dppf)Cl₂.CH₂Cl₂ (208 mg, 0.25 mmol) and TEA (1.06 mL, 7.6 mmol). The suspension was degassed and purged with CO three times. The mixture was stirred under CO (50 Psi) at 80° C. for 20 h. After cooling to rt the mixture was filtered, and the solvent was removed under reduced pressure. The residue was purified by column chromatography to give methyl 6-amino-4-(trifluoromethyl)pyridine-2-carboxylate (410 mg, 73% yield). LCMS (ESI): m/z: [M+H] calculated for $C_8H_8F_3N_2O_2$: 221.1 found 221.2.

Step 3
To a solution of methyl 6-amino-4-(trifluoromethyl)pyridine-2-carboxylate (200 mg, 0.91 mmol) in DCM (2 mL) was added acetyl acetate (0.26 mL, 2.7 mmol) and TEA (0.19 mL, 1.36 mmol). The mixture was stirred at rt for 10 h before H₂O was added and the mixture was extracted with EtOAc. The combined organic phases were washed with brine, dried with Na₂SO₄, and the solvent was removed under reduced pressure. The crude residue was purified by column chromatography to give methyl 6-acetamido-4-(trifluoromethyl)pyridine-2-carboxylate (100 mg, 42% yield). LCMS (ESI): m/z: [M+H] calculated for $C_{10}H_{10}F_3N_2O_3$: 263.1; found 263.1.

Step 4
To a solution of ethyl methyl 6-acetamido-4-(trifluoromethyl)pyridine-2-carboxylate (90 mg, 0.34 mmol) and N-methoxymethanamine (67 mg, 687 mmol) in 1,4-dioxane (1 mL) was added 2M Al(CH₃)₃ (0.34 mL, 0.69 mmol). The reaction was stirred at rt for 6 h before H₂O was added and the mixture was extracted with EtOAc. The combined organic phases were washed with brine, dried over Na₂SO₄, and the solvent was removed under reduced pressure. The crude residue was purified by column chromatography to give 6-acetamido-N-methoxy-N-methyl-4-(trifluoromethyl)pyridine-2-carboxamide (66 mg, 66% yield). LCMS (ESI): m/z: [M+H] calculated for $C_{11}H_{13}F_3N_3O_3$: 292.08; found 292.05.

Step 5
To a solution of 6-acetamido-N-methoxy-N-methyl-4-(trifluoromethyl)pyridine-2-carboxamide (50 mg, 0.17 mmol) in THF (1 mL) at 0° C. was added 1M LiHMDS (0.17 mL, 0.17 mmol). The reaction mixture was stirred at 0° C. for 30 min before 2M MeMgBr (0.3 mL, 0.6 mmol) was added and the reaction was stirred at rt for another 30 min. H₂O was then added and the mixture was extracted with EtOAc, washed with brine, dried with Na₂SO₄, filtered, and the solvent was removed under reduced pressure. The crude residue was purified by prep-TLC to give N-[6-acetyl-4-(trifluoromethyl)-2-pyridyl]acetamide (27 mg, 64% yield). LCMS (ESI): m/z: [M+H] calculated for $C_{10}H_{10}F_3N_2O_2$: 247.1; found 247.0. $^1$H NMR (400 MHz, methanol-d4) δ ppm 8.66 (s, 1H) 7.90 (s, 1H) 2.68 (s, 3H) 2.23 (s, 3H).

Step 6
To a solution of N-[6-acetyl-4-(trifluoromethyl)-2-pyridyl]acetamide (150 mg, 609.30 mmol) and (R)-2-methylpropane-2-sulfinamide (89 mg, 0.73 mmol) in THF (1.5 mL) was added Ti(OEt)₄ (0.25 mL, 1.2 mmol). The reaction stirred at 80° C. for 11 h before being cooled to −20° C. and MeOH (25 μL, 0.61 mmol) and LiBH₄ (13 mg, 0.61 mmol) were added. The mixture was stirred at rt for 1 h. Ice water was added, and the resulting solids were filtered off. The filtrate was extracted with EtOAc, washed with brine, dried with Na₂SO₄ and the solvent was removed under reduced pressure. The crude residue was purified by column chromatography to give N-[6-[(1R)-1-(1,1-dimethylethylsulfinylamino)ethyl]-4-(trifluoromethyl)-2-pyridyl]acetamide (50 mg, 23% yield). ¹H NMR (400 MHz, methanol-d4) δ ppm 8.33 (s, 1H) 7.49 (s, 1H) 4.57 (q, J=6.91 Hz, 1H) 2.20 (s, 3H) 1.54 (d, J=6.84 Hz, 3H) 1.26 (s, 9H).

Step 7

To a solution of N-[6-[(1R)-1-(1,1-dimethylethylsulfinylamino)ethyl]-4-(trifluoromethyl)-2-pyridyl]acetamide (45 mg, 0.13 mmol) in MeOH (0.5 mL) was added 4M HCl in MeOH (0.16 mL, 0.640 mmol). The mixture was stirred at rt for 3 h. The solvent was removed under reduced pressure to give 6-[(1R)-1-aminoethyl]-4-(trifluoromethyl)pyridin-2-amine (26 mg, crude). LCMS (ESI): m/z: [M+H] calculated for C₈H₁₁F₃N₃: 206.1; found 206.2.

Step 8

To a solution of 6-[(1R)-1-aminoethyl]-4-(trifluoromethyl)pyridin-2-amine (26 mg, 126.72 mmol) in DMF (1 mL) was added BOP (90 mg, 0.2 mmol) and DBU (57 mL, 0.38 mmol) followed by 6-(1-acetyl-4-piperidyl)-4-hydroxy-8-methyl-pyrido[2,3-d]pyrimidin-7-one (57 mg, 0.19 mmol). The mixture was stirred at rt for 4 h and then filtered. The solvent was removed under reduced pressure and the crude residue was purified by prep-HPLC to give 6-(1-acetyl-4-piperidyl)-4-[1-[6-amino-4-(trifluoromethyl)-2-pyridyl]ethylamino]-8-methyl-pyrido[2,3-d]pyrimidin-7-one (5.7 mg, 7% yield). LCMS (ESI): m/z: [M+H] calculated for C₂₃H₂₇F₃N₇O₂: 490.2; found 490.3. ¹H NMR (400 MHz, methanol-d4) δ ppm 8.32 (s, 1H) 8.14 (s, 1H) 6.74 (s, 1H) 6.63 (s, 1H) 5.38-5.37 (m, 1H) 4.72 (d, J=14.06 Hz, 1H) 4.07 (d, J=13.08 Hz, 1H) 3.77-3.69 (m, 3H) 3.25-3.09 (m, 2H) 2.76 (t, J=12.59 Hz, 1H) 2.15 (s, 3H) 2.07-1.89 (m, 2H) 1.72-1.62 (m, 2H) 1.60 (d, J=6.97 Hz, 3H).

Examples 45 and 46: Synthesis of [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide and [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide

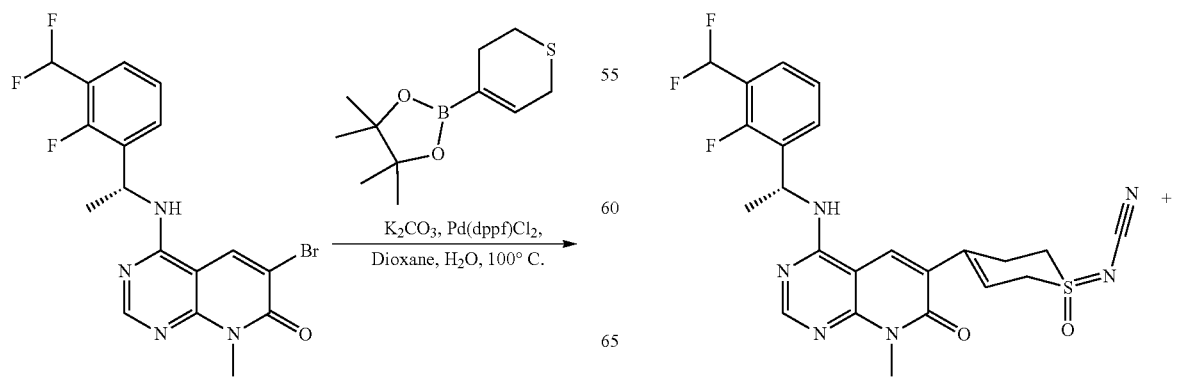

-continued

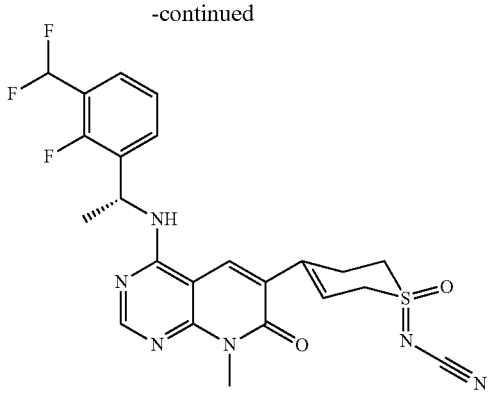

Step 1

A mixture of 6-bromo-4-[[(1R)-1-[3-(difluoromethyl)-2-fluoro-phenyl]ethyl]amino]-8-methyl-pyrido[2,3-d]pyrimidin-7-one (5 g, 11.7 mmol), 2-(3,6-dihydro-2H-thiopyran-4-yl)-4,4,5,5-tetramethyl-1,3,2-dioxaborolane (5.3 g, 23.4 mmol), Pd(dppf)Cl$_2$ (856 mg, 1.17 mmol), and K$_2$CO$_3$ (4.85 g, 35 mmol) in dioxane (50 mL) and H$_2$O (10 mL) was degassed and purged with N$_2$ three times. The reaction was stirred under N$_2$ at 100° C. for 12 h. After cooling to rt the reaction mixture was filtered, and the solvent was removed under reduced pressure. The crude residue was purified by column chromatography to give 4-[[(1R)-1-[3-(difluoromethyl)-2-fluoro-phenyl]ethyl]amino]-6-(3,6-dihydro-2H-thiopyran-4-yl)-8-methyl-pyrido[2,3-d]pyrimidin-7-one (4.2 g, 80% yield). $^1$H NMR (400 MHz, methanol-d$_4$) δ ppm 8.29 (s, 1H) 8.20 (s, 1H) 7.55 (t, J=7.4 Hz, 1H) 7.47 (t, J=7.0 Hz, 1H) 7.22 (t, J=7.8 Hz, 1H) 7.00 (t, J=55.0 Hz, 1H) 6.21-6.19 (m, 1H) 5.76 (q, J=7.0 Hz, 1H) 3.68 (s, 3H) 3.34-3.31 (m, 2H) 2.86-2.83 (m, 2H) 2.70-2.68 (m, 2H) 1.64 (d, J=6.8 Hz, 3H).

Step 2

To a solution of 4-[[(1R)-1-[3-(difluoromethyl)-2-fluoro-phenyl]ethyl]amino]-6-(3,6-dihydro-2H-thiopyran-4-yl)-8-methyl-pyrido[2,3-d]pyrimidin-7-one (4 g, 9.0 mmol) in THF (50 mL) and H$_2$O (10 mL) at 0° C. was added oxone (2.8 g, 4.6 mmol). The mixture was stirred at rt for 2 h and then quenched with aq. Na$_2$S$_2$O$_3$, extracted with EtOAc, washed with brine, dried over Na$_2$SO$_4$, and the solvent was removed under reduced pressure. The crude residue was purified by column chromatography to give 4-[[(1R)-1-[3-(difluoromethyl)-2-fluoro-phenyl]ethyl]amino]-8-methyl-6-(1-oxo-3,6-dihydro-2H-thiopyran-4-yl)pyrido[2,3-d]pyrimidin-7-one (3 g, 72% yield). $^1$H NMR (400 MHz, methanol-d$_4$) δ ppm 8.30 (s, 1H) 8.26 (s, 1H) 7.56 (t, J=7.4 Hz, 1H) 7.47 (t, J=7.0 Hz, 1H) 7.22 (t, J=7.6 Hz, 1H) 7.00 (t, J=54.8 Hz, 1H) 6.09-6.05 (m, 1H) 5.79-5.73 (m, 1H) 3.78-3.73 (m, 1H) 3.67 (s, 3H) 3.50-3.44 (m, 1H) 3.28-3.22 (m, 1H) 3.12-3.05 (m, 1H) 2.98-2.93 (m, 2H) 1.64 (d, J=6.8 Hz, 3H).

Step 3

To a solution of 4-[[(1R)-1-[3-(difluoromethyl)-2-fluoro-phenyl]ethyl]amino]-8-methyl-6-(1-oxo-3,6-dihydro-2H-thiopyran-4-yl)pyrido[2,3-d]pyrimidin-7-one (2.6 g, 5.6 mmol) in MeOH (60 mL) was added (diacetoxyiodo)benzene (5.4 g, 16.9 mmol) and ammonia carbamic acid (1.76 g, 22.5 mmol). The mixture was stirred at rt for 12 h. The solvent was removed under reduced pressure and the crude residue was purified by prep-HPLC to give 4-[[(1R)-1-[3-(difluoromethyl)-2-fluoro-phenyl]ethyl]amino]-6-(1-imino-1-oxo-3,6-dihydro-2H-thiopyran-4-yl)-8-methyl-pyrido[2,3-d]pyrimidin-7-one (560 mg, 21% yield). LCMS (ESI): m/z: [M+H] calculated for C$_{22}$H$_{23}$F$_3$N$_5$O$_2$S: 478.1; found 478.0.

Step 4

To a solution of 4-[[(1R)-1-[3-(difluoromethyl)-2-fluoro-phenyl]ethyl]amino]-6-(1-imino-1-oxo-3,6-dihydro-2H-thiopyran-4-yl)-8-methyl-pyrido[2,3-d]pyrimidin-7-one (100 mg, 0.21 mmol) in DCM (2 mL) at 0° C. was added DMAP (28 mg, 0.23 mmol) and cyanogen bromide (31 μL, 0.42 mmol). The mixture was stirred at 0° C. for 4 h. The reaction mixture was quenched with H$_2$O, extracted with DCM, dried over Na$_2$SO$_4$, and the solvent was removed under reduced pressure. The crude residue was purified by prep SFC to give [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide (29.2 mg, 28% yield, sulfoximine configuration assigned arbitrarily) and [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide (25.3 mg, 24% yield, sulfoximine configuration assigned arbitrarily).

[4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide LCMS (ESI): m/z: [M+H] calculated for C$_{23}$H$_{22}$F$_3$N$_6$O$_2$S: 503.1; found 503.1; $^1$H NMR (400 MHz, acetonitrile-d$_3$) δ ppm 8.29 (s, 1H) 7.98 (s, 1H) 7.61 (t, J=7.0 Hz, 1H) 7.49 (t, J=7.0 Hz, 1H) 7.25 (t, J=7.4 Hz, 1H) 7.01 (t, J=54.8 Hz, 1H) 6.87 (br d, J=5.6, 1H) 6.19-6.17 (m, 1H) 5.75-5.68 ((m, 1H) 4.29-4.18 (m, 2H) 3.69-3.63 (m, 2H) 3.61 (s, 3H) 3.33-3.36 (m, 1H) 3.21-3.12 (m, 1H) 1.63 (d, J=7.2 Hz, 3H).

[4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide LCMS (ESI): m/z: [M+H] calculated for C$_{23}$H$_{22}$F$_3$N$_6$O$_2$S: 503.1; found 503.0. $^1$H NMR (400 MHz, acetonitrile-d$_3$) δ ppm 8.29 (s, 1H) 8.00 (s, 1H) 7.62 (t, J=7.2 Hz, 1H) 7.49 (t, J=7.0 Hz, 1H) 7.25 (t, J=7.8 Hz, 1H) 7.01 (t, J=54.8 Hz, 1H) 6.92 (br d, J=6.8 Hz, 1H) 6.20 (t, J=4.4 Hz, 1H) 5.76-5.68 (m, 1H) 4.29-4.17 (m, 2H) 3.69-3.65 (m, 2H) 3.61 (s, 3H) 3.31-3.15 (m, 2H) 1.63 (d, J=7.2 Hz, 3H).

Example 47: Synthesis of [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-thian-1-ylidene]cyanamide

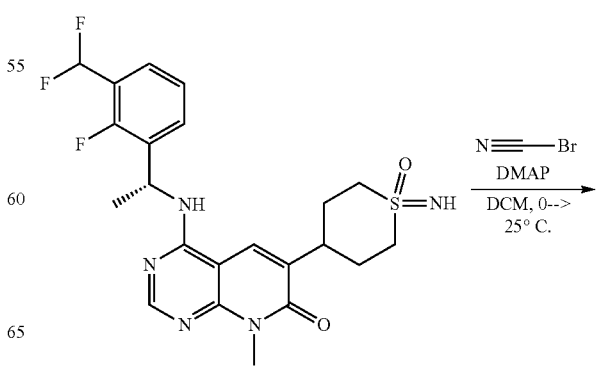

-continued

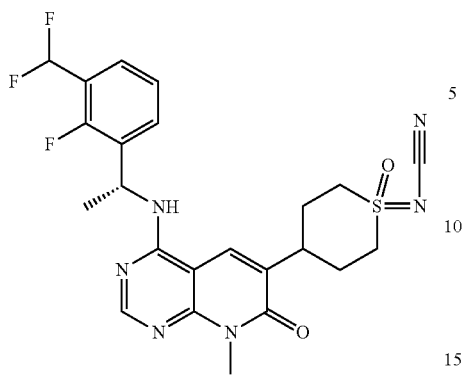

Step 1

To a solution of 4-[[(1R)-1-[3-(difluoromethyl)-2-fluoro-phenyl]ethyl]amino]-6-(1-imino-1-oxo-thian-4-yl)-8-methyl-pyrido[2,3-d]pyrimidin-7-one (150 mg, 0.31 mmol) in DCM (3 mL) at 0° C. was added DMAP (42 mg, 0.34 mmol) and cyanogen bromide (46 μL, 0.63 mmol). The mixture was stirred at rt for 5 h before H₂O was added and the mixture was extracted with DCM. The combined organic phases were dried with Na₂SO₄, and the solvent was removed under reduced pressure. The residue was purified by prep-HPLC to give [4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-thian-1-ylidene]cyanamide (17.3 mg, 11% yield). LCMS (ESI): m/z: [M+H] calculated for C₂₃H₂₄F₃N₆O₂S: 505.2; found 505.1. ¹H NMR (400 MHz, DMSO-d₆) δ ppm 8.44 (br, d, J=7.2 Hz, 1H) 8.34 (s, 1H) 8.28 (s, 1H) 7.61 (t, J=7.2 Hz, 1H) 7.52 (t, J=7.0 Hz, 1H) 7.31 (t, J=7.8 Hz, 1H) 7.25 (t, J=54.4 Hz, 1H) 5.76-5.68 ((m, 1H) 3.81-3.76 (m, 4H) 3.59 (s, 3H) 3.38-3.11 (m, 1H) 2.35-2.15 (m, 4H) 1.60 (d, J=7.2 Hz, 3H).

Example 48: Synthesis of 6-(1-acetyl-4-piperidyl)-4-[[(1R)-1-[4-(difluoromethyl)-1H-indol-6-yl] ethyl] amino]-8-methyl-pyrido[2,3-d]pyrimidin-7-one

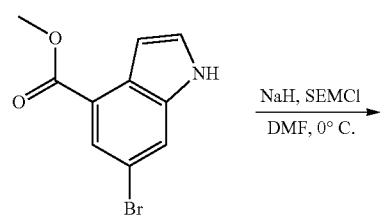

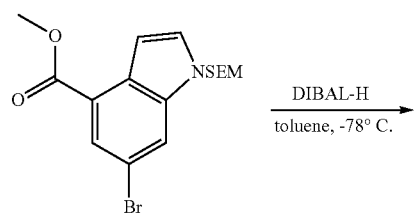

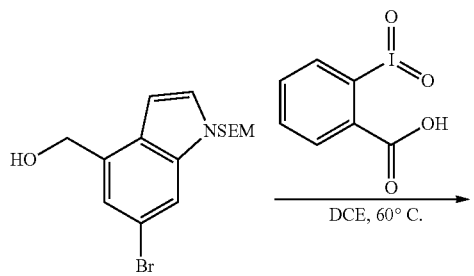

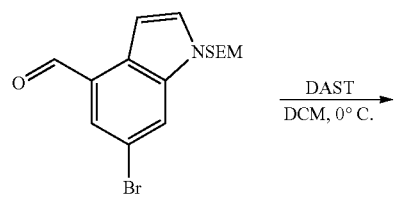

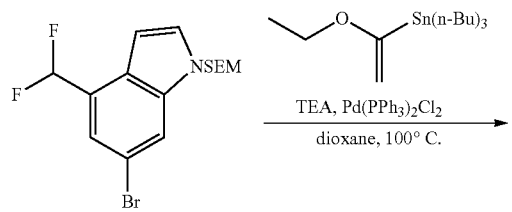

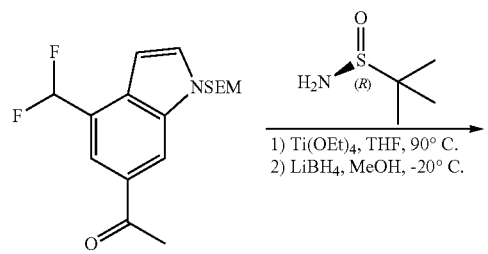

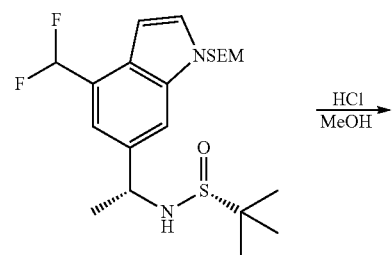

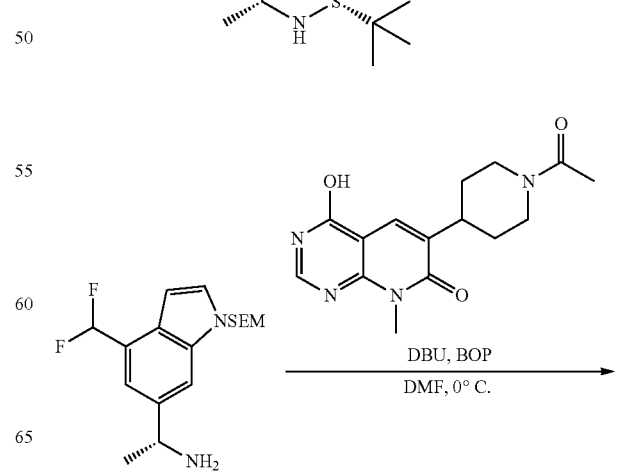

-continued

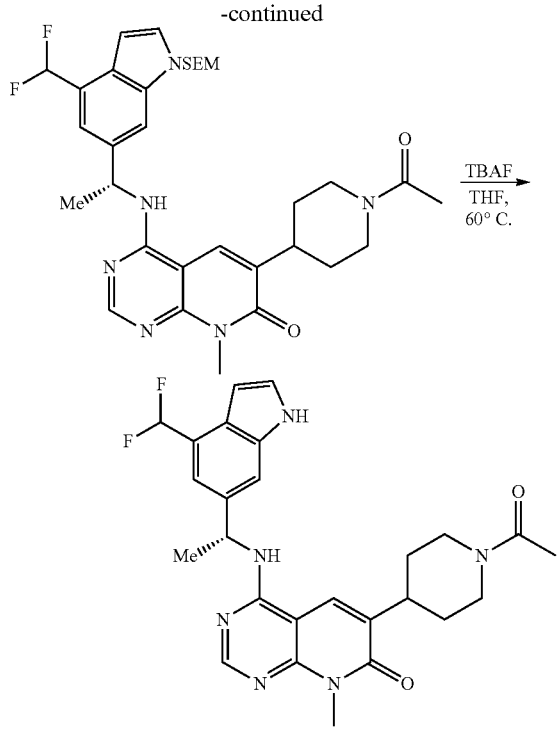

Step 1

To a solution of methyl 6-bromo-1H-indole-4-carboxylate (3 g, 11.8 mmol) in DMF (36 mL) at 0° C. was added NaH (60 wt %, 708 mg, 17.7 mmol). The mixture was stirred for 30 min and then SEM-C$_1$ (3.1 mL, 17.7 mmol) was added. After an additional 2 h the reaction was poured into water and extracted with EtOAc. The combined organic phases were washed with aq. sat. NH$_4$Cl, dried with Na$_2$SO$_4$, and the solvent was removed under reduced pressure. The crude residue was purified by column chromatography to give methyl 6-bromo-1-(2-trimethylsilylethoxymethyl) indole-4-carboxylate (3.6 g, 79% yield). $^1$H NMR (400 MHz, methanol-d$_4$) δ ppm 7.98-7.91 (m, 2H), 7.48 (d, J=4 Hz, 1H), 7.06 (d, J=4 Hz, 1H), 5.66 (s, 2H), 3.96 (s, 3H), 3.51-3.46 (m, 2H), 0.87-0.82 (m, 2H), −0.08 (s, 9H).

Step 2

To a solution of methyl 6-bromo-1-(2-trimethylsilylethoxymethyl)indole-4-carboxylate (3.6 g, 9.4 mmol) in toluene (130 mL) at −78° C. was added DIBAL-H (37.5 mL, 37.5 mmol). The mixture was stirred for 2 h. The reaction was quenched with 1M HCl, extracted with EtOAc, dried with Na$_2$SO$_4$, and the solvent was removed under reduced pressure. The crude residue was purified by column chromatography to give [6-bromo-1-(2-trimethylsilylethoxymethyl) indol-4-yl] methanol (2.7 g, 81% yield). $^1$H NMR (400 MHz, methanol-d$_4$) δ ppm 7.62 (s, 1H), 7.36-7.24 (m, 2H), 6.59 (d, J=2 Hz, 1H), 5.51 (s, 2H), 4.86 (s, 2H), 3.48 (t, J=8.0 Hz, 2H), 0.85 (t, J=8.0 Hz, 2H), −0.08 (s, 9H).

Step 3

To a solution of [6-bromo-1-(2-trimethylsilylethoxymethyl) indol-4-yl]methanol (2.7 g, 7.6 mmol) in DCE (220 mL) was added 2-iodylbenzoic acid (3.2 g, 11.4 mmol). The mixture was stirred at 60° C. for 8 h. After cooling to rt the mixture was filtered, and the filtrate was concentrated under reduced pressure. The crude residue was purified by column chromatography to give 6-bromo-1-(2-trimethylsilyl ethoxy methyl) indole-4-carbaldehyde (2.17 g, 81% yield). $^1$H NMR (400 MHz, methanol-d$_4$) δ ppm 10.15 (s, 1H), 8.05 (s, 1H), 7.81 (d, J=2 Hz, 1H), 7.57 (d, J=2 Hz, 1H), 7.24-7.16 (m, 1H), 5.60 (s, 2H), 3.54-3.46 (m, 2H), 0.86 (t, J=8 Hz, 2H), −0.08 (s, 9H).

Step 4

To a solution of 6-bromo-1-(2-trimethylsilylethoxymethyl) indole-4-carbaldehyde (1.3 g, 3.7 mmol) in DCM (13 mL) at 0° C. was added DAST (4.8 mL, 37 mmol). The reaction mixture was stirred at rt for 16 h and then quenched with H$_2$O and extracted with EtOAc. The combined organic phases were washed with brine, dried with Na$_2$SO$_4$, and the solvent was removed under reduced pressure. The crude residue was purified by column chromatography to give 2-[[6-bromo-4-(difluoromethyl)indol-1-yl]methoxy]ethyl-trimethyl-silane (590 mg, 43% yield). LCMS (ESI): m/z: [M+H] calculated for C$_{15}$H$_{21}$BrF$_2$NOSi: 376.1; found: 376.2.

Step 5

To a solution of tributyl(1-ethoxyvinyl)stannane (0.79 mL, 2.4 mmol) and 2-[[6-bromo-4-(difluoromethyl)indol-1-yl]methoxy]ethyl-trimethyl-silane (590 mg, 1.57 mmol) in dioxane (6 mL) under N$_2$ was added TEA (0.54 mL, 3.9 mmol) and Pd(PPh$_3$)$_2$Cl$_2$ (110 mg, 0.16 mmol). The mixture was purged with N$_2$ three times and then stirred at 100° C. for 3 h. After cooling to rt the reaction was acidified to pH=2 with 1M HCl and stirred for 16 h. The mixture was filtered, and the filtrate was extracted with EtOAc. The combined organic layers were stirred for 2 h with aq. KF. Solids were removed by filtration and the organic layer of the filtrate was washed with brine, dried with Na$_2$SO$_4$, and the solvent was removed under reduced pressure. The crude residue was purified by column chromatography to give 1-[4-(difluoromethyl)-1-(2-trimethylsilylethoxymethyl)indol-6-yl]ethanone (460 mg, 86% yield). LCMS (ESI): m/z: [M+H] calculated for C$_{17}$H$_{24}$F$_2$NO$_2$Si: 340.2; found: 340.2.

Step 6

To a solution of 2-methylpropane-2-sulfinamide (107 mg, 0.88 mmol) and 1-[4-(difluoromethyl)-1-(2-trimethylsilylethoxymethyl)indol-6-yl]ethanone (150 mg, 0.44 mmol) in THF (2 mL) was added Ti(OEt)$_4$ (0.34 mL, 1.8 mmol). The reaction was stirred at 90° C. for 8 h and then cooled to −20° C., before LiBH$_4$ (11 mg, 0.49 mmol) and methanol (18 μL, 0.44 mmol) were added. The reaction was stirred at −20° C. for 30 min. Water was added and the mixture was extracted with EtOAc. The combined organic phases were washed with brine, dried with Na$_2$SO$_4$ and the solvent was removed under reduced pressure. The crude residue was purified by column chromatography to give (R)—N-[(1R)-1-[4-(difluoromethyl)-1-(2-trimethylsilylethoxymethyl)indol-6-yl] ethyl]-2-methyl-propane-2-sulfinamide (80 mg, 41% yield). LCMS (ESI): m/z: [M+H] calculated for C$_{21}$H$_{35}$F$_2$N$_2$O$_2$SSi: 445.2; found: 445.2.

Step 7

To a solution of (R)—N-[(1R)-1-[4-(difluoromethyl)-1-(2-trimethylsilylethoxymethyl)indol-6-yl] ethyl]-2-methyl-propane-2-sulfinamide (50 mg, 0.11 mmol) in methanol (0.5 mL) was added HCl in methanol (4 M in MeOH, 42 mL, 0.17 mmol). The mixture was stirred for 30 min at rt and then adjusted to pH ~8 using NaOH in MeOH. The solvent was removed under reduced pressure to give (1R)-1-[4-(difluoromethyl)-1-(2-trimethylsilylethoxymethyl)indol-6-yl]ethanamine (30 mg, crude). $^1$H NMR (400 MHz, methanol-d4) δ ppm 7.79 (s, 1H), 7.50 (d, J=4 Hz, 1H), 7.38 (s, 1H), 7.03 (t, J=55.6 Hz, 1H), 6.67 (d, J=2 Hz, 1H), 5.62-5.54 (m, 2H), 4.64-4.56 (m, 1H), 3.48 (t, J=8 Hz, 2H), 1.69 (d, J=8 Hz, 3H), 0.83 (t, J=8 Hz, 2H), −0.10 (s, 9H).

Step 8

To a solution of 6-(1-acetyl-4-piperidyl)-4-hydroxy-8-methyl-pyrido[2,3-d]pyrimidin-7-one (48 mg, 0.16 mmol) and (1R)-1-[4-(difluoromethyl)-1-(2-trimethylsilyl ethoxy methyl)indol-6-yl]ethanamine (30 mg, 0.09 mmol) in DMF (1 mL) at 0° C. was added DBU (66 µL, 0.44 mmol) and BOP (58 mg, 0.13 mmol). The mixture was stirred for 30 min. The reaction was quenched with H$_2$O, extracted with EtOAc, washed with brine, dried with Na$_2$SO$_4$, and the solvent was removed under reduced pressure. The crude residue was purified by prep-TLC to give 6-(1-acetyl-4-piperidyl)-4-[[(1R)-1-[4-(difluoromethyl)-1-(2-trimethylsilylethoxymethyl)indol-6-yl]ethyl]amino]-8-methyl-pyrido[2,3-d]pyrimidin-7-one (40 mg, 63% yield). LCMS (ESI): m/z: [M+H] calculated for C$_{32}$H$_{43}$F$_2$N$_6$O$_3$Si: 625.3; found; 625.4.

Step 9

To a solution of 6-(1-acetyl-4-piperidyl)-4-[[(1R)-1-[4-(difluoromethyl)-1-(2-trimethylsilyl ethoxymethyl)indol-6-yl]ethyl]amino]-8-methyl-pyrido[2,3-d]pyrimidin-7-one (32 mg, 51 µmol) in THF (3 mL) was added 1M TBAF in TH (256 µL, 256 µmol). The mixture was stirred at 60° C. for 48 h. After cooling to rt H$_2$O was added and the mixture was extracted with EtOAc. The combined organic phases were washed with brine, dried with Na$_2$SO$_4$, and the solvent was removed under reduced pressure. The crude residue was purified by prep-HPLC to give 6-(1-acetyl-4-piperidyl)-4-[[(1R)-1-[4-(difluoromethyl)-1H-indol-6-yl] ethyl]amino]-8-methyl-pyrido[2,3-d]pyrimidin-7-one (2.5 mg, 10% yield). LCMS (ESI): m/z: [M+H] calculated for C$_{26}$H$_{29}$F$_2$N$_6$O$_2$: 495.2; found; 495.2. $^1$H NMR (400 MHz, methanol-d$_4$) δ ppm 8.34 (d, J=4 Hz, 1H), 8.15 (d, J=3.6 Hz, 1H), 7.58 (d, J=2.6 Hz, 1H), 7.33-7.25 (m, 2H), 6.96 (t, J=55.8 Hz, 1H), 6.58 (d, J=1.8 Hz, 1H), 5.75-5.65 (m, 1H), 4.70 (d, J=12 Hz, 2H), 4.10-3.99 (m, 1H), 3.72 (s, 3H), 3.20-3.11 (m, 1H), 2.74 (t, J=12 Hz, 1H), 2.13 (d, J=4 Hz, 3H), 2.05-1.88 (m, 2H), 1.70 (d, J=8.0 Hz, 3H), 1.65-1.50 (m, 2H).

Examples 49 and 50: Synthesis of 4-(((R)-1-(3-(difluoromethyl)-2-fluorophenyl)ethyl)amino)-6-((1S,4s)-1-imino-4-methoxy-1-oxidohexahydro-1λ$^6$-thiopyran-4-yl)-8-methylpyrido[2,3-d]pyrimidin-7(8H)-one and 4-(((R)-1-(3-(difluoromethyl)-2-fluorophenyl)ethyl)amino)-6-((1R,4r)-1-imino-4-methoxy-1-oxidohexahydro-1λ$^6$-thiopyran-4-yl)-8-methylpyrido[2,3-d]pyrimidin-7(8H)-one

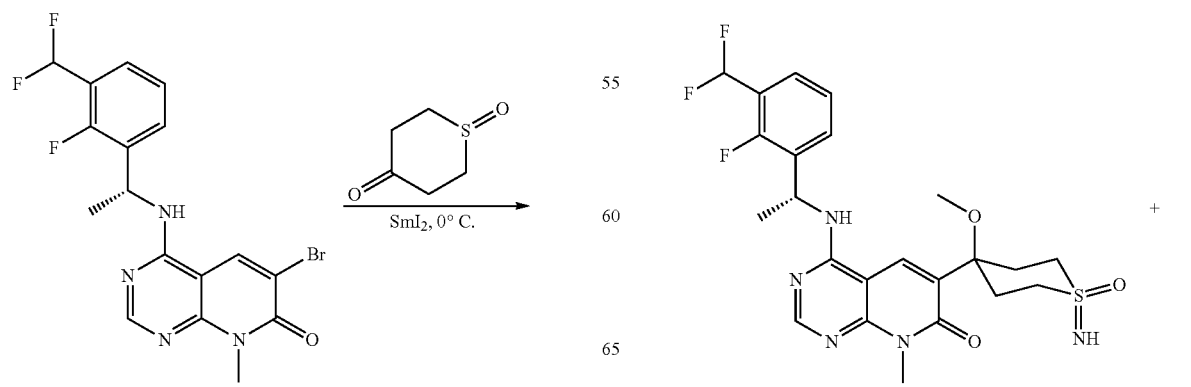

-continued

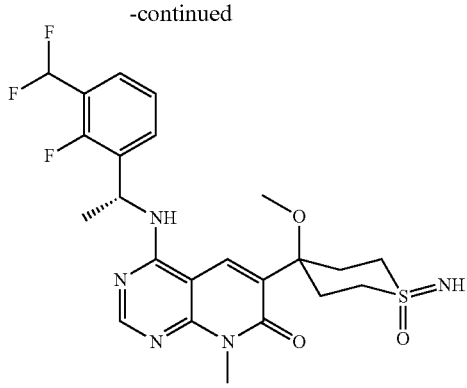

Step 1

To a solution of 6-bromo-4-{[(1R)-1-[3-(difluoromethyl)-2-fluorophenyl]ethyl]amino}-8-methyl-7H,8H-pyrido[2,3-d]pyrimidin-7-one (1.0 g, 2.3 mmol) and thian-4-one S-oxide (930 mg, 7.0 mmol) in THF (50 mL) samarium iodide (0.1 M solution in THF, 164 mL, 16.4 mmol) was added at 0° C. After 1 h stirring at 0° C. another portion of samarium iodide (0.1 M solution in THF, 50 mL, 5 mmol) was added and the mixture was stirred for an additional 1 h at 0° C. before sat. aq. NH$_4$Cl was added and the mixture was with EtOAc. The combined organic layers were dried over anhydrous Na$_2$SO$_4$, and the solvent was removed under reduced pressure. The crude product was purified via reverse phase flash column chromatography to give 4-{[(1R)-1-[3-(difluoromethyl)-2-fluorophenyl]ethyl]amino}-6-(4-hydroxy-1-oxo-1λ$^4$-thian-4-yl)-8-methyl-7H,8H-pyrido[2,3-d]pyrimidin-7-one (169 mg, 15% yield). $^1$H NMR (300 MHz, DMSO-d$_6$) δ 8.69 (d, J=7.3 Hz, 1H), 8.54 (s, 1H), 8.36 (s, 1H), 7.63 (t, J=7.5 Hz, 1H), 7.51 (t, J=7.1 Hz, 1H), 7.45-7.03 (m, 2H), 5.75 (t, J=7.2 Hz, 2H), 3.60 (s, 3H), 2.99 (d, J=9.6 Hz, 4H), 2.86-2.75 (m, 2H), 1.71 (s, 2H), 1.59 (d, J=7.1 Hz, 3H).

Step 2

A solution of 4-{[(1R)-1-[3-(difluoromethyl)-2-fluorophenyl]ethyl]amino}-6-(4-hydroxy-1-oxo-1λ$^4$-thian-4-yl)-8-methyl-7H,8H-pyrido[2,3-d]pyrimidin-7-one (150 mg, 0.31 mmol), trifluoroacetamide (71 mg, 0.6 mmol), rhodium (II) acetate dimer (6 mg, 0.01 mmol), (diacetoxyiodo)benzene (151 mg, 0.47 mmol) and magnesium oxide (50 mg, 1.25 mmol) in dry DCM (15 mL) was stirred at rt overnight. After this time trifluoroacetamide, rhodium (II) acetate dimer, (diacetoxyiodo)benzene and magnesium oxide were added again in the same portions and the reaction mixture was stirred at rt for an additional 72 h. The reaction mixture was filtered through a pad of Celite®, washed with DCM and concentrated. The crude product was purified by flash column chromatography to give N-[4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-hydroxy-1-oxo-1-thian-1-ylidene]-2,2,2-trifluoroacetamide (82 mg, 44% yield). $^1$H NMR (300 MHz, DMSO-d$_6$) δ 8.70 (d, J=9.8 Hz, 2H), 8.37 (s, 1H), 7.64 (t, J=7.4 Hz, 1H), 7.51 (t, J=7.2 Hz, 1H), 7.45-7.00 (m, 2H), 6.09 (s, 1H), 5.77 (t, J=7.1 Hz, 1H), 3.90-3.77 (m, 4H), 3.59 (s, 3H), 3.26-3.13 (m, 2H), 2.06-2.01 (m, 2H), 1.58 (d, J=7.0 Hz, 3H).

Step 3

To a solution of N-[4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-hydroxy-1-oxo-1λ$^6$-thian-1-ylidene]-2,2,2-trifluoroacetami-de (80 mg, 0.13 mmol) in dry DCM (2.4 mL) under argon atmosphere DAST (27 μL, 0.20 mmol) was added at 0° C. After 1 h stirring at rt the reaction mixture was quenched with 1.0 M aq. NaHCO$_3$ solution and extracted with DCM. The combined organic layers were dried over anhydrous Na$_2$SO$_4$. The solvent was removed under reduced pressure to give N-[4-(4-{[(1R)-1-[3-(difluoromethyl)-2-fluorophenyl]-ethyl]amino}-8-methyl-7-oxo-7H,8H-pyrido[2,3-d]pyrimidin-6-yl)-4-fluoro-1-oxo-1λ$^6$-thian-1-ylidene]-2,2,2-trifluoroacetamide (73 mg, crude). $^1$H NMR (300 MHz, DMSO-d$_6$) δ 8.78-8.70 (m, 1H), 8.63 (d, J=4.0 Hz, 1H), 8.38 (d, J=3.9 Hz, 1H), 7.62 (t, J=7.6 Hz, 1H), 7.51 (t, J=7.0 Hz, 1H), 7.44-7.03 (m, 2H), 5.73 (d, J=6.9 Hz, 1H), 4.11-3.83 (m, 4H), 3.66-3.46 (m, 2H), 3.56 (s, 3H), 2.38-2.21 (m, 2H), 1.57 (d, J=7.0 Hz, 3H).

Step 4

To a solution of N-[4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-fluoro-1-oxo-1λ$^6$-thian-1-ylidene]-2,2,2-trifluoroacetamide (60 mg, 0.10 mmol) in a mixture of acetonitrile (1.5 mL), methanol (750 μL) and water (300 μL) sodium methoxide (49 mg, 0.91 mmol) was added. After overnight stirring at rt the reaction mixture was quenched with sat. aq NH$_4$Cl solution and extracted with EtOAc. The combined organic layers were dried over anhydrous Na$_2$SO$_4$ and the crude product was purified by prep-HPLC to give 4-(((R)-1-(3-(difluoromethyl)-2-fluorophenyl)ethyl)amino)-6-((1S,4s)-1-imino-4-methoxy-1-oxidohexahydro-1λ$^6$-thiopyran-4-yl)-8-methylpyrido[2,3-d]pyrimidin-7(8H)-one (7.0 mg, 13% yield, sulfoximine configuration assigned arbitrarily) and 4-(((R)-1-(3-(difluoromethyl)-2-fluorophenyl)ethyl)amino)-6-((1R,4r)-1-imino-4-methoxy-1-oxidohexahydro-1-thiopyran-4-yl)-8-methylpyrido[2,3-d]pyrimidin-7(8H)-one (7.1 mg, 14% yield, sulfoximine configuration assigned arbitrarily).

4-(((R)-1-(3-(difluoromethyl)-2-fluorophenyl)ethyl)amino)-6-((1S,4s)-1-imino-4-methoxy-1-oxidohexahydro-1λ$^6$-thiopyran-4-yl)-8-methylpyrido[2,3-d]pyrimidin-7(8H)-one LCMS (ESI): m/z: [M+H] calculated for C$_{23}$H$_{26}$F$_3$N$_5$O$_3$S: 510.2; found 509.8; $^1$H NMR (300 MHz, DMSO-d$_6$) δ 8.64 (d, J=7.2 Hz, 1H), 8.35 (d, J=3.8 Hz, 2H), 7.62 (t, J=7.4 Hz, 1H), 7.51 (t, J=7.1 Hz, 1H), 7.30 (t, J=7.7 Hz, 1H), 7.24 (t, J=54.4 Hz, 1H), 5.74 (p, J=7.0 Hz, 1H), 3.55 (s, 4H), 3.20 (ddd, J=20.2, 6.5, 3.1 Hz, 2H), 3.12 (s, 3H), 2.99 (d, J=13.2 Hz, 2H), 2.85-2.69 (m, 2H), 2.38 (dd, J=22.9, 9.3 Hz, 2H), 1.58 (d, J=7.0 Hz, 3H).

4-(((R)-1-(3-(difluoromethyl)-2-fluorophenyl)ethyl)amino)-6-((1R,4r)-1-imino-4-methoxy-1-oxidohexahydro-1λ$^6$-thiopyran-4-yl)-8-methylpyrido[2,3-d]pyrimidin-7(8H)-one LCMS (ESI): m/z: [M+H] calculated for C$_{23}$H$_{26}$F$_3$N$_5$O$_3$S: 510.2; found 509.7; $^1$H NMR (300 MHz, DMSO-d$_6$) δ 8.62 (d, J=7.2 Hz, 1H), 8.35 (d, J=6.2 Hz, 2H), 7.62 (t, J=7.5 Hz, 1H), 7.50 (t, J=7.0 Hz, 1H), 7.30 (t, J=7.7 Hz, 1H), 7.24 (t, J=54.3 Hz, 1H), 5.74 (t, J=7.0 Hz, 1H), 3.78

(s, 1H), 3.56 (s, 3H), 3.30-3.14 (m, 2H), 3.12 (s, 3H), 2.93 (d, J=13.4 Hz, 2H), 2.78 (t, J=14.5 Hz, 2H), 2.39 (t, J=13.8 Hz, 2H), 1.58 (d, J=7.0 Hz, 3H).

Examples 51 and 52: Synthesis of 4-(((R)-1-(3-(difluoromethyl)-2-fluorophenyl)ethyl)amino)-6-((1S,4s)-4-fluoro-1-(methylimino)-1-oxidohexahydro-1λ⁶-thiopyran-4-yl)-8-methylpyrido[2,3-d]pyrimidin-7(8H)-one and 4-(((R)-1-(3-(difluoromethyl)-2-fluorophenyl)ethyl)amino)-6-((1R,4r)-4-fluoro-1-(methylimino)-1-oxidohexahydro-1λ-thiopyran-4-yl)-8-methylpyrido[2,3-d]pyrimidin-7(8H)-one

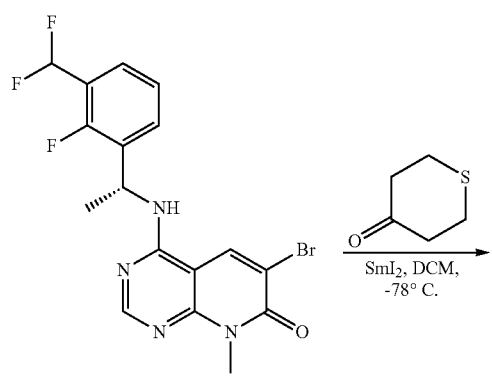

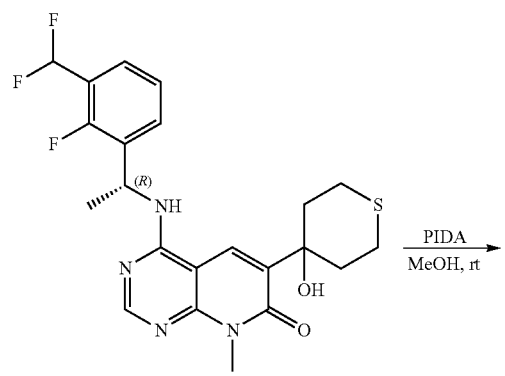

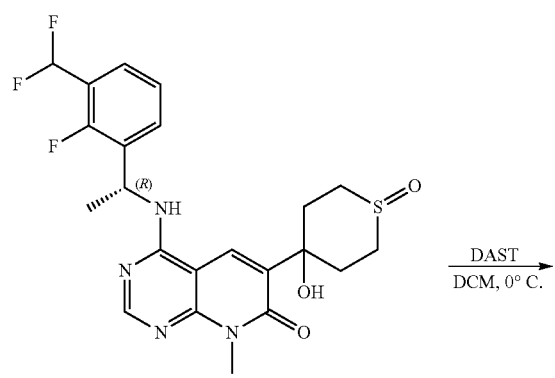

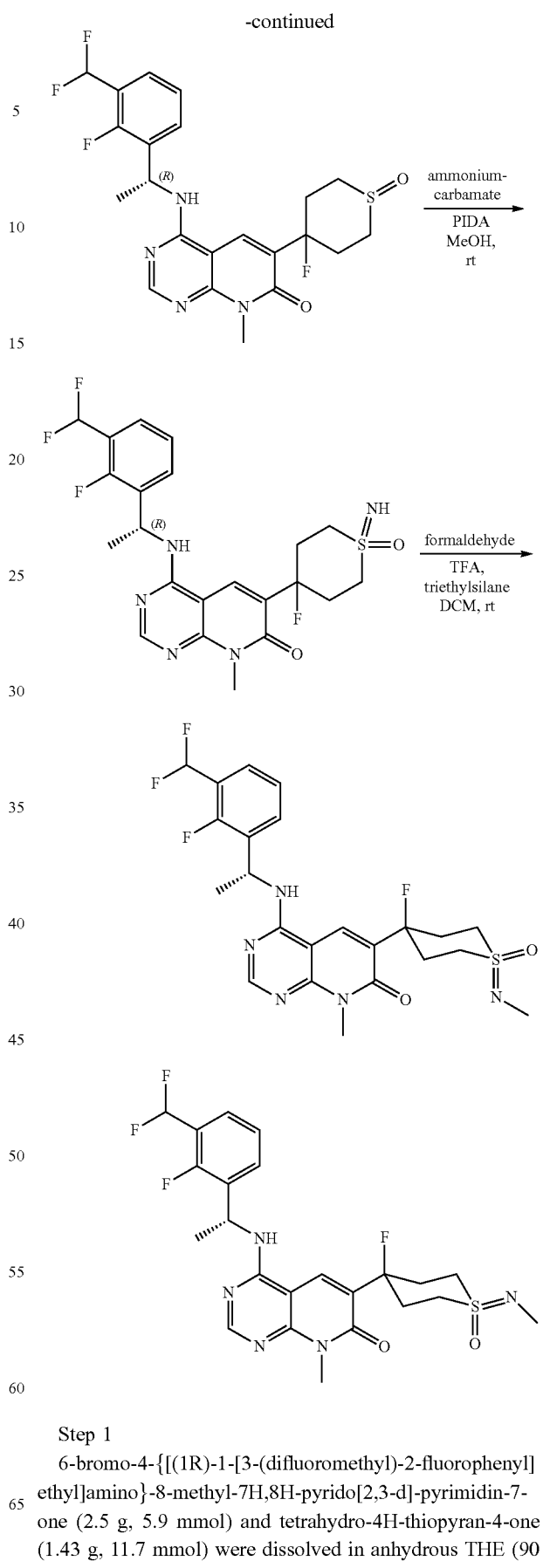

Step 1

6-bromo-4-{[(1R)-1-[3-(difluoromethyl)-2-fluorophenyl]ethyl]amino}-8-methyl-7H,8H-pyrido[2,3-d]-pyrimidin-7-one (2.5 g, 5.9 mmol) and tetrahydro-4H-thiopyran-4-one (1.43 g, 11.7 mmol) were dissolved in anhydrous THF (90 mL) and the solution was cooled at −78° C. SmI$_2$ (0.1 M solution in THF, 414 mL, 41.4 mmol) was cooled to −78° C. and cannulated into the reaction mixture. After stirring for 30 min at −78° C. the reaction was allowed to warm to rt, sat. aq NH$_4$Cl solution was added and the mixture was extracted with DCM. The combined organic phases were dried over anhydrous Na$_2$SO$_4$ and the solvent was removed under reduced pressure to give 4-{[(1R)-1-[3-(difluoromethyl)-2-fluorophenyl]ethyl]amino}-6-(4-hydroxythian-4-yl)-8-methyl-7H,8H-pyrido[2,3-d]pyrimidin-7-one (2.34 g, crude). LCMS (ESI): m/z: [M+H] calculated for C$_{22}$H$_{23}$F$_3$N$_4$O$_2$S: 464.2; found 464.6.

Step 2

4-{[(1R)-1-[3-(difluoromethyl)-2-fluorophenyl]ethyl]amino}-6-(4-hydroxythian-4-yl)-8-methyl-7H,8H-pyrido[2,3-d]pyrimidin-7-one (2.3 g, 5.0 mmol) and iodobenzene diacetate (2.5 g, 7.5 mmol) were dissolved in MeOH (67 mL) and stirred at rt overnight. The solvent was removed under reduced pressure and the crude residue was purified by flash column chromatography to afford 4-{[(1R)-1-[3-(difluoromethyl)-2-fluorophenyl]ethyl]amino}-6-(4-hydroxy-1-oxo-1λ$^6$-thian-4-yl)-8-methyl-7H,8H-pyrido[2,3-d]pyrimidin-7-one (1.3 g, yield=54%). $^1$H NMR (300 MHz, DMSO-d$_6$) δ 8.69 (d, J=7.2 Hz, 1H), 8.54 (s, 1H), 8.36 (s, 1H), 7.63 (t, J=7.5 Hz, 1H), 7.51 (t, J=7.1 Hz, 1H), 7.30 (t, J=7.7 Hz, 1H), 7.24 (t, J=54.3 Hz, 1H), 5.81-5.69 (m, 2H), 3.60 (s, 3H), 3.03-2.75 (m, 6H), 1.77-1.65 (m, 2H), 1.59 (d, J=7.0 Hz, 3H).

Step 3

4-{[(1R)-1-[3-(difluoromethyl)-2-fluorophenyl]ethyl]amino}-6-(4-fluoro-1-oxo-1λ$^4$-thian-4-yl)-8-methyl-7H,8H-pyrido[2,3-d]pyrimidin-7-on (1.08 g, 2.24 mmol), iodobenzene diacetate (1.80 g, 5.60 mmol) and ammonium carbamate (860 mg, 8.95 mmol) were dissolved in MeOH (27 mL). The reaction mixture was stirred at rt overnight and then diluted with 1.0 M aq. HCl (75 mL) and EtOAc (75 mL). The phases were separated and the organic phase was extracted with 1.0 M aq. HCl. The aqueous phase was neutralized with 2.0 M aq NaHCO$_3$ and extracted with DCM. The combined organic layers were dried over anhydrous Na$_2$SO$_4$ and the solvent was removed under reduced pressure to afford 4-{[(1R)-1-[3-(difluoromethyl)-2-fluorophenyl]ethyl]amino}-6-(4-fluoro-1-imino-1-oxo-1λ$^6$-thian-4-yl)-8-methyl-7H,8H-pyrido[2,3-d]pyrimidin-7-one (830 mg, yield=74%). $^1$H NMR (300 MHz, DMSO-d$_6$) δ 8.70 (d, J=7.1 Hz, 1H), 8.60 (s, 1H), 8.36 (d, J=1.3 Hz, 1H), 7.63 (t, J=7.5 Hz, 1H), 7.51 (t, J=7.1 Hz, 1H), 7.30 (t, J=7.7 Hz, 1H), 7.24 (t, J=54.4 Hz, 1H), 5.74 (t, J=7.0 Hz, 1H), 3.93 (s, 0.5H), 3.70 (s, 0.5H), 3.57 (d, J=2.3 Hz, 3H), 3.11-3.02 (m, 6H), 2.14-2.00 (m, 2H), 1.57 (d, J=7.0 Hz, 3H).

Step 4

4-{[(1R)-1-[3-(difluoromethyl)-2-fluorophenyl]ethyl]amino}-6-(4-hydroxy-1-oxo-1λ$^6$-thian-4-yl)-8-methyl-7H,8H-pyrido[2,3-d]pyrimidin-7-one (1.33 µg, 2.78 mmol) was dissolved in anhydrous DCM (40 mL) and cooled to 0° C. DAST (622 µL, 4.7 mmol) was added and the reaction mixture was left to stir at rt overnight. Then, the reaction mixture was diluted with DCM and washed with 1.0 M aq NaHCO$_3$ solution. The combined organic layers were dried over anhydrous Na$_2$SO$_4$, and the solvent was removed under reduced pressure to afford 4-{[(1R)-1-[3-(difluoromethyl)-2-fluorophenyl]ethyl]amino}-6-(4-fluoro-1-oxo-1λ$^4$-thian-4-yl)-8-methyl-7H,8H-pyrido[2,3-d]pyrimidin-7-on (1.08 g, crude). $^1$H NMR (300 MHz, DMSO-d$_6$) δ 8.67 (t, J=8.0 Hz, 1H), 8.61-8.54 (m, 1H), 8.36 (s, 1H), 7.63 (t, J=7.1 Hz, 1H), 7.51 (t, J=7.1 Hz, 1H), 7.34-7.26 (m, 1H), 7.24 (t, J=54.4 Hz, 1H), 5.76-5.71 (t, J=7.0 Hz, 1H), 3.57 (s, 3H), 3.33-2.74 (m, 6H), 2.17-2.02 (m, 1H), 1.93-1.78 (m, 1H), 1.57 (d, J=7.0 Hz, 3H).

Step 5

4-{[(1R)-1-[3-(difluoromethyl)-2-fluorophenyl]ethyl]amino}-6-(4-fluoro-1-imino-1-oxo-1λ$^6$-thian-4-yl)-8-methyl-7H,8H-pyrido[2,3-d]pyrimidin-7-one (300 mg, 0.6 mmol) was suspended in acetonitrile (12 mL). To the stirred mixture aq. formaldehyde (37% wt, 190 µL, 2.41 mmol) and trifluoroacetic acid (185 µL, 2.42 mmol) were added. The resulting solution was stirred at rt for 30 min. Triethylsilane (385 µL, 2.41 mmol) was added and the reaction mixture was left to stir at rt overnight. The solvent was removed under reduced pressure and the crude residue was divided between water and DCM. NaHCO$_3$ (solid) was added to adjust to neutral pH. The aqueous phase was washed with DCM and the combined organic layers were dried over anhydrous Na$_2$SO$_4$. The solvent was removed under reduced pressure and the crude residue was purified by prep-HPLC to give 4-(((R)-1-(3-(difluoromethyl)-2-fluorophenyl)ethyl)amino)-6-((1S,4s)-4-fluoro-1-(methylimino)-1-oxidohexahydro-1λ$^6$-thiopyran-4-yl)-8-methylpyrido[2,3-d]pyrimidin-7(8H)-one (32 mg, 11% yield, sulfoximine configuration assigned arbitrarily) and 4-(((R)-1-(3-(difluoromethyl)-2-fluorophenyl)ethyl)amino)-6-((1R,4r)-4-fluoro-1-(methylimino)-1-oxidohexahydro-1λ$^6$-thiopyran-4-yl)-8-methylpyrido[2,3-d]pyrimidin-7(8H)-one (73 mg, 25% yield, sulfoximine configuration assigned arbitrarily).

4-(((R)-1-(3-(difluoromethyl)-2-fluorophenyl)ethyl)amino)-6-((1S,4s)-4-fluoro-1-(methylimino)-1-oxidohexahydro-1λ$^6$-thiopyran-4-yl)-8-methylpyrido[2,3-d]pyrimidin-7(8H)-one LCMS (ESI): m/z: [M+H] calculated for C$_{23}$H$_{26}$F$_4$N$_5$O$_2$S: 512.2; found 511.8; $^1$H NMR (300 MHz, DMSO-d$_6$) δ 8.75 (d, J=7.2 Hz, 1H), 8.65 (s, 1H), 8.41 (s, 1H), 7.67 (t, J=7.4 Hz, 1H), 7.56 (t, J=7.1 Hz, 1H), 7.35 (t, J=7.7 Hz, 1H), 7.28 (t, J=54.4 Hz, 1H), 5.79 (p, J=7.0 Hz, 1H), 3.64-3.56 (m, 5H), 3.18 (dt, J=43.0, 13.8 Hz, 4H), 2.79 (s, 3H), 2.17 (dd, J=14.1, 7.6 Hz, 2H), 1.62 (d, J=7.0 Hz, 3H).

4-(((R)-1-(3-(difluoromethyl)-2-fluorophenyl)ethyl)amino)-6-((1R,4r)-4-fluoro-1-(methylimino)-1-oxidohexahydro-1λ$^6$-thiopyran-4-yl)-8-methylpyrido[2,3-d]pyrimidin-7(8H)-one LCMS (ESI): m/z: [M+H] calculated for C$_{23}$H$_{26}$F$_4$N$_5$O$_2$S: 512.2; found 511.8; $^1$H NMR (400 MHz, DMSO-d$_6$) δ 8.69 (d, J=7.3 Hz, 1H), 8.60 (s, 1H), 8.37 (s, 1H), 7.63 (t, J=7.6 Hz, 1H), 7.51 (t, J=7.2 Hz, 1H), 7.30 (t, J=7.7 Hz, 1H), 7.23 (t, J=54.4 Hz, 1H), 5.74 (p, J=6.9 Hz, 1H), 3.58 (s, 3H), 3.30-3.10 (m, 6H), 2.73 (s, 3H), 2.21-2.11 (m, 2H), 1.57 (d, J=7.0 Hz, 3H).

The following Examples 51-1 to 51-6 shown in Table 16 were synthesized in the manner similar to Examples 51 and 52.
TABLE 16
Examples 51-1 to 51-6
| Example # | Structure | Mass Found |
|---|---|---|
| 51-1 | 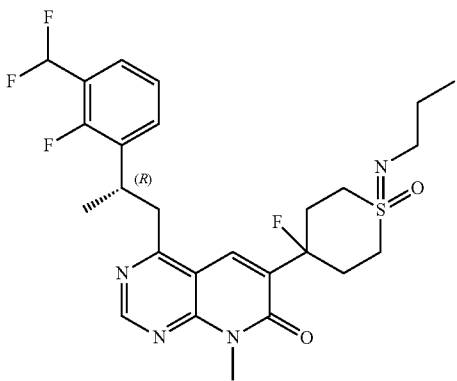 | 540.1 |
| 51-2 | 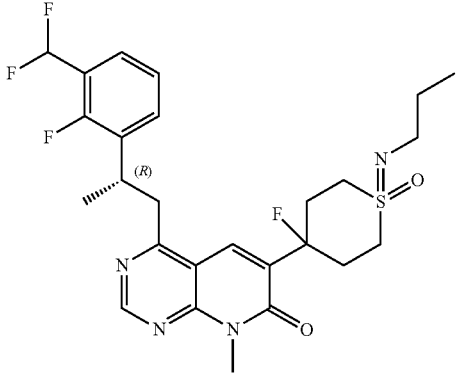 | 540.1 |
| 51-3 | 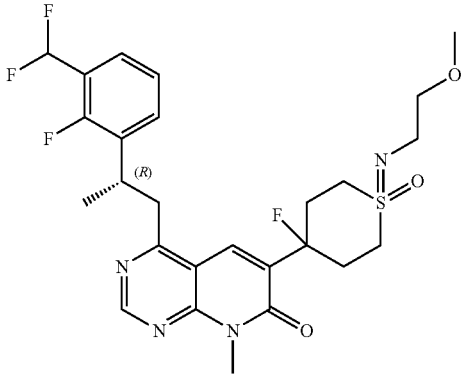 | 556.1 |

TABLE 16-continued
Examples 51-1 to 51-6
| Example # | Structure | Mass Found |
|---|---|---|
| 51-4 | 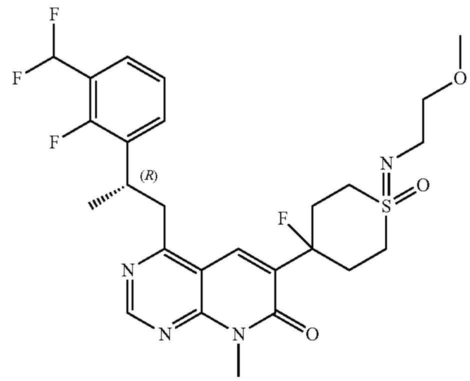 | 556.1 |
| 51-5 | 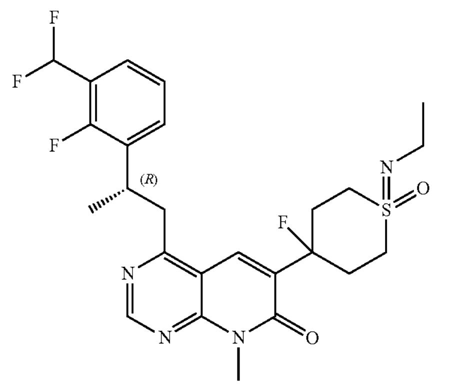 | 526.1 |
| 51-6 | 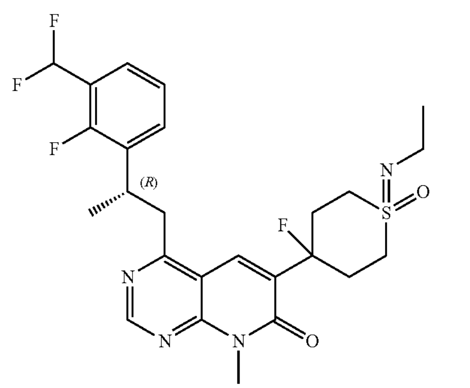 | 526.1 |
Example 53: Synthesis of 4-(4-{[(1R)-1-[3-(difluoromethyl)-2-fluorophenyl]ethyl]amino}-8-methoxy-7-oxo-7H,8H-pyrido[2,3-d]pyrimidin-6-yl)-1λ⁶-thiane-1,1-dione
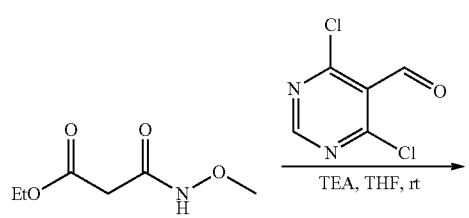
-continued
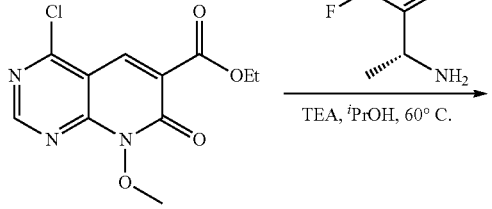

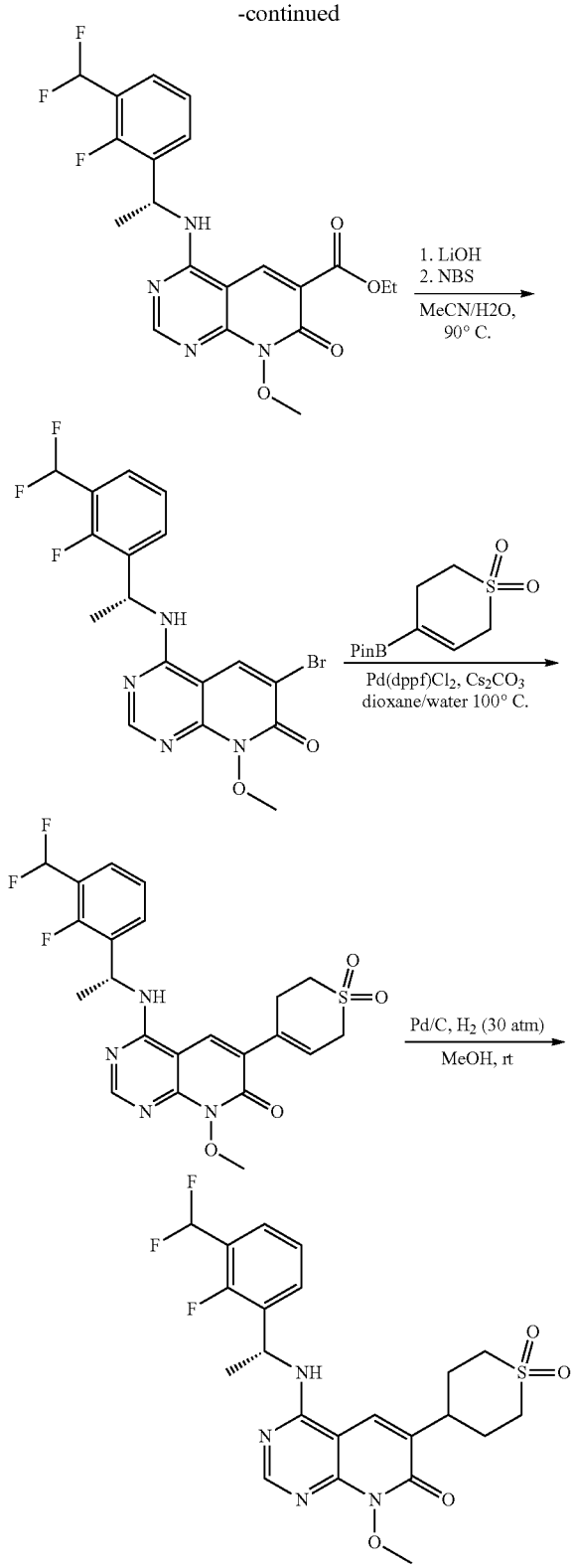

-continued

Step 1

To a solution of 4,6-dichloropyrimidine-5-carbaldehyde (3.45 g, 19.49 mmol) in anhydrous THF (100 mL) ethyl 2-[(methoxy)carbamoyl]acetate (4.17 g, 25.34 mmol) and triethylamine (6.22 mL, 44.84 mmol) were added and reaction mixture was stirred at rt for 2 h. The solvent was removed under reduced pressure and the residue was suspended in water and extracted with EtOAc. The combined organic layers were dried over anhydrous $Na_2SO_4$, and the solvent was removed under reduced pressure. The crude residue was purified by flash column chromatography to afford ethyl 4-chloro-8-methoxy-7-oxo-7H,8H-pyrido[2,3-d]pyrimidine-6-carboxylate (2.8 g, yield=51%). $^1$H NMR (300 MHz, DMSO-$d_6$) δ 9.05 (s, 1H), 8.48 (s, 1H), 4.34 (d, J=7.1 Hz, 2H), 4.01 (s, 3H), 1.32 (t, J=7.1 Hz, 3H).

Step 2

To a solution of ethyl 4-chloro-8-methoxy-7-oxo-7H,8H-pyrido[2,3-d]pyrimidine-6-carboxylate (2.80 g, 9.87 mmol) in isopropanol (84 mL) (1R)-1-[3-(difluoromethyl)-2-fluorophenyl]ethan-1-amine hydrochloride (2.23 g, 9.87 mmol) and triethylamine (4.13 mL, 29.61 mmol) were added. The reaction mixture was stirred for 2 h at 60° C. The reaction was diluted with EtOAc and washed with water. The aqueous layer was extracted with EtOAc and the combined organic phases were dried over $Na_2SO_4$. The solvent was removed under reduced pressure and the crude residue was purified by flash column chromatography to afford ethyl 4-{[(1R)-1-[3-(difluoromethyl)-2-fluorophenyl]ethyl]amino}-8-methoxy-7-oxo-7H,8H-pyrido[2,3-d]pyrimidine-6-carboxylate (3.3 g, 76% yield). $^1$H NMR (300 MHz, DMSO-$d_6$) δ 9.05 (s, 1H), 8.96 (d, J=6.5 Hz, 1H), 8.43 (s, 1H), 7.71-7.61 (m, 1H), 7.52 (t, J=7.2 Hz, 1H), 7.32 (d, J=7.7 Hz, 1H), 7.24 (t, J=54.4 Hz, 1H), 5.80-5.66 (m, 1H), 4.33 (q, J=7.1 Hz, 2H), 3.92 (s, 3H), 1.59 (s, 3H), 1.32 (t, J=7.1 Hz, 3H).

Step 3

To a solution of ethyl 4-{[(1R)-1-[3-(difluoromethyl)-2-fluorophenyl]ethyl]amino}-8-methoxy-7-oxo-7H,8H-pyrido[2,3-d]pyrimidine-6-carboxylate (3.3 g, 7.6 mmol) in a mixture of acetonitrile (50 mL) and water (50 mL) lithium hydroxide monohydrate (825 mg, 19.7 mmol) was added and the reaction mixture was stirred at 90° C. for 1 h. The reaction mixture was cooled to 35° C. and NBS (1.35 g, 7.56 mmol) was added keeping the internal temperature at 35-45° C. The resulting mixture was stirred at rt for 1 h and then another portion of NBS (1.35 g, 7.56 mmol) was added. The reaction mixture was stirred overnight at rt. The precipitate was filtered off, dried and purified via flash chromatography to give 6-bromo-4-{[(1R)-1-[3-(difluoromethyl)-2-fluorophenyl]ethyl]amino}-8-methoxy-7H,8H-pyrido[2,3-d]pyrimidin-7-one (1.2 g, yield=24%). $^1$H NMR (300 MHz, DMSO-$d_6$) δ 9.00 (s, 1H), 8.58 (d, J=7.1 Hz, 1H), 8.42 (s, 1H), 7.64 (t, J=7.3 Hz, 1H), 7.52 (t, J=7.1 Hz, 1H), 7.30 (t, J=7.7 Hz, 1H), 7.24 (t, J=56 Hz, 1H), 5.74-5.65 (m, 1H), 3.94 (s, 3H), 1.57 (d, J=7.1 Hz, 3H).

Step 4

6-bromo-4-{[(1R)-1-[3-(difluoromethyl)-2-fluorophenyl]ethyl]amino}-8-methoxy-7H,8H-pyrido[2,3-d]pyrimidin-7-one (821 mg, 1.24 mmol) was dissolved in 1,4-dioxane (23 mL) and water (2.8 mL). 1,1-Dioxo-1,2,3,6-tetrahydro-2H-thiopyran-4-yl-boronic acid pinacol ester (384 mg, 1.49 mmol) and cesium carbonate (930 mg, 2.85 mmol) were added. The solution was purged with Ar for 10 min before Pd(dppf)$Cl_2$ (61 mg, 0.06 mmol) was added and the mixture was purged with Ar for an additional 10 min. The mixture was heated in a microwave reactor at 100° C. for 1 h. After cooling to rt all solids were filtered off and the solvent was removed from the filtrate under reduced pressure to give 4-(4-{[(1R)-1-[3-(difluoromethyl)-2-fluorophenyl]ethyl]amino}-8-methoxy-7-oxo-7H,8H-pyrido[2,3-d]pyrimidin-6-yl)-3,6-dihydro-2H-1-thiopyran-1,1-dione (889 mg, crude). LCMS (ESI): m/z: [M+H] calculated for $C_{22}H_{22}F_3N_4O_4S$: 495.1; found 495.1.

Step 5

4-(4-{[(1R)-1-[3-(difluoromethyl)-2-fluorophenyl]ethyl]amino}-8-methoxy-7-oxo-7H,8H-pyrido[2,3-d]pyrimidin-6-yl)-3,6-dihydro-2H-1-thiopyran-1,1-dione (877 mg, 1.17 mmol) was dissolved in MeOH (23 mL). Then Pd/C (20 wt %, 175 mg) was added and the reaction mixture was placed into a Parr reactor under $H_2$ atmosphere (30 bars) and stirred at rt overnight. The reaction mixture was filtered through a pad of Celite® and the solvent was removed under reduced pressure. The crude residue was purified by prep-HPLC to give 4-(4-{[(1R)-1-[3-(difluoromethyl)-2-fluorophenyl]ethyl]amino}-8-methoxy-7-oxo-7H,8H-pyrido[2,3-d]pyrimidin-6-yl)-1$\lambda^6$-thiane-1,1-dione (128 mg, 26% yield). LCMS (ESI): m/z: [M+H] calculated for $C_{22}H_{24}F_3N_4O_4S$: 497.1; found 497.0; $^1$H NMR (300 MHz, DMSO-$d_6$) δ 8.57 (d, J=7.1 Hz, 1H), 8.36 (s, 1H), 8.26 (s, 1H), 7.63 (t, J=7.5 Hz, 1H), 7.52 (t, J=7.0 Hz, 1H), 7.32 (t, J=7.7 Hz, 1H), 7.25 (t, J=54.3 Hz, 1H), 5.73 (p, J=6.8 Hz, 1H), 3.92 (s, 3H), 3.48-3.38 (m, 3H, overlapped with $H_2O$ peak), 3.21-3.11 (m, 2H), 2.24-2.11 (m, 4H), 1.60 (d, J=7.0 Hz, 3H).

Example 54: Synthesis of 6-{3-acetyl-3-azabicyclo[3.1.0]hexan-1-yl}-4-{[(1R)-1-[3-(difluoromethyl)-2-fluorophenyl]ethyl]amino}-8-methyl-7H,8H-pyrido[2,3-d]pyrimidin-7-one

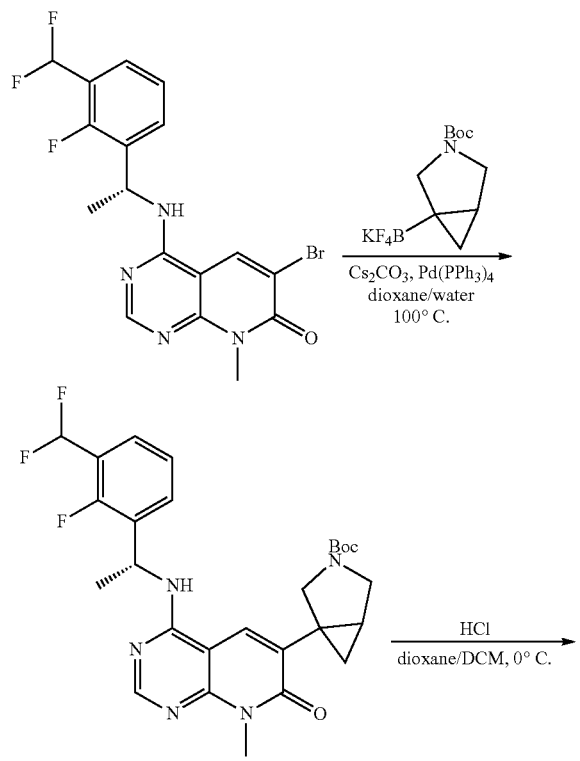

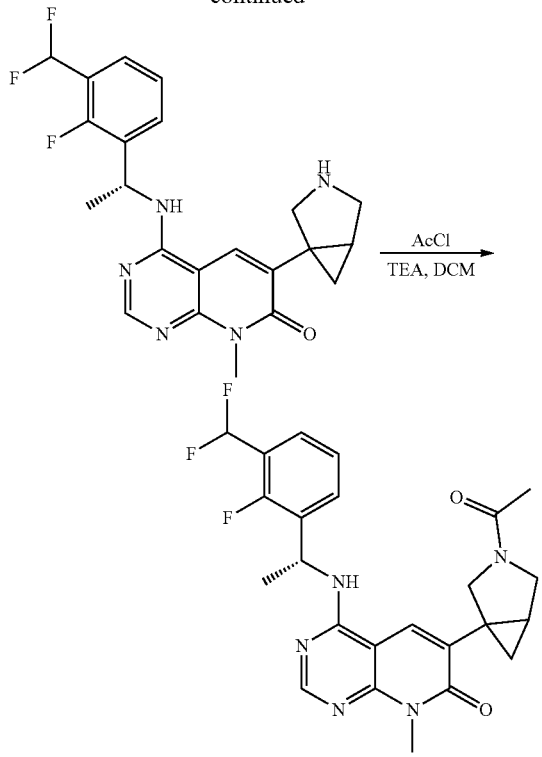

Step 1

6-bromo-4-{[(1R)-1-[3-(difluoromethyl)-2-fluorophenyl]ethyl]amino}-8-methoxy-7H,8H-pyrido[2,3-d]pyrimidin-7-one (700 mg, 1.64 mmol) was dissolved in 1,4-dioxane (17.5 mL) and water (5.6 mL). Potassium (3-(tert-butoxycarbonyl)-3-azabicyclo[3.1.0]hexan-1-yl)trifluoroborate (710 mg, 2.46 mmol) and cesium carbonate (2.67 g, 8.19 mmol) were added. The solution was purged with Ar for 10 min before Pd(PPh$_3$)$_4$ (322 mg, 0.27 mmol) was added and the mixture was stirred overnight at 100° C. After cooling to rt the mixture was filtered and the solvent was removed under reduced pressure. The crude residue was purified by flash column chromatography to give tert-butyl 1-(4-{[(1R)-1-[3-(difluoromethyl)-2-fluorophenyl]ethyl]amino}-8-methyl-7-oxo-7H,8H-pyrido[2,3-d]pyrimidin-6-yl)-3-azabicyclo[3.1.0]hexane-3-carboxylate (930 mg, 99% yield). LCMS (ESI): m/z: [M+H] calculated for $C_{27}H_{31}F_3N_5O_3$: 530.2; found 530.8.

Step 2

To a solution of tert-butyl 1-(4-{[(1R)-1-[3-(difluoromethyl)-2-fluorophenyl]ethyl]amino}-8-methyl-7-oxo-7H,8H-pyrido[2,3-d]pyrimidin-6-yl)-3-azabicyclo[3.1.0]hexane-3-carboxylate (846 mg, 1.6 mmol) in DCM (4.2 mL) HCl (4 M in dioxane, 4.0 mL, 16 mmol) was added at 0° C. and the reaction mixture was stirred at rt overnight. The solvent was removed under reduced pressure to give 6-{3-azabicyclo[3.1.0]hexan-1-yl}-4-{[(1R)-1-[3-(difluoromethyl)-2-fluorophenyl]ethyl]amino}-8-methyl-7H,8H-pyrido[2,3-d]pyrimidin-7-one hydrochloride (1.05 g, crude). LCMS (ESI): m/z: [M+H] calculated for $C_{22}H_{23}F_3N_5O$: 430.2; found 430.4.

Step 3

To the solution of 6-{3-azabicyclo[3.1.0]hexan-1-yl}-4-{[(1R)-1-[3-(difluoromethyl)-2-fluorophenyl]ethyl]amino}-8-methyl-7H,8H-pyrido[2,3-d]pyrimidin-7-one hydrochloride (882 mg, 1.89 mmol) and triethylamine (1.32 mL, 9.47 mmol) in DCM (26.5 mL) acetyl chloride (122 µL, 1.70 mmol) was added dropwise. The reaction was stirred for 20 min at rt before being quenched with water. The organic layer was dried over $Na_2SO_4$, and the solvent was removed under reduced pressure. The crude residue was purified by flash column chromatography to give 6-{3-acetyl-3-azabicyclo[3.1.0]hexan-1-yl}-4-{[(1R)-1-[3-(difluoromethyl)-2-fluorophenyl]ethyl]amino}-8-methyl-7H,8H-pyrido[2,3-d]pyrimidin-7-one (580 mg, 64% yield). LCMS (ESI): m/z: [M+H] calculated for $C_{24}H_{25}F_3N_5O_2$: 472.2; found 472.2; $^1$H NMR (300 MHz, DMSO-$d_6$) δ 8.40-8.26 (m, 3H), 7.62 (t, 1H), 7.51 (t, J=7.1 Hz, 1H), 7.30 (t, J=7.7 Hz, 1H), 7.24 (t, J=54.4 Hz, 1H), 5.73 (q, J=7.2 Hz, 1H), 3.95-3.82 (m, 1H), 3.82-3.66 (m, 2H), 3.57 (d, J=4.2 Hz, 3H), 3.51-3.39 (m, 1H), 1.94 (d, J=8.9 Hz, 3H), 1.59 (d, J=6.9 Hz, 3H), 1.22-1.13 (m, 1H), 0.91-0.80 (m, 1H), 0.79-0.68 (m, 1H).

The following examples 54-1 to 54-4 shown in Table 17 were synthesized in the manner similar to Example 54.

TABLE 17

Examples 54-1 to 54-4

| Example # | Structure | Mass Found |
| --- | --- | --- |
| 54-1 | [structure] | 486.2 |
| 54-2 | [structure] | 445.1 |
| 54-3 | [structure] | 445.11 |

TABLE 17-continued
Examples 54-1 to 54-4
| Example # | Structure | Mass Found |
|---|---|---|
| 54-4 | 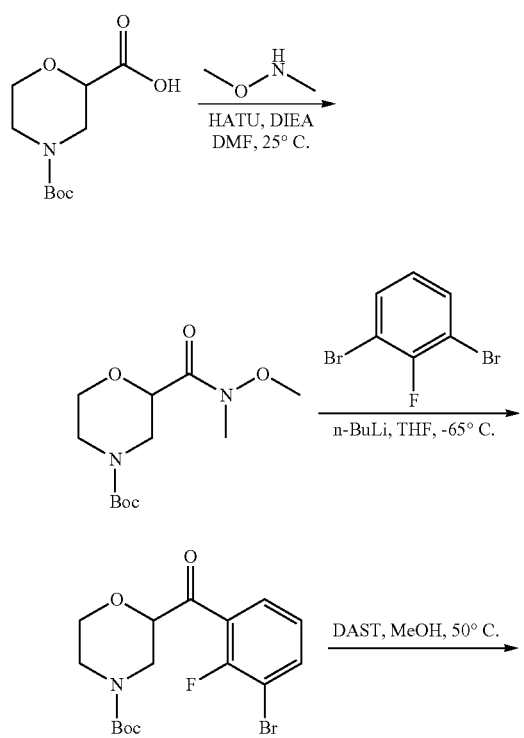 | 486.2 |
Example 55: Synthesis of 6-(1-acetyl-4-piperidyl)-4-[[(1R)-1-[3-[(4-cyclopropylmorpholin-2-yl)-difluoro-methyl]-2-fluoro-phenyl]ethyl]amino]-8-methyl-pyrido[2,3-d]pyrimidin-7-one
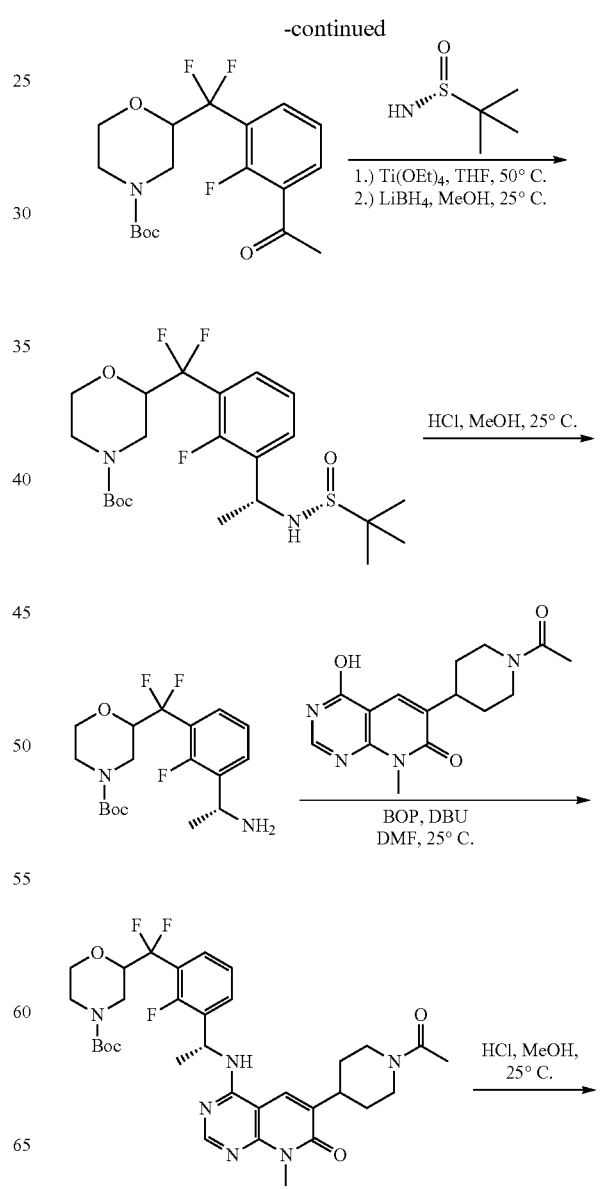

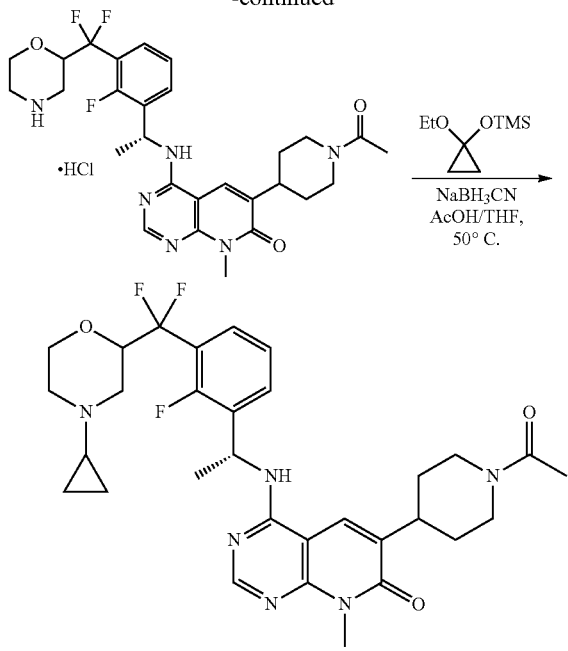

Step 1

To a solution of 4-tert-butoxycarbonylmorpholine-2-carboxylic acid (10 g, 43 mmol) in DMF (40 mL) were added HATU (25 g, 65 mmol), N,O-dimethylhydroxylamine hydrochloride (6.3 g, 65 mmol) and DIEA (38 mL, 216 mmol) at rt. The reaction mixture was stirred at rt for 12 h before H$_2$O was added and the mixture was extracted with EtOAc. The combined organic phases were treated with brine, dried over anhydrous Na$_2$SO$_4$, and the solvent was removed under reduced pressure. The crude residue was purified by column chromatography to give tert-butyl 2-[methoxy(methyl)carbamoyl]morpholine-4-carboxylate (5 g, 42% yield). $^1$H NMR (400 MHz, METHANOL-d$_4$) δ ppm 4.45-4.35 (m, 1H), 4.11-3.91 (m, 2H), 3.86-3.72 (m, 4H), 3.59 (td, J=11.4, 2.8 Hz, 1H), 3.21 (s, 3H), 3.09-2.86 (m, 2H), 1.47 (s, 9H).

Step 2

To a solution of 1,3-dibromo-2-fluoro-benzene (4.0 g, 15.7 mmol) in THF (10 mL) was added a 2.0 M solution of n-BuLi in hexanes (8.6 mL, 17.2 mmol) at −65° C. tert-Butyl 2-[methoxy(methyl)carbamoyl]morpholine-4-carboxylate (4.3 g, 15.7 mmol) in THF (10 mL) was then added at −65° C. over a period of 1 h before H$_2$O was added at rt and the mixture was extracted with EtOAc. The combined organic phases were treated with brine, dried over anhydrous Na$_2$SO$_4$, and concentrated under reduced pressure. The crude residue was purified by column chromatography to give tert-butyl 2-(3-bromo-2-fluoro-benzoyl)morpholine-4-carboxylate (4.0 g, 66% yield). LCMS (ESI): m/z: [M−55] calculated for C$_{12}$H$_{12}$BrFNO$_4$: 332.0; found 332.0.

Step 3

To a solution of tert-butyl 2-(3-bromo-2-fluoro-benzoyl)morpholine-4-carboxylate (2.00 g, 5.15 mmol) in DAST (5.0 mL, 37.8 mmol) was added MeOH (208 µL, 5.15 mmol) at rt. The reaction mixture was stirred at 50° C. for 3 h. The mixture was then diluted with H$_2$O and extracted with EtOAc. The combined organic phases were treated with brine, dried over anhydrous Na$_2$SO$_4$, and the solvent was removed under reduced pressure. The crude residue was purified by column chromatography to give tert-butyl 2-[(3-bromo-2-fluoro-phenyl)-difluoro-methyl] morpholine-4-carboxylate (1.5 g, 70% yield). LCMS (ESI): m/z: [M+H] calculated for C$_{16}$H$_{20}$BrF$_3$NO$_3$: 410.1; found 410.2.

Step 4

A mixture of tert-butyl 2-[(3-bromo-2-fluoro-phenyl)-difluoro-methyl]morpholine-4-carboxylate (1.50 g, 3.66 mmol), tributyl(1-ethoxyvinyl)stannane (1.85 mL, 5.5 mmol), TEA (1.27 mL, 9.14 mmol), and Pd(PPh$_3$)$_2$Cl$_2$ (257 mg, 366 µmol) in dioxane (10 mL) was degassed and purged with N$_2$ 3 times. The reaction mixture was stirred at 100° C. for 4 h under N$_2$. After cooling to rt aqueous HCl (2 M, 10 mL) was added to the mixture and stirred for an additional 1 h. Solids were filtered off and the filtrate was extracted with EtOAc. Into the combined organic extracts was poured an aqueous solution of KF (20 mL, ~1 g KF). The resulting mixture was stirred for 2 h, filtered, treated with brine, dried over Na$_2$SO$_4$, and concentrated under reduced pressure. The crude residue was purified by column chromatography to give tert-butyl 2-[(3-acetyl-2-fluoro-phenyl)-difluoro-methyl]morpholine-4-carboxylate (1.0 g, 73% yield). LCMS (ESI): m/z: [M+H] calculated for C$_{18}$H$_{23}$F$_3$NO$_4$: 374.2; found 374.2.

Step 5

To a solution of tert-butyl 2-[(3-acetyl-2-fluoro-phenyl)-difluoro-methyl]morpholine-4-carboxylate (1.0 g, 2.7 mmol) in THF (2 mL) were added Ti(OEt)$_4$ (1.7 mL, 8.0 mmol) and (R)-2-methylpropane-2-sulfinamide (649 mg, 5.4 mmol). The reaction mixture was stirred at 80° C. for 4 h. Subsequently, LiBH$_4$ (175 mg, 8.04 mmol) and MeOH (108 µL, 2.68 mmol) were added to the mixture at 0° C. and the reaction was stirred at rt for 4 h. The mixture was poured into a 1:1 mixture of H$_2$O (20 mL) and THF (20 mL). Solids were filtered off and the filtrate was concentrated under reduced pressure. The crude residue was purified by column chromatography to give tert-butyl 2-[[3-[(1R)-1-[[(R)-tert-butylsulfinyl]amino]ethyl]-2-fluoro-phenyl]-difluoro-methyl]morpholine-4-carboxylate (700 mg, 55% yield). $^1$H NMR (400 MHz, METHANOL-d$_4$) δ ppm 7.67 (t, J=6.4 Hz, 1H), 7.45 (t, J=7.2 Hz, 1H), 7.27 (t, J=15.6 Hz, 1H), 4.09-4.02 (m, 2H), 3.84-3.80 (m, 2H), 3.49-3.42 (m, 1H), 3.15-2.96 (m, 2H), 1.54 (d, J=6.8 Hz, 3H), 1.47 (s, 9H), 1.19 (s, 9H).

Step 6

To a solution of tert-butyl 2-[[3-[(1R)-1-[[(R)-tert-butylsulfinyl]amino]ethyl]-2-fluoro-phenyl]-difluoro-methyl]morpholine-4-carboxylate (550 mg, 1.15 mmol) in MeOH (2 mL) was added a 4 M solution of HCl in MeOH (287 µL, 1.15 mmol). The reaction was stirred at rt for 30 min before NaOH in MeOH was added to adjust the pH to ~7. The mixture was then was poured into MeOH (2 mL) and DCM (20 mL) and filtered. The filtrate was concentrated under reduced pressure to give tert-butyl 2-[[3-[(1R)-1-aminoethyl]-2-fluoro-phenyl]-difluoro-methyl]morpholine-4-carboxylate (300 mg, crude). $^1$H NMR (400 MHz, METHANOL-d4) δ ppm 7.66 (t, J=7.0 Hz, 1H), 7.42 (t, J=3.6 Hz, 1H), 7.32-7.23 (t, J=7.8 Hz, 1H), 4.41-4.40 (m, 1H), 4.09-4.07 (m, 2H), 3.86-3.83 (m, 2H), 3.51-3.46 (m, 1H), 3.10-2.89 (m, 2H), 1.47 (s, 9H), 1.42 (d, J=6.8 Hz, 3H).

Step 7

To a solution of tert-butyl 2-[[3-[(1R)-1-aminoethyl]-2-fluoro-phenyl]-difluoro-methyl] morpholine-4-carboxylate (150 mg, 0.4 mmol) in DMF (5 mL) were added DBU (181 µL, 1.20 mmol), BOP (230 mg, 0.52 mmol) and 6-(1-acetyl-4-piperidyl)-4-hydroxy-8-methyl-pyrido[2,3-d]pyrimidin-7-one (133 mg, 0.44 mmol). The mixture was stirred at rt for 3 h before H$_2$O (30 mL) was added and the mixture was extracted with EtOAc. The combined organic phases were filtered and treated with brine, dried over anhydrous Na$_2$SO$_4$, and concentrated under reduced pressure. The crude residue was purified by prep-TLC to give tert-butyl 2-[[3-[(1R)-1-[[6-(1-acetyl-4-piperidyl)-8-methyl-7-oxo-pyrido[2,3-d] pyrimidin-4-yl]amino]ethyl]-2-fluoro-phenyl]-difluoro-methyl]morpholine-4-carboxylate (150 mg, 57% yield). LCMS (ESI): m/z: [M+H] calculated for $C_{33}H_{42}F_3N_6O_5$: 659.3, found 659.4.

Step 8

To a solution of tert-butyl 2-[[3-[(1R)-1-[[6-(1-acetyl-4-piperidyl)-8-methyl-7-oxo-pyrido[2,3-d]pyrimidin-4-yl]amino]ethyl]-2-fluoro-phenyl]-difluoro-methyl]morpholine-4-carboxylate (150 mg, 228 μmol) in MeOH (5 mL) was added a 4 M solution of HCl in MeOH (228 μL, 0.91 mmol). The mixture was stirred at rt for 3 h before NaOH in MeOH was added to adjust the pH to ~7. The mixture was diluted with water and extracted with EtOAc. The combined organic phases were dried over $Na_2SO_4$, and the solvent was removed under reduced pressure. The crude residue was purified by prep-TLC to give 6-(1-acetyl-4-piperidyl)-4-[[(1R)-1-[3-[difluoro(morpholin-2-yl)methyl]-2-fluoro-phenyl]ethyl]amino]-8-methyl-pyrido[2,3-d]pyrimidin-7-one HCl salt (120 mg, 33% yield). LCMS (ESI): m/z: [M+H] calculated for $C_{28}H_{34}F_3N_6O_3$: 559.3; found 559.3.

Step 9

To a solution of 6-(1-acetyl-4-piperidyl)-4-[[(1R)-1-[3-[difluoro(morpholin-2-yl)methyl]-2-fluoro-phenyl]ethyl]amino]-8-methyl-pyrido[2,3-d]pyrimidin-7-one (120 mg, 215 μmol) in AcOH (2 mL) and THF (2 mL) were added $NaBH_3CN$ (27 mg, 430 μmol) and (1-ethoxycyclopropoxy)-trimethyl-silane (65 μL, 322 μmol) at rt. The reaction mixture was stirred at 50° C. for 3 h. The mixture was then filtered, and the filtrate was concentrated under reduced pressure. The crude residue was purified by prep-HPLC to give 6-(1-acetyl-4-piperidyl)-4-[[(1R)-1-[3-[(4-cyclopropylmorpholin-2-yl)-difluoro-methyl]-2-fluoro-phenyl]ethyl]amino]-8-methyl-pyrido[2,3-d]pyrimidin-7-one (25 mg, 19% yield). LCMS (ESI): m/z: [M+H] calculated for $C_{31}H_{38}F_3N_6O_3$: 599.3; found 599.3; $^1H$ NMR (400 MHz, METHANOL-$d_4$) δ ppm 8.31 (s, 1H), 8.18 (s, 1H), 7.54 (t, J=7.2 Hz, 1H), 7.40 (t, J=7.2 Hz 1H), 7.19 (t, J=7.7 Hz, 1H), 5.78-5.75 (m, 1H), 4.71 (d, J=14.6 Hz, 1H), 4.15-4.03 (m, 3H), 3.86-3.84 (m, 1H), 3.71 (s, 3H), 3.50 (t, J=4 Hz, 1H), 3.28-3.15 (m, 2H), 3.13-3.04 (m, 1H), 2.92-2.85 (m, 1H), 2.80-2.72 (m, 1H), 2.51-2.42 (m, 2H), 2.15 (s, 3H), 2.15-2.02 (m, 1H), 2.01-1.97 (m, 1H), 1.97-1.93 (m, 1H), 1.65-1.62 (m, 5H), 0.55-0.47 (m, 4H).

Examples 56 and 57: Synthesis of 6-((1R,4r)-1-(cyclopropylimino)-4-fluoro-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one and 6-((1S,4s)-1-(cyclopropylimino)-4-fluoro-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one

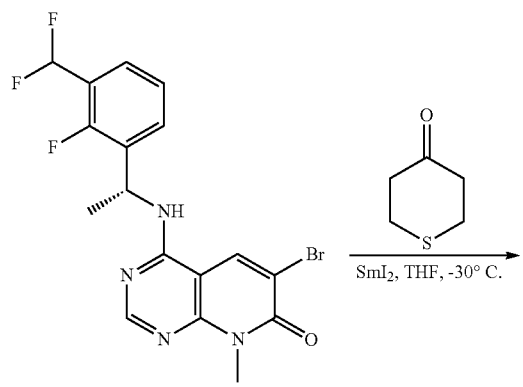

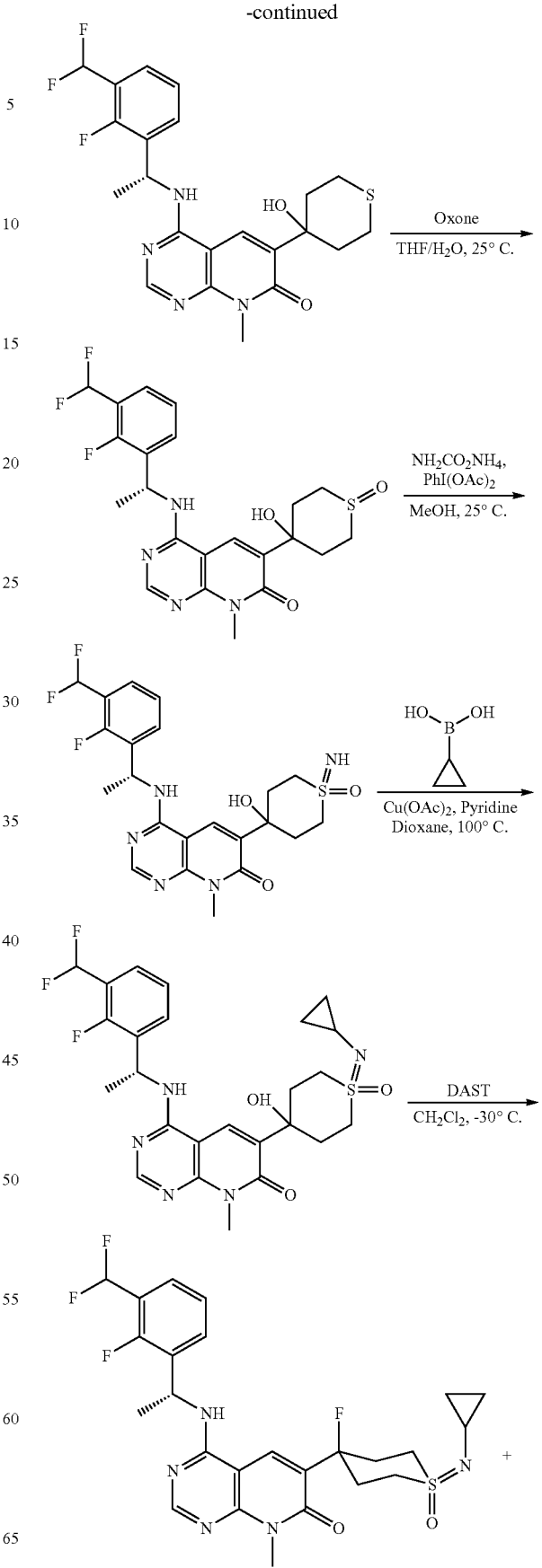

-continued

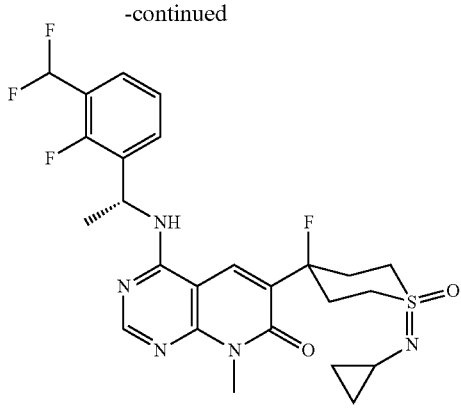

Step 1

To a solution of 6-bromo-4-[[(1R)-1-[3-(difluoromethyl)-2-fluoro-phenyl]ethyl]amino]-8-methyl-pyrido[2,3-d]pyrimidin-7-one (1.0 μg, 2.34 mmol) and tetrahydrothiopyran-4-one (272 mg, 2.34 mmol) in THF (10 mL) at −30° C. was added a 0.1 M solution of SmI$_2$ in THF (70.2 mL, 7.02 mmol) under N$_2$. The reaction was stirred at −30° C. for 2 h and then treated with aq. sat. NaHCO$_3$ (20 mL), filtered, and extracted with EtOAc. The combined organic extracts were washed with brine, dried over anhydrous Na$_2$SO$_4$, and the solvent was removed under reduced pressure. The crude residue was purified by column chromatography to give 4-[[(1R)-1-[3-(difluoromethyl)-2-fluoro-phenyl]ethyl]amino]-6-(4-hydroxytetrahydrothiopyran-4-yl)-8-methyl-pyrido[2,3-d]pyrimidin-7-one (720 mg, 65% yield). LCMS (ESI): m/z: [M+H] calculated for C$_{22}$H$_{24}$F$_3$N$_4$O$_2$S: 465.2; found 465.2.

Step 2

To a solution of 4-[[(1R)-1-[3-(difluoromethyl)-2-fluoro-phenyl]ethyl]amino]-6-(4-hydroxytetrahydrothiopyran-4-yl)-8-methyl-pyrido[2,3-d]pyrimidin-7-one (300 mg, 646 μmol) in THF (5 mL) and H$_2$O (1 mL) at 0° C. was added Oxone (198 mg, 323 μmol). The reaction mixture was stirred at rt for 2 h and then quenched by the addition aqueous Na$_2$S$_2$O$_3$ (10 mL) and extracted with EtOAc. The combined organic phases were washed with brine, dried over anhydrous Na$_2$SO$_4$, and the solvent was removed under reduced pressure. The crude residue was purified by column chromatography to give 4-[[(1R)-1-[3-(difluoromethyl)-2-fluoro-phenyl]ethyl]amino]-6-(4-hydroxy-1-oxo-thian-4-yl)-8-methyl-pyrido[2,3-d]pyrimidin-7-one (170 mg, 46% yield). LCMS (ESI): m/z: [M+H] calculated for C$_{22}$H$_{24}$F$_3$N$_4$O$_3$S: 481.1; found 481.1.

Step 3

4-[[(1R)-1-[3-(difluoromethyl)-2-fluoro-phenyl]ethyl]amino]-6-(4-hydroxy-1-oxo-thian-4-yl)-8-methyl-pyrido[2,3-d]pyrimidin-7-one (1.11 g, 2.31 mmol), PhI(OAc)$_2$ (2.23 g, 6.93 mmol) and ammonium carbamate (721 mg, 9.24 mmol) were suspended in MeOH (10 mL) and the reaction was stirred for 4 h at rt. The solvent was then removed under reduced pressure and the crude residue was purified by column chromatography to give 4-[[(1R)-1-[3-(difluoromethyl)-2-fluoro-phenyl]ethyl]amino]-6-(4-hydroxy-1-imino-1-oxo-thian-4-yl)-8-methyl-pyrido[2,3-d]pyrimidin-7-one (990 mg, 86% yield). $^1$H NMR (400 MHz, METHANOL-d$_4$) δ ppm 8.46 (s, 1H) 8.33 (s, 1H) 7.58 (t, J=8 Hz, 1H) 7.48 (t, J=6 Hz, 1H) 7.23 (t, J=8 Hz, 1H) 7.00 (t, J=56 Hz, 1H) 5.82-5.77 (m, 1H) 3.70 (s, 3H) 3.66-3.59 (m, 2H) 3.11-3.06 (m, 2H) 2.96-2.89 (m, 2H) 2.26-2.21 (m, 2H) 1.66 (d, J=8 Hz, 3H).

Step 4

A mixture of 4-[[(1R)-1-[3-(difluoromethyl)-2-fluoro-phenyl]ethyl]amino]-6-(4-hydroxy-1-imino-1-oxo-thian-4-yl)-8-methyl-pyrido[2,3-d]pyrimidin-7-one (1.00 g, 2.02 mmol), Cu(OAc)$_2$ (550 mg, 3.03 mmol) and pyridine (391 μL, 4.84 mmol) in dioxane (10 mL) was stirred for 5 min at rt under open air. Cyclopropylboronic acid (347 mg, 4.04 mmol) was added and the reaction was heated to 100° C. for 6 h. After cooling to rt the mixture was filtered, and the solvent was removed under reduced pressure. The crude residue was purified by column chromatography to give 6-(1-cyclopropylimino-4-hydroxy-1-oxo-thian-4-yl)-4-[[(1R)-1-[3-(difluoromethyl)-2-fluoro-phenyl]ethyl]amino]-8-methyl-pyrido[2,3-d]pyrimidin-7-one (800 mg, 73% yield). LCMS (ESI): m/z: [M+H] calculated for C$_{25}$H$_{29}$F$_3$N$_5$O$_3$S: 536.2; found 536.2.

Step 5

To a solution of 6-(1-cyclopropylimino-4-hydroxy-1-oxo-thian-4-yl)-4-[[(1R)-1-[3-(difluoromethyl)-2-fluoro-phenyl]ethyl]amino]-8-methyl-pyrido[2,3-d]pyrimidin-7-one (300 mg, 560 μmol) in DCM (3 mL) was added DAST (148 μL, 1.12 mmol) at −30° C. under N$_2$. The reaction was stirred at −30° C. for 5 h before aq. sat. NaHCO$_3$ solution (50 mL) was added and the mixture was extracted with DCM. The combined organic extracts were washed with brine, dried over anhydrous Na$_2$SO$_4$, and the solvent was removed under reduced pressure. The crude residue was purified by prep-HPLC to afford 6-((1R,4r)-1-(cyclopropylimino)-4-fluoro-1-oxidohexahydro-1λ$^6$-thiopyran-4-yl)-4-(((R)-1-(3-(difluoromethyl)-2-fluorophenyl)ethyl)amino)-8-methylpyrido[2,3-d]pyrimidin-7(8H)-one (18.6 mg, 6% yield, sulfoximine stereochemistry assigned arbitrarily) and 6-((1S,4s)-1-(cyclopropylimino)-4-fluoro-1-oxidohexahydro-1λ$^6$-thiopyran-4-yl)-4-(((R)-1-(3-(difluoromethyl)-2-fluorophenyl)ethyl)amino)-8-methylpyrido[2,3-d]pyrimidin-7(8H)-one (32.2 mg, 11% yield, sulfoximine stereochemistry assigned arbitrarily).

6-((1R,4r)-1-(cyclopropylimino)-4-fluoro-1-oxidohexahydro-1λ$^6$-thiopyran-4-yl)-4-(((R)-1-(3-(difluoromethyl)-2-fluorophenyl)ethyl)amino)-8-methylpyrido[2,3-d]pyrimidin-7(8H)-one LCMS (ESI): m/z: [M+H] calculated for C$_{25}$H$_{28}$F$_4$N$_5$O$_2$S: 538.2; found 538.1; $^1$H NMR (400 MHz, DMSO-d$_6$) δ ppm 8.68 (d, J=4 Hz, 1H), 8.59 (s, 1H) 8.37 (s, 1H) 7.63 (t, J=8 Hz, 1H) 7.51 (t, J=6 Hz, 1H) 7.37-7.10 (m, 2H) 5.77-5.70 (m, 1H) 3.57 (s, 3H) 3.42-3.39 (m, 2H) 3.28-3.08 (m, 4H) 2.56-2.53 (m, 1H) 2.09-2.04 (m, 2H) 1.57 (d, J=8 Hz, 3H) 0.54-0.47 (m, 2H) 0.45-0.40 (m, 2H).

6-((1S,4s)-1-(cyclopropylimino)-4-fluoro-1-oxidohexahydro-1λ$^6$-thiopyran-4-yl)-4-(((R)-1-(3-(difluoromethyl)-2-fluorophenyl)ethyl)amino)-8-methylpyrido[2,3-d]pyrimidin-7(8H)-one LCMS (ESI): m/z:[M+H] calculated for C$_{25}$H$_{28}$F$_4$N$_5$O$_2$S: 538.2; found 538.1; H NMR (400 MHz, DMO-d$_6$) δ ppm 8.69 (d, J=8 Hz, 1H) 8.59 (s, 1H) 8.37 (s, 1H) 7.63 (t, J=8 Hz, 1H) 7.51 (t, J=6 Hz, 1H) 7.37-7.10 (m, 2H) 5.78-5.71 (m, 1H) 3.58 (s, 3H) 3.30-3.13 (m, 6H) 2.59-2.55 (m, 1H) 2.16-2.14 (m, 2H) 1.57 (d, J=8 Hz, 3H) 0.51-0.47 (m, 2H) 0.37-0.34 (m, 2H).

The following examples 56-1 to 56-5 shown in Table 18 were synthesized in the manner similar to Examples 56 and 57.

TABLE 18

Examples 56-1 to 56-5

| Example # | Structure | Mass Found |
|---|---|---|
| 56-1 | 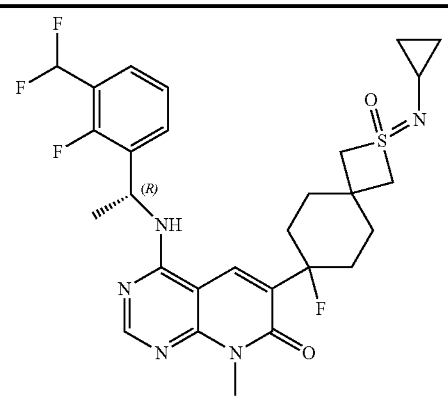 | 578.12 |
| 56-2 | 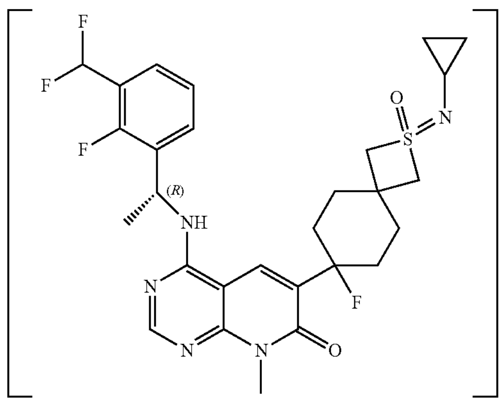 | 578.05 |
| 56-3 | 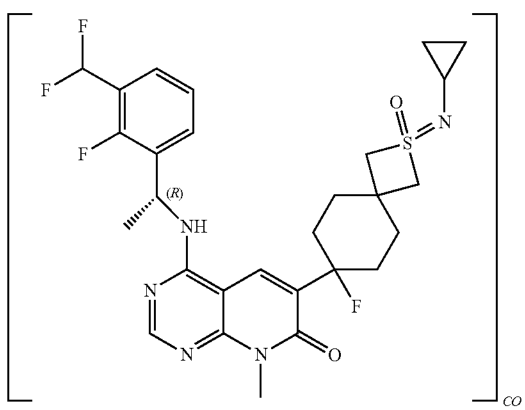 | 578.05 |
| 56-4 | 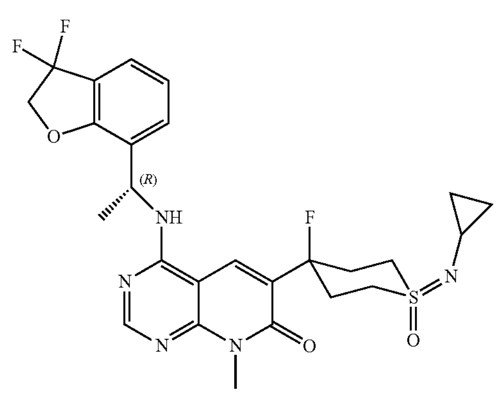 | 548.1 |

TABLE 18-continued

Examples 56-1 to 56-5

| Example # | Structure | Mass Found |
|---|---|---|
| 56-5 | 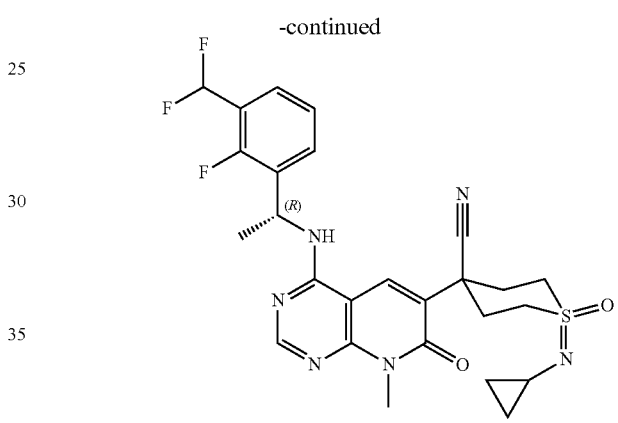 | 548.1 |

Examples 58 and 59. Synthesis of (1R,4r)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ$^6$-thiopyran-4-carbonitrile 1-oxide and (1S,4s)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ$^6$-thiopyran-4-carbonitrile 1-oxide

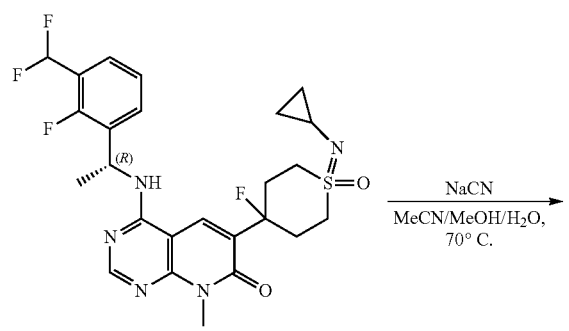

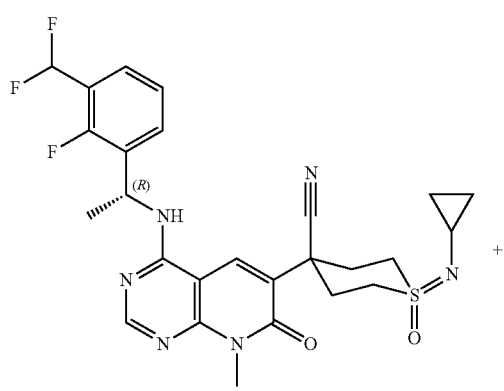

Step 1

To a solution of 6-(1-cyclopropylimino-4-fluoro-1-oxo-thian-4-yl)-4-[[(1R)-1-[3-(difluoromethyl)-2-fluoro-phenyl]ethyl]amino]-8-methyl-pyrido[2,3-d]pyrimidin-7-one (210 mg, 391 μmol) in MeCN (1 mL), MeOH (0.6 mL) and H$_2$O (0.2 mL) was added NaCN (115 mg, 2.34 mmol) at rt under N$_2$. The reaction was stirred at 70° C. for 10 h, and then poured into aqueous Na$_2$CO$_3$ to adjust the pH to ~10. The mixture was extracted with EtOAc, the combined organic extracts were washed with brine, dried over anhydrous Na$_2$SO$_4$, and the solvent was removed under reduced pressure. The crude residue was purified by prep-HPLC and prep-SFC to afford (1R,4r)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ$^6$-thiopyran-4-carbonitrile 1-oxide (9.1 mg, 15% yield, sulfoximine stereochemistry assigned arbitrarily) and (1S,4s)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ$^6$-thiopyran-4-carbonitrile 1-oxide (7.0 mg, 12% yield, sulfoximine stereochemistry assigned arbitrarily).

703

(1R,4r)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ⁶-thiopyran-4-carbonitrile 1-oxide LCMS (ESI): m/z: [M+H] calculated for $C_{26}H_{28}F_3N_6O_2S$: 545.2; found 545.1. ¹H NMR (400 MHz, DMSO-d₆) δ ppm 8.64 (d, J=4 Hz, 1H) 8.38 (d, J=8 Hz, 2H) 7.63 (t, J=6 Hz, 1H) 7.52 (t, J=6 Hz, 1H) 7.37-7.10 (m, 2H) 5.78-5.71 (m, 1H) 3.85-3.71 (m, 2H) 3.61 (s, 3H) 3.24-3.21 (m, 2H) 2.78 (d, J=12 Hz, 2H) 2.42-2.33 (m, 3H) 1.60 (d, J=8 Hz, 3H) 0.51-0.47 (m, 2H) 0.36-0.34 (m, 2H).

704

(1S,4s)-1-(cyclopropylimino)-4-(4-(((R)-1-(3-(difluoromethyl)-2-fluorophenyl)ethyl)amino)-8-methyl-7-oxo-7,8-dihydropyrido[2,3-d]pyrimidin-6-yl)hexahydro-1λ⁶-thiopyran-4-carbonitrile 1-oxide LCMS (ESI): m/z: [M+H] calculated for $C_{26}H_{28}F_3N_6O_2S$: 545.2.

The following examples 58-1 to 58-4 shown in Table 19 were synthesized in the manner similar to Examples 58 and 59.

TABLE 19

Examples 58-1 to 58-4

| Example # | Structure | Mass Found |
|---|---|---|
| 58-1 | 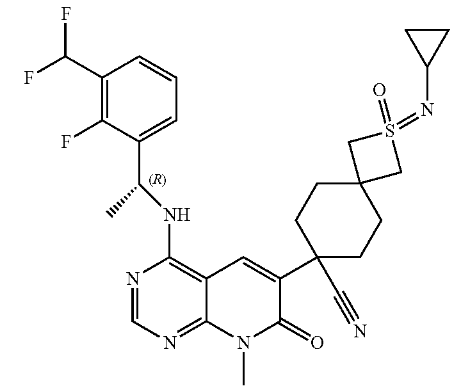 | 585.2 |
| 58-2 | | 585.21 |
| 58-3 | 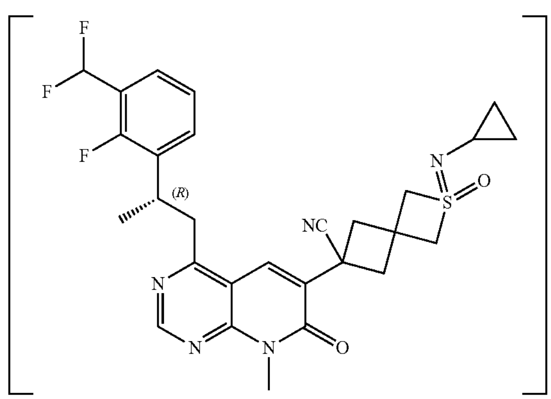 | 557.1 |

TABLE 19-continued

Examples 58-1 to 58-4

| Example # | Structure | Mass Found |
|---|---|---|
| 58-4 | 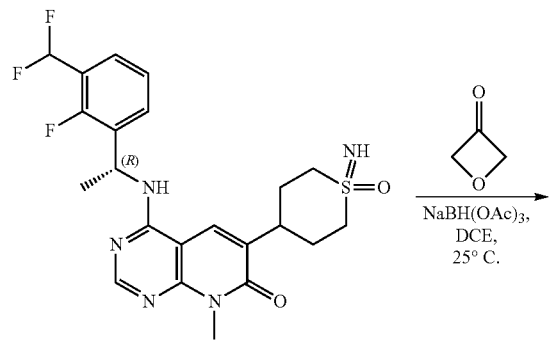 | 557.1 |

Example 60: Synthesis of 4-[[(1R)-1-[3-(difluoromethyl)-2-fluoro-phenyl]ethyl]amino]-8-methyl-6-[1-(oxetan-3-ylimino)-1-oxo-thian-4-yl]pyrido[2,3-d]pyrimidin-7-one

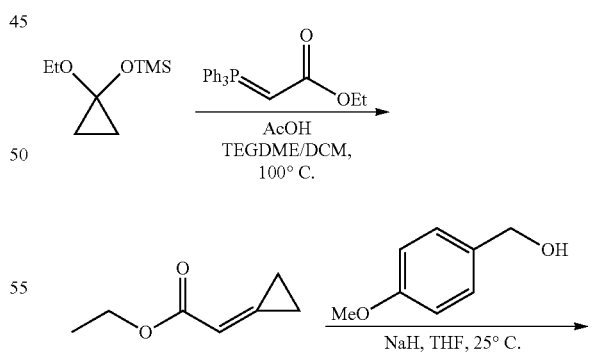

To a solution of 4-[[(1R)-1-[3-(difluoromethyl)-2-fluoro-phenyl]ethyl]amino]-6-(1-imino-1-oxo-thian-4-yl)-8-methyl-pyrido[2,3-d]pyrimidin-7-one (280 mg, 584 μmol) and oxetan-3-one (168 mg, 2.34 mmol) in DCE (5 mL) was added NaBH(OAc)$_3$ (371 mg, 1.75 mmol). The reaction was stirred at 50° C. for 36 h before being quenched with H$_2$O (10 mL) and extracted with DCM. The combined organic phases were treated with brine, dried over anhydrous Na$_2$SO$_4$, filtered, and concentrated under reduced pressure. The crude residue was purified by prep-HPLC, followed by prep-SFC, to give 4-[[(1R)-1-[3-(difluoromethyl)-2-fluoro-phenyl]ethyl]amino]-8-methyl-6-[1-(oxetan-3-ylimino)-1-oxo-thian-4-yl]pyrido[2,3-d]pyrimidin-7-one (9.8 mg, 3% yield). LCMS (ESI): m/z: [M+H] calculated for C$_{25}$H$_{29}$F$_3$N$_5$O$_3$S: 536.2; found 536.2; $^1$H NMR (400 MHz, DMSO-d$_6$) δ ppm 8.46 (br d, J=7.1 Hz, 1H) 8.32 (s, 1H) 8.26 (s, 1H) 7.60 (t, J=7.2 Hz, 1H) 7.51 (t, J=7.0 Hz, 1H) 7.30 (t, J=7.8 Hz, 1H) 7.24 (t, J=54.4 Hz, 1H) 5.76-5.68 (m, 1H) 4.70-4.60 (m, 3H) 4.43-4.41 (m, 2H) 3.58 (s, 3H) 3.24-3.18 (m, 5H) 2.19-2.10 (m, 4H) 1.59 (d, J=7.2 Hz, 3H).

Example 61: Synthesis of 4-[[(1R)-1-[3-(difluoromethyl)-2-fluoro-phenyl]ethyl]amino]-6-[1-[(4-methoxyphenyl)methoxy]cyclopropyl]-8-methyl-pyrido[2,3-d]pyrimidin-7-one

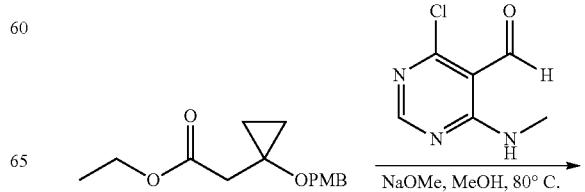

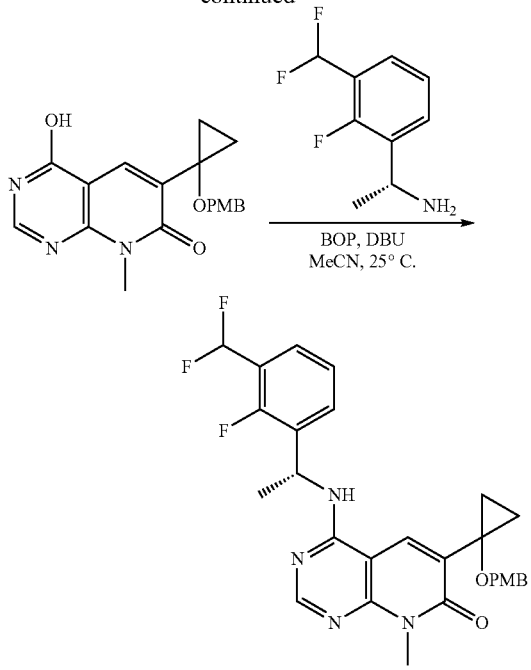

Step 1

To a solution of [(1-ethoxycyclopropyl)oxy]trimethylsilane (6.0 mL, 29.8 mmol) and acetic acid (853 mL, 14.9 mmol) in tetraethylene glycol dimethyl ether (20 mL) was added a solution of ethyl 2-(triphenylphosphoranylidene)acetate (9.35 g, 26.9 mmol) in DCM (10 mL). The reaction mixture was stirred at 100° C. for 3 h in a pressure tube. After cooling to rt DCM the solvent was removed under reduced pressure and the crude residue purified by column chromatography to give ethyl 2-cyclopropylideneacetate (3.0 g, 80% yield). $^1$H NMR (400 MHz, CHLOROFORM-d) δ ppm 6.23-6.18 (m, 1H), 4.20 (q, J=7.1 Hz, 2H), 1.47-1.40 (m, 2H), 1.29 (t, J=7.1 Hz, 3H), 1.25-1.17 (m, 2H).

Step 2

To a solution of NaH (60 wt %, 159 mg, 3.96 mmol) in THF (5 mL) was added (4-methoxyphenyl)methanol (7.4 mL, 59.5 mmol). The mixture was stirred for 30 min before ethyl 2-cyclopropylideneacetate (2.5 g, 19.8 mmol) in THF (2.5 mL) was added and the reaction was stirred at rt for 2 h. H$_2$O was added and the mixture was extracted with EtOAc. The combined organic phases were washed with brine, dried over anhydrous Na$_2$SO$_4$, and the solvent was removed under reduced pressure. The crude residue was purified by column chromatography to give ethyl 2-[1-[(4-methoxyphenyl)methoxy]cyclopropyl]acetate (160 mg, 3% yield). $^1$H NMR (400 MHz, CHLOROFORM-d) δ ppm 7.17-7.12 (m, 2H), 6.80-6.75 (m, 2H), 4.41 (s, 2H), 4.18 (q, J=8.0 Hz, 2H), 3.72 (s, 3H), 2.58 (s, 2H), 1.20 (t, J=8.0 Hz, 3H), 0.92-0.86 (m, 2H), 0.64-0.58 (m, 2H).

Step 3

To a solution of 4-chloro-6-(methylamino)pyrimidine-5-carbaldehyde (300 mg, 1.75 mmol) and (4-methoxyphenyl)methyl 2-[1-[(4-methoxyphenyl)methoxy]cyclopropyl]acetate (748 mg, 2.10 mmol) in MeOH (3 mL) was added NaOMe in MeOH (30%, 1.57 g, 8.74 mmol). The reaction was stirred at 80° C. for 1 h. After cooling to rt the mixture was filtered, and the filtrate was concentrated under reduced pressure. The crude residue was purified by prep-HPLC to give 4-hydroxy-6-[1-[(4-methoxyphenyl)methoxy]cyclopropyl]-8-methyl-pyrido[2,3-d]pyrimidin-7-one (150 mg, 24% yield). LCMS (ESI): m/z: [M+H] calculated for C$_{19}$H$_{20}$N$_3$O$_4$: 354.1; found: 354.0.

Step 4

To a solution of 4-hydroxy-6-[1-[(4-methoxyphenyl)methoxy]cyclopropyl]-8-methyl-pyrido[2,3-d]pyrimidin-7-one (90 mg, 255 μmol) in MeCN (2 mL) were added DBU (115 μL, 764 μmol), BOP (169 mg, 382 μmol) and (1R)-1-[3-(difluoromethyl)-2-fluoro-phenyl]ethanamine (72 mg, 382 μmol). The reaction mixture was stirred at rt for 1 h and then diluted with H$_2$O and extracted with EtOAc. The combined organic phases were washed with brine, dried over anhydrous Na$_2$SO$_4$, and concentrated under reduced pressure. The crude residue was purified by column chromatography to give 4-[[(1R)-1-[3-(difluoromethyl)-2-fluoro-phenyl]ethyl]amino]-6-[1-[(4-methoxyphenyl)methoxy]cyclopropyl]-8-methyl-pyrido[2,3-d]pyrimidin-7-one (100 mg, 85% yield). LCMS (ESI): m/z: [M+H] calculated for C$_{28}$H$_{28}$F$_3$N$_4$O$_3$: 525.2; found: 525.1; $^1$H NMR (400 MHz, DMSO-d$_6$) δ ppm 8.52 (s, 1H), 8.45 (br d, J=7.4 Hz, 1H), 8.34 (s, 1H), 7.68-7.62 (m, 1H), 7.55-7.48 (m, 1H), 7.40-7.11 (m, 4H), 6.84-6.78 (m, 2H), 5.78-5.69 (m, 1H), 4.40 (s, 2H), 3.68 (s, 3H), 3.56 (s, 3H), 1.60 (d, J=7.1 Hz, 3H), 1.18-1.13 (m, 2H), 1.07-1.02 (m, 2H).

Example 62: Synthesis of 6-(1-acetyl-4-methoxy-4-piperidyl)-4-[[(1R)-1-[4-(difluoromethyl)-3-fluoro-2-pyridyl]ethyl]amino]-8-methyl-pyrido[2,3-d]pyrimidin-7-one

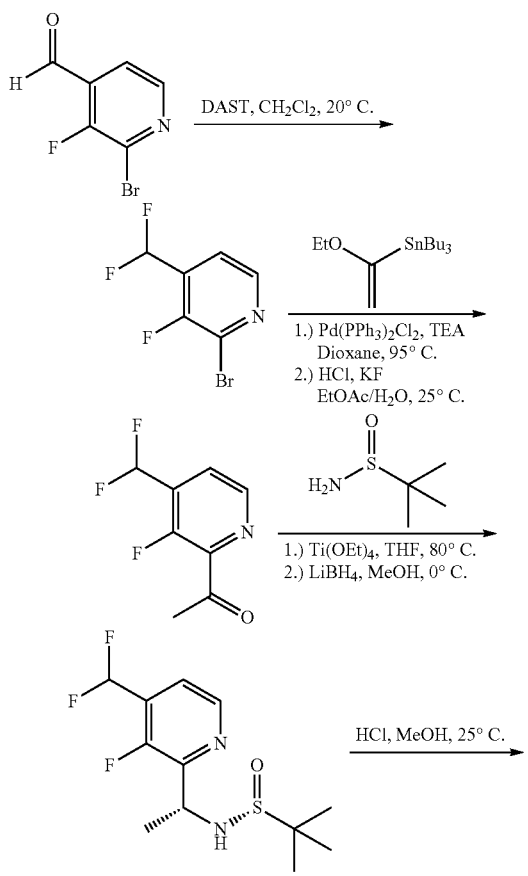

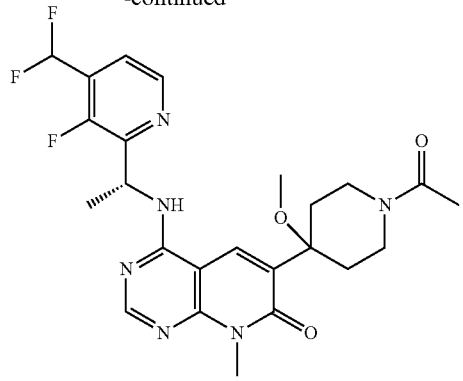

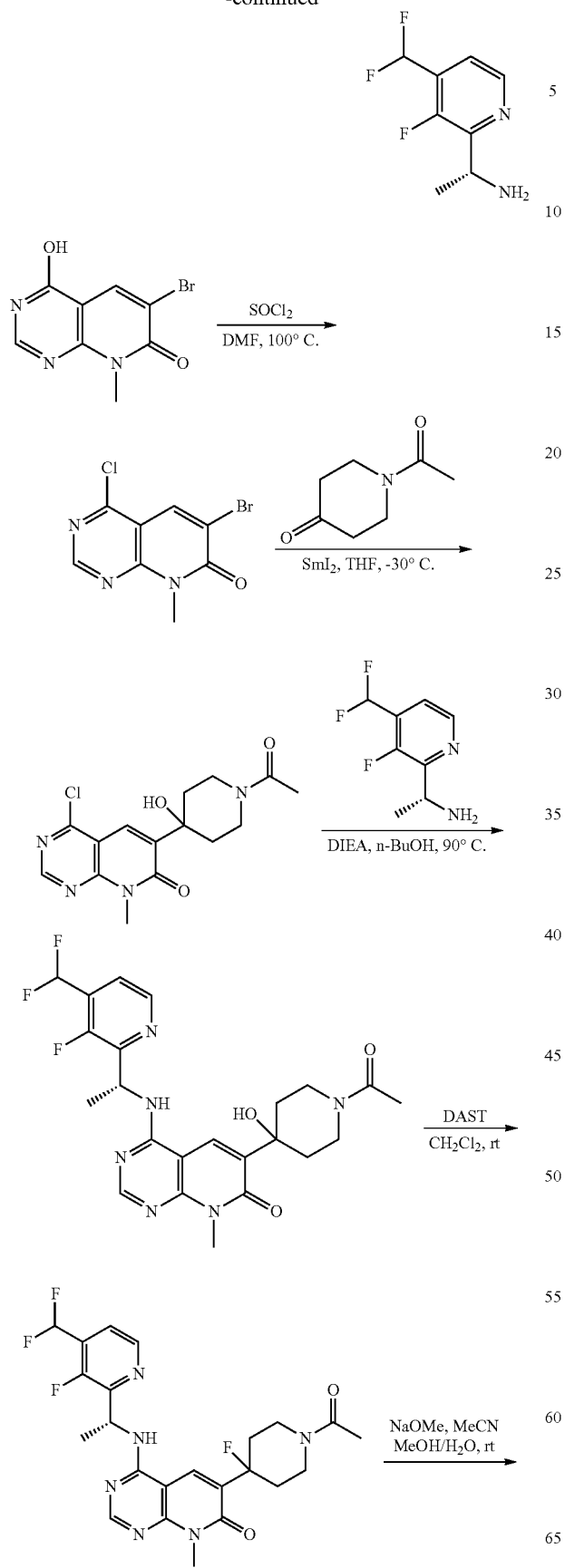

Step 1

To a solution of 2-bromo-3-fluoro-pyridine-4-carbaldehyde (4.5 g, 22.1 mmol) in DCM (50 mL) was added DAST (5.8 mL, 44.1 mmol) at 0° C. The reaction mixture was stirred at rt for 2 h before H$_2$O was added and the mixture was extracted with DCM. The combined organic phases were washed with brine, dried over anhydrous Na$_2$SO$_4$, and the solvent was removed under reduced pressure. The crude residue was purified by silica gel chromatography to give 2-bromo-4-(difluoromethyl)-3-fluoro-pyridine (3.5 g, 70% yield). $^1$H NMR (400 MHz, DMSO-d$_6$) δ ppm 8.45 (d, J=4 Hz, 1H), 7.73 (t, J=4 Hz, 1H), 7.46-7.19 (m, 1H).

Step 2

To a mixture of 2-bromo-4-(difluoromethyl)-3-fluoro-pyridine (3.5 g, 15.5 mmol) and TEA (5.4 mL, 38.7 mmol) in dioxane (36 mL) were added tributyl(1-ethoxyvinyl)stannane (7.8 mL, 23.2 mmol) and Pd(PPh$_3$)$_2$Cl$_2$ (544 mg, 774 μmol). The mixture was purged with N$_2$ three times then stirred at 95° C. for 3 h. After cooling to rt aqueous HCl (4 M, 54 mL) was added (pH ~2) and the reaction was stirred for 1 h at rt before being filtered and extracted with EtOAc. The combined organic extracts were poured over aqueous KF and stirred for 2 h. Any solids were removed by filtration and the filtrate was treated with brine, dried over Na$_2$SO$_4$, and the solvent was removed under reduced pressure. The crude residue was purified by column chromatography to give 1-[4-(difluoromethyl)-3-fluoro-2-pyridyl]ethanone (2.7 g, 92% yield). $^1$H NMR (400 MHz, DMSO-d$_6$) δ ppm 8.70 (d, J=4 Hz, 1H), 7.95-7.92 (m, 1H), 7.49-7.23 (m, 1H), 2.64 (s, 3H).

Step 3

To a solution of 1-[4-(difluoromethyl)-3-fluoro-2-pyridyl]ethanone (1.7 g, 9.0 mmol), (R)-2-methylpropane-2-sulfinamide (2.2 g, 18.0 mmol) in THF (17 mL) was added Ti(OEt)$_4$ (7.46 mL, 36.0 mmol). The reaction mixture was stirred at 80° C. for 1 h. After cooling to 0° C. MeOH (364 μL, 9.0 mmol) and LiBH$_4$ (783 mg, 36.0 mmol) were added and the mixture was stirred at 0° C. for 1 h before being diluted with water and extracted with EtOAc. The combined organic extracts were washed with brine, dried over anhydrous Na$_2$SO$_4$, and the solvent was removed under reduced pressure. The crude residue was purified by silica gel chromatography followed by prep-HPLC to give N-[(1R)-1-[4-(difluoromethyl)-3-fluoro-2-pyridyl]ethyl]-2-methylpropane-2-sulfinamide (410 mg, 15% yield). $^1$H NMR (400 MHz, DMSO-d$_6$) δ ppm 8.58 (d, J=4 Hz, 1H), 7.62-7.59 (m, 1H), 7.46-7.19 (m, 1H), 5.65 (d, J=8 Hz, 1H), 4.84-4.77 (m, 1H), 1.47 (d, J=8 Hz, 3H), 1.08 (s, 9H).

Step 4

To a solution of N-[(1R)-1-[4-(difluoromethyl)-3-fluoro-2-pyridyl]ethyl]-2-methyl-propane-2-sulfinamide (200 mg, 680 µmol) in MeOH (8 mL) was added HCl in MeOH (4 M, 340 µL). The reaction was stirred at rt for 1 h. A solution of NaOH in MeOH was then added to adjust the pH to ~8, the mixture was concentrated under reduced pressure to remove most of the solvent, and the mixture was filtered to give (1R)-1-[4-(difluoromethyl)-3-fluoro-2-pyridyl]ethanamine (130 mg, 85% yield). $^1$H NMR (400 MHz, DMSO-$d_6$) δ ppm 8.62 (d, J=4 Hz, 1H), 7.67-7.64 (m, 1H), 7.49-7.21 (m, 1H), 4.59-4.54 (m, 1H), 1.42 (d, J=8 Hz, 3H).

Step 5

A solution of 6-bromo-4-hydroxy-8-methyl-pyrido[2,3-d]pyrimidin-7-one (1.80 g, 7.03 mmol) and DMF (1.08 mL, 14.1 mmol) and SOCl$_2$ (36 mL) was heated to 100° C. for 2 h. The mixture was then concentrated under reduced pressure. Aqueous NaHCO$_3$ solution was added until pH ~7 and the mixture was stirred for 30 min. After extraction with EtOAc the combined organic phases were washed with brine, dried over anhydrous Na$_2$SO$_4$ and the solvent was removed under reduced pressure to give 6-bromo-4-chloro-8-methyl-pyrido[2,3-d]pyrimidin-7-one (2.0 g, crude). LCMS (ESI): m/z: [M+H] calculated for C$_8$H$_6$BrClN$_3$O: 273.9; found: 275.1.

Step 6

A mixture of 6-bromo-4-chloro-8-methyl-pyrido[2,3-d]pyrimidin-7-one (0.50 g, 1.82 mmol) and 1-acetylpiperidin-4-one (224 µL, 1.82 mmol) in THF (5 mL) was degassed and purged with N$_2$. Samarium(II) iodide solution in THF (0.1 M, 55 mL, 5.5 mmol) was added at −30° C. and the mixture was stirred at −30° C. for 1 h before aq. sat. NaHCO$_3$ was added and the mixture was extracted with EtOAc. The combined organic phases were washed with brine, dried with anhydrous Na$_2$SO$_4$, and the solvent was removed under reduced pressure. The crude residue was purified by column chromatography to give 6-(1-acetyl-4-hydroxy-4-piperidyl)-4-chloro-8-methyl-pyrido[2,3-d]pyrimidin-7-one (0.5 g, 21% yield over 2 steps). LCMS (ESI): m/z: [M+H] calculated for C$_{15}$H$_{18}$ClN$_4$O$_3$: 337.1; found: 337.1.

Step 7

To a solution of 6-(1-acetyl-4-hydroxy-4-piperidyl)-4-chloro-8-methyl-pyrido[2,3-d]pyrimidin-7-one (276 mg, 820 µmol) in n-BuOH (2 mL) were added (1R)-1-[4-(difluoromethyl)-3-fluoro-2-pyridyl]ethanamine (130 mg, 684 µmol) and DIEA (238 µL, 1.37 mmol). The reaction mixture was stirred at 90° C. for 3 h. After cooling to rt the solvent was removed under reduced pressure and the crude residue was purified by column chromatography to give 6-(1-acetyl-4-hydroxy-4-piperidyl)-4-[[(1R)-1-[4-(difluoromethyl)-3-fluoro-2-pyridyl]ethyl]amino]-8-methyl-pyrido[2,3-d]pyrimidin-7-one (280 mg, 84% yield). LCMS (ESI): m/z: [M+H] calculated for C$_{23}$H$_{26}$F$_3$N$_6$O$_3$: 491.2; found: 491.1.

Step 8

To a solution of 6-(1-acetyl-4-hydroxy-4-piperidyl)-4-[[(1R)-1-[4-(difluoromethyl)-3-fluoro-2-pyridyl]ethyl]amino]-8-methyl-pyrido[2,3-d]pyrimidin-7-one (140 mg, 285 µmol) in DCM (2 mL) was added DAST (75 µL, 0.57 mmol) at 0° C. The reaction mixture was stirred at rt for 2 h. TEA and H$_2$O were added, and the mixture was extracted with DCM. The combined organic extracts were washed with brine, dried over anhydrous Na$_2$SO$_4$, filtered, and concentrated under reduced pressure. The crude residue was purified by silica gel chromatography to give 6-(1-acetyl-4-fluoro-4-piperidyl)-4-[[(1R)-1-[4-(difluoromethyl)-3-fluoro-2-pyridyl]ethyl]amino]-8-methyl-pyrido[2,3-d]pyrimidin-7-one (140 mg, crude). LCMS (ESI): m/z: [M+H] calculated for C$_{24}$H$_{25}$F$_4$N$_6$O$_2$: 493.2; found: 493.2.

Step 9

To a solution of 6-(1-acetyl-4-fluoro-4-piperidyl)-4-[[(1R)-1-[4-(difluoromethyl)-3-fluoro-2-pyridyl]ethyl]amino]-8-methyl-pyrido[2,3-d]pyrimidin-7-one (140 mg, crude) in MeOH (0.6 mL), MeCN (1 mL), and H$_2$O (0.2 mL) was added NaOMe (138 mg, 2.56 mmol). The reaction was stirred at rt for 2 h and then diluted with H$_2$O and extracted with EtOAc. The combined organic phases were washed with brine, dried over anhydrous Na$_2$SO$_4$, filtered, and the solvent was removed under reduced pressure. The crude residue was purified by prep-HPLC to give 6-(1-acetyl-4-methoxy-4-piperidyl)-4-[[(1R)-1-[4-(difluoromethyl)-3-fluoro-2-pyridyl]ethyl]amino]-8-methyl-pyrido[2, 3-d]pyrimidin-7-one (23 mg, 16% yield over 2 steps). LCMS (ESI): m/z: [M+H] calculated for C$_{24}$H$_{28}$F$_3$N$_6$O$_3$: 505.2; found: 505.2; $^1$H NMR (400 MHz, DMSO-$d_6$) δ ppm 8.74 (d, J=7.1 Hz, 1H), 8.52 (d, J=4.8 Hz, 1H), 8.32 (s, 1H), 8.29 (s, 1H), 7.57 (t, J=4.9 Hz, 1H), 7.48-7.20 (m, 1H), 5.84 (q, J=7.0 Hz, 1H), 4.30 (d, J=11.4 Hz, 1H), 3.70 (d, J=13.4 Hz, 1H), 3.54 (s, 3H), 3.40-3.34 (m, 1H), 3.10 (s, 3H), 2.89-2.76 (m, 1H), 2.30-1.96 (m, 7H), 1.60 (d, J=7.0 Hz, 3H).

Example 63: Synthesis of 2-[2-(difluoromethyl)-6-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]phenyl]acetonitrile

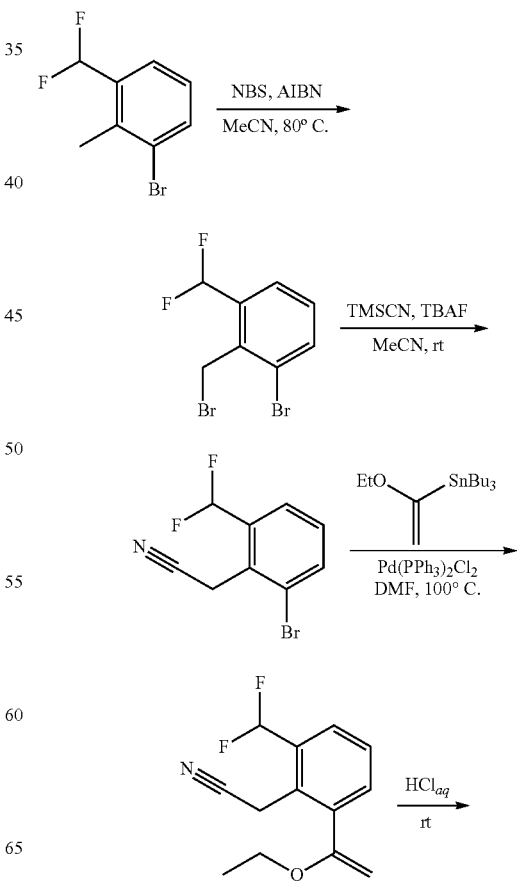

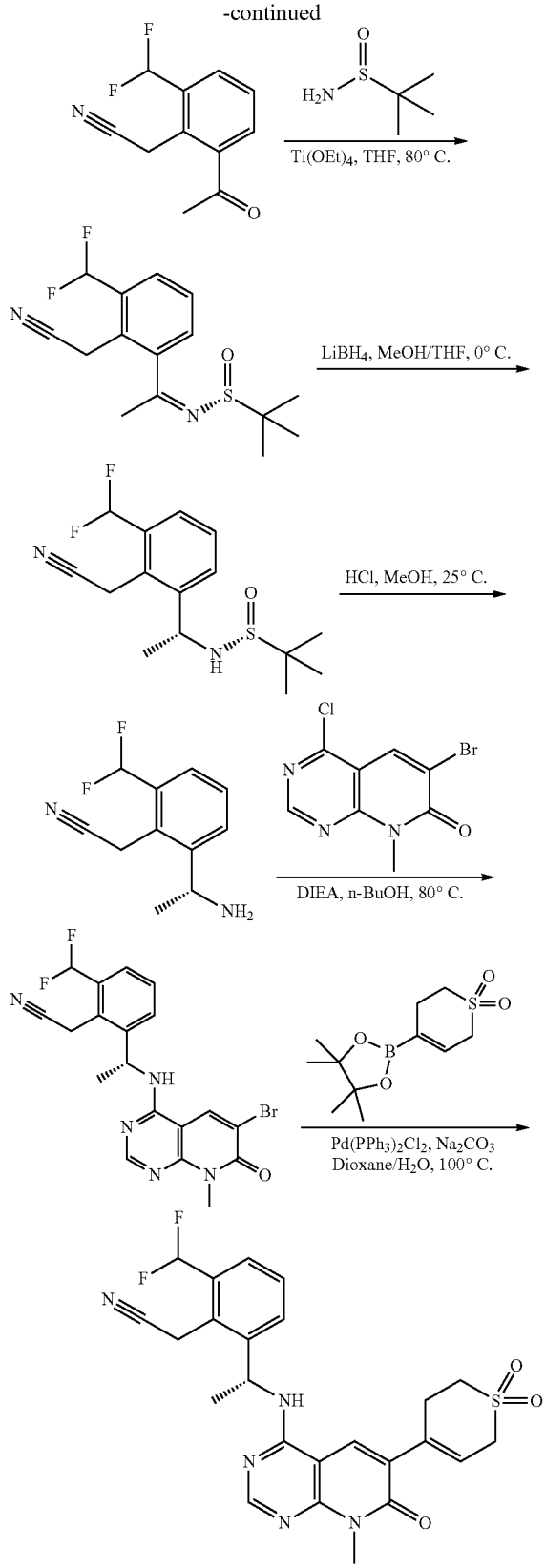

Step 1

N-Bromosuccinimide (4.06 g, 22.80 mmol) and AIBN (1.25 g, 7.60 mmol) was added to a solution of 1-bromo-3- (difluoromethyl)-2-methyl-benzene (4.20 g, 19.0 mmol) in MeCN (42 mL). The was stirred at 80° C. for 3 h and then poured into water and extracted with MTBE. The combined organic phases were treated with brine, dried over $Na_2SO_4$, and the solvent was removed under reduced pressure. The crude residue was purified by column chromatography on silica gel to give 1-bromo-2-(bromomethyl)-3-(difluoromethyl)-benzene (5.5 g, 97% yield). $^1$H NMR (400 MHz, $CDCl_3$) δ ppm 7.74 (d, J=8.0 Hz, 1H), 7.58 (d, J=7.6 Hz, 1H), 7.30 (t, J=8.0 Hz, 1H), 6.94 (t, J=54.8 Hz, 1H), 4.76 (s, 2H).

Step 2

Trimethylsilyl cyanide (1.63 mL, 13.0 mmol) was added to a solution of 1-bromo-2-(bromomethyl)-3-(difluoromethyl)benzene (3.00 g, 10.0 mmol) in MeCN (30 mL). TBAF solution (1 M in THF, 13 mL, 13 mmol) was added to the mixture at 0° C. and stirred at rt for 20 h. The reaction was poured into water and extracted with MTBE. The combined organic layers were washed with brine, dried over $Na_2SO_4$, and the solvent was removed under reduced pressure. The crude residue was purified by column chromatography on silica gel to give 2-[2-bromo-6-(difluoromethyl)phenyl]acetonitrile (2.3 g, 93% yield). $^1$H NMR (400 MHz, CDCl3) δ ppm 7.80 (d, J=8.0 Hz, 1H), 7.49 (d, J=7.6 Hz, 1H), 7.35 (t, J=8.0 Hz, 1H), 6.76 (t, J=54.4 Hz, 1H), 4.05 (s, 2H).

Step 3

To a mixture of 2-[2-bromo-6-(difluoromethyl)phenyl] acetonitrile (1.00 g, 4.06 mmol) in DMF (10 mL) were added $Pd(PPh_3)_2Cl_2$ (143 mg, 203 μmol) and tributyl(1-ethoxyvinyl)stannane (1.65 mL, 4.88 mmol). The mixture was stirred at 100° C. for 2 h under $N_2$. After cooling to rt the mixture was treated with saturated aqueous CsF solution, stirred for 10 min, then filtered. The aqueous phase of the filtrate was extracted with MTBE, washed with brine, dried over anhydrous $Na_2SO_4$, and the solvent was removed under reduced pressure to give 2-[2-(difluoromethyl)-6-(1-ethoxyvinyl)phenyl]acetonitrile (2.0 g, crude). LCMS (ESI): m/z: [M+H] calculated for $C_{13}H_{14}F_2NO$: 238.1; found: 238.4.

Step 4

2-[2-(difluoromethyl)-6-(1-ethoxyvinyl)phenyl]acetonitrile (2 g, crude) was dissolved in aqueous HCl (2 M, 20.00 mL, 40 mmol) and was stirred at rt for 3 h. The reaction was then diluted with water and extracted with EtOAc. The combined organic layers were treated with brine, dried over $Na_2SO_4$, and the solvent was removed under reduced pressure. The residue was purified by column chromatography to give 2-[2-acetyl-6-(difluoromethyl)phenyl]acetonitrile (0.76 g, 89% yield over two steps). $^1$H NMR (400 MHz, $CDCl_3$) δ ppm 7.95 (d, J=8.0 Hz, 1H), 7.72 (d, J=8.0 Hz, 1H), 7.59 (t, J=8.0 Hz, 1H), 6.87 (t, J=54.4 Hz, 1H), 4.20 (s, 2H), 2.70 (s, 3H).

Step 5

To a mixture of 2-[2-acetyl-6-(difluoromethyl)phenyl] acetonitrile (500 mg, 2.39 mmol) and (R)-2-methylpropane-2-sulfinamide (579 mg, 4.78 mmol) in THF (5 mL) was added $Ti(OEt)_4$ (1.98 mL, 9.56 mmol). The mixture was stirred at 70° C. for 10 h. The reaction mixture was quenched by the addition of water, filtered, and extracted with EtOAc. The combined organic phases were treated with brine, dried over $Na_2SO_4$, and the solvent was removed under reduced pressure. The crude residue was purified by column chromatography to give (R)—N-(1-(2-(cyanomethyl)-3-(difluoromethyl)phenyl)ethylidene)-2-methylpropane-2-sulfinamide (700 mg, 94% yield). LCMS (ESI): m/z: [M+H] calculated for $C_{15}H_{19}F_2N_2OS$: 313.1; found: 313.1.

Step 6

To a solution of (R)—N-(1-(2-(cyanomethyl)-3-(difluoromethyl)phenyl)ethylidene)-2-methylpropane-2-sulfinamide (700 mg, 2.24 mmol) and MeOH (91 μL, 2.24 mmol) in THF (7 mL) was added LiBH$_4$ (73 mg, 3.36 mmol). The mixture was stirred at 0° C. for 2 h and then poured into water and extracted with EtOAc. The combined organic phases were treated with brine, dried over Na$_2$SO$_4$, and the solvent was removed under reduced pressure. The crude residue was purified by column chromatography on silica gel followed by prep-HPLC to give (R)—N—((R)-1-(2-(cyanomethyl)-3-(difluoromethyl)phenyl)ethyl)-2-methylpropane-2-sulfinamide (350 mg, 50% yield). LCMS (ESI): m/z: [M+H] calculated for C$_{15}$H$_2$F$_2$N$_2$OS: 315.1; found: 315.1.

Step 7

To a solution of (R)—N—((R)-1-(2-(cyanomethyl)-3-(difluoromethyl)phenyl)ethyl)-2-methylpropane-2-sulfinamide (350 mg, 1.11 mmol) in MeOH (3.5 mL) was added HCl in MeOH (4 M, 557 μL, 2.23 mmol). The mixture was stirred at rt for 1 h before a solution of NaOH in MeOH was added until pH ~8 and the solvent was removed under reduced pressure. The residue was diluted in a mixture of MeOH/DCM, solids were filtered off and the solvent was removed under reduced pressure to give 2-[2-[(1R)-1-aminoethyl]-6-(difluoromethyl)phenyl]acetonitrile (0.30 g, crude). LCMS (ESI): m/z: [M+H] calculated for C$_1$H$_{13}$F$_2$N$_2$: 211.1; found: 211.2.

Step 8

To a solution of 2-[2-[(1R)-1-aminoethyl]-6-(difluoromethyl)phenyl]acetonitrile (150 mg, crude) in n-BuOH (1.5 mL) was added 6-bromo-4-chloro-8-methyl-pyrido[2,3-d]pyrimidin-7-one (196 mg, 714 μmol) and DIEA (621 μL, 3.57 mmol). The reaction mixture was stirred at 80° C. for 2 h and then poured into water, extracted with EtOAc, washed with brine, dried over Na$_2$SO$_4$, and the solvent was removed under reduced pressure. The crude residue was triturated with EtOAc to give 2-[2-[(1R)-1-[(6-bromo-8-methyl-7-oxo-pyrido[2,3-d]pyrimidin-4-yl)amino]ethyl]-6-(difluoromethyl)phenyl]acetonitrile (70 mg, 28% yield over two steps). LCMS (ESI): m/z: [M+H] calculated for C$_{19}$H$_{17}$BrF$_2$N$_5$O: 448.1; found: 448.1.

Step 9

To a mixture of 2-[2-[(1R)-1-[(6-bromo-8-methyl-7-oxo-pyrido[2,3-d]pyrimidin-4-yl)amino] ethyl]-6-(difluoromethyl)phenyl]acetonitrile (60 mg, 134 μmol) and 4-(4,4,5,5-tetramethyl-1,3,2-dioxaborolan-2-yl)-3,6-dihydro-2H-thiopyran 1,1-dioxide (69 mg, 268 μmol) in dioxane (2 mL) and H$_2$O (0.4 mL) were added Na$_2$CO$_3$ (28 mg, 268 μmol) and Pd(PPh$_3$)$_2$Cl$_2$ (9 mg, 13 μmol). The reaction was stirred under N$_2$ at 100° C. for 5 h. After cooling to rt the mixture was poured into water, extracted with EtOAc, washed with brine, dried over Na$_2$SO$_4$, and the solvent was removed under reduced pressure. The crude residue was purified by prep-HPLC to give 2-[2-(difluoromethyl)-6-[(1R)-1-[[6-(1,1-dioxo-3,6-dihydro-2H-thiopyran-4-yl)-8-methyl-7-oxo-pyrido[2,3-d]pyrimidin-4-yl]amino]ethyl]phenyl]acetonitrile formic acid salt (15 mg, 22% yield). LCMS (ESI): m/z: [M+H] calculated for C$_{24}$H$_{24}$F$_2$N$_5$O$_3$S: 500.2; found: 500.3; $^1$H NMR (400 MHz, DMSO-d$_6$) δ ppm 8.64 (s, 1H), 7.39-7.27 (m, 2H), 7.15 (s, 1H), 6.99 (s, 1H), 6.04 (t, J=54.8 Hz, 1H), 5.89-5.50 (m, 1H), 4.51-4.46 (m, 1H), 3.78-3.65 (m, 2H), 3.61 (s, 3H), 3.31-3.25 (m, 2H), 3.11-3.10 (m, 2H), 2.37-2.06 (m, 2H), 1.68-1.23 (m, 3H).

Example 64: Synthesis of 4-(((R)-1-(3-(difluoromethyl)-2-fluorophenyl)ethyl)amino)-8-methyl-6-((1R,4r)-1-(methylimino)-1-oxidohexahydro-1λ$^6$-thiopyran-4-yl)pyrido[2,3-d]pyrimidin-7(8H)-one

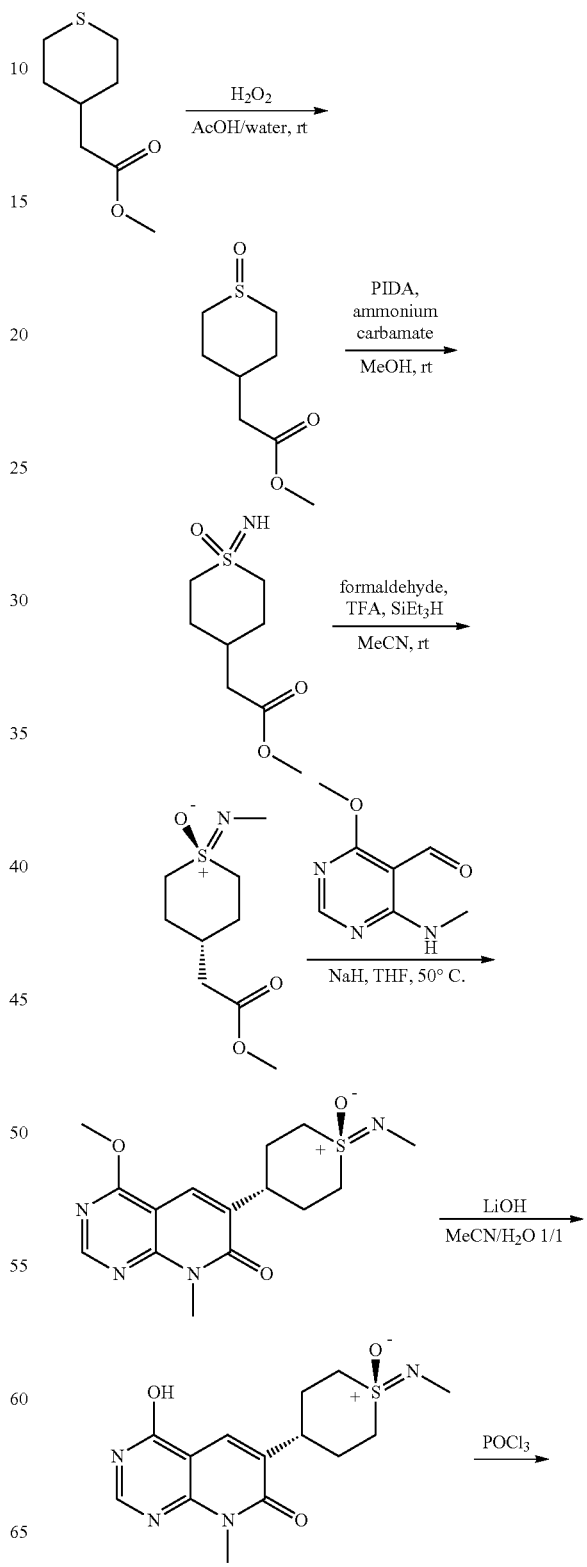

-continued

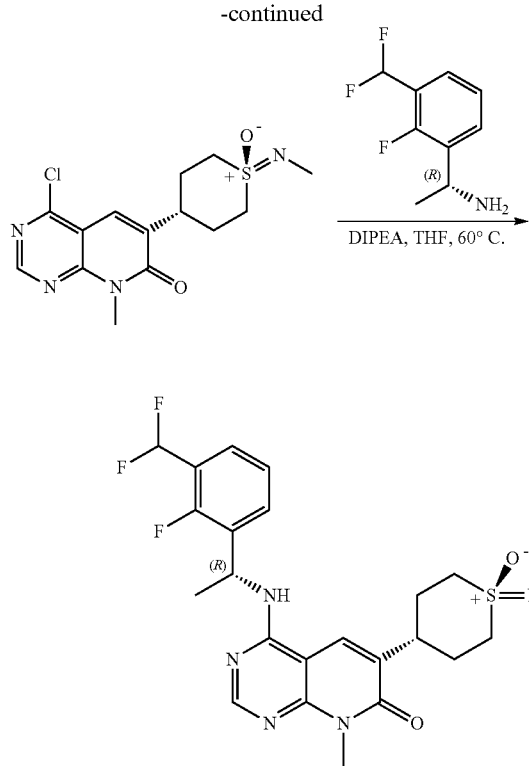

Step 1
Methyl 2-(tetrahydro-2H-thiopyran-4-yl)acetate (20.0 g, 115 mmol) was dissolved in AcOH (125 mL). Aqueous hydrogen peroxide (35 wt %, 13.8 mL, 161 mmol) was added and the mixture was stirred for 1 h. The mixture was diluted with EtOAc and water and the pH was adjusted to ~8 using NaHCO$_3$. Any remaining peroxide was quenched with excess aq. sat. Na$_2$SO$_3$. The aqueous layer was saturated with NaCl and extracted with EtOAc. The combined organic phases were dried over Na$_2$SO$_4$ and the solvent was removed under reduced pressure to afford methyl 2-(1-oxidotetrahydro-2H-thiopyran-4-yl)acetate (13 g, crude). $^1$H NMR (300 MHz, CDCl3) δ ppm 3.67 (s, 6H), 3.38-3.27 (d, 2H), 3.05-2.98 (d, 2H), 2.78-2.68 (t, 2H), 2.55-2.40 (t, 2H), 2.29 (d, 2H), 2.25 (d, 2H), 2.20-2.08 (m, 4H), 2.05-1.95 (m, 2H), 1.80-1.70 (d, 2H), 1.54-1.39 (q, 2H).

Step 2
Methyl 2-(1-oxidotetrahydro-2H-thiopyran-4-yl)acetate (10.70 g, 56.24 mmol), iodobenzene diacetate (39.85 g, 123.7 mmol) and ammonium carbamate (17.56 g, 225.0 mmol) were dissolved in methanol (80 mL) and the reaction was stirred overnight at rt. Any solids were removed by filtration and the filtrate was washed with heptane. The solvent as removed under reduced pressure and the crude product was triturated with MeCN to give 2-(1-imino-1-oxidohexahydro-1λ$^6$-thiopyran-4-yl)acetic acid (11.54 g, crude). $^1$H NMR (300 MHz, DMSO-d6) δ ppm 8.19 (s, 2H), 3.60 (s, 6H), 3.10-2.88 (m, 8H), 2.34 (d, 2H), 2.28 (d, 2H), 2.05-2.00 (m, 2H), 1.95-1.85 (m, 4H), 1.72-1.58 (m, 4H).

Step 3
To a solution of methyl 2-(1-imino-1-oxidohexahydro-1λ$^6$-thiopyran-4-yl)acetate (11.54 g, 56.20 mmol) in MeCN (200 mL) was added formaldehyde in water (37 wt %, 16.85 mL, 224.8 mmol) and TFA (17.32 mL, 224.8 mmol). After 30 min at rt triethylsilane (35.9 mL, 224.8 mmol) was added and the mixture was stirred overnight. The solvent volume was reduced under reduced pressure until 2 phases separated upon which 200 mL aq. sat NaHCO$_3$ and 250 mL EtOAc were added. The aqueous phase was extracted with EtOAc and the combined organic phases were dried over Na$_2$SO$_4$, and the solvent was removed under reduced pressure. The crude residue was dissolved in 200 mL methanol and washed with heptane. The solvent was removed under reduced pressure and the crude residue was purified by flash column chromatography to give methyl 2-((1r,4r)-1-(methylimino)-1-oxidohexahydro-1λ$^6$-thiopyran-4-yl)acetate (3.8 g, 31% yield, stereochemistry assigned arbitrarily) and methyl 2-((1s,4s)-1-(methylimino)-1-oxidohexahydro-1λ$^6$-thiopyran-4-yl)acetate 3.1 g, 25% yield, stereochemistry assigned arbitrarily).

2-((1r,4r)-1-(methylimino)-1-oxidohexahydro-1λ$^6$-thiopyran-4-yl)acetate: $^1$H NMR (300 MHz, CDCl$_3$) δ ppm 3.58 (s, 3H), 3.15-3.02 (d, 2H), 2.98-2.85 (t, 2H), 2.60 (s, 3H), 2.34 (d, 2H), 2.05-1.95 (m, 1H), 1.98-1.85 (d, 2H), 1.68-1.53 (q, 2H).

2-((1s,4s)-1-(methylimino)-1-oxidohexahydro-1λ$^6$-thiopyran-4-yl)acetate: $^1$H NMR (300 MHz, CDCl$_3$) δ ppm 3.58 (s, 3H), 3.21-3.08 (d, 2H), 3.04-2.95 (t, 2H), 2.55 (s, 3H), 2.16 (d, 2H), 2.08-1.95 (m, 1H), 1.90-1.80 (d, 2H), 1.62-1.43 (q, 2H).

Step 4/5
NaH (60 wt %, 287 mg, 7.18 mmol) was added to a solution of 4-methoxy-6-(methylamino)pyrimidine-5-carbaldehyde (400 mg, 2.39 mmol) in THF (15 mL) at 0° C. under N$_2$. Methyl 2-((1r,4r)-1-(methylimino)-1-oxidohexahydro-1λ$^6$-thiopyran-4-yl)acetate (1.05 g, 4.79 mmol) was then added and the mixture was stirred at 50° C. for 8 h. After cooling to rt the solvent was removed under reduced pressure and the residue was dissolved in DCM. The organic phase was washed with H$_2$O and brine. Lithium hydroxide monohydrate (150 mg, 3.57 mmol) was added and the mixture was stirred at 50° C. for 8 h, cooled to rt and the solvent was partially removed under reduced pressure. HCl (5 N) was added until pH ~7. The precipitate was filtered off and dried under vacuum to give 4-methoxy-8-methyl-6-((1r,4r)-1-(methylimino)-1-oxidohexahydro-1λ$^6$-thiopyran-4-yl)pyrido[2,3-d]pyrimidin-7(8H)-one (210 mg, 41%). LCMS (ESI): m/z: [M+H] calculated for C$_{14}$H$_{19}$N$_4$O$_3$S: 323.1; found: 323.1.

Step 6
4-hydroxy-8-methyl-6-((1r,4r)-1-(methylimino)-1-oxidohexahydro-1λ$^6$-thiopyran-4-yl)pyrido[2,3-d]pyrimidin-7(8H)-one (210 mg, 0.99 mmol) was suspended in POCl$_3$ (4 mL). The suspension was stirred at 110° C. for 6 h. After cooling to rt excess POCl$_3$ was removed under reduced pressure and crude 4-chloro-8-methyl-6-((1r,4r)-1-(methylimino)-1-oxidohexahydro-1-thiopyran-4-yl)pyrido[2,3-d]pyrimidin-7(8H)-one was used directly in the next step assuming quantitative yield. LCMS (ESI): m/z: [M+H] calculated for C$_{14}$H$_8$N$_4$O$_3$S: 341.1; found: 341.4.

Step 7
4-chloro-8-methyl-6-((1r,4r)-1-(methylimino)-1-oxidohexahydro-1λ$^6$-thiopyran-4-yl)pyrido[2,3-d]pyrimidin-7(8H)-one (337 mg, 0.99 mmol) was suspended in THF (5 mL). DIPEA (660 mg, 5.11 mmol) was added and the mixture was stirred for 30 min at rt before (R)-1-(3-(difluoromethyl)-2-fluorophenyl)ethan-1-amine (322 mg, 1.70 mmol) was added. The reaction was stirred at 60° C. for 12 h. After cooling to rt and diluted with DCM the organic phase was washed with sat. aq. NH₄Cl, and brine. Sodium methoxide (362 mg, 6.70 mmol) was added and the reaction was stirred at rt overnight. After adding sat. aq NH₄Cl the mixture was extracted with DCM and the combined organic phases were dried over Na₂SO₄. The solvent was removed under reduced pressure and the crude residue was purified by prep-HPLC to give 6-((1R,4r)-1-(cyclopropylimino)-4-methoxy-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one (47.3 mg, 12% yield, sulfoximine stereochemistry assigned arbitrarily). LCMS (ESI): m/z: [M+H]calculated for $C_{23}H_{27}F_3N_5O_2S$: 494.2; found: 494.2; ¹ NMR (300 MHz, CDCl₃) δ 8.44 (s, 1H), 7.78 (s, 1H), 7.59 (t, 1H), 7.52 (t, 1H), 7.23 (t, 1H), 6.94 (t, 1H), 6.30 (d, 1H), 5.81 (p, 1H), 3.75 (s, 3H), 3.50-3.32 (m, 5H), 2.90 (s, 3H), 2.50 (q, 2H), 2.32 (d, 2H), 1.74 (d, 3H).

The following examples 64-1 to 64-3 shown in Table 20 were synthesized in the manner similar to Example 64.

TABLE 20

Examples 64-1 to 64-3

| Example # | Structure | Mass Found |
| --- | --- | --- |
| 64-1 | 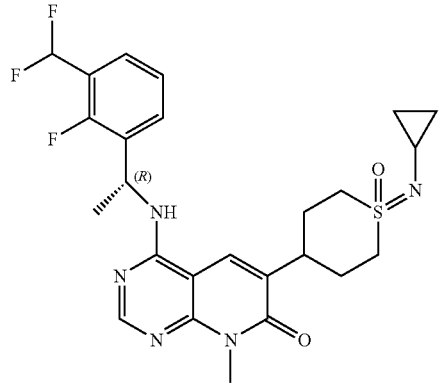 | 520.2 |
| 64-2 | 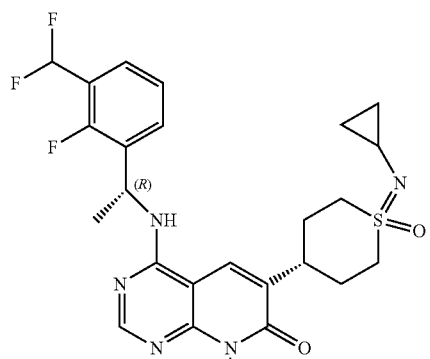 | 520.2 |
| 64-3 | 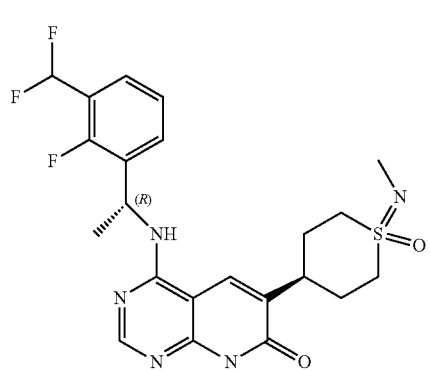 | 494.2 |

Examples 65 and 66: Synthesis of 4-(((R)-1-(3-(difluoromethyl)-2-fluorophenyl)ethyl)amino)-8-methyl-6-((S)-1-(oxetan-3-ylimino)-1-oxido-1,2,3,6-tetrahydro-1λ$^6$-thiopyran-4-yl)pyrido[2,3-d]pyrimidin-7(8H)-one and 4-(((R)-1-(3-(difluoromethyl)-2-fluorophenyl)ethyl)amino)-8-methyl-6-((R)-1-(oxetan-3-ylimino)-1-oxido-1,2,3,6-tetrahydro-1λ$^6$-thiopyran-4-yl)pyrido[2,3-d]pyrimidin-7(8H)-one

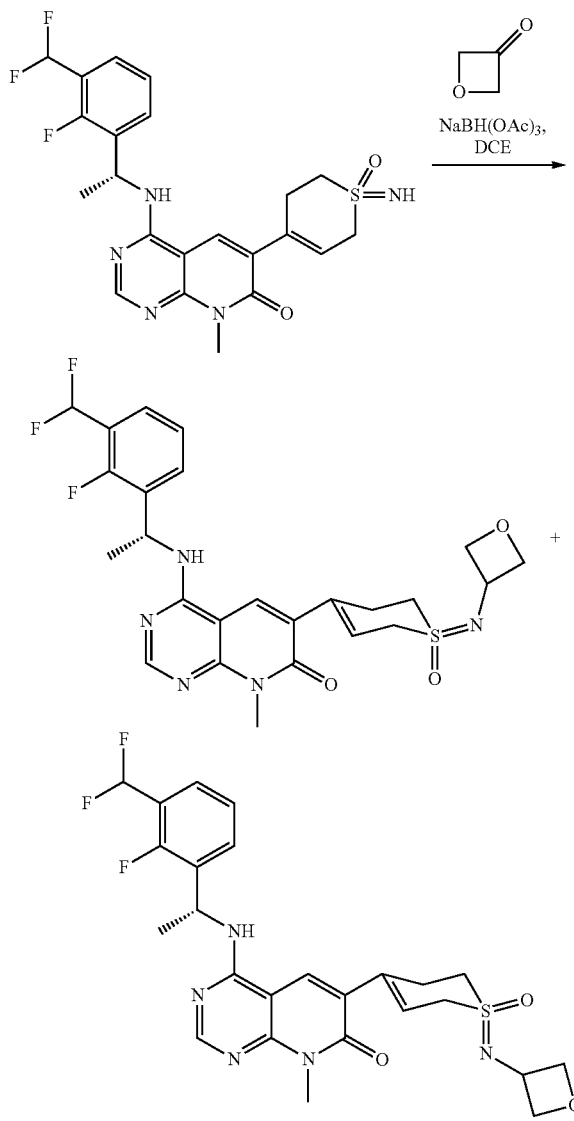

Step 1

To a solution of 4-[[(1R)-1-[3-(difluoromethyl)-2-fluoro-phenyl]ethyl]amino]-6-(1-imino-1-oxo-3,6-dihydro-2H-thiopyran-4-yl)-8-methyl-pyrido[2,3-d]pyrimidin-7-one (200 mg, 419 µmol) and oxetan-3-one (60 mg, 838 µmol) in DCE (4 mL) was added NaBH(OAc)$_3$ (266 mg, 1.26 mmol). The mixture was stirred at rt for 12 h before being diluted with H$_2$O and extracted with DCM. The combined organic layers were washed with brine, dried over Na$_2$SO$_4$, and the solvent was removed under reduced pressure. The crude residue was purified by prep-HPLC to give 4-(((R)-1-(3-(difluoromethyl)-2-fluorophenyl)ethyl)amino)-8-methyl-6-((S)-1-(oxetan-3-ylimino)-1-oxido-1,2,3,6-tetrahydro-1λ$^6$-thiopyran-4-yl)pyrido[2,3-d]pyrimidin-7(8H)-one (17 mg, 34% yield, sulfoximine stereochemistry assigned arbitrarily) and 4-(((R)-1-(3-(difluoromethyl)-2-fluorophenyl)ethyl)amino)-8-methyl-6-((R)-1-(oxetan-3-ylimino)-1-oxido-1,2,3,6-tetrahydro-1λ$^6$-thiopyran-4-yl)pyrido[2,3-d]pyrimidin-7(8H)-one (11 mg, 22% yield, sulfoximine stereochemistry assigned arbitrarily).

4-(((R)-1-(3-(difluoromethyl)-2-fluorophenyl)ethyl)amino)-8-methyl-6-((S)-1-(oxetan-3-ylimino)-1-oxido-1,2,3,6-tetrahydro-1λ$^6$-thiopyran-4-yl)pyrido[2,3-d]pyrimidin-7(8H)-one LCMS (ESI): m/z: [M+H] calculated for C$_{25}$H$_{27}$F$_3$N$_5$O$_3$S: 534.2; found 534.1; $^1$H NMR (400 MHz, ACETONITRILE-d$_3$) δ ppm 8.28 (s, 1H) 7.95 (s, 1H) 7.60 (t, J=7.2 Hz, 1H) 7.49 (t, J=7.0 Hz, 1H) 7.25 (t, J=7.6 Hz, 1H) 7.01 (t, J=54.6 Hz, 1H) 6.85 (d, J=7.4 Hz, 1H) 6.14-6.11 (m, 1H) 5.75-5.66 ((m, 1H) 4.76-4.72 (m, 2H) 4.69-4.62 (m, 1H) 4.49-4.45 (m, 2H) 3.87-3.49 (m, 2H) 3.61 (s, 3H) 3.24 (t, J=6.2 Hz, 2H) 3.12-2.98 (m, 2H) 1.62 (d, J=7.2 Hz, 3H).

4-(((R)-1-(3-(difluoromethyl)-2-fluorophenyl)ethyl)amino)-8-methyl-6-((R)-1-(oxetan-3-ylimino)-1-oxido-1,2,3,6-tetrahydro-1λ$^6$-thiopyran-4-yl)pyrido[2,3-d]pyrimidin-7(8H)-one LCMS (ESI): m/z: [M+H] calculated for C$_{25}$H$_{27}$F$_3$N5O$_3$S: 534.2; found 534.1; $^1$H NMR (400 MHz, ACETONITRILE-d$_3$) δ ppm 8.28 (s, 1H) 7.95 (s, 1H) 7.60 (t, J=7.2 Hz, 1H) 7.49 (t, J=7.0 Hz, 1H) 7.25 (t, J=7.6 Hz, 1H) 7.01 (t, J=54.8 Hz, 1H) 6.85 (d, J=6.8 Hz, 1H) 6.14-6.11 (m, 1H) 5.75-5.66 ((m, 1H) 4.76-4.72 (m, 2H) 4.68-4.62 (m, 1H) 4.49-4.45 (m, 2H) 3.87-3.74 (m, 2H) 3.61 (s, 3H) 3.26-3.22 (m, 2H) 3.06-3.03 (m, 2H) 1.62 (d, J=7.2 Hz, 3H).

Example 67: Synthesis of 4-[[(1R)-1-[3-(difluoromethyl)-2-fluoro-phenyl]ethyl]amino]-6-(1-imino-1-oxo-thian-4-yl)-8-methyl-pyrido[2,3-d]pyrimidin-7-one

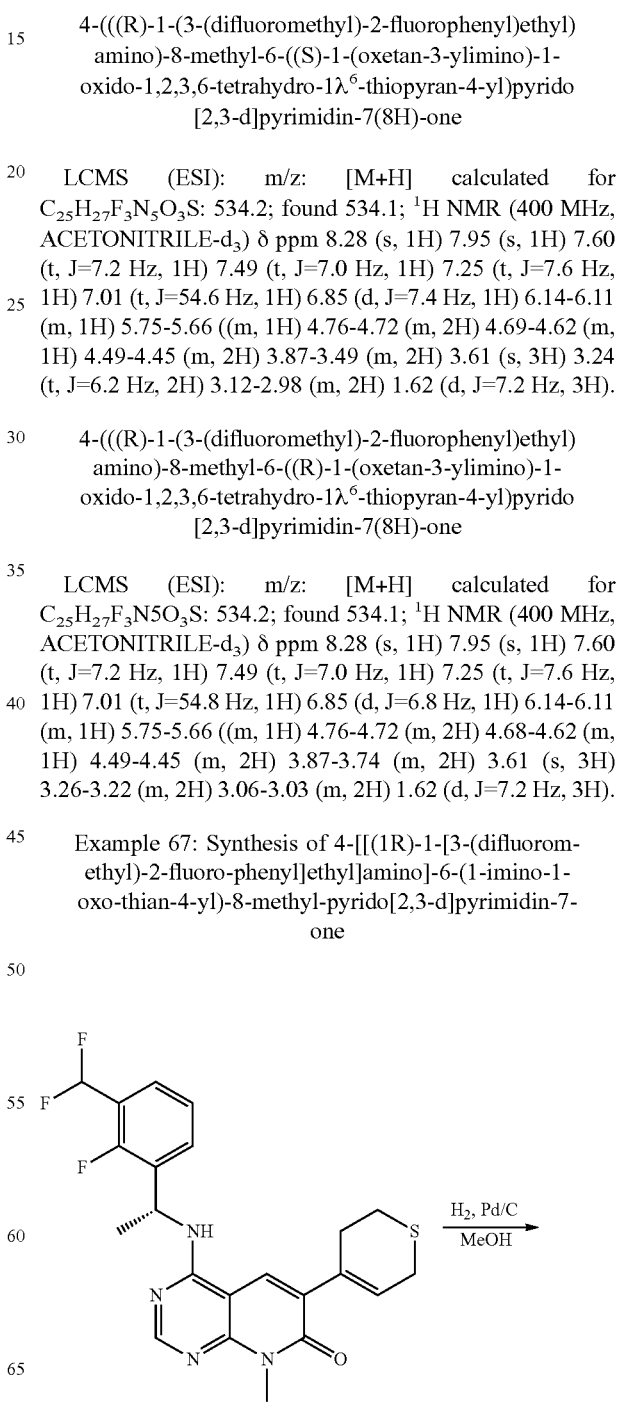

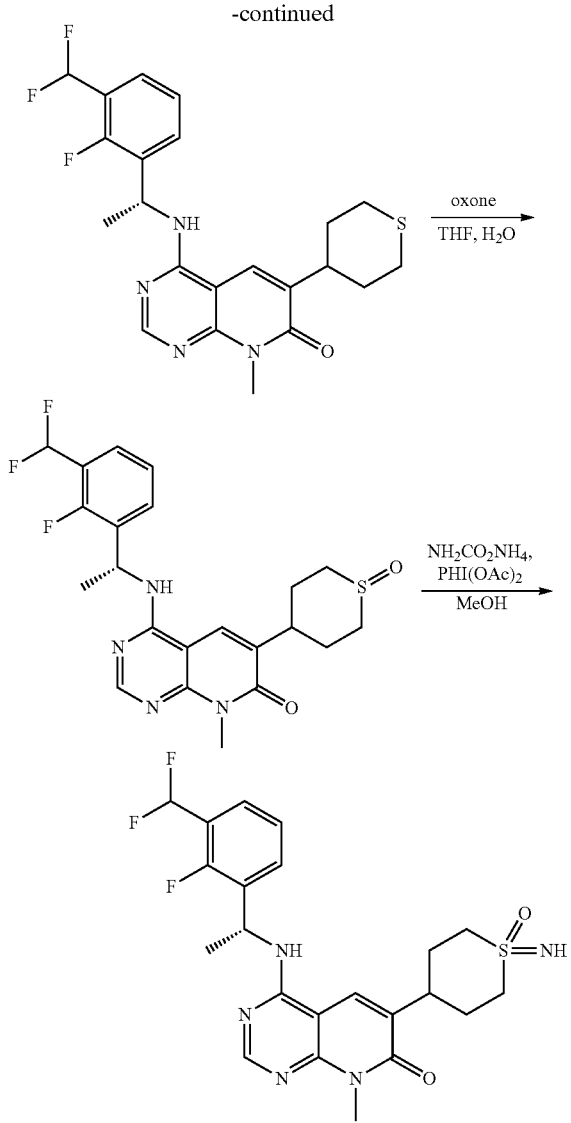

Step 1

To a solution of 4-[[(1R)-1-[3-(difluoromethyl)-2-fluoro-phenyl]ethyl]amino]-6-(3,6-dihydro-2H-thiopyran-4-yl)-8-methyl-pyrido[2,3-d]pyrimidin-7-one (1 g, 2.24 mmol) in MeOH (100 mL) was added Pd/C (1 g, 10 wt %) under Ar. The mixture was degassed under vacuum and purged with H₂ 3 times. The reaction was stirred under H₂ (50 psi) at 80° C. for 24 h. After cooling to rt the mixture was filtered and the solvent was removed under reduced pressure. The residue was purified by column chromatography to give 4-[[(1R)-1-[3-(difluoromethyl)-2-fluoro-phenyl]ethyl]amino]-8-methyl-6-tetrahydrothiopyran-4-yl-pyrido[2,3-d]pyrimidin-7-one (550 mg, 55% yield). ¹H NMR (400 MHz, METHANOL-$d_4$) δ ppm 8.28 (s, 1H) 8.17 (s, 1H) 7.56 (t, J=7.4 Hz, 1H) 7.47 (t, J=6.8 Hz, 1H) 7.22 (t, J=7.8 Hz, 1H) 7.00 (t, J=55.0 Hz, 1H) 5.77 (q, J=7.0 Hz, 1H) 3.69 (s, 3H) 3.00-2.86 (m, 3H) 2.70-2.66 (m, 2H) 2.20-2.16 (m, 2H) 1.90-1.79 (m, 2H) 1.66 (d, J=7.2 Hz, 3H).

Step 2

To a solution of 4-[[(1R)-1-[3-(difluoromethyl)-2-fluoro-phenyl]ethyl]amino]-8-methyl-6-tetrahydrothiopyran-4-yl-pyrido[2,3-d]pyrimidin-7-one (250 mg, 557 μmol) in THF (5 mL) and H₂O (1 mL) was added Oxone (175 mg, 284 μmol) at 0° C. The mixture was stirred at rt for 2 h before aqueous Na₂S₂O₃ was added (10 mL). After extraction with EtOAc the combined organic phases were washed with brine, dried over Na₂SO₄, and the solvent was removed under reduced pressure. The residue was purified by column chromatography to give 4-[[(1R)-1-[3-(difluoromethyl)-2-fluoro-phenyl]ethyl]amino]-8-methyl-6-(1-oxothian-4-yl) pyrido[2,3-d]pyrimidin-7-one (200 mg, 75% yield). ¹H NMR (400 MHz, METHANOL-$d_4$) δ ppm 8.29 (s, 1H) 8.24 (s, 1H) 7.57 (t, J=7.2 Hz, 1H) 7.47 (t, J=7.0 Hz, 1H) 7.00 (t, J=55.0 Hz, 1H) 5.78 (q, J=7.0 Hz, 1H) 3.69 (s, 3H) 3.22-3.14 (m, 3H) 2.96-2.88 (m, 2H) 2.48-2.35 (m, 2H) 1.99-1.95 (m, 2H) 1.66 (d, J=7.2 Hz, 3H).

Step 3

To a solution of 4-[[(1R)-1-[3-(difluoromethyl)-2-fluoro-phenyl]ethyl]amino]-8-methyl-6-(1-oxothian-4-yl)pyrido[2,3-d]pyrimidin-7-one (320 mg, 689 μmol) in MeOH (5 mL) was added (diacetoxyiodo)benzene (665 mg, 2.07 mmol) and ammonia carbamic acid (215 mg, 2.76 mmol). The mixture was stirred at rt for 4 h, the solvent was removed under reduced pressure and the crude residue was purified by prep-HPLC to give 4-[[(1R)-1-[3-(difluoromethyl)-2-fluoro-phenyl]ethyl]amino]-6-(1-imino-1-oxo-thian-4-yl)-8-methyl-pyrido[2,3-d]pyrimidin-7-one (206 mg, 62% yield). LCMS (ESI): m/z: [M+H] calculated for $C_{22}H_{25}F_3N_5O_2S$: 480.2; found 480.1; ¹H NMR (400 MHz, METHANOL-$d_4$) δ ppm 8.30 (s, 1H) 8.28 (s, 1H) 7.57 (t, J=7.4 Hz, 1H) 7.48 (t, J=7.0 Hz, 1H) 7.23 (t, J=7.8 Hz, 1H) 7.01 (t, J=54.8 Hz, 1H) 5.77 (q, J=7.0 Hz, 1H) 3.71 (s, 3H) 3.38-3.33 (m, 2H) 3.27-3.23 (m, 3H) 2.35-2.25 (m, 4H) 1.66 (d, J=7.2 Hz, 3H).

Examples 68 and 69: Synthesis of 6-((1R,4r)-1-(cyclopropylimino)-4-methoxy-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one and 6-((1S,4s)-1-(cyclopropylimino)-4-methoxy-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one

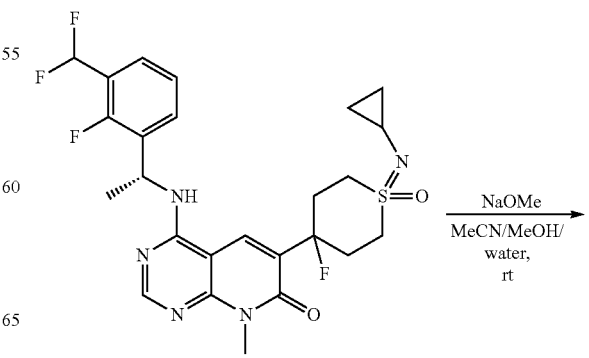

-continued

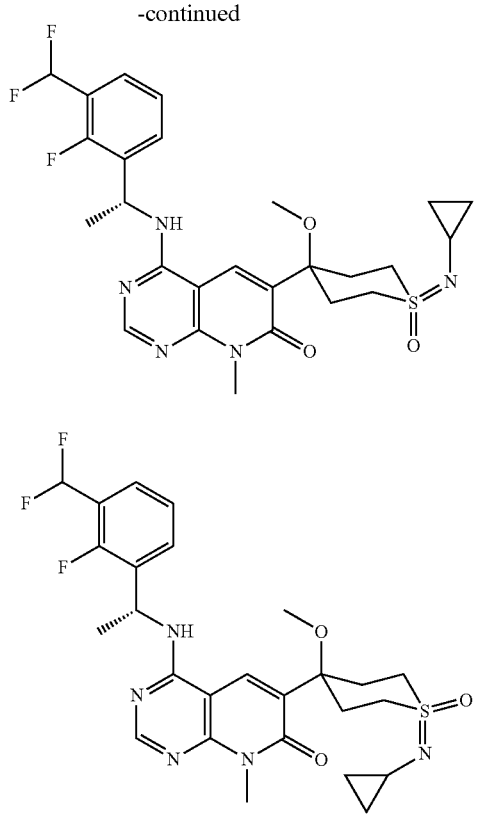

Step 1

To a solution of 6-[1-(cyclopropylimino)-4-fluoro-1-oxo-1λ⁶-thian-4-yl]-4-{[(1R)-1-[3-(difluoromethyl)-2-fluorophenyl]ethyl]amino}-8-methyl-7H,8H-pyrido[2,3-d]pyrimidin-7-one (400 mg, 0.74 mmol) in mixture of ACN (50 mL), MeOH (30 mL) and water (10 mL) sodium methoxide (362 mg, 6.7 mmol) was added. The reaction mixture was stirred at rt overnight and then quenched with sat. aq NH₄C₁. After extraction with DCM the combined organic layers were dried over Na₂SO₄ and the solvent was removed under reduced pressure. The crude material was purified by prep-HPLC to give 6-((1R,4r)-1-(cyclopropylimino)-4-methoxy-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one (47.3 mg, yield=12%, sulfoximine stereochemistry assigned arbitrarily) and 6-((1S,4s)-1-(cyclopropylimino)-4-methoxy-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one (60.2 mg, yield=15%, sulfoximine stereochemistry assigned arbitrarily).

6-((1R,4r)-1-(cyclopropylimino)-4-methoxy-1-oxido-hexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one: LCMS (ESI): m/z: [M+H] calculated for $C_{26}H_3F_3N_5O_3S$: 550.2; found: 550.2; ¹H NMR (300 MHz, DMSO-d₆) δ 8.63 (d, J=7.1 Hz, 1H), 8.35 (d, J=3.8 Hz, 2H), 7.66-7.57 (m, 1H), 7.51 (t, J=7.1 Hz, 1H), 7.30 (t, J=7.7 Hz, 1H), 7.24 (t, J=54.4 Hz, 1H), 5.80-5.69 (m, 1H), 3.56 (s, 3H), 3.30-3.11 (m, 7H), 2.82-2.67 (m, 2H), 2.43-2.22 (m, 3H), 1.59 (d, J=7.1 Hz, 3H), 0.55-0.32 (m, 4H).

6-((1S,4s)-1-(cyclopropylimino)-4-methoxy-1-oxidohexahydro-1λ⁶-thiopyran-4-yl)-4-(((R)-1-(3-(difluoromethyl)-2-fluorophenyl)ethyl)amino)-8-methylpyrido[2,3-d]pyrimidin-7(8H)-one LCMS (ESI): m/z: [M+H] calculated for $C_{26}H_{30}F_3N_5O_3S$: 550.2; found: 550.2; ¹H NMR (300 MHz, DMSO-d₆) δ 8.63 (d, J=7.2 Hz, 1H), 8.41-8.31 (m, 2H), 7.63 (t, J=7.6 Hz, 1H), 7.51 (t, J=7.0 Hz, 1H), 7.30 (t, J=7.7 Hz, 1H), 7.24 (t, J=54.4 Hz, 1H), 5.80-5.71 (m, 1H), 3.57 (s, 3H), 3.24-3.09 (m, 7H), 2.86-2.75 (m, 2H), 2.60-2.54 (m, 1H), 2.45-2.36 (m, 2H), 1.59 (d, J=7.1 Hz, 3H), 0.54-0.29 (m, 4H).

The following examples 68-1 to 68-3 shown in Table 21 were synthesized in the manner similar to Examples 68 and 69.

TABLE 21

Examples 68-1 to 68-3

| Example # | Structure | Mass Found |
|---|---|---|
| 68-1 | 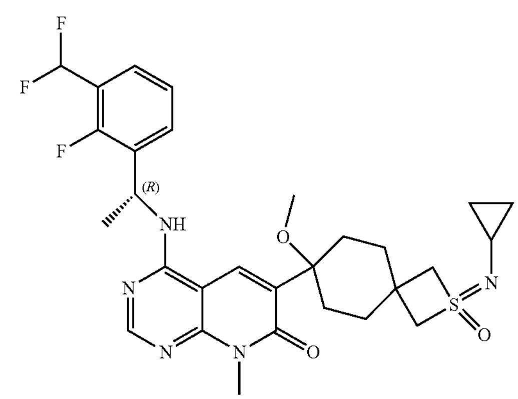 | 590.19 |

TABLE 21-continued
Examples 68-1 to 68-3
| Example # | Structure | Mass Found |
|---|---|---|
| 68-2 | 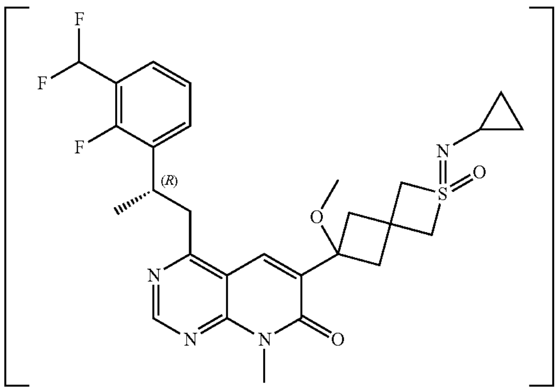 | 561.9 |
| 68-3 | 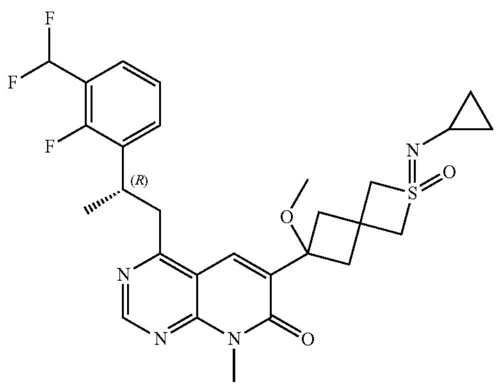 | 561.9 |
Example 70: Synthesis of N-[3-(4-{[(1R)-1-[3-(difluoromethyl)-2-fluorophenyl]ethyl]amino}-8-methyl-7-oxo-7H,8H-pyrido[2,3-d]pyrimidin-6-yl)bicyclo[1.1.1]pentan-1-yl]acetamide
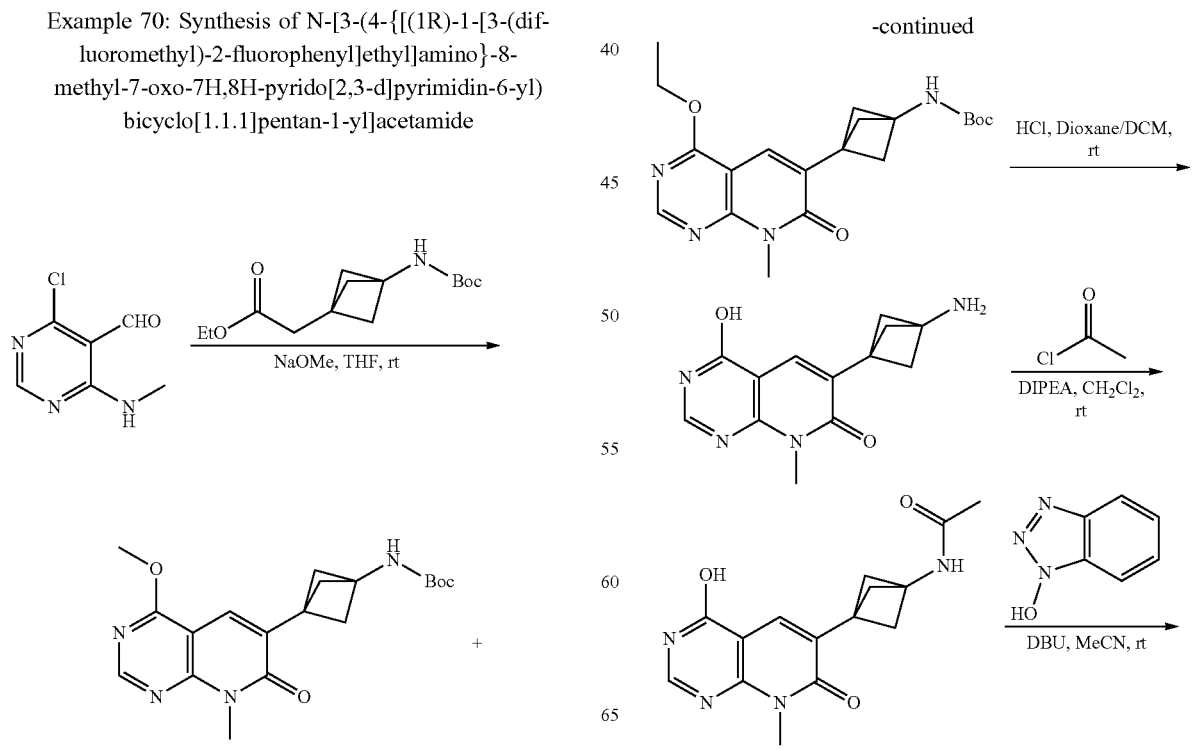

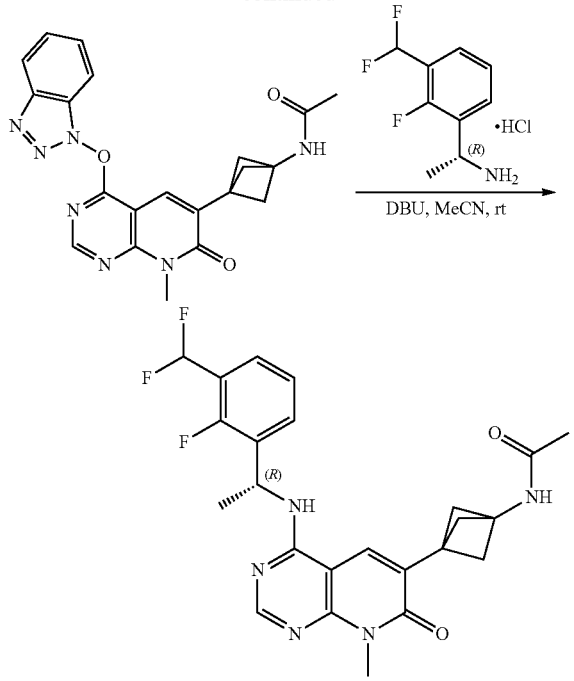

Step 1

To a solution of 4-chloro-6-(methylamino)pyrimidine-5-carbaldehyde (1.40 g, 8.17 mmol) in THF (55 mL), ethyl 2-(3-{[(tert-butoxy)carbonyl]amino}bicyclo[1.1.1]pentan-1-yl)acetate (2.20 g, 8.17 mmol, 1.0 eq) and sodium methoxide (880 mg, 16.3 mmol) were added. The reaction mixture was stirred for 18 hours at room temperature. The solvent was removed in vacuo and the residue was partitioned between water and EtOAc. The layers were separated and aqueous phase was extracted with EtOAc and DCM. The combined organic extracts were dried over anhydrous $Na_2SO_4$, filtered and concentrated. The crude residue was purified by flash column chromatography over silica gel to give a mixture of tert-butyl N-(3-{4-ethoxy-8-methyl-7-oxo-7H,8H-pyrido[2,3-d]pyrimidin-6-yl}bicyclo[1.1.1]pentan-1-yl)carbamate and tert-butyl N-(3-{4-methoxy-8-methyl-7-oxo-7H,8H-pyrido[2,3-d]pyrimidin-6-yl}bicyclo[1.1.1]pentan-1-yl)carbamate (combined 2.55 g, crude). UPLC (ESI) for product 1: m/z: [M+H] calculated for $C_{20}H_{26}N_4O_4$: 387.2; found 387.3; UPLC (ESI) for product 2: m/z: [M+H] calculated for $C_{19}H_{24}N_4O_4$: 373.2; found 373.3.

Step 2

To a mixture of tert-butyl N-(3-{4-methoxy-8-methyl-7-oxo-7H,8H-pyrido[2,3-d]pyrimidin-6-yl}bicyclo[1.1.1]pentan-1-yl)carbamate and tert-butyl N-(3-{4-ethoxy-8-methyl-7-oxo-7H,8H-pyrido[2,3-d]pyrimidin-6-yl}bicyclo[1.1.1]pentan-1-yl)carbamate (1.20 g, crude) in anhydrous DCM (66 mL), HCl (4.0 M in dioxane, 8.05 mL, 32.2 mmol) was added dropwise at 0° C. The reaction mixture was stirred at room temperature over 3 days. The mixture was concentrated under reduced pressure. The crude residue was triturated with diethyl ether, filtered, and washed with diethyl ether to give 6-{3-aminobicyclo[1.1.1]pentan-1-yl}-4-hydroxy-8-methyl-7H,8H-pyrido[2,3-d]pyrimidin-7-one hydrochloride (800 mg, crude). UPLC (ESI): m/z: [M+H] calculated for $C_{13}H_{14}N_4O_2$: 258.1; found 259.3.

Step 3

To a suspension of 6-{3-aminobicyclo[1.1.1]pentan-1-yl}-4-hydroxy-8-methyl-7H,8H-pyrido[2,3-d]pyrimidin-7-one hydrochloride (850 mg, crude) in anhydrous DCM (21.0 mL), DIPEA (1.51 mL, 8.65 mmol) was added. The reaction mixture was cooled to 0° C. and acetyl chloride (226 µL, 3.17 mmol) was added dropwise. The reaction mixture was warmed to room temperature and stirred for 1 hour. The mixture was then treated with sat. aq $NaHCO_3$ solution and extracted with DCM. The combined organic layers were dried over anhydrous $Na_2SO_4$, filtered and concentrated under reduced pressure. The crude product was purified by flash column chromatography to give N-(3-{4-hydroxy-8-methyl-7-oxo-7H,8H-pyrido[2,3-d]pyrimidin-6-yl}bicyclo[1.1.1]pentan-1-yl)acetamide (335 mg, 29% yield over 3 steps). UPLC (ESI): m/z: [M+H] calculated for $C_{15}H_{16}N_4O_3$: 301.1; found 301.3.

Step 4

To a solution of N-(3-{4-hydroxy-8-methyl-7-oxo-7H,8H-pyrido[2,3-d]pyrimidin-6-yl}bicyclo[1.1.1]pentan-1-yl)acetamide (390 mg, 1.3 mmol) and BOP (740 mg, 1.69 mmol) in acetonitrile (39.0 mL), DBU (291 µL, 1.95 mmol) was added. The reaction mixture was stirred for 1 hour at room temperature. The mixture was then concentrated under reduced pressure and the crude material was purified by flash column chromatography to give of N-{3-[4-(1H-1,2,3-benzotriazol-1-yloxy)-8-methyl-7-oxo-7H,8H-pyrido[2,3-d]pyrimidin-6-yl]bicyclo[1.1.1]pentan-1-yl}acetamide (360 mg, 66% yield). UPLC (ESI): m/z: [M+H] calculated for $C_{21}H_{19}N_7O_3$: 418.2; found 418.5.

Step 5

To a solution of (1R)-1-[3-(difluoromethyl)-2-fluorophenyl]ethan-1-amine hydrochloride (290 mg, 1.29 mmol) and DBU (387 µL, 2.59 mmol) in anhydrous acetonitrile (36.0 mL) was added N-{3-[4-(1H-1,2,3-benzotriazol-1-yloxy)-8-methyl-7-oxo-7H,8H-pyrido[2,3-d]pyrimidin-6-yl]bicyclo[1.1.1]pentan-1-yl}acetamide (360 mg, 860 µmol). The reaction mixture was stirred for 18 hours at room temperature. The mixture was concentrated under reduced pressure then the residue was suspended in water and extracted with DCM. The combined organic layers were washed with sat. aq. $NaHCO_3$ solution, $NaHSO_4$ solution, brine, then were dried over anhydrous $Na_2SO_4$ and concentrated under reduced pressure. The crude residue was purified by flash column chromatography to give 73 mg (Y=18%) of N-[3-(4-{[(1R)-1-[3-(difluoromethyl)-2-fluorophenyl]ethyl]amino}-8-methyl-7-oxo-7H,8H-pyrido[2,3-d]pyrimidin-6-yl)bicyclo[1.1.1]pentan-1-yl]acetamide (60 mg, 15% yield). UPLC (ESI): m/z: [M+H] calculated for $C_{24}H_{24}F_3N_5O_2$: 472.2; found 472.7; $^1$H NMR (400 MHz, DMSO-$d_6$) δ ppm 8.48 (s, 1H), 8.40-8.28 (m, 2H), 8.19 (s, 1H), 7.62 (t, J=7.5 Hz, 1H), 7.51 (t, J=7.1 Hz, 1H), 7.32 (t, J=7.7 Hz, 1H), 7.24 (t, J=55.0 Hz, 1H), 5.79-5.65 (m, 1H), 3.54 (s, 3H), 2.33 (d, J=1.8 Hz, 6H), 1.80 (s, 3H), 1.59 (d, J=7.0 Hz, 3H).

Example 71: Synthesis of N-[3-(4-{[(1R)-1-[3-(difluoromethyl)-2-fluorophenyl]ethyl]amino}-8-methyl-7-oxo-7H,8H-pyrido[2,3-d]pyrimidin-6-yl)bicyclo[1.1.1]pentan-1-yl]acetamide

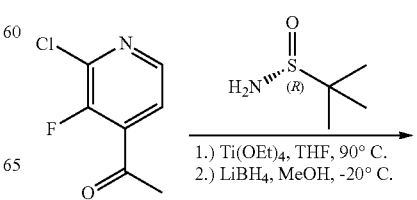

731
-continued

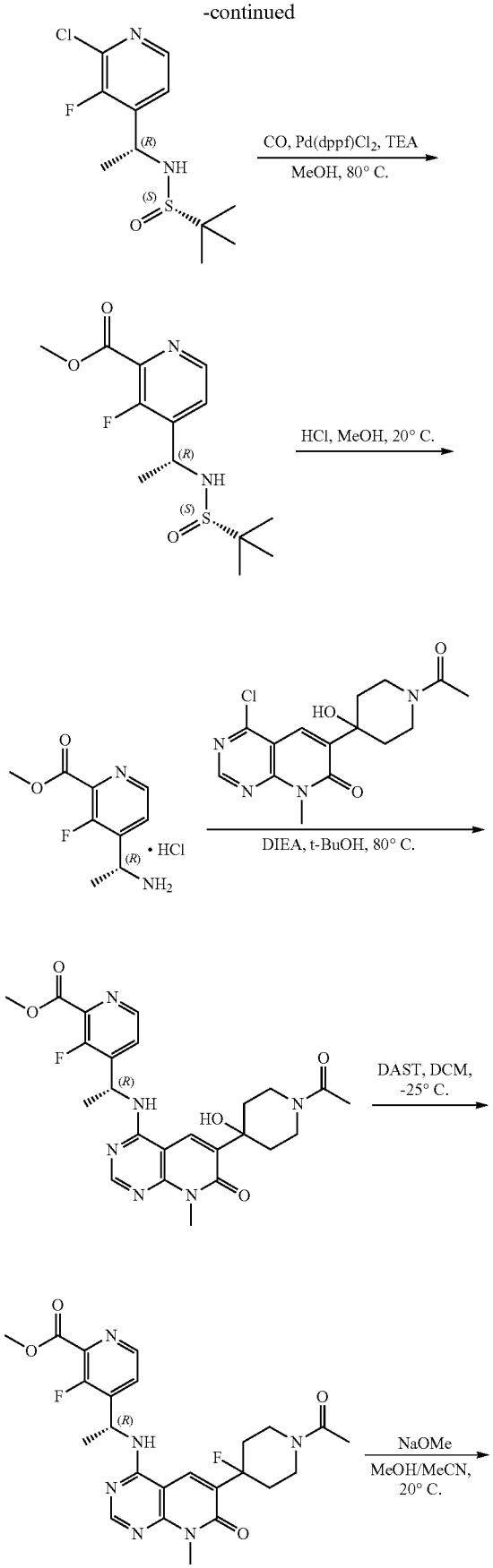

732
-continued

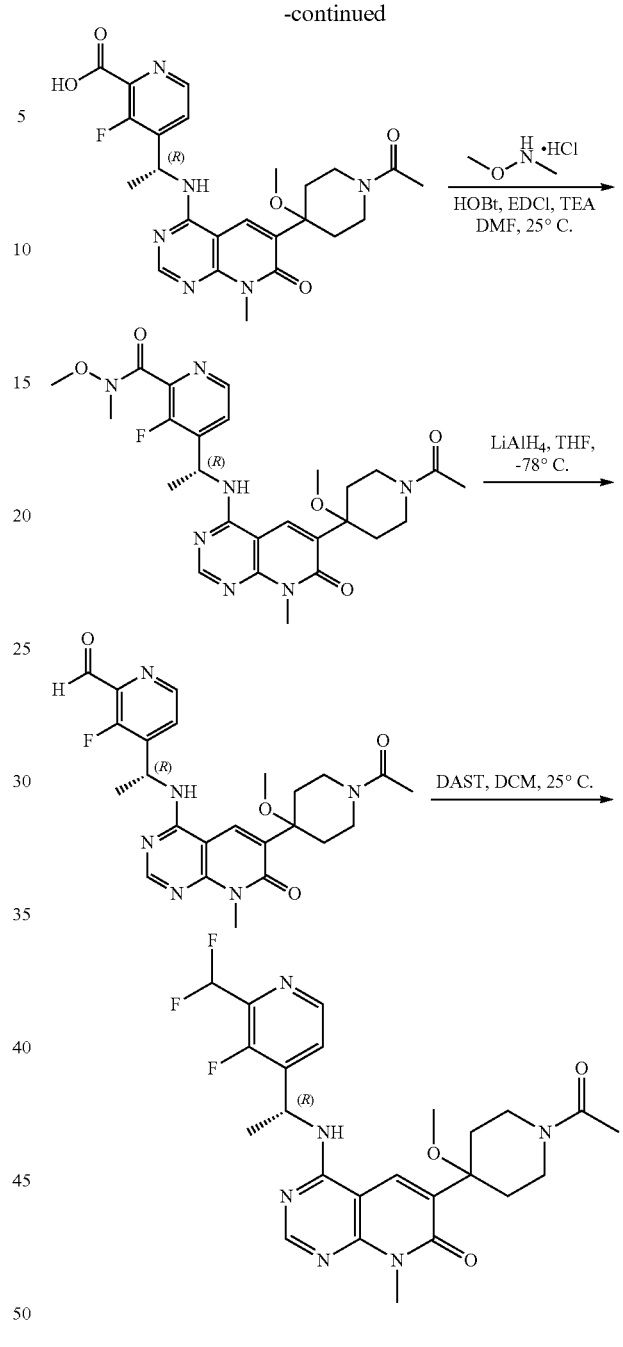

Step 1

To a solution of 1-(2-chloro-3-fluoro-4-pyridyl)ethanone (20.0 g, 115 mmol) and (R)-2-methylpropane-2-sulfinamide (27.9 g, 230 mmol) in THF (200 mL) was added Ti(OEt)$_4$ (95.6 mL, 461 mmol) at 25° C. The reaction mixture was stirred at 90° C. for 8 h. After the mixture was cooled to −20° C., LiBH$_4$ (2.76 g, 127 mmol) and MeOH (4.66 mL, 115 mmol) were added and the reaction mixture was stirred at −20° C. for 30 min. The reaction was quenched by H$_2$O then was extracted with ethyl acetate, washed with brine, dried over Na$_2$SO$_4$, and concentrated under reduced pressure. The residue was purified by prep-HPLC to give N-[(1R)-1-(2-chloro-3-fluoro-4-pyridyl)ethyl]-2-methyl-propane-2-sulfinamide (10 g, 31% yield). LCMS (ESI): m/z: [M+H] calculated for C$_{11}$H$_{17}$ClFN$_2$OS: 279.1; found: 278.9.

Step 2

To a solution of N-[(1R)-1-(2-chloro-3-fluoro-4-pyridyl)ethyl]-2-methyl-propane-2-sulfinamide (10.0 g, 35.9 mmol) in MeOH (200 mL) were added TEA (15.0 mL, 108 mmol) and Pd(dppf)Cl$_2$.CH$_2$Cl$_2$(2.93 g, 3.59 mmol). The mixture was degassed and purged with CO for then was stirred at 80° C. for 2 h under an atmosphere of CO (50 psi). The mixture was filtered and concentrated under reduced pressure. The residue was then purified by column chromatography to give methyl 4-[(1R)-1-(1,1-dimethylethylsulfinylamino)ethyl]-3-fluoro-pyridine-2-carboxylate (9.0 g, 83% yield). LCMS (ESI): m/z: [M+H] calculated for C$_{13}$H$_{2}$FN$_2$O$_3$S: 303.1; found: 302.9.

Step 3

To a solution of methyl 4-[(1R)-1-(1,1-dimethylethylsulfinylamino)ethyl]-3-fluoro-pyridine-2-carboxylate (5.00 g, 16.5 mmol) in MeOH (50 mL) was added a solution of HCl (4 M in MeOH, 12.40 mL). The reaction mixture was stirred at 20° C. for 2 h. The mixture was concentrated under reduced pressure to give methyl 4-[(1R)-1-aminoethyl]-3-fluoro-pyridine-2-carboxylate (3.0 g, crude). LCMS (ESI): m/z: [M+H] calculated for C$_9$H$_{12}$FN$_2$O$_2$: 199.1; found: 198.9.

Step 4

To a solution of 6-(1-acetyl-4-hydroxy-4-piperidyl)-4-chloro-8-methyl-pyrido[2,3-d]pyrimidin-7-one (2.00 g, 5.94 mmol) in t-BuOH (20 mL) was added DIEA (4.14 mL, 23.8 mmol) and methyl 4-[(1R)-1-aminoethyl]-3-fluoro-pyridine-2-carboxylate (1.41 g, 7.13 mmol). The reaction mixture was stirred at 80° C. for 12 h. The reaction mixture was quenched with H$_2$O and extracted with ethyl acetate. The combined organic extracts were washed with brine, dried over anhydrous Na$_2$SO$_4$, filtered, and concentrated under reduced pressure. The residue was purified by column chromatography to give methyl 4-[(1R)-1-[[6-(1-acetyl-4-hydroxy-4-piperidyl)-8-methyl-7-oxo-pyrido[2,3-d]pyrimidin-4-yl]amino]ethyl]-3-fluoro-pyridine-2-carboxylate (2.0 g, 68% yield). LCMS (ESI): m/z: [M+H] calculated for C$_{24}$H$_{27}$FN$_6$O$_5$: 499.2; found: 499.2.

Step 5

To a solution of methyl 4-[(1R)-1-[[6-(1-acetyl-4-hydroxy-4-piperidyl)-8-methyl-7-oxo-pyrido [2,3-d]pyrimidin-4-yl]amino]ethyl]-3-fluoro-pyridine-2-carboxylate (1.00 g, 2.01 mmol) in DCM (10 mL) was added DAST (530 µL, 4.01 mmol) at −25° C. The reaction mixture was stirred at −25° C. for 2 h. The mixture was then treated with TEA to pH=8, diluted with H$_2$O, and extracted with DCM. The combined organic extracts were washed with brine, dried with anhydrous Na$_2$SO$_4$, filtered, and concentrated under reduced pressure to give methyl 4-[(1R)-1-[[6-(1-acetyl-4-fluoro-4-piperidyl)-8-methyl-7-oxo-pyrido[2,3-d]pyrimidin-4-yl]amino]ethyl]-3-fluoro-pyridine-2-carboxylate (1.2 g, crude). LCMS (ESI): m/z: [M+H] calculated for C$_{24}$H$_{27}$F$_2$N$_6$O$_4$: 501.2; found: 501.1.

Step 6

To a solution of methyl 4-[(1R)-1-[[6-(1-acetyl-4-fluoro-4-piperidyl)-8-methyl-7-oxo-pyrido [2,3-d]pyrimidin-4-yl]amino]ethyl]-3-fluoro-pyridine-2-carboxylate (1.00 g, 2.00 mmol) in MeCN (10 mL) and MeOH (6 mL) was added NaOMe (324 mg, 5.99 mmol). The reaction mixture was stirred at 20° C. for 12 h. The mixture was then quenched by H$_2$O and extracted with ethyl acetate. The combined organic extracts were treated with brine, dried with anhydrous Na$_2$SO$_4$, and concentrated under reduced pressure. The residue was purified by prep-HPLC to give 4-[(1R)-1-[[6-(1-acetyl-4-methoxy-4-piperidyl)-8-methyl-7-oxo-pyrido[2,3-d]pyrimidin-4-yl]amino]ethyl]-3-fluoro-pyridine-2-carboxylic acid (250 mg, 25% yield). LCMS (ESI): m/z: [M+H] calculated for C$_{24}$H$_{28}$FN$_6$O$_5$: 499.2; found: 499.1.

Step 7

To a solution of 4-[(1R)-1-[[6-(1-acetyl-4-methoxy-4-piperidyl)-8-methyl-7-oxo-pyrido [2,3-d]pyrimidin-4-yl]amino]ethyl]-3-fluoro-pyridine-2-carboxylic acid (250 mg, 502 µmol) in DMF (3 mL) were added N-methoxymethanamine hydrochloride (53.8 mg, 552 µmol), HOBt (81.3 mg, 602 µmol), TEA (209 µL, 1.50 mmol) and EDCI (115 mg, 602 µmol) at 0° C. The reaction mixture was stirred at 25° C. for 16 h. The mixture was diluted with H$_2$O and extracted with ethyl acetate. The combined organic extracts were treated with brine, dried over anhydrous Na$_2$SO$_4$, filtered, and concentrated under reduced pressure. The residue was purified by prep-TLC to give 4-[(1R)-1-[[6-(1-acetyl-4-methoxy-4-piperidyl)-8-methyl-7-oxo-pyrido[2,3-d]pyrimidin-4-yl]amino]ethyl]-3-fluoro-N-methoxy-N-methyl-pyridine-2-carboxamide (150 mg, 55% yield). LCMS (ESI): m/z: [M+H] calculated for C$_{26}$H$_{33}$FN$_7$O$_5$: 542.2; found: 542.2.

Step 8

To a solution of 4-[(1R)-1-[[6-(1-acetyl-4-methoxy-4-piperidyl)-8-methyl-7-oxo-pyrido[2,3-d]pyrimidin-4-yl]amino]ethyl]-3-fluoro-N-methoxy-N-methyl-pyridine-2-carboxamide (50.0 mg, 92.3 µmol) in THF (1 mL) was added LiAlH$_4$ (2.5 M in THF, 18.46 µL) at −78° C. The mixture was stirred at −78° C. for 30 min. The reaction was diluted with H$_2$O and extracted with ethyl acetate. The combined organic extracts were treated with brine, dried over anhydrous Na$_2$SO$_4$, filtered, and concentrated under reduced pressure. The residue was purified by prep-TLC to give 4-[(1R)-1-[[6-(1-acetyl-4-methoxy-4-piperidyl)-8-methyl-7-oxo-pyrido[2,3-d]pyrimidin-4-yl]amino]ethyl]-3-fluoro-pyridine-2-carbaldehyde (60 mg, crude). LCMS (ESI): m/z: [M+H] calculated for C$_{24}$H$_{28}$FN$_6$O$_4$: 483.2; found: 483.1.

Step 9

To a solution of 4-[(1R)-1-[[6-(1-acetyl-4-methoxy-4-piperidyl)-8-methyl-7-oxo-pyrido [2,3-d]pyrimidin-4-yl]amino]ethyl]-3-fluoro-pyridine-2-carbaldehyde (30.0 mg, 62.2 µmol) in DCM (0.5 mL) was added DAST (16.4 µL, 124 µmol) at 0° C. The reaction mixture was stirred at 25° C. for 1 h. The reaction was quenched by the addition of TEA then was diluted with H$_2$O and extracted with DCM. The combined organic extracts were treated with brine, dried over anhydrous Na$_2$SO$_4$, filtered, and concentrated under reduced pressure. The residue was purified by prep-HPLC to give 6-(1-acetyl-4-methoxy-4-piperidyl)-4-[[(1R)-1-[2-(difluoromethyl)-3-fluoro-4-pyridyl]ethyl]amino]-8-methyl-pyrido-[2,3-d]pyrimidin-7-one (6.0 mg, 19% yield). LCMS (ESI): m/z: [M+H] calculated for C$_{24}$H$_{28}$F$_3$N$_6$O$_3$: 505.2; found: 505.2; $^1$H NMR (400 MHz, DMSO-d$_6$) δ ppm 8.64 (br d, J=6.8 Hz, 1H), 8.45 (d, J=4.8 Hz, 1H), 8.33 (s, 2H), 7.64 (d, J=3.5 Hz, 1H), 7.17 (d, J=52.8 Hz, 1H), 5.69 (t, J=7.0 Hz, 1H), 4.38-4.28 (m, 1H), 3.77-3.67 (m, 1H), 3.55 (s, 3H), 3.42-3.33 (m, 1H), 3.13 (d, J=3.8 Hz, 3H), 2.90-2.70 (m, 1H), 2.31-1.97 (m, 7H), 1.61 (d, J=7.1 Hz, 3H).

Biological Examples

Potency Assay: Measurement of the Binding Affinity of Compounds of the Invention to SOS1 Using Surface Plasmon Resonance (SPR)

The purpose of the SPR assay was to measure the direct binding of compounds to SOS1 catalytic domain (residues 564-1049) immobilized on a sensor chip. Data was reported as equilibrium dissociation constant ($K_d$) values.

Using a GE Biacore 8K SPR instrument, avi-tagged SOS1 catalytic domain protein was immobilized to a level of approximately 6000 response units (RU) on a streptavidin-coated SPR sensor chip in assay buffer containing 0.01 M HEPES, 0.15 M NaCl and 0.05% v/v Surfactant P20. In assay buffer containing 2% DMSO, concentration series of test compounds were generated spanning 5 µM to 4.9 nM over ten 2-fold dilutions. For each test compound, a separate 0 µM sample was generated for use during subsequent double reference subtraction. Serially for each test compound, individual dilution samples were flowed over the immobilized SOS1 protein at a flow rate of 50 µL/minute to monitor the association with SOS1. Dissociation of bound test compound from the SOS1 protein was immediately monitored by flowing assay buffer over the sensor surface and monitoring the decrease in binding signal back to the baseline level seen in the absence of compound. This was repeated for all compound dilutions in each series. The binding level response for each test compound concentration was noted immediately prior to the end of the association phase, and a secondary plot generated showing binding response level versus test compound concentration generated for each compound dilution series. This data was fitted to a model describing reversible equilibrium 1:1 binding between test compound and SOS1, yielding an estimate of the $K_d$ value for the interaction.

SOS1 using Surface Plasmon Resonance (SPR) results are shown in the Table 22 below.

TABLE 22

| Example # | SOS1 SPR Equilibrium Kd (µM) |
|---|---|
| Example 1. | 0.0062 |
| Example 1-1. | 0.0591 |
| Example 1-2. | 0.0134 |
| Example 1-3. | 0.00786 |
| Example 1-4. | |
| Example 1-5. | 0.0163 |
| Example 1-6. | 0.0182 |
| Example 1-7. | 0.353 |
| Example 1-8. | 0.0200 |
| Example 1-9. | 0.074 |
| Example 1-10. | 0.0232 |
| Example 1-11. | 0.0546 |
| Example 1-12. | 0.0368 |
| Example 1-13. | 0.0138 |
| Example 1-14. | 0.019 |
| Example 1-15. | 0.00629 |
| Example 1-16. | 0.0282 |
| Example 1-17. | 0.0213 |
| Example 1-18. | 0.022 |
| Example 1-19. | 0.144 |
| Example 1-20. | 0.0559 |
| Example 1-21. | 0.137 |
| Example 1-22. | 0.0151 |
| Example 1-23. | 0.122 |
| Example 1-24. | 0.0749 |
| Example 1-25. | 0.101 |
| Example 1-26. | 0.0610 |
| Example 1-27. | 0.0486 |
| Example 1-28. | |
| Example 1-29. | 0.157 |
| Example 1-30. | 0.0201 |
| Example 1-31. | 0.0982 |
| Example 1-32. | |
| Example 1-33. | |
| Example 2. | 0.00736 |
| Example 2-1. | |
| Example 2-2. | |
| Example 2-3. | 0.0890 |
| Example 2-4. | 0.153 |
| Example 2-5. | 0.097 |
| Example 3. | 0.0218 |
| Example 4. | 0.00797 |
| Example 5. | |
| Example 6. | 0.0173 |
| Example 7. | 0.117 |
| Example 8. | |
| Example 8-1. | 0.0242 |
| Example 8-2. | 0.0644 |
| Example 8-3. | 0.0309 |
| Example 8-4. | 0.0294 |
| Example 8-5. | 0.0376 |
| Example 8-6. | |
| Example 8-7. | |
| Example 8-8. | 0.0620 |
| Example 8-9. | 0.120 |
| Example 8-10. | |
| Example 8-11. | |
| Example 8-12. | 0.0834 |
| Example 8-13. | 0.156 |
| Example 8-14. | 0.200 |
| Example 8-15. | 0.0904 |
| Example 8-16. | 0.136 |
| Example 8-17. | 0.796 |
| Example 9. | 0.000366 |
| Example 10. | |
| Example 11. | |
| Example 11-1. | 0.0813 |
| Example 11-2. | |
| Example 11-3. | |
| Example 11-4. | |
| Example 12. | 0.00794 |
| Example 13. | 0.0283 |
| Example 14. | |
| Example 15. | 0.168 |
| Example 16. | |
| Example 17. | |
| Example 18. | 0.016 |
| Example 19. | 0.0324 |
| Example 20. | |
| Example 20-1. | |
| Example 20-2. | |
| Example 20-3. | |
| Example 20-4. | |
| Example 21. | 0.0327 |
| Example 21-1. | 1.16 |
| Example 21-2. | 0.0854 |
| Example 21-3. | 0.330 |
| Example 21-4. | 0.272 |
| Example 21-5. | 0.115 |
| Example 21-6. | 0.118 |
| Example 21-7. | 0.0925 |
| Example 21-8. | 0.336 |
| Example 21-9. | 0.338 |
| Example 21-10. | 0.849 |
| Example 21-11. | 0.234 |
| Example 21-12. | 0.216 |
| Example 21-13. | |
| Example 21-14. | |
| Example 21-15. | |
| Example 22. | 0.0342 |
| Example 23. | 0.0198 |
| Example 23-1. | 0.0862 |
| Example 24. | |
| Example 25. | 0.0194 |
| Example 26. | 0.115 |
| Example 26-1. | 0.285 |
| Example 26-2. | 0.118 |
| Example 26-3. | 0.404 |
| Example 26-4. | 0.0732 |
| Example 26-5. | |
| Example 26-6. | |
| Example 26-7. | 0.0775 |
| Example 26-8. | |

TABLE 22-continued

| Example # | SOS1 SPR Equilibrium Kd (µM) |
|---|---|
| Example 26-9. | 0.178 |
| Example 26-10. | |
| Example 26-11. | 0.0978 |
| Example 26-12. | 0.158 |
| Example 26-13. | |
| Example 26-14. | |
| Example 26-15. | |
| Example 26-16. | |
| Example 26-17. | |
| Example 26-18. | 0.150 |
| Example 26-19. | 0.148 |
| Example 26-20. | 1.465 |
| Example 26-21. | 0.114 |
| Example 26-22. | 0.474 |
| Example 26-23. | |
| Example 26-24. | 0.160 |
| Example 26-25. | 0.350 |
| Example 26-26. | 0.269 |
| Example 26-27. | |
| Example 26-28. | |
| Example 26-29. | 0.136 |
| Example 26-30. | 0.26 |
| Example 26-31. | 0.322 |
| Example 26-32. | |
| Example 26-33. | |
| Example 26-34. | |
| Example 26-35. | |
| Example 26-36. | |
| Example 26-37. | |
| Example 26-38. | 0.235 |
| Example 26-39. | |
| Example 26-40. | |
| Example 26-41. | 0.420 |
| Example 26-42. | |
| Example 26-43. | 0.0536 |
| Example 26-44. | |
| Example 26-45. | |
| Example 26-46. | |
| Example 26-47. | 0.136 |
| Example 26-48. | |
| Example 26-49. | 0.311 |
| Example 26-50. | |
| Example 26-51. | |
| Example 26-52. | |
| Example 27. | 0.550 |
| Example 28. | 0.0451 |
| Example 28-1. | 0.0704 |
| Example 28-2. | 0.14 |
| Example 28-3. | 0.128 |
| Example 28-4. | |
| Example 28-5. | 0.118 |
| Example 28-6. | 0.021 |
| Example 28-7. | |
| Example 28-8. | |
| Example 28-9. | |
| Example 29. | 0.0360 |
| Example 29-1. | |
| Example 29-2. | |
| Example 29-3. | 0.0416 |
| Example 29-4. | 0.0522 |
| Example 29-5. | 0.0374 |
| Example 29-6. | |
| Example 29-7. | |
| Example 29-8. | |
| Example 29-9. | |
| Example 29-10. | |
| Example 29-11. | |
| Example 29-12. | |
| Example 29-13. | |
| Example 29-14. | |
| Example 29-15. | |
| Example 30. | |
| Example 31. | 0.0428 |
| Example 31-1. | 0.0164 |
| Example 31-2. | |
| Example 31-3. | |
| Example 31-4. | |
| Example 31-5. | |
| Example 31-6. | |
| Example 31-7. | |
| Example 31-8. | |
| Example 31-9. | |
| Example 31-10. | |
| Example 31-11. | |
| Example 32. | 0.0396 |
| Example 32-1. | |
| Example 32-2. | |
| Example 32-3. | |
| Example 32-4. | |
| Example 32-5. | |
| Example 32-6. | |
| Example 32-7. | |
| Example 32-8. | |
| Example 32-9. | |
| Example 32-10. | |
| Example 32-11. | |
| Example 32-12. | |
| Example 32-13. | |
| Example 32-14. | |
| Example 32-15. | |
| Example 32-16. | |
| Example 32-17. | |
| Example 32-18. | |
| Example 32-19. | 0.00692 |
| Example 32-20. | |
| Example 32-21. | |
| Example 32-22. | |
| Example 32-23. | |
| Example 32-24. | |
| Example 32-25. | |
| Example 32-26. | |
| Example 32-27. | |
| Example 32-28. | |
| Example 32-29. | |
| Example 32-30. | |
| Example 32-31. | |
| Example 32-32. | |
| Example 32-33. | |
| Example 32-34. | |
| Example 32-35. | |
| Example 32-36. | |
| Example 32-37. | |
| Example 32-38. | |
| Example 32-39. | |
| Example 32-40. | |
| Example 32-41. | |
| Example 32-42. | |
| Example 32-43. | |
| Example 32-44. | |
| Example 32-45. | |
| Example 32-46. | |
| Example 32-47. | |
| Example 32-48. | |
| Example 32-49. | |
| Example 32-50. | |
| Example 32-51. | |
| Example 32-52. | |
| Example 32-53. | |
| Example 32-54. | |
| Example 32-55. | |
| Example 32-56. | |
| Example 32-57. | |
| Example 32-58. | |
| Example 32-59. | |
| Example 32-60. | |
| Example 32-61. | |
| Example 32-62. | |
| Example 32-63. | |
| Example 32-64. | |
| Example 32-65. | |
| Example 32-66. | |
| Example 32-67. | |

TABLE 22-continued

| Example # | SOS1 SPR Equilibrium Kd (μM) |
|---|---|
| Example 32-68. | |
| Example 32-69. | |
| Example 32-70. | |
| Example 32-71. | |
| Example 32-72. | |
| Example 32-73. | |
| Example 32-74. | |
| Example 32-75. | |
| Example 32-76. | |
| Example 32-77. | |
| Example 32-78. | |
| Example 32-79. | |
| Example 32-80. | |
| Example 32-81. | |
| Example 32-82. | |
| Example 32-83. | |
| Example 32-84. | |
| Example 32-85. | |
| Example 32-86. | |
| Example 32-87. | |
| Example 32-88. | |
| Example 32-89. | |
| Example 32-90. | |
| Example 32-91. | |
| Example 32-92. | |
| Example 32-93. | |
| Example 32-94. | |
| Example 32-95. | |
| Example 32-96. | |
| Example 32-97. | |
| Example 32-98. | |
| Example 32-99. | |
| Example 32-100. | |
| Example 32-101. | |
| Example 32-102. | |
| Example 32-103. | |
| Example 32-104. | |
| Example 32-105. | |
| Example 32-106. | |
| Example 32-107. | |
| Example 32-108. | |
| Example 32-109. | |
| Example 32-110. | |
| Example 32-111. | |
| Example 32-112. | |
| Example 32-113. | |
| Example 32-114. | |
| Example 32-115. | |
| Example 33. | 0.0334 |
| Example 33-1. | 0.486 |
| Example 33-2. | |
| Example 33-3. | |
| Example 33-4. | |
| Example 33-5. | |
| Example 33-6. | |
| Example 33-7. | |
| Example 33-8. | |
| Example 33-9. | |
| Example 33-10. | |
| Example 33-11. | |
| Example 33-12. | |
| Example 33-13. | |
| Example 33-14. | |
| Example 33-15. | |
| Example 33-16. | |
| Example 33-17. | |
| Example 33-18. | |
| Example 33-19. | |
| Example 33-20. | |
| Example 33-21. | |
| Example 33-22. | |
| Example 33-23. | |
| Example 33-24. | |
| Example 33-25. | |
| Example 33-26. | |
| Example 33-27. | |
| Example 33-28. | |
| Example 33-29. | |
| Example 33-30. | |
| Example 33-31. | |
| Example 33-32. | |
| Example 33-33. | |
| Example 33-34. | |
| Example 33-35. | |
| Example 33-36. | |
| Example 33-37. | |
| Example 34. | 0.0729 |
| Example 35. | |
| Example 36. | |
| Example 36-1. | |
| Example 36-2. | |
| Example 36-3. | |
| Example 36-4. | |
| Example 36-5. | |
| Example 36-6. | |
| Example 36-7. | |
| Example 36-8. | |
| Example 36-9. | |
| Example 36-10. | |
| Example 36-11. | |
| Example 36-12. | |
| Example 36-13. | |
| Example 36-14. | |
| Example 36-15. | |
| Example 36-16. | |
| Example 37. | |
| Example 38. | |
| Example 39. | |
| Example 40. | |
| Example 41. | |
| Example 41-1. | |
| Example 42. | |
| Example 43. | |
| Example 44. | |
| Example 45. | |
| Example 46. | |
| Example 47. | |
| Example 48. | |
| Example 49. | |
| Example 50. | |
| Example 51. | |
| Example 51-1. | |
| Example 51-2. | |
| Example 51-3. | |
| Example 51-4. | |
| Example 51-5. | |
| Example 51-6. | |
| Example 52. | |
| Example 53. | |
| Example 54. | |
| Example 54-1. | |
| Example 54-2. | |
| Example 54-3. | |
| Example 54-4. | |
| Example 55. | |
| Example 56. | |
| Example 56-1. | |
| Example 56-2. | |
| Example 56-3. | |
| Example 56-4. | |
| Example 56-5. | |
| Example 57. | 0.00919 |
| Example 58. | |
| Example 58-1. | |
| Example 58-2. | |
| Example 58-3. | |
| Example 58-4. | |
| Example 59. | |
| Example 60. | |
| Example 61. | |
| Example 62. | |
| Example 63. | |

TABLE 22-continued

| Example # | SOS1 SPR Equilibrium Kd (μM) |
|---|---|
| Example 64. | |
| Example 64-1. | |
| Example 64-2. | |
| Example 64-3. | |
| Example 65. | |
| Example 66. | |
| Example 67. | |
| Example 68. | |
| Example 68-1. | |
| Example 68-2. | |
| Example 68-3. | |
| Example 69. | |
| Example 70. | |
| Example 71. | |

Blank = not determined

Potency Assay: pERK

The purpose of this assay is to measure the ability of test compounds to inhibit SOS1 function in cells. SOS1 activates RAS proteins by catalyzing the conversion of RAS-GDP to RAS.GTP in response to receptor tyrosine kinase activation. Activation of RAS induces a sequence of cellular signaling events that results in increased phosphorylation of ERK at Threonine 202 and Tyrosine 204 (pERK). The procedure described below measures the level of cellular pERK in response to test compounds in PC-9 cells (EGFR Ex19Del).

PC-9 cells were grown and maintained using media and procedures recommended by the ATCC. On the day prior to compound addition, cells were plated in 384-well cell culture plates (40 μL/well) and grown overnight in a 37° C., 5% $CO_2$ incubator. Test compounds were prepared in 10, 3-fold dilutions in DMSO, with a top concentration of 10 mM. On the day of the assay, 40 nL of test compound was added to each well of cell culture plate using an Echo550 liquid handler (LabCyte). Concentrations of test compound were tested in duplicate with highest test concentration being 10 μM. After compound addition, cells were incubated for 1 hour at 37° C., 5% $CO_2$. Following incubation, culture medium was removed and cells were washed once with phosphate buffered saline.

Cellular pERK level was determined using the AlphaLISA SureFire Ultra p-ERK1/2 Assay Kit (PerkinElmer). Cells were lysed in 25 μL lysis buffer, with shaking at 600 RPM at room temperature for 15 minutes. Lysate (10 μL) was transferred to a 384-well Opti-plate (PerkinElmer) and 5 μL acceptor mix was added. The plate was centrifuged at 1000 RPM for 1 minute, and incubated in the dark for 2 hours. Following this incubation, 5 μL of donor mix was added, the plate was sealed and centrifuged at 1000 RPM for 1 minute, and the mixture was incubated for 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

SOS1 pERK IC50 Assay results are shown in the Table 23 below.

TABLE 23

| Example # | SOS1 pERK IC50 (μM) |
|---|---|
| Example 1. | 0.0546 |
| Example 1-1. | 0.14 |
| Example 1-2. | 0.114 |
| Example 1-3. | 0.0503 |
| Example 1-4. | 0.0431 |
| Example 1-5. | 0.222 |
| Example 1-6. | 0.18 |
| Example 1-7. | 0.693 |
| Example 1-8. | 0.169 |
| Example 1-9. | 0.666 |
| Example 1-10. | 0.425 |
| Example 1-11. | 0.077 |
| Example 1-12. | 0.125 |
| Example 1-13. | 0.195 |
| Example 1-14. | 0.218 |
| Example 1-15. | 0.217 |
| Example 1-16. | 0.119 |
| Example 1-17. | 0.0507 |
| Example 1-18. | 0.067 |
| Example 1-19. | 0.091 |
| Example 1-20. | 0.0785 |
| Example 1-21. | 0.173 |
| Example 1-22. | 0.416 |
| Example 1-23. | 0.0702 |
| Example 1-24. | 0.106 |
| Example 1-25. | 0.0837 |
| Example 1-26. | 0.26 |
| Example 1-27. | 0.313 |
| Example 1-28. | 0.125 |
| Example 1-29. | 0.309 |
| Example 1-30. | 0.143 |
| Example 1-31. | 0.568 |
| Example 1-32. | 0.0931 |
| Example 1-33. | 0.201 |
| Example 2. | 0.0598 |
| Example 2-1. | 0.112 |
| Example 2-2. | 0.427 |
| Example 2-3. | 0.188 |
| Example 2-4. | 0.906 |
| Example 2-5. | 0.824 |
| Example 3. | 0.0794 |
| Example 4. | 0.481 |
| Example 5. | 0.134 |
| Example 6. | 0.188 |
| Example 7. | 0.0724 |
| Example 8. | 2.13 |
| Example 8-1. | 0.0684 |
| Example 8-2. | 0.265 |
| Example 21-9. | 0.335 |
| Example 21-10. | 0.611 |
| Example 21-11. | 0.452 |
| Example 21-12. | 0.588 |
| Example 21-13. | 0.486 |
| Example 21-14. | 0.119 |
| Example 21-15. | 0.212 |
| Example 22. | 0.122 |
| Example 23. | 0.0485 |
| Example 23-1. | 0.076 |
| Example 24. | 0.0614 |
| Example 25. | 0.122 |
| Example 26. | 0.388 |
| Example 26-1. | 0.994 |
| Example 26-2. | 0.314 |
| Example 26-3. | 0.659 |
| Example 26-4. | 0.423 |
| Example 26-5. | 0.396 |
| Example 26-6. | 8.83 |
| Example 26-7. | 0.186 |
| Example 26-8. | 0.252 |
| Example 26-9. | 0.479 |
| Example 26-10. | 2.09 |
| Example 26-11. | 0.251 |
| Example 26-12. | 0.861 |
| Example 26-13. | 1.13 |
| Example 26-14. | 0.122 |
| Example 26-15. | 0.256 |

TABLE 23-continued

| Example # | SOS1 pERK IC50 (μM) |
|---|---|
| Example 26-16. | 0.729 |
| Example 26-17. | 0.195 |
| Example 26-18. | 0.589 |
| Example 26-19. | 0.295 |
| Example 26-20. | 1.75 |
| Example 26-21. | 0.52 |
| Example 26-22. | 2.61 |
| Example 26-23. | 0.275 |
| Example 26-24. | 0.794 |
| Example 26-25. | 0.605 |
| Example 26-26. | 0.228 |
| Example 26-27. | 0.803 |
| Example 26-28. | 0.766 |
| Example 26-29. | 1.45 |
| Example 26-30. | 0.656 |
| Example 26-31. | 2.82 |
| Example 26-32. | 0.216 |
| Example 26-33. | 0.152 |
| Example 26-34. | 0.122 |
| Example 26-35. | 0.193 |
| Example 26-36. | |
| Example 26-37. | 0.747 |
| Example 26-38. | 0.392 |
| Example 26-39. | >10.0 |
| Example 26-40. | 0.453 |
| Example 26-41. | 1.4 |
| Example 26-42. | 0.194 |
| Example 26-43. | 0.181 |
| Example 26-44. | 0.401 |
| Example 26-45. | 0.521 |
| Example 26-46. | 0.322 |
| Example 26-47. | 0.585 |
| Example 26-48. | 0.22 |
| Example 26-49. | 0.959 |
| Example 26-50. | 0.88 |
| Example 26-51. | 0.445 |
| Example 26-52. | 0.152 |
| Example 27. | 0.852 |
| Example 28. | 0.0937 |
| Example 28-1. | 0.187 |
| Example 28-2. | 0.572 |
| Example 28-3. | 0.111 |
| Example 28-4. | 0.0837 |
| Example 28-5. | 0.157 |
| Example 28-6. | 0.123 |
| Example 28-7. | 0.322 |
| Example 28-8. | 0.0326 |
| Example 28-9. | 0.369 |
| Example 29. | 0.0346 |
| Example 29-1. | 0.122 |
| Example 29-2. | 0.0915 |
| Example 29-3. | 0.12 |
| Example 29-4. | 0.144 |
| Example 29-5. | 0.0373 |
| Example 29-6. | 0.47 |
| Example 29-7. | 0.0811 |
| Example 29-8. | 0.0534 |
| Example 29-9. | 0.163 |
| Example 29-10. | 0.14 |
| Example 29-11. | 0.0443 |
| Example 29-12. | 0.0536 |
| Example 29-13. | 0.196 |
| Example 29-14. | 0.0355 |
| Example 29-15. | 0.0422 |
| Example 30. | 2.76 |
| Example 31. | .0145 |
| Example 31-1. | 0.0456 |
| Example 31-2. | 0.0162 |
| Example 31-3. | 0.777 |
| Example 31-4. | 0.18 |
| Example 31-5. | 0.0267 |
| Example 31-6. | 0.191 |
| Example 31-7. | 0.0456 |
| Example 31-8. | 0.0394 |
| Example 31-9. | 0.168 |
| Example 31-10. | 0.0518 |
| Example 31-11. | 0.575 |
| Example 32. | 0.0584 |
| Example 32-1. | 0.124 |
| Example 32-2. | 0.01 |
| Example 32-3. | 2.24 |
| Example 32-4. | 0.00929 |
| Example 32-5. | 0.0357 |
| Example 32-6. | 0.0391 |
| Example 32-7. | 0.0714 |
| Example 32-8. | 0.186 |
| Example 32-9. | 0.0163 |
| Example 32-10. | 0.436 |
| Example 32-11. | 0.0345 |
| Example 32-12. | 0.0286 |
| Example 32-13. | 0.044 |
| Example 32-14. | 1.31 |
| Example 32-15. | 0.0493 |
| Example 32-16. | 0.268 |
| Example 32-17. | 0.0299 |
| Example 32-18. | 0.947 |
| Example 32-19. | 0.0113 |
| Example 32-20. | 0.143 |
| Example 32-21. | 0.393 |
| Example 32-22. | 0.18 |
| Example 32-23. | 0.0527 |
| Example 32-24. | 0.0697 |
| Example 32-25. | 1.44 |
| Example 32-26. | 0.0418 |
| Example 32-27. | 0.0879 |
| Example 32-28. | 0.0921 |
| Example 32-29. | 0.0537 |
| Example 32-30. | 0.236 |
| Example 32-31. | 0.0101 |
| Example 32-32. | 0.00979 |
| Example 32-33. | 0.0859 |
| Example 32-34. | 0.0711 |
| Example 32-35. | 0.244 |
| Example 32-36. | 0.0931 |
| Example 32-37. | 0.0118 |
| Example 32-38. | 0.172 |
| Example 32-39. | 0.0542 |
| Example 32-40. | 0.382 |
| Example 32-41. | 0.461 |
| Example 32-42. | 0.355 |
| Example 32-43. | 0.181 |
| Example 32-44. | 0.0321 |
| Example 32-45. | 0.249 |
| Example 32-46. | 0.148 |
| Example 32-47. | 0.0776 |
| Example 32-48. | 0.0054 |
| Example 32-49. | 0.102 |
| Example 32-50. | 0.153 |
| Example 32-51. | 0.00579 |
| Example 32-52. | 0.0181 |
| Example 32-53. | 0.199 |
| Example 32-54. | 0.0402 |
| Example 32-55. | 0.0816 |
| Example 32-56. | 0.0937 |
| Example 32-57. | 0.0839 |
| Example 32-58. | 0.0133 |
| Example 32-59. | 0.0203 |
| Example 32-60. | 0.0211 |
| Example 32-61. | 0.115 |
| Example 32-62. | 0.0108 |
| Example 32-63. | 0.0115 |
| Example 32-64. | 0.154 |
| Example 32-65. | 0.0503 |
| Example 32-66. | 0.127 |
| Example 32-111. | 0.189 |
| Example 32-112. | 0.092 |
| Example 32-113. | 0.015 |
| Example 32-114. | 0.434 |
| Example 32-115. | 0.350 |
| Example 33. | 0.145 |
| Example 33-1. | 0.0621 |
| Example 33-2. | 0.0716 |

TABLE 23-continued

| Example # | SOS1 pERK IC50 (μM) |
|---|---|
| Example 33-3. | 0.0348 |
| Example 33-4. | 0.0925 |
| Example 33-5. | 0.0412 |
| Example 33-6. | 0.0397 |
| Example 33-7. | 0.521 |
| Example 33-8. | 0.0547 |
| Example 33-9. | 0.27 |
| Example 33-10. | 0.335 |
| Example 33-11. | 0.169 |
| Example 33-12. | 0.0407 |
| Example 33-13. | 0.021 |
| Example 33-14. | 0.271 |
| Example 33-15. | 0.113 |
| Example 33-16. | 0.0879 |
| Example 33-17. | 0.285 |
| Example 33-18. | 0.0532 |
| Example 33-19. | 0.182 |
| Example 33-20. | 0.0527 |
| Example 33-21. | 0.0522 |
| Example 33-22. | 1.2 |
| Example 33-23. | 0.0854 |
| Example 33-24. | 0.293 |
| Example 33-25. | 0.0738 |
| Example 33-26. | |
| Example 33-27. | |
| Example 33-28. | |
| Example 33-29. | |
| Example 33-30. | 0.263 |
| Example 33-31. | 0.204 |
| Example 33-32. | 0.027 |
| Example 33-33. | 0.182 |
| Example 33-34. | 0.297 |
| Example 33-35. | 0.146 |
| Example 33-36. | 0.053 |
| Example 33-37. | 0.034 |
| Example 34. | |
| Example 35. | 0.127 |
| Example 36. | 0.0281 |
| Example 36-1. | 0.0116 |
| Example 36-2. | 0.063 |
| Example 36-3. | 0.181 |
| Example 36-4. | 0.091 |
| Example 36-5. | 0.124 |
| Example 36-6. | 0.0333 |
| Example 36-7. | 0.772 |
| Example 36-8. | 0.0388 |
| Example 36-9. | 0.0869 |
| Example 36-10. | 0.044 |
| Example 36-11. | 0.268 |
| Example 36-12. | 0.448 |
| Example 36-13. | 0.0812 |
| Example 36-14. | 0.207 |
| Example 36-15. | 0.0589 |
| Example 36-16. | 0.222 |
| Example 37. | 0.0499 |
| Example 38. | 0.137 |
| Example 39. | 1.56 |
| Example 40. | 1.37 |
| Example 41. | 4.48 |
| Example 41-1. | >10.0 |
| Example 42. | 0.242 |
| Example 43. | >7.29 |
| Example 44. | 0.179 |
| Example 45. | 0.0291 |
| Example 46. | 0.0433 |
| Example 47. | 0.0547 |
| Example 48. | 1.52 |
| Example 49. | 0.0755 |
| Example 50. | 0.112 |
| Example 51. | 0.0411 |
| Example 51-1. | 0.086 |
| Example 51-2. | 0.087 |
| Example 51-3. | 0.144 |
| Example 51-4. | 0.315 |
| Example 51-5. | 0.072 |
| Example 51-6. | 0.047 |
| Example 52. | 0.0706 |
| Example 53. | 0.0367 |
| Example 54. | 0.0463 |
| Example 54-1. | 0.0537 |
| Example 54-2. | 0.0828 |
| Example 54-3. | 0.376 |
| Example 54-4. | 0.301 |
| Example 55. | 0.109 |
| Example 56. | 0.0572 |
| Example 56-1. | 0.121 |
| Example 56-2. | 0.294 |
| Example 56-3. | 0.0862 |
| Example 56-4. | 0.05 |
| Example 56-5. | 0.0441 |
| Example 57. | 0.0426 |
| Example 58. | 0.271 |
| Example 58-1. | 0.386 |
| Example 58-2. | 0.0562 |
| Example 58-3. | 0.148 |
| Example 58-4. | 0.104 |
| Example 59. | 0.0288 |
| Example 60. | 0.0231 |
| Example 61. | 0.647 |
| Example 62. | 0.262 |
| Example 63. | >10.0 |
| Example 64. | 0.131 |
| Example 64-1. | 0.0263 |
| Example 64-2. | 0.494 |
| Example 64-3. | 0.0583 |
| Example 65. | 0.0668 |
| Example 66. | 0.0291 |
| Example 67. | 0.0161 |
| Example 68. | 0.201 |
| Example 68-1. | 0.0241 |
| Example 68-2. | 0.136 |
| Example 68-3. | 0.100 |
| Example 69. | 0.094 |
| Example 70. | 0.121 |
| Example 71. | 0.528 |

Blank = not determined

Mode of Action Assay: Inhibition of SOS1 Nucleotide Exchange Activity

The purpose of this assay was to characterize the inhibitory activity of compounds on SOS1 nucleotide exchange of KRAS. Data was reported as $IC_{50}$ values based on the TR-FRET signal.

Note—the Following Protocol Describes a Procedure for Monitoring the Inhibition of SOS1 Nucleotide Exchange Activity of Wild-Type KRAS in Response to a Compound of the Invention. Other KRAS Mutants and RAS Isoforms May be Employed.

In assay buffer containing 20 mM HEPES, pH 7.5, 150 mM NaCl, 5 mM $MgCl_2$, 0.05% Tween-20, 0.1% BSA, 1 mM DTT, concentration series of test compounds were generated spanning 100 μM to 1.7 nM over eleven 3-fold serial dilutions in a 384-well assay plate at a volume of 20 μL. The purified tagless catalytic domain of SOS1 (residues 564-1049) was first diluted in assay buffer at a concentration of 100 nM, and then 20 μL of the SOS1 containing solution was directly dispensed into compound plates. The SOS1/compound mixture was incubated at room temperature with constant mixing on an orbital shaker for 20 minutes to allow the reaction to reach equilibrium. A KRAS mixture was prepared by diluting 66.7 nM avi-tagged KRAS (residue 1-169), 3.33 nM Streptavidin-Tb and 333 nM EDA-GTP-DY-647P1 in assay buffer. This mixture was prepared immediately before addition to the SOS1/compound mixture to prevent intrinsic nucleotide exchange. Then 5 μL of the pre-incubated SOS1/compound mixture and 7.5 μL of the KRAS mixture were added sequentially in a 384-well low volume black round bottom plate and incubated at room temperature with constant shaking for 30 minutes. Time-resolved fluorescence was measured on a PerkinElmer Envision plate reader. DMSO and 10 μM of compound (i) were used as negative and positive controls, respectively.

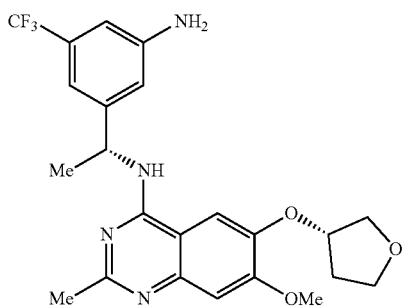

compound (i)

Three replicates were performed for each compound. Data were normalized by the following: (Positive control−Sample signal)/(Positive control−negative control)*100. The data were fit using a four-parameter logistic fit.

SOS1 TR-FRET IC50 Assay results are shown in the Table 24 below.

TABLE 24

| Example # | TR-FRET IC50 (μM) |
|---|---|
| Example 1. | 0.009 |
| Example 1-1. | 0.0415 |
| Example 1-2. | 0.0238 |
| Example 1-3. | 0.0212 |
| Example 1-4. | 0.0456 |
| Example 1-5. | 0.032 |
| Example 1-6. | 0.0236 |
| Example 1-7. | 0.257 |
| Example 1-8. | 0.0201 |
| Example 1-9. | 0.0489 |
| Example 1-10. | 0.0429 |
| Example 1-11. | 0.0293 |
| Example 1-12. | 0.034 |
| Example 1-13. | 0.0193 |
| Example 1-14. | 0.053 |
| Example 1-15. | 0.0398 |
| Example 1-16. | 0.0204 |
| Example 1-17. | 0.013 |
| Example 1-18. | 0.0128 |
| Example 1-19. | 0.0443 |
| Example 1-20. | 0.0267 |
| Example 1-21. | 0.0956 |
| Example 1-22. | 0.0207 |
| Example 1-23. | 0.094 |
| Example 1-24. | 0.0364 |
| Example 1-25. | 0.0673 |
| Example 1-26. | 0.0264 |
| Example 1-27. | 0.0786 |
| Example 1-28. | |
| Example 1-29. | 0.129 |
| Example 1-30. | 0.0458 |
| Example 1-31. | 0.0714 |
| Example 1-32. | |
| Example 1-33. | |
| Example 2. | 0.0129 |
| Example 2-1. | 0.0441 |
| Example 2-2. | 2.08 |
| Example 2-3. | 0.183 |
| Example 2-4. | 0.0892 |

TABLE 24-continued

| Example # | TR-FRET IC50 (μM) |
|---|---|
| Example 2-5. | 0.112 |
| Example 3. | 0.0349 |
| Example 4. | 0.0108 |
| Example 5. | 0.113 |
| Example 6. | 0.0209 |
| Example 7. | 0.155 |
| Example 8. | 0.0222 |
| Example 8-1. | 0.0246 |
| Example 8-2. | 0.0212 |
| Example 8-3. | 0.015 |
| Example 8-4. | 0.00766 |
| Example 8-5. | 0.0128 |
| Example 8-6. | |
| Example 8-7. | |
| Example 8-8. | 0.0305 |
| Example 8-9. | 0.0536 |
| Example 8-10. | |
| Example 8-11. | |
| Example 8-12. | 0.065 |
| Example 8-13. | 0.0398 |
| Example 8-14. | 0.0812 |
| Example 8-15. | 0.0401 |
| Example 8-16. | 0.0775 |
| Example 8-17. | 0.708 |
| Example 9. | 0.0119 |
| Example 10. | 0.178 |
| Example 11. | 0.0328 |
| Example 11-1. | 0.183 |
| Example 11-2. | |
| Example 11-3. | |
| Example 11-4. | |
| Example 12. | 0.0136 |
| Example 13. | 0.0294 |
| Example 14. | |
| Example 15. | 0.0904 |
| Example 16. | |
| Example 17. | |
| Example 18. | 0.00579 |
| Example 19. | 0.0123 |
| Example 20. | >20.0 |
| Example 20-1. | 6.17 |
| Example 20-2. | |
| Example 20-3. | |
| Example 20-4. | |
| Example 21. | 0.018 |
| Example 21-1. | 1.07 |
| Example 21-2. | 0.0429 |
| Example 21-3. | 0.12 |
| Example 21-4. | 0.172 |
| Example 21-5. | 0.126 |
| Example 21-6. | 0.0864 |
| Example 21-7. | 0.0471 |
| Example 21-8. | 0.235 |
| Example 21-9. | 0.099 |
| Example 21-10. | 0.532 |
| Example 21-11. | 0.173 |
| Example 21-12. | 0.123 |
| Example 21-13. | |
| Example 21-14. | |
| Example 21-15. | |
| Example 22. | 0.298 |
| Example 23. | 0.0209 |
| Example 23-1. | 0.0783 |
| Example 24. | 0.0135 |
| Example 25. | 0.0159 |
| Example 26. | 0.0702 |
| Example 26-1. | 0.162 |
| Example 26-2. | 0.102 |
| Example 26-3. | 0.407 |
| Example 26-4. | 0.0387 |
| Example 26-5. | |
| Example 26-6. | >20.0 |
| Example 26-7. | 0.0508 |
| Example 26-8. | |
| Example 26-9. | 0.122 |
| Example 26-10. | |

TABLE 24-continued

| Example # | TR-FRET IC50 (μM) |
|---|---|
| Example 26-11. | 0.0461 |
| Example 26-12. | 0.107 |
| Example 26-13. | |
| Example 26-14. | |
| Example 26-15. | |
| Example 26-16. | |
| Example 26-17. | |
| Example 26-18. | 0.0786 |
| Example 26-19. | 0.0654 |
| Example 26-20. | 0.331 |
| Example 26-21. | 0.0249 |
| Example 26-22. | 0.113 |
| Example 26-23. | |
| Example 26-24. | 0.0541 |
| Example 26-25. | 0.106 |
| Example 26-26. | 0.0722 |
| Example 26-27. | |
| Example 26-28. | |
| Example 26-29. | 0.0978 |
| Example 26-30. | 0.0861 |
| Example 26-31. | 0.23 |
| Example 26-32. | |
| Example 26-33. | |
| Example 26-34. | |
| Example 26-35. | |
| Example 26-36. | |
| Example 26-37. | |
| Example 26-38. | 0.156 |
| Example 26-39. | |
| Example 26-40. | |
| Example 26-41. | 0.17 |
| Example 26-42. | |
| Example 26-43. | 0.037 |
| Example 26-44. | |
| Example 26-45. | |
| Example 26-46. | |
| Example 26-47. | 0.0561 |
| Example 26-48. | |
| Example 26-49. | 0.176 |
| Example 26-50. | |
| Example 26-51. | |
| Example 26-52. | |
| Example 27. | 0.192 |
| Example 28. | 0.0206 |
| Example 28-1. | 0.0659 |
| Example 28-2. | 0.0491 |
| Example 28-3. | 0.0998 |
| Example 28-4. | |
| Example 28-5. | 0.0244 |
| Example 28-6. | 0.014 |
| Example 28-7. | |
| Example 28-8. | |
| Example 28-9. | |
| Example 29. | 0.0501 |
| Example 29-1. | |
| Example 29-2. | |
| Example 29-3. | 0.0424 |
| Example 29-4. | 0.0159 |
| Example 29-5. | 0.0148 |
| Example 29-6. | |
| Example 29-7. | |
| Example 29-8. | |
| Example 29-9. | |
| Example 29-10. | |
| Example 29-11. | |
| Example 29-12. | |
| Example 29-13. | |
| Example 29-14. | |
| Example 29-15. | |
| Example 30. | 10.9 |
| Example 31. | 0.0315 |
| Example 31-1. | 0.015 |
| Example 31-2. | |
| Example 31-3. | |
| Example 31-4. | |
| Example 31-5. | |
| Example 31-6. | |
| Example 31-7. | |
| Example 31-8. | |
| Example 31-9. | |
| Example 31-10. | |
| Example 31-11. | |
| Example 32. | |
| Example 32-1. | |
| Example 32-2. | |
| Example 32-3. | |
| Example 32-4. | |
| Example 32-5. | |
| Example 32-6. | |
| Example 32-7. | |
| Example 32-8. | |
| Example 32-9. | |
| Example 32-10. | |
| Example 32-11. | |
| Example 32-12. | |
| Example 32-13. | |
| Example 32-14. | |
| Example 32-15. | |
| Example 32-16. | |
| Example 32-17. | |
| Example 32-18. | |
| Example 32-19. | 0.00882 |
| Example 32-20. | |
| Example 32-21. | |
| Example 32-22. | |
| Example 32-23. | |
| Example 32-24. | 0.0191 |
| Example 32-25. | |
| Example 32-26. | |
| Example 32-27. | |
| Example 32-28. | |
| Example 32-29. | |
| Example 32-30. | |
| Example 32-31. | 0.00353 |
| Example 32-32. | 0.00477 |
| Example 32-33. | |
| Example 32-34. | |
| Example 32-35. | |
| Example 32-36. | |
| Example 32-37. | |
| Example 32-38. | |
| Example 32-39. | |
| Example 32-40. | |
| Example 32-41. | |
| Example 32-42. | |
| Example 32-43. | |
| Example 32-44. | |
| Example 32-45. | |
| Example 32-46. | |
| Example 32-47. | |
| Example 32-48. | |
| Example 32-49. | |
| Example 32-50. | |
| Example 32-51. | 0.00677 |
| Example 32-52. | |
| Example 32-53. | |
| Example 32-54. | |
| Example 32-55. | |
| Example 32-56. | |
| Example 32-57. | |
| Example 32-58. | |
| Example 32-59. | |
| Example 32-60. | |
| Example 32-61. | |
| Example 32-62. | |
| Example 32-63. | |
| Example 32-64. | |
| Example 32-65. | |
| Example 32-66. | |
| Example 32-67. | |
| Example 32-68. | |
| Example 32-69. | |

TABLE 24-continued

| Example # | TR-FRET IC50 (μM) |
|---|---|
| Example 32-70. | |
| Example 32-71. | |
| Example 32-72. | |
| Example 32-73. | |
| Example 32-74. | |
| Example 32-75. | |
| Example 32-76. | |
| Example 32-77. | |
| Example 32-78. | |
| Example 32-79. | |
| Example 32-80. | |
| Example 32-81. | |
| Example 32-82. | |
| Example 32-83. | |
| Example 32-84. | |
| Example 32-85. | |
| Example 32-86. | |
| Example 32-87. | |
| Example 32-88. | |
| Example 32-89. | |
| Example 32-90. | |
| Example 32-91. | |
| Example 32-92. | |
| Example 32-93. | |
| Example 32-94. | |
| Example 32-95. | |
| Example 32-96. | |
| Example 32-97. | |
| Example 32-98. | |
| Example 32-99. | |
| Example 32-100. | |
| Example 32-101. | |
| Example 32-102. | |
| Example 32-103. | |
| Example 32-104. | |
| Example 32-105. | |
| Example 32-106. | |
| Example 32-107. | |
| Example 32-108. | |
| Example 32-109. | |
| Example 32-110. | |
| Example 32-111. | |
| Example 32-112. | |
| Example 32-113. | |
| Example 32-114. | |
| Example 32-115. | |
| Example 33. | 0.0295 |
| Example 33-1. | 0.0427 |
| Example 33-2. | |
| Example 33-3. | |
| Example 33-4. | |
| Example 33-5. | |
| Example 33-6. | |
| Example 33-7. | |
| Example 33-8. | |
| Example 33-9. | |
| Example 33-10. | |
| Example 33-11. | |
| Example 33-12. | |
| Example 33-13. | |
| Example 33-14. | |
| Example 33-15. | |
| Example 33-16. | |
| Example 33-17. | |
| Example 33-18. | |
| Example 33-19. | |
| Example 33-20. | |
| Example 33-21. | |
| Example 33-22. | |
| Example 33-23. | |
| Example 33-24. | |
| Example 33-25. | |
| Example 33-26. | |
| Example 33-27. | |
| Example 33-28. | |
| Example 33-29. | |
| Example 33-30. | |
| Example 33-31. | |
| Example 33-32. | |
| Example 33-33. | |
| Example 33-34. | |
| Example 33-35. | |
| Example 33-36. | |
| Example 33-37. | |
| Example 34. | 0.0627 |
| Example 35. | |
| Example 36. | |
| Example 36-1. | |
| Example 36-2. | |
| Example 36-3. | |
| Example 36-4. | |
| Example 36-5. | |
| Example 36-6. | |
| Example 36-7. | |
| Example 36-8. | |
| Example 36-9. | |
| Example 36-10. | |
| Example 36-11. | |
| Example 36-12. | |
| Example 36-13. | |
| Example 36-14. | |
| Example 36-15. | |
| Example 36-16. | |
| Example 37. | |
| Example 38. | |
| Example 39. | |
| Example 40. | |
| Example 41. | |
| Example 41-1. | |
| Example 42. | |
| Example 43. | |
| Example 44. | |
| Example 45. | |
| Example 46. | |
| Example 47. | |
| Example 48. | |
| Example 49. | |
| Example 50. | |
| Example 51. | |
| Example 51-1. | |
| Example 51-2. | |
| Example 51-3. | |
| Example 51-4. | |
| Example 51-5. | |
| Example 51-6. | |
| Example 52. | |
| Example 53. | |
| Example 54. | |
| Example 54-1. | |
| Example 54-2. | |
| Example 54-3. | |
| Example 54-4. | |
| Example 55. | |
| Example 56. | |
| Example 56-1. | |
| Example 56-2. | |
| Example 56-3. | |
| Example 56-4. | |
| Example 56-5. | |
| Example 57. | 0.00765 |
| Example 58. | |
| Example 58-1. | |
| Example 58-2. | |
| Example 58-3. | |
| Example 58-4. | |
| Example 59. | |
| Example 60. | |
| Example 61. | |
| Example 62. | |
| Example 63. | |
| Example 64. | |
| Example 64-1. | |

TABLE 24-continued

| Example # | TR-FRET IC50 (μM) |
|---|---|
| Example 64-2. | |
| Example 64-3. | |
| Example 65. | |
| Example 66. | |
| Example 67. | |
| Example 68. | |
| Example 68-1. | |
| Example 68-2. | |
| Example 68-3. | |
| Example 69. | |
| Example 70. | |
| Example 71. | |

Blank = not determined

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:
1. A compound selected from the group consisting of:
(R)-4-((1-(3-amino-5-(trifluoromethyl)phenyl)ethyl)amino)-8-methyl-6-(1,2,3,6-tetrahydropyridin-4-yl)pyrido[2,3-d]pyrimidin-7(8H)-one;
(R)-4-((1-(3-(1,1-difluoro-2-hydroxyethyl)phenyl)ethyl)amino)-8-methyl-6-morpholinopyrido[2,3-d]pyrimidin-7(8H)-one;
(R)-6-(3,6-dihydro-2H-pyran-4-yl)-8-methyl-4-((1-(3-(trifluoromethyl)phenyl)ethyl)amino)pyrido[2,3-d]pyrimidin-7(8H)-one;
4-{[(1R)-1-[3-amino-5-(trifluoromethyl)phenyl]ethyl]amino}-8-methyl-6-(morpholin-4-yl)-7H,8H-pyrido[2,3-d]pyrimidin-7-one;
8-methyl-6-(morpholin-4-yl)-4-{[(1R)-1-[3-(trifluoromethyl)phenyl]-ethyl]amino}-7H,8H-pyrido[2,3-d]pyrimidin-7-one;
4-{[(1R)-1-[3-(difluoromethyl)-2-fluorophenyl]ethyl]amino}-6-(1-methanesulfonyl-3-methylazetidin-3-yl)-8-methyl-7H,8H-pyrido[2,3-d]pyrimidin-7-one;
6-(1-acetyl-4-piperidyl)-4-[[(1R)-1-[3-amino-2-fluoro-5-(trifluoromethyl)phenyl]ethyl]amino]-8-methyl-pyrido[2,3-d]pyrimidin-7-one;
6-(1-acetyl-4-piperidyl)-4-[[(1R)-1-[5-amino-2-fluoro-3-(trifluoromethyl)phenyl]ethyl]amino]-8-methyl-pyrido[2,3-d]pyrimidin-7-one;
(R)-4-((1-(3-(difluoromethyl)-2-fluorophenyl)ethyl)amino)-8-methyl-6-(pyridazin-4-yl)pyrido[2,3-d]pyrimidin-7(8H)-one;
4-(((R)-1-(3-(difluoromethyl)-2-fluorophenyl)ethyl)amino)-8-methyl-6-(1-oxido-3,6-dihydro-2H-thiopyran-4-yl)pyrido[2,3-d]pyrimidin-7(8H)-one;
4-(((R)-1-(3-(difluoromethyl)-2-fluorophenyl)ethyl)amino)-6-(1-imino-1-oxido-1,2,3,6-tetrahydro-1λ⁶-thiopyran-4-yl)-8-methylpyrido[2,3-d]pyrimidin-7(8H)-one;
4-(((R)-1-(3-(difluoromethyl)-2-fluorophenyl)ethyl)amino)-8-methyl-6-(1-(methylimino)-1-oxido-1,2,3,6-tetrahydro-1λ⁶-thiopyran-4-yl)pyrido[2,3-d]pyrimidin-7(8H)-one;
(R)-4-((1-(3-(difluoromethyl)-2-fluorophenyl)ethyl)amino)-8-methyl-6-(1-oxidotetrahydro-2H-thiopyran-4-yl)pyrido[2,3-d]pyrimidin-7(8H)-one;
4-(4-{[(1R)-1-[3-(difluoromethyl)-2-fluorophenyl]-ethyl]amino}-8-methyl-7-oxo-7H,8H-pyrido[2,3-d]pyrimidin-6-yl)-4-hydroxy-1λ⁶-thiane-1,1-dione;
4-(4-{[(1R)-1-[3-(difluoromethyl)-2-fluorophenyl]ethyl]amino}-8-methyl-7-oxo-7H,8H-pyrido[2,3-d]-pyrimidin-6-yl)-4-fluoro-1λ⁶-thiane-1,1-dione;
4-{[(1R)-1-[3-(difluoromethyl)-2-fluorophenyl]ethyl]amino}-8-methyl-6-(phenylsulfanyl)-7H,8H-pyrido[2,3-d]pyrimidin-7-one;
6-(4-aminooxan-4-yl)-4-{[(1R)-1-[3-(difluoromethyl)-2-fluorophenyl]ethyl]amino}-8-methyl-7H,8H-pyrido-[2,3-d]pyrimidin-7-one;
4-(4-{[(1R)-1-[3-(difluoro-methyl)-2-fluorophenyl]ethyl]amino}-8-methyl-7-oxo-7H,8H-pyrido[2,3-d]pyrimidin-6-yl)-4-methoxy-1λ⁶-thiane-1,1-dione;
6-(4-{[(1R)-1-[3-(difluoromethyl)-2-fluorophenyl]ethyl]amino}-8-methyl-7-oxo-7H,8H-pyrido[2,3-d]pyrimidin-6-yl)-2λ⁶-thiaspiro[3.3]heptane-2,2-dione;
4-(((R)-1-(3-(difluoromethyl)-2-fluorophenyl)ethyl)amino)-6-(3-hydroxypiperidin-4-yl)-8-methylpyrido[2,3-d]pyrimidin-7(8H)-one;
(R)-4-((1-(3-(difluoromethyl)-2-fluorophenyl)ethyl)amino)-6-(1-imino-1-oxidohexahydro-1λ⁶-thiopyran-4-yl)-8-methylpyrido[2,3-d]pyrimidin-7(8H)-one;
1-acetyl-4-(4-{[(1R)-1-[3-(difluoromethyl)-2-fluorophenyl]ethyl]amino}-8-methyl-7-oxo-7H,8H-pyrido[2,3-d]pyrimidin-6-yl)piperidine-4-carbonitrile;
4-(4-{[(1R)-1-[3-(difluoromethyl)-2-fluorophenyl]ethyl]amino}-8-methyl-7-oxo-7H,8H-pyrido[2,3-d]pyrimidin-6-yl)-4-methyl-1λ⁶-thiane-1,1-dione;
6-(1-acetylpiperidin-4-yl)-4-{[(1R)-1-[2,3-bis(difluoromethyl)phenyl]ethyl]amino}-8-methyl-7H,8H-pyrido[2,3-d]pyrimidin-7-one;
6-(1-acetylpiperidin-4-yl)-4-{[(1R)-1-[3-(difluoromethyl)-2-(fluoromethyl)phenyl]ethyl]amino}-8-methyl-7H,8H-pyrido[2,3-d]pyrimidin-7-one;
2-{3-[(1R)-1-{[6-(1,1-dioxo-3,6-dihydro-2H-1λ⁶-thiopyran-4-yl)-8-methyl-7-oxo-7H,8H-pyrido[2,3-d]pyrimidin-4-yl]amino}ethyl]phenyl}-2,2-difluoroacetonitrile;
2-{3-[(1R)-1-{[6-(1,1-dioxo-3,6-dihydro-2H-1λ⁶-thiopyran-4-yl)-8-methyl-7-oxo-7H,8H-pyrido[2,3-d]pyrimidin-4-yl]amino}ethyl]-2-fluorophenyl}-2,2-difluoroacetonitrile;
4-(4-{[(1R)-1-[3-(2-amino-1,1-difluoroethyl)-2-fluorophenyl]ethyl]amino}-8-methyl-7-oxo-7H,8H-pyrido[2,3-d]pyrimidin-6-yl)-3,6-dihydro-2H-1λ⁶-thiopyran-1,1-dione;
6-(1-acetyl-4-piperidyl)-4-[[(1R)-1-[3-(difluoromethyl)-5-(3-fluoroazetidin-3-yl)phenyl]ethyl]amino]-8-methyl-pyrido[2,3-d]pyrimidin-7-one;
[4-[4-[[(1R)-1-[3-(difluoromethyl)-2-fluoro-phenyl]ethyl]amino]-8-methyl-7-oxo-pyrido[2,3-d]pyrimidin-6-yl]-1-oxo-3,6-dihydro-2H-thiopyran-1-ylidene]cyanamide;

[4-[4-[[(1R)-1-[3-(difluoromethyl)-2-fluoro-phenyl]
ethyl]amino]-8-methyl-7-oxo-pyrido[2,3-d]pyrimidin-
6-yl]-1-oxo-thian-1-ylidene]cyanamide;

4-(((R)-1-(3-(difluoromethyl)-2-fluorophenyl)ethyl)
amino)-6-((1S,4s)-1-imino-4-methoxy-1-oxidohexa-
hydro-1λ⁶-thiopyran-4-yl)-8-methylpyrido[2,3-d]py-
rimidin-7(8H)-one;

4-(((R)-1-(3-(difluoromethyl)-2-fluorophenyl)ethyl)
amino)-6-((1R,4r)-1-imino-4-methoxy-1-oxidohexa-
hydro-1λ⁶-thiopyran-4-yl)-8-methylpyrido[2,3-d]py-
rimidin-7(8H)-one;

4-(((R)-1-(3-(difluoromethyl)-2-fluorophenyl)ethyl)
amino)-6-((1S,4s)-4-fluoro-1-(methylimino)-1-oxido-
hexahydro-1λ⁶-thiopyran-4-yl)-8-methylpyrido[2,3-d]
pyrimidin-7(8H)-one;

4-(((R)-1-(3-(difluoromethyl)-2-fluorophenyl)ethyl)
amino)-6-((1R,4r)-4-fluoro-1-(methylimino)-1-oxido-
hexahydro-1λ⁶-thiopyran-4-yl)-8-methylpyrido[2,3-d]
pyrimidin-7(8H)-one;

6-{3-acetyl-3-azabicyclo[3.1.0]hexan-1-yl}-4-{[(1R)-1-
[3-(difluoromethyl)-2-fluorophenyl]ethyl]amino}-8-
methyl-7H,8H-pyrido[2,3-d]pyrimidin-7-one;

6-(1-acetyl-4-piperidyl)-4-[[(1R)-1-[3-[(4-cyclopropy-
lmorpholin-2-yl)-difluoro-methyl]-2-fluoro-phenyl]
ethyl]amino]-8-methyl-pyrido[2,3-d]pyrimidin-7-one;

6-((1R,4r)-1-(cyclopropylimino)-4-fluoro-1-oxidohexa-
hydro-1λ⁶-thiopyran-4-yl)-4-(((R)-1-(3-(difluorom-
ethyl)-2-fluorophenyl)ethyl)amino)-8-methylpyrido[2,
3-d]pyrimidin-7(8H)-one;

6-((1S,4s)-1-(cyclopropylimino)-4-fluoro-1-oxidohexa-
hydro-1λ⁶-thiopyran-4-yl)-4-(((R)-1-(3-(difluorom-
ethyl)-2-fluorophenyl)ethyl)amino)-8-methylpyrido[2,
3-d]pyrimidin-7(8H)-one;

(1R,4r)-1-(cyclopropylimino)-4-(4-(((R)-1-(3-(difluo-
romethyl)-2-fluorophenyl)ethyl)amino)-8-methyl-7-
oxo-7,8-dihydropyrido[2,3-d]pyrimidin-6-yl)hexa-
hydro-1λ⁶-thiopyran-4-carbonitrile 1-oxide;

(1S,4s)-1-(cyclopropylimino)-4-(4-(((R)-1-(3-(difluo-
romethyl)-2-fluorophenyl)ethyl)amino)-8-methyl-7-
oxo-7,8-dihydropyrido[2,3-d]pyrimidin-6-yl)hexa-
hydro-1λ⁶-thiopyran-4-carbonitrile 1-oxide;

4-[[(1R)-1-[3-(difluoromethyl)-2-fluoro-phenyl]ethyl]
amino]-8-methyl-6-[1-(oxetan-3-ylimino)-1-oxo-
thian-4-yl]pyrido[2,3-d]pyrimidin-7-one;

4-[[(1R)-1-[3-(difluoromethyl)-2-fluoro-phenyl]ethyl]
amino]-6-[1-[(4-methoxyphenyl)methoxy]cyclopro-
pyl]-8-methyl-pyrido[2,3-d]pyrimidin-7-one;

2-[2-(difluoromethyl)-6-[(1R)-1-[[6-(1,1-dioxo-3,6-di-
hydro-2H-thiopyran-4-yl)-8-methyl-7-oxo-pyrido[2,3-
d]pyrimidin-4-yl]amino]ethyl]phenyl]acetonitrile;

4-(((R)-1-(3-(difluoromethyl)-2-fluorophenyl)ethyl)
amino)-8-methyl-6-((1R,4r)-1-(methylimino)-1-oxido-
hexahydro-1λ⁶-thiopyran-4-yl)pyrido[2,3-d]pyrimi-
din-7(8H)-one;

4-(((R)-1-(3-(difluoromethyl)-2-fluorophenyl)ethyl)
amino)-8-methyl-6-((S)-1-(oxetan-3-ylimino)-1-
oxido-1,2,3,6-tetrahydro-1λ⁶-thiopyran-4-yl)pyrido[2,
3-d]pyrimidin-7(8H)-one;

4-(((R)-1-(3-(difluoromethyl)-2-fluorophenyl)ethyl)
amino)-8-methyl-6-((R)-1-(oxetan-3-ylimino)-1-
oxido-1,2,3,6-tetrahydro-1λ⁶-thiopyran-4-yl)pyrido[2,
3-d]pyrimidin-7(8H)-one;

4-[[(1R)-1-[3-(difluoromethyl)-2-fluoro-phenyl]ethyl]
amino]-6-(1-imino-1-oxo-thian-4-yl)-8-methyl-pyrido
[2,3-d]pyrimidin-7-one;

6-((1R,4r)-1-(cyclopropylimino)-4-methoxy-1-oxido-
hexahydro-1λ⁶-thiopyran-4-yl)-4-(((R)-1-(3-(difluo-
romethyl)-2-fluorophenyl)ethyl)amino)-8-meth-
ylpyrido[2,3-d]pyrimidin-7(8H)-one;

6-((1S,4s)-1-(cyclopropylimino)-4-methoxy-1-oxido-
hexahydro-1λ⁶-thiopyran-4-yl)-4-(((R)-1-(3-(difluo-
romethyl)-2-fluorophenyl)ethyl)amino)-8-meth-
ylpyrido[2,3-d]pyrimidin-7(8H)-one; and N-[3-(4-{[(1R)-1-[3-(difluoromethyl)-2-fluorophenyl]
ethyl]amino}-8-methyl-7-oxo-7H,8H-pyrido[2,3-d]py-
rimidin-6-yl)bicyclo[1.1.1]pentan-1-yl]acetamide;

or a pharmaceutically acceptable salt or a stereoisomer
thereof.

2. The compound of claim 1, or a pharmaceutically
acceptable salt thereof.

3. A compound, or a pharmaceutically acceptable salt or
a stereoisomer thereof, selected from among the compounds
in the following table:

| Structure | Structure |
|---|---|
| 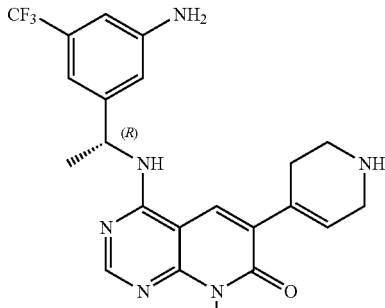 | 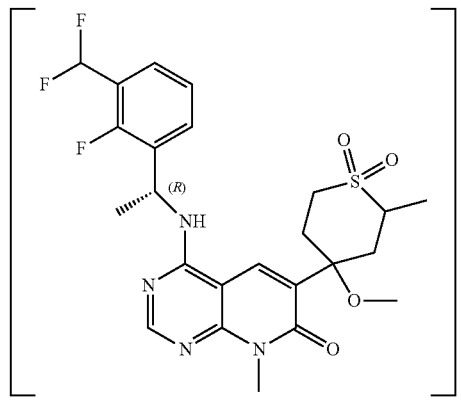 |

| Structure | Structure |
|---|---|
| 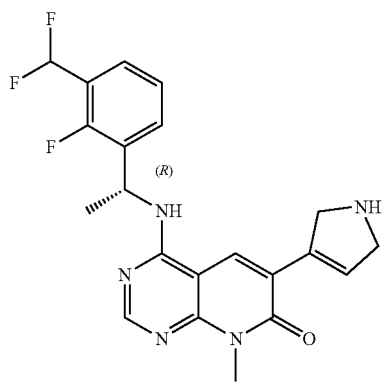 | |
| 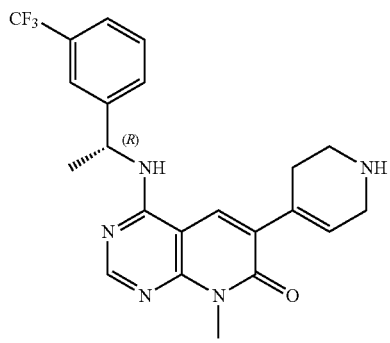 | |
| 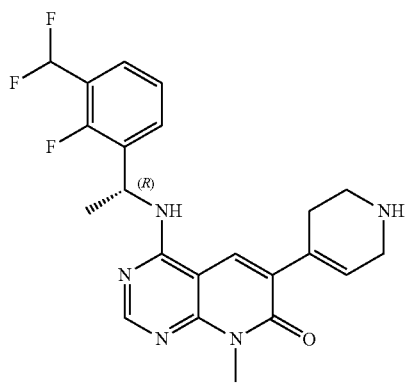 | 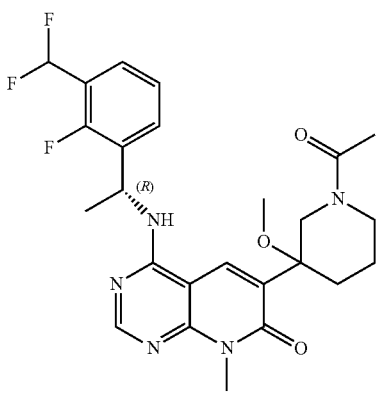 |
| 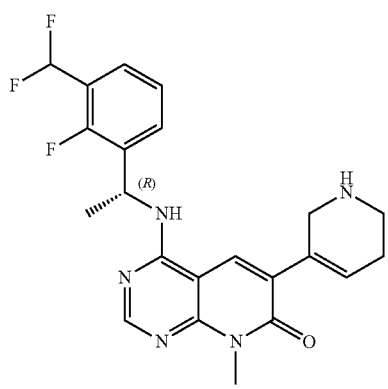 | 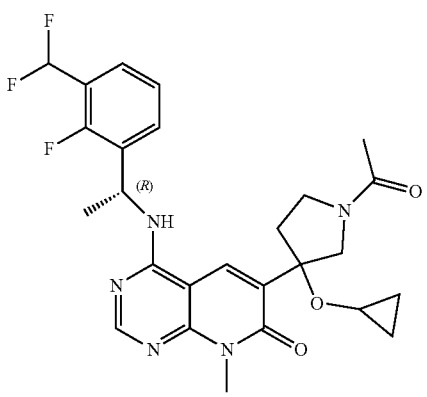 |

| Structure | Structure |
|---|---|
| 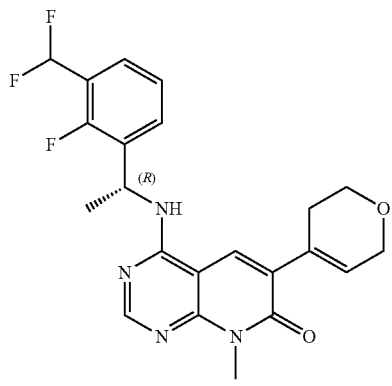 | 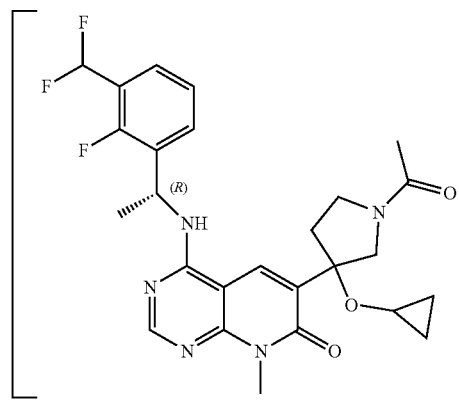 |
| 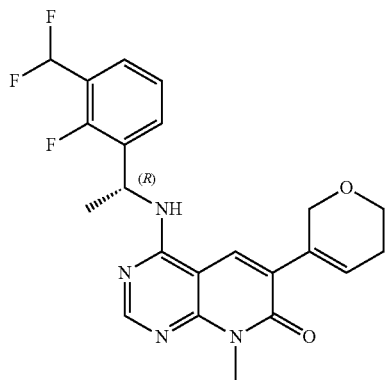 | 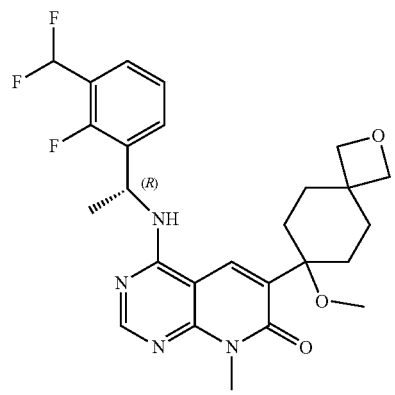 |
| 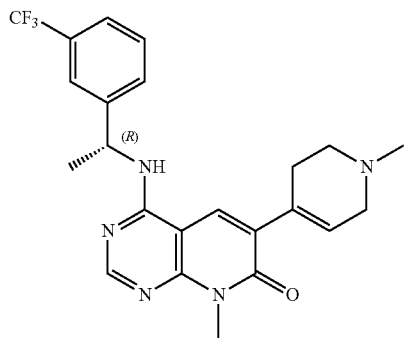 | 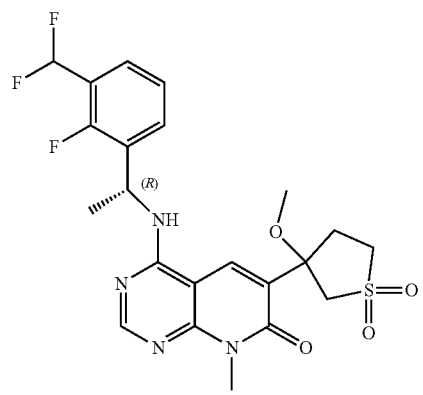 |
| 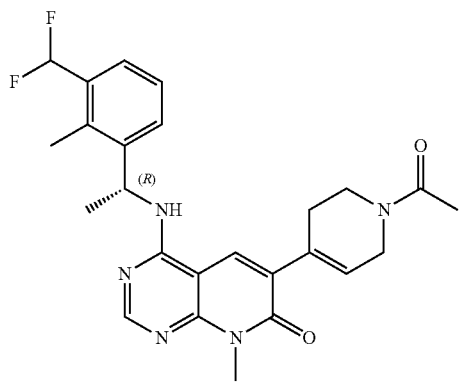 | 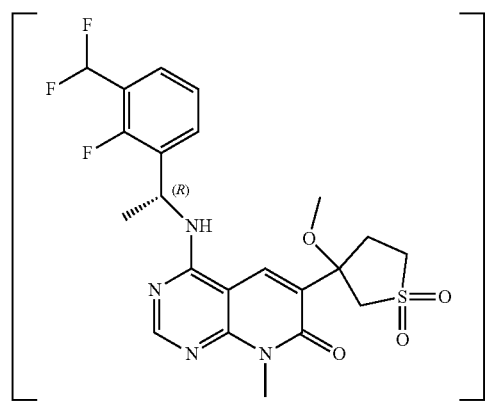 |

| Structure | Structure |
|---|---|
| 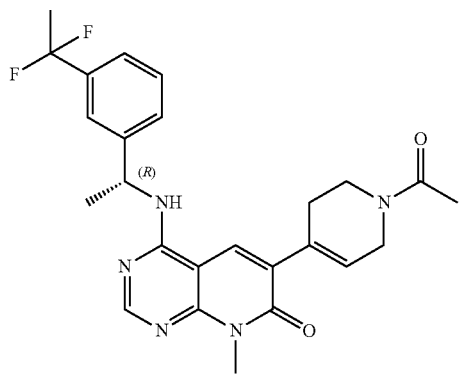 | 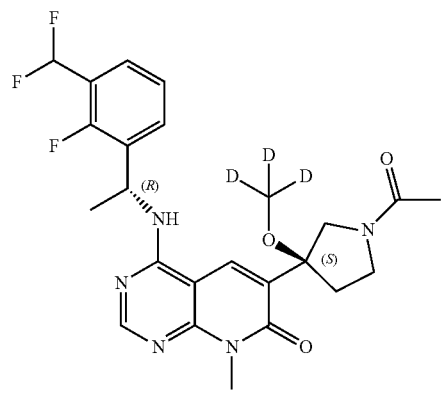 |
| 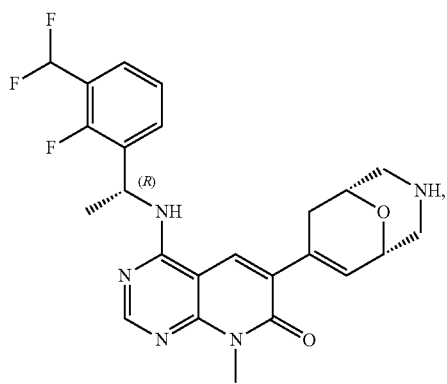 | 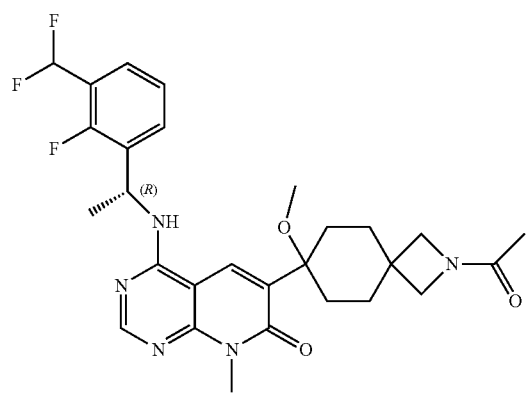 |
| 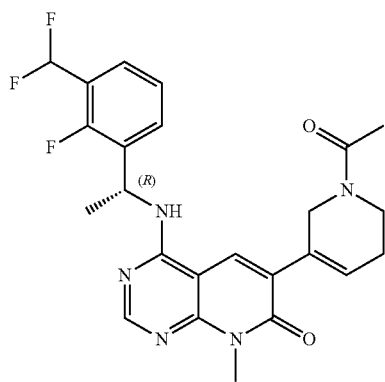 | 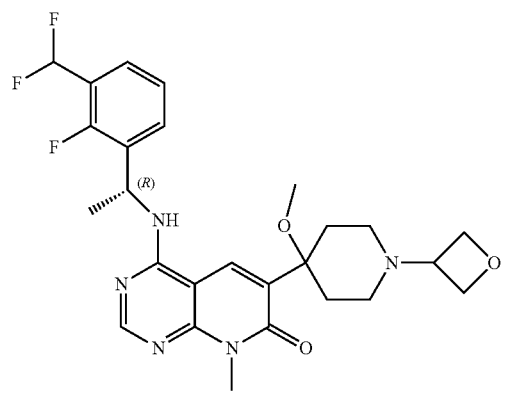 |
| 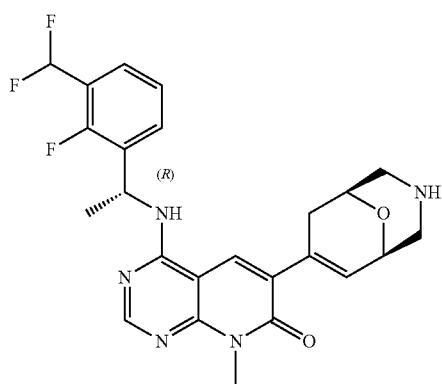 | 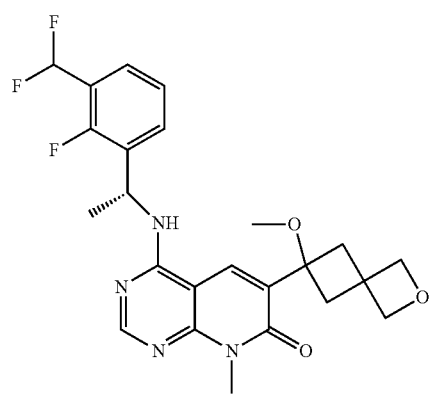 [SMILES: COC1(c2cc3c(N[C@H](C)c4cccc(C(F)F)c4F)ncnc3n(C)c2=O)CC2(COC2)C1] |

| Structure | Structure |
|---|---|
| 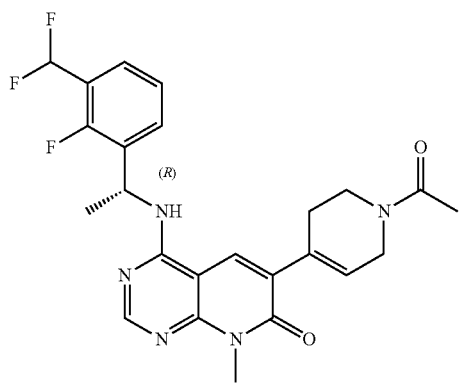 | 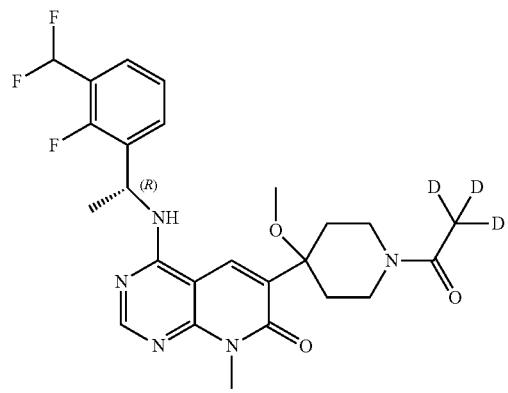 |
| 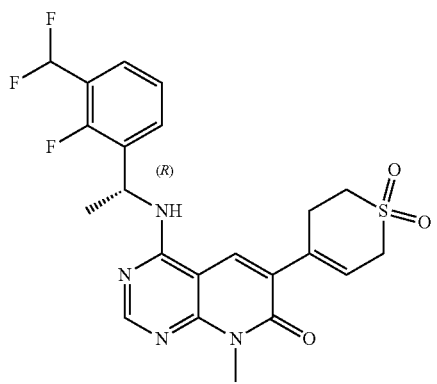 | 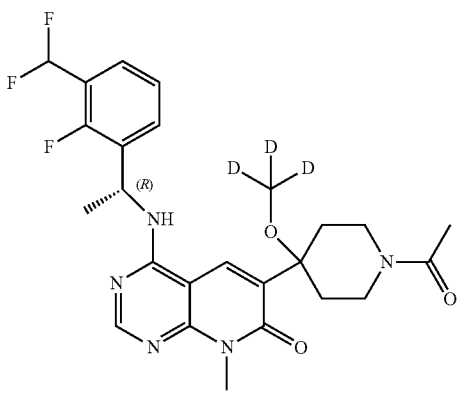 |
| 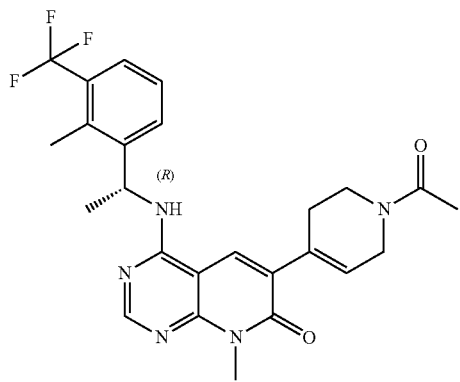 | 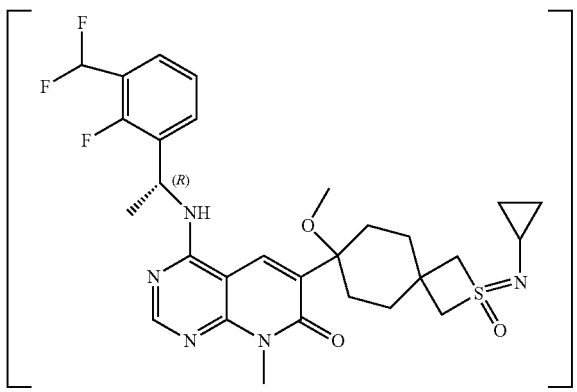 |
| 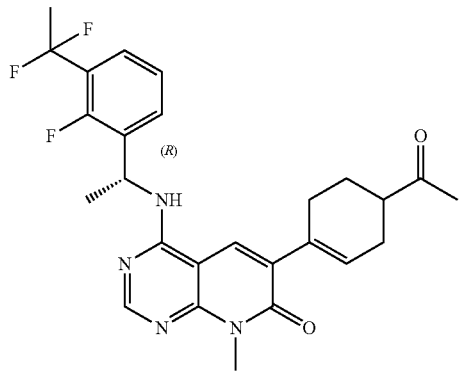 | 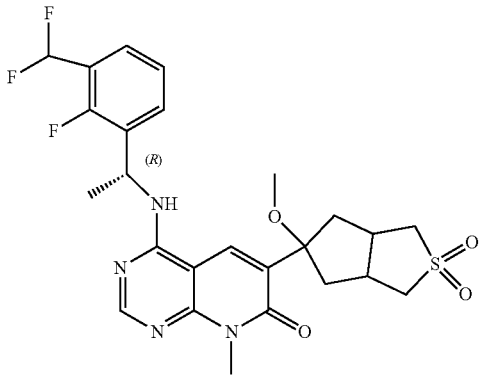 |

| Structure | Structure |
|---|---|
| 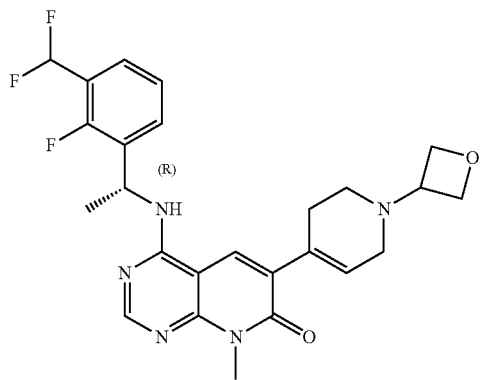 | 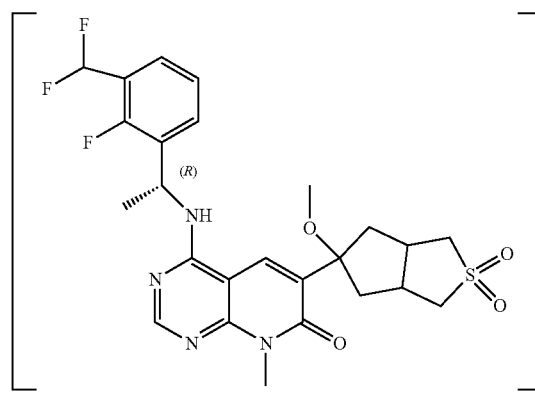 |
| 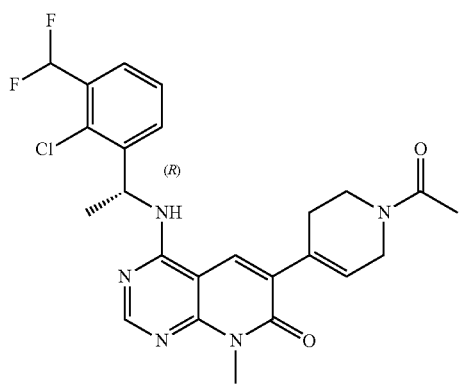 | 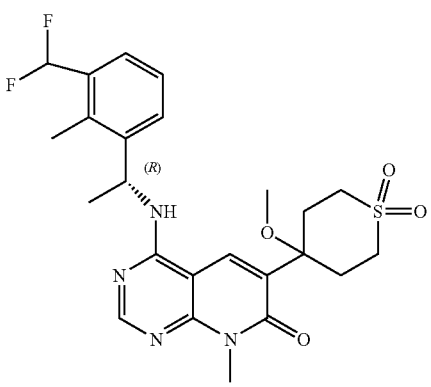 |
| 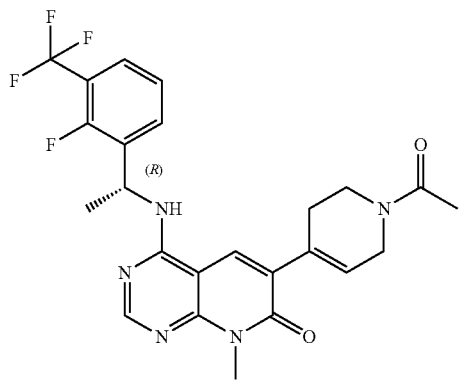 | 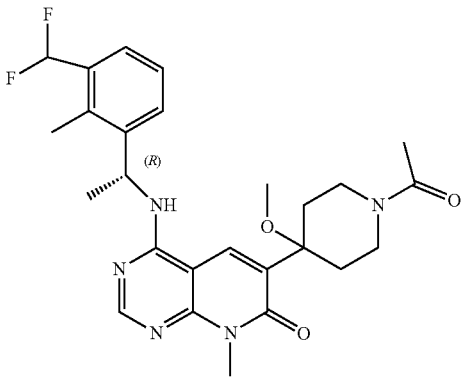 |
| 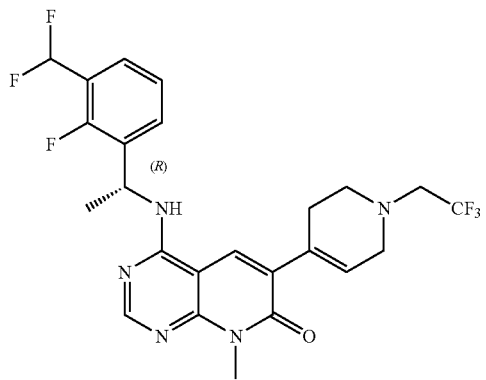 | 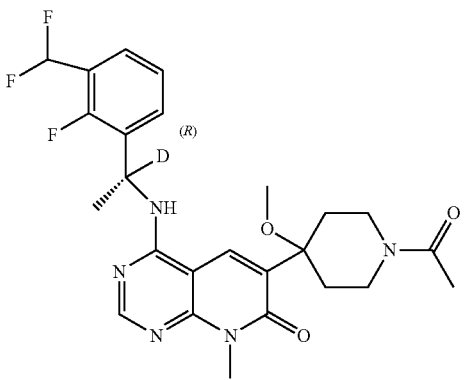 |

| Structure | Structure |
|---|---|
| 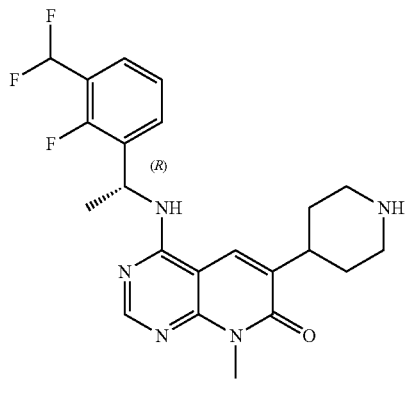 | 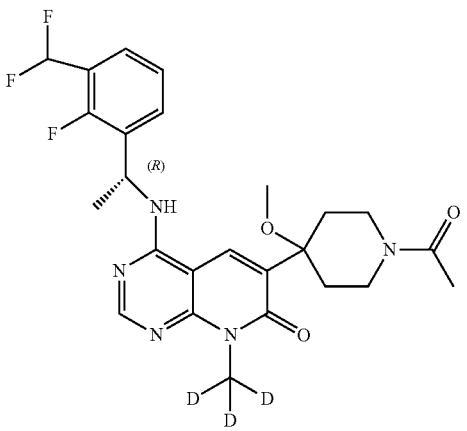 |
| 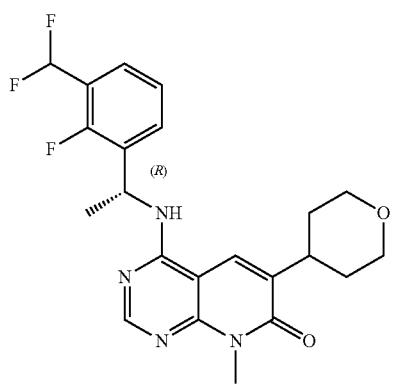 | 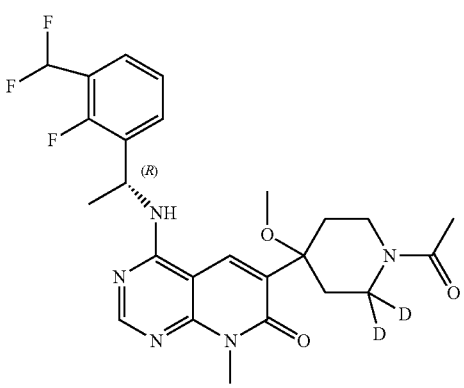 |
| 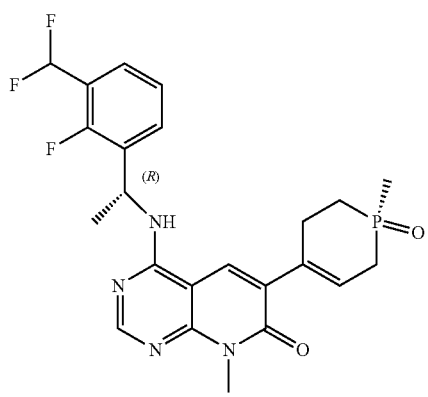 | 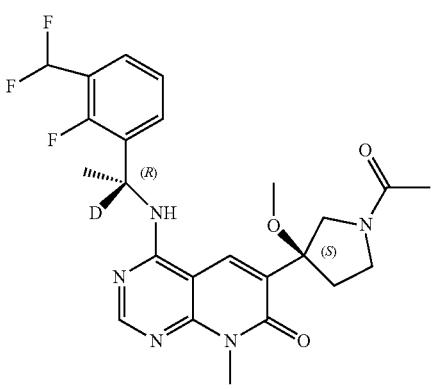 |
| 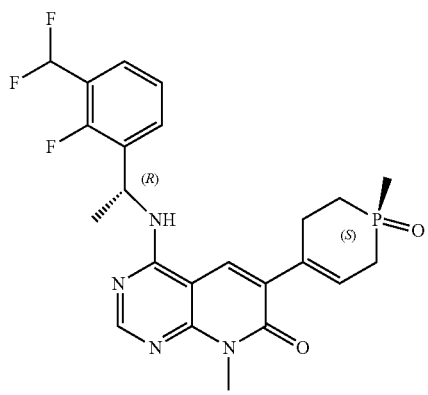 | 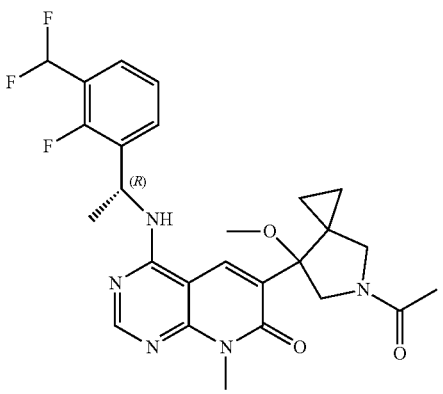 |

-continued
| Structure | Structure |
|---|---|
| 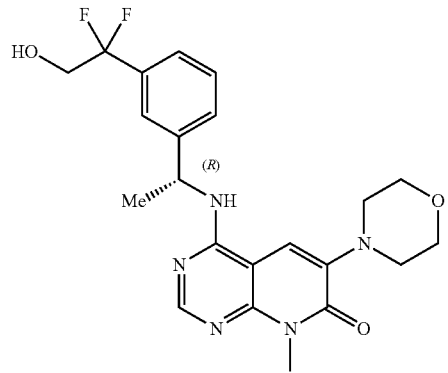 | 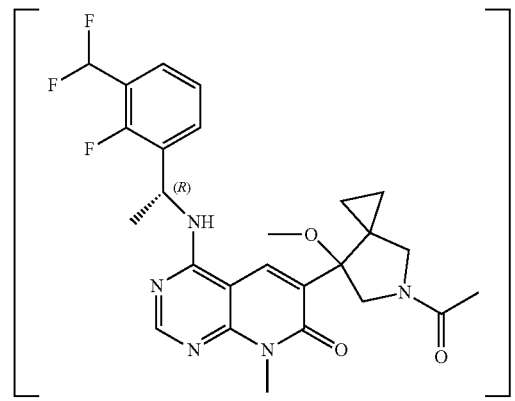 |
| 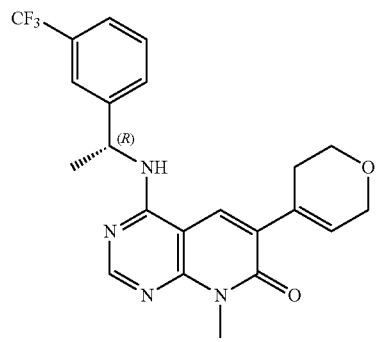 | 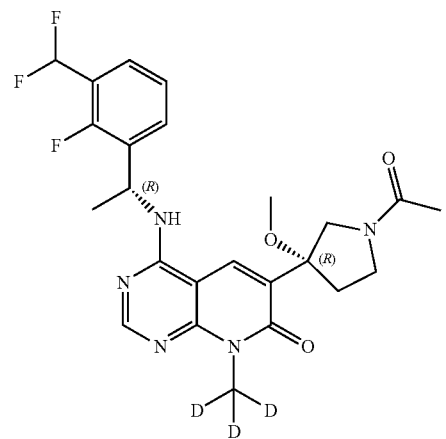 |
| 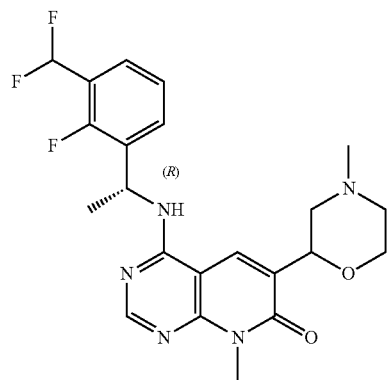 | 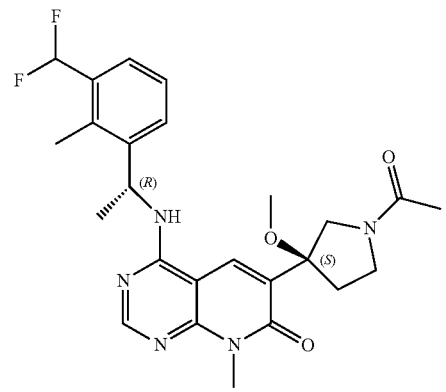 |

| Structure | Structure |
|---|---|
| 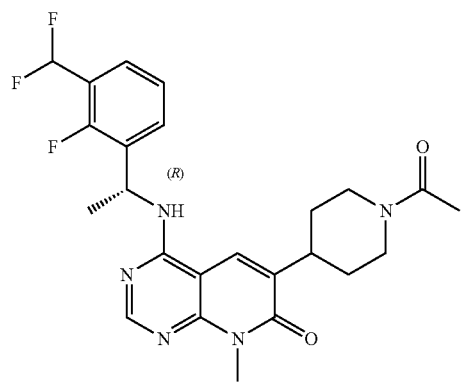 | 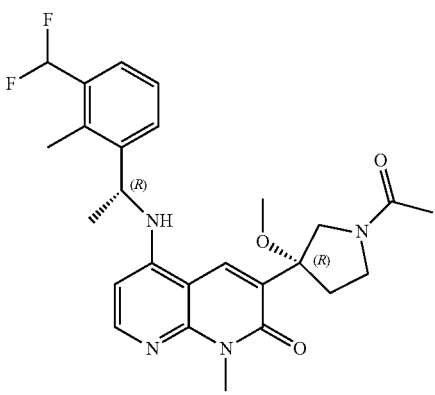 |
| 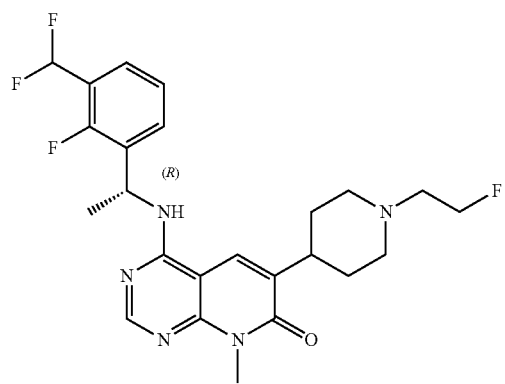 | 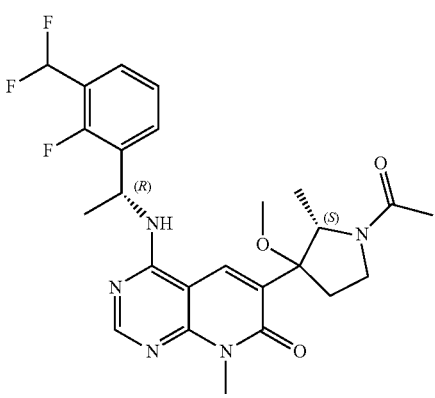 |
| 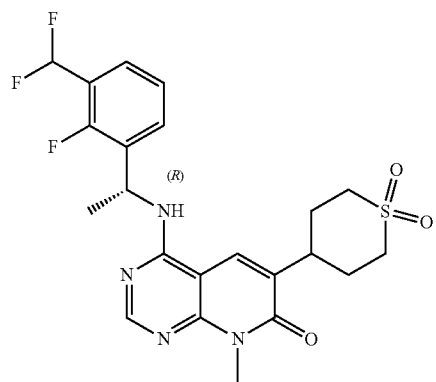 | 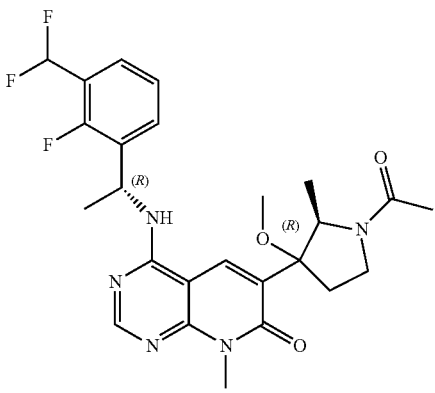 |
| 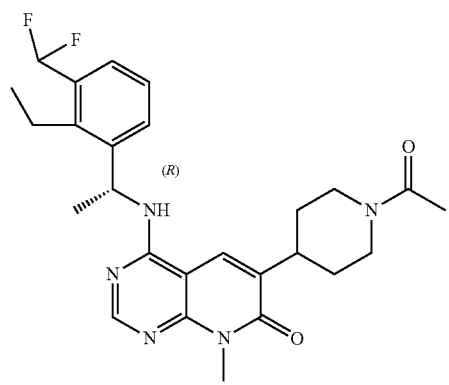 | 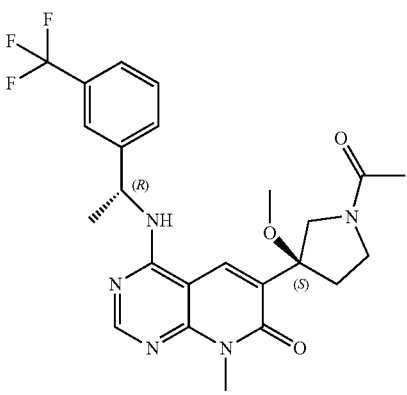 |

-continued
| Structure | Structure |
|---|---|
| 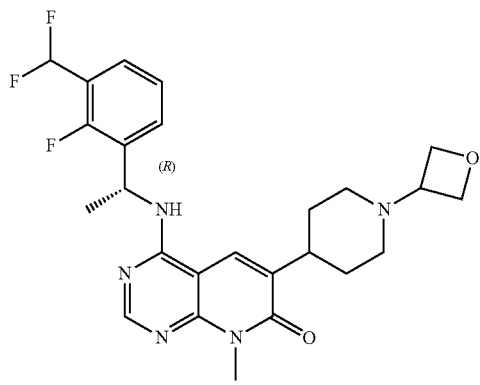 | 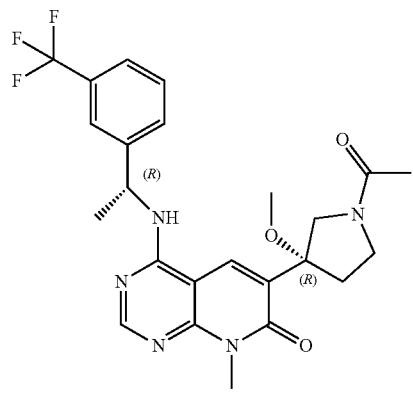 |
| 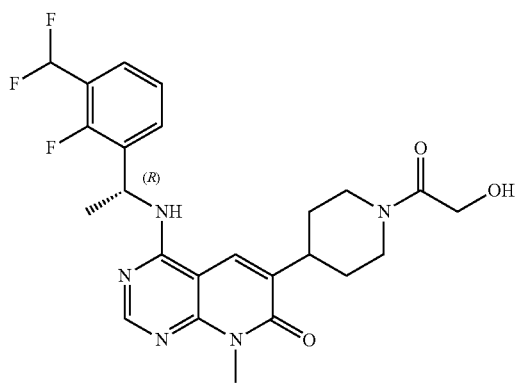 | 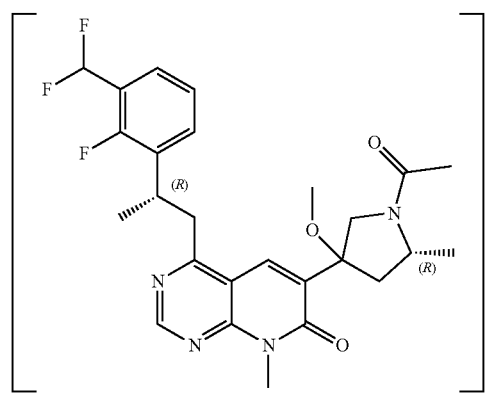 |
| 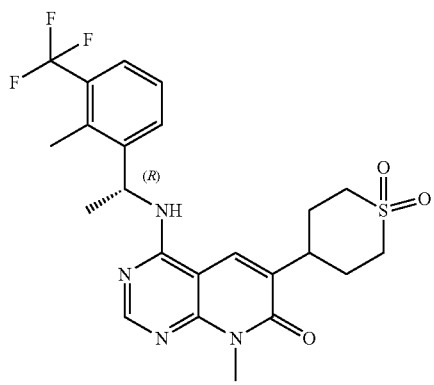 | 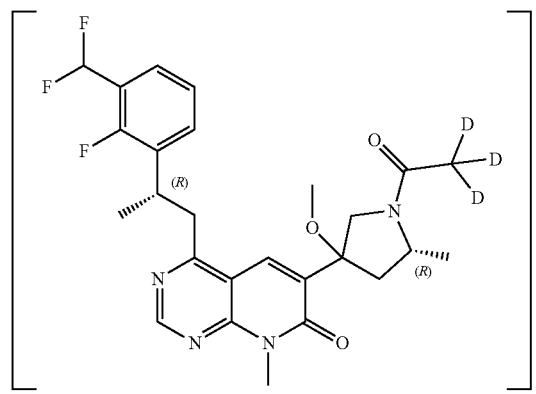 |
| 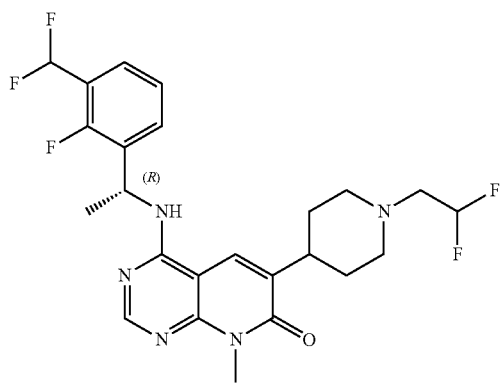 | 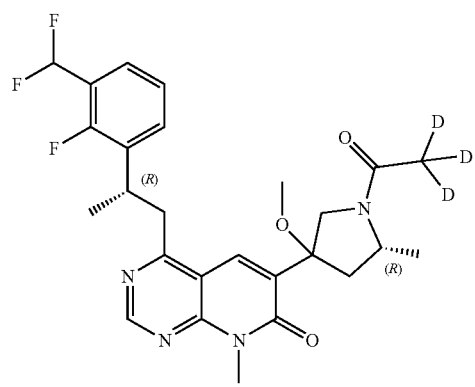 |

| Structure | Structure |
|---|---|
| 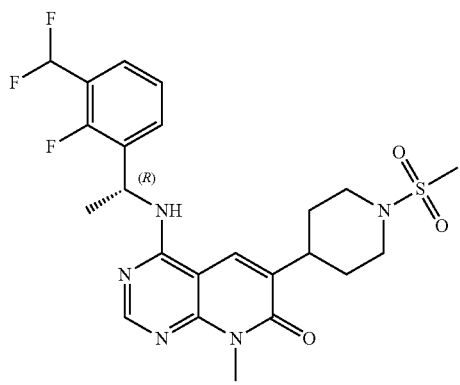 | 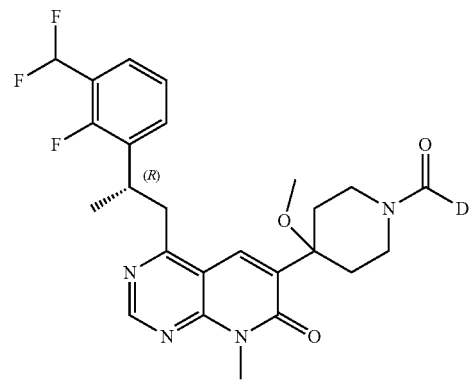 |
| 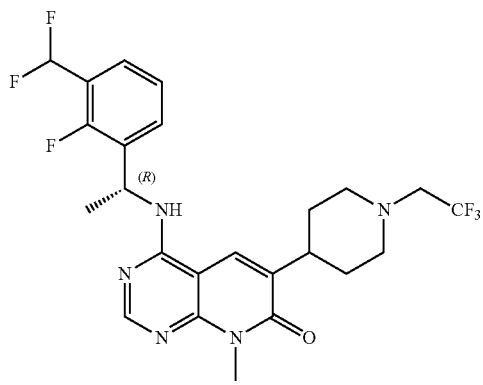 | 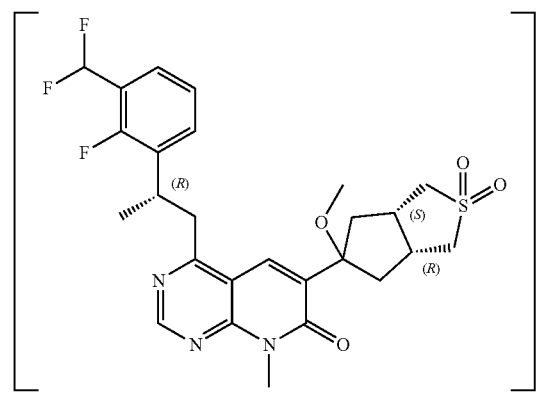 |
| 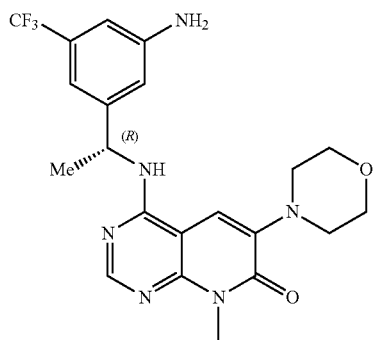 | 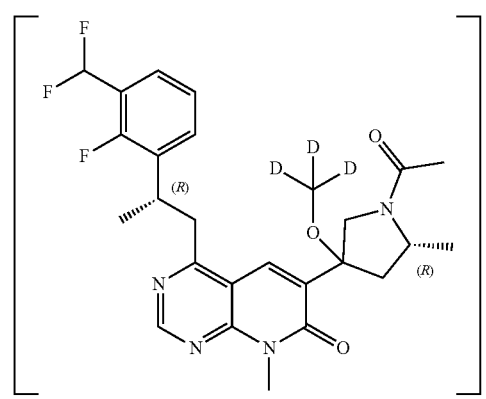 |
| 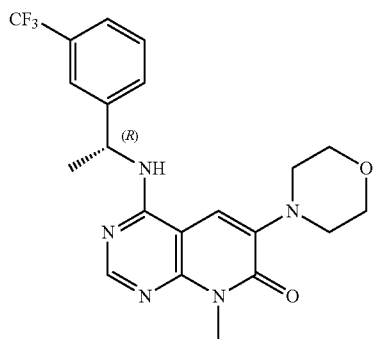 | 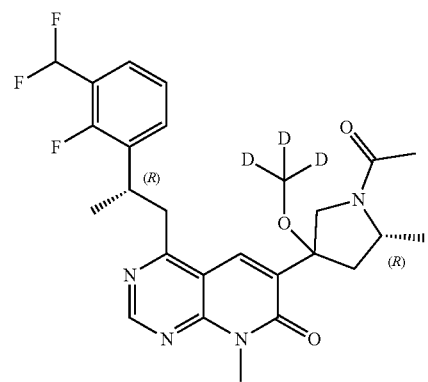 |

| Structure | Structure |
|---|---|
| 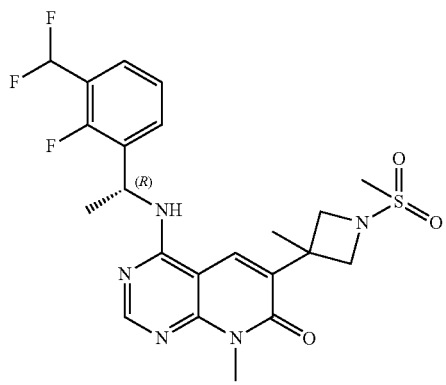 | 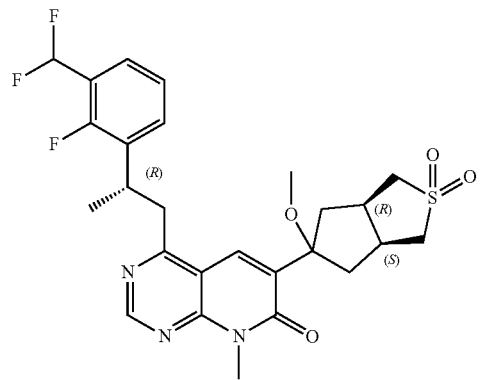 |
| 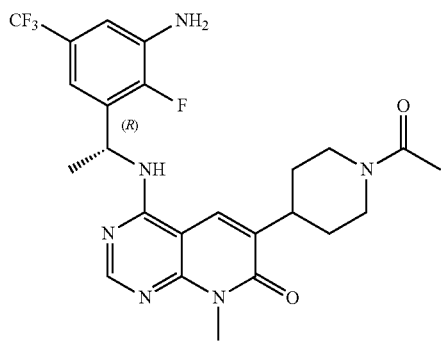 | 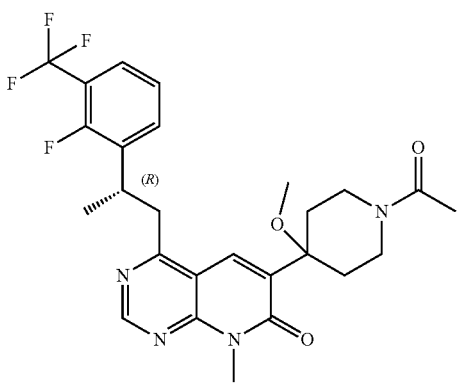 |
| 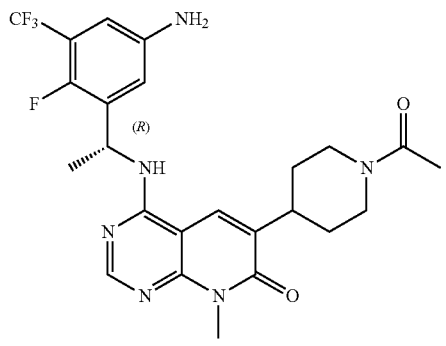 | 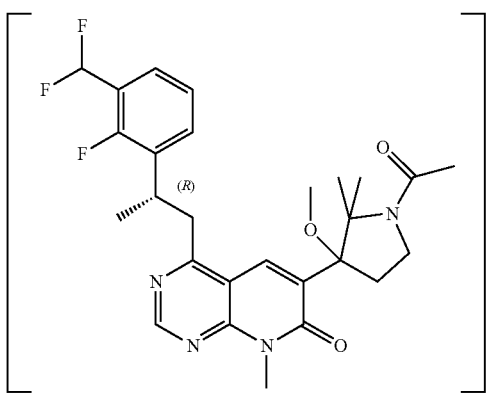 |
| 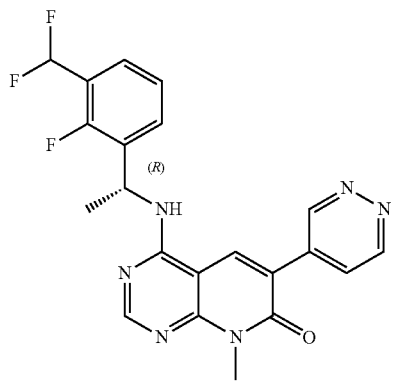 | 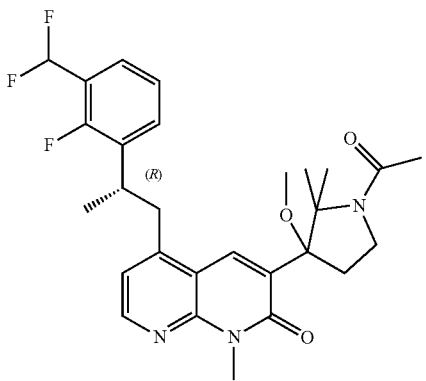 |

| Structure | Structure |
|---|---|
| 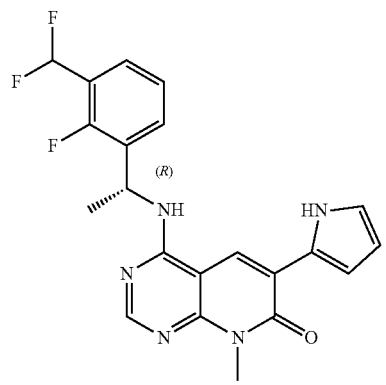 | 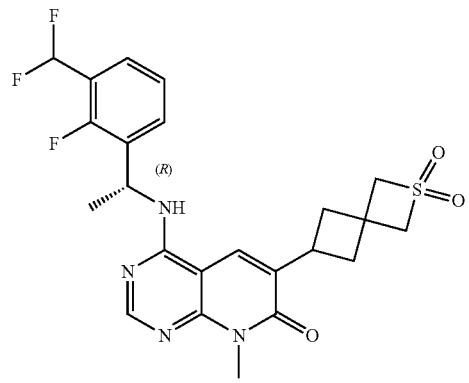 |
| 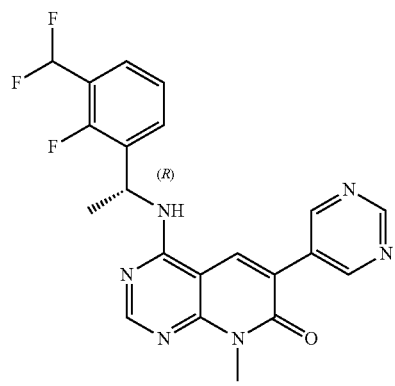 | 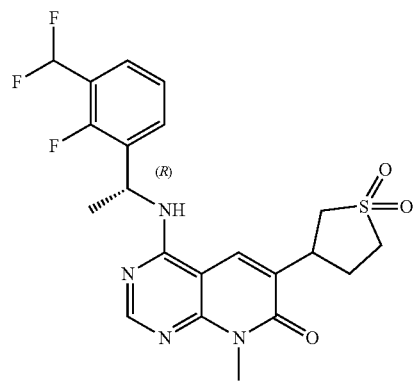 |
| 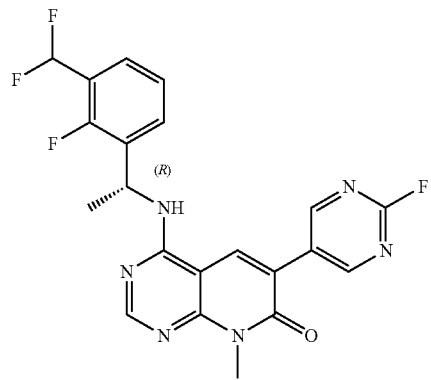 | 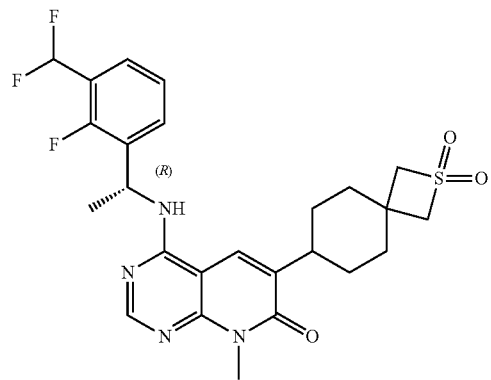 |
| 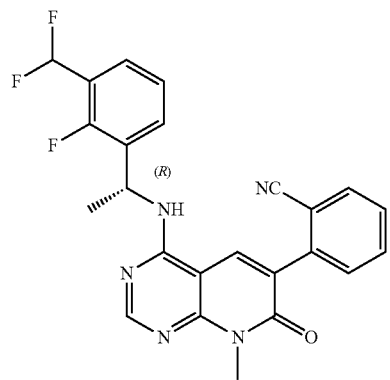 | 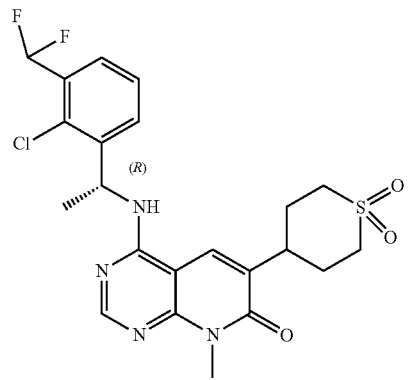 |

-continued
| Structure | Structure |
|---|---|
| 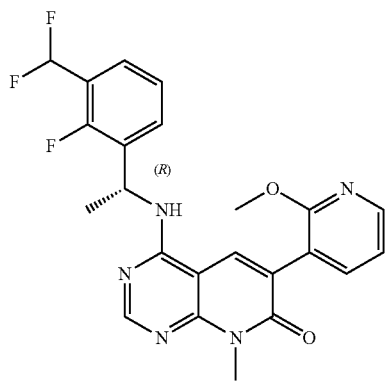 | 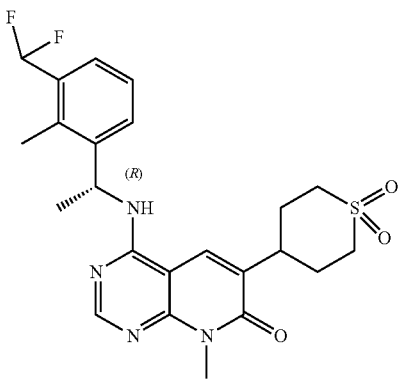 |
| 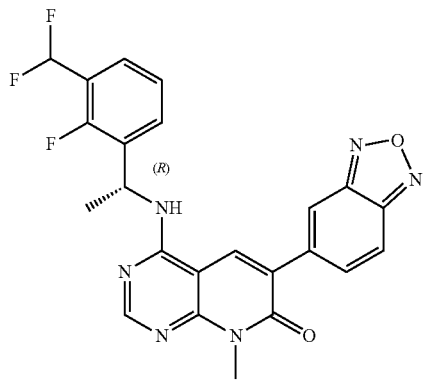 | 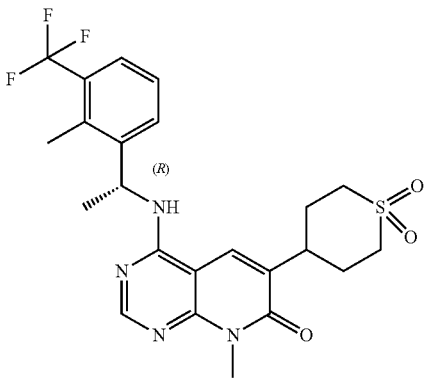 |
| 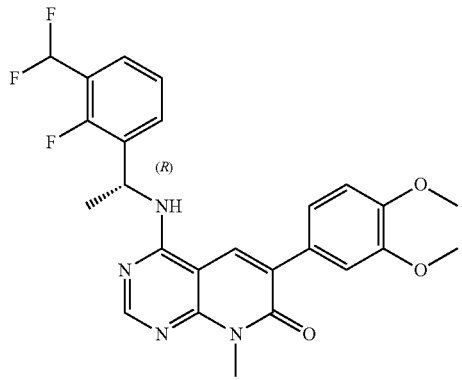 | 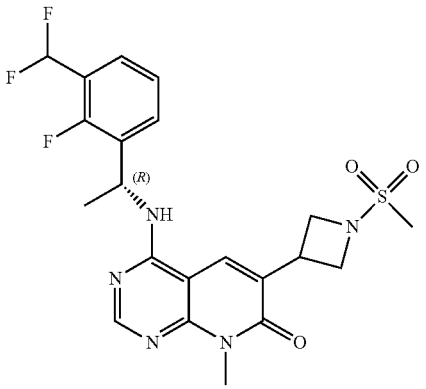 |
| 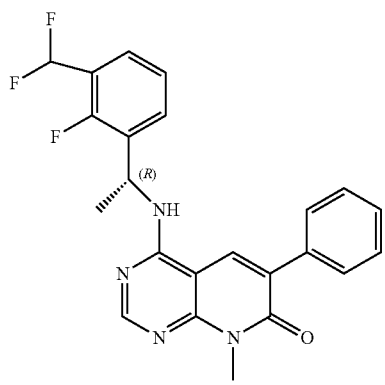 | 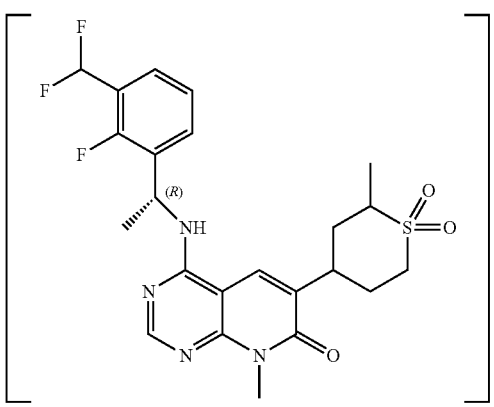 |

| Structure | Structure |
|---|---|
| 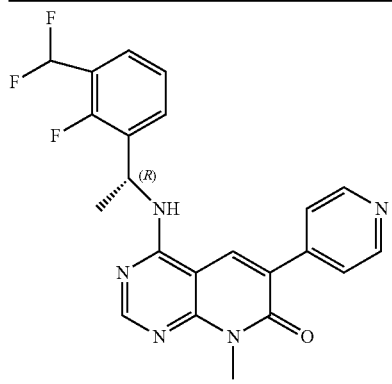 | |
| 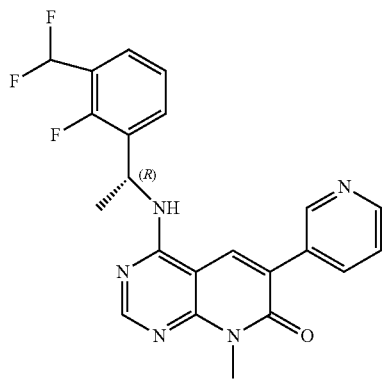 | 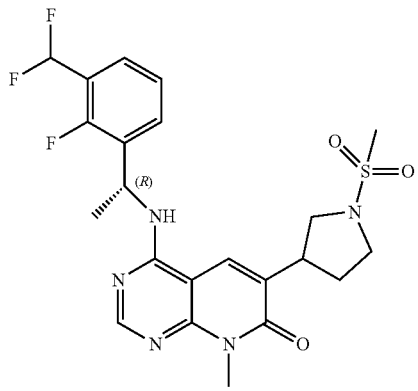 |
| 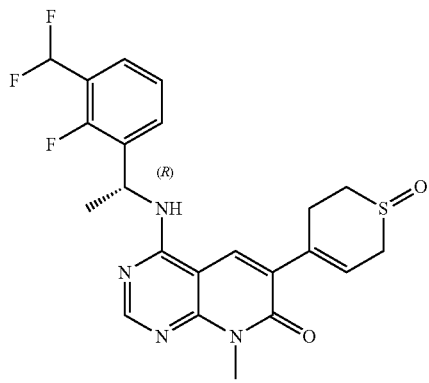 | 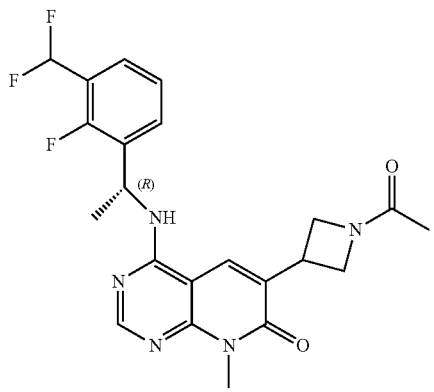 |
| 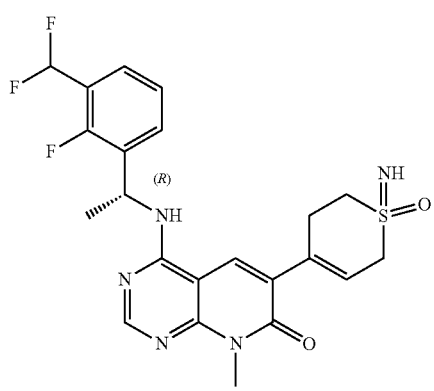 | 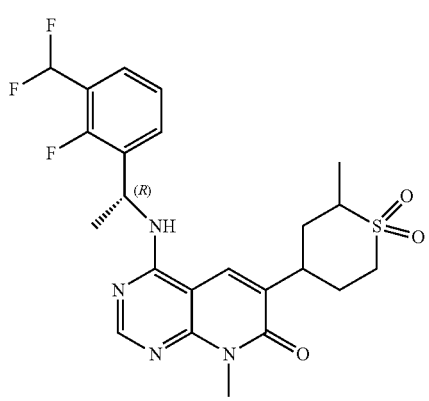 |

| Structure | Structure |
|---|---|
| 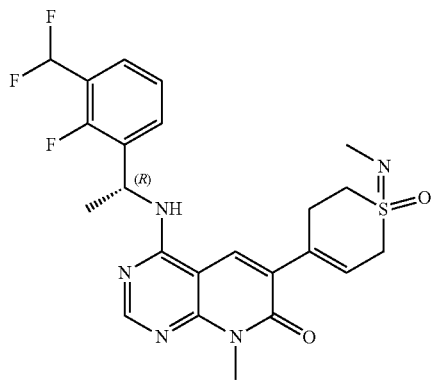 | |
| 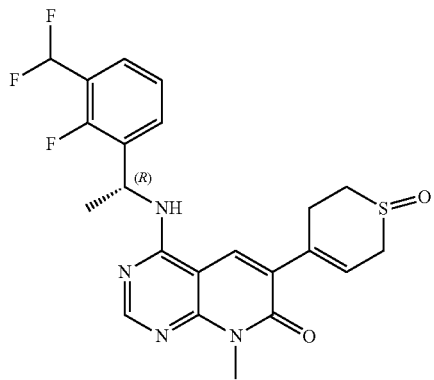 | 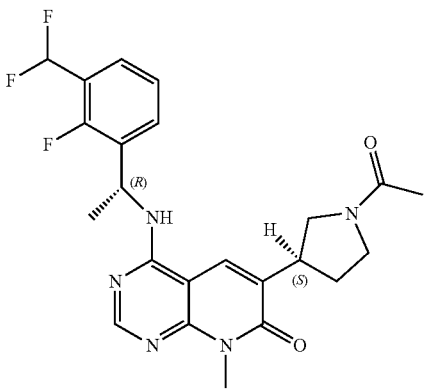 |
| 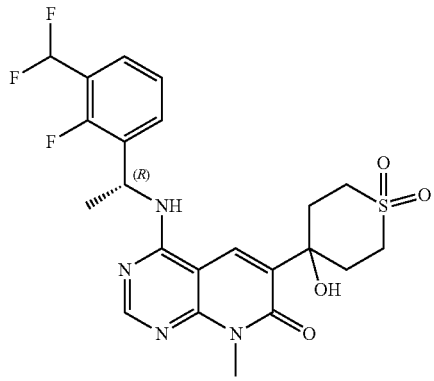 | 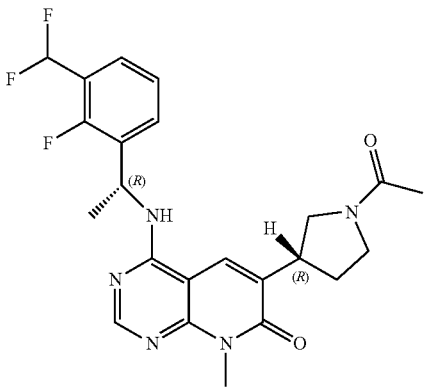 |
| 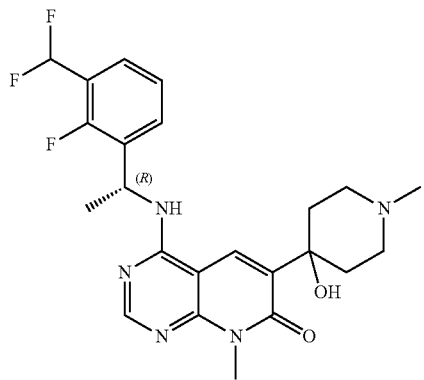 | 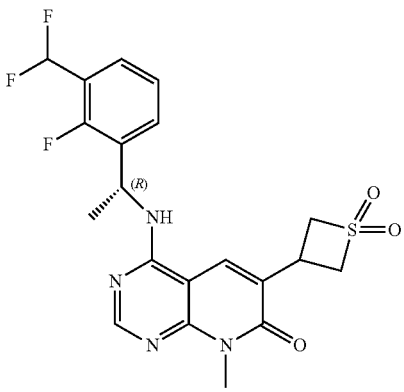 |

| Structure | Structure |
|---|---|
| 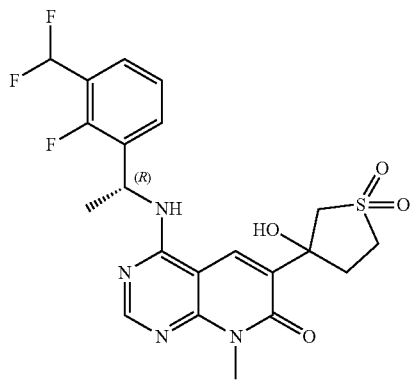 | 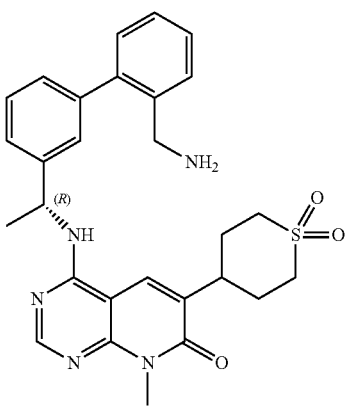 |
| 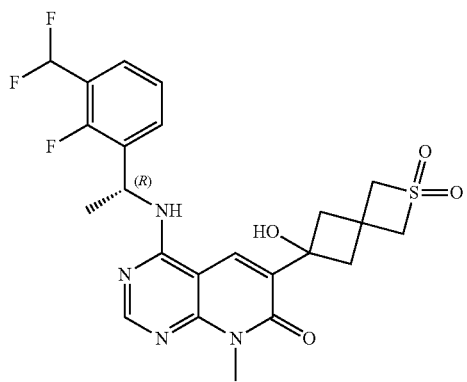 | 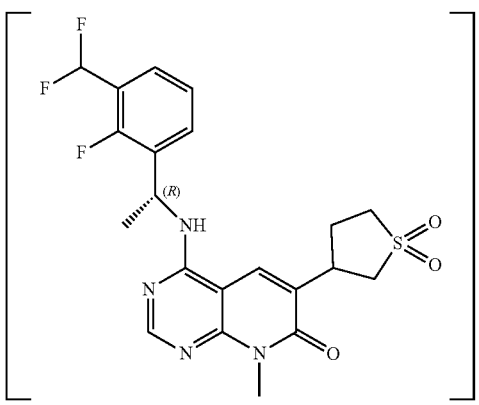 |
| 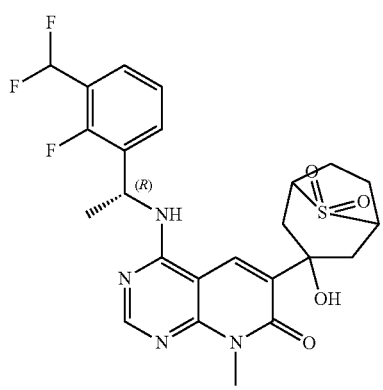 | |
| 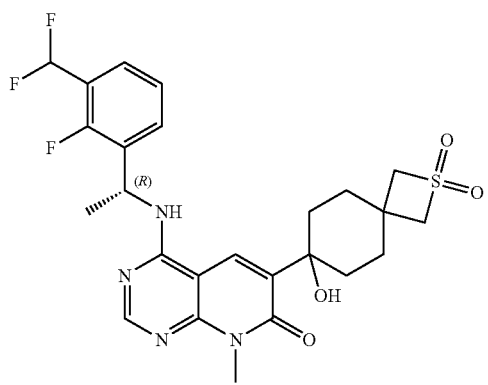 | 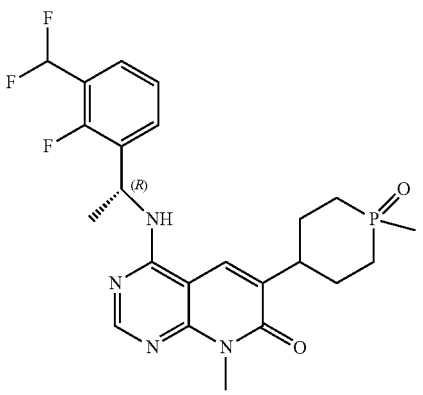 |

| Structure | Structure |
|---|---|
| 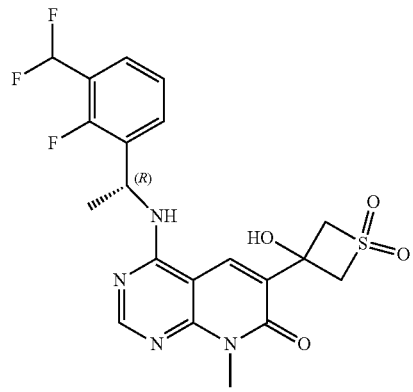 | 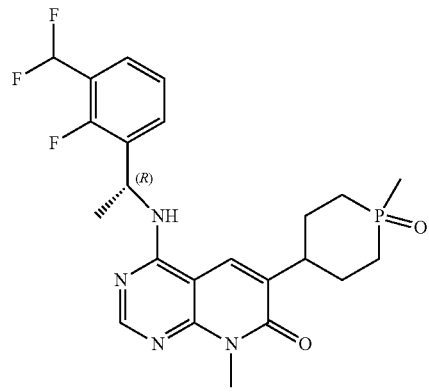 |
| 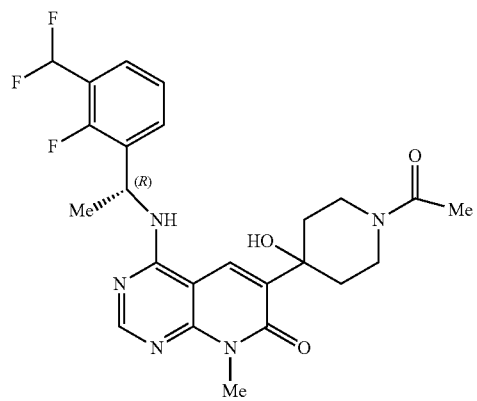 | 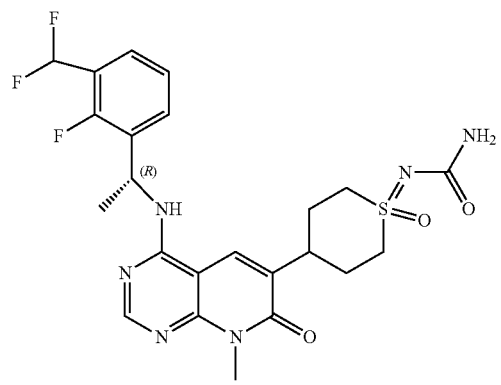 |
| 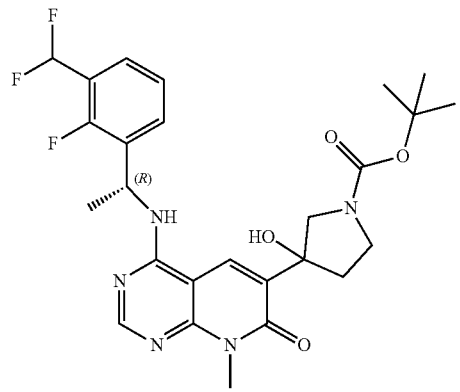 | 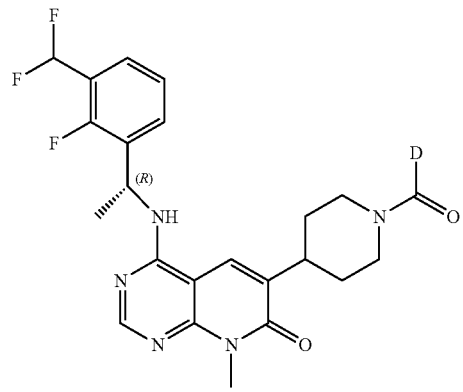 |
| 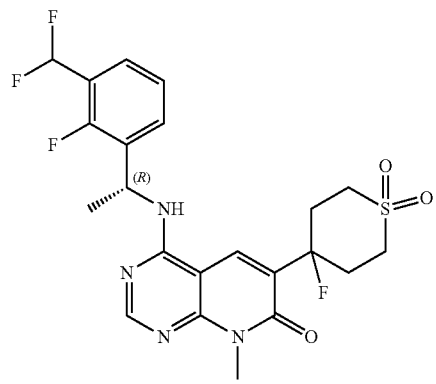 | 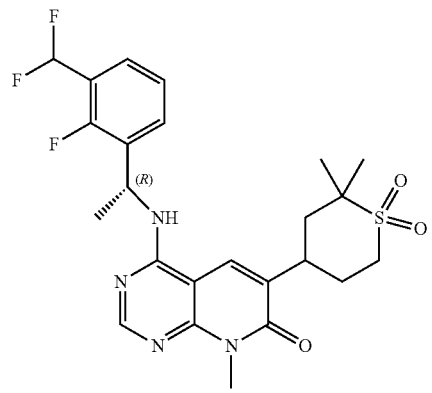 |

| Structure | Structure |
|---|---|
| 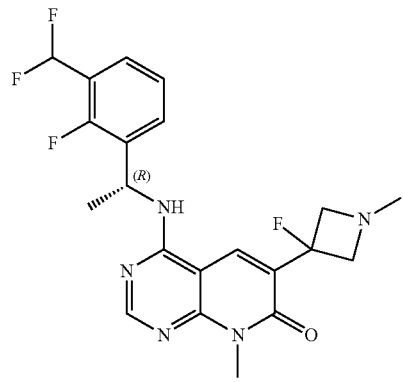 | 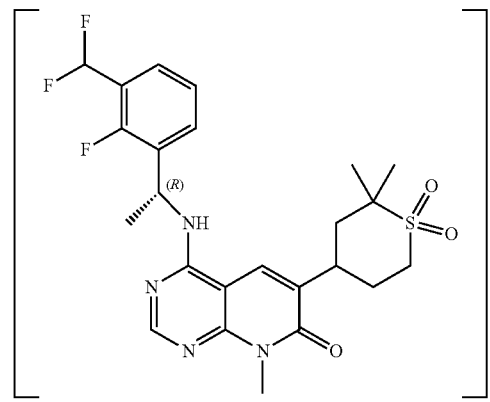 |
| 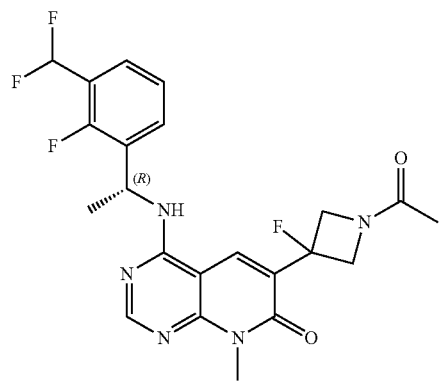 | 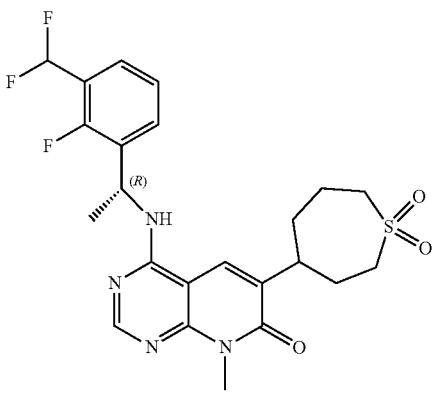 |
| 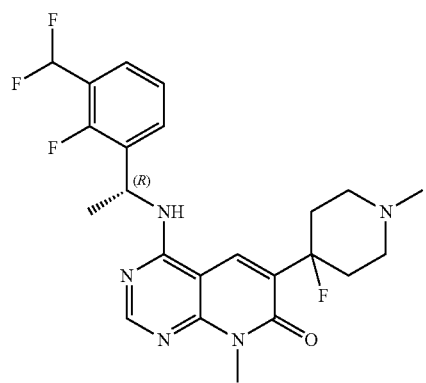 | 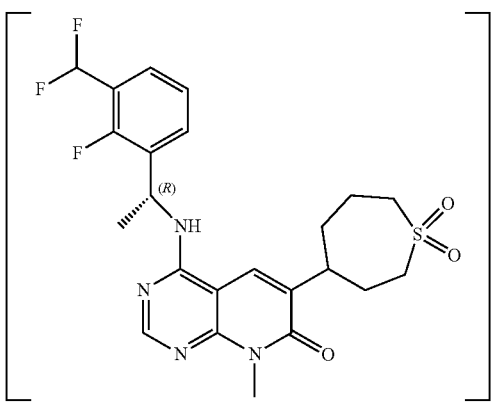 |
| 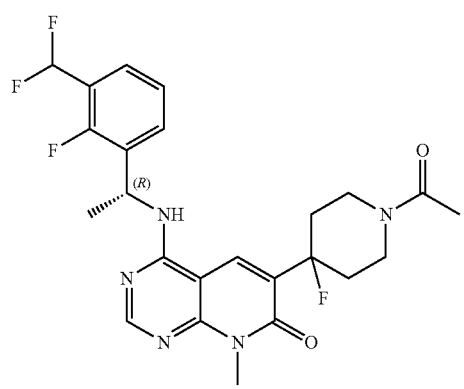 | 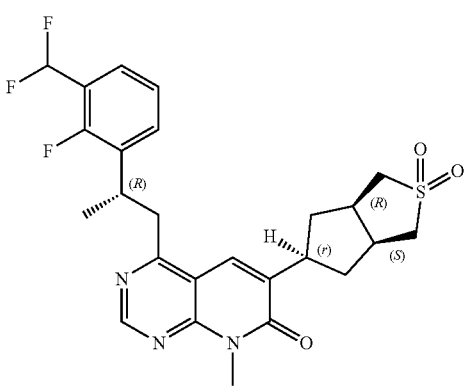 |

| Structure | Structure |
|---|---|
| 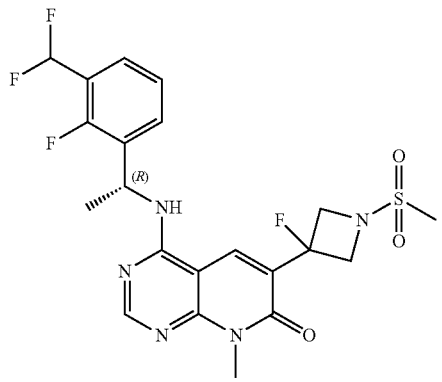 | 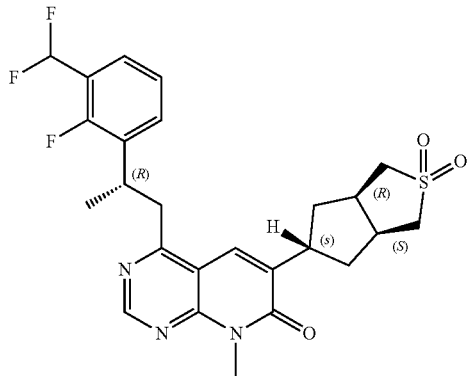 |
| 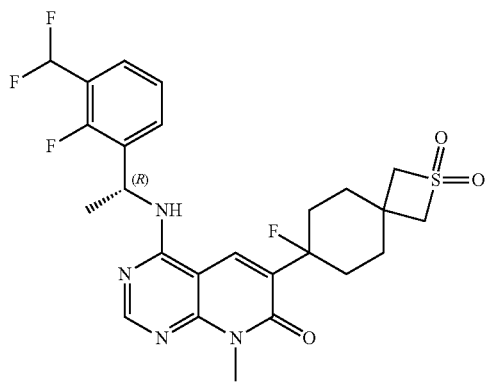 | |
| 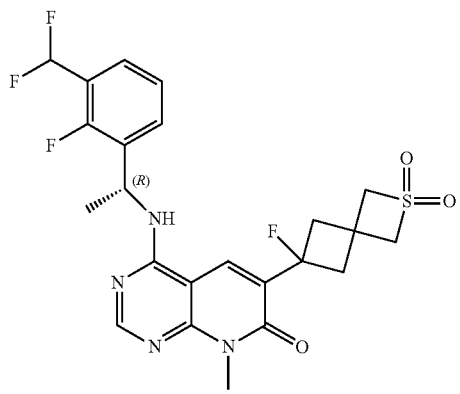 | |
| 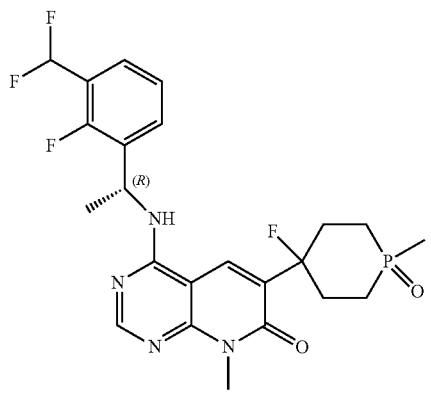 | 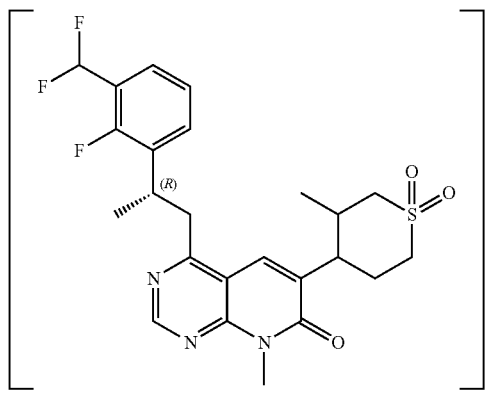 |

-continued
| Structure | Structure |
|---|---|
| 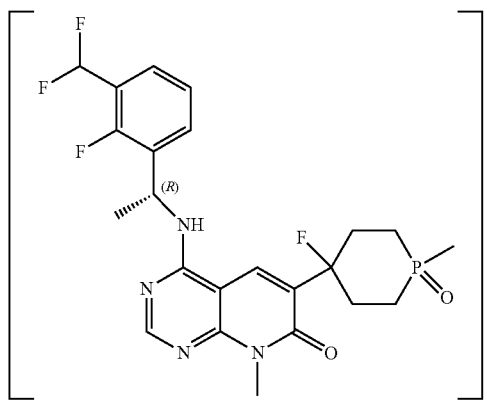 | 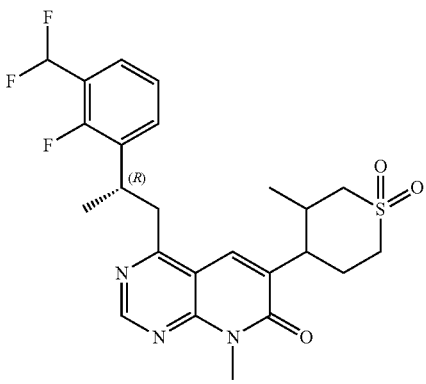 |
| 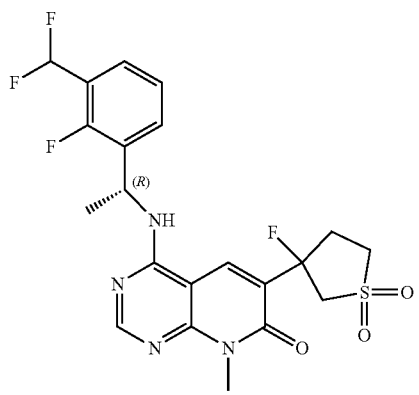 | 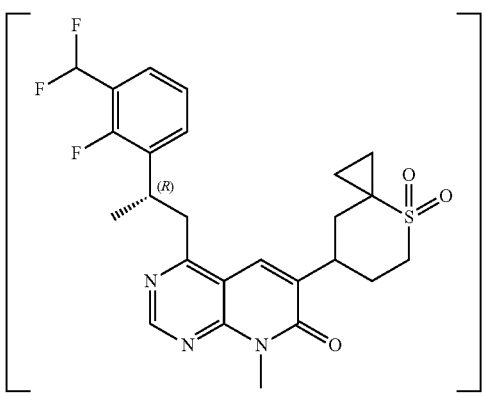 |
| 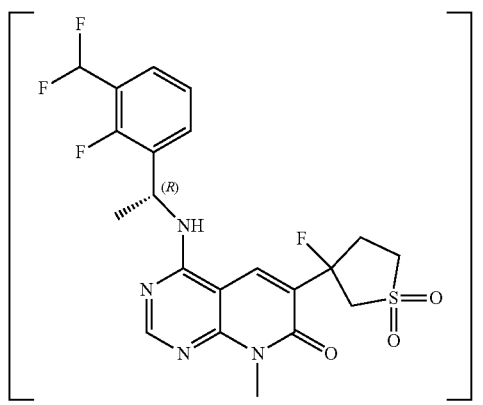 | 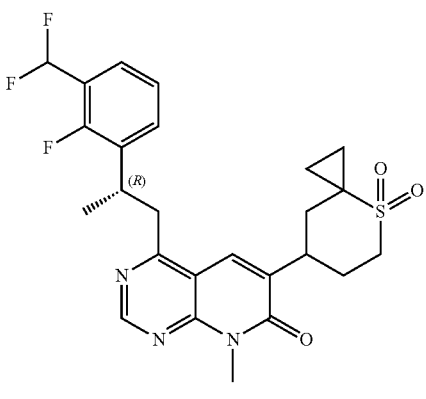 |
| 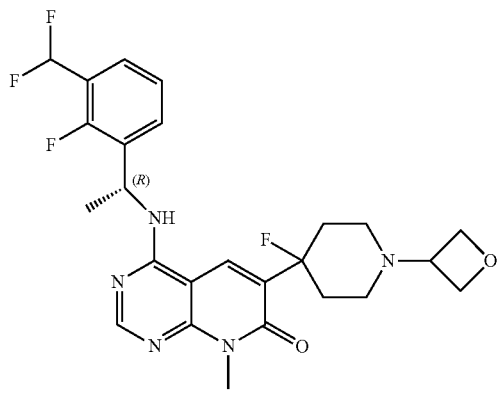 | 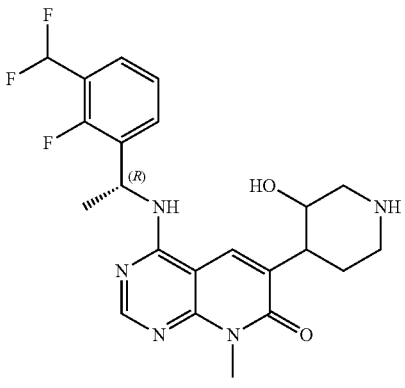 |

| Structure | Structure |
|---|---|
| 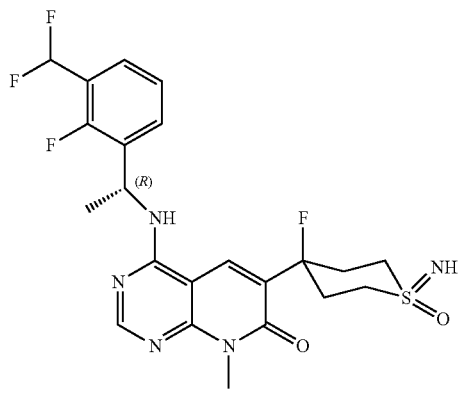 | 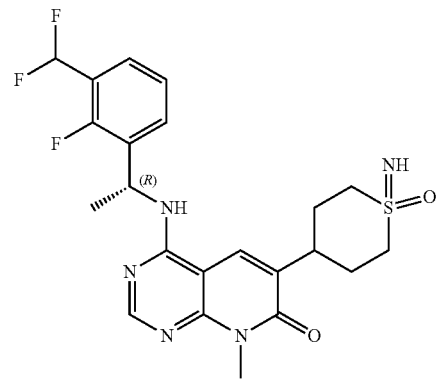 |
| 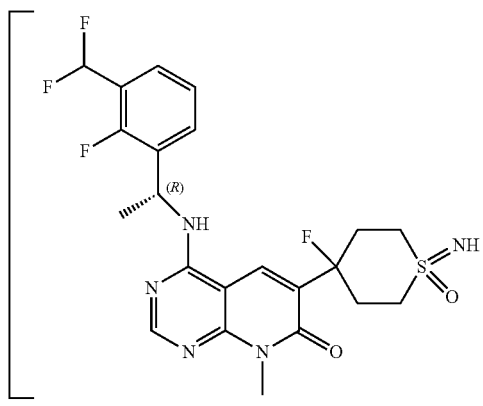 | 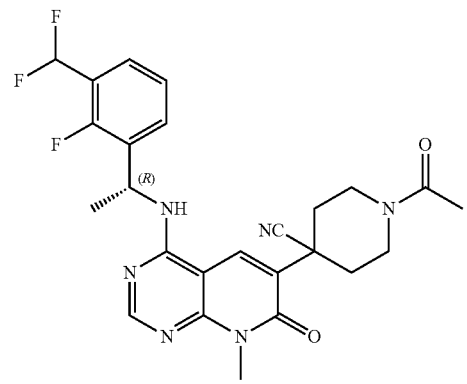 |
| 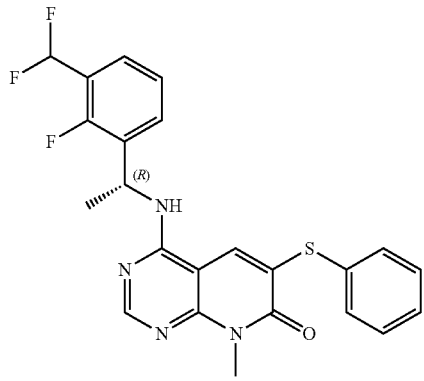 | 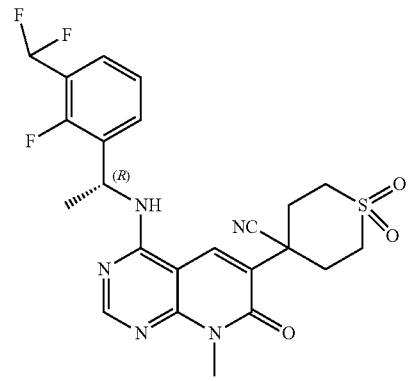 |
| 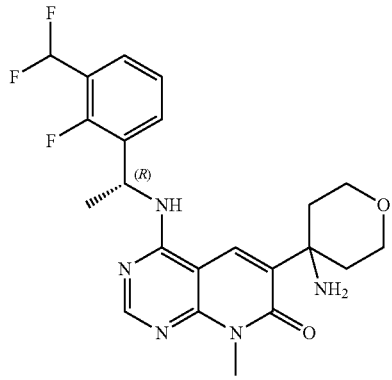 | 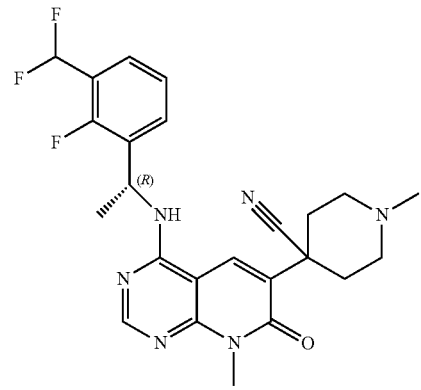 |

| Structure | Structure |
|---|---|
| 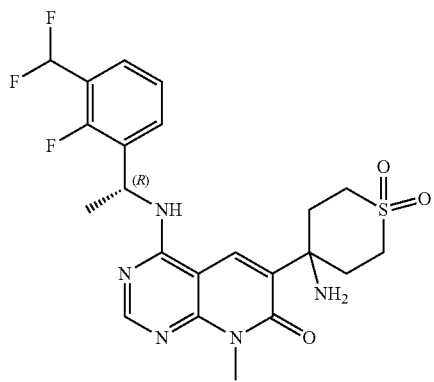 | 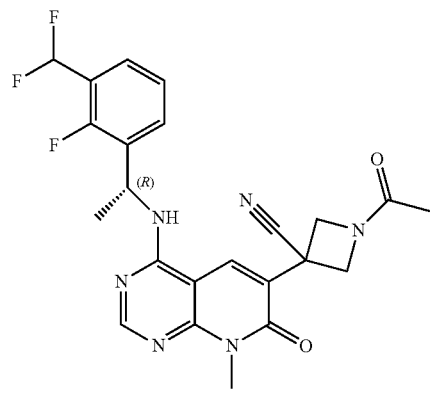 |
| 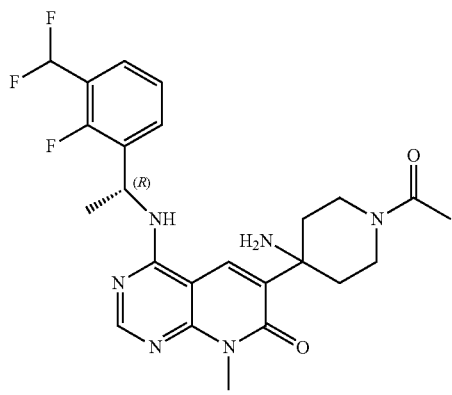 | 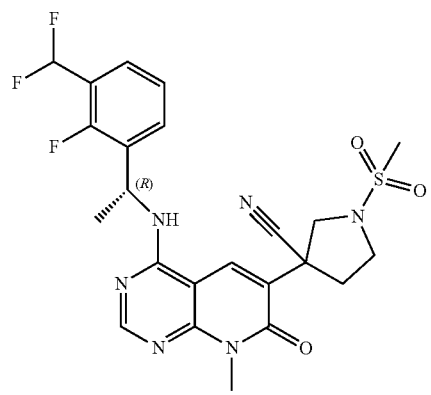 |
| 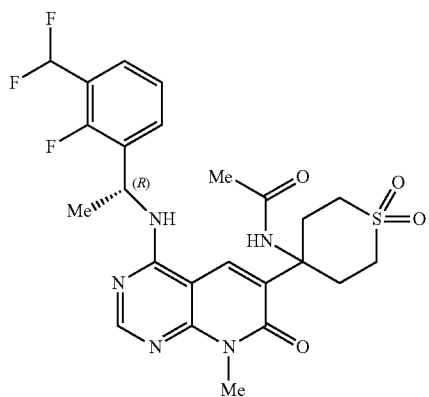 | 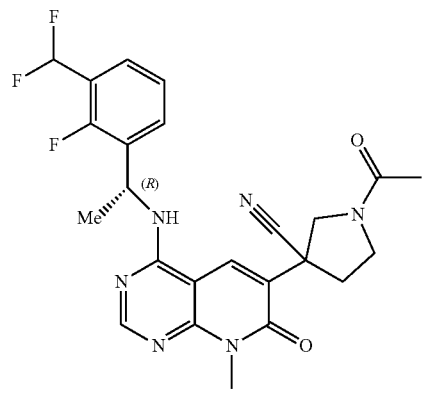 |
| 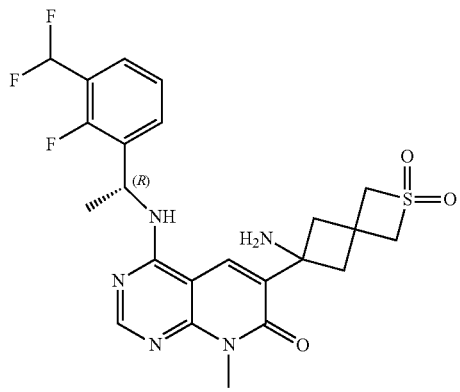 | 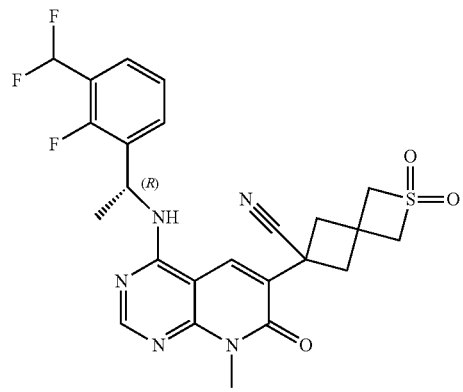 |

| Structure | Structure |
|---|---|
| 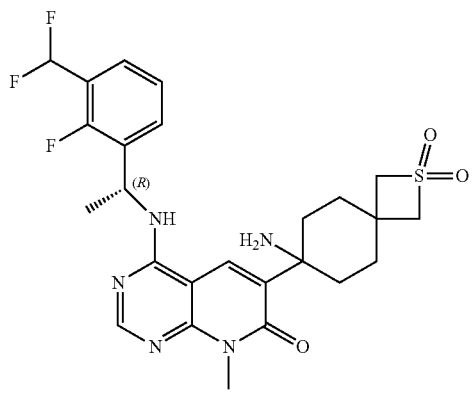 | 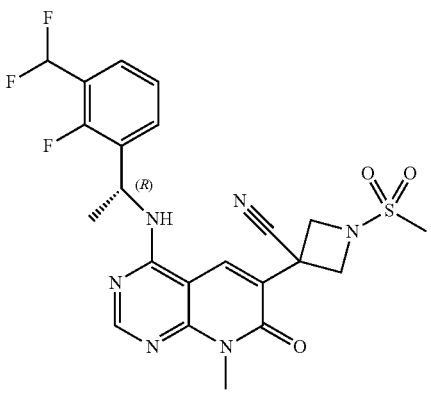 |
| 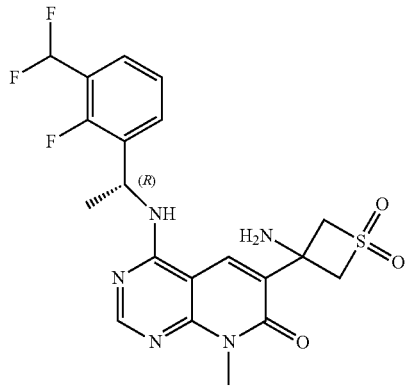 | 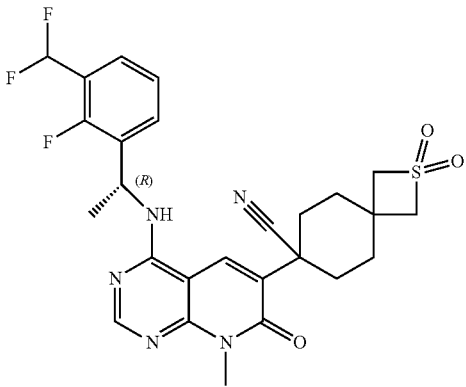 |
| 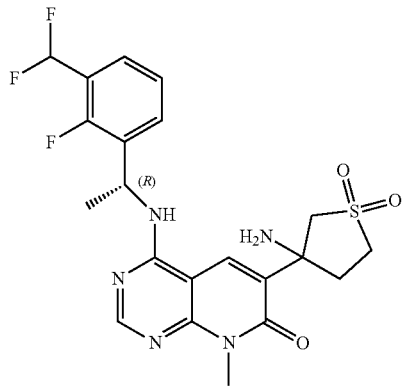 | 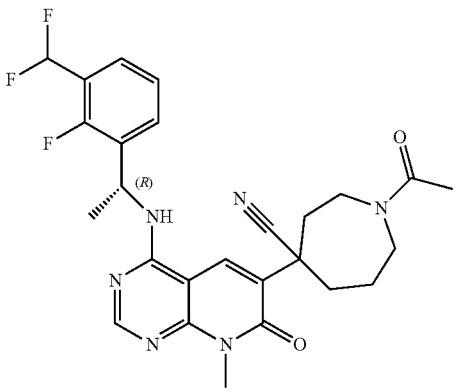 |
| 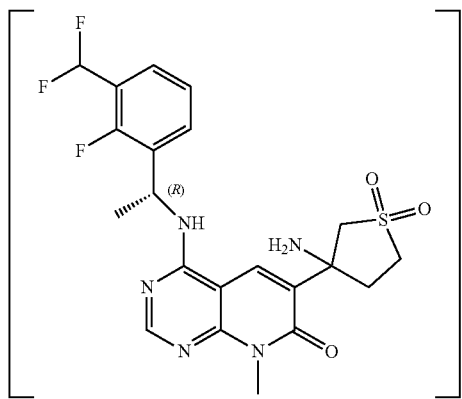 | 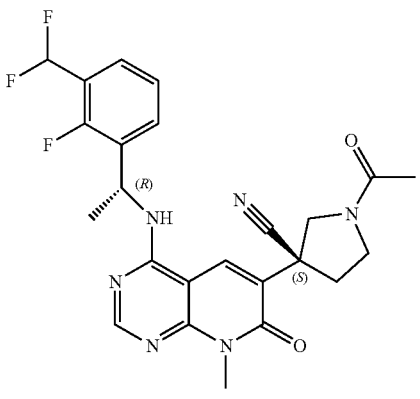 |

803
804
-continued
| Structure | Structure |
|---|---|
| 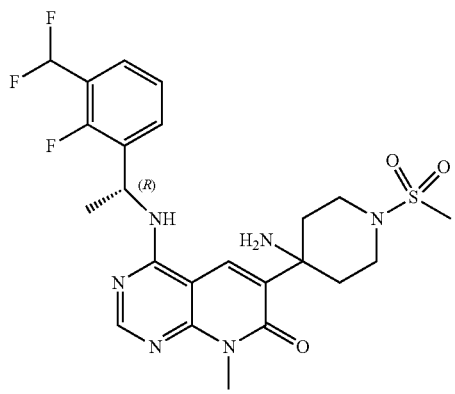 | 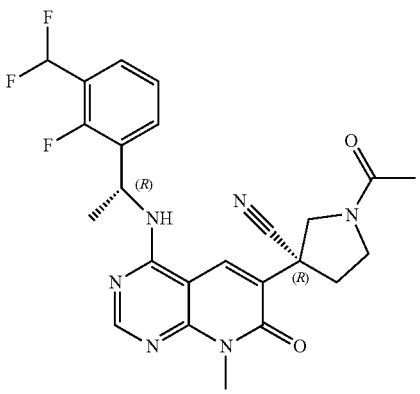 |
| 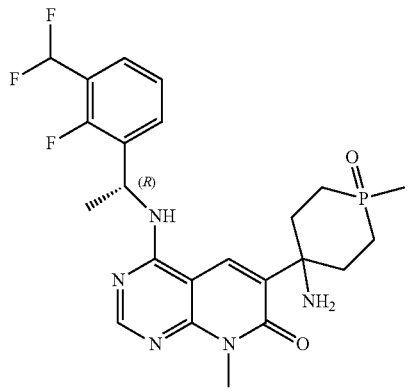 | 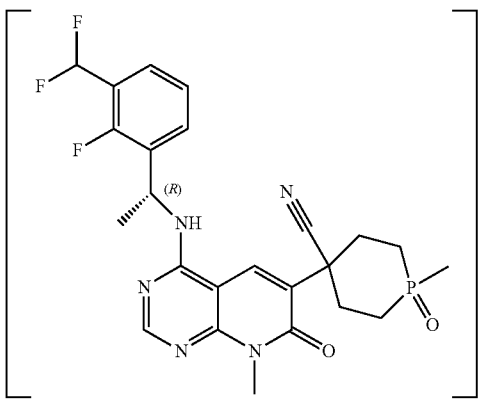 |
| 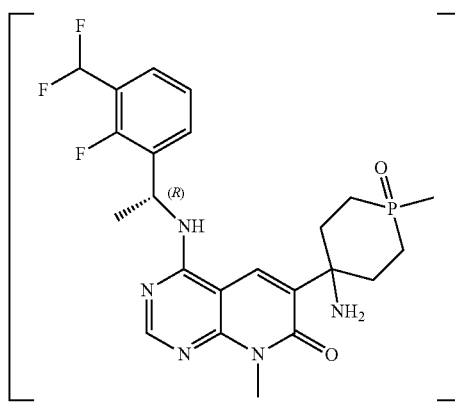 | 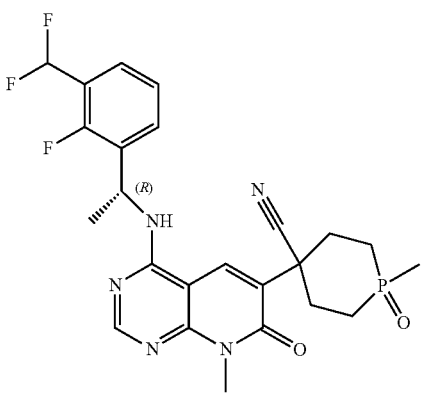 |
| 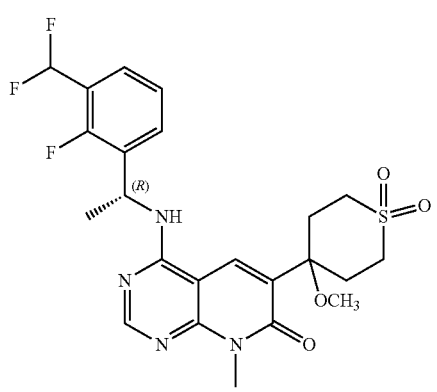 | 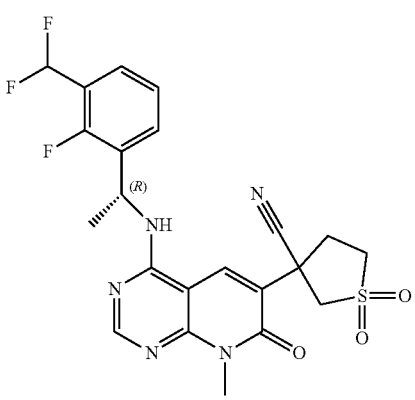 |

US 11,168,102 B1
805 806
-continued
| Structure | Structure |
|---|---|
| 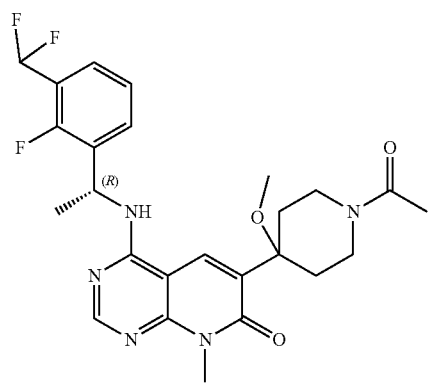 | 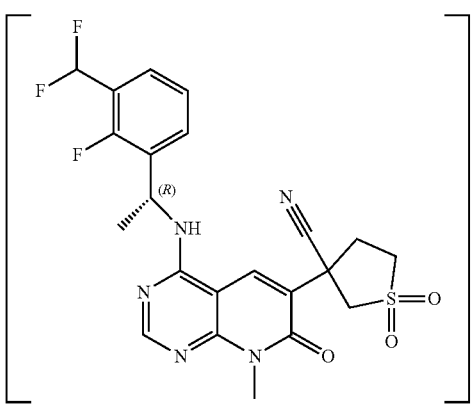 |
| 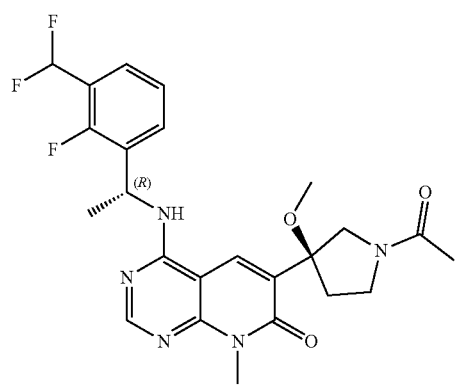 | 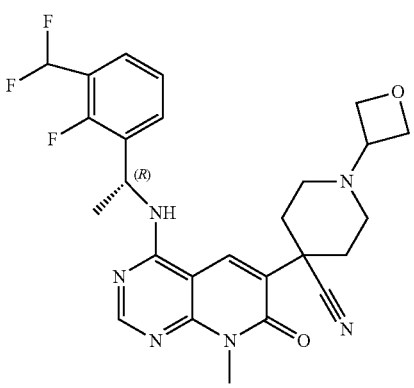 |
| 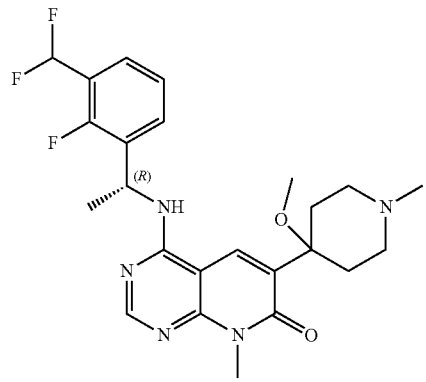 | 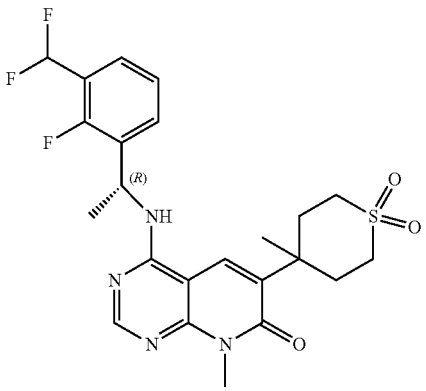 |
| 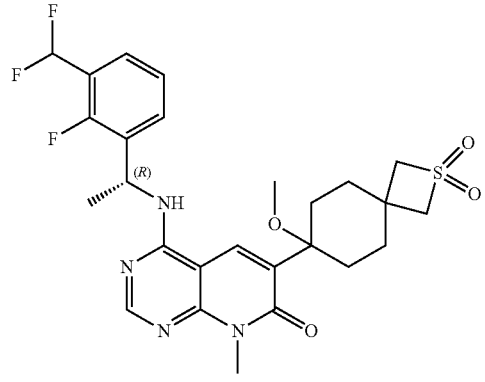 | 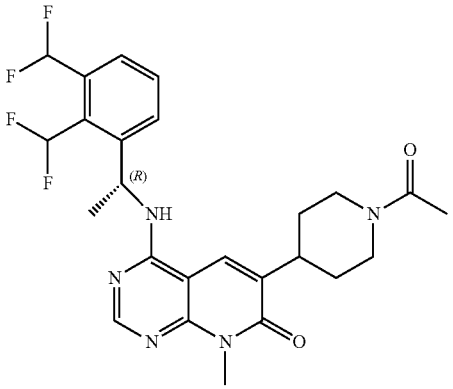 |

| 807 | 808 |
|---|---|
| Structure | Structure |
| 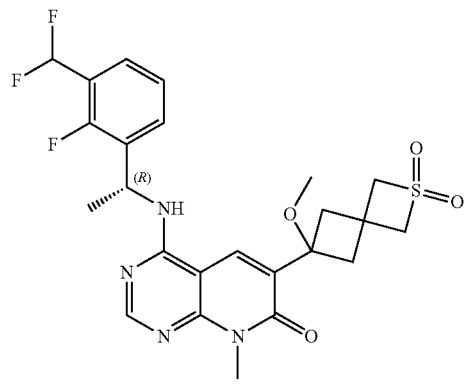 | 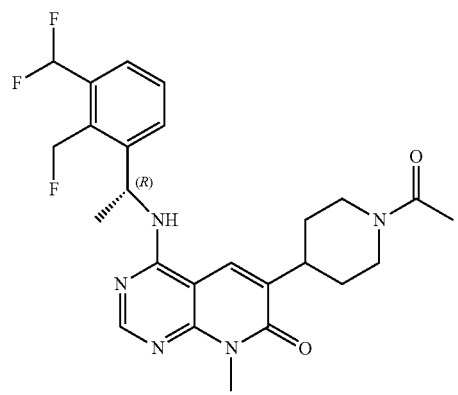 |
| 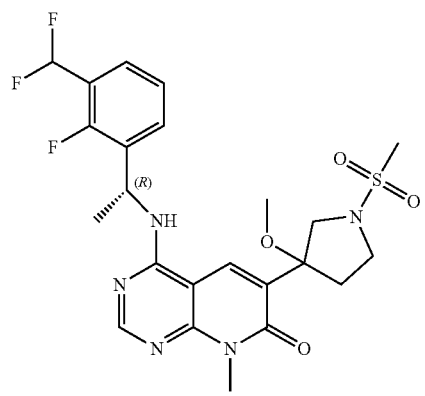 | 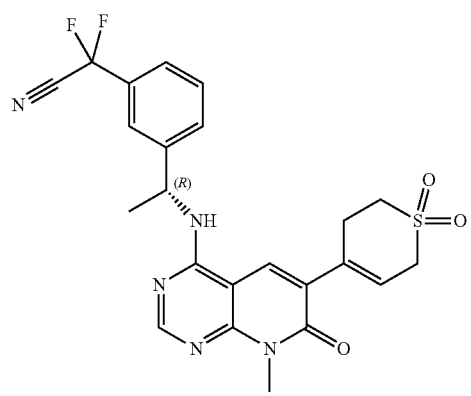 |
| 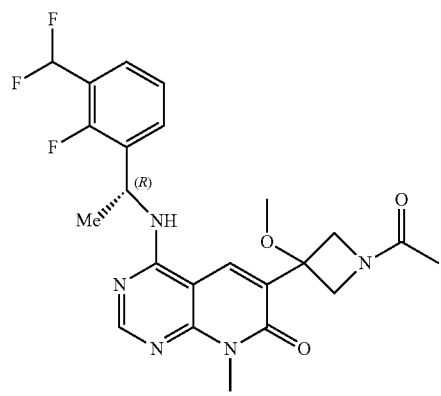 | 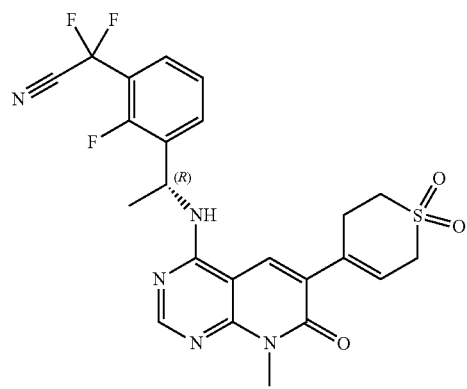 |
| 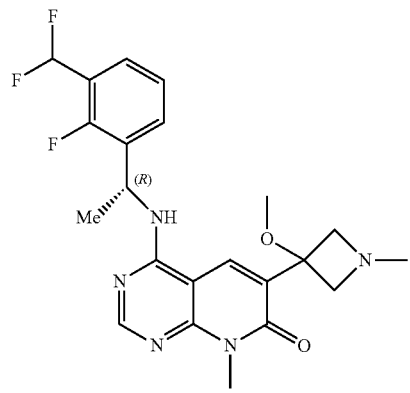 | 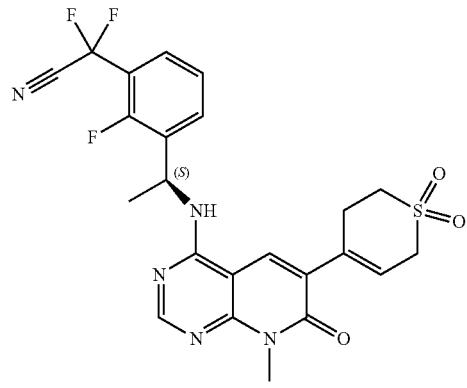 |

| Structure | Structure |
|---|---|
| 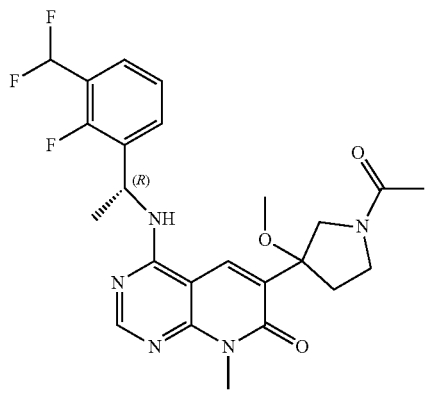 | 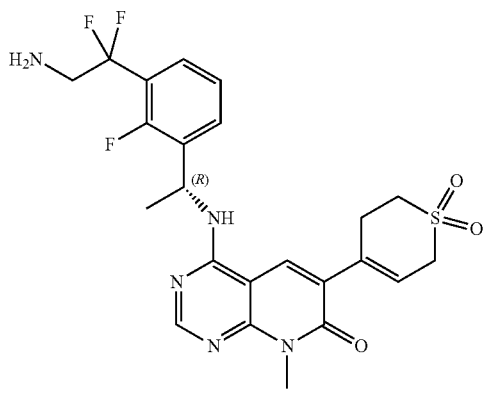 |
| 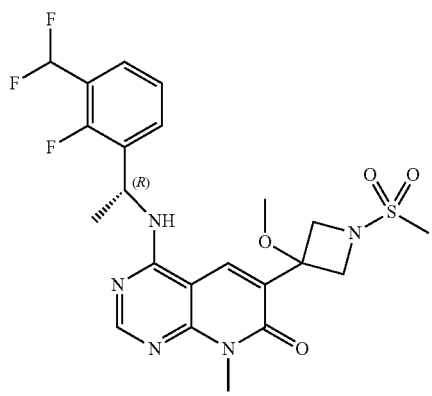 | 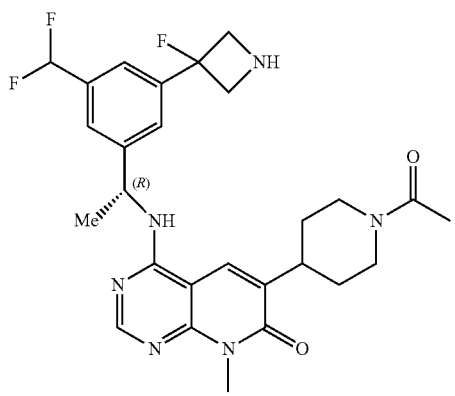 |
| 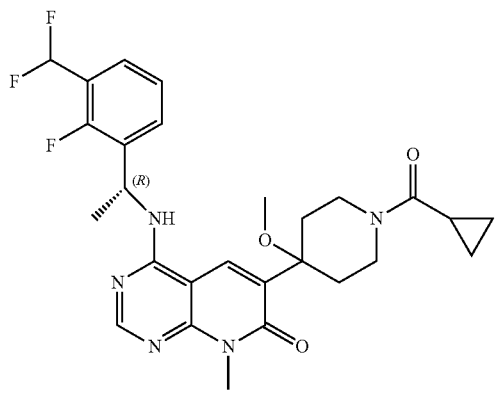 | 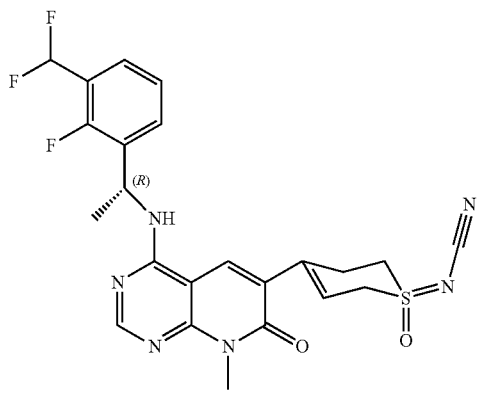 |
| 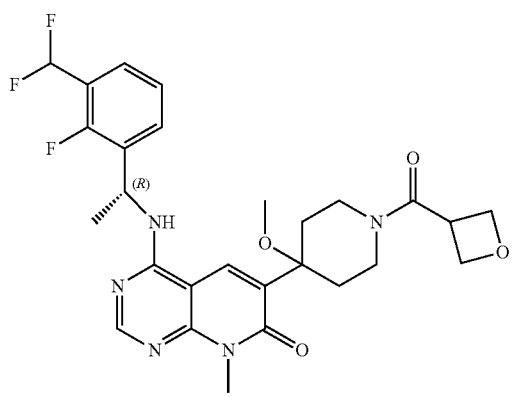 | |

| 811 | 812 |
|---|---|
| Structure | Structure |
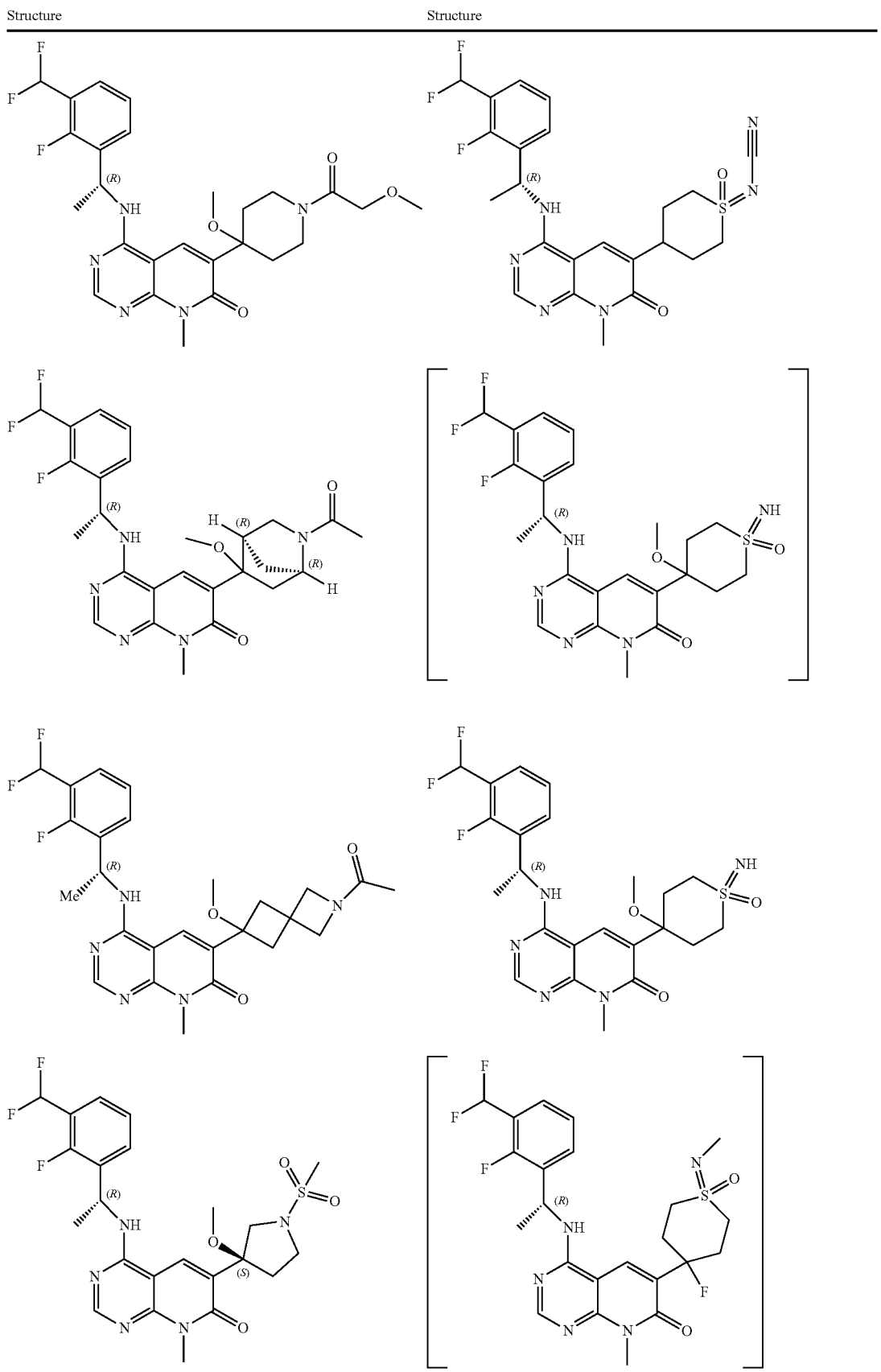

| Structure | Structure |
|---|---|
| 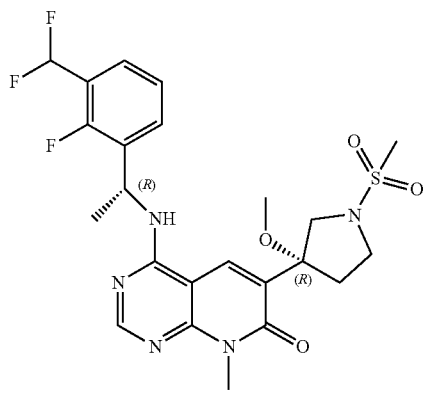 | 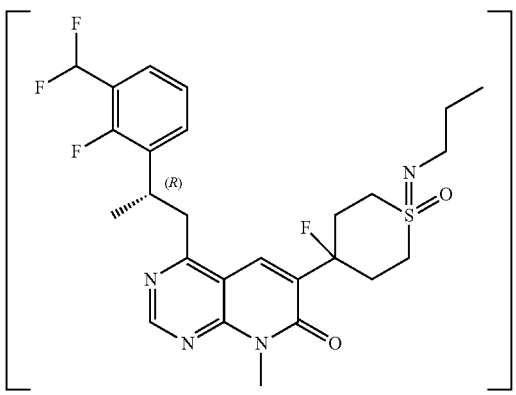 |
| 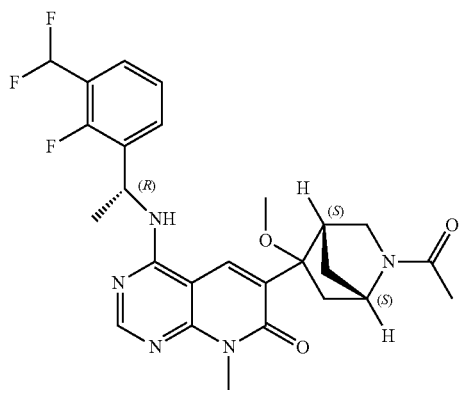 | 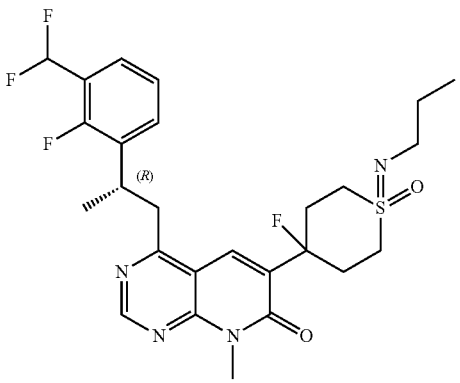 |
| 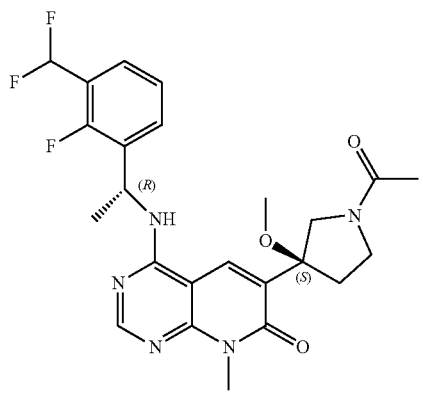 | 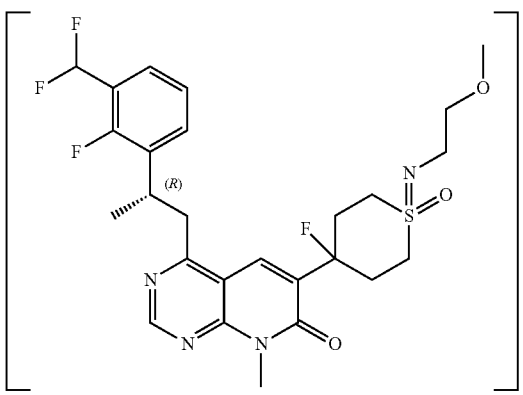 |
| 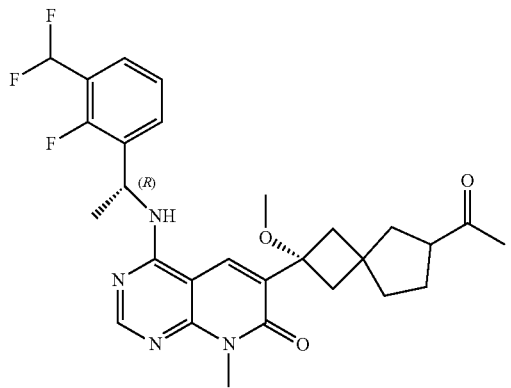 | 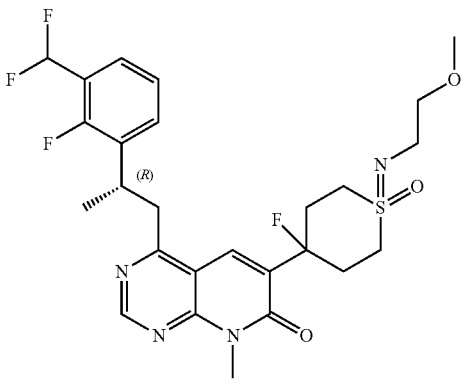 |

| Structure | Structure |
|---|---|
| 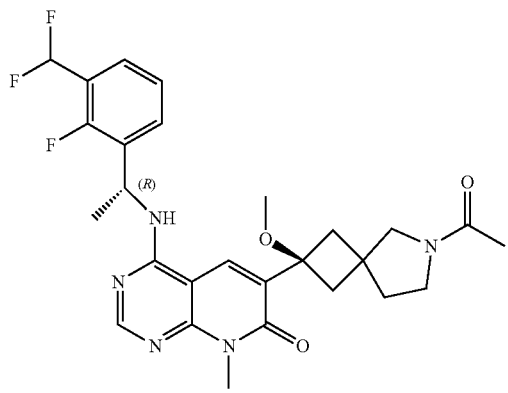 | 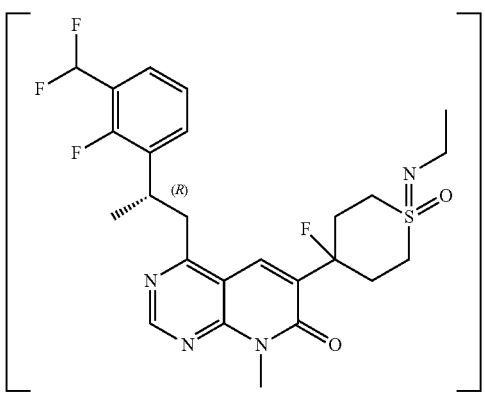 |
| 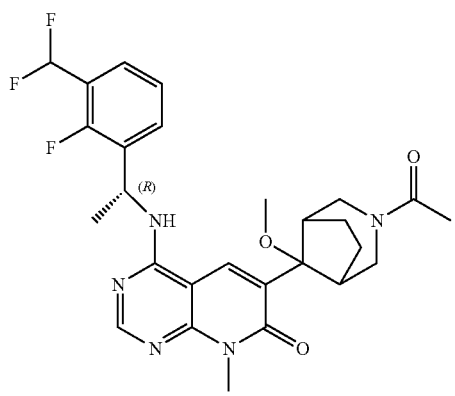 | 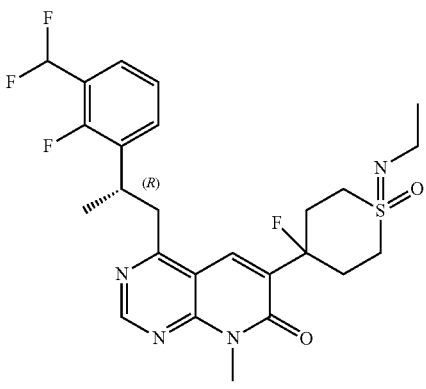 |
| 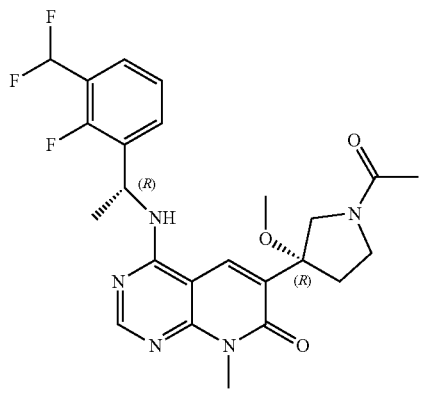 | 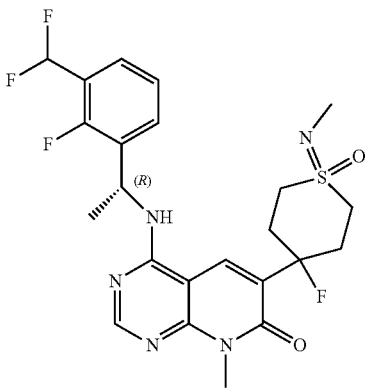 |
| 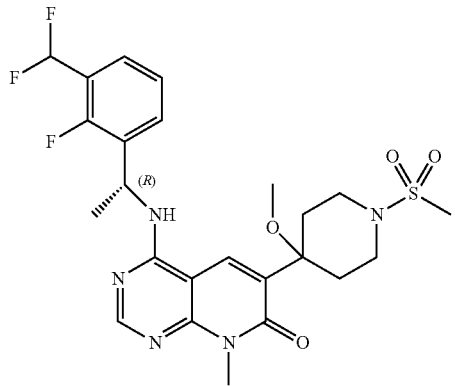 | 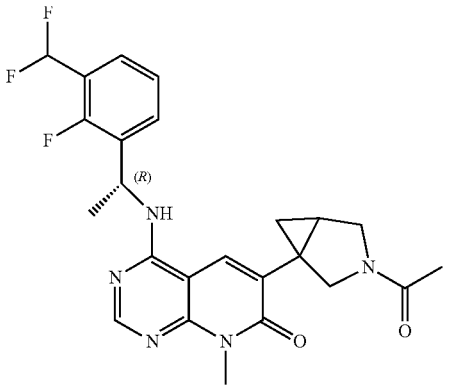 |

-continued
| Structure | Structure |
|---|---|
| 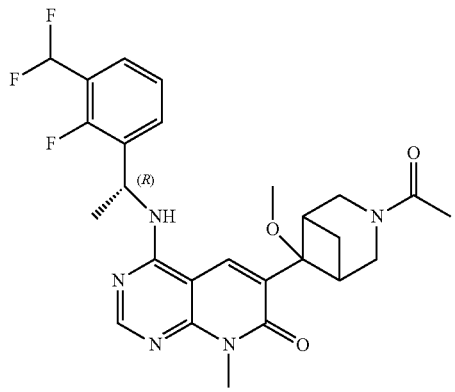 | 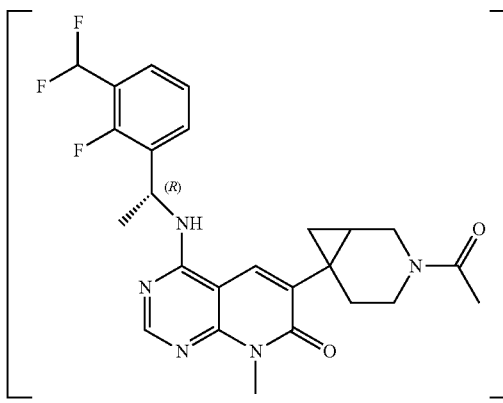 |
| 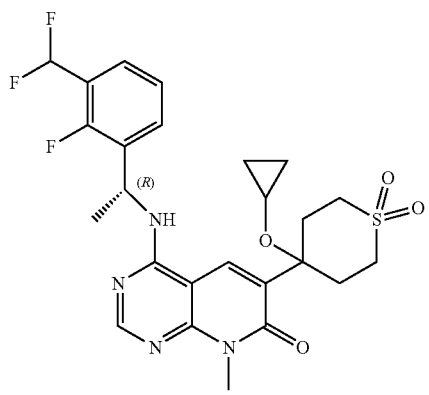 | 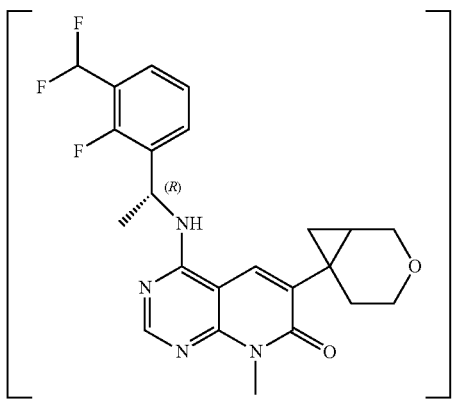 |
| 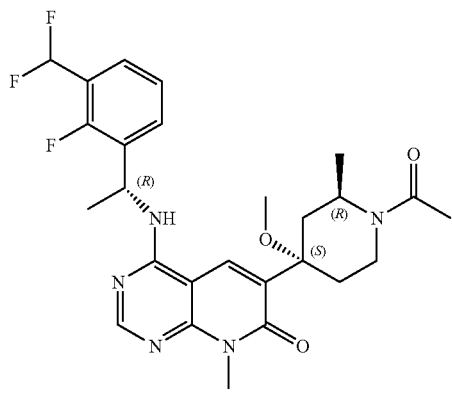 | 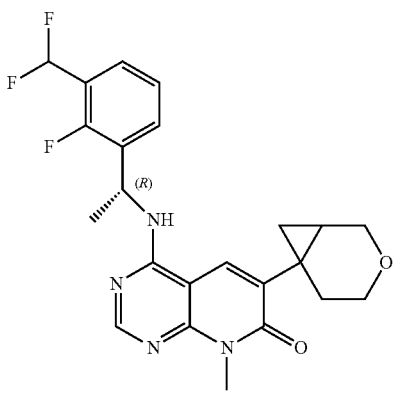 |
| 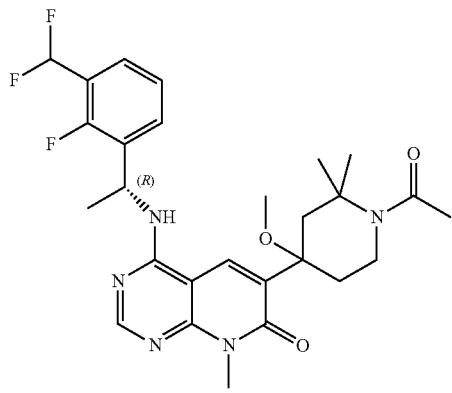 | 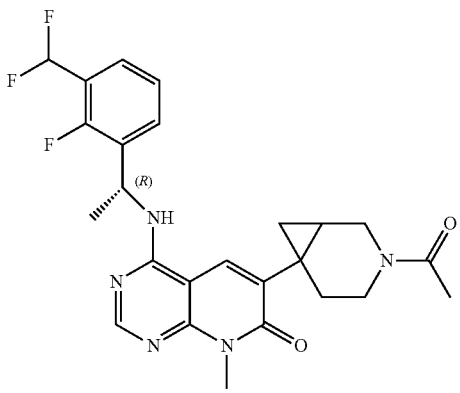 |

-continued
| Structure | Structure |
|---|---|
| 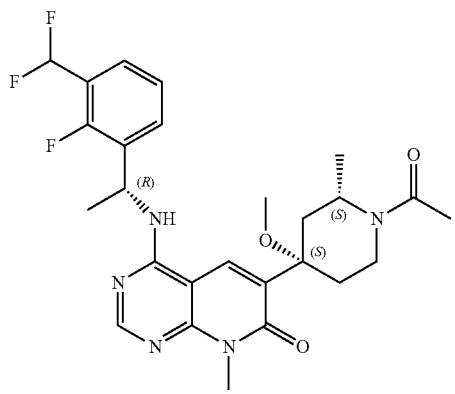 | 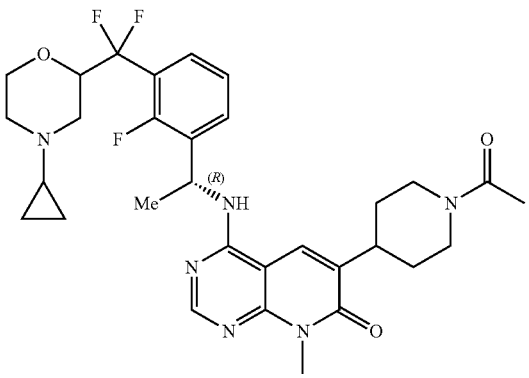 |
| 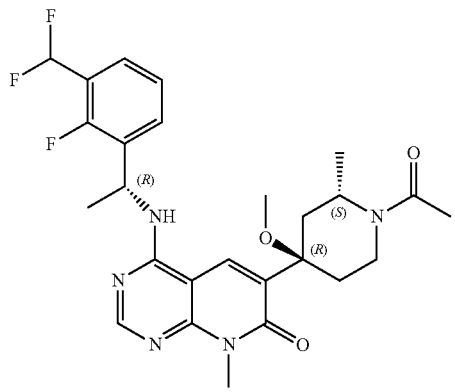 | 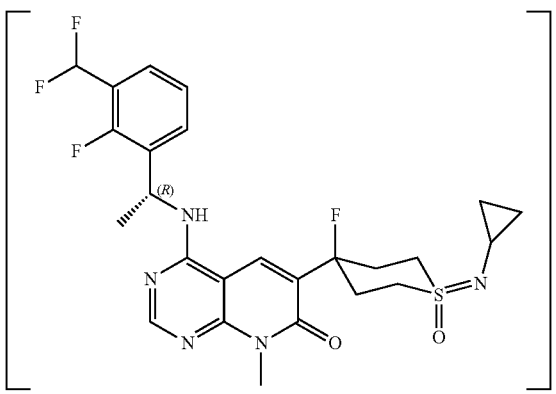 |
| 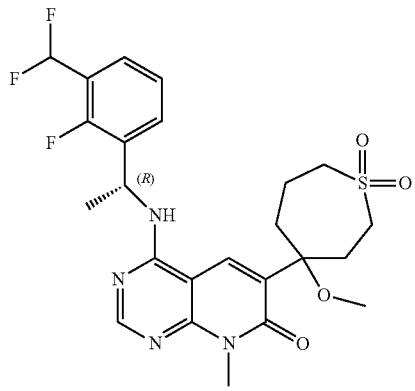 | 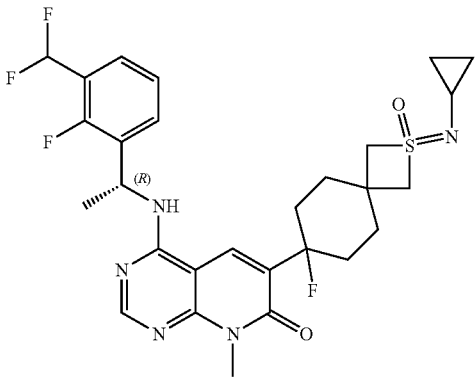 |
| 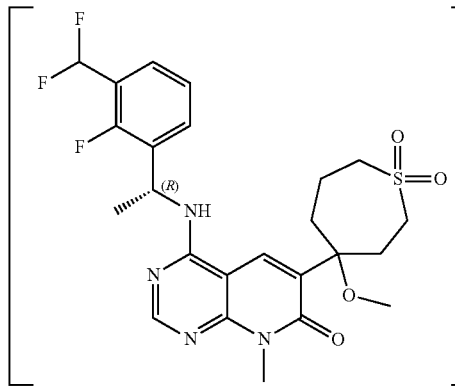 | 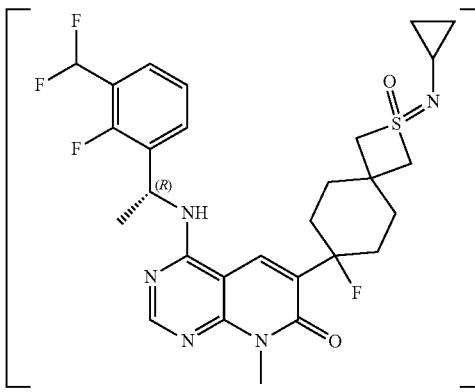 |

| Structure | Structure |
|---|---|
| 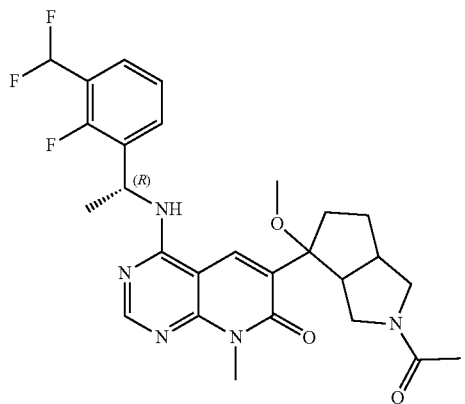 | |
| 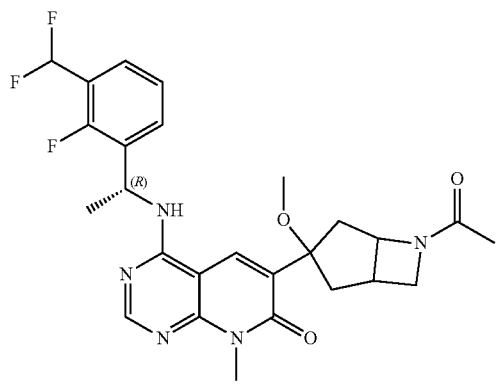 | 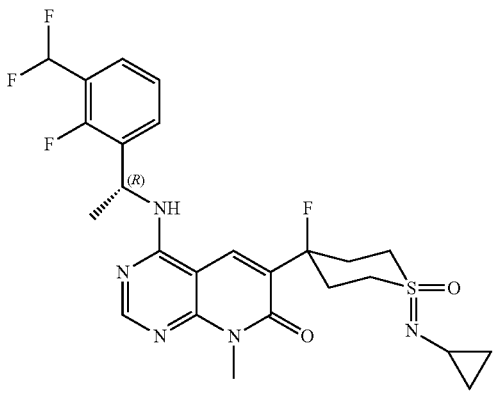 |
| 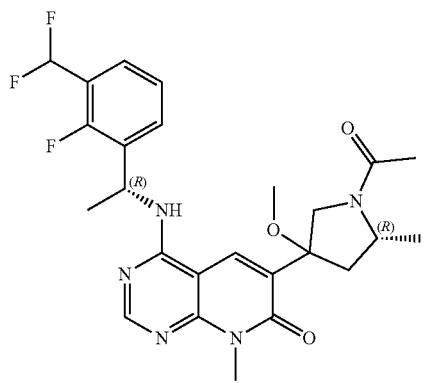 | 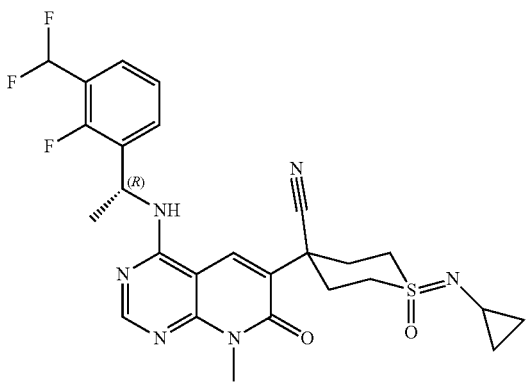 |
| 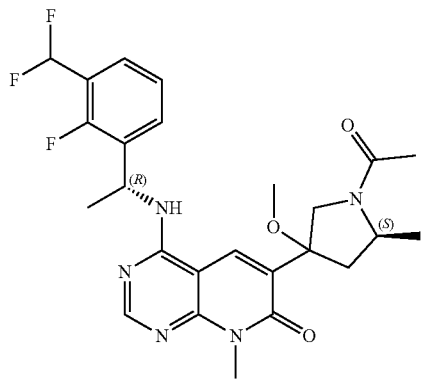 | 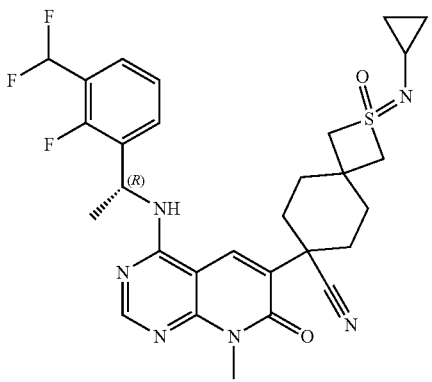 |

-continued
| Structure | Structure |
|---|---|
| 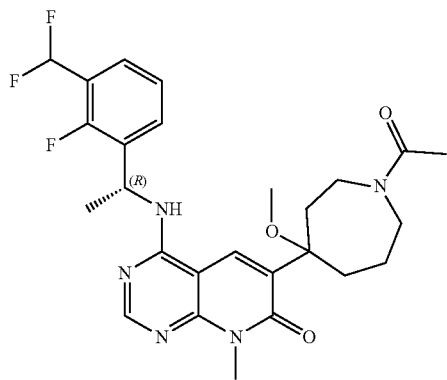 | 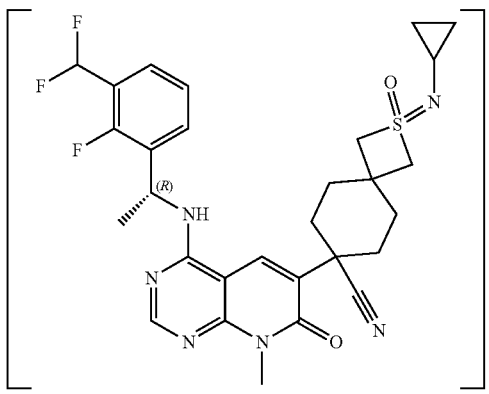 |
| 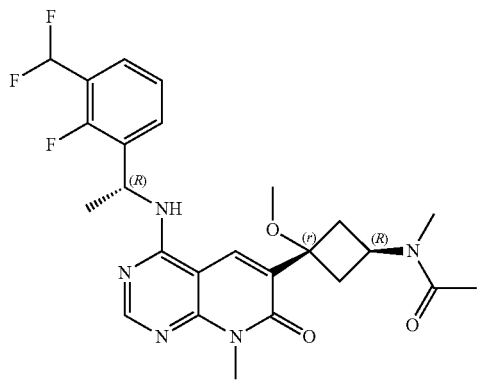 | 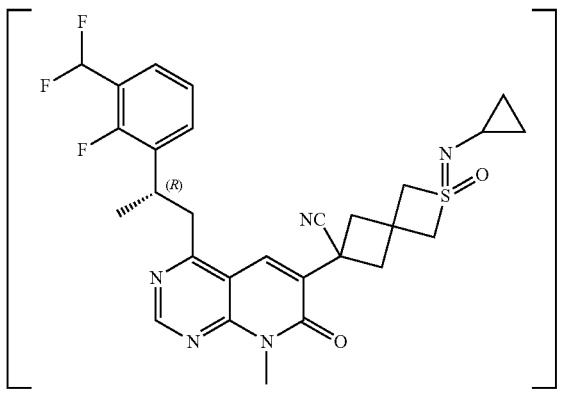 |
| 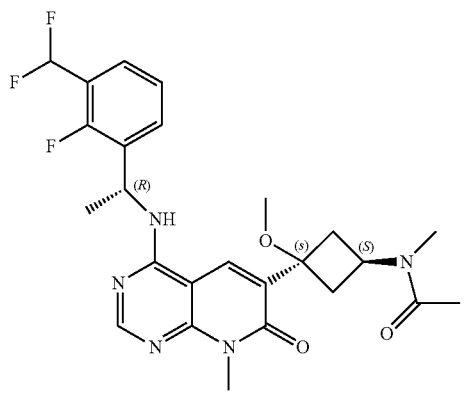 | 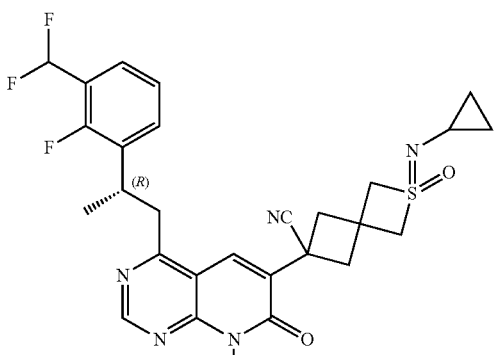 |
| 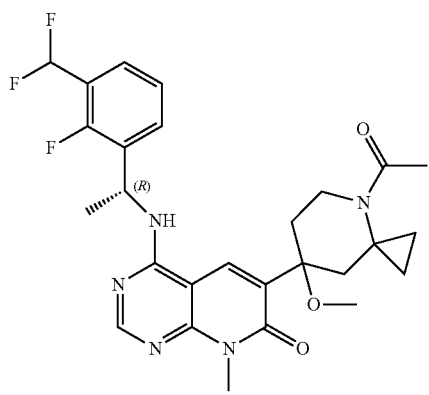 | 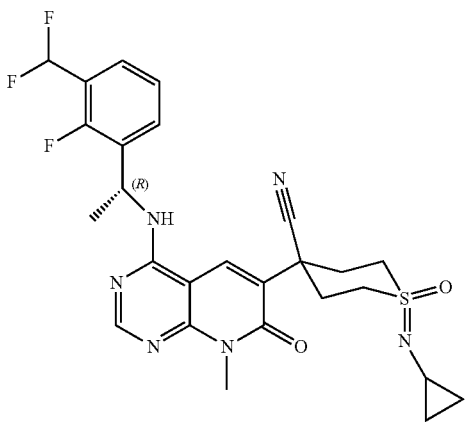 |

| Structure | Structure |
|---|---|
| 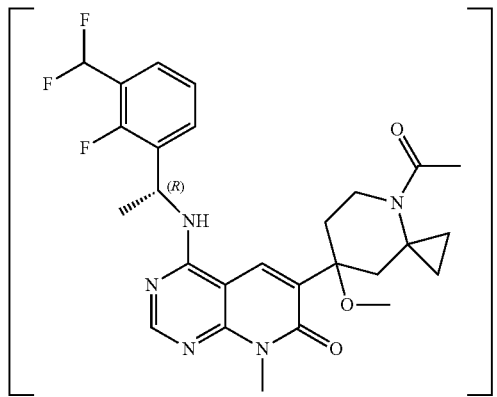 | 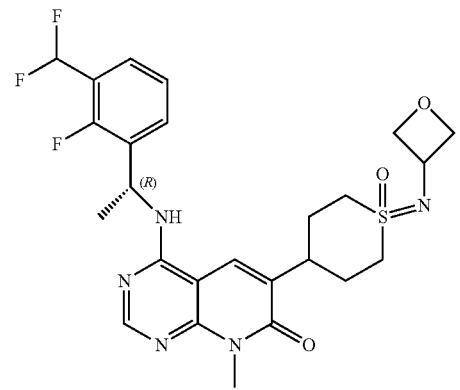 |
| 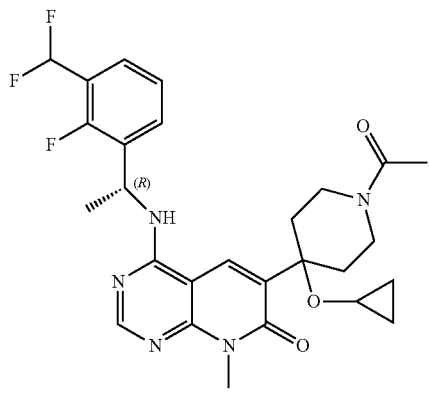 | 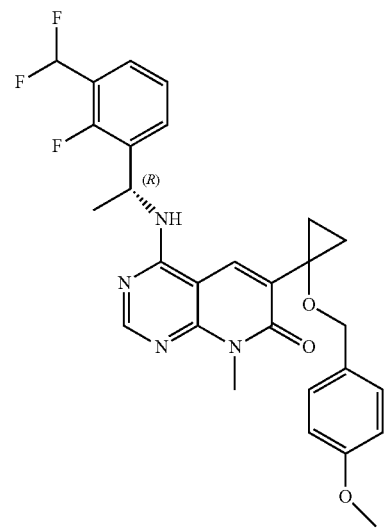 |
| 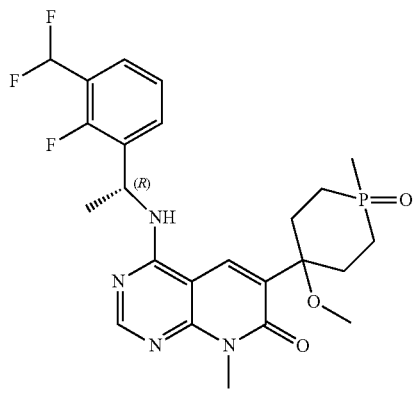 | 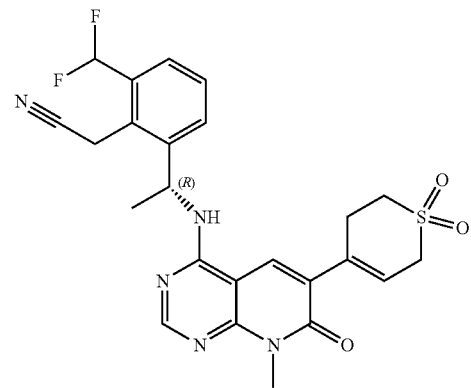 |

| Structure | Structure |
|---|---|
| 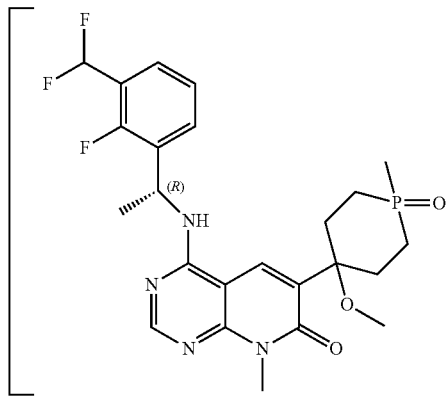 | 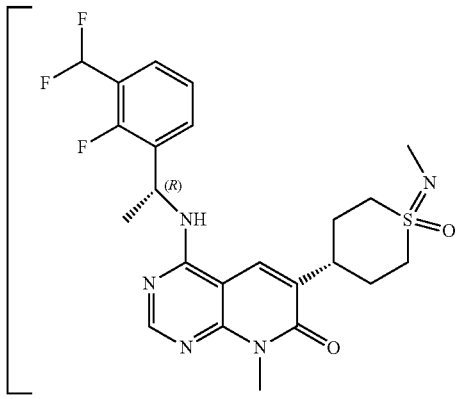 |
| 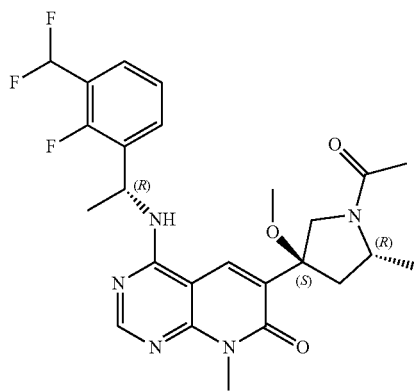 | 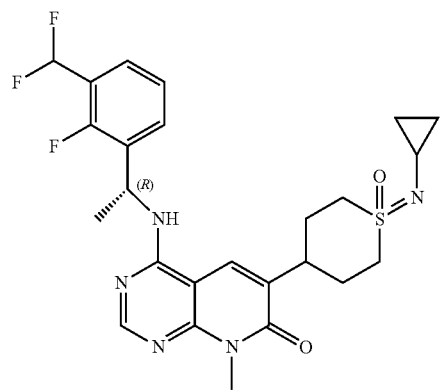 |
| 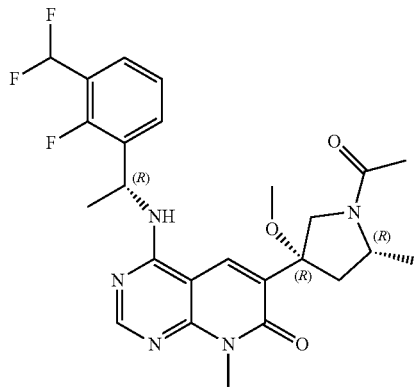 | 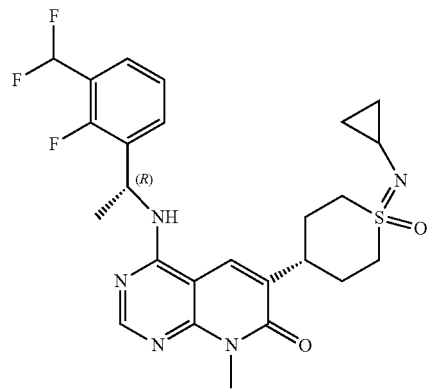 |
| 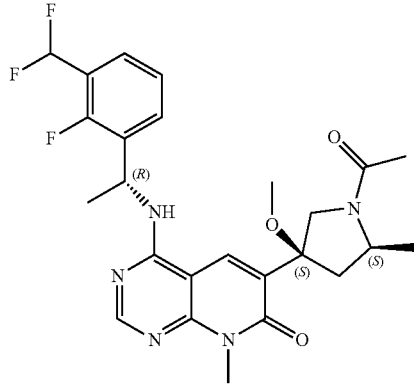 | 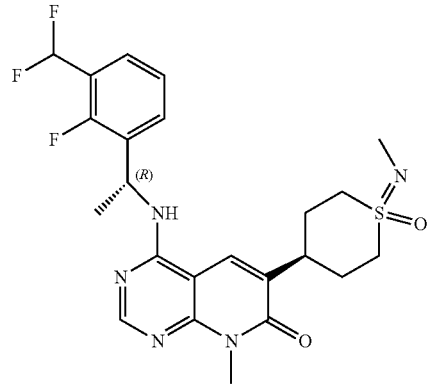 |

-continued
| Structure | Structure |
|---|---|
| 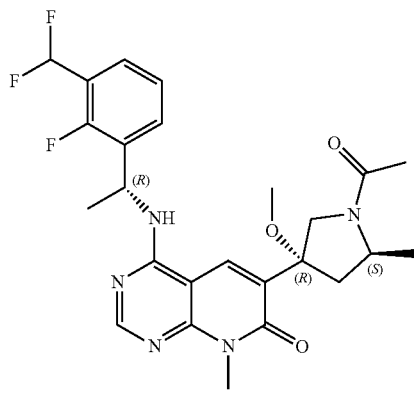 | 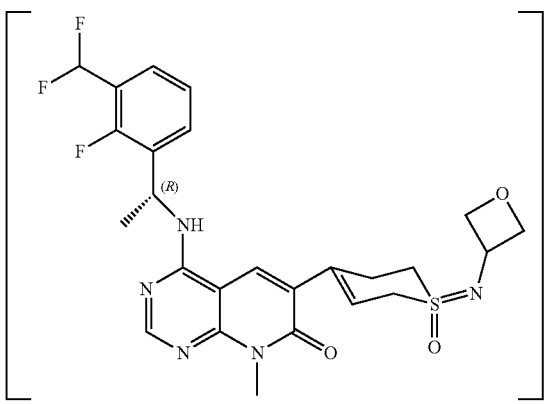 |
| 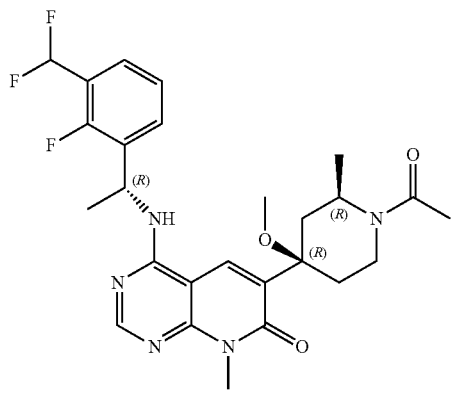 | |
| 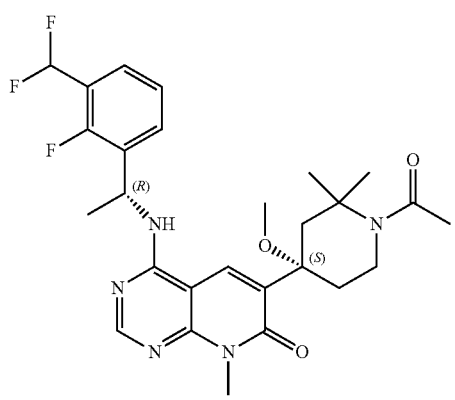 | 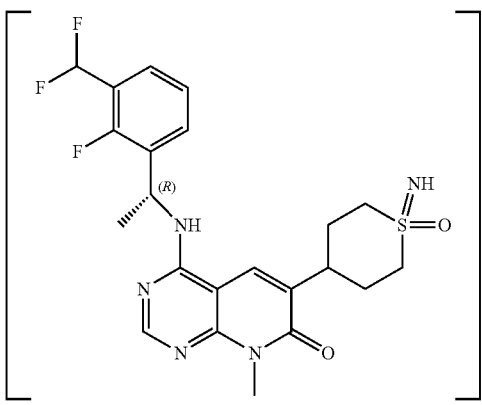 |
| | 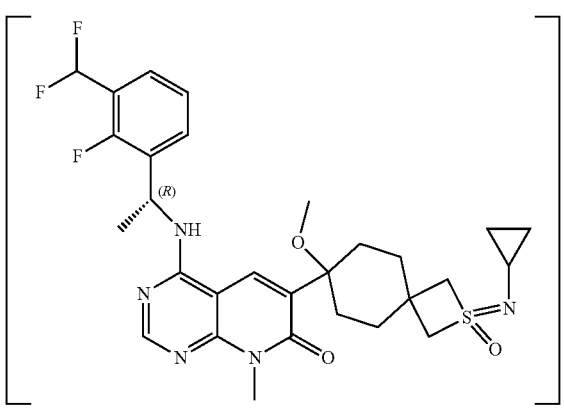 |

| Structure | Structure |
|---|---|
| 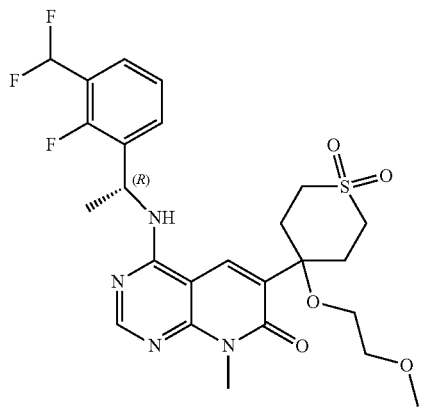 | 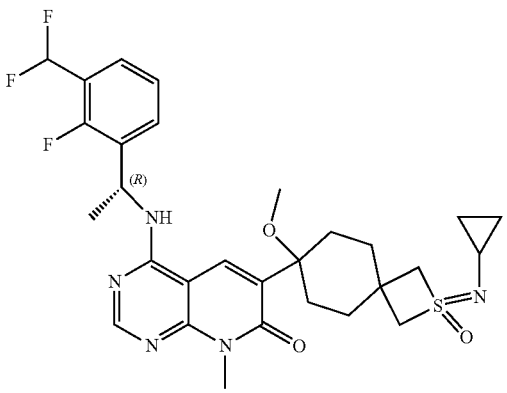 |
| 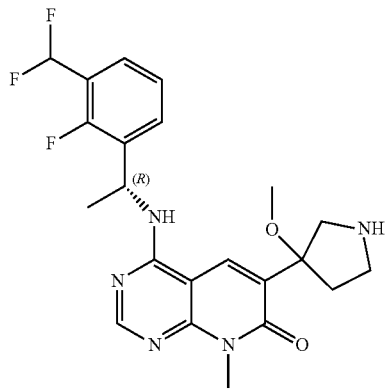 | 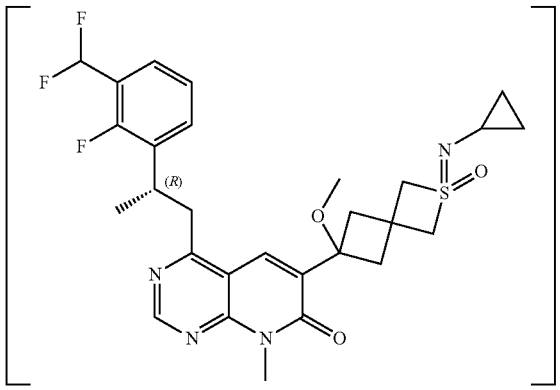 |
| 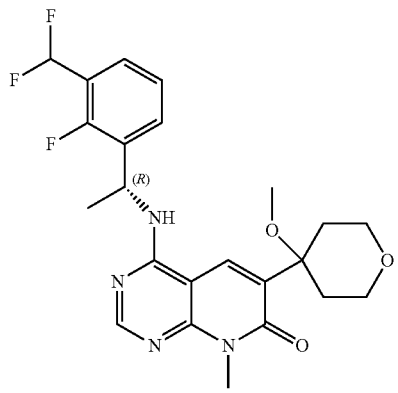 | 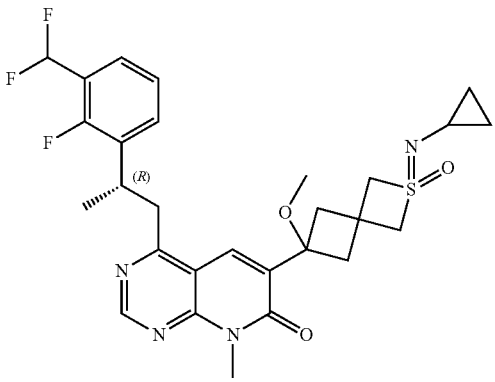 |
| 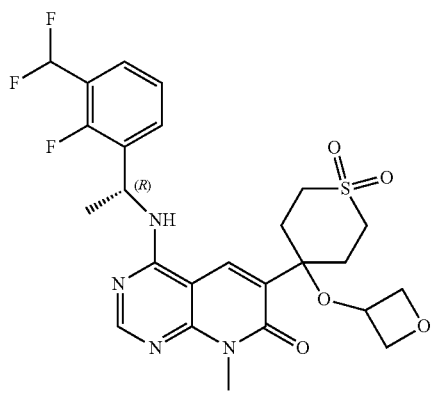 | 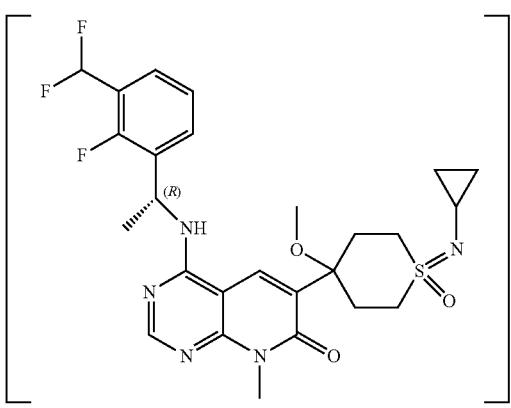 |

| Structure | Structure |
|---|---|
| 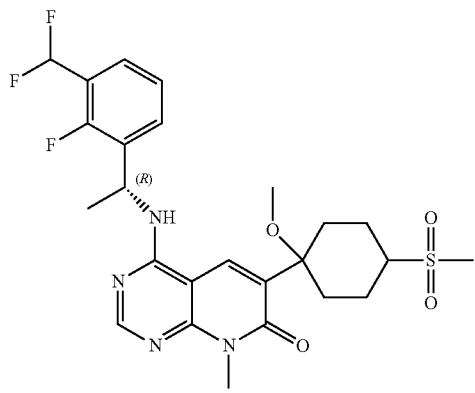 | 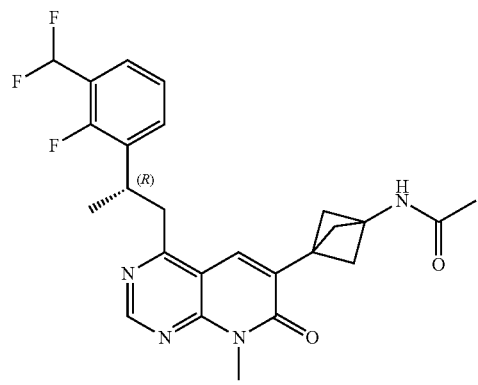 |
| 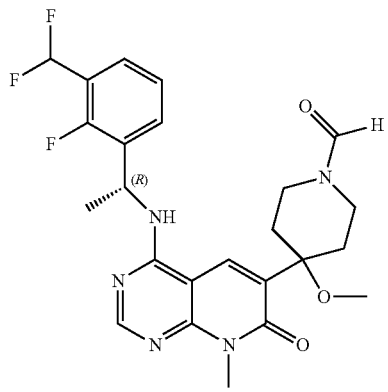 | 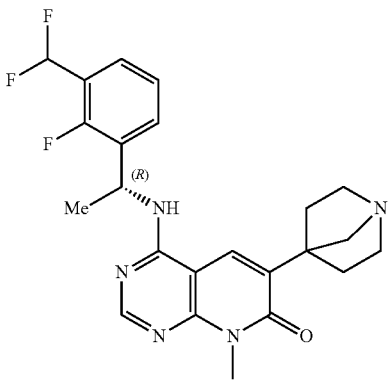 |
| 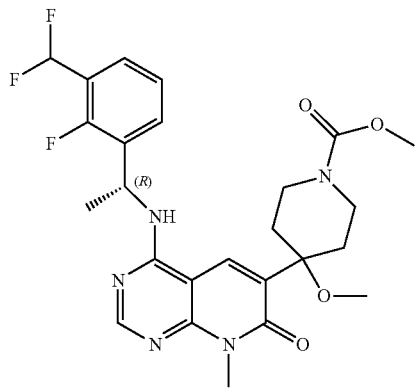 | 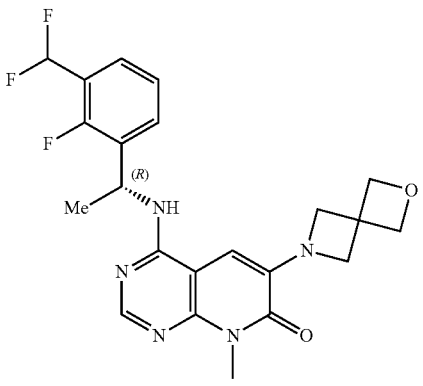 |

| Structure | Structure |
|---|---|
| 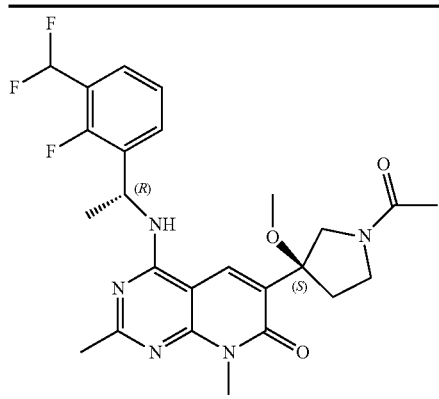 | 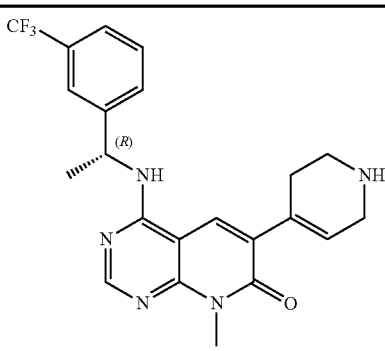 |
| 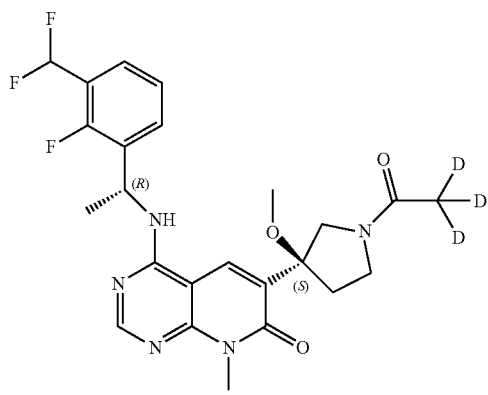 | 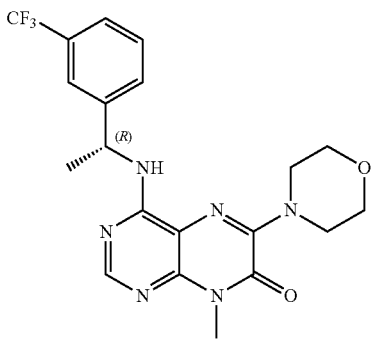 |
| 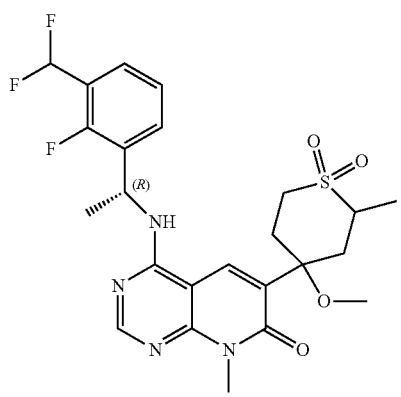 | |
4. The compound of claim 3, or a pharmaceutically acceptable salt thereof.

5. A compound, or a pharmaceutically acceptable salt or a stereoisomer thereof, selected from among the compounds in the following table:

| Structure |
|---|
| 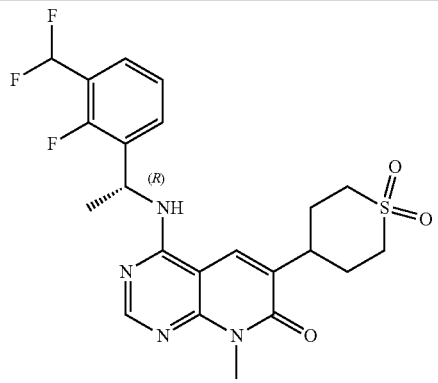 |
| 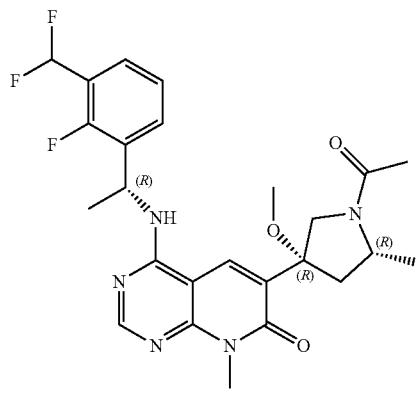 |
| 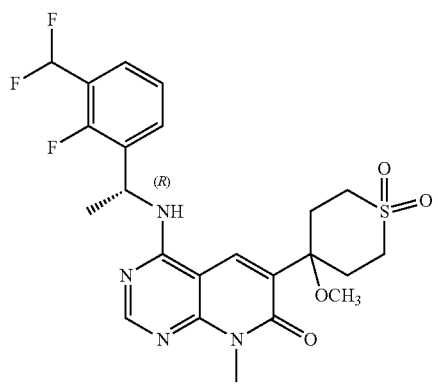 |
| 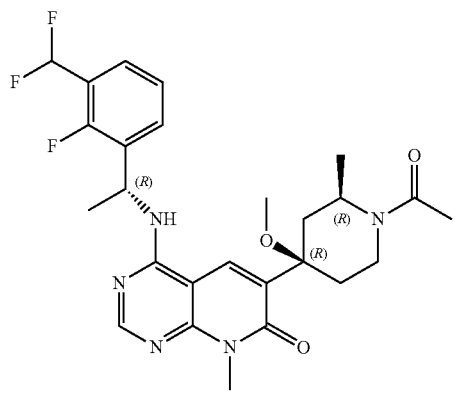 |

-continued

| Structure |
|---|
| 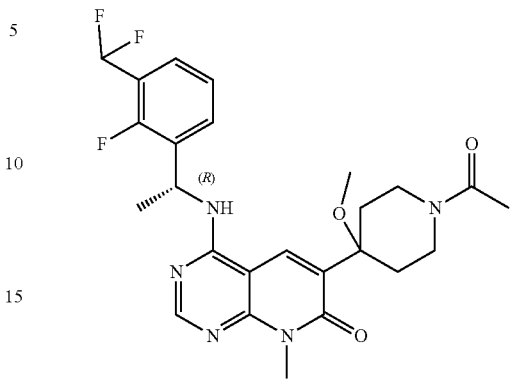 |
| 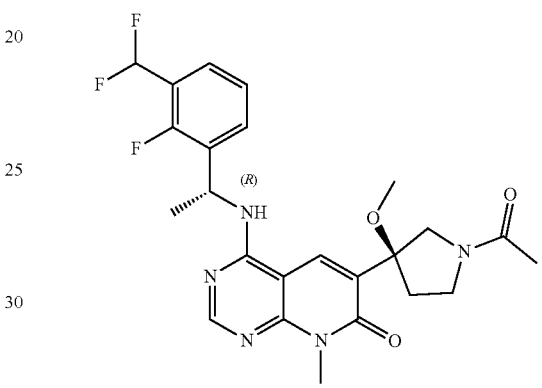 |
| 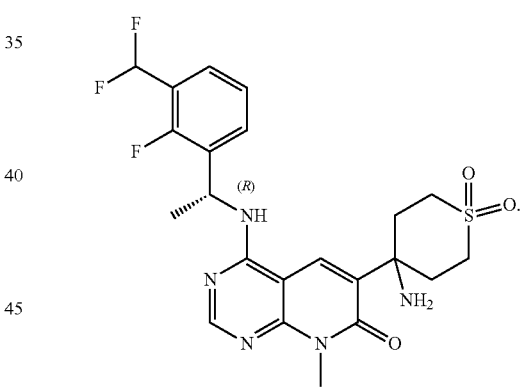 |

6. The compound of claim 5, or a pharmaceutically acceptable salt thereof.

7. A pharmaceutical composition comprising a compound of claim 1, or a pharmaceutically acceptable salt or stereoisomer thereof, and a pharmaceutically acceptable carrier.

8. The compound of claim 1, or a stereoisomer thereof.

9. The compound of claim 1, or a pharmaceutically acceptable salt of a stereoisomer thereof.

10. The pharmaceutically acceptable salt of a stereoisomer of claim 1.

11. The compound of claim 3, or a stereoisomer thereof.

12. The compound of claim 3, or a pharmaceutically acceptable salt of a stereoisomer thereof.

13. The pharmaceutically acceptable salt of a stereoisomer of claim 3.

14. The compound of claim 5, or a stereoisomer thereof.

15. The compound of claim 5, or a pharmaceutically acceptable salt of a stereoisomer thereof.

16. The pharmaceutically acceptable salt of a stereoisomer of claim 5.

17. A pharmaceutical composition comprising a compound of claim 3, or a pharmaceutically acceptable salt or stereoisomer thereof, and a pharmaceutically acceptable carrier.

18. A pharmaceutical composition comprising a compound of claim 5, or a pharmaceutically acceptable salt or stereoisomer thereof, and a pharmaceutically acceptable carrier.

* * * * *